US007198924B2

(12) United States Patent
Chesnut et al.

(10) Patent No.: US 7,198,924 B2
(45) Date of Patent: Apr. 3, 2007

(54) METHODS AND COMPOSITIONS FOR SYNTHESIS OF NUCLEIC ACID MOLECULES USING MULTIPLE RECOGNITION SITES

(75) Inventors: Jonathan D. Chesnut, Carlsbad, CA (US); John Carrino, San Diego, CA (US); Louis Leong, Mission Viejo, CA (US); Knut Madden, Carlsbad, CA (US); Martin A. G. Gleeson, San Diego, CA (US); James Fan, Carlsbad, CA (US); Michael A. Brasch, Gaithersburg, MD (US); David Cheo, Kensington, MD (US); James L. Hartley, Frederick, MD (US); Devon R. N. Byrd, Fredericksburg, VA (US); Gary F. Temple, Washington Grove, MD (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 10/792,035

(22) Filed: Mar. 4, 2004

(65) Prior Publication Data

US 2004/0265863 A1 Dec. 30, 2004

Related U.S. Application Data

(63) Continuation of application No. 10/454,793, filed on Jun. 5, 2003, now abandoned, and a continuation-in-part of application No. 10/014,128, filed on Dec. 7, 2001, now Pat. No. 7,033,801, and a continuation-in-part of application No. 10/005,876, filed on Dec. 7, 2001, and a continuation-in-part of application No. 09/732,914, filed on Dec. 11, 2000.

(60) Provisional application No. 60/385,613, filed on Jun. 5, 2002, provisional application No. 60/333,124, filed on Nov. 27, 2001, provisional application No. 60/318,902, filed on Sep. 14, 2001.

(51) Int. Cl.
*C12P 19/34* (2006.01)
*C12Q 1/68* (2006.01)

(52) U.S. Cl. ...................................... 435/91.5; 435/462

(58) Field of Classification Search ..................... None
See application file for complete search history.

(56) References Cited

U.S. PATENT DOCUMENTS

| | | | |
|---|---|---|---|
| 4,626,505 | A | 12/1986 | Falco |
| 4,673,640 | A | 6/1987 | Backman |
| 4,683,195 | A | 7/1987 | Mullis et al. |
| 4,683,202 | A | 7/1987 | Mullis |
| 4,743,546 | A | 5/1988 | Backman et al. |
| 4,808,537 | A | 2/1989 | Stroman et al. |
| 4,855,231 | A | 8/1989 | Stroman et al. |
| 4,959,217 | A | 9/1990 | Sanders et al. |
| 4,959,317 | A | 9/1990 | Sauer |
| 4,965,188 | A | 10/1990 | Mullis et al. |
| 5,093,257 | A | 3/1992 | Gray |
| 5,102,797 | A | 4/1992 | Tucker et al. |
| 5,159,062 | A | 10/1992 | Knapp et al. |
| 5,227,288 | A | 7/1993 | Blattner |
| 5,286,632 | A | 2/1994 | Jones |
| 5,334,375 | A | 8/1994 | Nabi et al. |
| 5,334,575 | A | 8/1994 | Noonan et al. |
| 5,348,886 | A | 9/1994 | Lee et al. |
| 5,354,668 | A | 10/1994 | Auerbach |
| 5,378,618 | A | 1/1995 | Sternberg et al. |
| 5,434,066 | A | 7/1995 | Bebee et al. |
| 5,451,513 | A | 9/1995 | Maliga et al. |
| 5,470,727 | A | 11/1995 | Mascarenhas et al. |

(Continued)

FOREIGN PATENT DOCUMENTS

| | | |
|---|---|---|
| CA | 2141412 | 2/1994 |

(Continued)

OTHER PUBLICATIONS

Abremski, K., et al., "Bacteriophage P1 Cre-*laxP* Site-specific Recombination: Site-specific DNA Topoisomerase Activity of the Cre Recombination Protein," *J. Biol. Chem. 261*:391-396, American Society for Biochemistry and Molecular Biology (1986).

(Continued)

*Primary Examiner*—James Ketter
(74) *Attorney, Agent, or Firm*—Sterne, Kessler, Goldstein and Fox PLLC

(57) ABSTRACT

The present invention provides compositions and methods for recombinational cloning. The compositions include vectors having multiple recombination sites and/or multiple topoisomerase recognition sites. The methods permit the simultaneous cloning of two or more different nucleic acid molecules. In some embodiments the molecules are fused together while in other embodiments the molecules are inserted into distinct sites in a vector. The invention also generally provides for linking or joining through recombination a number of molecules and/or compounds (e.g., chemical compounds, drugs, proteins or peptides, lipids, nucleic acids, carbohydrates, etc.) which may be the same or different. The invention also provides host cells comprising nucleic acid molecules of the invention or prepared according to the methods of the invention, and also provides kits comprising the compositions, host cells and nucleic acid molecules of the invention, which may be used to synthesize nucleic acid molecules according to the methods of the invention.

25 Claims, 59 Drawing Sheets

U.S. PATENT DOCUMENTS

| | | | |
|---|---|---|---|
| 5,527,695 | A | 6/1996 | Hodges et al. |
| 5,552,314 | A | 9/1996 | Greener |
| 5,591,609 | A | 1/1997 | Auerbach |
| 5,605,793 | A | 2/1997 | Stemmer |
| 5,614,389 | A | 3/1997 | Auerbach |
| 5,635,381 | A | 6/1997 | Hooykaas et al. |
| 5,650,308 | A | 7/1997 | Baum |
| 5,650,557 | A | 7/1997 | Hannah et al. |
| 5,654,182 | A | 8/1997 | Wahl et al. |
| 5,658,772 | A | 8/1997 | Odell et al. |
| 5,677,170 | A | 10/1997 | Devine et al. |
| 5,677,177 | A | 10/1997 | Wahl et al. |
| 5,695,971 | A | 12/1997 | Kadokami et al. |
| 5,710,248 | A | 1/1998 | Grose |
| 5,723,765 | A | 3/1998 | Oliver et al. |
| 5,728,551 | A | 3/1998 | Devine et al. |
| 5,733,733 | A | 3/1998 | Auerbach |
| 5,733,743 | A | 3/1998 | Johnson et al. |
| 5,744,336 | A | 4/1998 | Hodges et al. |
| 5,766,891 | A | 6/1998 | Shuman |
| 5,776,449 | A | 7/1998 | Baum et al. |
| 5,801,030 | A | 9/1998 | McVey et al. |
| 5,814,300 | A | 9/1998 | Scott et al. |
| 5,830,707 | A | 11/1998 | Bushman |
| 5,837,242 | A | 11/1998 | Holliger et al. |
| 5,837,458 | A | 11/1998 | Minshull et al. |
| 5,843,772 | A | 12/1998 | Devine et al. |
| 5,851,808 | A | 12/1998 | Elledge et al. |
| 5,858,657 | A | 1/1999 | Winter et al. |
| 5,871,907 | A | 2/1999 | Winter et al. |
| 5,874,259 | A | 2/1999 | Szybalski |
| 5,888,732 | A | 3/1999 | Hartley et al. |
| 5,910,438 | A | 6/1999 | Bernard et al. |
| 5,916,804 | A | 6/1999 | Bushman |
| 5,919,676 | A | 7/1999 | Graham et al. |
| 5,928,914 | A | 7/1999 | Leboulch et al. |
| 5,929,307 | A | 7/1999 | Hodges et al. |
| 5,962,255 | A | 10/1999 | Griffiths et al. |
| 5,965,408 | A | 10/1999 | Short |
| 5,981,177 | A | 11/1999 | Demirjian et al. |
| 5,989,872 | A | 11/1999 | Luo et al. |
| 5,994,136 | A | 11/1999 | Naldini et al. |
| 6,010,884 | A | 1/2000 | Griffiths et al. |
| 6,025,192 | A | 2/2000 | Beach et al. |
| 6,040,138 | A | 3/2000 | Lockhart et al. |
| 6,040,430 | A | 3/2000 | Stewart |
| 6,063,627 | A | 5/2000 | McVey et al. |
| 6,066,778 | A | 5/2000 | Ginsburg et al. |
| 6,080,576 | A | 6/2000 | Zambrowicz et al. |
| 6,110,735 | A | 8/2000 | Chartier et al. |
| 6,120,764 | A | 9/2000 | Graham et al. |
| 6,121,043 | A | 9/2000 | Cochran et al. |
| 6,140,087 | A | 10/2000 | Graham et al. |
| 6,143,557 | A | 11/2000 | Hartley et al. |
| 6,156,497 | A | 12/2000 | Kaleko |
| 6,165,782 | A | 12/2000 | Naldini et al. |
| 6,171,820 | B1 | 1/2001 | Short |
| 6,171,861 | B1 | 1/2001 | Hartley et al. |
| 6,225,121 | B1 | 5/2001 | Savakis et al. |
| 6,228,646 | B1 | 5/2001 | Hardy |
| 6,238,884 | B1 | 5/2001 | Short et al. |
| 6,262,341 | B1 | 7/2001 | Baszczynski et al. |
| 6,270,969 | B1 | 8/2001 | Hartley et al. |
| 6,271,436 | B1 | 8/2001 | Piedrahita et al. |
| 6,277,608 | B1 | 8/2001 | Hartley et al. |
| 6,277,620 | B1 | 8/2001 | Gwynn et al. |
| 6,281,000 | B1 | 8/2001 | Chartier et al. |
| 6,303,301 | B1 | 10/2001 | Mack |
| 6,309,822 | B1 | 10/2001 | Fodor et al. |
| 6,333,155 | B1 | 12/2001 | Lockhart et al. |
| 6,352,842 | B1 | 3/2002 | Short et al. |
| 6,358,709 | B1 | 3/2002 | Short et al. |
| 6,361,972 | B1 | 3/2002 | Harrington et al. |
| 6,361,974 | B1 | 3/2002 | Short et al. |
| 6,365,377 | B1 | 4/2002 | Patten et al. |
| 6,410,266 | B1 | 6/2002 | Harrington et al. |
| 6,410,317 | B1 | 6/2002 | Farmer |
| 6,436,707 | B1 | 8/2002 | Zambrowicz et al. |
| 6,455,254 | B1 | 9/2002 | Short |
| 6,479,258 | B1 | 11/2002 | Short |
| 6,489,145 | B1 | 12/2002 | Short |
| 6,537,776 | B1 | 3/2003 | Short |
| 6,544,790 | B1 | 4/2003 | Sabatini |
| 6,548,277 | B1 | 4/2003 | Shuman |
| 6,576,463 | B1 | 6/2003 | Kasahara et al. |
| 6,605,449 | B1 | 8/2003 | Short |
| 6,632,600 | B1 | 10/2003 | Short |
| 6,709,841 | B2 | 3/2004 | Short |
| 6,713,279 | B1 | 3/2004 | Short |
| 6,713,282 | B2 | 3/2004 | Short et al. |
| 6,720,140 | B1 | 4/2004 | Hartley et al. |
| 6,740,506 | B2 | 5/2004 | Short et al. |
| 6,773,900 | B2 | 8/2004 | Short et al. |
| 6,916,632 | B2 | 7/2005 | Chesnut et al. |
| 6,964,861 | B1 | 11/2005 | Gerard et al. |
| 2002/0007051 | A1 | 1/2002 | Cheo et al. |
| 2002/0068290 | A1 | 6/2002 | Yarovinsky |
| 2002/0094574 | A1 | 7/2002 | Hartley et al. |
| 2002/0106797 | A1 | 8/2002 | Miles et al. |
| 2002/0162126 | A1 | 10/2002 | Beach et al. |
| 2002/0172997 | A1 | 11/2002 | Hartley et al. |
| 2002/0182731 | A1 | 12/2002 | Ji et al. |
| 2002/0192819 | A1 | 12/2002 | Hartley et al. |
| 2003/0022179 | A1 | 1/2003 | Chesnut et al. |
| 2003/0027289 | A1 | 2/2003 | Farmer |
| 2003/0027337 | A1 | 2/2003 | Droge et al. |
| 2003/0054552 | A1 | 3/2003 | Hartley et al. |
| 2003/0054555 | A1 | 3/2003 | Farmer et al. |
| 2003/0059900 | A1 | 3/2003 | Farmer |
| 2003/0064515 | A1 | 4/2003 | Hartley et al. |
| 2003/0068799 | A1 | 4/2003 | Hartley et al. |
| 2003/0077804 | A1 | 4/2003 | Byrd et al. |
| 2003/0100110 | A1 | 5/2003 | Hartley et al |
| 2003/0124555 | A1 | 7/2003 | Brasch et al. |
| 2003/0135888 | A1 | 7/2003 | Zhu et al. |
| 2003/0153055 | A1 | 8/2003 | Miles et al. |
| 2003/0157662 | A1 | 8/2003 | Gerard et al. |
| 2003/0157716 | A1 | 8/2003 | Hartley et al. |
| 2003/0175772 | A1 | 9/2003 | Wang |
| 2003/0175970 | A1 | 9/2003 | Hartley et al. |
| 2003/0176644 | A1 | 9/2003 | Byrd et al. |
| 2003/0186233 | A1 | 10/2003 | Chesnut et al. |
| 2003/0220249 | A1 | 11/2003 | Hackett et al. |
| 2004/0040053 | A1 | 2/2004 | Nomura et al. |
| 2004/0053412 | A1 | 3/2004 | Hartley et al. |
| 2004/0063207 | A1 | 4/2004 | Hartley et al. |
| 2004/0132133 | A1 | 7/2004 | Bennett |
| 2004/0171156 | A1 | 9/2004 | Hartley et al. |
| 2004/0171157 | A1 | 9/2004 | Hartley et al. |
| 2004/0219516 | A1 | 11/2004 | Bennett et al. |
| 2004/0219673 | A1 | 11/2004 | Hartley et al. |
| 2004/0229229 | A1 | 11/2004 | Cheo et al. |
| 2004/0253620 | A1 | 12/2004 | Leong et al. |
| 2004/0253631 | A1 | 12/2004 | Hartley et al. |
| 2004/0265863 | A1 | 12/2004 | Chesnut et al. |
| 2005/0009091 | A1 | 1/2005 | Hartley et al. |
| 2005/0069929 | A1 | 3/2005 | Chestnut et al. |
| 2005/0095615 | A1 | 5/2005 | Welsch et al. |
| 2005/0176065 | A1 | 8/2005 | Hanson |
| 2005/0181417 | A1 | 8/2005 | Miles et al. |
| 2005/0208530 | A1 | 9/2005 | Chesnut et al. |
| 2006/0035269 | A1 | 2/2006 | Hartley et al. |
| 2006/0035272 | A1 | 2/2006 | Brasch et al. |

FOREIGN PATENT DOCUMENTS

| | | |
|---|---|---|
| EP | 0 160 571 | 11/1985 |
| EP | 0 220 009 | 4/1987 |
| EP | 0 300 422 | 1/1989 |
| EP | 0 427 074 | 5/1991 |
| EP | 0 542 466 | 5/1993 |
| EP | 1 035 208 | 9/2000 |
| FR | 2 670 502 | 6/1992 |
| WO | WO 90/11375 | 10/1990 |
| WO | WO 91/02801 | 3/1991 |
| WO | WO 91/09957 | 7/1991 |
| WO | WO 91/16427 | 10/1991 |
| WO | WO 92/10577 | 6/1992 |
| WO | WO 92/15694 | 9/1992 |
| WO | WO 92/20791 | 11/1992 |
| WO | WO 92/22650 | 12/1992 |
| WO | WO 93/15191 | 8/1993 |
| WO | WO 93/19172 | 9/1993 |
| WO | WO 94/03624 | 2/1994 |
| WO | WO 94/09127 | 4/1994 |
| WO | WO 94/17176 | 8/1994 |
| WO | WO 94/18333 | 8/1994 |
| WO | WO 94/20604 | 9/1994 |
| WO | WO 95/00555 | 1/1995 |
| WO | WO 96/04393 | 2/1996 |
| WO | WO 96/19497 | 6/1996 |
| WO | WO 96/23904 A1 | 8/1996 |
| WO | WO 96/30498 | 10/1996 |
| WO | WO 96/40722 | 12/1996 |
| WO | WO 96/40724 | 12/1996 |
| WO | WO 97/06265 | 2/1997 |
| WO | WO 97/09436 | 3/1997 |
| WO | WO 97/25446 | 7/1997 |
| WO | WO 97/32481 | 9/1997 |
| WO | WO 97/47758 A1 | 12/1997 |
| WO | WO 98/10086 | 3/1998 |
| WO | WO 98/38326 A1 | 9/1998 |
| WO | WO 98/53056 | 11/1998 |
| WO | WO 98/56943 A1 | 12/1998 |
| WO | WO 99/10488 | 3/1999 |
| WO | WO 99/21977 | 5/1999 |
| WO | WO 99/25851 | 5/1999 |
| WO | WO 99/55851 | 11/1999 |
| WO | WO00/12687 | 3/2000 |
| WO | WO 00/29000 | 5/2000 |
| WO | WO 00/52027 | 9/2000 |
| WO | WO 00/52141 | 9/2000 |
| WO | WO 00/60091 | 10/2000 |
| WO | WO 01/05961 | 1/2001 |
| WO | WO 01/07572 | 2/2001 |
| WO | WO 01/11058 | 2/2001 |
| WO | WO 01/25466 | 4/2001 |
| WO | WO 01/31039 | 5/2001 |
| WO | WO 01/42509 | 6/2001 |
| WO | WO 01/62892 | 8/2001 |
| WO | WO 01/68836 | 9/2001 |
| WO | WO 02/00875 | 1/2002 |
| WO | WO 02/05294 | 1/2002 |
| WO | WO 02/08291 | 1/2002 |
| WO | WO 02/16594 | 2/2002 |
| WO | WO 02/46372 | 6/2002 |
| WO | WO 02/061034 | 8/2002 |
| WO | WO 02/062957 | 8/2002 |
| WO | WO 02/086144 | 10/2002 |
| WO | WO 02/095055 | 11/2002 |
| WO | WO 03/025161 | 3/2003 |
| WO | WO 03/044207 | 5/2003 |
| WO | WO 03/103600 | 12/2003 |
| WO | WO 04/009768 | 1/2004 |
| WO | WO 04/13290 | 2/2004 |
| WO | WO 2005/012487 A2 | 2/2005 |
| WO | WO 2005/014796 A2 | 2/2005 |

OTHER PUBLICATIONS

Abremski, K., and Hoess, R., "Bacteriophage P1 Site-specific Recombination. Purification and Properties of the Cre Recombinase Protein," *J. Biol. Chem. 259*:1509-1514, American Society for Biochemistry and Molecular Biology (1984).

Abremski, K., et al., "Studies on the Properties of P1 Site-Specific Recombination: Evidence for Topologically Unlinked Products Following Recombination," *Cell 32*:1301-1311, Cell Press (1993).

Abremski, K., and Gottesman, S., "Purification of the Bacteriophage λ Excisive Recombination," *J. Biol. Chem. 257*:9658-9662, American Society for Biochemistry and Molecular Biology (1982).

Adams, D.E., et al., "Cre-*lox* Recombination in *Escherichia coli* Cells: Mechanistic Differences from the *in Vitro* Reaction," *J. Mol. Biol. 226*:661-673, Academic Press (1992).

Akagi, K., et al., "Cre-mediated somatic site-specific recombination in mice," *Nucl. Acids Res. 25*:1766-1773, Oxford University Press (May 1997).

Aladjem, M.I., et al., "Positive Selection of FLP-Mediated Unequal Sister Chromatid Exchange Products in Mammalian Cells," *Mol. Cell. Biol. 17*:857-861, American Society for Microbiology (Feb. 1997).

Albert, H., et al., "Site-specific Integration of DNA into wild-type and mutant *lox* sites placed in the plant genome," *Plant J. 7*:649-659, Blackwell Science Ltd. (1995).

Andrews, B.J., et al., "The FLP Recombinase of the 2μ Circle DNA of Yeast: Interaction with Its Target Sequences," *Cell 40*:795-803, Cell Press (1985).

Andrews, B.J., et al., "Interaction of the FLP Recombinase of the *Saccharomyces cerevisiae* 2μm Plasmid with Mutated Target Sequences," *Mol. Cell. Biol. 6*:2482-2489, American Society for Microbiology (1986).

Angelastro, J. M., et al., "Identification of diverse nerve growth factor-regulated genes by serial analysis of gene expression (SAGE) profiling," *Proc. Natl. Acad. Sci. USA* 97 :10424-10429, National Acadmey of Sciences (Sep. 2000).

Angrand, P.O., et al., "Inducible expression based on regulated recombination: a single vector strategy for stable for stable expression in cultured cells," *Nucl. Acids Res. 26*:3263-3269, Oxford University Press (Jul. 1998).

Anton, M., and Graham, F.L. "Site-Specific Recombination Mediated by an Adenovirus Vector Expressing the Cre Recombinase Protein: a Molecular Switch for Control of Gene Expression," *J. Virol. 69*:4600-4606, American Society for Microbiology (1995).

Araki, H., et al., "Site-specific Recombinase, R, Encoded by Yeast Plasmid pSR1," *J. Mol. Biol. 225*:25-37, Academic Press, Inc., New York, NY (1992).

Astumian, J.H., et al., "Site-specific recombination between cloned attP and attB sites from the *Haemophilus influenza* bacteriophage HP1 propagated in recombination deficient *Escherichia coli*," *J. Bacteriol. 171*:1747-1750, American Society for Micribiology (1989).

Atlung, T., et al., "A versatile method for integration of genes and gene fusions into the λ attachment site of *Escherichia coli,*" *Gene 107*:11-17, Elsevier Science (1991).

Ausubel, F.M., et al., "Maps of Plasmids pBR322 and pUC19," in *Short Protocols in Molecular Biology, Third Edition*, John Wiley & Sons, Inc., Boston, MA, pp. 1.12-1.13 (1995).

Ayres, E.K., et al., "Precise Deletions in Large Bacterial Genomes by Vector-mediated Excision (VEX) The *trfA* Gene of Promiscuous Plasmid RK2 is Essential for Replication in Several Gram-negative Hosts," *J. Mol. Biol. 230*:174-185, Academic Press (1993).

Babineau, D., et al., "The FLP Protein of the 2-micron Plasmid of Yeast," *J. Biol. Chem. 260*:12313-12391, American Society for Biochemistry and Molecular Biology, Inc. (1985).

Backman, K., et al., "Use of Synchronous Sie-Specific Recombination *In Vivo* to Regulate Gene Expression," *BioTechnology 2*:1045-1049 (1984).

Bai, C., et al., "*SKP1* Connects Cell Cycle Regulators to the Ubiquitin Proteolysis Machinery through a Novel Motif, the F-Box," *Cell 86*:263-274, Cell Press (Jul. 1996).

Balakrishnan, R., et al., "A gene cassette for adapting *Escherichia coli* strains as hosts for *att*-Int-mediated rearrangement and $p_L$ expression vectors," *Gene 138*:101-104, Elsevier Science (Jan. 1994).

Ball, C.A., and Johnson, R.C., "Efficient Excision of Phage λ from the *Escherichia coli* Chromosome Requires the Fis Protein," *J. Bacteriol. 173*: 4027-4031, American Society for Microbiology (Jul. 1991).

Barnes, G., and Rine, J., "Regulated expression of endonuclease *Eco*RI in *Saccharomyces cerevisiae*: Nuclear entry and biological consequences," *Proc. Natl. Acad. Sci. USA 82*: 1354-1358, National Academy of Sciences (1985).

Bauer, C.E., et al., "Extent of Sequence Homology Required for Bacteriophage Lambda Site-specific Recombination," *J. Mol. Biol. 181*:187-197, Academic Press Inc. (1985).

Bayley, C.C., et al., "Exchange of gene activity in transgenic plants catalyzed by the Cre-*lox* site specific recombination system," *Plant Mol. Biol.* , 18:353-361, Dordrecht Kluwer Academic (1992).

Bernard, P., and Couturier, M., "Cell Killing by the F plasmid Ccdb Protein Involves Poisoning of DNA-topoisomerase II Complexes," *J. Mol. Biol. 226*:735-745, Academic Press, Inc. (1992).

Bernard, P., "Positive Selection of Recombinant DNA by CcdB," *BioTechniques 21*:320-323, Eaton Publishing Company (1996).

Bernard, P. et al., "The F Plasmid CcdB Protein Induces Efficient ATP-dependent DNA Cleavage by Gyrase," *J. Mol. Biol. 234*:534-541, Academic Press, Inc. (1993).

Bernard, P., et al., "Positive selection of vectors using the F plasmid *ccdB* killer gene," *Gene 148*: 71-74, Elsevier Science (1994).

Bethke, B., and Sauer, B., "Segmental genomic replacement by Cre-mediated recombination: genotoxic stress activation of the p53 promoter in single-copy transformants," *Nucl. Acids Res. 25*:2828-2834, Oxford University Press (1997).

Betz, U.A.K., et al., "Bypass of lethality with mosaic mice generated by Cre-*loxP*-mediated recombination," *Curr. Biol. 6*:1307-1316, Current Biology Ltd. (Oct. 1996).

Bhandari, P., and Gowrishankar, J., "An *Escherichia coli* host strain useful for efficient overporduction of cloned gene products with NaCl as the inducer," *J. Bacteriol 179*:4403-4406, American Society for Microbiology (Jul. 1997).

Black, L. W., "In vitro packaging into phage T4 particles and specific recircularization of phage lambda DNAs," *Gene 46*:97-101, Elsevier Science (1986).

Bloch, C.A., et al., "Purification of *Escherichia coli* Chromosomal Segments without Cloning," *Biochem. Biophys. Res. Comm. 223*:104-111, Academic Press, Inc. (1996).

Bochner, B.R., et al., "Positive Selection for Loss of Tetracycline Resistance," *J. Bacteriol. 143*:926-933, American Society for Microbiology (1980).

Boshart, M.., et al., "A Very Strong Enhancer is Located Upstream of an Immediate Early Gene of Human Cytomegalovirus," *Cell 41*:521-530, MIT (1985).

Bouhassira, E.E., et al., "Transcriptional Behavior of LCR Enhancer Elements Integrated at the Same Chromosomal Locus by Recombinase-Mediated Cassette Exchange," *Blood 90*:3332-3344, The American Society of Hematology (Nov. 1997).

Boyd, A.C., "Turbo cloning: a fast, efficient method for cloning PCR products and other blunt-ended DNA fragments into plasmids," *Nucl. Acids Res. 21*:817-821, Oxford University Press (1993).

Brent, R., and Ptashne, M., "A bacterial repressor protein or a yeast transcriptional terminator can block upstream activation of a yeast gene," *Nature 312*: 612-615, Macmillan Journals Ltd. (1984).

Broach, J. R., et al., "Recombination within the Yeast Plasmid 2µ Circle is Site-Specific," *Cell 29*:227-234, Cell Press (1982).

Bruckner, R.C., and Cox, M.M., "The Histone-like H Protein of *Escherichia coli* is a ribosomal protein s3," *Nucl. Acid Res. 17*:3145-3161 (1989).

Brunelli, J.P., and Pall, M.L., "Lambda/Plasmid Vector Construction by *In Vivo* cre/*lox*-Mediated Recombination," *BioTechniques 16*:1061-1064, Eaton Publishing Company (Jun. 1994).

Brunelli, J.P., and Pall, M.L., "A Series of Yeast/*Escherichia coli* λ Expression Vectors Designed for Directional Cloning of cDNAs and cre/*lox*-Mediated Plasmid Excision," *Yeast 9*:1309-1318, John Wiley (1993).

Bubeck, P., et al., "Rapid cloning by homologous recombination *in vivo,*" *Nucl. Acids Res. 21*:3601-3602, Oxford University Press (1993).

Buchholz, F., et al., "A simple assays to determine the functionality of Cre or FLP recombination targets in genomic manipulation constructs," *Nucl. Acids Res. 24*:3118-3119, Oxford University Press (1996).

Buchholz, F., et al., "Different thermostabilities of FLP and CRE recombinases: implications for applied site-specific recombination," *Nucl. Acids Res. 24*:4256-4262, Oxford Univeristy Press (1996).

Bushman, W., et al., "Control of Directionality in Lambda Site Specific Recombination," *Science 230*:906-911, American Association for the Advancement of Science (1985).

Burioni, R., et al., "An improved phage display vector for antibody repertoire cloning by construction of combinatoral libraries" *Res. Virol. 148*:161-164, Elsevier (1997).

Campbell, A. M., "Chromosomal Insertion Sites for Phages and Plasmids," *J. Bacteriol. 174*:7495-7499, American Society For Microbiology (1992).

Capone, J.P., et al., "Introduction of UAG, UAA, and UGA Nonsense Mutations at a Specific Site in the *Escherichia coli* Chloramphenicol Acetyltransferase Gene: Use in Measurement of Amber, Ochre, and Opal Suppression in Mammalian Cells," *Mol. Cell. Biol. 6*:3059-3067, American Society for Microbiology (1986).

Chanock, R.M., et al., "Human Monoclonal Antibody Fab Fragments Cloned from Combinatorial Libraries: Potential Usefulness in Prevention and/or Treatment of Major Human Viral Diseases," *Infect. Agents Dis. 2*:118-131, Raven Press (1993).

Chapin, S.J., et al., "Differential expression of alternatively spliced forms of MAP4: a repertoire of structurally different microtubule-binding domains," *Biochem. 34*:2289-2301, American Chemical Society (1995).

Chatterjee, P.K., and Coren, J.S., "Isolating large nested deletion in bacterial and P1 artificial chromosmes by *in vivo*P1 packaging of products of Cre-catalyzed recombination between the endogenous and transposed *loxP* site," *Nucl. Acids Res.* , 25:2205-2212, Oxford University Press (1997).

Cherepanov, P.P., and Wackernagel, W., "Gene disruption in *Escherichia coli*: Tc$^R$ and Km$^R$ cassettess with the option of Flp-catalyzed excision of the antibiotic-resistance determinant," *Gene 158*:9-14, Elsevier Science (1995).

Chong, S., et al., "Single-column purification of free recombinant proteins using a self-cleavable affinity tag derived from a protein splicing element," *Gene 192*:271-281, Elsevier Science B.V. (1997).

Choulika, A., et al., "Transfer of single gene-containing long terminal repeats into the genome of mammalian cells by a retroviral vector carrying the cre gene and the loxP site." *J Virol. 70*:1792-1798, American Society For Microbiology (1996).

Chuang, C-F., et al., "Specific and heritable genetic interference by double-stranded RNA in *Arabidopsis thaliana,*" *Proc. Natl. Acad. Sci. USA 97*:4985-4990, National Academy of Sciences of the USA (Apr. 2000).

Cigan, A.M., et al., "Mutational Analysis of the *HIS4* Translational Initiator Region in *Saccharomyces cerevisiae,*" *Mol. Cell. Biol. 8*:2964-2975, American Society for Microbiology (1988).

CLONTECH, "Creator™ Gene Cloning & Expression System," *CLONTECHniques 15*:7-11, CLONTECH (Apr. 2000).

CLONTECH, "New Additions to the Creator™ Platform," *CLONTECHniques 16*:3 pages, CLONTECH (Jan. 2001).

CLONTECH, "New Creator™ -Compatible Expression System," *CLONTECHniques 15*:2 pages, CLONTECH (Oct. 2000).

CLONTECH, "Creator™ Acceptor Vector Construction Kits" *CLONTECHniques 16*:2 pages, CLONTECH (Oct. 2000).

CLONTECH, "Creator™ SMART™ Library Construction Kit," *CLONTECHniques 16*:2 pages, CLONTECH (Oct. 2000).

CLONTECH, "Creator™: The Universal Platform for Analysis of Gene Function," Powerpoint Presentation, pp. 1-9, CLONTECH, (Jul. 2001), available at http://www.clontech.com/products/families/creator/popups/s1page1.html.
CLONTECH, "Creator™ pDNR-Dual Cloning Kit," *CLONTECHniques 16*:3 pages, CLONTECH (Oct. 2001).
Collis, C.M., and Hall, R.M., "Expression of Antibiotic Resistance Genes in the Integrated Cassettes of Integrons," *Antimicrob Agents Chemother 39*:155-162, American Society For Microbiology (1995).
Cormack, B., "Directed Mutagenesis Using the Polymerase Chain Reaction," in *Cuttent Protocols in Molecular Biology, Supplement 37*, Ausubel, F.M., et al., eds., John Wiley & Sons, Inc., Boston, MA, pp. 8.5.1-8.5.10 (1997).
Cormack, B., "Mutagenesis by the Polymerase Chain Reaction," in *Current Protocols in Molecular Biology, vol. 1, Supplement 15*, Ausubel, F.M., et al., eds., John Wiley & Sons, Inc., Boston, MA, pp. 8.5.1-8.5.9 (1991).
Cox, M.M., "The FLP protein of the yeast 2-μm plasmid: Expression of a eukaryotic genetic recombination system in *Escherichia coli," Proc. Natl. Acad. Sci. USA 80*:4223-4227, National Academy of Sciences (1983).
Craig, N.L., and Nash, H.A., "The Mechanism of Phage λ Site-Specific Recombination: Site-Specific Breakage of DNA by Int Topoisomerase," *Cell 35*:795-803, Cell Press (1983).
Curcio, M.J., and Garfinkel, D.J., "Single-Step selection for Ty1 element retrotransposition," *Proc. Natl. Acad. Sci. USA 88*:936-940, National Academy of Sciences (1991).
Dale, E.C., and Ow, D.W., "Intra- and intermolecular site-specific recombination in plant cells mediated by bacteriophage P1 recombinase," *Gene 91*:79-85, Elsevier Science (1990).
Dale, E.C., and Ow. D.W., "Gene transfer with subsequent removal of the selection gene from the host genome," *Proc. Natl. Acad. Sci. USA 88*:10558-10562, National Academy of Sciences (1991).
Dale, E.C., and Ow. D.W., "Mutations in the Cre/lox Recombination Site Enhance the Stability of Recombination Products: Applications for Gene Targeting in Plants," *J. Cell. Biochem.* 16 (Suppl. F):206, abstract No. Y108, Wiley-Liss, Inc. (1992).
Dang, D.T., and Perrimon, N., "Use of a Yeast Site-Specific Recombinase to Generate Embryonic Mosaics in *Drosophila," Dev. Genet. 13*:367-375, Wiley-Liss (1992).
Datson, N.A., et al., "MicroSAGE: a modified procedure for serial analysis of gene expression in limited amounts of tissue," *Nucl. Acids Res. 27*:1300-1307, Oxford University Press (Mar. 1999).
Davies, J., and Reichmann, L., "An Antibody VH Domain with a *lox*-Cre Site Integrated Into its Coding Region: Bacterial Recombination within a Single Polypeptide Chain," *FEBS Letts. 377*:92-96, Elsevier Science (1995).
Davis, C.R., et al., "Analysis of the Mechanisms of Action of the *Saccharomyces cerevisiae* Dominant Lethal cdc42$^{G12V}$ and Dominant Negative cdc42$^{D118A}$ Mutations," *J. Biol. Chem. 273*:849-858, The American Society for Biochemistry and Molecular Biology (1998).
Degryse, E., "In vivo intermolecular recombination in *Escherichia coli*: application to plasmid constructions," *Gene 170*:45-50, Elsevier Science (1996).
Deng, M-D., and Coleman, J.R., "Ethanol Synthesis by Genetic Engineering in Cyanobacteria," *Appl. Environ. Microbiol. 65*:523-528, American Society for Microbiology (Feb. 1999).
Derbyshire, V., and Belfort, M., "Lighning strikes twice: Intron-intein coincidence," *Proc. Natl. Acad. Sci. USA 95*:1356-1357, National Academy of Sciences of the USA (1998).
Devine, S.E., and Boeke, J.D., "Efficient integration of artificial transposons into plasmid targets *in vitro*: a useful tool for DNA mapping, sequencing and genetic analysis," *Nucl. Acids Res. 22*:3765-3772, Oxford University Press (Sep. 1994).
Diederich, L., et al., "New Cloning Vectors for Integration into the λ Attachment Site *attB* of the *Escherichia coli* Chromosome," *Plasmid 28*:14-24, Academic Press (1992).
Dijkema, R., et al., "Cloning and Expression of the Chromosomal Immune Interferon Gene of the Rat." *EMBO J. 4*:761-767, IRL Press Limited (1985).
Dymecki, S.M., "A modular set of *Flp, FRT* and *lacZ* fusion vectors for manipulating genes by site-specific recombination," *Gene 171*:197-201, Elsevier North-Holland (Jun. 1996).
Elledge, S.J., et al., "λYES: A multifunctional cDNA expression vector for the isolation of genes by complementation of yeast and *Escherichia coli* mutations," *Proc. Natl. Acad. Sci. USA 88*:1731-1735, National Academy of Sciences (1991).
Enquist, L.W., and Weisberg, R.A., "The Red Plaque Test: A Rapid Method for Identificiation of Excision Defective Variants of Bacteriophage Lambda," *Virology 72*:147-153, Academic Press, Inc. (1976).
Esposito, D., et al., "The integrase family of tyrosine recombinases: evolution of a conserved active site domain," *Nucl. Acids. Res. 25*:3605-3614, Oxford University Press (1997).
Feil, R., et al., "Regulations of Cre Recombinase Activity by Mutated Estrogen Receptor Ligand-Binding Domains," *Biochem. Biophys. Res. Comm. 237*:752-757, Academic Press (1997).
Feinbaum, R., "Vectors Derived from Plasmids," in *Current Protocols in Molecular Biology*, Ausubel, F.M., et al., John Wiley & Sons, Inc., Boston, MA, pp. 1:1.5.1-1.5.17 (1998).
Ferguson, J., et al., "Construction and characterization of three yeast-*Escherichia coli* shuttle vectors designed for rapid subcloning of yeast genes on small DNA fragments," *Gene 16*:191-197, Elsevier Science (1981).
Fiering, S., et al., "An 'in-out' strategy using gene targeting and FLP recombinase for the functional dissection of complex DNA regulatory elements: Analysis of the β-globin locus control region," *Proc. Natl. Acad. Sci. USA 90*:8469-8473, National Academy of Sciences (1993).
Filutowicz, M., et al., "Purification of the *Escherichia coli* integration host factor (IHF) in one chromatographic step," *Gene 147*:149-150, Elsevier Science (Sep. 1994).
Flanagan, P.M., and Fennwald, M.A., "Analysis of Inhibitors of the Site-specific Recombination Reaction Mediated by TN3 Resolvase," *J. Mol. Biol. 206*:295-304, Academic Press Limited (1989).
Flores, A., et al., "A protein-protein interaction map of yeast RNA polymerase III," *Proc. Natl. Acad. Sci. USA 96*:7815-7820, National Academy of Sciences (Jul. 1999).
Francia, M.V., et al., "Gene Integration in the *Escherichia coli* Chromosome Mediated by Tn21 Integrase (Int21)," *J. Bacteriol. 178*:894-898, American Society For Microbiology (Feb. 1996).
Francia, M.V., et al., "The IntIl Integron Preferentially Binds Single-Stranded DNA of the *att*C Site," *J. Bacteriol. 181*:6844-6849, American Society for Microbiology (1999).
Fukushige, S., and Sauer, B., "Genomic targeting with a positive-selection *lox* integration vector allows highly reproducible gene expression in mammalian cells," *Proc. Natl. Acad. Sci. USA 89*:7905-7909, National Academy of Sciences (1992).
Gage, P.J., et al., "A Cell-Free Recombination System for Site-Specific integration of Multigenic Shuttle Plasmids into Herpes Simplex Type 1 Genome," *J. Virol. 66*:5509-5515, American Society for Microbiology (1992).
Gateway™ Cloning Technology, Version 1, GIBCO BRL, Life Technologies Instruction Manual, pp. 1-60 (Nov. 1999), available at http://lifetech.com/gateway.
Gay, P., et al., "Positive Selection Procedure for Entrapment of Insertion Sequence Elements in Gram-Negative Bacteria," *J. Bacterial. 164*:918-921, American Society for Microbiology (1985).
Gay, P., et al., "Cloning Structural Gene *sacB*, which Codes for Exoenzyme Levansucrase of *Bacillus subtilis*: Expression of the Gene in *Escherichia coli," J. Bacteriol. 153*:1424-1431, American Society for Microbiology (1983).
Geoffroy, F., et al., "A new phage display system to construct multicombinatorial libraries of very large antibody repertoires," *Gene 151*:109-113, Elsevier Science (Dec. 1994).
Glasgow, A.C., et al., "DNA-binding Properties of the Hin Recombinase," *J. Biol. Chem. 264*:10072-10082, American Society for Biochemistry and Molecular Biology (1989).
Golic, K.G., and Lindquist, S., "The FLP Recombinase of Yeast Catalyzes Site-Specific Recombination in the *Drosophila* Genome," *Cell 59*:499-509, Cell Press (1989).
Gorman, C. M., et al., "The Rous Sarcoma Virus Long Terminal Repeat is a Strong Promoter when Introduced into a Variety of Eukaryotic Cells by DNA-mediated Transfection," *Proc. Natl. Acad. Sci. USA 79*:6777-6781, National Academy of Sciences (1982).
Götz, F., et al., "*Escherichia coli* 30S mutants lacking protein S20 are defective in translation initiation," *Biochim. Biophys. Acta 1050*:93-97, Elsevier Publishing Co. (1990).
Green, R., and Noller, H.F., "Ribosomes and Translation," *Ann. Rev. Biochem. 66*:679-716, Annual Reviews, Inc. (1997).
Grindley, N.D.F., and Kelley, W.S., "Effects of Different Alleles of the *E. coli* K12 *polA* Gene on the Replication of Non-transferring Plasminds," *Molec. Gen. Genet. 143*:311-318, Springer Verlag (1976).
Gronostajski, R.M., and Sadowski, P.D., "The FLP Protein of the 2-micron Plasmid of Yeast Inter- and Intramlecular Reactions," *J. Biol. Chem. 260*:12328-12335, The American Society of Biological Chemists, Inc. (1985).
Gu, H., et al., "Deletion of a DNA polymerase beta gene segment in T cells using cell type-specific gene targeting," *Science 265*:103-106, American Association for the Advancement of Science (1994).
Guo, F., et al., "Asymmetric DNA bending in the Cre-*loxP* site-specific recombination synapse," *Proc. Natl. Acad. Sci. USA 96*:7143-7148, National Academy of Sciences (1999).
Haffter, P., and Bickle, T.A., "Enhancer-Independent mutants of the Cin Recombinase have a Relaxed Topological Specificty," *EMBO J. 7*:3991-3996, IRL Press Limited (1988).
Hall, R.M., and Collis, C.M., "Mobile Gene Cassettes and Integrons: Capture and Spread of Genes by Site-specific Recombination," *Molec. Mircobiol. 15*:593-600, Blackwell Science Ltd. (Feb. 1995).
Hancock, R.E.W., and Scott, M.G., "The role of antimicrobila peptides in animal defenses," *Proc. Natl. Acad. Sci. USA 97*:8856-8861, National Academy of Sciences (Aug. 2000).
Hardy, S., et al., "Constructiuon of Adenvirus Vectors through Cre-*lox* Recombination," *J. Virol. 71*:1842-1849, American Society for Microbiology (1997).
Hartley, J.L., et al., "DNA Cloning Using In Vitro Site-Specific Recombination," *Genome Res. 10*:1788-1795, Cold Spring Harbor Laboratory Press (Nov. 2000).
Hasan, N., et al., "*Escherichia coli* genome targeting, I. Cre-*lox*-mediated in vitro generation of *ori* plasmids and their in vivo chromosomal integration and retrieval," *Gene 150*:51-56, Elsevier Science (Dec. 1994).
Hasan, N., and Szybalski, W., "Control of cloned gene expression by promoter inversion in vivo: construction of improved vectors with a multiple cloning site and the $p_{tac}$ promoter," *Gene 56*:145-151, Elsevier Science (1987).
Hashimoto-Gotoh, t., et al., "Improved vector, pHSG664, for direct streptomycin-resistance selection cDNA cloning with G:C-tailing procedure and subcloning of double-digested DNA fragments," *Gene 41*:125-128, Elsevier Science (1986).
Hehl, R., et al., "Structural analysis of Tam3, a transposable element from *Antirrhunu, majus*, reveals homologies to the Ac element from maize," *Plant Mol. Biol. 16*:369-371, Kluwer Academics Pres (1991).
Henikoff, S., "Unidirectional digestion with exonuclease III creates targeted breakpoints for DNA sequencing," *Gene 28*:351-359, Elsevier Science Publishers (1984).
Heyman, J.A., et al., "Genome-Scale Cloning and Expression of Individual Open Reading Frames Using Topoisomerase I-Mediated Ligation," *Genome Res. 9*:383-392, Cold Spring Harbor Laboratory Press (Apr. 1999).
Hochuli, E., et al. "Genetic Approach to Facilitate Purification of Recombinant Proteins with a Novel Metal Chelate Adsorbent." *BioTechnology 6*:1321-1325, Nature Pub. Co. (1988).
Hoekstra, M.F., et al., "Shuttle Mutagenesis: Bacterial Transposons for Genetic Manipulations in Yeast," *Meth. Enzymol. 194*:329-342, Academic Press (1991).
Hoess, R.H., et al., "Mechanism of Strand Cleavage and Exchange in the Cre-*lox* Site-specific Recombination System," *J. Mol. Biol. 181*:351-362, Academic Press (1985).
Hoess, R., et al., "Formation of small circular DNA molecules via an in vitro site-specific recombination system," *Gene 40*:325-329, Elsevier Science (1985).
Hoess, R.H., et al., "P1 site-specific recombination: Nucleotide sequence of the recombining sites," *Proc. Natl. Acad. Sci. USA 79*:3398-3402, National Academy of Sciences (1982).
Hoess, R.H., et al., "The role of the *loxP* spacer region in P1 site-specific recombination," *Nucl. Acids Res. 14*:2287-2300, Oxford University Press (1986).
Hoess, R. H., and Abremski, K., "The Cre-*lox* Recombination System," in *Nucleic Acids and Molecular Biology*, vol. 4, ed. by Eckstein, F., and Lilley, D.M.J., Springer-Verlag, Berlin, pp. 99-109 (1990).
Hoess, R.H., and Abremski, K., "Interaction of the Bacteriophage P1 Recombinase Cre with the Recombining Site *loxP," Proc. Natl. Acad. Sci. USA 81*:1026-1029, National Academy of Sciences (1984).
Holt, C.L., and May, G.S., "A Novel phange λ replacement Cre-*lox* vector that has automatic subcloning capabilities," *Gene 133*:95-97, Elsevier Science (1993).
Hoogenboom, H.R., et al., "Multi-subunit proteins on the surface of filamentous phage: methodologies for displaying antibody (Fab) heavy and light chains," *Nucl. Acids Res. 19*:4133-4137, Oxford University Press (1991).
Iida, S., et al., "A site specific, conservative recombination system carried by bacteriophage P1, Mapping of the recombinase gene cin and the crossover sites cix for the inversion of the c segment," *EMBO J. 1*:1445-1453, Oxford University Press (1982).
Iino, T., and Kutsukake, K., "*Trans*-acting Genes of Bacteriophages P1 and Mu Mediate inversion of a Specific DNA Segment Involved in Flagellar Phase Variation of *Salmonella," Cold Spring Harbor Symposia on Quantitative Biology 45*:11-16, Cold Spring Harbor Laboratory Press (1981).
Institut Pasteur Website, Introduction: http://www.pasteur.fr/recherche/unites/pmtg/integ/intro.html (accessed Jun. 19, 2003).
Institut Pasteur Website, Figure 1: http://www.pasteur.fr/recherche/unites/pmtg/integ/fig1.html (accessed Jun. 19, 2003).
Institut Pasteur Website, Figure 2: http://www.pasteur.fr/recherche/unites/pmtg/integ/fig2.html (accessed Jun. 19, 2003).
Institut Pasteur Website, Figure 3: http://www.pasteur.fr/recherche/unites/pmtg/integ/fig3.html (accessed Jun. 19, 2003).
Institut Pasteur Website, Main Page: http://www.pasteur.fr/recherche/unites/pmtg/ (accessed Jun. 19, 2003).
Invitrogen Online Catalog, "The Echo™ Cloning System: The Future of Cloning is Here," available at: http://web.archive.org/web/20010112191100/www.invitrogen.com/catalog_project/cat_echo.html (accessed Jul. 7, 2004).
Jaffé, A., et al., "Effects of the *ccd* Function of the F Plasmid on Bacterial Growth," *J. Bacteriol. 163*:841-849, American Society For Microbiology (1985).
Jayaram, M., "The *Int* Family of Site-specific Recombinases: Some thoughts on a General Reaction Mechanism," *J. Genet. 67*:29-36, Indian Academy of Sciences (1988).
Jeong, J-H., et al., "Cloning and nucleotide sequencing of the genes, *rplU* and *rpmA*, for ribosomal proteins L21 and L27 of *Escherichia coli," J. DNA Sequencing and Mapping 4*:59-67, Harwood Academic Publishers GmbH (1993).
Johnson, R.C., et al., "Isolation of the gene encoding the Hin recombinational enhancer binding protein," *Proc. Natl. Acad. Sci. USA 85*:3484-3488, National Academy of Sciences (1988).
Kanaar, R., et al., "Gin-Mediated Recombination of Catenated and Knotted DNA Substrates: Implications for the Mechanism of Interaction Between *Cis*-Acting Sites," *Cell 58*:147-159, Cell Press (1989).
Kaniga, K., et al., "A wide-host-range suicide vector for improving reverse genetics in Gram-negative bacteria: inactivation of the *blsa* gene of *Yersinia enterocolitica," Gene 109*:137-141, Elsevier Science (1991).
Katz, L., et al., "Site-specific recombination in *Esherichia coli* between the *att* sites of plasmid pSE211 from *Saccharopolyspora erhthraea," Mol. Gen. Genet. 227*: 155-159, Springer-Verlag (1991).
Kealey, J.T., et al., "Production of Polyketide Natural Product in Nonpolyketide-producing Prokaryotic and Eukaryotic Hosts," *Proc. Natl. Acad. Sci. USA 95*:505-509, National Academy of Sciences (Jan. 1998).

Kholodenko, B.N., et al., "Metabolic Design: How to Engineer a Living Cell to Desired Metabolite Concentrations and Fluxes," *Biotechnol. Bioengineer. 59*:239-247, John Wiley & Son (1998).
Kilby, N.J., et al., "Site-specific recombinases: tools for genome engineering," *Trends Genet. 9*:413-421, Elsevier Trends Journals (1993).
Kim, S., and Landy, A., "Lambda Int Protein Bridges Between Highter Order Complexes at Two Distant Chromosomal Loci *att*L and *att*R," *Science 256*:198-203, American Association for the Advancement of Science (1992).
Kim, D.W., "Use of the Human Elongation Factor 1a Promoter as a Versatile and Efficient Expression System," *Gene 91*:217-223, Elsevier Science (1990).
Kitts, P.A., and Nash, H.A., "Bacteriophage Lambda Site-Specific Recombination Proceeds with a Defined Order of Strand Exchanges," *J. Mol. Biol. 204*:95-107, Academic Press, Inc. (1988).
Klippel, A., et al., "Isolation and characterization of unusual *gin* mutants," *The EMBO Journal 7*: 3938-3989, IRL Press Inc. (1988).
Koch, C., et al., "*Escherichia coli* host factor for site-specific DNA inversion: Cloning and characterization of the *fis* gene," *Proc. Natl. Acad. Sci. USA 85*:4237-4241, National Academy of Sciences (1988).
Kolb, A.F., and Siddell, S.G., "Genomic Targeting with an MBP-Cre Fusion Protein," *Gene 183*:53-60, Elsevier Science (Dec. 1996).
Kouprina, N., et al., "Rescue of Targeted Regions of Mammalian Chromosomes by in Vivo Recombination in Yeast," *Genome Res. 8*:666-672, Cold Spring Harbor Research Laboratory Press (1998).
Kozak, M., "Comparison of initiation of protein synthesis in procaryotes, eucaryotes, and organelles," *Microbiol. Rev. 47*:1-45, American Society For Microbiology (1983).
Kozak, M., "An analysis of 5'-noncoding sequences from 699 vertebrate messenger RNAs," *Nucl. Acids Res. 15*:8125-8132, Oxford University Press (1987).
Kozak, M., "Structural features in eukaryotic mRNAs that modulate the initiation of translation," *J. Biol. Chem. 266*:19867-19870, American Society for Biochemistry and Molecular Biology (1991).
Krafte, D.S., et al., "Stable Expression and Functional Characterization of a Human Cardiac $Na^{+}$Channel Gene in Mammalian Cells," *J. Mol. Cell. Cardiol. 27*:823-830, Academic Press Ltd. (1995).
Krautwald, S., and Baccarini, M., "Bacterially expressed murine CSF-1 possesses agonistic activity in its monomeric form." *Biochem. Biophys. Res. Commun. 192*:720-727, Elsevier Science (1993).
Kuempel, P., et al., "Use of a transposon (Tn*dif*) to obtain suppressing and nonsuppressing insertions of the *dif* resolvase site of *Eschericia coli," Genes & Development 10*:1162-1171, Cold Spring Harbor Laboratory Press (May 1, 1996).
Kühn, R., et a., "Inducible Gene Targeting in Mice," *Science 269*:1427-1429, American Association for the Advancement of Science (Sep. 1995).
Lafontaine, D., and Tollervey, D., "One-step PCR Mediated Strategy for the Construction of Conditionally Expressed and Epitope Tagged Yeast Proteins," *Nucl. Acids Res. 24*:3469-3472, Oxford University Press (1996).
Lake, J.A., "Evolving Ribosome Structure: Domains in Archaebacteria, Eubacteria, Eocytes and Eukaryotes," *Ann. Rev. Biochem. 54*:507-530, Annual Reviews, Inc. (1985).
Lakso, M., et al., "Targeted oncogene activation by site-specific recombination in transgenic mice," *Proc. Natl. Acad. Sci. USA 89*:6232-6236, National Academy of Sciences (1992).
Lander, E.S., "The new genomics: global views of biology," *Science 274*:536-539, American Association for the Advancement of Science (Oct. 1996).
Landy, A., "Mechanistic and structural complexity in the site-specific recombination pathways of Int and FLP," *Curr. Opin. Genet. Dev. 3*:699-707, Current Biology (1993).
Landy, A., "Dynamic, Structural, and Regulatory Aspects of λ Site-Specific Recombination," *Annu. Rev. Biochem. 58*:913-949, Annual Reviews (1989).
Langeveld, S.A., et al., "Expression of an *Escherichia coli phr* gene in the yeast *Saccharomyces cerevisiae," Mol. Gen. Genet. 199*:396-400, Springer-Verlag (1985).
Lebreton, B., et al., "Mutations That Improve the Binding of Yeast FLP Recombinase to Its Substrate," *Genetics 118*:393-400, Genetics Society of America (1988).
Lee, E.C., et al., "Genetic Analysis of *Escherichia coli* Integration Host Factor Interactions with Its Bacteriophage λ H' Recognition Site," *J. Bacteriol. 173*:609-617, American Society for Microbiology (1991).
Lee, G., and Saito, I., "Role of Nucleotide Sequences of *loxP* Spacer Region in Cre-mediated Recombination," *Gene 216*:55-65, Elsevier Science (1998).
Lee, M.H., et al., "Site-specific integration of mycobacteriophage L5: Integration-proficient vectors for *Mycobacterium smegnatis, Mycobacterium tuberculosis*, and bacille Calmette-Guérin," *Proc. Natl. Acad. Sci. USA 88*:3111-3115, National Acadmey of Sciences (1991).
Lenski, R.E., et al., "Genetic Analysis of a Plasmid-Encoded, Host Genotype-Specific Enhancement of Bacterial Fitness," *J. Bacteriol. 176*:3140-3147, American Society For Microbiology (1994).
Leong, J.M., et al., "Generation of single base-pair deletions, insertions, and substitutions by a site-specific recombination system," *Proc. Natl. Acad. Sci. USA 82*:6990-6994, national Academy of Sciences (1985).
Leslie, N.R., and Sherratt, D.H., "Site-specific Recombination in the Replication Terminus Region of *Escherichia coli*: Functional Replacement of *dif," EMBO J. 14*:1561-1570, Oxford University Press (Apr. 1995).
Leung, L.L.K., "Application of Combinatorial Libraries and Protein Engineering to the Discovery of Novel Anti-Thrombotic Drugs," *Thromb. Haemost. 74*:373-376, F.K. Schattauer Verlagsgesellschafrt mbH (1995).
Li, Z.W., et al., Generation of mice with a 200-kb amyloid precursor protein gene deletion by Cre recombinase-medicated site-specific recombination in embryonic stem cells. *Proc. Natl. Acad. Sci. USA 93*:6158-6162, National Academy of Sciences (1996).
Liu, Q., et al., "The univector plasmid-fusion system, a method for rapid construction of recombinant DNA without restriction enzymes," *Curr. Biol. 8*:1300-1309, Cell Press (1998).
Lorbach, E., et al., "Site-specific Recombination in Human Cells Catalyzed by Phage λ Integrase Mutants," *J. Mol. Biol. 296*:1175-1181, Academic Press (Mar. 2000).
Lu, F., and Churchward, G., "Conjugative transponsition: Tn916 integrase contains two independent DNA binding domain that recognize different DNA sequences," *EMBO J. 13*:1541-1548, Oxford University Press (Apr. 1994).
Luckow, V.A., et al., "Efficient Generation of Infectious Recombinant Baculoviruses by Site-Specific Transposon-Mediated Insertion of Foreing Genes into a Baculovirus Genome Propagated in *Escherichia coli," J. Virol. 67*:4566-4579, American Society For Microbiology (1993).
Mackie, G.A., "Nucleotide Sequence of the Gene for Ribosomal Protein S20 and Its Flanking Regions," *J. Biol. Chem. 256*:8177-8182, American Society for Biochemistry and Molecular Biology, Inc. (1981).
Madison, L.L., and Huisman, G.W., "Metabolic Engineering of Poly(3-Hydroxyalkanoates): From DNA to Plastic," *Microbiol. Mol. Biol. Reviews 63*:21-53, American Society for Microbiology (Mar. 1999).
Maemura, K., et al., "Generation of a Dominant-negative Mutant of Endothelial PAS Domain Protein 1 by Deletion of a Potent C-terminal Transactivation Domain," *J. Biol. Chem. 27*:31565-31570, The American Society for Biochemistry and Molecular Biology, Inc. (1999).
Maeser, S., and Kahmann, R., "The Gin recombinase of phage Mu can catalyse site-specific recombination in plant protoplasts," *Mol. Gen. Genet. 230*:170-176, Springer-Verlag (1991).
Mahillon, J., et al., "IS231 and other *Bacillus thuringiensis* transposable elements: a review," *Genetica 93*:13-26, Kluwer Academic (Nov. 1994).
Mahillon, J., et al., "Subdivision of the *Escherichia coli* K-12 genome for sequencing: manipulation and DNA sequence of transposable elements introducing unique restriction sites," *Gene 223*:47-54, Elsevier Science B.V. (1998).

Malynn, B.A., et al., "The *scid* Defect Affects the Final Step of the Immunoglobulin VDJ Recombinase Mechanism," *Cell 54*:453-460, Cell Press (1988).

Maniatis, T., et al., "Regulation of Inducible and Tissue-specific Gene Expressionds," *Science 236*:1237-1245, American Association for the Advancement of Science (1987).

Manning, P.A., et al., "Gene Capture in *Vibrio cholerae," Trends in Microbiology 7*:93-95, Elsevier Science (1999).

Matsuzaki, H., et al., "Chromosome Engineering in *Saccharomyces cerevisiae* by Using a Site-Specific Recombination System of a Yeast Plasmid," *J. Bacteriol. 172*:610-618, American Society for Microbiology (1990).

McCarthy, J.E., and Brimacombe, R., "Prokaryotic translation: the interactive pathway leading to initiation," *Trends Genet. 10*:10:402-407, Elsevier Trends Journals (Nov. 1994).

Medberry, S.L., et al., "Intra-chromosomal rearrangements generated by Cre-*lox* site-specific recombination," *Nucl. Acids Res. 23*:485-490, Oxford University Press (1995).

Mendiola, M.W., and de la Cruz, F., "Specificity of Insertion of IS91, an Insertion Sequence Present in α-haemolysis Plasmides of *Escherichia coli," Mol. Microbiol. 3*:979-984, Blackwell Scientific Publications (1989).

Mercier, J., et al., "Structural and Functional Characterization of *tnpI*, a Recombinase Locus in Tn21 and Related β-Lactamase Transposons," *J. Bacteriol. 172*:3745-3757, American Society for Microbiology (1990).

Metcalf, W.W., et al., "Conditionally Replicative and Conjugative Plasmids Carrying *lacZa* for Cloning, Mutagenesis, and Allele Replacement in Bacteria," *Plasmid 35*:1-13, Academic Press, Inc. (Jan. 1996).

Mette, M.F., et al., "Transcriptional silencing and promoter methylation triggered by double-stranded RNA," *EMBO J. 19*:5194-5201, European Molecular Biology Organization (Oct. 2000).

Meyer-Leon, L., et al., "Purification of the FLP Site-specific Recombinase by Affinity Chromatography and Re-examination of Basic Properties of the System," *Nucl. Acids Res. 15*:6469-6488, IRL Press Limited (1987).

Miki, T., et al., "Control of segregation of chromosomal DNA by sex factor F in *Escherichia coli* . Mutantants of DNA gyrase subunit A suppress letD (ccdB) product growth inhibition," *J. Mol. Biol. 225*:39-52, Academic Press (1992).

Miller, H.I., et al., "*int*-h: an *int* Mutation of Phage λ That Enhances Site-Specific Recombination," *Cell 20*:721-729, Cell Press (1980).

Mizushima, S., and Nagat, S., "pEF-BOS, a Powerful Mammalian Expression Vector," *Nucl. Acids Res. 18*:5322, Oxford University Press (1990).

Mizuuchi, K., and Mizuuchi, M., "Integrative Recombination of Bacteriophage λ: In Vitro Study of the Intermolecular Reaction," *Cold Spring Harb. Symp. Quant. Biol. 43*:1111-1114, Cold Spring Harbor Laboratory Press (1979).

Mizuuchi, M., and Mizuuchi, K., "The extent of DNA sequence required for a functional bacterial attachment site of phage lambda," *Nucl. Acids Res. 13*:1193-1208, Oxford University Press (1985).

Mozo, T., and Hooykaas, P.J.J., "Design of a novel system for the construction of vectors for Agrobacterium-mediated plant transformation," *Mol. Gen. Genet 236*:1-7, Springer-Verlag (1992).

Mullins, L.J., et al., "Efficient Cre-lox linearisation of BACs: applications to physical mapping and generation of transgenenic animals," *Nucl. Acids Res. 25*:2539-2540, Oxford University Press (1997).

Murayama, N., et al. "Evidence for Involvement of *Escherichia coli* Genes pmbA, csrA and a Previously unrecognized Gene tldD, in the Control of DNA Gyrase by letD (ccdb) of Sex Factor F," *J. Mol. Biol. 256*:483-502, Academic Press Limited (Mar. 1, 1996).

Nagaraja, R., and Weisberg, R.A., "Specificity Determinants in the Attachment Sites of Bacteriophages HK022 and λ," *J. Bacteriol. 172*:6540-6550, American Society for Microbiology (1990).

Nagy, A., "Cre Recombinase: The Universal Reagent for Genome Tailoring," *Genesis 26*:99-109, Wiley-Liss (2000).

Nash, H.A., "Integrative Recobination of Bacteriophage Lambda DNA *In Vitro," Proc. Natl. Acad. Sci. USA 72*:1072-1076, National Acadmey of Sciences (1975).

Nash, H.A., "Bending and supercoiling of DNA at the attachment site of bacteriophage lambda," *Trands Biochem. Sci 15*:222-227, Elsevier Trends Journals (1990).

Nash, H.A., "Purification and Properties of the Bacteriophage Lambda Int Protein," *Meth. Enzymol. 100*:210-216, Academic Press (1983).

Nash, H.A., and Robertson, C.A., "Heteroduplex substrates for bacteriophage lambda site-specific recombination: cleavage and strand transfer products," *EMBO J. 8*:3523-3533, Oxford University Press (1989).

Nash, H.A., et al., "Role of homology in site-specific recombination of bacteriophage λ: Evidence against joining of cohesive ends," *Proc. Natl. Acad. Sci. USA 84*:4049-4053, National Academy of Sciences (1987).

Nash, H.A., and Robertson, C.A., "Purification and properties of the *Escherichia coli* prote factor required for lambda integra tive recombination," *J. Biol. Chem. 256*:9246-9253, American Society for Biochemistry and Molecular Biology (1981).

Nomura, M., et al., "Regulation of Synthesis of Ribosomes and Ribosomal Components," *Ann. Rev. Biochem. 53*:75-117, Annual Reviews, Inc. (1984).

Numrych, T.E., et al., "A comparison of the effects of single-base and triple-base changes in the integarse arm-type binding sites on the site-specific recombination of bacteriophage lambda," *Nucl. Acids Res. 18*:3953-3959, Oxford University Press (1990).

Numrych, T.E., et al., "Characterization of the bacteriophage lambda excisionase (Xis) protein: the C-terminus is required for Xis—integrase cooperativity but not for DNA binding," *EMBO J. 11*:3797-3806, Oxford University Press (1992).

Nunes-Düby, S.E., et al., "Similarities and differences among 105 members of the Int family of site-specific recombinases," *Nucl. Acids. Res. 26*:391-406, Oxford University Press (1998).

Nunes-Düby, S.E., et al., "Half-*att* Site Substrates Reveal the Homology Independence and Minimal Protein Requirements for Productive Synapsis in λ Excisive Recombination," *Cell 59*:197-206, Cell Press (1989).

Oberto, J., et al., "A segment of the phage HK022 chromosome is a mosaic of other lambdoid chromosomes," *Nucl. Acids. Res. 22*:354-356, Oxford University Press (Feb. 1994).

Odell, J.T., et al., "Seed-specific Gene Activation Mediated by the *Cre/lox* Site Specific Recombination System," *Plant Physiol. 106*:447-458, American Society of Plant Physiologists (Oct. 1994).

O'Gara, J.P., et al., "Identification and Molecular Genetic Analysis of Multiple Loci Contributing to High-Level Tellurite Resistance in *Rhodobacter sphaeroides* 2.4.1," *Appl. Environ. Microbiol. 63*:4713-4720, American Society for Microbiology (1997).

Ohara, O., and Temple, G., "Directional cDNA library construction assisted by the *in vitro* recombination reaction," *Nucl. Acids Research 29*:e22(1-8), Oxford University Press (2001).

Okayama, H., and Berg, P., "Bacteriophage Lambda Vector for Transducing a cDNA Clone Library into Mammalian Cells," *Mol. Cell. Biol. 5*:1136-1142, American Society for Microbiology (1985).

Oliner, J.D., et al., "*In vivo* cloning of PCR products in *E. coli," Nucl. Acids. Res. 21*:5192-5197, Oxford University Press (1993).

Orban, P.C., et al., "Tissue- and site-specific DNA recombination in transgenic mice," *Proc. Natl. Acad. Sci. USA 89*:6861-6865, National Academy of Sciences (1992).

Osborne, B.I., et al., "A system for insertional mutagenesis and chromosmal rearrangement using the Ds transponon and Cre-*lox," Plant J. 7*:687-701, Blackwell Scientific Publishers (1995).

Osuna, R., et al., "Identification of two functional regions in Fis: the N-terminus is required to promote Hin-mediated DNA inversion by not 1 excision," *EMBO J. 10*1593-1603, Oxford University Press (1991).

Padgett, K.A., and Sorge, J.A., "Creating seamless junction independent of restriction sites in PCR cloning," *Gene 168*, 31-35, Elsevier Science (Feb. 1996).

Pal, S.K., et al., "P1 Plasmid Replication of Initiator Titration in Copy Number Control," *J. Mol. Biol. 192*:275-285, Academic Press Inc. (1986).

Palazzolo, M.J., et al., "Phage lambda cDNA cloning vectors for substractive hybridization, fusion-protein synthesis and Cre-*loxP* automatic plasmid subcloning," *Gene 88*:25-36, Elsevier Science (1990).

Pan, G., et al., "Ligation of Synthetic Activated DNA Substrates by Site-specific Recombinases and Topoisomerase I," *J. Biol. Chem. 268*:3683-3689, American Society for Biochemistry and Molecular Biology (1993).

Panke, S., et al., "Engineering of Quasi-Natural *Pseudomas putida* Strains for Toluene Metabolism through an *ortho*-Cleavage Pathway," *Appl. Environ. Microbiol. 64*:748-751, American Society for Microbiology (1998).

Parks, R.J., and Graham, F.L., "A Helper-Dependent System for Adenovirus Vector Production Helps Define a Lower Limit for Efficient DNA Packaging," *J. Virol. 71*3293-3298, American Society For Microbiology (1997).

Patel, P.H., and Loeb, L.A., "DNA polymerase active site is highly mutable: Evolutionary consequences," *Proc. Natl. Acad. Sci. USA 97*:5095-5100, National Academy of Sciences (May 2000).

Peakman, T. C., et al., "Highly efficient generation of recombinant baculoviruses by enzymatically mediated site specific *in virto* recombination," *Nucl. Acids Res. 20*:495-500, Oxford University Press (1992).

Peredelchuk, M.Y., and Bennett, G.N., "A method for construction of *E. coli* strains with multiple DNA insertions in the chromosome," *Gene 187*:231-238, Elsevier Science (1997).

Perler, F.B., "InBase, the New England Biolabs Intein Database," *Nucl. Acids Res. 27*:346-347, Oxford University Press (Jan. 1999).

Persson, M.A.A., "Combinatorial Libraries," *Intern. Rev. Immunol. 10*153-63, Harwood Academic Publishers GmbH (1993).

Phillips-Jones, M.K., et al., "Context Effects on Misreading and Suppression at UAG Codons in Human Cells," *Mol. Cell. Biol. 15*:6593-6600, American Society for Microbiology (1995).

Pichel, J.G., et al., "Timining of SV40 oncogene activation by site-specific recombination determines subsequent tumor progression during murine lens development," *Gene 8*:3333-3342, Elsevier Science (1993).

Pierce, J.C., et al., "A positive selection vector for cloning high molecular weight DNA by the bacteriophage P1 system: Improved cloning efficacy," *Proc. Natl. Acad. Sci. USA 89*:2056-2060, National Academy of Sciences (1992).

Podhajska, A.J., et al., "Control of cloned gene expression by promoter inversion in vivo: construction of the heat-pulse-activated *att-nut*L-*p-att-N* module," *Gene 40*:163-168, Elsevier Science (1985).

Pósfai, G., et al., "In vivo excision and amplification of large segments of the *Escherichia coli* genome," *Nucl. Acids Res. 22*:2392-2398, Oxford University Press (Jun. 1994).

Powell, J., "Enhanced concatemer cloning-a modification to the SAGE (Serial Analysis of Gene Expression) technique," *Nucl. Acids Res. 26*:3445-3446, Oxford Univeristy Press (1998).

Prasad, P.V., et al., "Substrate Recognition by the 2 μm Circle Site-Specific Recombinase: Effect of Mutations within the Symmetry of the Minimal Substrate," *Mol. Cell. Biol. 6*:4329-4334, American Society for Mircobiology (1986).

Prieto, M.A., et al., "Molecular Characterization of the 4-Hydroxyphenylacetate Catabolic Pathway of *Escherichia coli* W: Engineering a Mobile Aromatic Degradative Cluster," *J. Bacteriol. 178*:111-120, American Society for Microbiology (1996).

Qian, X., et al., "Reactions between Half- and Full-FLP Recombination Target Sites: A Model System for Analyzing Early Steps in FLP Protein-Mediated Site-Specific Recombination," *J. Biol. Chem 267*:7794-7805, American Society for Biochemistry and Molecular Biology (1992).

Qin, M., et al., "Cre recombinase-mediated site-specific recombination between plant chromosomes," *Proc. Natl. Acad. Sci. USA 91*:1706-1710, National Academy of Sciences (1994).

Qin, M., et al., "Site-specific Cleavage of Chromosomes *in vitro* Through *Cre-lox* Recombination," *Nucl. Acids Res. 23*:1923-1927, Oxford University Press (Jun. 1995).

Reed, R.R., and Grindley, N.D., "Transponson-Mediated Site-Specific Recombination in Vitro: DNA Cleavage and Protein-DNA Linkage at the Recombination Site," *Cell 25*:721-728, Cell Press (1981).

Reed, R.R., "Transposon-Mediated Site-Specific Recombination: A Defined in Vitro System," *Cell 25*:713-719, Cell Press (1981).

Richet, E., et al., "Synapsis of Attachment Sites during Lambda Integrative Recombination Involves Capture of a Naked DNA by a Protein-DNA Complex," *Cell 52*:9-17, Cell Press (1988).

Richet, E., et al., "The Interaction of Recombination Proteins with Supercoiled DNA: Defining the Role of Supercoiling in Lambda Integrative Recombination," *Cell 46*:1011-1021, Cell Press (1986).

Ross, W., and Landy, A., "Patterns of λ Int Recognition in the Regions of Strand Exchange," *Cell 33*:261-272, Cell Press (1983).

Russell, M., "A recombination-based cloning system that decreases time to protein analysis," *Am. Biotechnol. Lab. 18*:8,10, International Scientific Communications, Inc. (Jun. 2000).

Sadowski, P.D., "The Flp recombinase of the 2-microns plasmid of *Saccharomyces cerevisiae," Prog. Nucl. Acid Res. Mol. Biol. 51*:53-91, Academic Press (1995).

Sadowski, P., "Site-Secific Recombinases: Changing Partners and Doing the Twist," *J. Bacteriol. 165*:341-347, American Society for Microbiology (1986).

Sambrook, J., et al., Molecular Cloning: A Laboratory Manual, 2nd ed., Cold Spring Harbor Laboratory Press, NY, pp. 16.6-16.8 (1989).

Sandhu, J.S., "Protein Engineering of Antibodies," *Crit. Rev. Biotechnol. 12*:437-462, CRC Press, Inc. (1992).

Sato, T., et al., "The *cisA* Cistron of *Bacillus subtilis* Sporulation Gene *spoIVC* Encodes a Protein Homologous to a Site-Specific Recombinase," *J. Bacteriol. 172*:1092-1098, American Society for Microbiology (1990).

Sauer, B., "Functional Expression of the *cre-lox* Site-Specific Recombination System in the Yeast *Saccharomyces cerevisiae," Mol. Cell. Biol. 7*:2087-2096, American Society for Microbiology (1987).

Sauer, B., et al., "Construction of Isogenic Cell Lines Expressing Human and Rat Angiotensin II AT1 Receptors by Cre-Mediated Site-Specific Recombination," *Methods 4*:143-149, Academic Press (1992).

Sauer, B., and Henderson, N., "Site-specific DNA recombination in mammalian cells by the Cre recombinase of bacteriophage P1," *Proc. Natl. Acad. Sci. USA 85*:5166-5170, National Academy of Sciences (1988).

Sauer, B., "Expression and Functioning in Yeast of a Bacterial Site Specific Recombination System," *J. Cell. Bio. Chem. Supp. 10(b)*:242 )(I340), Alan R. Liss, Inc. (1986).

Sauer, B., and Henderson, N., "Cre-stimulated recombination at *loxP*-containing DNA sequences placed into the mammalian genome," *Nucl. Acids Res. 17*:147-161, Oxford University Press (1989).

Sauer, B., "Manipulation of Transgenes by Site-Specific Recombination: User of Cre Recombinase," *Meth. Enzymol. 255*:890-900, Academic Press (1993).

Sauer, B., "Site-specific recombination: developments and applications," *Curr. Opin. Biotechnol. 5*:521-527, Current Biology (Oct. 1994).

Sauer, B., et al., "Site-specific insertion of DNA into a pseudorabies virus vector," *Proc. Natl. Acad. Sci. USA 84*:9108-9112, National Academy of Sciences (1987).

Sauer, B., and Henderson, N., "The cyclization of linear DNA in *Escherichia coli* by site-specfic recombination," *Gene 70*:331-341, Elsevier Science (1988).

Sauer, B., "Inducible gene targeting in mice using the Cre/*lox* system," *Methods 14* :381-392, Academic Press (Apr. 1998).

Sauer, B., "Multiplex Cre/*lox* recombination permits selective site-specific DNA targeting to both a natural and an engineered site in the yeast genome," *Nucl. Acids Res. 24*:4608-4613, Oxford University Press (1996).

Schild, D., et al., "Cloning of Three Human Multifunction *de novo* Purine Biosynthetic Genes by Functional Complementation of Yeast Mutations," *Proc. Natl. Acad. Sci. USA* 87:2916-2920, National Academy of Sciences (1990).

Schindelhauer, D., and Cooke, H.J., "Efficient combination of large DNA *in vitro*: in gel site specific recombination (IGSSR) of PAC fragments containing αsatellite DNA and the human HPRT gene locus," *Nucl. Acids Res. 25*:2241-2243, Oxford University Press (1997).

Schlake, T., and Bode, J., "Use of Mutated FLP Recognition Target (FRT) Sites for the Exchange of Expression Cassettes at Defined Chromosomal Loci," *Biochemistry 33*:12746-12751, American Chemical Society (Nov. 1994).

Schnepf, E., et al., "*Bacillus thuringiensis* and Its Pesticidal Crystal Proteins," *Microbiol. Mol. Biol. Rev. 62*:775-806, American Society for Microbiology (1998).

Scott, S.D., and Marples, B., "Comment on the use of the cre/*lox*P recombinase system for gene therapy vectors," *Gene Therapy 7*:1706, Macmillan Publishers Ltd. (2000).

Segall, A.M., et al., "Architectural Elements in Nucleoprotein Complexes: Interchangeability of Specific and Non-specific DNA Binding Proteins," *EMBO J. 13*:4536-4548, Oxford University Press (1994).

Segall, A.M., and Nash, H.A., "Architectural flexibility in lambda site-specific recombination: three alternate conformations channel the *attL* site into three distinct pathways," *Genes Cells 1* :453-463, Blackwell Science Ltd. (1996).

Segall, A.M., and Nash, H.A., "Synaptic intermediates in bacteriophage lambda site-specific recombination: integrase can align pairs of attachment sites," *EMBO J. 12*:4567-4576, Oxford University Press (1993).

Senecoff, J.F., et al., "DNA Recognition by the FLP Recombinase of the Yeast 2 μ Plasmid—A Mutational Analysis of the FLP Binding Site," *J. Mol. Biol. 201*:405-421, Academic Press (1988).

Sheffield, P., et al., "Overcoming expression and purification problems of RhoGDI using a family of "parallel" expression vectors," *Protein Expr. Purif. 15*:34-39, Academic Press (1999).

Shim, J., et al., "Distinct and Redundant Functions of μ1 Medium Chains of the AP-1 Clathrin-Associated Protein Complex in the Nematode *Caenorhabditis elegans," Mol. Biol. Cell 11*:2743-2756, American Society for Biology (Aug. 2000).

Shuman, S., "Recombination mediated by vaccinia virus DNA topoisomerase I on *Escherichia coli* is sequence specific," *Proc. Natl. Acad. Sci. USA 88*:10104-10108, National Acadmey of Sciences (1991).

Shuman, S., "Novel Approach to Molecular Cloning and Polynucleotide Synthesis Using Vaccinia DNA Topoisomerase," *J. Biol. Chem. 269*:32678-32684, American Society for Biochemistry and Molecular Biology, Inc. (1994).

Simpson, J.C., et al., "Systematic Subcellular Localization of Novel Proteins Identified by Large-scale cDNA Sequencing," *EMBO Rep. 1*287-292, Oxford University Press (Sep. 2000).

Sinclair, B., "Honing Your Cloning," *The Scientist 14*:29-32, The Scientist Inc. (Aug. 21, 2000) available at: http://www.the-scientist.com/yr2000/aug/profile1_000821.html.

Sizemore, C., et al., "Quantitative analysis of Tn*10* Tet repressor binding to a complete set of *tet* operator mutants," *Nucl. Acids Res. 18*:2875-2880, Oxford University Press (1990).

Skraly, F.A., et al., "Construction and Characterization of a 1,3-Propanediol Operon," *Appl. Environ Microbiol. 64*:98-105, American Society for Microbiology (1998).

Smith, A.J.H., et al., "A site-directed chromosomal translocation induced in embryonic stem cells by Cre-*lox*P recombination," *Nat. Genet. 9*:376-385, Nature Pub. Co. (Apr. 1995).

Snaith, M.R., et al., "Multiple cloning sites carrying *loxP* and *FRT* recognition sites for the Cre and Flp site-specific recombinases," *Gene 166*:173-174, Elsevier Science (Dec. 1, 1995).

Spengler, S.J., et al., "The Stereostructure of Knots and Catenanes Produced by Phage λ Integrative Recombination: Implications for Mechanism and DNA Structure," *Cell 42*:325-334, Cell Press (1985).

Spinella, D.G., et al., "Tandem arrayed ligation of expressed sequence tags (TALEST): a new method for generating global gene expression profiles," *Nucl. Acids Res. 27(e22)*:i-viii, Oxford University Press (1999).

Stark, W. M., et al., "Site-specific Recombination by TN3 Resolvase: Topological Changes in the Forward and Reverse Reactions," *Cell 58*:779-790, Cell Press (1989).

Stassi, D.L., et al., "Ethyl-substituted erythromycin derivatives produced by directed metalbolic engineering," *Proc. Natl. Acad. Sci. USA 95*:7305-7309, National Academy of Sciences of the USA (1998).

Stellwagen, A.E., and Craig, N.L., "Mobile DNA elements: controlling transposition with ATP-dependent molecular switches," *Trends Biochem. Sci. 23*:486-490, Elsevier Science Publishers (1998).

Stenzel, T. T., et al., "The Integration Host Factor of *Escherichia coli* Binds to Bent DNA at the Origin of Replication of the Plasmid pSC01," *Cell 49*:709-717, Cell Press (1987).

Stemberg, N., "Bacteriophage P1 cloning system for the isolation, amplification, and recovery of DNA fragments as large as 100 kilobase pairs,"*Proc. Natl. Acad. Sci. USA 87*:103-107, National Academy of Sciences (1990).

Sternberg, N., et al., "Bacteriophage P1 *cre* Gene and its Regulatory Region," *J. Mol. Biol. 187*:197-212, Academic Press (1986).

Sternberg, N., et al., "Site-specific Recombination and Its Role in the Life Cycle of Bacteriophage P1," *Cold Spring Harbor Symp. Quant. Biol. 45*:297-309, Cold Spring Harbor Laboratory Press (1981).

Storck, T., et al., "Rapid construction in yeast of complex targeting vectors for gene manipulation in the mouse," *Nucl. Acids Res. 24*:4594-4596, Oxford University Press (1996).

Strathmann, M., et al., "Transposon-facilitated DNA sequencing," *Proc. Natl. Acad. Sci. USA 88*:1247-1250, National Academy of Sciences (1991).

Stryer, L., *Biochemistry, 2nd ed.*, W.H. Freeman and Co., San Francisco, CA, p. 610 (1981).

Stuurman, J., et al., "Single-site manipulation of tomato chromosomes *in vitro* and *in vivo* using Cre-*lox* site-specific recombination," *Plant Molecular Biology 32*:901-913, Kluwer Academic Publishers (1996).

Sugiura, S., et al., "Minimal Essential Origin of Plasmid pSC101 Replication: Requirement of a Region Downstream of Iterons," *J. Bacteriol. 175*:5993-6001, American Society for Microbiology (1993).

Thompson, J.F., et al., "Helical-repeat dependence of integrative recombination of bacteriophage λ: Role of the *P1* and *H1* protein binding sites," *Proc. Natl. Acad. Sci. USA 85*:6323-6327, National Academy of Sciences (1988).

Thompson, J.F., et al., "Mutations in an Integration Host Factor-Binding Site: Effect on Lambda Site-Specific Recombination and Regulatory Implications," *J. Bacteriol. 168*:1343-1351, American Society For Microbiology (1986).

Thorpe, H.M., and Smith, M.C.M., "*In vitro* site-specific integration of bacteriophage DNA catalyzed by a recombinase of the resolvase/invertase family," *Proc. Natl. Acad. Sci. USA 95*:5505-5510, National Academy of Sciences (May 1998).

Tsurushita, N., et al., "Phage display vectors for in vivo recombination of immunoglobulin heavey and light chains genes to make large combinatorial libraries," *Gene 172*:59-63, Elsevier Science (1996).

Uetsuki, T., et al., "Isolation and Characterization of the Human Chromosomal Gene for Polypeptide Chain Elongation Factor-1a," *J. Biol. Chem. 264*:5791-5798, The American Society for Biochemistry and Molecular Biology, Inc. (1989).

van den Berg, A., et al., "Serial analysis of gene expression: rapid RT-PCR analysis of unknown SAGE tags," *Nucl. Acid Res. 27(e17)*:i-iii, Oxford Univeristy Press (1999).

Vanin, E.F., et al., "Development of High-Titer Retroviral Producer Cell Lines by Using Cre-Mediated Recombination," *J. Virol. 71*:7820-7826, American Society For Microbiology (1997).

Venkatesh, T.V., and Radding, C.M., "Ribosomal Protein S1 and NusA Protein Complexed to Recombination protein b of Phage 1," *J. Bacteriol. 175*:1844-1846, American Society of Microbiology (1993).

Vetter, D., et al., "Site-specific recombination of yeast 2- Ξm DNA *in vitro," Proc. Natl. Acad. Sci. USA 80*:7284-7288, National Acadmey of Sciences (1983).

Voss, S.D., et al., "The Role of Enhancers in the Regulation of Cell-type specific Transcriptional Control," *Trends Biochem. Sci. 11*:287-289, Elsevier Science (1986).
Voziyanov, Y., et al., "A general model for site-specific recombination by the integrase family recombinases," *Nucl. Acids. Res. 27*:930-941, Oxford University Press (1999).
Wang, G., et al., "pDual: A transposon-based cosmid cloning vector for generation nested deletions and DNA sequencing templates *in vivo," Proc. Natl. Acad. Sci. USA 90*:7874-7878, National Academy of Sciences (1993).
Wasserman, S.A., et al., "The helical repeat of double-stranded DNA varies as a function of catenation and supercoiling," *Nature 334*:448-450, Nature Pub. Co. (1988).
Waterhouse, P., et al., "Combinatorial infection and *in vivo* recombination: a strategy for making large phage antibody repertoires," *Nucl. Acids Res. 21*:2265-2266, Oxford University Press (1993).
Weisberg, R.A., and Landy, A., "Site-specific Recombination in Phage Lambda," in *Lambda II*, Hendrix, R.W., et al., eds., Cold Spring Harbor Laboratory Press, Cold Spring Harbor, NY, pp. 211-250 (1983).
Wierzbicki, A., et al., "A Mutational Analysis of the Bacteriophage P1 Recombinase Cre," *J. Mol. Biol. 195*:785-794, Academic Press (1987).
Wild, J., et al., "A broad-host-range *in vivo* pop-out and amplification system for generating large quantities of 50- to 100-kb genomic fragments for direct DNA sequencing," *Gene 179*:181-188, Elsevier Science (1996).
Wild, J., et al., "Targeting and retrofitting pre-existing libraries of transposon insertions with *FRT* and *oriV* elements for in-vivo generation of large quantities of any genomic fragment," *Gene 223*:55-66, Elsevier Science (1998).
Winoto, A., et al., "Directional Control of Site-specific Recombination by Bacteriophage λ," *J. Mol. Biol. 192*:677-680, Academic Press (1986).
Wittmann, H.G., "Components of Bacterial Ribosomes," *Ann. Rev. Biochem. 51*:155-183, Annual Reviews, Inc. (1982).
Wittmann, H.G., "Architecture of Prokaryotic Ribosomes," *Ann. Rev. Biochem. 52*:35-65, Annual Reviews, Inc. (1983).
Yang, W., and Mizuuchi, K., "Site-specific recombination in plane view," *Structure 5*:1401-1406, Cell Press (1997).
Yanisch-Perron, C., et al., "Improved M13 phage cloning vectors and host strains: nucleotide sequences of the M13mp18 and pUC19 vectors," *Gene 33*:103-119, Elsevier Science (1985).
Yoon, Y.G., et al., "Cre/*loxP*-mediated in vivo excision of large segments from yeast genome and their amplification based on the 2 Ξm plasmid-derived system," *Gene 223*:67-76, Elsevier Science (1998).
Yoon, H., et al., "*SSL1*, a Suppressor for a *HIS4* 5'-UTR Stem-loop Mutation, is Essential for Translation Initiation and Affects UV Resistance in Yeast," *Genes Dev. 6*:2463-2477, Cold Spring Harbor Laboratory Press (1992).
York, D., et al., "Simple and efficient generation *in vitro* of nested deletions and inversions: Tn5 intramolecular transposition," *Nucl. Acids Res. 26*:1927-1933, Oxford Univeristy Press (1998).
Zahra, D.G., et al., "Selectable in-vivo Recombination to Increase Antibody Library Size-an Improved Phage Display Vector System," *Gene 227*:49-54, Elsevier Science (1994).
Zechiedrich, E.L., et al., "Topoisomerase IV, not gyrase, decatenates products of site-specific recombination in *Escherichia coli," Genes Dev. 11*:2580-2592, Cold Spring Harbor Laboratory Press (1997).
Zhang, Y., et al., "A new logic for DNA engineering using recombination in *Escherichia coli," Nat. Genet. 20* : 123-128, Nature Pub. Co. (1998).
Zhu, X.D., et al., "Homology requirements for ligation and strand exchange by the FLP recombinase," *J. Biol. Chem. 270*:11646-11653, American Society for Biochemistry and Molecular Biology (1995).
U.S. Appl. No. 09/438,358, Gerard et al., filed Nov. 12, 1999, (Not Published).
U.S. Appl. No. 09/517,466, Hartley et al., filed Mar. 2, 2000 (Not Published).
U.S. Appl. No. 09/695,065, Brasch et al., filed Oct. 25, 2000 (Not Published).
U.S. Appl. No. 09/984,239, Brasch et al., filed Oct. 29, 2001 (Not Published).
U.S. Appl. No. 10/633,690, Byrd et al., filed Aug. 5, 2003 (Not Published).
U.S. Appl. No. 10/877,952, Welch et al., filed Jul. 28, 2004 (Not Published).
U.S. Appl. No. 10/913,501, Chesnut et al., filed Aug. 9, 2004 (Not Published).
U.S. Appl. No. 10/970,635, Hanson, filed Oct. 22, 2004 (Not Published).
U.S. Appl. No. 11/000,371, Chesnut et al., filed Dec. 1, 2004 (Not Published).
Dialog File 351, Derwent World Patent Index, Unverified English Language Abstract for PCT Patent No. WO 98/53056 (Document AL7), WPI Accession No. 12194396.
Dialog File 351, Derwent World Patent Index, Unverified English Language Abstract for PCT Patent No. WO 99/25851 (Document AO7), WPI Accession No. 12541379.
Argos, P., et al., "The integrase family of site-specific recombinases: regional similarities and global diveristy," *EMBO J. 5*:433-440, IRL Press Ltd. (1986).
invitrogen Online Catalog, "The Echo™ Cloning System: The Future of Cloning is Here," available at: http:invitrogen.com/content.cfm?pageid=3371&cfid=16767784&cftoken=62396683 (accessed Jul. 7, 2004).
Agah, R., et al., "Gene Recombination in Postmitotic Cells. Targeted Expression of Cre Recombinase Provokes Cardiac-restricted, Site-specific Rearrangement in Adult Ventricular Muscle In Vivo," *J. Clin. Invest. 100*:169-179, The American Society for Clinical Investigation, Inc. (Jul. 1997).
Benoist, C. and Chambon, P., "*In vivo* sequence requirements of the SV40 early promoter region," *Nature 290*:304-310, Macmillan Journal, Ltd. (1981).
Botstein, D., et al., "Making Mutations *In Vitro* and Putting Them Back Into Yeast," in *From Gene to Protein: Translation into Biotechnology*, Ahmad, F., et al., eds., Academic Press, New York, NY, pp. 265-274 (1982).
Broach, J.R., "The Yeast Plasmid 2 μ Circle," *Cell 28*:230-204, MIT (1982).
Cenatiempo, Y., "Prokaryotic gene expression *in vitro*: transcription-translation coupled systems," *Biochimie 68*:505-515, Elsevier (1986).
Christiansen, B., et al., "A Resolvase-Like Protein Is Required for the Site-Specific Integration of the Temperate Lactococcal Bacteriophage TP901-1," *J. Bacteriol. 178*:5164-5173, American Society for Microbiology (Sep. 1996).
Crellin, P.K. and Rood, J.I., "The Resolvase/Invertase Domain of the Site-Specific Recombinase TripX Is Functional and Recognizes a Target Sequence That Resembles a Target Sequence That Resembles the Junction of the Circular Form of the *Clostridium perfringens* Transposon Tn4451," *J. Bacteriol. 179*:5148-5156, American Society for Microbiology (Aug. 1997).
Ferrin, L.J. and Camerini-Otero, R.D., "Sequence-specific ligation of DNA using RecA protein," *Proc. Natl. Acad. Sci. USA 95*:2152-2157, National Academy of Science (Mar. 1998).
Golic, K.G. and Golic, M.M., "Engineering the Drosophilia Genome: Chromosome Rearrangement by Design," *Genetics 144*:1693-1711, The Genetics Society of America (1996).
Gottesman, S., "Bacterial Regulation: Global Regulatory Networks," *Ann. Rev. Genet. 18*:415-441, Annual Reviews, Inc. (1984).
Guo, R., et al., "Structure of Cre recombinase complexed with DNA in a site-specific recombination synapse," *Nature 389*:40-46, Nature Publishing Group (Sep. 1997).
Hallet, B. and Sherratt, D.J., "Transposition and site-specific recombination: adapting DNA cut-and-paste mechanisms to a variety of genetic rearrangements," *FEMS Microbiol. Rev. 21*:157-178, Elsevier Science B.V. (Sep. 1997).
Hamer, D.H. and Walling, M., "Regulation *In Vivo* of a Cloned Mammalian Gene: Cadmium Induces the Transcription of a Mouse Metallothionein Gene in SV40 Vectors," *J. Mol. Appl. Genet. 1*:273-288, Raven Press (1982).
Hanks, S.K. and Hunter, T., "The eukaryotic protein kinase superfamily: kinase (catalytic) domain structure and classification,"

*FASEB J. 9*:576-596, The Federation of American Societies for Experimental Biology (May 1995).
Huang, L-C., et al., "Convenient and Reversible Site-Specific Targeting of Exogenous DNA into a Bacterial Chromosome by Use of the FLP Recombinase: the FLIRT System," *J. Bacteriol. 179*:6076-6083, American Society for Microbiology (Oct. 1997).
John, Jr., J.F. and Twitty, J.A., "Plasmids as Epidemiologic Marker in Nosocomial Gram-Negative Bacilli: Experience at a University and Review of the Literature," *Rev. Infect. Dis. 8*:693-704, Univeristy of Chicago (1986).
Johnston, S.A. and Hopper, J.E., "Isolation of the yeast regulatory gene *GAL4* and analysis of its dosage effects on the galactose/melibiose regulon," *Proc. Natl. Acad. Sci. USA 79*:6971-6975, National Acadmey of Sciences (1982).
Kendall, K.J. and Cohen, S.N., "Plasmid Transfer in *Streptomyces lividans*: Identification of a *kil-kor* System Associated with Transfer Region of pIJ101," *J. Bacteriol. 169*:4177-4183, American Society for Microbiology (1987).
Lyznik, L.A., et al., "Activity of yeast FLP recombinase in maize and rice protoplasts," *Nucleic Acids Res. 21*:969-975, Oxford University Press (1993).
Maniatis, T., "Recombinant DNA Procedures in the Study of Eukaryotic Genes," in *Cell Biology: A Comprehensive Treatise, vol. 3, Gene Expression: The Production of RNA's*, Goldstein, L., and Prescott, D.M., eds., Academic Press, Inc., New York, NY, pp. 563-608 (1980).
Mayer, B.J. and Baltimore, D., "Signalling through SH2 and SH3 domains,"*Trends Cell biol. 3*:8-13, Elsevier Science (1993).
McKnight, S.L., "Functional Relationships between Transcriptional Control Signals of the Thymidine Kinase Gene of Herpes Simplex Virus," *Cell 31*:355-365, MIT (1982).
Nunes-Düby, S.E., et al., "λ Integrase cleaves DNA in *cis," EMBO J. 13*:4421-4430, Oxford University Press (1994).
Odell, J., et al., "Site-directed recombination in the genome of transgenic tobacco," *Mol. Gen. Genet. 223*:369-378, Springer-Verlag (1990).
Peterson, B.Ø. and Shuman, S., "Hisitidine 265 Is Important for Covalent Catalysis by Vacciania Topoisomerase and Is Conserved in All Eukaryotic Type I Enzymes," *J. Biol. Chem. 272*3891-3896, The American Society for Biochemistry and Molecular Biology, Inc. (Feb. 1997).
Rausch, H. and Lehmann, M., "Stuctural analysis of the actinophage ΦC31 attachment site," *Nucleic Acids Res. 19*:5187-5189, IRL Press (1991).
Sadowski, I., et al., "A Noncatalutic Domain Conserved among Cytoplasmic Protein-Tyrosine Kinases Modifies the Kinase and Transforming Activity of Fujinami Sarcoma Virus P130$^{gag-fps}$," *Mol. Cell. Biol. 6*:4396-4408, American Society for Microbiology (1986).
Sauer, B. and Henderson, N., "Targeted Insertion of Exogenous DNA into the Eukaryotic Genome by the Cre Recombinase," *New Biol. 2*:441-449, Saunders Scientific Publication/W.B. Saunders Company (1990).
Senecoff, J.F., et al., "The FLP recombinase of the yeast 2- μm plasmid: Characterization of its recombination site," *Proc. Natl. Acad. Sci. USA 82*:7270-7274, National Academy of Sciences (1985).
Shaikh, A.C. and Sadowski, P.D., "The Cre Recombinase Cleaves the *lox* Site in *trans," J. Biol. Chem. 272*:5695-5702, The American Society for Biochemistry and Molecular Biology, Inc. (Feb. 1997).
Shirai, M., et al., "Site-Specific Integration of the Actinophage R4 Genome into the Chromosome of *Streptomyces parvulus* Lysogenization," *J. Bacteriol. 173*:4237-4239, American Society for Microbiology (1991).
Shuman, S., et al., "Characterization of Vaccinia Virus DNA Topoisomerase I Expressed in *Escherichia coli," J. Biol. Chem. 263*:16401-16407, The American Soceity for Biochemistry and Molecular Biology, Inc. (1988).
Shuman, S., "Site-specific Interaction of Vaccinia Virus Topoisomerase I with Duplex DNA. Minimal DNA Substrate for Strand Cleavage *In Vitro," J. Biol. Chem. 266*:11372-11379, The American Society for Biochemistry and Molecular Biology, Inc. (1991).
Shuman, S., "Erratum: Site-specific Interaction of Vaccinia Virus Topoisomerase I with Duplex DNA. Minimal DNA Substrate for Strand Cleavage *In Vitro," J. Biol. Chem. 266*:20576-20577, The American Society for Biochemistry and Molecular Biology, Inc. (1991).
Silver, P.A., et al., "Amino terminus of the yeast *GAL4* gene product is sufficient for nuclear localization," *Proc. Natl. Acad. Sci. USA 81*:5951-5955, National Academy of Sciences (1984).
Stark, W.M., et al., "Catalysis by site-specific recombinases," *Trends Genet. 8*:432-439, Elsevier Science (1992).
Ulmanen, I., et al., "Transcription and Translation of Foreign Genes in *Bacillus subtilis* by the Aid of a Secretion Vector," *J. Bacteriol. 162*:176-182, American Society for Microbiology (1985).
van Deursen, J., et al., "Cre-mediated site-specific translocation between nonhomologous mouse chromosomes," *Proc. Natl. Acad. Sci. USA 92*:7376-7380, National Acadmey of Sciences (1995).
Ward, J.M., et al., "Construction and characterisation of a series of multi-copy promoter-probe plasmid vectors for *Streptomyces* using the aminoglycoside phosphotransferase gene from Tn5 as indicator," *Mol. Gen. Genet. 203*:468-478, Springer-Verlag (1986).
Invitrogen Life Technologies online catalog, "Directional TOPO Entry Vectors," 4 pages, accessed Sep. 27, 2002, available at: http://www.invitrogen.com/content.cfm?pageid=3799 &cfid=2897960&cftoken=88086554.
Dialog File 351, Derwent World Patent Index, English Language Abstract for French Patent No. FR 2 670 502 (Document AL20) and PCT Patent No. WO 92/10577 (Document AM20), WPI Accession No. 9107201.
Baum, J.A., "Tn*5401*, a New Class II Transposable Element From *Bacillus thuringiensis," J. Bacteriol. 176*:2835-2845, American Society for Microbiology (1994).
Short, J.M., et al., "λ ZAP: a bacteriophage λ expression vector with *in vivo* excision properties," *Nucleic Acids Res. 16*:7583-7600, Oxford University Press (1988).
U.S. Appl. No. 10/991,803, Carrino et al., filed Nov. 17, 2004.
Alonso, J.C., "Site-specific recombination in Gram-positive theta-replicating plasmids," *FEMS Microbiol. Lett. 142*:1-10, Elsevier, Science B.V. (1996).
Amin, A.A., et al., "Synthesis of an Enzymatically Active FLP Recombinase In Vitro: Search for a DNA-Binding Domain," *Molec. Cell. Biol. 9*: 1987-1995, American Society for Microbiology (1989).
Andersen, A.H., et al., "Studies if the Topisomerase II-mediated Cleavage and Religation Reactions by Use of a Suicidal Double-stranded DNA Substrate," *J. Biol. Chem. 266*:9203-9210, The American Society for Biochemistry and Molecular Biology, Inc. (1991).
Aoki, K., et al., "Efficient Generation of Recombinant Adenoviral Vectors bt Cre-lox Recombination In Vitro," *Molec. Med. 5*:224-231, Springer (1999).
Berger, J.M., "Structure of DNA topoisomerase," *Biochim. Biophys. Acta 1400*:3-18, Elsevier Science B.V. (1999).
Bliska, J.B and Cozzarelli, N.R., "Use of Site-Specific Recombination as a Prode of DNA Structure and Metabolism *in Vivo," J. Molec. Biol. 194*:205-218, Academic Pres Inc. (1987).
Caminci, P. and Hayashizaki, Y., "High-Efficiency Full-Length cDNA Cloning," *Meth. Enzmol. 303*:19-44, Academic Press (1999).
Caron, P.R. and Wang, J.C., "Appendix II: Alignment of Primary Sequences of DNA Topoisomerases," *Adv. Pharmacol. 29B*:271-297, Academic Press, Inc. (1994).
Chatterjee, P.K. and Sternberg, N.L., "Retrofitting High Molecular Weight DNA Cloned in P1: Introduction of Reporter Genes, Markers Selectable in Mammalian Cells and Generation of Nested Deletions," *Genet. Anal.: Biomolec. Eng. 13*:33-42, Elservier Science B.V. (1996).
Cheng, C. and Shuman, S., "Recombinogenic Flap Ligation Pathway for Intrinsic Repair of Topoisomerase IB-Induced Double-Strand Breaks," *Mol. Cell. Biol. 20*:8059-8068, American Society for Microbiology (2000).
Cheng, C., et al., "Conservation of Structure and Mechanism between Eukaryotic Topoisomerase I and Site Specific Recombinases," *Cell* 92841-850, Cell Press (1998).

DiGate, R.J. and Marians, K.J., "Molecular Cloning and DNA Sequence Analysis of *Escherichia coli* topB, and Gene Encoding Topoisomerase III," *J. Biol. Chem. 264*:17924-17930, The American Society for Biochemistry and Molecular Biology, Inc. (1989).
Gotou, N., et al., "Gateway™ Cloning Technology," *Exp. Med. Sci. 18*:2716-2717, Invitrogen Corporation (2000).
English language translation for Gotou, N., et al., "Gateway, Cloning Technology," *Exp. Med. Sci. 18*:2716-2717, Invitrogen Corporation (2000).
Gupta, M., et al., "Eukaryotic DNA topoisomerases I," *Biochim. Biophys. Acta. 1262*:1-14, Elsevier Science B.V. (1995).
Hanai R., et al., "Human TOP3: A single-copy gene encoding DNA topoisomerase III," *Proc. Natl. Acad. Sci. USA 93*:3653-3657, The National Academy of Sciences (1996).
Huang, L.-C., et al., "A bacterial model system for chromosomal targeting," *Nucl. Acids Res. 19*:443-448, Oxford University Press (1991).
Kanegae, Y., et al., "Efficient gene activation in mammalian cells by using recombinant adenovirus expressing site-specific Cre recombinase," *Nucl. Acids Res. 23*:3816-3821, Oxford University Press (1995).
Kijima, T., et al., "Application of the Cre Recombinase/*loxP* System Further Enhances Antitumor Effects in Cell Type-specific Gene Therapy against Carcinoembryonic Antigen-producing Cancer," *Canc. Res. 59*: 4906-4911, American Association for Cancer Research, Inc. (1999).
Kim, R.A. and Wang, J.C., "Identification of the Yeast TOP3 Gene Product as a Single Strans-specific DNA Topoisomerase," *J. Biol. Chem. 267*:17178-17185, The American Society for Biochemistry and Molecular Biology, Inc. (1992).
Kisu, Y., et al., "Development of high accuracy and high through put production multi purpose Gateway entry clones production. I. Improvement of the PCR condition for construction of the entry clone," abstract available at http://biotech.nikkeibp.co.jp/netlinl/Ito/gateway/new_info/contents9.html, (2000).
Kisu, Y., et al., "Development of high-throughput technology of entry clones of the multi-purpose Gateway cloning system (III): An Improved method for high-efficient and high-fidelity construction of the entry clones," *Poster Session of the Annual Meeting of Japan Society of Molecular Biology*, Abstract No. 2P-730 (Dec. 2001).
English language translation of Kisu, Y., et al., "Development of high-throughput technology of entry clones of the multi-purpose Gateway cloning system (III): An improved method for high-efficient and high-fidelity construction of the entry clones," *Poster Session of the Annual Meeting of Japan Society of Molecular Biology*, Abstract No. 2P-730 (Dec. 2001).
Li, Z., et al., "The traE Gene of Plasmid RP4 Encodes a Homologue of *Escherichia coli* DNA Topoisomerase III," *J. Biol. Chem. 272*:19582-19587, The American Society for Biochemistry and Molecular Biology, Inc. (1997).
Lieber, A., et al., "Recombinant Adenoviruses with Large Deletions Generated by Cre-Mediated Excision Exhibit Different Biological Properties Compared with First-Generation Vectors In Vitro and In Vivo," *J. Virol. 70*:8944-8960, American Society for Microbiology (1996).
Liu, X. and Gorovsky, M.A., "Mapping the 5' and 3' Ends of *Tetrahymena thermophelia* mRNAs Using RNA Ligase Mediated Amplification of cDNA Ends (RLM-RACE)," *Nucl. Acids Res. 21*:4954-4960, Oxford University Press (1993).
Ng, P., et al., "A High-Efficiency Cre//*loxP*-Based System for Construction of Adenoviral Vectors," *Human Gene Ther. 10*:2667-2672, Mary Ann Liebert, Inc. (1999).
"pENTR Directional TOPO® Cloning Kits," *Invitrogen Manual*, catalog Nos. K2400-20. K2400-480, K2400-500, K2420-20, K2420-80, K2420-500, Version B, Invitrogen Corporation, Carlsbad, CA, 48 pages (Jul. 2002).
Petersen, B.Ø., et al., "Characterization of a DNA Topoisomerase Encoded by *Amsacia moorer* Entomopoxvirus," *Virol. 230*:197-206, Academic Press (1997).
Pfeifer, A., et al., "Delivery of the Cre recombinase by a self-deleting lentiviral vector: Efficient gene targeting *in vivo," Proc. Natl. Acad. Sci. USA 98*:11450-11455, National Academy of Science (Sep. 2001).
"pLenti6/V5 Directional TOPO® Cloning Kit," *Invitrogen Manual*, catalog No. 54955-10, Version B, Invitrogen Corporation, Carlsbad, CA, 52 pages (May 2002).
Roca, J. and Wang, J.C., "The Capture of a DNA Double Helix by an ATP-Dependent Protein Clamp: A Key Step in DNA Transport by Type II DNA Topoisomerases," *Cell 71*:833-840, Cell Press (1992).
Sekiguchi, J. and Shuman, S., "Requirements for noncovalent binding of vaccinia topoisomerase I to duplex DNA," *Nucl. Acids Res. 22*:5360-5365, Oxford University Press (1994).
Shashikant, C.S., et al., "Recombinogenic targeting: a new approach to genomic analysis—a review," *Gene* 223:9-20, Elsevier Science B.V. (1998).
Shuman, S., "Vaccinia virus DNA topoisomerase: a model eukaryotic type IB enzyme," *Biochim. Biophys. Acta 1400*:321-337, Elsevier Science B.V. (1998).
Shuman, S. and Bernard M., "Identification of a vaccinia virus gene encoding a tyoe I DNA topoisomerase," *Proc. Natl. Acad. Sci. USA 84*:7478-7482, National Academy of Sciences (1987).
Walhout, A.J.M., "Protein Interaction Mapping in *C. elegans* Using Protein Involved in Vulval Development," *Science 287*:116-122, American Association for the Advancement of Science (2000).
Walhout, A.J.M., "GATEWAY Recombinational Cloning: Application to the Cloning of Large Numbers of Open Reading Frames or ORFeomes," *Meth. Enzymol. 328*:575-592, Academic Press (2000).
Wang, J.C., "DNA Topoisomerase: Why So Many?," *J. Biol. Chem. 2666*659-6662, The American Society for Biochemistry and Molecular Biology, Inc. (1991).
Wang, Y., et al., "Targeted DNA recombination in vivo using an adenvirus carrying the cre recombinase gene," *Proc. Natl. Acad. Sci. USA 93*:3932-3936, National Academy of Sciences (1996).
Wilson, T.M., et al., "Cloning and Charactization of *Drosophila* Topoisomerase IIIβ," *J. Biol. Chem. 275*:1533-1540, The American Society for Biochemistry and Molecular Biology, Inc. (2000).
Yahata, K., et al., "Development of high accuracy and high through put production of multi purpose Gateway entry clones. Very low mutation frequency in contructing 60 entry clones of human full length cDNAs," abstract available at http://biotech.nikkeibp.co.jp/netlink/Ito/gateway/new_info/contents9.html (2000).
Yahata, K., et al., "Development of high accuracy and high-throughput production method of the entry clone of multi-purpose Gateway system. (IV) Improvement of DNA sequencing method for Gateway entry clones," *Poster Session of the Annual Meeting of Japan Society of Molecular Biology*, Abstract No. 2P-731 (Dec. 2001).
English language translation of Yahata, K., et al., "Development of high accuracy and high-throughput production method of the entry clone of multi-purpose Gateway system. (IV) Improvement of DNA sequencing method for Gateway entry clones," *Poster Session of the Annual Meeting of Japan Society of Molecular Biology*, Abstract No. 2P-731 (Dec. 2001).
Zhang, H.L., et al., "*Escherichia coli* DNA Topoisomerase III Is a Site-specific DNA Binding Protein That Binds Asymmetrically to Its Cleavage Site," *J. Biol. Chem. 270*:23700-23705, The American Society for Biochemistry and Molecular Biology, Inc. (1995).
U.S. Appl. No. 11/106,715, Byrd et al., filed Apr. 15, 2005.
U.S. Appl. No, 11/290,804, Gray et al., filed Dec. 1, 2005.
2000 Invitrogen Catalog, "The Echo™ Cloning System," pp. cover page, vi, 1 and 4-8, Dec. 6, 1999.

TABLE 1

| Primer name | F# | Sequence (5'→ 3') | SEQ ID NO: |
|---|---|---|---|
| MTH1 | 10779 | TATGTATCATACACATACGATTTAGGT | 1 |
| MTH2 | 10780 | ACCGCCTCTCCCCGCGCGTT | 2 |
| GAL4r2 | 12667 | GTTCCGAAGGGGGCGATACAGTCAACTGTCTTTG | 3 |
| MTH5 | 12505 | TTGGCCAAGGGTATCTAGAAGCTTCTGCAGACGCGT | 4 |
| VP16r2 | 12668 | GTTCCGAAGGGCCACCGTACTCGTCAATTCCAAG | 5 |
| SV40pAf | 12016 | GGCCAAAAGGGAACTTGTTTATTGCAGCTTATAATG | 6 |
| SV40pAr | 561 | CTCTGACTTGAGCGTCGATTTT | 7 |
| p53f2 | 12669 | CGGAACAAGGGGAATTCCCTGTCACCGAGACC | 8 |
| SVTf2 | 12670 | CGGAACAAGGGGAATTCCCGGGGATCTGGAATTC | 9 |
| CMVr2 | 7221 | TCGAAAGGGTCGAGGTCGACCTGCAGCTG | 10 |
| CMVf | 6945 | AATTCACATTGATTATTGAGTAGTTA | 11 |
| GFP-Xhof | 7220 | TCGAAAGGGTAATGGCCAGCAAAGGAGAAG | 12 |
| GFP-Notr | 6682 | GGCCAAGGGTTTGTAGAGCTCATCCAT | 13 |
| BGHf2 | 7222 | GGCCAAGGGTCTGAATGGGGCCGCATAGT | 14 |
| BGHr | 6948 | AAGCCATAGAGCCCGGGCCA | 15 |
| CMVr3 | 8417 | GTTCCGAAGGGTCGAGGTCGACCTGCAGCTG | 16 |
| GFPf3 | 8418 | CGGAACAAGGGATGGCCAGCAAAGGAGAAG | 17 |
| GFPr3 | 8420 | TAGGCCAAGGGTTTGTAGAGCTCATCCATGC | 18 |
| BGHf3 | 8419 | GGCCTAAAGGGTGAATGGGGCCGCATAGT | 19 |
| T7top | 9304 | GAAGGAGTAATACGACTCACTATAGGGAGCCACCATGGGCCCTTCGGAAC | 20 |
| T7bottom | 9305 | GTTCCGAAGGGCCCATGGTGGCTCCCTATAGTGAGTCGTATTACTCCTTC | 21 |
| T7amp | 9306 | GAAGGAGTAATACGACTCACT | 22 |
| T3top | 9661 | GGCCTAAAGGGTCCCTTTAGTGAGGGTTAATTGCGCGC | 23 |
| T3bottom | 9662 | GCGCGCAATTAACCCTCACTAAAGGGACCCTTTAGGCC | 24 |
| lacZf2 | 10632 | CGGAACAAGGGATGATAGATCCCGTCGTTTTACA | 25 |
| lacZ1k2 | 10770 | TAGGCCAAGGGGACCATTTTCAATCCGCACCT | 26 |
| lacZ2k2 | 10771 | TAGGCCAAGGGGAGGCACTTCACCGCTTGCCA | 27 |
| lacZ3k2 | 10772 | TAGGCCAAGGGTTTGACACCAGACCAACTGGTA | 28 |

FIG. 9D

| SAMPLE # | GAL4+pA | VP16+pA | pGene/lacZ | GAL4+p53+pA | VP16+T+pA | p53-VP16 |
|---|---|---|---|---|---|---|
| 1 | | | 0.26 μg | p 0.37 μg | p 0.37 μg | |
| 2 | | | 0.4 μg | p 0.3 μg | p 0.3 μg | |
| 3 | | | 0.4 μg | | | p 0.6 μg |
| 4 | | | 0.4 μg | 10.3 μg | 10.3 μg | |
| 5 | | 10.3 μg | 0.4 μg | 10.3 μg | | |
| 6 | 10.3 μg | | 0.4 μg | | 10.3 μg | |
| 7 | | | 0.4 μg | 4.5 μl PCR | 4.5 μl PCR | |
| 8 | | 4.5 μl PCR | 0.4 μg | 4.5 μl PCR | | |
| 9 | 4.5 μl PCR | | 0.4 μg | | 4.5 μl PCR | |

| SAMPLE # | LacZ activity |
|---|---|
| 1 | 240000 |
| 2 | 140000 |
| 3 | 1800000 |
| 4 | 1400000 |
| 5 | 54000 |
| 6 | 80000 |
| 7 | 320000 |
| 8 | 12000 |
| 9 | 42000 |

MCS FOR pcDNAGW-DT(sc) AND pENTR-DT(sc)

...L Y K K A G S A A A G R A D P A F L Y K V
TTG TAC AAA AAA GCA GGC TCC GCG GCC GTA CTC GAG AAA GGG CGC GCC GAC CCA GCT TTC TTG TAC AAA GTG
BsrG I                 Not I       Xho I      Asc I                   BsrG I

AttL1/B1                                           AttL2/B2

```
   1 ctttcctgcg ttatcccctg attctgtgga taaccgtatt accgcctttg agtgagctga
  61 taccgctcgc cgcagccgaa cgaccgagcg cagcgagtca gtgagcgagg aagcggaaga
 121 gcgcccaata cgcaaaccgc ctctccccgc gcgttggccg attcattaat gcagctggca
 181 cgacaggttt cccgactgga aagcgggcag tgagcgcaac gcaattaata cgcgtaccgc
 241 tagccaggaa gagtttgtag aaacgcaaaa aggccatccg tcaggatggc cttctgctta
 301 gtttgatgcc tggcagttta tggcgggcgt cctgcccgcc accctccggg ccgttgcttc
 361 acaacgttca aatccgctcc cggcggattt gtcctactca ggagagcgtt caccgacaaa
 421 caacagataa aacgaaaggc ccagtcttcc gactgagcct ttcgttttat ttgatgcctg
 481 gcagttccct actctcgcgt taacgctagc atggatgttt tcccagtcac gacgttgtaa
 541 aacgacggcc agtcttaagc tcgggcccca aataatgatt ttattttgac tgatagtgac
 601 ctgttcgttg caacaaattg atgagcaatg cttttttata atgccaactt tgtacaaaaa
 661 agcaggctcc gcggccgccc cttcaccatg nnnnnnnnna agggtgggcg cgccgaccca
 721 gctttcttgt acaaagttgg cattataaga aagcattgct tatcaatttg ttgcaacgaa
 781 caggtcacta tcagtcaaaa taaaatcatt atttgccatc cagctgatat cccctatagt
 841 gagtcgtatt acatggtcat agctgtttcc tggcagctct ggcccgtgtc tcaaaatctc
 901 tgatgttaca ttgcacaaga taaaaatata tcatcatgaa caataaaact gtctgcttac
 961 ataaacagta atacaagggg tgttatgagc catattcaac gggaaacgtc gaggccgcga
1021 ttaaattcca acatggatgc tgatttatat gggtataaat gggctcgcga taatgtcggg
1081 caatcaggtg cgacaatcta tcgcttgtat gggaagcccg atgcgccaga gttgtttctg
1141 aaacatggca aaggtagcgt tgccaatgat gttacagatg agatggtcag actaaactgg
1201 ctgacggaat ttatgcctct tccgaccatc aagcatttta tccgtactcc tgatgatgca
1261 tggttactca ccactgcgat ccccggaaaa acagcattcc aggtattaga agaatatcct
1321 gattcaggtg aaaatattgt tgatgcgctg gcagtgttcc tgcgccggtt gcattcgatt
1381 cctgtttgta attgtccttt taacagcgat cgcgtatttc gtctcgctca ggcgcaatca
1441 cgaatgaata acggtttggt tgatgcgagt gattttgatg acgagcgtaa tggctggcct
1501 gttgaacaag tctggaaaga aatgcataaa cttttgccat tctcaccgga ttcagtcgtc
1561 actcatggtg atttctcact tgataacctt atttttgacg aggggaaatt aataggttgt
1621 attgatgttg gacgagtcgg aatcgcagac cgataccagg atcttgccat cctatggaac
1681 tgcctcggtg agttttctcc ttcattacag aaacggcttt ttcaaaaata tggtattgat
1741 aatcctgata tgaataaatt gcagtttcat ttgatgctcg atgagttttt ctaatcagaa
1801 ttggttaatt ggttgtaaca ctggcagagc attacgctga cttgacggga cggcgcaagc
1861 tcatgaccaa aatcccttaa cgtgagttac gcgtcgttcc actgagcgtc agaccccgta
1921 gaaaagatca aaggatcttc ttgagatcct ttttttctgc gcgtaatctg ctgcttgcaa
1981 acaaaaaaac caccgctacc agcggtggtt tgtttgccgg atcaagagct accaactctt
2041 tttccgaagg taactggctt cagcagagcg cagataccaa atactgtcct tctagtgtag
2101 ccgtagttag gccaccactt caagaactct gtagcaccgc ctacatacct cgctctgcta
2161 atcctgttac cagtggctgc tgccagtggc gataagtcgt gtcttaccgg gttggactca
2221 agacgatagt taccggataa ggcgcagcgg tcgggctgaa cggggggttc gtgcacacag
2281 cccagcttgg agcgaacgac ctacaccgaa ctgagatacc tacagcgtga gcattgagaa
2341 agcgccacgc ttcccgaagg gagaaaggcg gacaggtatc cggtaagcgg cagggtcgga
2401 acaggagagc gcacgaggga gcttccaggg ggaaacgcct ggtatcttta tagtcctgtc
2461 gggtttcgcc acctctgact tgagcgtcga tttttgtgat gctcgtcagg ggggcggagc
2521 ctatggaaaa acgccagcaa cgcggccttt ttacggttcc tggccttttg ctggcctttt
2581 gctcacatgt t
```

FIG.22B 1 ctttcctgcg ttatcccctg attctgtgga taaccgtatt accgcctttg agtgagctga
61 taccgctcgc cgcagccgaa cgaccgagcg cagcgagtca gtgagcgagg aagcggaaga
121 gcgcccaata cgcaaaccgc ctctccccgc gcgttggccg attcattaat gcagctggca
181 cgacaggttt cccgactgga aagcgggcag tgagcgcaac gcaattaata cgcgtaccgc
241 tagccaggaa gagtttgtag aaacgcaaaa aggccatccg tcaggatggc cttctgctta
301 gtttgatgcc tggcagttta tggcgggcgt cctgcccgcc accctccggg ccgttgcttc
361 acaacgttca aatccgctcc cggcggattt gtcctactca ggagagcgtt caccgacaaa
421 caacagataa aacgaaaggc ccagtcttcc gactgagcct ttcgttttat ttgatgcctg
481 gcagttccct actctcgcgt taacgctagc atggatgttt tcccagtcac gacgttgtaa
541 aacgacggcc agtcttaagc tcgggcccca aataatgatt ttattttgac tgatagtgac
601 ctgttcgttg caacaaattg atgagcaatg cttttttata atgccaactt tgtacaaaaa
661 agcaggctcc gcggccgcct tgtttaactt taagaaggag cccttcaccn nnnnnaaggg
721 tgggcgcgcc gacccagctt tcttgtacaa agttggcatt ataagaaagc attgcttatc
781 aatttgttgc aacgaacagg tcactatcag tcaaaataaa atcattattt gccatccagc
841 tgatatcccc tatagtgagt cgtattacat ggtcatagct gtttcctggc agctctggcc
901 cgtgtctcaa aatctctgat gttacattgc acaagataaa aatatatcat catgaacaat
961 aaaactgtct gcttacataa acagtaatac aaggggtgtt atgagccata ttcaacggga
1021 aacgtcgagg ccgcgattaa attccaacat ggatgctgat ttatatgggt ataaatgggc
1081 tcgcgataat gtcgggcaat caggtgcgac aatctatcgc ttgtatggga agcccgatgc
1141 gccagagttg tttctgaaac atggcaaagg tagcgttgcc aatgatgtta cagatgagat
1201 ggtcagacta aactggctga cggaatttat gcctcttccg accatcaagc attttatccg
1261 tactcctgat gatgcatggt tactcaccac tgcgatcccc ggaaaaacag cattccaggt
1321 attagaagaa tatcctgatt caggtgaaaa tattgttgat gcgctggcag tgttcctgcg
1381 ccggttgcat tcgattcctg tttgtaattg tccttttaac agcgatcgcg tatttcgtct
1441 cgctcaggcg caatcacgaa tgaataacgg tttggttgat gcgagtgatt ttgatgacga
1501 gcgtaatggc tggcctgttg aacaagtctg gaaagaaatg cataaacttt tgccattctc
1561 accggattca gtcgtcactc atggtgattt ctcacttgat aaccttattt ttgacgaggg
1621 gaaattaata ggttgtattg atgttggacg agtcggaatc gcagaccgat accaggatct
1681 tgccatccta tggaactgcc tcggtgagtt ttctccttca ttacagaaac ggctttttca
1741 aaaatatggt attgataatc ctgatatgaa taaattgcag tttcatttga tgctcgatga
1801 gtttttctaa tcagaattgg ttaattggtt gtaacactgg cagagcatta cgctgacttg
1861 acgggacggc gcaagctcat gaccaaaatc ccttaacgtg agttacgcgt cgttccactg
1921 agcgtcagac cccgtagaaa agatcaaagg atcttcttga gatccttttt ttctgcgcgt
1981 aatctgctgc ttgcaaacaa aaaaaccacc gctaccagcg gtggtttgtt tgccggatca
2041 agagctacca actctttttc cgaaggtaac tggcttcagc agagcgcaga taccaaatac
2101 tgtccttcta gtgtagccgt agttaggcca ccacttcaag aactctgtag caccgcctac
2161 atacctcgct ctgctaatcc tgttaccagt ggctgctgcc agtggcgata agtcgtgtct
2221 taccgggttg gactcaagac gatagttacc ggataaggcg cagcggtcgg gctgaacggg
2281 gggttcgtgc acacagccca gcttggagcg aacgacctac accgaactga gatacctaca
2341 gcgtgagcat tgagaaagcg ccacgcttcc cgaagggaga aaggcggaca ggtatccggt
2401 aagcggcagg gtcggaacag gagagcgcac gagggagctt ccagggggaa acgcctggta
2461 tctttatagt cctgtcgggt ttcgccacct ctgacttgag cgtcgatttt tgtgatgctc
2521 gtcagggggg cggagcctat ggaaaaacgc cagcaacgcg gcctttttac ggttcctggc
2581 cttttgctgg ccttttgctc acatgtt

FIG.23B

```
   1 gacggatcgg gagatctccc gatcccctat ggtcgactct cagtacaatc tgctctgatg
  61 ccgcatagtt aagccagtat ctgctccctg cttgtgtgtt ggaggtcgct gagtagtgcg
 121 cgagcaaaat ttaagctaca acaaggcaag gcttgaccga caattgcatg aagaatctgc
 181 ttagggttag gcgttttgcg ctgcttcgcg atgtacgggc cagatatacg cgttgacatt
 241 gattattgac tagttattaa tagtaatcaa ttacggggtc attagttcat agcccatata
 301 tggagttccg cgttacataa cttacggtaa atggcccgcc tggctgaccg cccaacgacc
 361 cccgcccatt gacgtcaata atgacgtatg ttcccatagt aacgccaata gggactttcc
 421 attgacgtca atgggtggac tatttacggt aaactgccca cttggcagta catcaagtgt
 481 atcatatgcc aagtacgccc cctattgacg tcaatgacgg taaatggccc gcctggcatt
 541 atgcccagta catgacctta tgggactttc ctacttggca gtacatctac gtattagtca
 601 tcgctattac catggtgatg cggttttggc agtacatcaa tgggcgtgga tagcggtttg
 661 actcacgggg atttccaagt ctccacccca ttgacgtcaa tgggagtttg ttttggcacc
 721 aaaatcaacg ggactttcca aaatgtcgta acaactccgc cccattgacg caaatgggcg
 781 gtaggcgtgt acggtgggag gtctatataa gcagagctct ctggctaact agagaaccca
 841 ctgcttactg gcttatcgaa attaatacga ctcactatag ggagacccaa gctggctagt
 901 taagctatca acaagtttgt acaaaaaagc aggctccgcg gccgcccctt caccatgnnn
 961 nnnnnnaagg gtgggcgcgc cgacccagct ttcttgtaca aagtggttga tctagagggc
1021 ccgcggttcg aaggtaagcc tatccctaac cctctcctcg gtctcgattc tacgcgtacc
1081 ggttagtaat gagtttaaac gggggaggct aactgaaaca cggaaggaga caataccgga
1141 aggaacccgc gctatgacgg caataaaaag acagaataaa acgcacgggt gttgggtcgt
1201 ttgttcataa acgcggggtt cggtcccagg gctggcactc tgtcgatacc ccaccgagac
1261 cccattgggg ccaatacgcc cgcgtttctt ccttttcccc accccacccc ccaagttcgg
1321 gtgaaggccc agggctcgca gccaacgtcg gggcggcagg ccctgccata gcagatctgc
1381 gcagctgggg ctctaggggg tatccccacg cgccctgtag cggcgcatta agcgcggcgg
1441 gtgtggtggt tacgcgcagc gtgaccgcta cacttgccag cgccctagcg cccgctcctt
1501 tcgctttctt cccttccttt ctcgccacgt tcgccggctt tccccgtcaa gctctaaatc
1561 ggggcatccc tttagggttc cgatttagtg ctttacggca cctcgacccc aaaaaacttg
1621 attagggtga tggttcacgt agtgggccat cgccctgata gacggttttt cgccctttga
1681 cgttggagtc cacgttcttt aatagtggac tcttgttcca aactggaaca acactcaacc
1741 ctatctcggt ctattctttt gatttataag ggattttggg gatttcggcc tattggttaa
1801 aaaatgagct gatttaacaa aaatttaacg cgaattaatt ctgtggaatg tgtgtcagtt
1861 agggtgtgga aagtccccag gctccccagc aggcagaagt atgcaaagca tgcatctcaa
1921 ttagtcagca accaggtgtg gaaagtcccc aggctcccca gcaggcagaa gtatgcaaag
1981 catgcatctc aattagtcag caaccatagt cccgccccta actccgccca tcccgcccct
2041 aactccgccc agttccgccc attctccgcc ccatggctga ctaatttttt ttatttatgc
2101 agaggccgag gccgcctctg cctctgagct attccagaag tagtgaggag gcttttttgg
2161 aggcctaggc ttttgcaaaa agctcccggg agcttgtata tccattttcg gatctgatca
2221 agagacagga tgaggatcgt ttcgcatgat tgaacaagat ggattgcacg caggttctcc
2281 ggccgcttgg gtggagaggc tattcggcta tgactgggca caacagacaa tcggctgctc
2341 tgatgccgcc gtgttccggc tgtcagcgca ggggcgcccg gttctttttg tcaagaccga
2401 cctgtccggt gccctgaatg aactgcagga cgaggcagcg cggctatcgt ggctggccac
2461 gacgggcgtt ccttgcgcag ctgtgctcga cgttgtcact gaagcgggaa gggactggct
2521 gctattgggc gaagtgccgg ggcaggatct cctgtcatct caccttgctc ctgccgagaa
2581 agtatccatc atggctgatg caatgcggcg gctgcatacg cttgatccgg ctacctgccc
2641 attcgaccac caagcgaaac atcgcatcga gcgagcacgt actcggatgg aagccggtct
2701 tgtcgatcag gatgatctgg acgaagagca tcaggggctc gcgccagccg aactgttcgc
2761 caggctcaag gcgcgcatgc ccgacggcga ggatctcgtc gtgacccatg gcgatgcctg
```

FIG.24B 2821 cttgccgaat atcatggtgg aaaatggccg cttttctgga ttcatcgact gtggccggct
2881 gggtgtggcg gaccgctatc aggacatagc gttggctacc cgtgatattg ctgaagagct
2941 tggcggcgaa tgggctgacc gcttcctcgt gctttacggt atcgccgctc ccgattcgca
3001 gcgcatcgcc ttctatcgcc ttcttgacga gttcttctga gcgggactct ggggttcgcg
3061 aaatgaccga ccaagcgacg cccaacctgc catcacgaga tttcgattcc accgccgcct
3121 tctatgaaag gttgggcttc ggaatcgttt tccgggacgc cggctggatg atcctccagc
3181 gcggggatct catgctggag ttcttcgccc accccaactt gtttattgca gcttataatg
3241 gttacaaata aagcaatagc atcacaaatt tcacaaataa agcatttttt tcactgcatt
3301 ctagttgtgg tttgtccaaa ctcatcaatg tatcttatca tgtctgtata ccgtcgacct
3361 ctagctagag cttggcgtaa tcatggtcat agctgtttcc tgtgtgaaat tgttatccgc
3421 tcacaattcc acacaacata cgagccggaa gcataaagtg taaagcctgg ggtgcctaat
3481 gagtgagcta actcacatta attgcgttgc gctcactgcc cgctttccag tcgggaaacc
3541 tgtcgtgcca gctgcattaa tgaatcggcc aacgcgcggg gagaggcggt ttgcgtattg
3601 ggcgctcttc cgcttcctcg ctcactgact cgctgcgctc ggtcgttcgg ctgcggcgag
3661 cggtatcagc tcactcaaag gcggtaatac ggttatccac agaatcaggg gataacgcag
3721 gaaagaacat gtgagcaaaa ggccagcaaa aggccaggaa ccgtaaaaag gccgcgttgc
3781 tggcgttttt ccataggctc cgcccccctg acgagcatca caaaaatcga cgctcaagtc
3841 agaggtggcg aaacccgaca ggactataaa gataccaggc gtttccccct ggaagctccc
3901 tcgtgcgctc tcctgttccg accctgccgc ttaccggata cctgtccgcc tttctccctt
3961 cgggaagcgt ggcgctttct caatgctcac gctgtaggta tctcagttcg gtgtaggtcg
4021 ttcgctccaa gctgggctgt gtgcacgaac cccccgttca gcccgaccgc tgcgccttat
4081 ccggtaacta tcgtcttgag tccaacccgg taagacacga cttatcgcca ctggcagcag
4141 ccactggtaa caggattagc agagcgaggt atgtaggcgg tgctacagag ttcttgaagt
4201 ggtggcctaa ctacggctac actagaagga cagtatttgg tatctgcgct ctgctgaagc
4261 cagttacctt cggaaaaaga gttggtagct cttgatccgg caaacaaacc accgctggta
4321 gcggtggttt ttttgtttgc aagcagcaga ttacgcgcag aaaaaaagga tctcaagaag
4381 atcctttgat cttttctacg gggtctgacg ctcagtggaa cgaaaactca cgttaaggga
4441 ttttggtcat gagattatca aaaaggatct tcacctagat ccttttaaat taaaaatgaa
4501 gttttaaatc aatctaaagt atatatgagt aaacttggtc tgacagttac caatgcttaa
4561 tcagtgaggc acctatctca gcgatctgtc tatttcgttc atccatagtt gcctgactcc
4621 ccgtcgtgta gataactacg atacgggagg gcttaccatc tggccccagt gctgcaatga
4681 taccgcgaga cccacgctca ccggctccag atttatcagc aataaaccag ccagccggaa
4741 gggccgagcg cagaagtggt cctgcaactt tatccgcctc catccagtct attaattgtt
4801 gccgggaagc tagagtaagt agttcgccag ttaatagttt gcgcaacgtt gttgccattg
4861 ctacaggcat cgtggtgtca cgctcgtcgt ttggtatggc ttcattcagc tccggttccc
4921 aacgatcaag gcgagttaca tgatccccca tgttgtgcaa aaaagcggtt agctccttcg
4981 gtcctccgat cgttgtcaga agtaagttgg ccgcagtgtt atcactcatg gttatggcag
5041 cactgcataa ttctcttact gtcatgccat ccgtaagatg cttttctgtg actggtgagt
5101 actcaaccaa gtcattctga gaatagtgta tgcggcgacc gagttgctct tgcccggcgt
5161 caatacggga taataccgcg ccacatagca gaactttaaa agtgctcatc attggaaaac
5221 gttcttcggg gcgaaaactc tcaaggatct taccgctgtt gagatccagt tcgatgtaac
5281 ccactcgtgc acccaactga tcttcagcat cttttacttt caccagcgtt tctgggtgag
5341 caaaaacagg aaggcaaaat gccgcaaaaa agggaataag ggcgacacgg aaatgttgaa
5401 tactcatact cttccttttt caatattatt gaagcattta tcagggttat tgtctcatga
5461 gcggatacat atttgaatgt atttagaaaa ataaacaaat aggggttccg cgcacatttc
5521 cccgaaaagt gccacctgac gtc

FIG.24C

```
   1 gacggatcgg gagatctccc gatcccctat ggtgcactct cagtacaatc tgctctgatg
  61 ccgcatagtt aagccagtat ctgctccctg cttgtgtgtt ggaggtcgct gagtagtgcg
 121 cgagcaaaat ttaagctaca acaaggcaag gcttgaccga caattgcatg aagaatctgc
 181 ttagggttag gcgttttgcg ctgcttcgcg atgtacgggc cagatatacg cgttgacatt
 241 gattattgac tagttattaa tagtaatcaa ttacggggtc attagttcat agcccatata
 301 tggagttccg cgttacataa cttacggtaa atggcccgcc tggctgaccg cccaacgacc
 361 cccgcccatt gacgtcaata atgacgtatg ttcccatagt aacgccaata gggactttcc
 421 attgacgtca atgggtggag tatttacggt aaactgccca cttggcagta catcaagtgt
 481 atcatatgcc aagtacgccc cctattgacg tcaatgacgg taaatggccc gcctggcatt
 541 atgcccagta catgacctta tgggactttc ctacttggca gtacatctac gtattagtca
 601 tcgctattac catggtgatg cggttttggc agtacatcaa tgggcgtgga tagcggtttg
 661 actcacgggg atttccaagt ctccacccca ttgacgtcaa tgggagtttg ttttggcacc
 721 aaaatcaacg ggactttcca aaatgtcgta acaactccgc cccattgacg caaatgggcg
 781 gtaggcgtgt acggtgggag gtctatataa gcagagctct ctggctaact agagaaccca
 841 ctgcttactg gcttatcgaa attaatacga ctcactatag ggagacccaa gctggctagt
 901 taagctatca acaagtttgt acaaaaaagc aggctccgcg gccgcccctt caccatgnnn
 961 nnnnnnaagg gtgggcgcgc cgacccagct ttcttgtaca aagtggttga tctagagggc
1021 ccgcggttcg aaggtaagcc tatccctaac cctctcctcg gtctcgattc tacgcgtacc
1081 ggttagtaat gagtttaaac gggggaggct aactgaaaca cggaaggaga caataccgga
1141 aggaacccgc gctatgacgg caataaaaag acagaataaa acgcacgggt gttgggtcgt
1201 ttgttcataa acgcggggtt cggtcccagg gctggcactc tgtcgatacc ccaccgagac
1261 cccattgggg ccaatacgcc cgcgtttctt ccttttcccc accccacccc ccaagttcgg
1321 gtgaaggccc agggctcgca gccaacgtcg gggcggcagg ccctgccata gcagatctgc
1381 gcagctgggg ctctaggggg tatccccacg cgccctgtag cggcgcatta agcgcggcgg
1441 gtgtggtggt tacgcgcagc gtgaccgcta cacttgccag cgccctagcg cccgctcctt
1501 tcgctttctt cccttccttt ctcgccacgt tcgccggctt tccccgtcaa gctctaaatc
1561 ggggcatccc tttagggttc cgatttagtg ctttacggca cctcgacccc aaaaaacttg
1621 attagggtga tggttcacgt agtgggccat cgccctgata gacggttttt cgccctttga
1681 cgttggagtc cacgttcttt aatagtggac tcttgttcca aactggaaca acactcaacc
1741 ctatctcggt ctattctttt gatttataag ggattttggg gatttcggcc tattggttaa
1801 aaaatgagct gatttaacaa aaatttaacg cgaattaatt ctgtggaatg tgtgtcagtt
1861 agggtgtgga aagtccccag gctccccagc aggcagaagt atgcaaagca tgcatctcaa
1921 ttagtcagca accaggtgtg gaaagtcccc aggctcccca gcaggcagaa gtatgcaaag
1981 catgcatctc aattagtcag caaccatagt cccgccccta actccgccca tcccgcccct
2041 aactccgccc agttccgccc attctccgcc ccatggctga ctaatttttt ttatttatgc
2101 agaggccgag gccgcctctg cctctgagct attccagaag tagtgaggag gcttttttgg
2161 aggcctaggc ttttgcaaaa agctcccggg agcttgtata tccattttcg gatctgatca
2221 gcacgtgttg acaattaatc atcggcatag tatatcggca tagtataata cgacaaggtg
2281 aggaactaaa ccatggccaa gcctttgtct caagaagaat ccaccctcat tgaaagagca
2341 acggctacaa tcaacagcat ccccatctct gaagactaca gcgtcgccag cgcagctctc
2401 tctagcgacg gccgcatctt cactggtgtc aatgtatatc attttactgg gggaccttgt
2461 gcagaactcg tggtgctggg cactgctgct gctgcggcag ctggcaacct gacttgtatc
2521 gtcgcgatcg gaaatgagaa caggggcatc ttgagcccct gcggacggtg ccgacaggtg
2581 cttctcgatc tgcatcctgg gatcaaagcc atagtgaagg acagtgatgg acagccgacg
2641 gcagttggga ttcgtgaatt gctgccctct ggttatgtgt gggagggcta agcacttcgt
2701 ggccgaggag caggactgac acgtgctacg agatttcgat tccaccgccg ccttctatga
2761 aaggttgggc ttcggaatcg ttttccggga cgccggctgg atgatcctcc agcgcgggga
```

FIG.25B 2821 tctcatgctg gagttcttcg cccaccccaa cttgtttatt gcagcttata atggttacaa
2881 ataaagcaat agcatcacaa atttcacaaa taaagcattt ttttcactgc attctagttg
2941 tggtttgtcc aaactcatca atgtatctta tcatgtctgt ataccgtcga cctctagcta
3001 gagcttggcg taatcatggt catagctgtt tcctgtgtga aattgttatc cgctcacaat
3061 tccacacaac atacgagccg gaagcataaa gtgtaaagcc tggggtgcct aatgagtgag
3121 ctaactcaca ttaattgcgt tgcgctcact gcccgctttc cagtcgggaa acctgtcgtg
3181 ccagctgcat taatgaatcg gccaacgcgc ggggagaggc ggtttgcgta ttgggcgctc
3241 ttccgcttcc tcgctcactg actcgctgcg ctcggtcgtt cggctgcggc gagcggtatc
3301 agctcactca aaggcggtaa tacggttatc cacagaatca ggggataacg caggaaagaa
3361 catgtgagca aaaggccagc aaaaggccag gaaccgtaaa aaggccgcgt tgctggcgtt
3421 tttccatagg ctccgccccc ctgacgagca tcacaaaaat cgacgctcaa gtcagaggtg
3481 gcgaaacccg acaggactat aaagatacca ggcgtttccc cctggaagct ccctcgtgcg
3541 ctctcctgtt ccgaccctgc cgcttaccgg atacctgtcc gcctttctcc cttcgggaag
3601 cgtggcgctt tctcatagct cacgctgtag gtatctcagt tcggtgtagg tcgttcgctc
3661 caagctgggc tgtgtgcacg aaccccccgt tcagcccgac cgctgcgcct tatccggtaa
3721 ctatcgtctt gagtccaacc cggtaagaca cgacttatcg ccactggcag cagccactgg
3781 taacaggatt agcagagcga ggtatgtagg cggtgctaca gagttcttga agtggtggcc
3841 taactacggc tacactagaa gaacagtatt tggtatctgc gctctgctga agccagttac
3901 cttcggaaaa agagttggta gctcttgatc cggcaaacaa accaccgctg gtagcggttt
3961 ttttgtttgc aagcagcaga ttacgcgcag aaaaaaagga tctcaagaag atcctttgat
4021 cttttctacg gggtctgacg ctcagtggaa cgaaaactca cgttaaggga ttttggtcat
4081 gagattatca aaaaggatct tcacctagat ccttttaaat taaaaatgaa gttttaaatc
4141 aatctaaagt atatatgagt aaacttggtc tgacagttac caatgcttaa tcagtgaggc
4201 acctatctca gcgatctgtc tatttcgttc atccatagtt gcctgactcc ccgtcgtgta
4261 gataactacg atacgggagg gcttaccatc tggccccagt gctgcaatga taccgcgaga
4321 cccacgctca ccggctccag atttatcagc aataaaccag ccagccggaa gggccgagcg
4381 cagaagtggt cctgcaactt tatccgcctc catccagtct attaattgtt gccgggaagc
4441 tagagtaagt agttcgccag ttaatagttt gcgcaacgtt gttgccattg ctacaggcat
4501 cgtggtgtca cgctcgtcgt ttggtatggc ttcattcagc tccggttccc aacgatcaag
4561 gcgagttaca tgatccccca tgttgtgcaa aaaagcggtt agctccttcg gtcctccgat
4621 cgttgtcaga agtaagttgg ccgcagtgtt atcactcatg gttatggcag cactgcataa
4681 ttctcttact gtcatgccat ccgtaagatg cttttctgtg actggtgagt actcaaccaa
4741 gtcattctga gaatagtgta tgcggcgacc gagttgctct tgcccggcgt caatacggga
4801 taataccgcg ccacatagca gaactttaaa agtgctcatc attggaaaac gttcttcggg
4861 gcgaaaactc tcaaggatct taccgctgtt gagatccagt tcgatgtaac ccactcgtgc
4921 acccaactga tcttcagcat cttttacttt caccagcgtt tctgggtgag caaaaacagg
4981 aaggcaaaat gccgcaaaaa agggaataag ggcgacacgg aaatgttgaa tactcatact
5041 cttccttttt caatattatt gaagcattta tcagggttat tgtctcatga gcggatacat
5101 atttgaatgt atttagaaaa ataaacaaat aggggttccg cgcacatttc cccgaaaagt
5161 gccacctgac gtc

FIG.25C

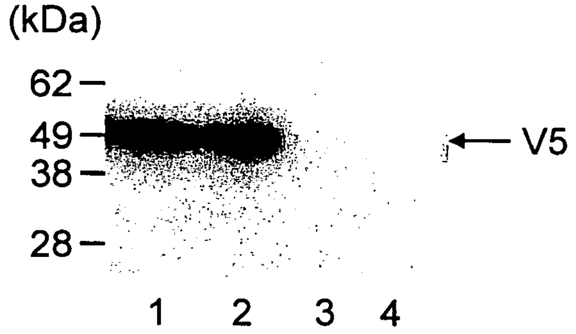

Lane 1: pCMVTetO/CAT/V5TKpA (without secondary PCR) + Tet
Lane 2: pCMVTetO/CAT/V5TKpA (with secondary PCR) + Tet
Lane 3: pCMVTetO/CAT/V5TKpA (with secondary PCR) - Tet
Lane 4: pCMVTetO/CAT/V5TKpA (without secondary PCR) - Tet

FIG.30A

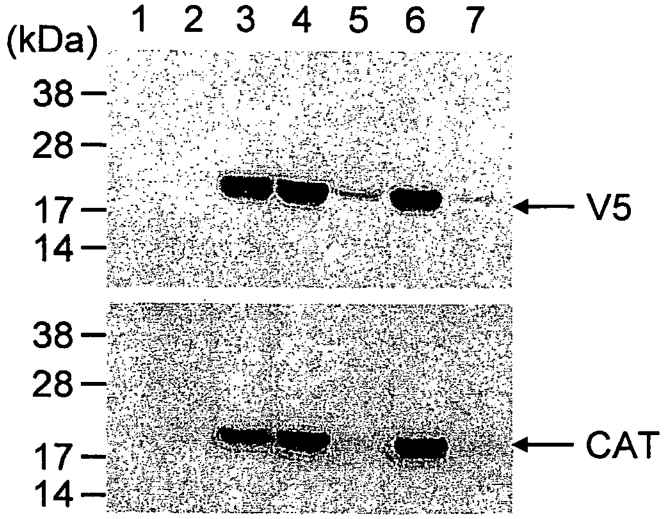

Lane 1: TRex-CHO Cells + Tet
Lane 2: without secondary PCR (with purified CAT ) - Tet
Lane 3: without secondary PCR (with purified CAT ) + Tet
Lane 4: without secondary PCR (with unpurified CAT ) + Tet
Lane 5: without secondary PCR (with unpurified CAT ) -Tet
Lane 6: with secondary PCR + Tet
Lane 7: with secondary PCR - Tet

FIG.30B

Lane 1: TRex-293 Cells + Tet
Lane 2: without secondary PCR (with purified CAT ) - Tet
Lane 3: without secondary PCR (with purified CAT ) + Tet
Lane 4: without secondary PCR (with unpurified CAT ) - Tet
Lane 5: without secondary PCR (with unpurified CAT ) +Tet
Lane 6: with secondary PCR - Tet
Lane 7: with secondary PCR + Tet Lane 1: negative control; lanes 2-11: test clones; M: 500 bp marker T7 promoter TOPO 5' pGACTCGTAATACGACTCACTATAGGGCCCTT 3'

3' AAAAAAAAAAAACTGAGCATTATGCTGAGTGATATCCCGGGAp 5'

T7-actin 1° PCR transcription actin 2° PCR transcription

T7-actin 1° PCR actin 2° PCR actin PCR + linker actin 1° PCR mock linking

METHODS AND COMPOSITIONS FOR SYNTHESIS OF NUCLEIC ACID MOLECULES USING MULTIPLE RECOGNITION SITES

CROSS-REFERENCE TO RELATED APPLICATIONS

The present application is a continuation of U.S. Application Ser. No. 10/454,793, filed Jun. 5, 2003 now abandoned, which claims the benefit of the filing date of U.S. provisional patent application No. 60/385,613, filed Jun. 5, 2002. U.S. Application Ser. No. 10/454,793 also is a continuation-in-part of U.S. Application Ser. No. 10/005,876, filed Dec. 7, 2001, which claims the benefit of the filing dates of U.S. provisional application Nos. 60/333,124, filed Nov. 27, 2001, and 60/318,902, filed Sep. 14, 2001, and also is a continuation-in-part of U.S. Application Ser. No. 10/014,128, filed Dec. 7, 2001 now U.S. Pat. No. 7,033,801, and of U.S. Application Ser. No. 09/732,914, filed Dec. 11, 2000. The present application also claims priority under 35 U.S.C. § 119(a) to International Application No. PCT/US03/18036, filed Jun. 5, 2003, which claims the benefit of U.S. provisional patent application No. 60/385,613, filed Jun. 5, 2002. The disclosures of all of the above-referenced applications are specifically incorporated herein by reference in their entireties.

U.S. patent application No. 09/935,280, filed Aug. 21, 2001, and U.S. provisional patent application Nos. 60/326,092, filed Sep. 28, 2001, 60/291,972, filed May 21, 2001, 60/254,510, filed Dec. 8, 2000, and 60/226,563, filed Aug. 21, 2000, also are specifically incorporated herein by reference.

BACKGROUND OF THE INVENTION

1. Field of the Invention

The present invention relates to the fields of biotechnology and molecular biology. In particular, the present invention relates to joining multiple nucleic acid molecules containing one or more recombination sites and/or one or more topoisomerase recognition sites. The present invention also relates to cloning such joined nucleic acid molecules using recombinational cloning methods such as those employing topoisomerase and/or recombination proteins. The invention also relates to joining multiple peptides, and combinations of peptides and nucleic acid molecules through the use of recombination sites and/or topoisomerase recognition sites. Other molecules and compounds or combinations of molecules and compounds may also be joined through recombination sites and/or topoisomerase recognition sites according to the invention. Such peptides, nucleic acids and other molecules and/or compounds (or combinations thereof) may also be joined or bound through recombination reactions and/or through topoisomerase joining reactions to one or a number of supports or structures in accordance with the invention.

Related Art

Site-Specific Recombinases

Site-specific recombinases are proteins that are present in many organisms (e.g. viruses and bacteria) and have been characterized as having both endonuclease and ligase properties. These recombinases (along with associated proteins in some cases) recognize specific sequences of bases in a nucleic acid molecule and exchange the nucleic acid segments flanking those sequences. The recombinases and associated proteins are collectively referred to as "recombination proteins" (see, e.g., Landy, A., *Current Opinion in Biotechnology* 3:699–707 (1993)).

Numerous recombination systems from various organisms have been described. See, e.g., Hoess, et al., *Nucleic Acids Research* 14(6):2287 (1986); Abremski, et al., *J. Biol. Chem.* 261(1):391 (1986); Campbell, J. Bacteriol. 174(23):7495 (1992); Qian, et al., *J. Biol. Chem.* 267(11):7794 (1992); Araki, et al., *J. Mol. Biol.* 225(1):25 (1992); Maeser and Kahnmann, *Mol. Gen. Genet.* 230:170–176) (1991); Esposito, et al., *Nucl. Acids Res.* 25(18):3605 (1997). Many of these belong to the integrase family of recombinases (Argos, et al., *EMBO J.* 5:433–440 (1986); Voziyanov, et al., *Nucl. Acids Res.* 27:930 (1999)). Perhaps the best studied of these are the Integrase/att system from bacteriophage (Landy, A. *Current Opinions in Genetics and Devel.* 3:699–707 (1993)), the Cre/loxP system from bacteriophage P1 (Hoess and Abremski (1990) In *Nucleic Acids and Molecular Biology*, vol. 4. Eds.: Eckstein and Lilley, Berlin-Heidelberg: Springer-Verlag; pp. 90–109), and the FLP/FRT system from the *Saccharomyces cerevisiae* 2 μ circle plasmid (Broach, et al., *Cell* 29:227–234 (1982)).

Recombination Sites

Whether the reactions discussed above are termed recombination, transposition or integration and are catalyzed by a recombinase, transposase or integrase, they share the key feature of specific recognition sequences, often termed "recombination sites," on the nucleic acid molecules participating in the reactions. These recombination sites are sections or segments of nucleic acid on the participating nucleic acid molecules that are recognized and bound by the recombination proteins during the initial stages of integration or recombination. For example, the recombination site for Cre recombinase is loxP which is a 34 base pair sequence comprised of two 13 base pair inverted repeats (serving as the recombinase binding sites) flanking an 8 base pair core sequence. See FIG. 1 of Sauer, B., *Curr. Opin. Biotech.* 5:521–527 (1994). Other examples of recognition sequences include the attB, attP, attL, and attR sequences which are recognized by the recombination protein (Int. attB is an approximately 25 base pair sequence containing two 9 base pair core-type Int binding sites and a 7 base pair overlap region, while attP is an approximately 240 base pair sequence containing core-type Int binding sites and arm-type Int binding sites as well as sites for auxiliary proteins integration host factor (IHF), FIS and excisionase (Xis). See Landy, *Curr. Opin. Biotech.* 3:699–707 (1993).

Conventional Nucleic Acid Cloning

The cloning of nucleic acid segments currently occurs as a daily routine in many research labs and as a prerequisite step in many genetic analyses. The purpose of these clonings is various, however, two general purposes can be considered: (1) the initial cloning of nucleic acid from large DNA or RNA segments (chromosomes, YACs, PCR fragments, mRNA, etc.), done in a relative handful of known vectors such as pUC, pGem, pBlueScript, and (2) the subcloning of these nucleic acid segments into specialized vectors for functional analysis. A great deal of time and effort is expended both in the transfer of nucleic acid segments from the initial cloning vectors to the more specialized vectors. This transfer is called subcloning.

The basic methods for cloning have been known for many years and have changed little during that time. A typical cloning protocol is as follows:

(1) digest the nucleic acid of interest with one or two restriction enzymes;

(2) gel purify the nucleic acid segment of interest when known;

(3) prepare the vector by cutting with appropriate restriction enzymes, treating with alkaline phosphatase, gel purify etc., as appropriate;

(4) ligate the nucleic acid segment to the vector, with appropriate controls to eliminate background of uncut and self-ligated vector;

(5) introduce the resulting vector into an *E. coli* host cell;

(6) pick selected colonies and grow small cultures overnight;

(7) make nucleic acid minipreps; and (8) analyze the isolated plasmid on agarose gels (often after diagnostic restriction enzyme digestions) or by PCR.

The specialized vectors used for subcloning nucleic acid segments are functionally diverse. These include but are not limited to: vectors for expressing nucleic acid molecules in various organisms; for regulating nucleic acid molecule expression; for providing tags to aid in protein purification or to allow tracking of proteins in cells; for modifying the cloned nucleic acid segment (e.g., generating deletions); for the synthesis of probes (e.g., riboprobes); for the preparation of templates for nucleic acid sequencing; for the identification of protein coding regions; for the fusion of various protein-coding regions; to provide large amounts of the nucleic acid of interest, etc. It is common that a particular investigation will involve subcloning the nucleic acid segment of interest into several different specialized vectors.

As known in the art, simple subclonings can be done in one day (e.g., the nucleic acid segment is not large and the restriction sites are compatible with those of the subcloning vector). However, many other subclonings can take several weeks, especially those involving unknown sequences, long fragments, toxic genes, unsuitable placement of restriction sites, high backgrounds, impure enzymes, etc. One of the most tedious and time consuming type of subcloning involves the sequential addition of several nucleic acid segments to a vector in order to construct a desired clone. One example of this type of cloning is in the construction of gene targeting vectors. Gene targeting vectors typically include two nucleic acid segments, each identical to a portion of the target gene, flanking a selectable marker. In order to construct such a vector, it may be necessary to clone each segment sequentially, i.e., first one gene fragment is inserted into the vector, then the selectable marker and then the second fragment of the target gene. This may require a number of digestion, purification, ligation and isolation steps for each fragment cloned. Subcloning nucleic acid fragments is thus often viewed as a chore to be done as few times as possible.

Several methods for facilitating the cloning of nucleic acid segments have been described, e.g., as in the following references.

Ferguson, J., et al., *Gene* 16:191 (1981), disclose a family of vectors for subcloning fragments of yeast nucleic acids. The vectors encode kanamycin resistance. Clones of longer yeast nucleic acid segments can be partially digested and ligated into the subcloning vectors. If the original cloning vector conveys resistance to ampicillin, no purification is necessary prior to transformation, since the selection will be for kanamycin.

Hashimoto-Gotoh, T., et al., *Gene* 41:125 (1986), disclose a subcloning vector with unique cloning sites within a streptomycin sensitivity gene; in a streptomycin-resistant host, only plasmids with inserts or deletions in the dominant sensitivity gene will survive streptomycin selection.

Notwithstanding the improvements provided by these methods, traditional subclonings using restriction and ligase enzymes are time consuming and relatively unreliable. Considerable labor is expended, and if two or more days later the desired subclone can not be found among the candidate plasmids, the entire process must then be repeated with alternative conditions attempted.

Recombinational Cloning

Cloning systems that utilize recombination at defined recombination sites have been previously described in U.S. Pat. Nos. 5,888,732, 6,143,557, 6,171,861, 6,270,969, and 6,277,608 which are specifically incorporated herein by reference. In brief, the Gateway™ Cloning System, described in this application and the applications referred to in the related applications section, utilizes vectors that contain at least one and preferably at least two different site-specific recombination sites based on the bacteriophage lambda system (e.g., att1 and att2) that are mutated from the wild type (att0) sites. Each mutated site has a unique specificity for its cognate partner att site of the same type (for example attB1 with attP1, or attL1 with attR1) and will not cross-react with recombination sites of the other mutant type or with the wild-type att0 site. Nucleic acid fragments flanked by recombination sites are cloned and subcloned using the Gateway™ system by replacing a selectable marker (for example, ccdB) flanked by att sites on the recipient plasmid molecule, sometimes termed the Destination Vector. Desired clones are then selected by transformation of a ccdB sensitive host strain and positive selection for a marker on the recipient molecule. Similar strategies for negative selection (e.g., use of toxic genes) can be used in other organisms such as thymidine kinase (TK) in mammals and insects.

Mutating specific residues in the core region of the att site can generate a large number of different att sites. As with the att1 and att2 sites utilized in Gateway™, each additional mutation potentially creates a novel att site with unique specificity that will recombine only with its cognate partner att site bearing the same mutation and will not cross-react with any other mutant or wild-type att site. Novel mutated att sites (e.g., attB 1–10, attP 1–10, attR 1–10 and attL 1–10) are described in commonly owned U.S. application Ser. No. 09/517,466, filed Mar. 2, 2000, which is specifically incorporated herein by reference. Other recombination sites having unique specificity (i.e., a first site will recombine with its corresponding site and will not recombine or not substantially recombine with a second site having a different specificity) may be used to practice the present invention. Examples of suitable recombination sites include, but are not limited to, loxP sites and derivatives such as loxP511 (see U.S. Pat. No. 5,851,808), frt sites and derivatives, dif sites and derivatives, psi sites and derivatives and cer sites and derivatives. The present invention provides novel methods using such recombination sites to join or link multiple nucleic acid molecules or segments and more specifically to clone such multiple segments into one or more vectors containing one or more recombination sites (such as any Gateway™ Vector including Destination Vectors).

SUMMARY OF THE INVENTION

The invention relates; in part, to nucleic acid molecules which comprise one or more (e.g., one, two, three, four, five, etc.) recombination sites (e.g., one or more att sites, one or more lox sites, etc.) and/or one or more (e.g., one, two, three, four, five, etc.) topoisomerase recognition sites (e.g., one or more recognition sites for a type IA topoisomerase, a type IB topoisomerase, a type II topoisomerase, etc.), as well as nucleic acid molecules which have undergone cleavage with a topoisomerase (e.g., a site specific topoisomerase). The invention also relates to nucleic acid molecules which comprise one or more recombination sites and/or one or more topoisomerases. The invention more specifically relates to combining or joining at least a first nucleic acid molecule which comprises at least a first nucleic acid molecule which comprises at least one recombination site and at least a second nucleic acid molecule which comprises at least one topoisomerase recognition site and/or at least one topoisomerase. Upon joining these at least first and second molecules, at least a third (or chimeric) molecule may be produced which comprises (1) at least one recombination site and (2) at least one topoisomerase recognition site and/or at least one topoisomerase. These nucleic acid molecules may be linear or closed circular (e.g., relaxed, supercoiled, etc.). Such recombination sites, topoisomerase recognition sites and topoisomerase can be located at any position on any number of nucleic acid molecules of the invention, including at or near the termini of the nucleic acid molecules and/or within the nucleic acid molecules. Moreover, any combination of the same or different recombination sites, topoisomerase recognition sites and/or topoisomerases may be used in accordance with the invention.

The invention includes, in part, nucleic acid molecules and compositions comprising nucleic acid molecules (e.g., reaction mixtures), wherein the nucleic acid molecules comprise (1) at least one (e.g., one, two, three, four, five, six, seven eight, etc.) recombination site and (2) at least one (e.g., one, two, three, four, five, six, seven eight, etc.) topoisomerase (e.g., a covalently linked topoisomerase) or at least one (e.g., one, two, three, four, five, six, seven eight, etc.) toposiomerase recognition site. In particular embodiments, the topoisomerases or toposiomerase recognition sites, as well as the recombination sites, of the nucleic acid molecules referred to above can be either internal or at or near one or both termini. For example, one or more (e.g., one, two, three, four, five, six, seven eight, etc.) of the at least one topoisomerase or the at least one topoisomerase recognition site, as well as one or more of the at least one recombination site, can be located at or near a 5' terminus, at or near a 3' terminus, at or near both 5' termini, at or near both 3' termini, at or near a 5' terminus and a 3' terminus, at or near a 5' terminus and both 3' termini, or at or near a 3' terminus and both 5' termini. The invention further provides methods for preparing and using nucleic acid molecules and compositions of the invention.

In specific aspects, the invention provides nucleic acid molecules (1) to which topoisomerases of various types (e.g., a type IA toposiomerase, a type IB toposiomerase, a type II topoisomerase, etc.) are attached (e.g., covalently bound) and/or (2) which contain two or more topoisomerase recognition sites which are recognized by various types of topoisomerases, as well as methods for preparing and using compositions comprising such nucleic acid molecules. In many embodiments, these nucleic acid molecules will further comprise one or more (e.g., one, two, three, four, five, six, seven eight, etc.) recombination site.

The invention further provides methods for joining two or more nucleic acid segments, wherein at least one of the nucleic acid segments contains at least one toposiomerase or topoisomerase recognition site and/or one or more recombination sites. Further, when nucleic acid segments used in methods of the invention contain more than one (e.g., two, three, four, five, six, seven eight, etc.) toposiomerase, either on the same or different nucleic acid segments, these toposiomerase may be of the same type or of different types. Similarly, when nucleic acid segments used in methods of the invention contain more than one toposiomerase recognition site, either on the same or different nucleic acid segments, these toposiomerase recognition sites may be recognized by topoisomerases of the same type or of different types. Additionally, when nucleic acid segments used in methods of the invention contain one or more recombination sites, these recombination sites may be able to recombine with one or more recombination sites on the same or different nucleic acid segments. Thus, the invention provides methods for joining nucleic acid segments using methods employing any one toposiomerase or topoisomerase recognition site. The invention provides further methods for joining nucleic acid segments using methods employing (1) any combination of topoisomerases or topoisomerase recognition sites and/or (2) any combination of recombination sites. The invention also provides nucleic acid molecules produced by the methods described above, as well as uses of these molecules and compositions comprising these molecules.

In general, the invention provides, in part, methods for joining any number of nucleic acid segments (e.g., two, three, four, five, six, seven, eight, nine, ten, etc.) which contain different functional or structural elements. The invention thus provides, in part, methods for bringing together any number of nucleic acid segments (e.g., two, three, four, five, six, seven, eight, nine, ten, etc.) which confer different properties upon a nucleic acid molecule product. In many instances, methods of the invention will result in the formation of nucleic acid molecules wherein there is operable interaction between properties and/or elements of individual nucleic acid segments which are joined (e.g., operable interaction/linkage between an expression control sequence and an open reading frame). Examples of (1) functional and structural elements and (2) properties which may be conferred upon product molecules include, but are not limited to, multiple cloning sites (e.g., nucleic acid regions which contain at least two restriction endonuclease cleavage sites), packaging signals (e.g., adenoviral packaging signals, alphaviral packaging signals, etc.), restriction endonuclease cleavage sites, open reading frames (e.g., intein coding sequence, affinity purification tag coding sequences, etc.), expression control sequences (e.g., promoters, operators, etc.), etc. Additional elements and properties which can be conferred by nucleic acid segments upon a product nucleic acid molecule are described elsewhere herein. The invention also provides nucleic acid molecules produced by the methods described above, as well as uses of these molecules and compositions comprising these molecules.

The invention further includes, in part, methods for joining two or more (e.g., 2, 3, 4, 5, 6, 7, 8, etc.) nucleic acid segments, wherein at least one (e.g., 1, 2, 3, 4, 5, 6, 7, 8, etc.) of the nucleic acid segments comprises one or more (e.g., 1, 2, 3, 4, 5, 6, 7, 8, etc.) topoisomerases and/or one or more topoisomerase recognition sites and at least one of the nucleic acid segments comprises one or more recombination sites. In particular embodiments, the invention provides methods for joining at least two (e.g., 2, 3, 4, 5, 6, 7, 8, etc.) nucleic acid molecules (e.g., methods employing recombination and/or mediated by one or more topoisomerases), wherein one of the nucleic acid segments comprises one or more topoisomerases or topoisomerase recognition sites but does not contain a recombination site and the other nucleic acid segments comprises one or more recombination site but does not contain a topoisomerase or topoisomerase recognition site. Thus, methods of the invention can be used to prepare joined or chimeric nucleic acid molecules by the joining of nucleic acid segments, wherein the product nucleic acid molecules comprise (1) one or more (e.g., 1, 2, 3, 4, 5, 6, 7, 8, etc.) topoisomerases and/or one or more (e.g., 1, 2, 3, 4, 5, 6, 7, 8, etc.) topoisomerase recognition sites and (2) one or more (e.g., 1, 2, 3, 4, 5, 6, 7, 8, etc.) recombination sites. The invention further provides nucleic acid molecules prepared by such methods, compositions comprising such nucleic acid molecules, and methods for using such nucleic acid molecules.

The invention also provides compositions comprising one or more nucleic acid segments and/or nucleic acid molecules described herein. Such compositions may comprise one or a number of other components selected from the group consisting of one or more other nucleic acid molecules (which may comprise recombination sites, topoisomerase recognition sites, topoisomerases, etc.), one or more nucleotides, one or more polymerases, one or more reverse transcriptases, one or more recombination proteins, one or more topoisomerases, one or more buffers and/or salts, one or more solid supports, one or more polyamines, one or more vectors, one or more restriction enzymes and the like. For example, compositions of the invention include, but are not limited to, mixtures (e.g., reaction mixtures) comprising a nucleic acid segment which comprises at least one topoisomerase recognition site and at least one topoisomerase which recognizes at least one of the at least one topoisomerase recognition sites of the nucleic acid segment. Compositions of the invention further include at least one nucleic acid segment comprising (1) at least one topoisomerase recognition site or at least one nucleic acid segment to which at least one topoisomerase is attached (e.g., covalently bound) and (2) one or more additional components. Examples of such additional components include, but are not limited to, topoisomerases; additional nucleic acid segments, which may or may not comprise one or more topoisomerases or topoisomerase recognition sites; buffers; salts; polyamines (e.g., spermine, spermidine, etc.); water; etc. Nucleic acid segments present in compositions of the invention may further comprise one or more recombination sites and/or one or more recombinase.

Nucleic acid molecules or segments produced by or used in conjunction with the methods of the invention, as well as nucleic acid molecules or segments thereof of the invention, include those molecules or segments specifically described herein as well as those molecules or segments that have substantial sequence identity to those molecules or segments specifically described herein. By a molecule or segment having "substantial sequence identity" to a given molecule or segment is meant that the molecule or segment is at least 65%, at least 70%, at least 75%, at least 80%, at least 85%, at least about 90%, 91%, 92%, 93%, 94%, 95%, 96%, 97%, 98% or 99%, identical to the given (or "reference") molecule or segment. By a nucleic acid molecule or segment having a nucleotide sequence at least, for example, 65% "identical" to a reference nucleic acid molecule or segment is intended that the nucleotide sequence of the nucleic acid molecule or segment is identical to that of the reference sequence except that the nucleic acid molecule or segment may include up to 35 point mutations per each 100 nucleotides of the reference nucleotide sequence. In other words, to obtain a polynucleotide having a nucleotide sequence at least 65% identical to a reference nucleotide sequence, up to 5% of the nucleotides in the reference sequence may be deleted or substituted with another nucleotide, or a number of nucleotides up to 35% of the total nucleotides in the reference sequence may be inserted into the reference sequence. These mutations of the reference sequence may occur at the 5' or 3' terminal positions (or both) of the reference nucleotide sequence, or anywhere between those terminal positions, interspersed either individually among nucleotides in the reference sequence or in one or more contiguous groups within the reference sequence.

As a practical matter, whether any particular nucleic acid molecule or segment is at least about 65%, 70%, 75%, 80%, 85%, 90%, 95%, 96%, 97%, 98% or 99% identical to a given reference molecule or segment can be determined conventionally using known computer programs such as FASTA (Heidelberg, Germany), BLAST (Washington, D.C.) or BESTFIT (Wisconsin Sequence Analysis Package, Version 8 for Unix, Genetics Computer Group, University Research Park, 575 Science Drive, Madison, Wis. 53711), which employs a local homology algorithm (Smith and Waterman, *Advances in Applied Mathematics* 2: 482–489 (1981)) to find the best segment of homology between two sequences. When using FASTA, BLAST, BESTFIT or any other sequence alignment program to determine whether a particular sequence is, for instance, 65% identical to a reference sequence according to the present invention, the parameters are set such that the percentage of identity is calculated over the full length of the reference nucleotide sequence and that gaps in homology of up to 35% of the total number of nucleotides in the reference sequence are allowed.

Often, nucleic acid molecules which have undergone cleavage with a topoisomerase (e.g., a site specific topoisomerase) will further have a topoisomerase molecule covalently bound to a phosphate group of the nucleic acid molecules. The invention further includes methods for preparing nucleic acid molecules described above and elsewhere herein, as well as recombinant methods for using such molecules.

In particular embodiments, nucleic acid molecules of the invention will be vectors. In additional embodiments, the invention includes host cells which contain nucleic acid molecules of the invention, as well as methods for making and using such host cells, for example, to produce expression products (e.g., proteins, polypeptides, antigens, antigenic determinants, epitopes, and the like, or fragments thereof).

In specific embodiments, nucleic acid molecules of the invention comprise two or more recombination sites with one or more (e.g., one, two, three, four, five, etc.) topoisomerase recognition site located between the recombination sites. In additional specific embodiments, nucleic acid molecules of the invention may comprise two or more topoisomerase recognition sites with one or more (e.g., one, two, three, four, five, etc.) recombination sites located between the two or more topoisomerase recognition sites.

In additional specific embodiments, nucleic acid molecules of the invention comprise two recombination sites with two topoisomerase recognition sites located between the two recombination sites. Thus, if such molecules are linearized by cleavage between the topoisomerase recognition sites, the topoisomerase recognition sites in the resulting linear molecule will be located distal (i.e., closer to the two ends of the linear molecule) to the recombination sites. The invention thus provides linear nucleic acid molecules which contain one or more recombination sites and one or more topoisomerase recognition sites. In particular embodiments, the one or more topoisomerase recognition sites are located distal to the one or more recombination sites. Examples of such molecules are set out below in Example 8.

The positioning of recombination sites and topoisomerase recognition sites of a first nucleic acid molecule can be such that topoisomerase mediated linkage of this molecule to a second nucleic acid molecule results in the second nucleic acid molecule being positioned between the two or more recombination sites. As an example, a linear first nucleic acid molecule may contain one recombination site at or near each end and may further comprise a topoisomerase recognition site located distal to one of the two recombination sites. In such a case, incubation of the linear first nucleic acid molecule with a topoisomerase can be designed to result in the covalent linkage of the topoisomerase to the first nucleic acid molecule, wherein the topoisomerase is positioned at or near the end of the first nucleic acid molecule and distal to the adjacent/nearest recombination site. This end of the first nucleic acid molecule may be blunt or may have either a 5' or 3' overhang. When incubated with a suitable second nucleic acid molecule (e.g., a molecule with sequence complementarity to at least one strand of the topoisomerase modified end of the first nucleic acid molecule), one or both strands of one end of the second nucleic acid molecule can be covalently joined to one or both strands of one end of the first nucleic acid molecule. Further, if a circular nucleic acid molecule is desired, then the second end of the second nucleic acid molecule can be joined to the second end of the first nucleic acid molecule by a topoisomerase, a ligase or other method. The result of the process described above is the generation of a nucleic acid molecule which contains a nucleic acid insert positioned between two recombination sites. Specific examples of related processes are set out below in Example 8. Methods for covalently linking nucleic acid molecules using topoisomerase are described in more detail elsewhere herein.

Once a nucleic acid insert has been positioned between one or more recombination sites, this insert, as well as adjacent nucleic acid, may be transferred to other nucleic acid molecules by recombinational cloning. The invention thus also provides methods for generating the nucleic acid molecules described above and elsewhere herein.

The distance, in terms of the number of nucleotides, between recombination sites and topoisomerase recognition sites which reside in a nucleic acid molecule of the invention will vary with the particular application for which the molecule is to be used, but can be zero, one, two, three, four, five, six, seven, eight, nine, ten, eleven, twelve, thirteen, fourteen, fifteen, sixteen, twenty, twenty-five, thirty, forty, fifty, sixty, eighty, one hundred, one hundred fifty, two hundred, three hundred, five hundred, seven hundred, nine hundred, one thousand, etc., or more, nucleotides. Further, the distance, in terms of the number of nucleotides, between recombination sites and topoisomerase recognition sites which reside in a nucleic acid molecule of the invention may fall within the following ranges: 0–10 nucleotides, 10–30 nucleotides, 20–50 nucleotides, 40–80 nucleotides, 70–100 nucleotides, 90–200 nucleotides, 120–400 nucleotides, 200–400 nucleotides, 200–1000 nucleotides, 200–2,000 nucleotides, etc.

The present invention also generally provides materials and methods for joining or combining two or more (e.g., three or more, four or more, five or more etc.) segments or molecules of nucleic acid of the invention. In one aspect, for such molecules to be combined, at least one of the segments or molecules may comprise at least one recombination site and at least one of the segments or molecules may comprise at least one topoisomerase recognition site. Such methods for joining multiple nucleic acid molecules according to the invention may be conducted in vivo or in vitro. Accordingly, the invention relates to methods to create novel or unique combinations of sequences and to the sequences created by such methods. The nucleic acid molecules created by the methods of the invention may be used for any purpose known to those skilled in the art. In one aspect, at least one (and often two or more) of the nucleic acid molecules or segments to be joined by the methods of the invention comprise at least one, and preferably at least two, recombination sites, although each molecule may comprise multiple recombination sites (e.g., three or more, four or more, five or more, etc.). In another aspect, the nucleic acid molecules may comprise at least one topoisomerase recognition site and/or at least one topoisomerase. In yet another aspect, the molecules may comprise (1) at least one recombination site and (2) at least one topoisomerase recognition site and/or at least one topoisomerase. Such recombination sites and topoisomerase recognition sites (which may be the same or different) may be located at various positions in each nucleic acid molecule or segment and the nucleic acid used in the invention may have various sizes and be in different forms including circular, supercoiled, linear, and the like. The nucleic acid molecules used in the invention may also comprise one or more vectors or one or more sequences allowing the molecule to function as a vector in a host cell (such as an origin of replication). In one aspect, nucleic acid molecules or segments for use in the invention are linear molecules having at least one recombination site at or near at least one termini of the molecule and preferably comprise at least one recombination site at or near both termini of the molecule. In another aspect, when multiple recombination sites are located on a nucleic acid molecule of interest, such sites do not substantially recombine or do not recombine with each other on that molecule. In this embodiment, the corresponding binding partner recombination sites preferably are located on one or more other nucleic acid molecules to be linked or joined by the methods of the invention. For instance, a first nucleic acid molecule used in the invention may comprise at least a first and second recombination site and a second nucleic acid molecule may comprise at least a third and fourth recombination site, wherein the first and second sites do not recombine with each other and the third and fourth sites do not recombine with each other, although the first and third and/or the second and fourth sites may recombine.

The nucleic acid molecules to be joined by the methods of the invention (e.g., the "starting molecules") may be used to produce one or more hybrid molecules containing all or a portion of the starting molecules (e.g., the "product nucleic acid molecules"). The starting molecules can be any nucleic acid molecule derived from any source or produced by any method. Such molecules may be derived from natural sources (such as cells, tissue, and organs from any animal or non-animal source) or may be non-natural (e.g., derivative nucleic acids) or synthetically derived. The segments or molecules for use in the invention may be produced by any means known to those skilled in the art including, but not limited to, amplification such as by PCR, isolation from natural sources, chemical synthesis, shearing or restriction digest of larger nucleic acid molecules (such as genomic or cDNA), transcription, reverse transcription and the like, and recombination sites and/or topoisomerase recognition sites and/or topoisomerases may be added to such molecules by any means known to those skilled in the art including ligation of adapters containing recombination sites and/or topoisomerase recognition sites and/or topoisomerases, amplification or nucleic acid synthesis using primers containing recombination sites and/or topoisomerase recognition sites and/or topoisomerases, insertion or integration of nucleic acid molecules (e.g., transponsons or integration sequences) containing recombination sites and/or topoisomerase recognition sites and/or topoisomerases, etc. In one aspect, the nucleic acid molecules used in the invention are populations of molecules such as nucleic acid libraries or cDNA libraries.

Once nucleic acid molecules are joined by recombination using methods such as those described herein, these nucleic acid molecules may then be joined to other nucleic acid molecules using topoisomerase-mediated joining methods and/or recombination-mediated joining methods also described herein.

Recombination sites for use in the invention may be any recognition sequence on a nucleic acid molecule which participates in a recombination reaction catalyzed or facilitated by recombination proteins. In those embodiments of the present invention utilizing more than one recombination site, such recombination sites may be the same or different and may recombine with each other or may not recombine or not substantially recombine with each other. Recombination sites contemplated by the invention also include mutants, derivatives or variants of wild-type or naturally occurring recombination sites. Preferred recombination site modifications include those that enhance recombination, such enhancement selected from the group consisting of substantially (i) favoring integrative recombination; (ii) favoring excisive recombination; (iii) relieving the requirement for host factors; (iv) increasing the efficiency of co-integrate or product formation; and (v) increasing the specificity of co-integrate or product formation. Preferred modifications include those that enhance recombination specificity, remove one or more stop codons, and/or avoid hair-pin formation. Desired modifications can also be made to the recombination sites to include desired amino acid changes to the transcription or translation product (e.g., mRNA or protein) when translation or transcription occurs across the modified recombination site. Recombination sites that may be used in accordance with the invention include att sites, frt sites, dif sites, psi sites, cer sites, and lox sites or mutants, derivatives and variants thereof (or combinations thereof). Recombination sites contemplated by the invention also include portions of such recombination sites.

Each starting nucleic acid molecule may comprise, in addition to one or more recombination sites and/or one or more topoisomerase recognition sites and/or one or more topoisomerases, a variety of sequences (or combinations thereof) including, but not limited to sequences suitable for use as primer sites (e.g., sequences which a primer such as a sequencing primer or amplification primer may hybridize to initiate nucleic acid synthesis, amplification or sequencing), transcription or translation signals or regulatory sequences such as promoters and/or operators, ribosomal binding sites, topoisomerase recognition sequences (or sites), Kozak sequences, and start codons, transcription and/or translation termination signals such as stop codons (which may be optimally suppressed by one or more suppressor tRNA molecules), tRNAs (e.g., suppressor tRNAs), origins of replication, selectable markers, and genes or portions of genes which may be used to create protein fusion (e.g., N-terminal or carboxy terminal) such as GST, GUS, GFP, open reading frame (orf) sequences, and any other sequence of interest which may be desired or used in various molecular biology techniques including sequences for use in homologous recombination (e.g., gene targeting).

The present invention also relates to methods of generating a covalently linked recombinant nucleic acid molecule by contacting two or more (e.g., 2, 3, 4, 5, 6, 7, 8, 9, 10, etc) nucleic acid molecules (which may be alternatively and equivalently referred to herein as “nucleotide sequences”), The nucleic acid molecules (e.g., ds or ss nucleic acid molecules) to be linked can be in any form, for example, single-stranded or double-stranded, linear, circular, or supercoiled, and are characterized, in part, in that each nucleic acid molecule to be linked is a substrate for a topoisomerase or can be modified to be such a substrate. The topoisomerase can be any topoisomerase that can covalently link at least one strand of a nucleic acid molecule to at least one strand of another nucleic acid molecule, preferably through a phosphodiester bond. The topoisomerase can be a site specific topoisomerase or can have relaxed specificity, and preferably forms a stable complex (e.g., a covalent complex) with one strand of the nucleic acid molecule at or near the site at which cleavage is effected.

A method of the invention generally is performed by contacting topoisomerase and the nucleic acid molecules (e.g., ds or ss nucleic acid molecules) to be joined under conditions such that both strands of an end of one nucleic acid molecule are ligated to both strands of an end of at least one (e.g., 1, 2, 3, 4, 5, 6, 7, 8, 9, 10, etc.) other nucleic acid molecule. As such, a method of the invention generates a covalently linked recombinant nucleic acid molecule (which may be either single-stranded or double-stranded), which does not contain a nick at the site or sites at which the substrate nucleic acid molecules are ligated. The present invention also provides recombinant nucleic acid molecules prepared by such a method. In certain such aspects of the invention, such recombinant nucleic acid molecules will further comprise one or more recombination sites.

A method of the invention can be performed using various combinations of components. For example, the method can be performed by contacting two or more substrate nucleic acid molecules (e.g., ss nucleic acid molecules or ds nucleic acid molecules) to be covalently linked and at least one topoisomerase, wherein the topoisomerase cleaves one or both strands of the nucleic acid molecules and forms a stable complex with a nucleotide at a terminus of the cleavage site. The topoisomerase-charged ends or topoisomerase-charged nucleic acid molecules are then contacted with each other such that each strand of the substrate nucleic acid molecules are linked, thereby generating one or more covalently linked recombinant nucleic molecules. Preferably, the topoisomerase mediates the formation of phosphodiester bond at each linkage site. The method also can be performed by contacting two or more topoisomerase-charged nucleic acid molecules, either alone, or in the presence of excess topoisomerase, or by contacting one or more topoisomerase-charged nucleic acid molecules (which may be ss or ds) with one or more nucleic acid molecules (which may also be ss or ds) that contain a topoisomerase cleavage site, and a topoisomerase. The present invention also provides recombinant nucleic acid molecules prepared by such a method. In certain such aspects of the invention, such recombinant nucleic acid molecules will further comprise one or more recombination sites. In various embodiments, the topoisomerase can have a relatively relaxed specificity such that it can bind to and cleave a variety of different nucleotide sequences, or the topoisomerase can be a site specific topoisomerase, which binds to and cleaves a specific nucleotide sequence. The topoisomerase also can be a type I topoisomerase, which cleaves one strand of a ds nucleic acid molecule, or can be a type II topoisomerase, which cleaves both strands of a ds nucleic acid molecule. Where the topoisomerase is a type II topoisomerase, cleavage is effected such that a linear ds nucleic acid molecule is produced, and is topoisomerase-charged at one or both ends. In certain such aspects, the strand of the ds nucleic acid molecule that is complementary to the strand containing the bound topoisomerase will form an overhanging sequence.

An advantage of performing a method of the invention is that the ligation reaction performed by a topoisomerase occurs very quickly and over a wide range of temperatures. An additional advantage is that recombinant nucleic acid molecules generated according to the methods of the invention do not contain nicks at the sites where two nucleic acid molecules are joined together. As such, the covalently linked recombinant nucleic acid molecules can be used directly in a subsequent procedure, for example, as a substrate for an amplification reaction such as a polymerase chain reaction (PCR).

By way of example, a method of the invention can be performed by contacting 1) a first nucleic acid molecule (which may be ss or ds) having a first end and a second end, wherein, at the first end or second end or both, the first nucleic acid molecule has a topoisomerase recognition site at or near the 3' terminus; 2) at least a second nucleic acid molecule (which may also be ss or ds) having a first end and a second end, wherein, at the first end or second end or both, the at least second double stranded nucleotide sequence has a topoisomerase recognition site at or near the 3' terminus; and 3) a site specific topoisomerase, under conditions such that all components are in contact and the topoisomerase can effect its activity. The strand complementary to that containing the topoisomerase recognition sequence may comprise a 5' hydroxyl group and, upon cleavage by the topoisomerase, may further comprise a 5' overhanging sequence.

A method of the invention also can be performed by contacting 1) a nucleic acid molecule (which may be ss or ds) having a first end and a second end, wherein each of the first end and second end contains a topoisomerase recognition site at or near the 3' terminus, and 2) a site specific topoisomerase, under conditions such that the components are in contact and the topoisomerase can effect its activity. For example, the topoisomerase can be a type IB topoisomerase such as a *Vaccinia* topoisomerase or an *S. cerevisiae* topoisomerase. Such a method provides a means to prepare a covalently closed circular or supercoiled ds nucleic acid molecule.

A method of the invention also can be performed by contacting 1) a first nucleic acid molecule (which may be ss or ds) having a first end and a second end, wherein the first nucleic acid molecule has a topoisomerase recognition site at or near the 5' terminus of the first end or the second end or both; 2) at least a second nucleic acid molecule (which may also be ss or ds) having a first end and a second end, wherein the at least second double stranded nucleotide sequence has a topoisomerase recognition site at or near the 5' terminus of the first end or the second end or both; and 3) at least one site specific topoisomerase, under conditions such that all components are in contact and the at least one topoisomerase can effect its activity. For example, the topoisomerase can be a type IA topoisomerase such as an *E. coli* topoisomerase I or topoisomerase III, or eukaryotic topoisomerase III. Upon cleavage of a nucleic acid molecule, the topoisomerase preferably is stably bound to the 5' terminus. The 3' terminus of the end containing the topoisomerase recognition site, or bound topoisomerase, can comprise a 3' hydroxyl group, or can be modified to comprise a 3' hydroxyl group. Upon cleavage by the topoisomerase, the cleaved nucleic acid molecule may comprise a 3' overhanging sequence.

The methods as exemplified herein can be performed using two or more site specific topoisomerases, wherein the first, second or other nucleic acid substrates correspondingly have, at or near a 3' terminus or 5' terminus of an end, a topoisomerase recognition site for one of the two or more topoisomerases. The use of two or more topoisomerases, and corresponding topoisomerase recognition sites, can facilitate the joining of the nucleic acid molecules (which may be ss or ds) in a predetermined order, orientation, or combination thereof. Thus, it will be recognized that, where a method of the invention is exemplified using a topoisomerase, the method similarly can be performed using two or more topoisomerases. In some cases, reference is made to the use of at least one topoisomerase, although, unless indicated otherwise, the methods can be performed using one, two, three or more topoisomerases, provided the substrate nucleic acid molecules contain the appropriate topoisomerase recognition sites. Similar considerations are relevant to topoisomerase-charged nucleic acid substrates, in that the topoisomerases can be the same or different.

In another embodiment, a method of the invention can be performed by contacting 1) a first nucleic acid molecule (which may be ss or ds) having a first end and a second end, wherein the first nucleic acid molecule has a topoisomerase recognition site at or near the 3' terminus and a topoisomerase recognition site at or near the 5' terminus of the first end or of the second end or of both ends; 2) at least a second nucleic acid molecule (which may also be ss or ds) having a first end and a second end; and 3) at least two (e.g., 2, 3, 4, 5, 6, 7, 8, 9, 10, etc.) site specific topoisomerases, under conditions such that all components are in contact and each of the topoisomerases can effect its activity. Upon cleavage of the termini of the substrate first nucleic acid molecule by the topoisomerases, the 5' terminus or the 3' terminus of one or both ends can comprise an overhanging sequence, or can be blunt ended, or one end can contain an overhang and the second end can be blunt ended. Where present, an overhanging sequence generally has sufficient complementarity to an overhanging sequence of the second (or other) nucleic acid molecule to allow for specific hybridization of the two molecules to each other.

Once nucleic acid molecules are joined by topoisomerase mediated joining methods of the invention, the resulting nucleic acid molcules may then be used in recombination reactions, such as those described elsewhere herein.

The number of different topoisomerases useful in such an embodiment will depend, in part, on whether the first nucleic acid molecule contains topoisomerase recognition sites at only the first end or the second end, or contains topoisomerase recognition sites at both ends, and further, where the nucleic acid molecule contains topoisomerase recognition sites on both ends, whether at least the 3' recognition sites or the 5' recognition sites are different. In addition, the method can be performed such that one or more of the at least second nucleic acid molecule also can contain a topoisomerase recognition site at or near the 3' terminus and/or a topoisomerase recognition site at or near the 5' terminus of the first end or of the second end or of both ends, wherein the topoisomerase recognition sites at or near the 3' terminus or the 5' terminus or both of the other nucleic acid molecule can the same as or different from the topoisomerase recognition sites in the first nucleic acid molecule. As such, the number of different topoisomerase further will depend on the number of different substrate nucleic acid molecules being linked according to a method of the invention.

An advantage of performing a method of the invention using a site specific topoisomerase is that the first nucleic acid molecule, the second nucleic acid molecule, and one or more additional nucleic acid molecules (which may be ss or ds) can be covalently linked in a predetermined directional orientation. An additional advantage is that a functional product can be selected in vitro by performing an amplification reaction using primers specific for the termini of the desired covalently linked recombinant nucleic acid molecule. As such, a covalently linked recombinant nucleic acid molecule (which may be ss or_ds) generated according to a method of the invention can be used directly in further procedures, for example, for transfecting a cell, or as a template for performing amplification (e.g., PCR), a recombination reaction (e.g., a recombination reaction such as those described herein), an in vitro transcription reaction, or a coupled transcription/translation reaction. Accordingly, the covalently linked recombinant nucleic acid molecule is useful, without further manipulation, for various purposes.

In an aspect of the invention, the first nucleic acid molecules, as well as other nucleic acids used in methods of the invention, may be derived from at least a first population of nucleic acid molecules, for example, from a cDNA library or a combinatorial library such as a combinatorial library of synthetic oligonucleotides, and the second nucleic acid molecules, as well as other nucleic acids used in methods of the invention, may be derived from at least a second population of source nucleic acid molecules. According to such a method, linking of first nucleic acid molecules with second nucleic acid molecules provides a means to generate combinatorial populations of covalently linked recombinant nucleic acid molecules (which may be ss or ds). In accordance with such a method, one or more target nucleic acid molecules also can be linked with the recombinant nucleic acid molecules of the population to produce additional populations. Such populations of combinatorial molecules can be further manipulated or analyzed, for example, by protein expression and screening for fusion proteins having desirable characteristics.

In one embodiment, a method of the invention is performed such that the first nucleic acid molecule (which may be ss or ds), as well as other nucleic acids used in methods of the invention, comprises an open reading flame, for example, an isolated cDNA or coding sequence of a gene, and a second nucleic acid molecule (which may be ss or ds) comprises a regulatory element such as a promoter, which can be operably covalently linked to the 5' end of the coding sequence such that the coding sequence can be transcribed therefrom. A second nucleic acid molecule, as well as other nucleic acids used in methods of the invention, also can comprise two or more regulatory elements, for example, a promoter (e.g., a GAL4 promoter), an operator (e.g., a tet operator, a galactose operon operator, a lac operon operator, and the like), an internal ribosome entry site and an ATG initiator methionine codon, in operative linkage with each other, which can be operably covalently linked to the 5' end of a first nucleic acid molecule comprising a coding sequence according to a method of the invention. Such a method can further include contacting a third nucleic acid molecule (which may be ss or ds) comprising, for example, a polyadenylation signal, which can be operably covalently linked to the 3' end of the coding sequence. Such a method can be useful for generating an expressible nucleic acid molecule, which can be transcribed, translated, or both as a functional unit. In addition, or alternatively, a nucleic acid molecule encoding a detectable marker, for example, an epitope tag, can be operably linked to a first or second (or other) nucleic acid molecule(s) according to a method of the invention. The generation of a recombinant nucleic acid molecule (which may be ss or ds) having a desired directional orientation of the nucleotide sequences in such a construct may be facilitated, for example, by including complementary 5' overhanging sequences at the termini of the nucleic acid molecules to be covalently linked together by the topoisomerase.

In another embodiment, a method of the invention is performed such that at least the first nucleic acid molecule or the at least second nucleic acid molecule, as well as other nucleic acids used in methods of the invention, is one of a plurality of nucleotide sequences, for example, a cDNA library, a combinatorial library of nucleotide sequences, or a variegated population of nucleotide sequences. In another embodiment, a method of the invention includes further contacting a generated covalently linked ds recombinant nucleic acid molecule (e.g., a recombinant nucleic acid molecule which is covalently linked in one or both strands) with a PCR primer pair, and amplifying all or a portion of the covalently linked recombinant nucleic acid molecule. In addition to generating a large amount of product, the amplification reaction can be selective for constructs comprising a desired covalently linked ds recombinant nucleic acid molecule, particularly where the nucleic acid molecules to be covalently linked comprise complementary overhanging sequences. As such, a method of the invention provides an in vitro selection means that is suitable for high throughput analysis.

A method of the invention is also exemplified by contacting 1) a first nucleic acid molecule (which may be ss or ds) having a first end and a second end, wherein, at the first end or second end or both, the first nucleic acid molecule has a topoisomerase covalently bound to the 3' terminus ("topoisomerase-charged"); and 2) at least a second topoisomerase-charged nucleic acid molecule (which may be ss or ds). Preferably, the topoisomerase-charged nucleic acid molecules contain a 5' hydroxyl group at the ends containing the bound topoisomerase, although 5' hydroxy groups also can be generated using a phosphatase. The methods of the invention can be performed using only a first nucleic acid molecule and a second nucleic acid molecule, or can include a third, fourth or more nucleic acid molecules (which may be ss or ds) as desired, wherein each nucleotide sequence is as defined. A first or second (or other) nucleic acid molecule independently can have a topoisomerase covalently bound to a 3' terminus of one end or at both ends of the nucleotide sequence, and, unless indicated otherwise, the first and second (or other) nucleic acid molecules can be the same or can be different. In certain such aspects, at least one of the nucleic acid molecules used in the methods described herein will comprise at least one recombination site. Further, nucleic acid molecules generated by methods described above may be used in recombination reactions, such as those described elsewhere herein.

Methods of the invention are further exemplified by contacting 1) a first nucleic acid molecule (which may be ss or ds) having a first end and a second end, wherein, at the first end or second end or both, the first nucleic acid molecule has a topoisomerase covalently bound to a 5' terminus (i.e., a topoisomerase-charged 5' terminus); and 2) at least a second topoisomerase-charged nucleic acid molecule (which may be ss or ds) comprising at least one topoisomerase-charged 5' terminus. The topoisomerase-charged nucleic acid molecules can contain a 3' hydroxyl group at the ends containing the bound topoisomerase, or a 3' hydroxyl group can be generated using a phosphatase. As disclosed herein, such a method can be performed using only a first nucleic acid molecule and a second nucleic acid molecule, or can include a third, fourth or more nucleic acid molecules (which may be ss or ds) as desired, wherein each nucleotide sequence is as defined, including comprising at least one topoisomerase-charged 5' terminus. A first or second (or other) nucleic acid molecule independently can have a topoisomerase covalently bound to a 5' terminus of one end or at both ends of the nucleic acid molecule, and, unless indicated otherwise, the first and second (or other) nucleic acid molecules can be the same or can be different. In certain such aspects, at least one of the nucleic acid molecules used in the methods described herein will comprise at least one recombination site. Further, nucleic acid molecules generated by methods described above and elsewhere herein may also be used in recombination reactions, such as those described elsewhere herein.

A method of the invention is additionally exemplified by contacting 1) a first nucleic acid molecule having a first end and a second end, wherein, at the first end or second end or both, the first nucleic acid molecule has a first topoisomerase covalently bound to the 5' terminus and a second topoisomerase covalently bound to the 3' terminus of the first end or the second end or both (i.e., one or both ends contain a topoisomerase charged 5' terminus and a topoisomerase-charged 3' terminus); and 2) at least a second nucleic acid molecule, which, preferably, has or can be made to have hydroxyl groups at the 5' terminus and 3' terminus of an end to be covalently linked to an end of the first nucleic acid molecule containing the topoisomerases. Th method also can be performed wherein either the 5' terminus or 3' terminus of the end containing a topoisomerase-charged 3' terminus or topoisomerase-charged 5' terminus, respectively, contains a topoisomerase recognition site, wherein the method further includes contacting the components with a topoisomerase that can effect its activity with respect to the topoisomerase recognition site. In certain such aspects, at least one of the nucleic acid molecules used in the methods described herein will comprise at least one recombination site. Further, nucleic acid molecules generated by methods described above and elsewhere herein may also be used in recombination reactions, such as those described elsewhere herein.

Such a method of the invention can be performed using only a first nucleic acid molecule and a second nucleic acid molecule, or can include a third, fourth or more nucleic acid molecule as desired, wherein the nucleic acid molecules are as defined for the first nucleic acid molecule, the second nucleic acid molecule, or a combination thereof. A first or second (or other) nucleic acid molecule independently can, but need not, have one or more topoisomerases covalently bound to a 5' terminus, 3' terminus, or both 5' and 3' termini of the second end (i.e., the undefined end). Further, one or more of these nucleic acid molecules may additionally comprise one or more recombination sites. Unless indicated otherwise, the first and second (or other) nucleic acid molecules can be the same or can be different.

The present invention further relates to a method of generating a covalently linked ds recombinant nucleic acid molecule by 1) amplifying a portion of a first nucleic acid molecule using a PCR primer pair, wherein at least one primer of the primer pair encodes a complement of a topoisomerase recognition site, and, optionally, of one or more recombination sites, thereby producing an amplified first nucleic acid molecule having a first end and a second end, wherein the first end or second end or both has a topoisomerase e.g., double-stranded ("ds") or single-stranded ("ss") nucleic acid molecules, with at least one (e.g., 1, 2, 3, 4, 5, 6, 7, 8, 9, 10, etc.) topoisomerase. As will be understood by the ordinarily skilled artisan, any and all of the nucleic acid molecules or nucleotide sequences referred to herein, for example those used in or generated by the methods, compositions and kits disclosed herein, may be ss or ds nucleic acid molecules or nucleotide sequences, whether or not the molecules or sequences are specifically referred to herein as being ss and/or ds.

In one such aspect, the methods of the invention allow joining of such nucleic acid sequences in a desired orientation and/or order, which, if desired, can be further manipulated or used in a variety of assays or procedures, including, for example, for a transcription or transfection procedure, which can be performed in vitro or in vivo, a translation reaction or other protein expression procedure, recombination reactions, and the like. In another aspect, three or more, four or more, five or more, etc., or a population or library of the same or different nucleic acid sequences can be linked according to a method of the invention. In still another aspect, the methods of the invention can be used to link each end of a single nucleic acid molecule to form a covalently closed circular or supercoiled molecule.

The nucleic acid sequences to be linked can be derived from any source, and can be naturally occurring and chemically or recombinantly synthesized nucleic acid molecules such as cDNA, genomic DNA, vectors, oligonucleotides, and the like. Furthermore, the nucleic acid sequences can, but need not, contain one or more functional sequences such as gene regulatory elements, origins of replication, splice sites, polyadenylation sites, open reading frames, which can encode, for example, tag sequences, detectable or selectable markers, cell localization domains, or other peptide or polypeptide, and the like. As such, the invention allows any number of nucleic acid sequences, which can be the same or different, to be linked, including, if desired, in a predetermined order or orientation or both. recognition site at or near the 3' terminus; and 2) contacting a) the amplified first nucleic acid molecule; b) at least a second nucleic acid molecule having a first end and a second end, wherein the first end or second end or both has a topoisomerase recognition-site, or cleavage product thereof, at or near the 3' terminus and has, or can be made to have, a hydroxyl group at the 5' terminus of the same end; and c) a site specific topoisomerase, under conditions such that the topoisomerase can cleave the end of the amplified first nucleic acid molecule having a topoisomerase recognition site and the end (or ends) of the at least second nucleic acid molecule having a topoisomerase recognition site, and can effect its ligating activity. The PCR primer that encodes a complement of topoisomerase recognition site can have a hydroxyl group at its 5' terminus, or the amplified first nucleic acid molecule generated using the primer can be contacted with a phosphatase to generate a hydroxyl group at its 5' terminus. The PCR primer encoding the complement of a topoisomerase recognition site also can comprise a nucleotide sequence at its 5' terminus such that, upon cleavage by a site specific topoisomerase of a first nucleic acid molecule amplified using the primer, the nucleic acid molecule contains a 5' overhanging sequence, which is complementary to a 5' overhanging sequence of a second (or other) nucleic acid molecule to which the first nucleic acid molecule is to be covalently linked according to a method of the invention. In certain such aspects, at least one of the nucleic acid molecules used in the methods described herein will comprise at least one recombination site. Further, nucleic acid molecules generated by methods described above and elsewhere herein may also be used in recombination reactions, such as those described elsewhere herein.

The present invention also relates to a method of generating a covalently linked ds recombinant nucleic acid molecule by 1) amplifying a portion of a first nucleic acid molecule using a PCR primer pair, wherein at least one primer of the primer pair encodes a topoisomerase recognition site, and, optionally, one or more recombination sites, thereby producing an amplified first nucleic acid molecule having a first end and a second end, wherein the first end or second end or both has a topoisomerase recognition site at or near the 5' terminus; and 2) contacting a) the amplified first nucleic acid molecule; b) at least a second nucleic acid molecule having a first end and a second end, wherein the first end or second end or both has a topoisomerase recognition site at or near the 5' terminus and has, or can be made to have, a hydroxyl group at the 3' terminus of the same end; and c) at least one site specific topoisomerase, under conditions such that the at least one topoisomerase can cleave the end of the amplified first nucleic acid molecule having a topoisomerase recognition site and the end (or ends) of the at least second nucleic acid molecule having a topoisomerase recognition site, and can effect its ligating activity. The amplified first nucleic acid molecule generally has a hydroxyl group at the 3' terminus of the end containing the topoisomerase recognition site, or can be modified to contain such a 3' hydroxyl group. The PCR primer encoding the topoisomerase recognition site can further comprise a nucleotide sequence at its 5' terminus, i.e., 5' to the topoisomerase recognition site, such that, upon cleavage of the amplified first nucleic acid molecule by a site specific topoisomerase, the nucleic acid molecule contains a 3' overhanging sequence, which is complementary to a 3' overhanging sequence of a second (or other) nucleic acid molecule to which the first nucleic acid molecule is to be covalently linked according to a method of the invention. In certain such aspects, at least one of the nucleic acid molecules used in the methods described herein will comprise at least one recombination site. Further, nucleic acid molecules generated by methods described above and elsewhere herein may also be used in recombination reactions, such as those described elsewhere herein.

The present invention further relates to a method of generating a covalently linked ds recombinant nucleic acid molecule by 1) amplifying a portion of a first nucleic acid molecule using a PCR primer pair, wherein at least one primer of the primer pair includes a topoisomerase recognition site, a nucleotide sequence complementary to a topoisomerase recognition site, such that PCR introduces a functional recognition site in the opposite strand (see primer sequences in FIG. 9D), and, optionally, a recombination site, thereby producing an amplified first nucleic acid molecule having a first end and a second end, wherein the amplified first nucleic acid molecule has a topoisomerase recognition site at or near the 5' terminus and a topoisomerase recognition site at or near the 3' terminus of the first end or of the second end or of both ends; and 2) contacting a) the amplified first nucleic acid molecule; b) at least a second nucleic acid molecule having a first end and a second end, wherein the second nucleic acid molecule has, or can be made to have, a 5' hydroxyl group and a 3' hydroxyl group at the first end or at second end or at both ends; and c) at least two site specific topoisomerases, under conditions such that i) at least one topoisomerase can cleave the topoisomerase recognition site at or near the 5' terminus of the end of the amplified first nucleic acid molecule, and can effect its ligating activity, and ii) at least one topoisomerase can cleave the topoisomerase recognition site at or near the 3' terminus of the end of the amplified first nucleic acid molecule, and can effect its ligating activity. Accordingly, the present invention provides a nucleic acid molecule containing, at one or both ends, a topoisomerase recognition site at or near the 5' terminus and a topoisomerase recognition site at or near the 3' terminus. In addition, the invention provides such a nucleic acid molecule, which is topoisomerase charged at the 5' terminus or the 3' terminus or both. In certain such aspects, at least one of the nucleic acid molecules used in the methods described herein will comprise at least one recombination site. Further, nucleic acid molecules generated by methods described above and elsewhere herein may also be used in recombination reactions, such as those described elsewhere herein.

The present invention further relates to an oligonucleotide containing at least one recognition site of one or more type IA site specific topoisomerases, at least one nucleotide sequence complementary to a recognition site of one or more type IB site specific topoisomerases and, optionally, at least one recombination site. Such an oligonucleotide is useful, for example, as a primer for a primer extension reaction or as one of a primer pair for performing an amplification reaction such as PCR. Such an oligonucleotide, referred to herein as an oligonucleotide primer, can be one of a primer pair, which can be useful for generating a ds nucleic acid amplification product that contains, at one end, a type IA topoisomerase recognition site at or near the 5' terminus and, at the same end, a type IB topoisomerase recognition site at or near the 3' terminus. The oligonucleotide primer can further contain a nucleotide sequence encoding (or complementary to) any other nucleotide sequence or peptide of interest, for example, a restriction endonuclease recognition site, a peptide tag, and, if desired, one or more additional type IA or type IB topoisomerase recognition sites, thereby allowing selection of one or more convenient or readily available topoisomerases for practicing a method of the invention. The oligonucleotide primer can further comprise a nucleotide sequence at its 5' terminus, i.e., 5' to the type IA topoisomerase recognition site or to the nucleotide sequence complementary to the type IB topoisomerase recognition site, such that, upon cleavage of the amplified first nucleic acid molecule by a site specific topoisomerase, the nucleic acid molecule contains a 3' or 5' overhanging sequence, respectively, which is complementary to a 3' or 5' overhanging sequence, respectively, of a second (or other) nucleic acid molecule to which the first nucleic acid molecule is to be covalently linked according to a method of the invention, or the oligonucleotide primer can be designed such that, upon cleavage of an amplified nucleic acid molecule generated therefrom, a blunt end topoisomerase charged nucleic acid molecule is generated.

The invention further relates to an oligonucleotide which contains at least one topoisomerase recognition site, or a nucleotide sequence complementary thereto, and at least one recombination site. Such an oligonucleotide may be used as described above, for example as one member of a primer pair.

Oligonucleotides of the invention will often be between 15–20, 15–30, 15–50, 20–30, 20–50, 30–40, 30–50, 30–80, 30–100, 40–50, 40–70, 40–80, 40–100, 50–60, 50–80, 50–100, 15–80, 15–100, or 20–100 (or the like) nucleotides in length.

The present invention also provides a primer pair, which includes at least-one oligonucleotide primer as defined above, wherein one of the primers is useful as a forward primer and the primer is useful as a reverse primer in an amplification reaction. The second primer in such a primer pair can, but need not, include a type IA topoisomerase recognition site, a nucleotide sequence complementary to a type IB topoisomerase recognition site, or both, and can include any other nucleotide sequence of interest and/or at least one recombination site. In one embodiment, the primer pair includes two oligonucleotide primers of the invention, wherein one oligonucleotide primer is useful as a forward primer and the second oligonucleotide primer is useful as a reverse primer, such a primer pair being useful, for example, for generating a nucleic acid molecule amplification product having topoisomerase recognition sites at both termini of both ends and/or one or more recombination sites, wherein the type IA or type IB or both topoisomerase recognition sites at the termini are the same or different.

Accordingly, the present invention further relates to a nucleic acid molecule, which has a first end and a second end, and which contains a type IA topoisomerase recognition site at or near the 5' terminus and a type IB topoisomerase recognition site at or near the 3' terminus of the first end or of the second end or of both ends. In addition, the present invention provides a nucleic acid molecule as defined above, except wherein the nucleic acid molecule is a topoisomerase charged molecule, comprising a stably bound type IA topoisomerase or a type IB topoisomerase or both, at one or both ends, as desired. These nucleic acid molcules may further comprise one or more recombination sites.

In one embodiment, the first nucleic acid molecule, as well as other nucleic acids used in methods of the invention, comprises an expressible nucleotide sequence which encodes molecules such as a polypeptide (which may be, e.g., a polypeptide with an intein), an antisense nucleotide sequence, interference RNA (i.e., "RNAi") molecule(s), a ribozyme, a transfer RNA (i.e., a tRNA, including but not limited to a supressor tRNA), a triplexing nucleotide sequence, and the like, and the second (or other) nucleic acid molecule comprises a transcription regulatory element such as a promoter (e.g., a GAL4 operator), an operator (e.g., a tet operator, a galactose operon operator, a lac operon operator, and the like), an enhancer, a silencer, a translation start site, or a polyadenylation signal, or encodes a translation regulatory element such as an initiator methionine, a STOP codon, a cell compartmentalization domain, a homology domain, or the like, or a combination thereof in operative linkage. A second (or other) nucleic acid molecule, as well as other nucleic acids used in methods of the invention, which can be an amplified second (or other) nucleic acid molecule prepared as for the amplified first nucleic acid molecule, also can comprise one or more multiple cloning sites ("MCS"), a detectable label, for example, an enzyme, a substrate for an enzyme, a fluorescent compound, a luminescent compound, a chemiluminescent compound, a radionuclide, a paramagnetic compound, and biotin; or can include a tag, which can be an oligonucleotide tag or can be a peptide tag, for example, a polyhistidine tag, a V5 epitope, or a myc epitope.

In another embodiment, a method of the invention is performed using a first nucleic acid molecule that encodes a polypeptide (e.g., a polypeptide which contains an intein), or a domain thereof, and a second (or other) nucleic acid molecule that encodes a transcription activation domain or a DNA binding domain. Such a method can be used to generate covalently linked ds recombinant nucleic acid molecules that encode chimeric polypeptides useful for performing a two hybrid assay system, particularly a high throughput two hybrid assay. In still another embodiment, the first nucleic acid molecules comprises a plurality of nucleotide sequences, which can be a cDNA library, a combinatorial library of nucleotide sequences, a variegated population of nucleotide sequences, or the like.

A method of the invention provides a means to generate a covalently linked ds recombinant nucleic acid molecule useful for site specific insertion into a target genomic DNA sequence. The target genomic DNA sequence can be any genomic sequence, particularly a gene, and preferably a gene for which some or all of the nucleotide sequence is known. The method can be performed utilizing two sets of PCR primer pairs and a nucleic acid molecule. The nucleic acid molecule has a first end and a second end and encodes a polypeptide, for example, a selectable marker, wherein the nucleic acid molecule comprises a topoisomerase recognition site or cleavage product thereof at the 3' terminus of each end and, optionally, a hydroxyl group at the 5' terminus of each end, and wherein, preferably, the 5' termini comprise overhanging sequences, which are different from each other. Similarly, the nucleic acid molecule can comprise a topoisomerase recognition site or cleavage product thereof at or near the 5' terminus of one or both ends and, optionally, a hydroxyl group at the 3' terminus of one or both end, and wherein one or both the 3' termini can comprise overhanging sequences, which can be the same as or, preferably, different from each other; or the 5' terminus and 3' terminus of one or both ends of the nucleic acid molecule each can comprise a topoisomerase recognition site or cleavage product thereof (see FIG. 11). In certain such aspects, at least one of the nucleic acid molecules used in the methods described herein will comprise at least one recombination site. Further, nucleic acid molecules generated by methods described above and elsewhere herein may also be used in recombination reactions, such as those described elsewhere herein.

The two sets of PCR primer pairs will generally be selected such that, in the presence of an appropriate DNA polymerase such as Taq polymerase and a template comprising the sequences to be amplified, the primers amplify portions of a genomic DNA sequence that are upstream (and adjacent to) and downstream (and adjacent to) of the target site for insertion of the polypeptide (e.g., selectable marker). The sets of PCR primer pairs also are designed such that the amplification products contain a topoisomerase recognition site at least at the end to be covalently linked to the selectable marker, including at or near the 5' terminus, or the 3' terminus, or both, as appropriate for the particular method of the invention being practiced. As such, the first PCR primer pair can include, for example, 1) a first primer, which comprises, in an orientation from 5' to 3', a nucleotide sequence complementary to a 5' overhanging sequence of the end of the selectable marker to which the amplification product is to be covalently linked, a nucleotide sequence complementary to a topoisomerase recognition site, such that PCR introduces a functional recognition site in the opposite strand (see primer sequences in FIG. 9D), and a nucleotide sequence complementary to a 3' sequence of a target genomic DNA sequence; and 2) a second primer, which comprises a nucleotide sequence of the target genomic DNA upstream of the 3' sequence to which the first primer is complementary. The second PCR primer pair includes 1) a first primer, which comprises, from 5' to 3', a nucleotide sequence complementary to the 5' overhanging sequence of the end of the selectable marker to which it is to be covalently linked, a nucleotide sequence complementary to a topoisomerase recognition site, such that PCR introduces a functional recognition site in the opposite strand (see primer sequences in FIG. 9D), and a nucleotide sequence of a 5' sequence of a target genomic DNA sequence, wherein the 5' sequence of the target genomic DNA is downstream of the 3' sequence of the target genomic DNA to which the first primer of the first PCR primer pair is complementary; and 2) a second primer, which comprises a nucleotide sequence complementary to a 3' sequence of the target genomic DNA that is downstream of the 5' sequence of the target genomic DNA contained in the first primer.

Upon contact of the nucleic acid molecule comprising the selectable marker, the PCR amplification products, and at least one topoisomerase, a covalently linked ds recombinant nucleic acid molecule is generated according to a method of the invention. The generated ds recombinant nucleic acid molecule is useful for performing homologous recombination in a genome, for example, to knock-out the function of a gene in a cell, or to confer a novel phenotype on the cell containing the generated ds recombinant nucleic acid molecule. The method can further be used to produce a transgenic non-human organism having the generated recombinant nucleic acid molecule stably maintained in its genome.

The present invention also relates to compositions prepared according to the methods of the invention, and to compositions useful for practicing the methods. Such compositions can include one or more reactants used in the methods of the invention and/or one or more ds recombinant nucleic acid molecules produced according to a method of the invention. Such compositions can include, for example, one or more nucleic acid molecules with one or more topoisomerase recognition sites; one or more topoisomerase-charge nucleic acid molecules; one or more nucleic acid molecules comprising one or more recombination sites; one or more primers useful for preparing a nucleic acid molecule containing a topoisomerase recognition site at one or both termini of one or both ends of an amplification product prepared using the primer; one or more topoisomerases; one or more substrate nucleic acid molecules, including, for example, nucleotide sequences encoding tags, markers, regulatory elements, or the like; one or more covalently linked ds recombinant nucleic acid molecules produced according to a method of the invention; one or more cells containing or useful for containing a nucleic acid molecule, primer, or recombinant nucleic acid molecule as disclosed herein; one or more polymerases for performing a primer extension or amplification reaction; one or more reaction buffers; and the like. In one embodiment, a composition of the invention comprises two or more different topoisomerase-charged nucleic acid molecules and/or two or more different recombination sites. The composition can further comprise at least one topoisomerase. A composition of the invention also can comprise a site specific topoisomerase and a covalently linked ds recombinant nucleic acid molecule, wherein the recombinant nucleic acid molecule contains at least one topoisomerase recognition site for the site specific topoisomerase in each strand, and wherein a topoisomerase recognition site in one strand is within about 100 nucleotides of a topoisomerase recognition site in the complementary strand, generally within about five, ten, twenty or thirty nucleotides.

Product molecules produced by methods of the invention may comprise any combination of starting molecules (or portions thereof) and can be any size and be in any form (e.g., circular, linear, supercoiled, etc.), depending on the starting nucleic acid molecule or segment, the location of the recombination sites on the molecule, and the order of recombination of the sites.

Any of the product molecules of the invention may be further manipulated, analyzed or used in any number of standard molecular biology techniques or combinations of such techniques (in vitro or in vivo). These techniques include sequencing, amplification, nucleic acid synthesis, protein or peptide expression (for example, fusion protein expression, antibody expression, hormone expression etc.), protein-protein interactions (2-hybrid or reverse 2-hybrid analysis), homologous recombination or gene targeting, and combinatorial library analysis and manipulation. The invention also relates to cloning the nucleic acid molecules of the invention (preferably by recombination) into one or more vectors or converting the nucleic acid molecules of the invention into a vector by the addition of certain functional vector sequences (e.g., origins of replication). In one aspect, recombination and/or topoisomerase-mediated joining is accomplished in vitro and further manipulation or analysis is performed directly in vitro. Thus, further analysis and manipulation will not be constrained by the ability to introduce the molecules of the invention into a host cell and/or maintained in a host cell. Thus, less time and higher throughput may be accomplished by further manipulating or analyzing the molecules of the invention directly in in vitro, although in vitro analysis or manipulation can be done after passage through host cells or can be done directly in vivo (while in the host cells).

Nucleic acid synthesis steps, according to the invention, may comprise:

(a) mixing a nucleic acid molecule of interest or template with one or more primers and one or more nucleotides to form a mixture; and (b) incubating said mixture under conditions sufficient to synthesize a nucleic acid molecule complementary to all or a portion of said molecule or template.

The synthesized molecule may then be used as a template for further synthesis of a nucleic acid molecule complementary to all or a portion of the first synthesized molecule. Accordingly, a double stranded nucleic acid molecule (e.g., DNA) may be prepared. Preferably, such second synthesis step is preformed in the presence of one or more primers and one or more nucleotides under conditions sufficient to synthesize the second nucleic acid molecule complementary to all or a portion of the first nucleic acid molecule. Typically, synthesis of one or more nucleic acid molecules is performed in the presence of one or more polymerases (preferably DNA polymerases which may be thermostable or mesophilic), although reverse transcriptases may also be used in such synthesis reactions. Accordingly, the nucleic acid molecules used as templates for the synthesis of additional nucleic acid molecules may be RNA, mRNA, DNA or non-natural or derivative nucleic acid molecules. Nucleic acid synthesis, according to the invention, may be facilitated by incorporating one or more primer sites into the product molecules through the use of starting nucleic acid molecules containing such primer sites. Thus, by the methods of the invention, primer sites may be added at one or a number of desired locations in the product molecules, depending on the location of the primer site within the starting molecule and the order of addition of the starting molecule in the product molecule.

Sequencing steps, according to the invention, may comprise:

(a) mixing a nucleic acid molecule to be sequenced with one or more primers, one or more nucleotides and one or more termination agents to form a mixture;

(b) incubating said mixture under conditions sufficient to synthesize a population of molecules complementary to all or a portion of said molecules to be sequenced; and (c) separating said population to determine the nucleotide sequence of all or a portion of said molecule to be sequenced.

Such sequencing steps are preferably performed in the presence of one or more polymerases (e.g., DNA polymerases and/or reverse transcriptases) and one or more primers. Preferred terminating agents for sequencing include derivative nucleotides such as dideoxynucleotides (ddATP, ddTTP, ddGTP, ddCTP and derivatives thereof). Nucleic acid sequencing, according to the invention, may be facilitated by incorporating one or more sequencing primer sites into the product molecules through the use of starting nucleic acid molecules containing such primer sites. Thus, by the methods of the invention, sequencing primer sites may be added at one or a number of desired locations in the product molecules, depending on the location of the primer site within the starting molecule and the order of addition of the starting molecule in the product molecule.

Protein expression steps, according to the invention, may comprise:

(a) obtaining a nucleic acid molecule to be expressed which comprises one or more expression signals; and (b) expressing all or a portion of the nucleic acid molecule under control of said expression signal thereby producing a peptide or protein encoded by said molecule or portion thereof.

In this context, the expression signal may be said to be operably linked to the sequence to be expressed. The protein or peptide expressed is preferably expressed in a host cell (in vivo), although expression may be conducted in vitro using techniques well known in the art. Upon expression of the protein or peptide, the protein or peptide product may optionally be isolated or purified. Moreover, the expressed protein or peptide may be used in various protein analysis techniques including 2-hybrid interaction, protein functional analysis and agonist/antagonist-protein interactions (e.g., stimulation or inhibition of protein function through drugs, compounds or other peptides). The novel and unique hybrid proteins or peptides (e.g., fusion proteins) produced by the invention and particularly from expression of the combinatorial molecules of the invention may generally be useful for therapeutics. Protein expression, according to the invention, may be facilitated by incorporating one or more transcription or translation signals or regulatory sequences, start codons, termination signals, splice donor/acceptor sequences (e.g., intronic sequences) and the like into the product molecules through the use of starting nucleic acid molecules containing such sequences. Thus, by the methods of the invention, expression sequences may be added at one or a number of desired locations in the product molecules, depending on the location of such sequences within the starting molecule and the order of addition of the starting molecule in the product molecule.

Homologous recombination, according to the invention, may comprise:

(a) mixing at least a first nucleic acid molecule of the invention (which is preferably a product molecule) comprising one or more recombination sites and/or one or more toposiomerase recognition sites with at least one target nucleic molecule, wherein said first and target molecules have one or more homologous sequences; and (b) causing said first and target nucleic acid molecules to recombine by homologous recombination. One example of a nucleic acid construct that can be used for homologous recombination is depicted in FIG. 37. The invention further includes methods for preparing nucleic acid molecules which can be used for homologous recombination, and nucleic acid molecules prepared by such methods, as well as cells which have undergone homologous recombination according to methods of the invention.

Such homologous recombination may occur in vitro, but preferably is accomplished in vivo (e.g., in a host cell). Preferably, homologous recombination causes transfer of all or a portion of a nucleic acid molecule of the invention containing recombination sites (the first nucleic acid molecule) into one or more positions of the target nucleic acid molecule containing homologous sequences. Selection of such homologous recombination may be facilitated by positive or negative selection (e.g., using selectable markers) to select for a desired product and/or against an undesired product. In a preferred aspect, the nucleic acid molecule of the invention comprises at least one selectable marker and at least two sequences which are homologous to the target molecule. Preferably, the first molecule comprises at least two homologous sequences flanking at least one selectable marker.

The present invention thus facilitates construction of gene targeting nucleic acid molecules or vectors which may be used to knock-out or mutate a sequence or gene of interest (or alter existing sequences, for example to convert a mutant sequence to a wild type sequence), particularly genes or sequences within a host or host cells such as animal, plant, human, insect, bacteria, and the like or sequences of adventitious agents such as viruses within such host or host cells. Such gene targeting may preferably comprise targeting a sequence on the genome of such host cells. Such gene targeting may be conducted in vitro or in vivo. Thus, in a preferred aspect, the invention relates to a method of targeting or mutating a sequence or a gene comprising:

(a) obtaining at least one nucleic acid molecule of the invention comprising one or more recombination sites and/or one or more topoisomerase recognition sites (and preferably one or more selectable markers), wherein said molecule comprises one or more sequences homologous to the target gene or sequence of interest (said one or more homologous sequences preferably flank one or more selectable markers on the molecule of the invention); and (b) contacting said molecule with one or more target genes or sequences of interest under conditions sufficient to cause homologous recombination at one or more sites between said target sequence or gene of interest and said molecule of the invention, thereby causing insertion of all or a portion of the molecule of the invention within the target sequence or gene.

Such targeting method may cause deletion, inactivation or partial inactivation of the sequence or target gene such that an expression product (typically a protein or peptide) normally expressed by such sequence is not produced or produced at a higher or lower level or to the extent produced is has an altered protein sequence which may result in more or less activity or in an inactive or partially inactive expression product. The selectable marker preferably present on the molecule of the invention facilitates selection of candidates (for example host cells) in which the homologous recombination event was successful. Thus, the present invention provides a method to produce host cells, tissues, organs, and animals (e.g., transgenic animals) containing the modified gene or sequence produced by the targeting methods of the invention. The modified sequence or gene preferably comprises at least one recombination site and/or at least one selectable marker provided by the molecule of the invention.

Thus, the present invention more specifically relates to a method of targeting or mutating a sequence or a gene comprising:

(a) obtaining at least one nucleic acid molecule of the invention comprising one or more recombination sites, at least one selectable marker flanked by one or more sequences homologous to the target gene or sequence of interest and, optionally, one or more topoisomerase recognition sites;

(b) contacting said molecule with one or more target genes or sequences of interest under conditions sufficient to cause homologous recombination at one or more sites between said target sequence or gene of interest and said molecule, thereby causing insertion of all or a portion of the molecule of the invention (and preferably causing insertion of at least one selectable marker and/or at least one recombination site) within the target sequence or gene; and (c) optionally selecting for said sequence or gene comprising all or a portion of the molecule of the invention or for a host cell containing said gene or sequence containing all or a portion of said molecule of the invention.

In another aspect of the invention, recombination sites introduced into targeted sequences according to the invention may be used to excise or remove all or a portion of the molecule inserted into the target sequence. Thus, the invention allows for in vitro or in vivo removal of such sequences and thus may allow for reactivation of the target gene or sequence. In some embodiments, after identification and isolation of a sequence containing the alterations introduced as above, a selectable marker present on the molecule of the present invention may be removed.

The present invention also provides methods for cloning the starting or product nucleic acid molecules of the invention into one or more vectors or converting the product molecules of the invention into one or more vectors. In one aspect, the starting molecules are recombined to make one or more product molecules and such product molecules are cloned, (preferably by recombination) into one or more vectors. In another aspect, the starting molecules are cloned directly into one or more vectors such that a number of starting molecules are joined within the vector, thus creating a vector containing the product molecules of the invention. In another aspect, the starting molecules are cloned directly into one or more vectors such that the starting molecules are not joined within the vector (i.e., the starting molecules are separated by vector sequences). In yet another aspect, a combination of product molecules and starting molecules may be cloned in any order into one or more vectors, thus creating a vector comprising a new product molecule resulting from a combination of the original starting and product molecules.

Thus, the invention relates to a method of cloning comprising:

(a) obtaining at least one nucleic acid molecule of the invention comprising one or more recombination sites and/or one or more topoisomerase recognition sites; and (b) transferring all or a portion of said molecule into one or more vectors. The invention further includes vectors prepared by such methods, compositions comprising these vectors, and methods using these vectors.

Such vectors will often comprise one or more recombination sites and/or one or more topoisomerase recognition sites, and the transfer of the molecules into such vectors is preferably accomplished by recombination between one or more sites on the vectors and one or more sites on the molecules of the invention. In another aspect, the product molecules of the invention may be converted to molecules which function as vectors by including the necessary vector sequences (e.g., origins of replication). Thus, according to the invention, such vectors sequences may be incorporated into the product molecules through the use of starting molecules containing such sequences. Such vector sequences may be added at one or a number of desired locations in the product molecules, depending on the location of the sequence within the starting molecule and the order of addition of the starting molecules in the product molecule. The product molecule containing the vector sequences may be in linear form or may be converted to a circular or supercoiled form by causing recombination of recombination sites within the product molecule or by a topoisomerase-mediated joining reaction. Often, circularization of such product molecule is accomplished by recombining recombination sites at or near both termini of the product molecule.

The vector sequences used in the invention may comprise one or a number of elements and/or functional sequences and/or sites (or combinations thereof) including one or more sequencing or amplification primer sites, one or more multiple cloning sites, one or more selectable markers (e.g., toxic genes, antibiotic resistance genes, selectable markers etc.), one or more transcription or translation sites or signals, one or more transcription or translation termination sites, one or more topoisomerase recognition sites, one or more topoisomerases, one or more origins of replication, one or more recombination sites (or portions thereof), etc. The vector sequences used in the invention may also comprise stop codons which may be suppressed to allow expression of desired fusion proteins as described herein. Thus, according to the invention, vector sequences may be used to introduce one or more of such elements, functional sequences and/or sites into any of the nucleic acid molecule of the invention, and such sequences may be used to further manipulate or analyze any such nucleic acid molecule cloned into such vectors. For example, primer sites provided by a vector (preferably located on both sides of the insert cloned in such vector) allow sequencing or amplification of all or a portion of a product molecule cloned into the vector. Additionally, transcriptional or regulatory sequences contained by the vector allows expression of peptides, polypeptides or proteins encoded by all or a portion of the product molecules cloned to the vector. Likewise, genes, portion of genes or sequence tags (such as GUS, GST, GFP, His tags, epitope tags and the like) provided by the vectors allow creation of populations of gene fusions with the product molecules cloned in the vector or allows production of a number of peptide, polypeptide or protein fusions encoded by the sequence tags provided by the vector in combination with the product sequences cloned in such vector. Such genes, portions of genes or sequence tags may be used in combination with optionally suppressed stop codons to allow controlled expression of fusion proteins encoded by the sequence of interest being cloned into the vector and the vector supplied gene or tag sequence. In a construct, the vector may comprise one or more recombination sites, one or more stop codons and one or more tag sequences. In some embodiments, the tag sequences may be adjacent to a recombination site. Optionally, a stop codon may be incorporated into the sequence of the tag or in the sequence of the recombination site in order to allow controlled addition of the tag sequence to the gene of interest. In embodiments of this type, the gene of interest may be inserted into the vector by recombinational cloning such that the tag and the coding sequence of the gene of interest are in the same reading frame. The gene of interest may be provided with translation initiation signals, e.g., Shine-Delgarno sequences, Kozak sequences and/or IRES sequences, in order to permit the expression of the gene with a native N-terminal when the stop codon is not suppressed. The gene of interest may also be provided with a stop codon at the 3'-end of the coding sequence. In some embodiments, a tag sequence may be provided at both the N- and C-terminals of the gene of interest. Optionally, the tag sequence at the N-terminal may be provided with a stop codon and the gene of interest may be provided with a stop codon and the tag at the C-terminal may be provided with a stop codon. The stop codons may be the same or different. In some embodiments, the stop codon of the N-terminal tag is different from the stop codon of the gene of interest. In embodiments of this type, suppressor tRNAs corresponding to one or both of the stop codons may be provided. When both are provided, each of the suppressor tRNAs may independently be provided on the same vector, a different vector or in the host cell genome. The suppressor tRNAs need not both be provided in the same way, for example, one may be provided on the vector containing the gene of interest while the other may be provided in the host cell genome. In this way, the nucleic acid molecules of one such aspect of the invention may comprise a suppressible stop codon that separates two coding regions. Depending on the location of the expression signals (e.g., promoters), expression of the suppressor tRNA results in suppression of the stop codon(s), thereby allowing the production of a fusion peptide, for example a fusion peptide having an affinity tag sequence at the N- and/or C-terminus of the expressed protein. By not suppressing the stop codon(s), expression of the sequence of interest without the N- and/or C-terminal tag sequence may be accomplished. Thus, the invention allows through recombination efficient construction of vectors containing a gene or sequence of interest (e.g., one or more open reading frames or "orfs") for controlled expression of fusion proteins depending on the need. Preferably, the starting nucleic acid molecules or product molecules of the invention which are cloned into one or more vectors comprise at least one open reading frame (orf). Such starting or product molecules may also comprise functional sequences (e.g., primer sites, transcriptional or translation sites or signals, termination sites (e.g., stop codons which may be optionally suppressed), origins of replication, and the like) and preferably comprises sequences that regulate gene expression including transcriptional regulatory sequences and sequences that function as internal ribosome entry sites (IRES). Preferably, at least one of the starting or product molecules and/or vectors comprise sequences that function as a promoter. Such starting or product molecules and/or vectors may also comprise transcription termination sequences, selectable markers, restriction enzyme recognition sites, and the like.

In some embodiments, the vector comprises two copies of the same selectable marker, each copy flanked by recombination sites and/or topoisomerase recognition sites. In other embodiments, the vector comprises two different selectable markers each flanked by two recombination sites. In some embodiments, one or more of the selectable markers may be a negative selectable marker.

In a specific aspect, the invention provides a method of cloning comprising providing at least a first nucleic acid molecule comprising at least a first and a second recombination site and at least a second nucleic acid molecule comprising at least a third and a fourth recombination site, wherein either the first or the second recombination site is capable of recombining with either the third or the fourth recombination site and conducting a recombination reaction such that the two nucleic acid molecules are recombined into one or more product nucleic acid molecules and cloning the product nucleic acid molecules into one or more vectors. In certain such embodiments, the recombination sites flank the first and/or second nucleic acid molecules. Moreover, the cloning step is often accomplished by the recombination reaction of the product molecule into a vector comprising one or more recombination sites. In one aspect, the cloning step comprises conducting a recombination reaction between the sites in the product nucleic acid molecule that did not react in the first recombination reaction with a vector having recombination sites capable of recombining with the unreacted sites.

In some embodiments, a recombination site and/or a topoisomerase recognition site may be attached to a molecule of interest using conventional conjugation technology. For example, oligonucleotides comprising the recombination site and/or topoisomerase recognition site can be synthesized so as to include one or more reactive functional moieties which may be the same or different. Suitable reactive functional moieties include, but are not limited to, amine groups, epoxy groups, vinyl groups, thiol groups and the like. The synthesis of oligonucleotides comprising one or more reactive functional moieties is routine in the art. Once synthesized, oligonucleotides comprising one or more reactive functional moieties may be attached to one or more reactive groups present on the molecule or compound of interest. The oligonucleotides may be attached directly by reacting one or more of the reactive functional moieties with one or more of the reactive functional groups. In some embodiments, the attachment may be effected using a suitable linking group capable of reacting with one or more of the reactive functional moieties present on the oligonucleotide and with one or more of the reactive groups present on the molecule of interest. In other embodiments, both direct attachment and attachment through a linking group may be used. Those skilled in the art will appreciate that the reactive functional moieties on the oligonucleotide may be the same or different as the reactive functional moieties on the molecules and/or compounds of interest. Suitable reagents and techniques for conjugation of the oligonucleotide to the molecule of interest may be found in Hermanson, *Bioconjugate Techniques*, Academic Press Inc., San Diego, Calif., 1996.

The invention also relates to compositions for carrying out the methods of the invention, and kits comprising such compositions, and to compositions created while carrying out the methods of the invention.

Compositions, methods and kits of the invention may be prepared and carried out using a phage-lambda site-specific recombination system. Further, such compositions, methods and kits may be prepared and carried out using the GATEWAY™ Recombinational Cloning System and/or the TOPO® Cloning System and/or the pENTR Directional TOPO® Cloning System, which are available from Invitrogen Corporation (Carlsbad, Calif.).

In other aspects, the invention provides isolated nucleic acid molecules comprising one or more (e.g., one, two, three, four, five, etc.) recombination sites and/or one or more (e.g., one, two, three, four, five, etc.) topoisomerase recognition sites. One such molecule of the invention will contain two or more recombination sites flanking one topoisomerase recognition site. Another such molecule of the invention will contain two or more recombination sites and two or more topoisomerase recognition sites, wherein each recombination site may flank a topoisomerase recognition site. Nucleic acid molecules according to this aspect of the invention may be linear, circular, or have any of a variety of geometries and structures, such as coiled, supercoiled, etc. Recombination sites advantageously used in nucleic acid molecules according to this aspect of the invention include, but are not limited to, att sites (including, but not limited to, attB sites, attP sites, attL sites, attR sites, and the like), lox sites (including, but not limited to, loxP sites, loxP511 sites, and the like), psi sites, dif sites, cer sites, frt sites, and mutants, variants, and derivatives of these recombination sites that retain the ability to undergo recombination. Topoisomerase recognition sites advantageously used in the nucleic acid molecules of this aspect of the invention are preferably recognized and bound by a type I topoisomerase (such as type IA topoisomerases (including but not limited to *E. coli* topoisomerase I, *E. coli* topoisomerase III, eukaryotic topoisomerase II, archeal reverse gyrase, yeast topoisomerase III, *Drosophila* topoisomerase III, human topoisomerase III, *Streptococcus pneumoniae* topoisomerase III, and the traE protein of plasmid RP4) and type IB topoisomerases (including but not limited to eukaryotic nuclear type I topoisomerase and a poxvirus (such as that isolated from or produced by vaccinia virus, Shope fibroma virus, ORF virus, fowlpox virus, molluscum contagiosum virus and *Amsacta moorei* entomopoxvirus)), and type II topoisomerase (including, but not limited to, bacterial gyrase, bacterial DNA topoisomerase IV, eukaryotic DNA topoisomerase II (such as calf thymus type II topoisomerase), and T-even phage-encoded DNA topoisomerase).

The invention also provides vectors (which may be expression vectors) comprising such isolated nucleic acid molecules. Exemplary vectors according to this aspect of the invention include, but are not limited to, pcDNAGW-DT (sc), pENTR-DT(sc), pcDNA-DEST41, pENTR/D-TOPO, pENTR/SD/D-TOPO, pcDNA3.2/V5/GWD-TOPO and pcDNA6.2/V5/GWD-TOPO. The invention also provides host cells comprising such the isolated nucleic acid molecules or vectors of the invention.

In related aspects, the invention provides in vitro methods of cloning a nucleic acid molecule. Methods according to this aspect of the invention may comprise one or more steps, including:

(a) obtaining a nucleic acid molecule to be cloned (which in certain embodiments may be a linear molecule (and which may be blunt-ended or not) such as a PCR product, and which may optionally comprise one or more genes or open reading frames);

(b) mixing the nucleic acid molecule to be cloned in vitro with a vector (which may be an expression vector) comprising at least a first topoisomerase recognition site flanked by at least a first recombination site and at least a second recombation site, wherein the first and second recombination sites do not recombine with each other, and with at least one topoisomerase; and (c) incubating the mixture under conditions such that the nucleic acid molecule to be cloned is inserted into the vector between the first and second topoisomerase recognition sites, thereby producing a first product molecule comprising the nucleic acid molecule localized between the first and second recombination sites. The invention further includes nucleic acid molecules prepared by the above methods.

Methods according to this aspect of the invention may comprise one or more additional steps, including, for example, contacting the first product molecule with at least one vector comprising at least a third and fourth recombination sites that do not recombine with each other, under conditions favoring recombination between the first and third and between the second and fourth recombination sites, thereby producing at least one second product molecule. According to the invention, the first and/or second product molecules produced by these methods may be inserted into a host cell. The vectors used in this aspect of the invention may comprise at least one additional nucleic acid sequence selected from the group consisting of a selectable marker, a cloning site, a restriction site, a promoter, an operon, an origin of replication, and a gene or partial gene (i.e., a gene fragment or element).

Recombination sites and topoisomerase recognition sites used in the methods of this aspect of the invention include, but are not limited to, those described elsewhere herein. In particular methods, the second product nucleic acid molecule and the vector are combined in the presence of at least one recombination protein, which may be but is not limited to Cre, Int, IHF, Xis, Fis, Hin, Gin, Cin, Tn3 resolvase, TndX, XerC, or XerD. In certain such embodiments, the recombination protein is Cre, Int, Xis, IHF or Fis.

The invention also provides kits comprising these isolated nucleic acid molecules of the invention, which may optionally comprise one or more additional components selected from the group consisting of one or more topoisomerases, one or more recombination proteins, one or more vectors, one or more polypeptides having polymerase activity, and one or more host cells.

Other preferred embodiments of the invention will be apparent to one or ordinary skill in the art in light of what is known in the art, in light of the following drawings and description of the invention, and in light of the claims.

BRIEF DESCRIPTION OF THE DRAWINGS/FIGURES

Figure 8A:
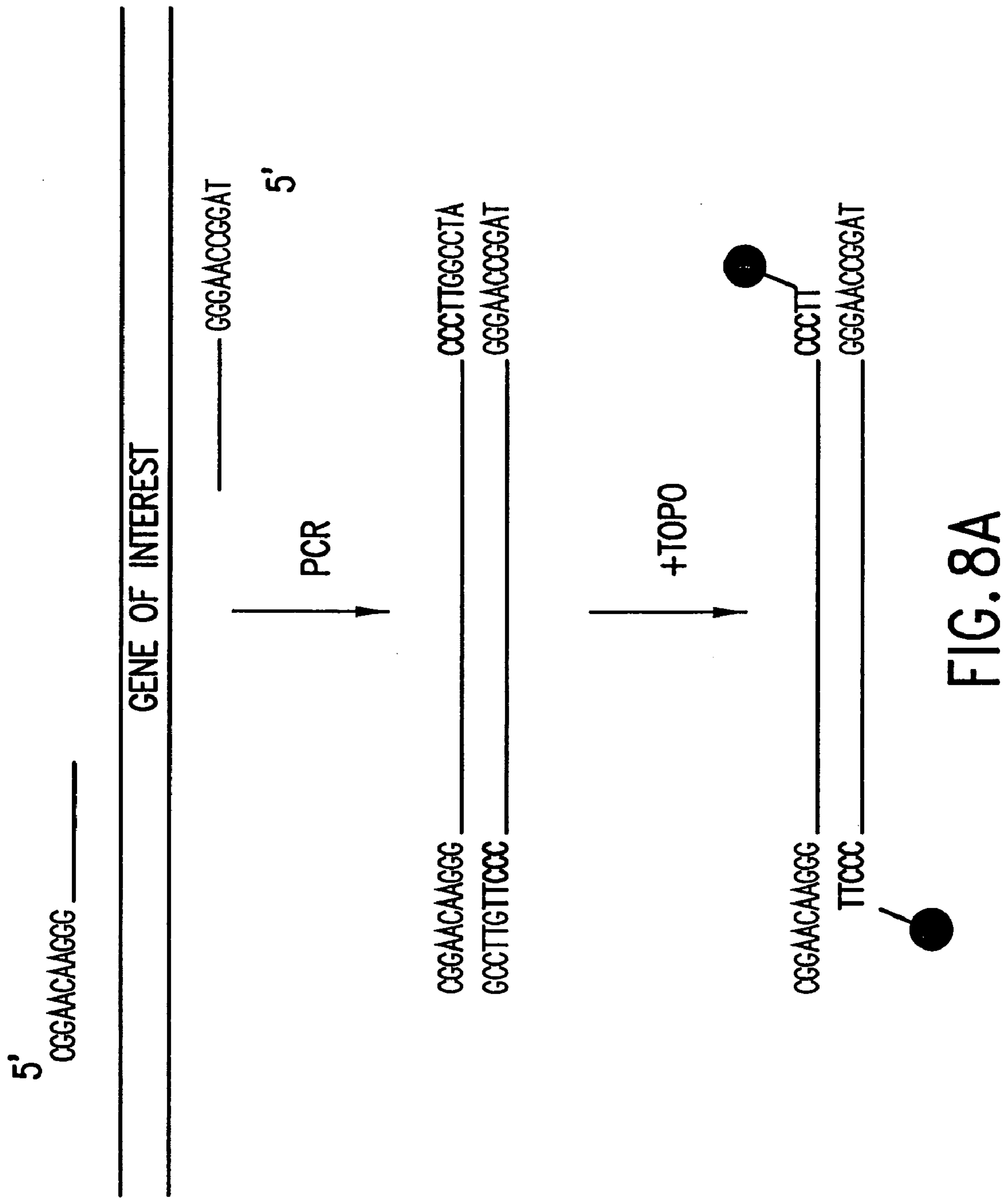
Figure 8B:
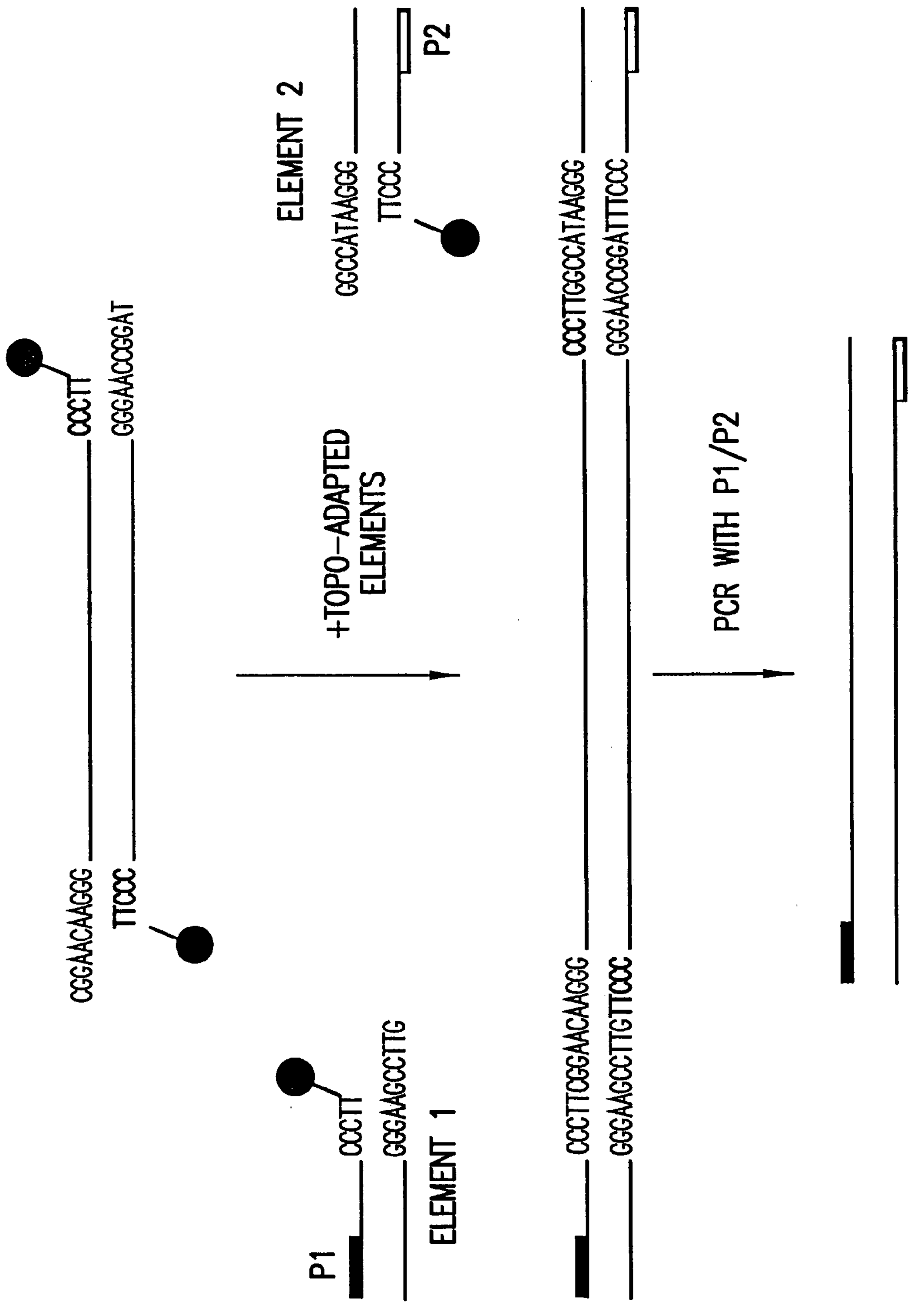

FIGS. 8A and 8B depict generating a covalently linked double stranded nucleotide sequence containing an element on each end according to a method of the invention. "PCR" indicates polymerase chain reaction; "TOPO" indicates topoisomerase; topoisomerase shown as circle attached to sequence; "P1" and "P2" indicate PCR primers. Topoisomerase recognition site is indicated in bold print. (5'-CGGAACAAGGG (SEQ ID NO: 63); 3'-GGGAACCG-GAT (SEQ ID NO: 64); 5'-CCCTTCGGAACAAGGG (SEQ ID NO: 65); 5'-CCCTTGGCCATAAGGG (SEQ ID NO: 66); 5'-GGCCATAAGGG (SEQ ID NO: 135); 3'-GG-GAAGCCTTG (SEQ ID NO: 136))

Figures 9A, 9B, 9C:
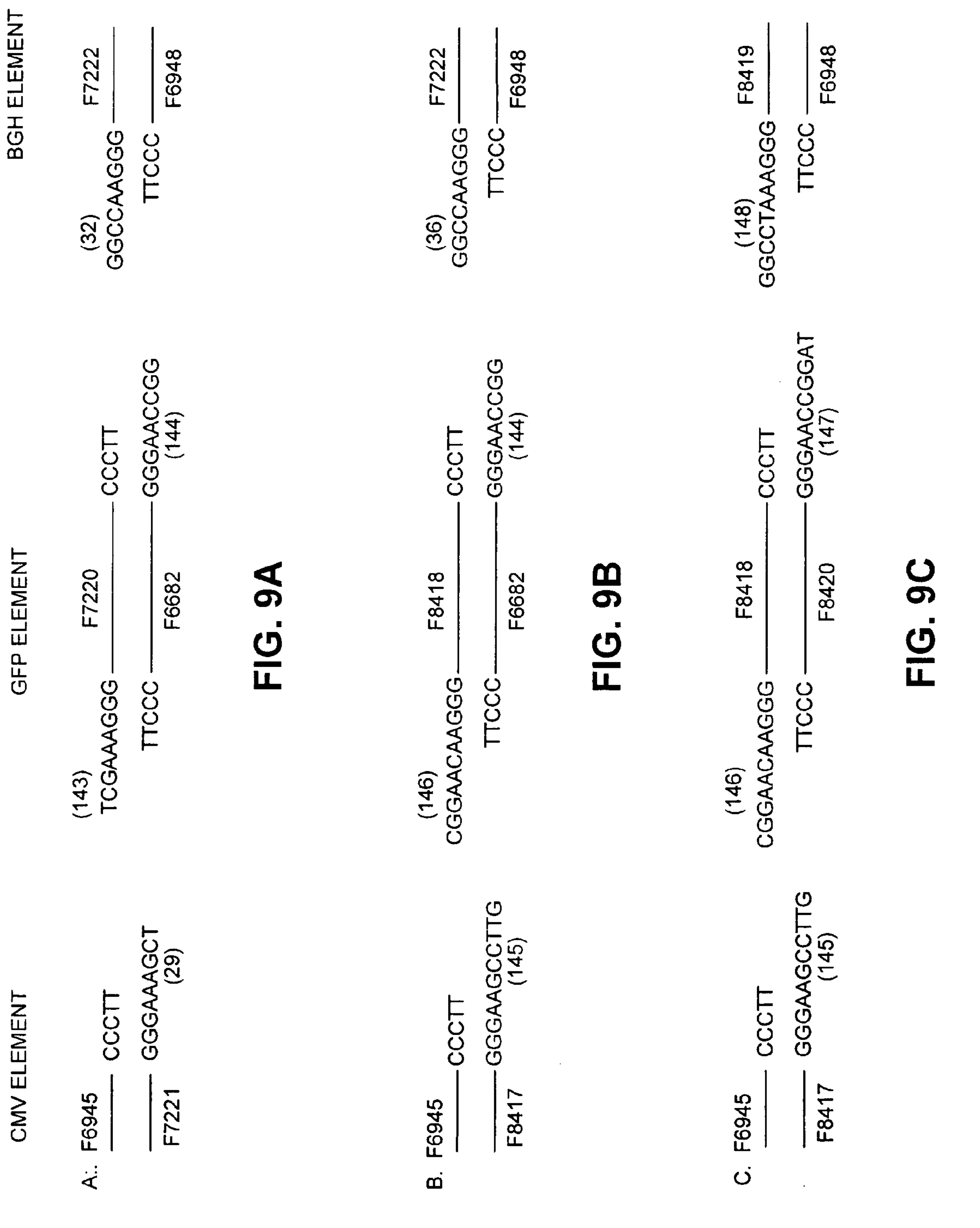

FIGS. 9A–9C show the ends of PCR products representing a cytomegalovirus promoter element ("CMV"), a green fluorescent protein element ("GFP"), and a bovine growth hormone polyadenylation signal ("BGH") element. Primers used to construct the PCR products of FIGS. 9A, 9B and 9C are indicated by an "F" number (see FIG. 9D). The portion of one or both ends including the topoisomerase recognition site (CCCTT) is shown. Bold print indicates overhanging sequences. In FIGS. 9A and 9B, one (FIG. 9B) or both (FIG. 9A) of the overhang sequences are palindromic in nature. Sequences are shown in conventional orientation, with the top strand in a 5' to 3' orientation from left to right, and the bottom strand in a 3' to 5' orientation from left to right. Number in parentheses above or below sequences indicates SEQ ID NOs.

Figures 10A, 10B:
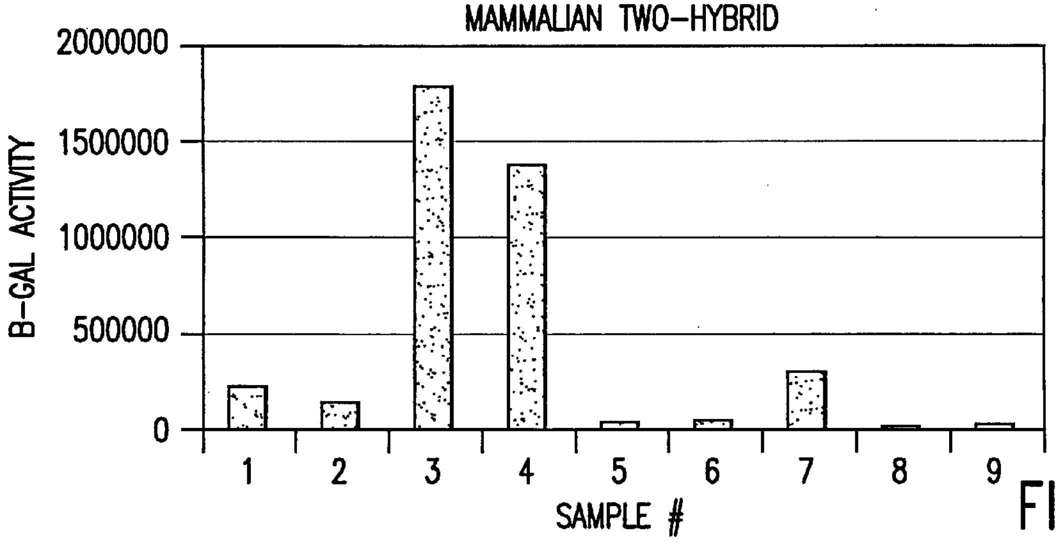

FIGS. 10A and 10B show constructs (FIG. 10A) and results (FIG. 10B) of studies examining the ability to use covalently linked ds recombinant nucleic acid molecules that encode polypeptides for performing a two hybrid assay. FIG. 10A shows the amount of each construct used for transfection. A "p" preceding an amount or volume of reactant indicates plasmid form, "l" indicates linear form, and "PCR" indicates PCR amplification reaction mixture. FIG. 10B shows the level of β-galactosidase activity ("LacZ activity") associated with each transfected sample. Increased LacZ activity is indicative of a positive interaction.

FIGS. 11A to 11F represent various embodiments of the composition and methods for generating a ds recombinant nucleic acid molecule covalently linked in one strand. Note nicks in one or both strands of the molecules shown in FIGS. 11B–11F.

FIGS. 12A to 12D illustrate various embodiments of compositions and methods of the invention for generating a covalently linked ds recombinant nucleic acid molecule. Topoisomerase is shown as a solid circle, and is either attached to a terminus of a substrate nucleic acid molecule or is released following a linking reaction. As illustrated, the substrate nucleic acid molecules have 5' overhangs, although they similarly can have 3' overhangs or can be blunt ended. In addition, while the illustrated nucleic acid molecules are shown having the topoisomerases bound thereto (topoisomerase-charged), one or more of the termini shown as having a topoisomerase bound thereto also can be represented as having a topoisomerase recognition site, in which case the joining reaction would further require addition of one or more site specific topoisomerases, as appropriate.

Figure 12A:
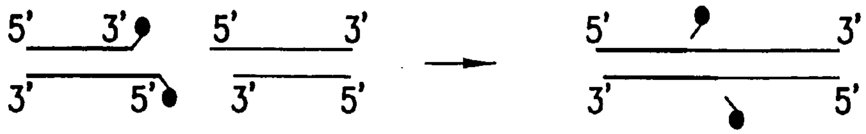

FIG. 12A shows a first nucleic acid molecule having a topoisomerase linked to each of the 5' terminus and 3' terminus of one end, and further shows linkage of the first nucleic acid molecule to a second nucleic acid molecule.

Figure 12B:
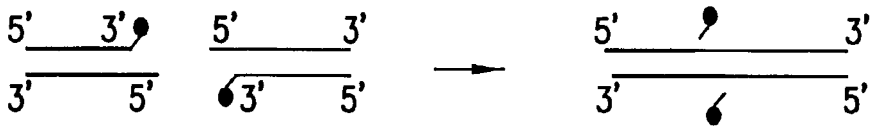

FIG. 12B shows a first nucleic acid molecule having a topoisomerase bound to the 3' terminus of one end, and a second nucleic acid molecule having a topoisomerase bound to the 3' terminus of one end, and further shows a covalently linked ds recombinant nucleic acid molecule generated due to contacting the ends containing the topoisomerase-charged substrate nucleic acid molecules.

Figure 12C:

FIG. 12C shows a first nucleic acid molecule having a topoisomerase bound to the 5' terminus of one end, and a second nucleic acid molecule having a topoisomerase bound to the 5' terminus of one end, and further shows a covalently linked ds recombinant nucleic acid molecule generated due to contacting the ends containing the topoisomerase-charged substrate nucleic acid molecules.

Figure 12D:
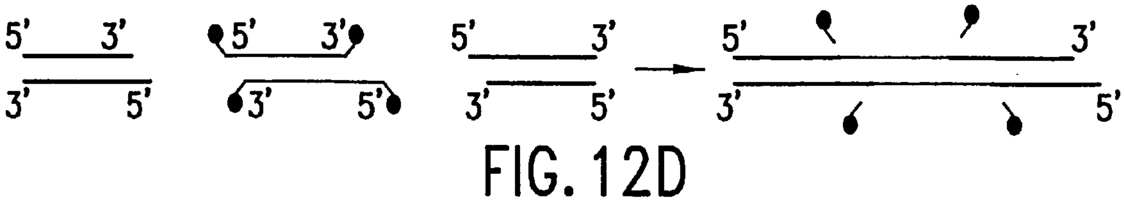

FIG. 12D shows a nucleic acid molecule having a topoisomerase linked to each of the 5' terminus and 3' terminus of both ends, and further shows linkage of the topoisomerase-charged nucleic acid molecule to two nucleic acid molecules, one at each end. The topoisomerases at each of the 5' termini and/or at each of the 3' termini can be the same or different.

Figure 13:
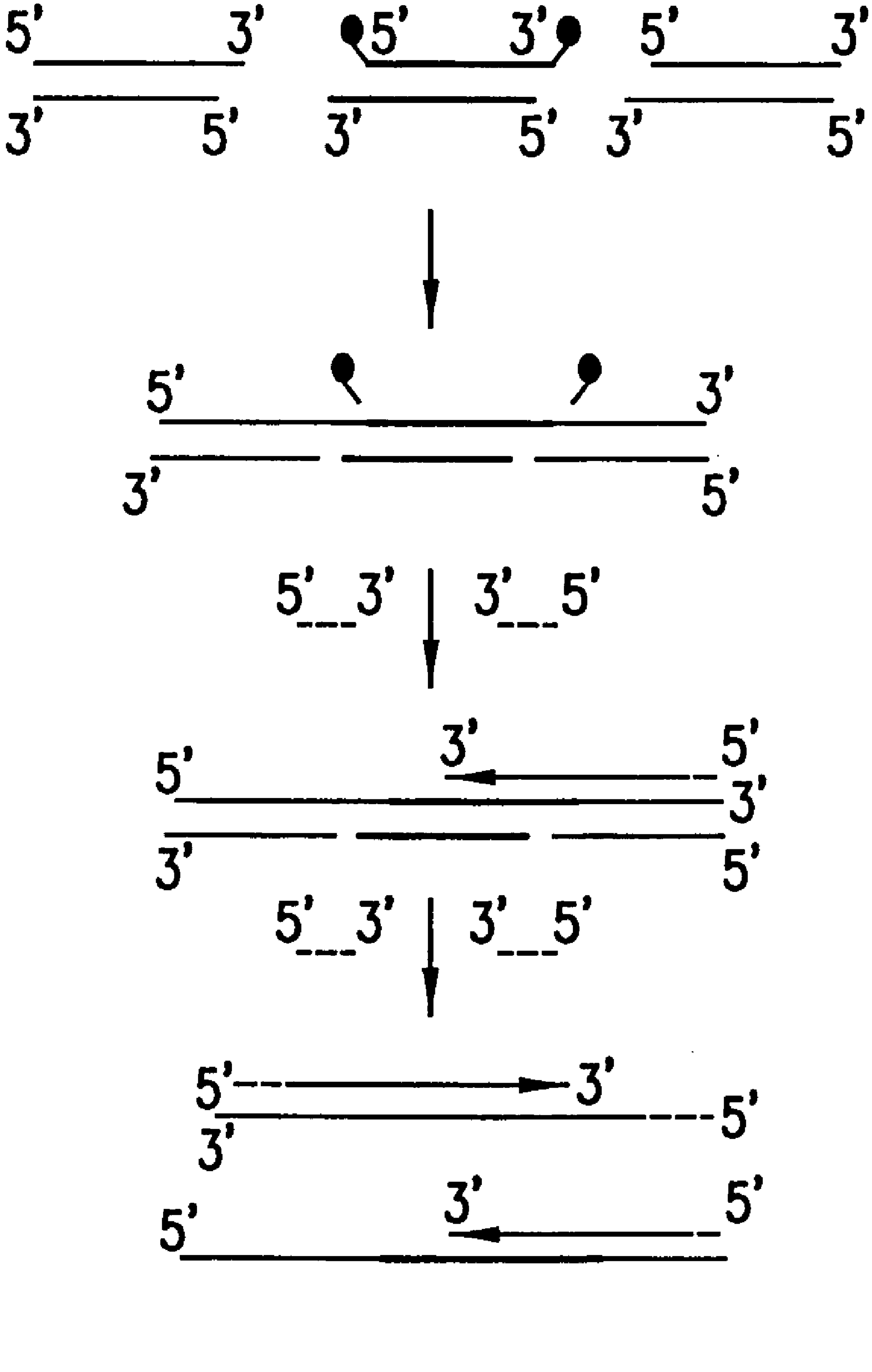

FIG. 13 illustrates the generation of an expressible ds recombinant nucleic acid molecule and amplification of the expressible ds recombinant nucleic acid molecule. The expressible ds recombinant nucleic acid molecule is generated from three nucleic acid molecules, including a nucleotide sequence comprising a promoter, a nucleotide sequence comprising a coding sequence, and a nucleotide sequence comprising a polyadenylation signal. Generation of the nucleic acid molecule can be facilitated by the incorporation of complementary 5' and/or 3' overhanging sequences at the ends of the ds nucleotides sequences to be joined. The expressible ds recombinant nucleic acid molecule is generated by contacting a first nucleic acid molecule having a type IA topoisomerase at a 5' terminus of a first end and a type IB topoisomerase at a 3' terminus of a second end, with a second nucleic acid molecule and a third double stranded nucleotide sequence. The expressible ds recombinant nucleic acid molecule is amplified using a first primer that hybridizes to the second ds recombinant nucleic acid molecule upstream of the promoter, and a second primer that hybridizes to the third ds recombinant nucleic acid molecule downstream of the polyadenylation signal.

Figure 14:
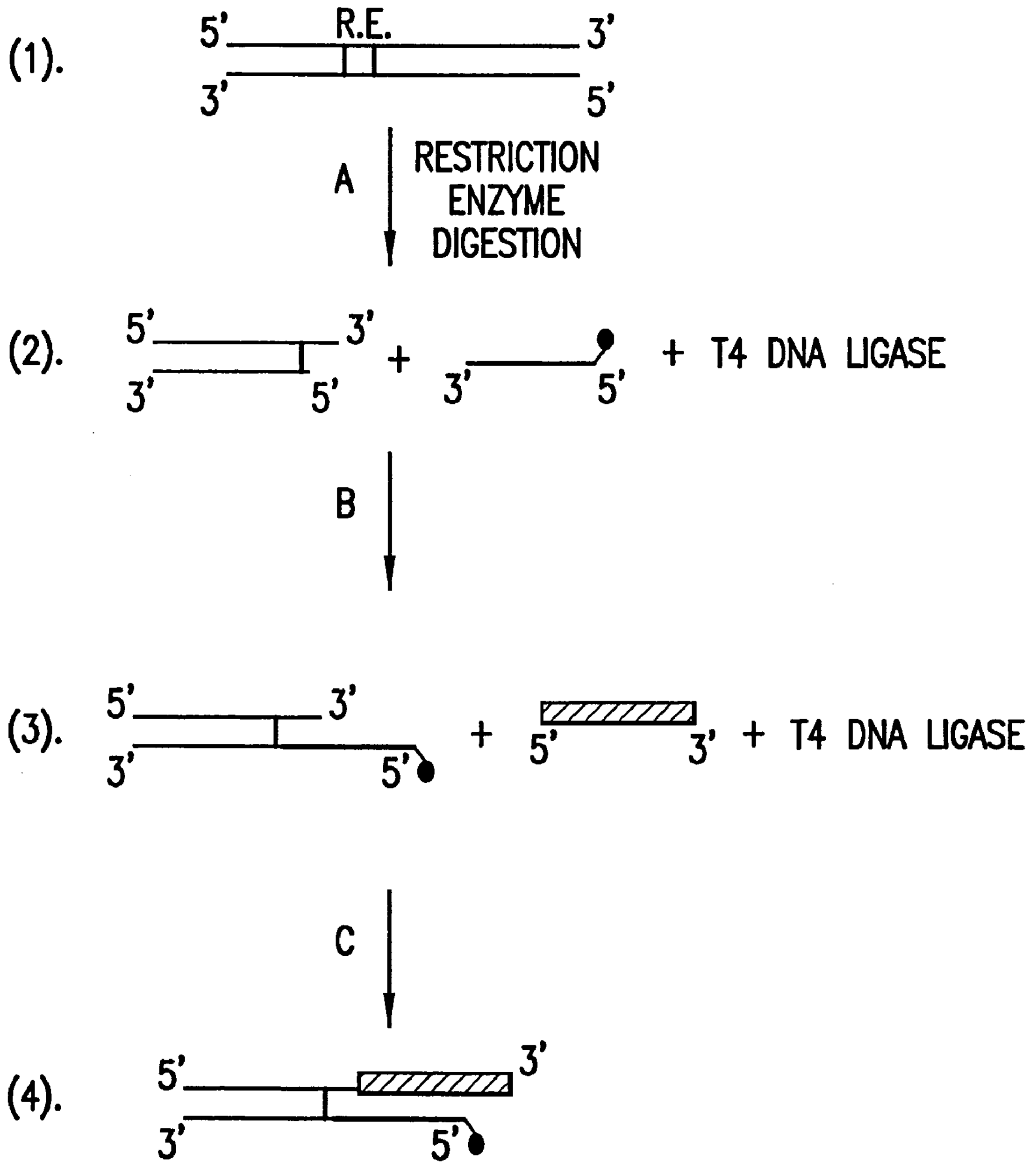

FIG. 14 shows one example of a process for preparing a double stranded nucleic acid molecule which contains a topoisomerase (e.g., a type IA topoisomerase) bound to the 5' terminus of one end of the molecule, wherein the same end of the molecule further comprise a 3' overhang (see (4) in this figure).

Figure 15:
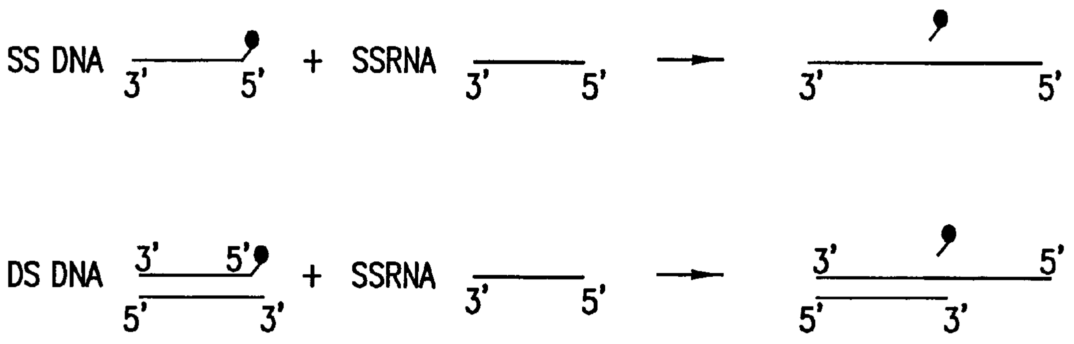

FIG. 15 shows two embodiments of the invention in which a single stranded or double stranded DNA nucleotide sequence is joined with single stranded RNA nucleotide sequence.

Figure 16:
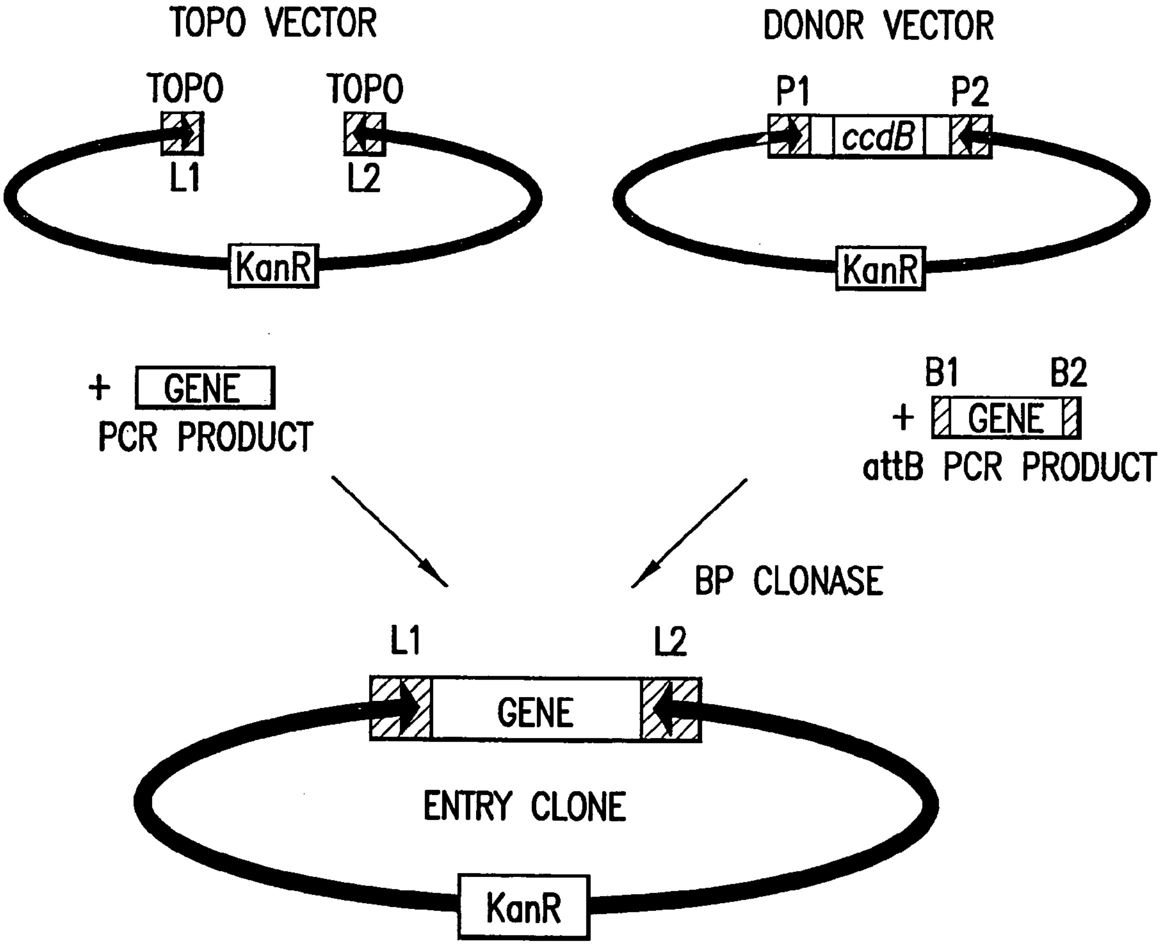

FIG. 16 is a schematic demonstrating the flexibility in entry point for PCR cloning using the TOPO-Gateway™ or standard Gateway™ cloning methodologies.

Figure 17:
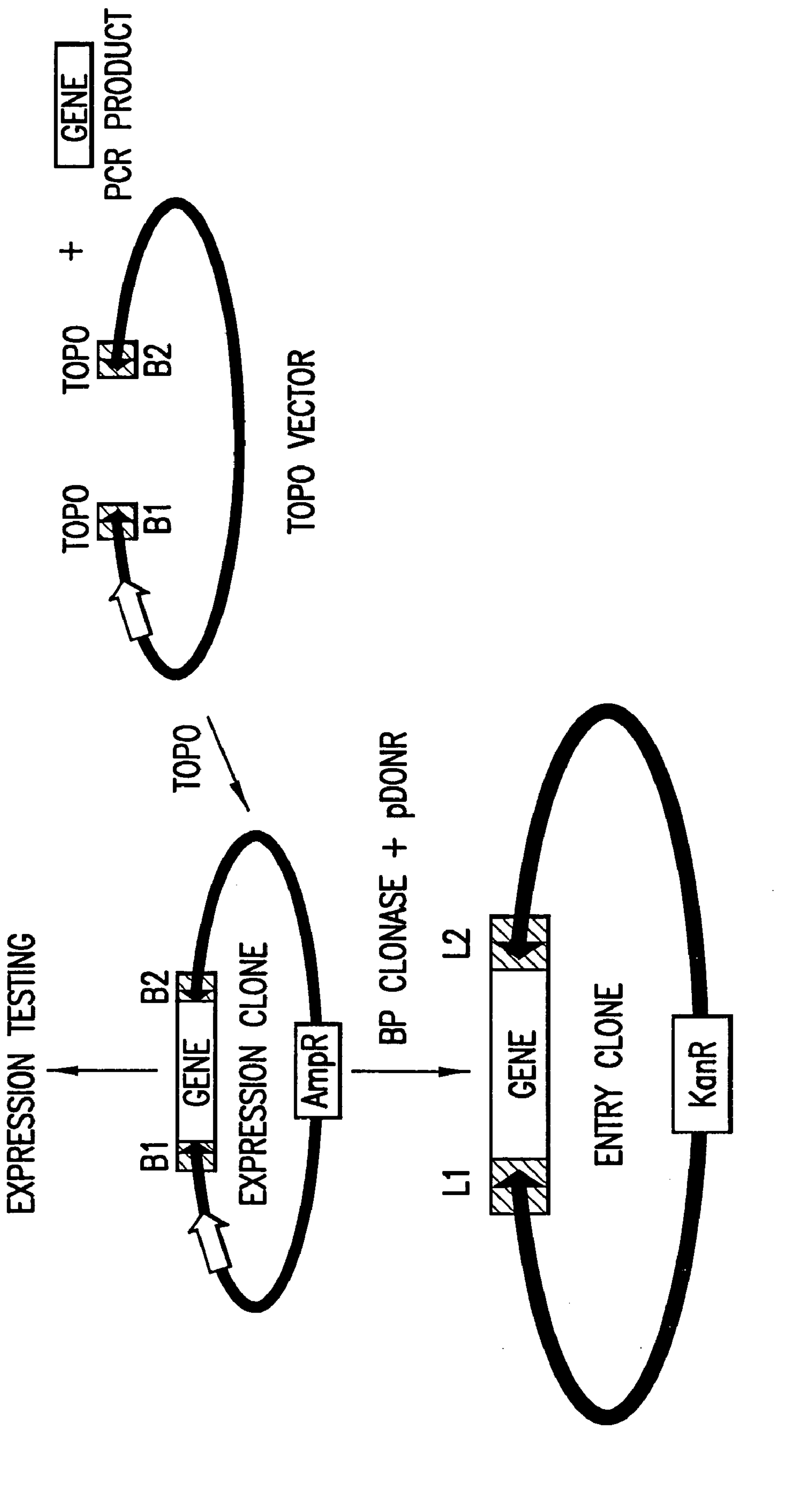

FIG. 17 is a schematic diagram of the production of expression clones using the Gateway™ system and a directional TOPO-Gateway™ expression vector.

Figure 18:
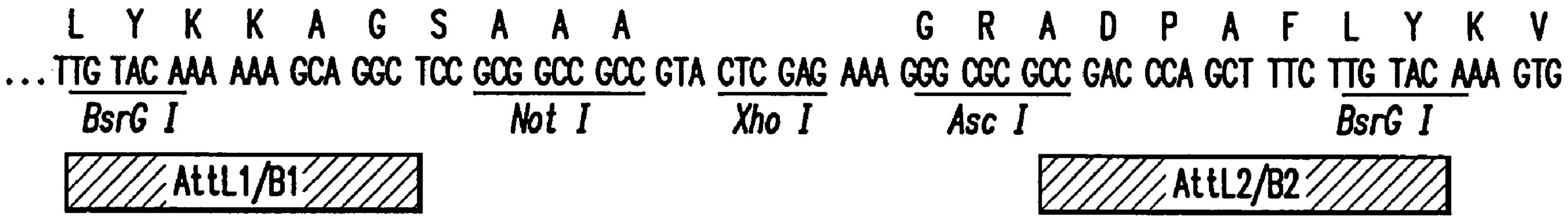

FIG. 18 is a map of the multiple cloning site in plasmids pcDNAGW-DT(sc) and pENTR-DT(sc). (SEQ ID NO: 67; amino acid sequences SEQ ID NO: 68 and SEQ ID NO: 69)

Figure 19:
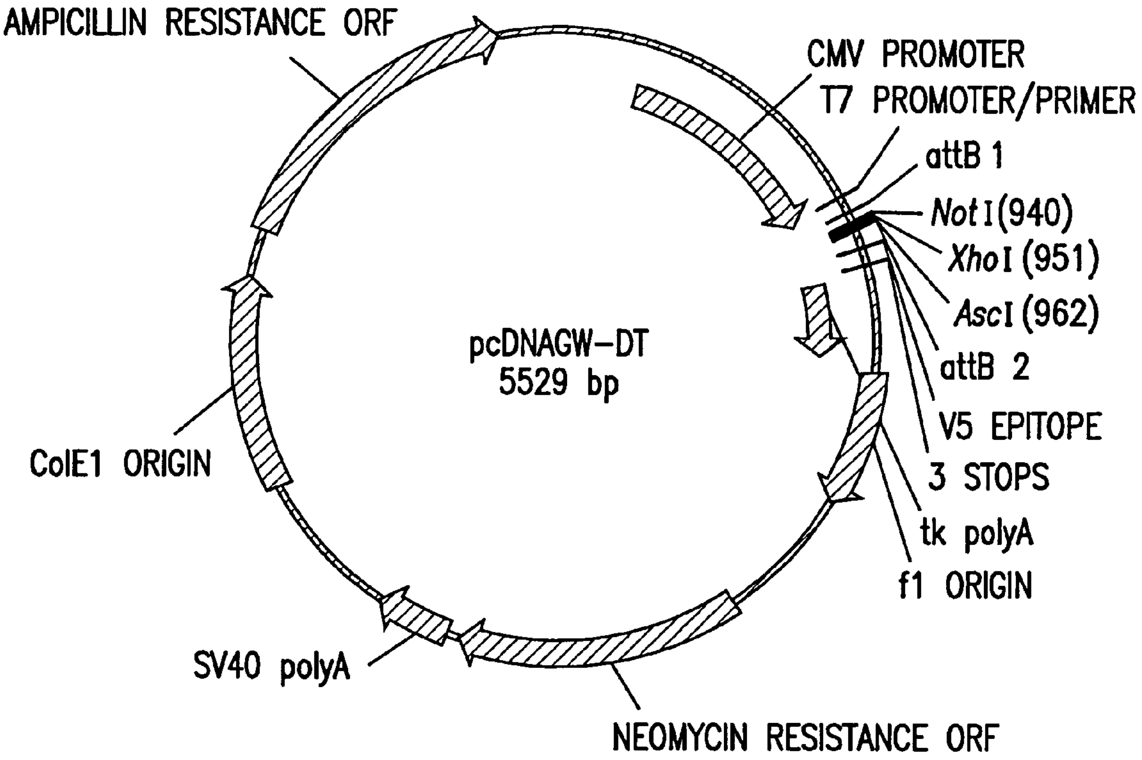

FIG. 19 is a physical map of plasmid pcDNAGW-DT.

Figure 20:
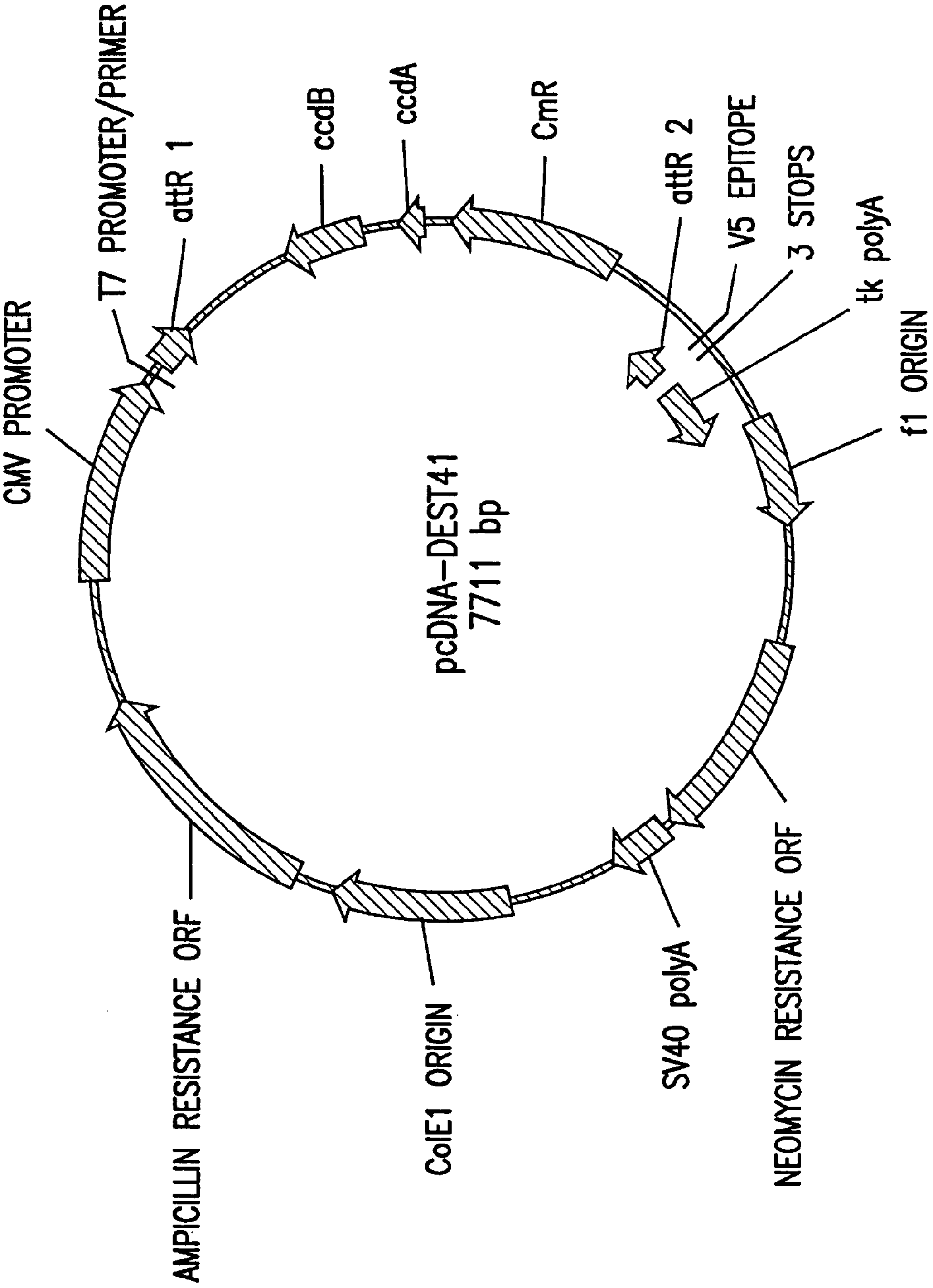

FIG. 20 is a physical map of plasmid pcDNA-DEST41.

Figure 21:
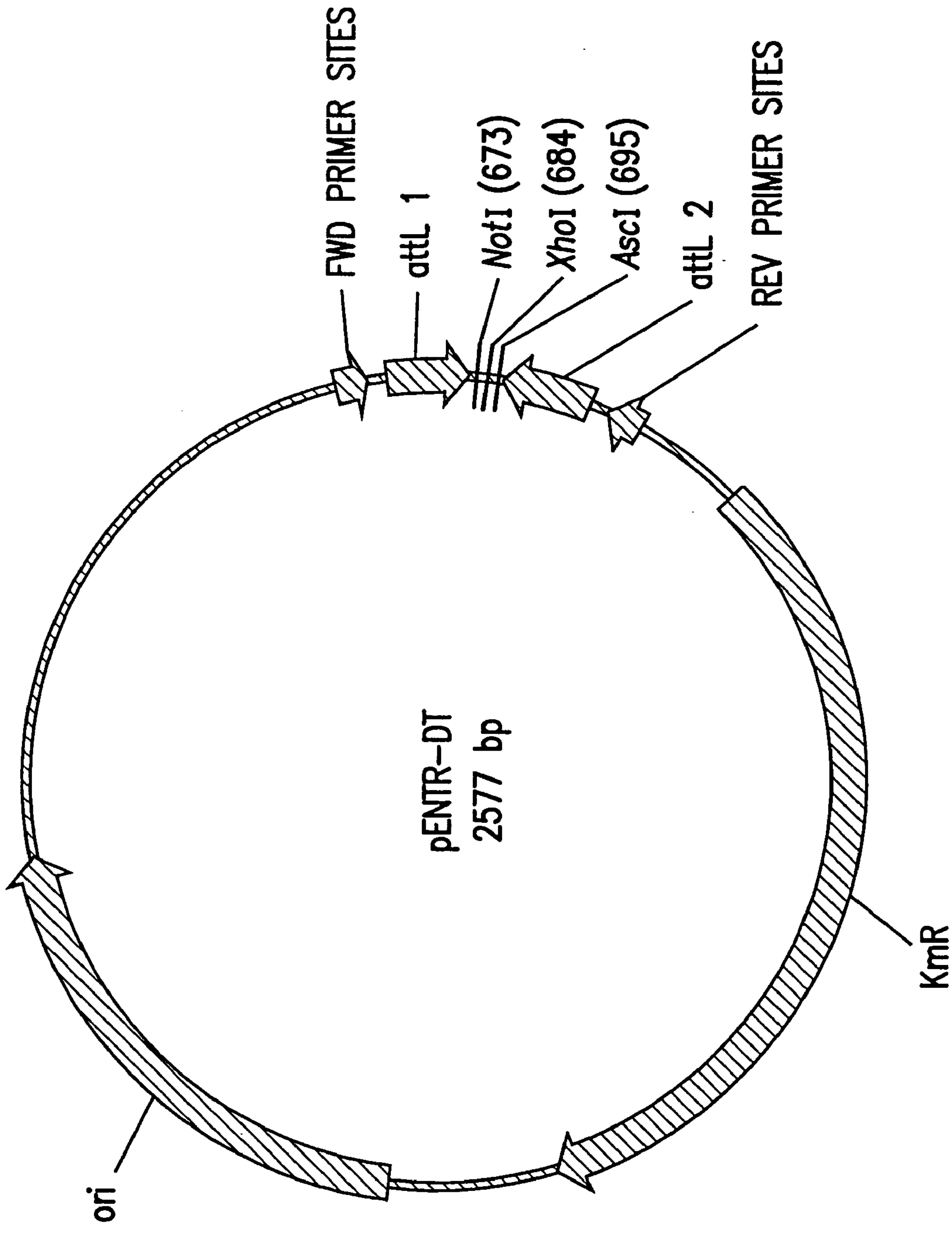

FIG. 21 is a physical map of plasmid pENTR-DT.

Figure 22A:
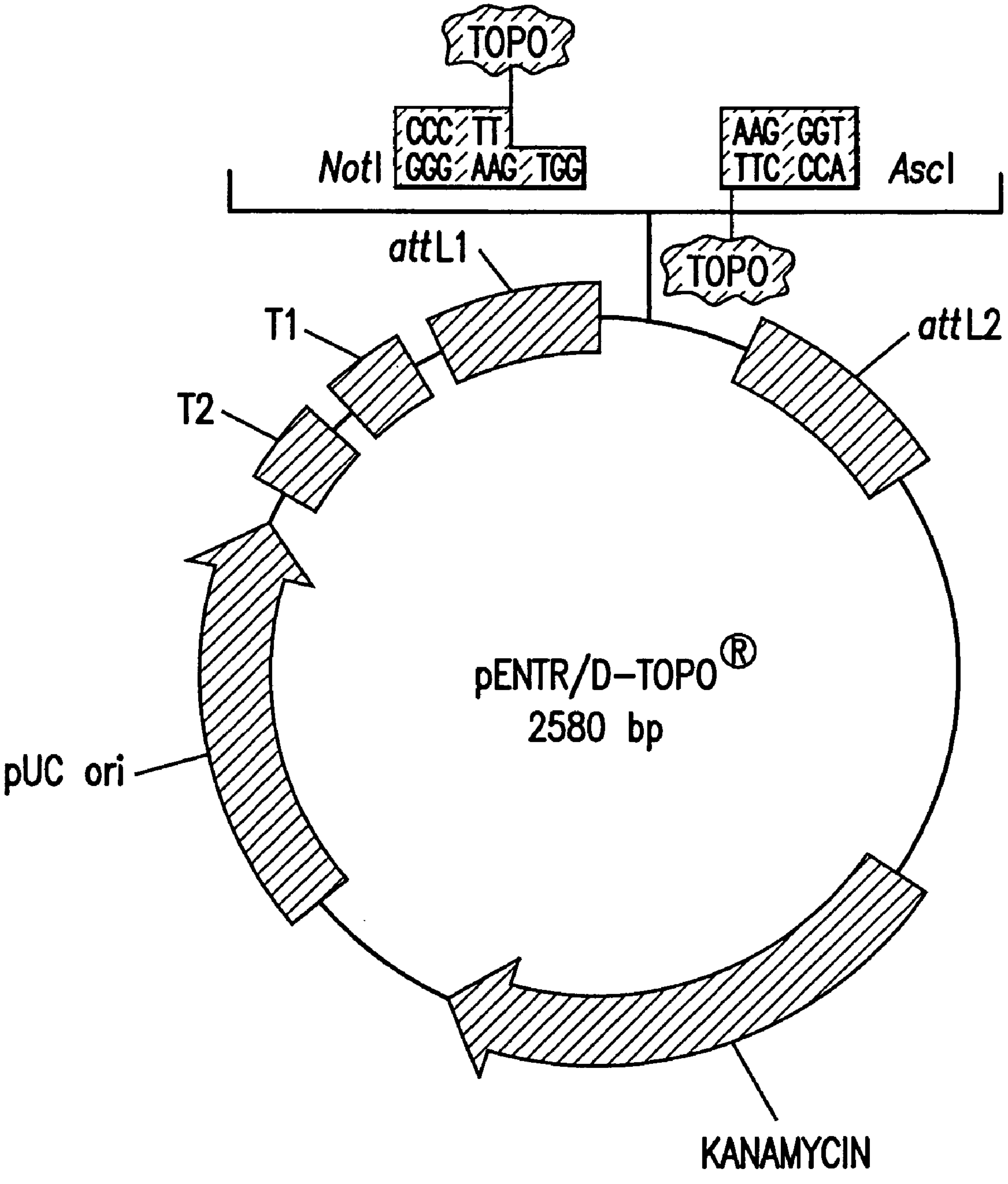

FIG. 22 is a depiction of the physical map (FIG. 22A) showing the TOPO cloning site in, and the nucleotide sequence (FIG. 22B) of, plasmid pENTR/D-TOPO. The physical map depicts the adapted, supercoiled form of the vector, while the nucleotide sequence depicts the vector containing a start codon and an open reading frame (atgnnnnnn . . . ). Restriction sites are labeled to indicate the actual cleavage site. The boxed region indicates attL sequences in the entry clone that will be transferred into the destination vector following recombination.

Figure 23A:
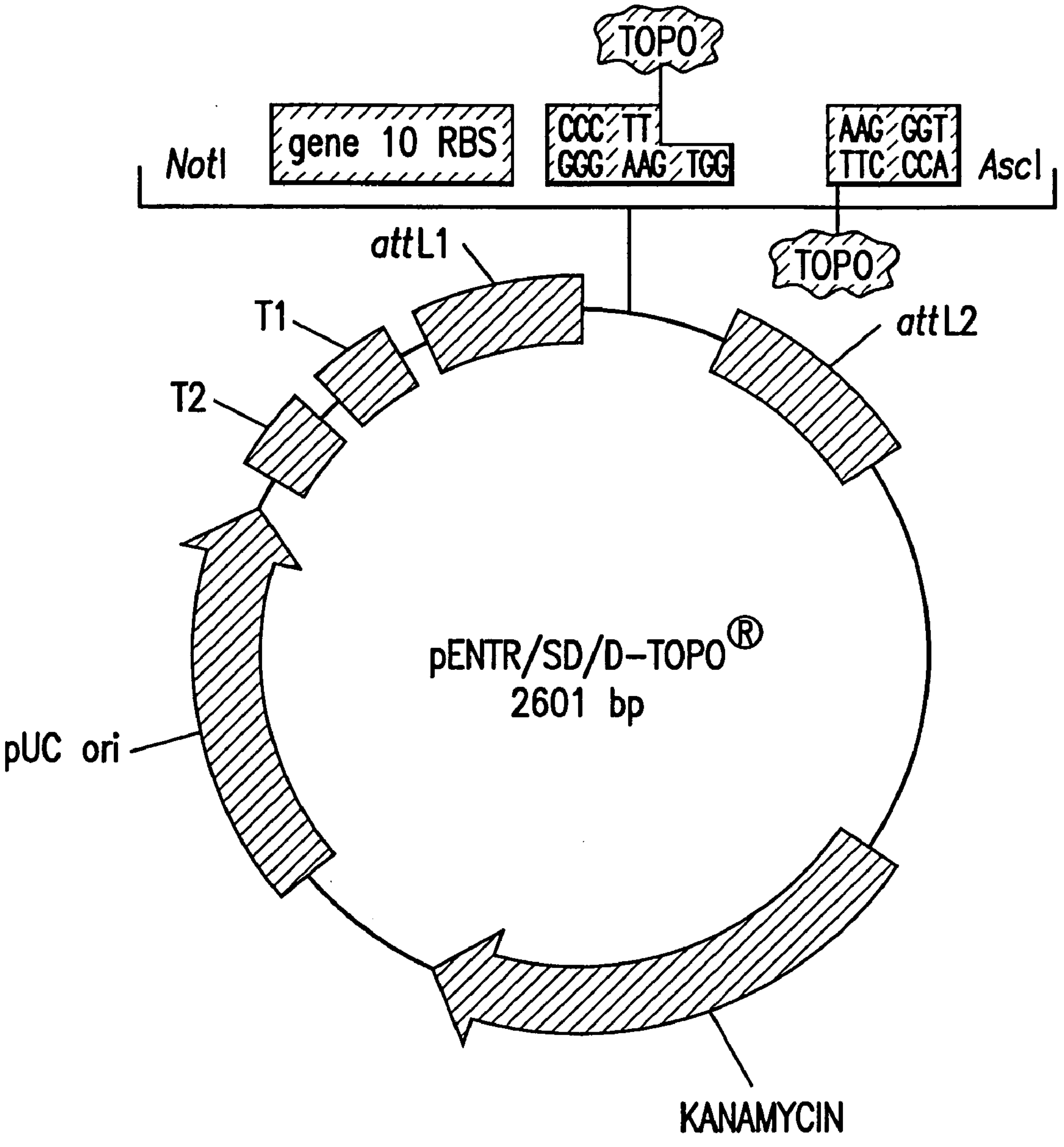

FIG. 23 is a depiction of the physical map (FIG. 23A) showing the TOPO cloning site in, and the nucleotide sequence (FIG. 23B) of, plasmid pENTR/SD/D-TOPO. The physical map depicts the adapted, supercoiled form of the vector, while the nucleotide sequence depicts the vector containing a start codon and an open reading frame (atgnnnnnn . . . ). Restriction sites are labeled to indicate the actual cleavage site. The boxed region indicates attL sequences in the entry clone that will be transferred into the destination vector following recombination.

Figure 24A:
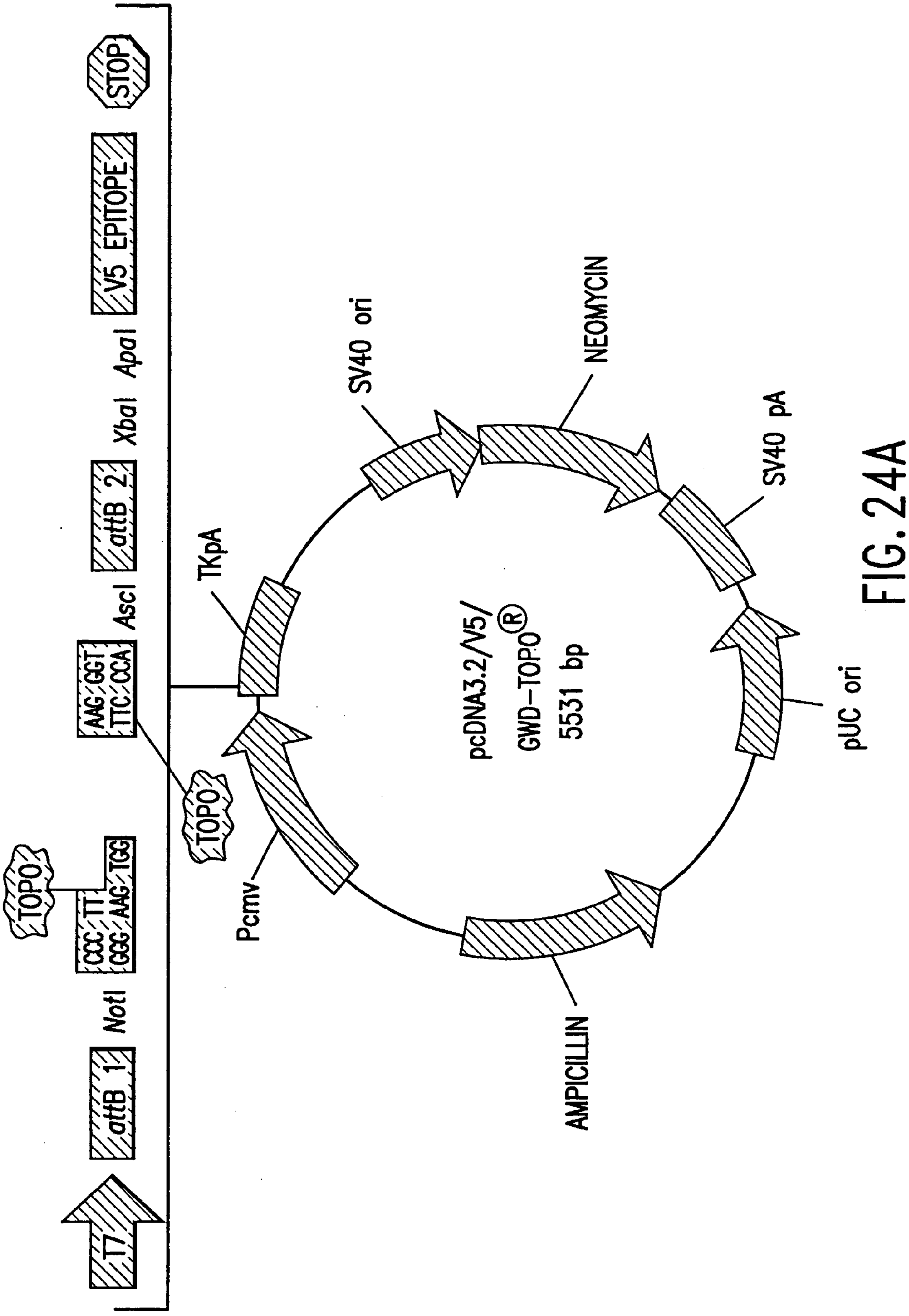

FIG. 24 is a depiction of the physical map (FIG. 24A) and the nucleotide sequence (FIG. 24B–C) (SEQ ID NO: 72) of plasmid pcDNA3.2/V5/GWD-TOPO7. The physical map depicts the adapted, supercoiled form of the vector, while the nucleotide sequence depicts the vector containing a start codon and an open reading frame (atgnnnnnn . . . ).

Figure 25A:
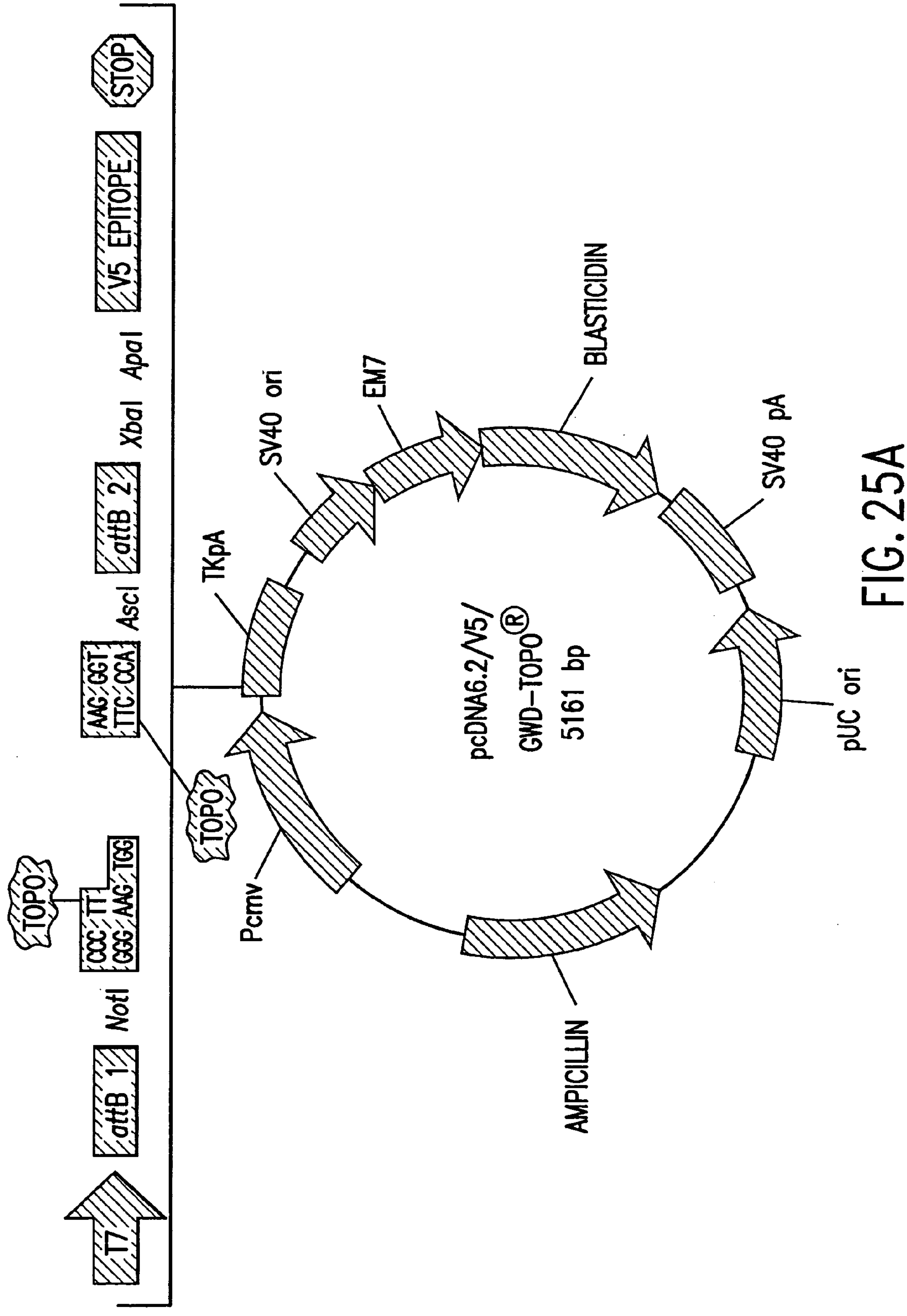

FIG. 25 is a depiction of the physical map (FIG. 25A) and the nucleotide sequence (FIG. 25B–C) (SEQ ID NO: 73) of plasmid pcDNA6.2/V5/GWD-TOPO7. The physical map depicts the adapted, supercoiled form of the vector, while the nucleotide sequence depicts the vector containing a start codon and an open reading frame (atgnnnnnn . . . ).

Figure 26:
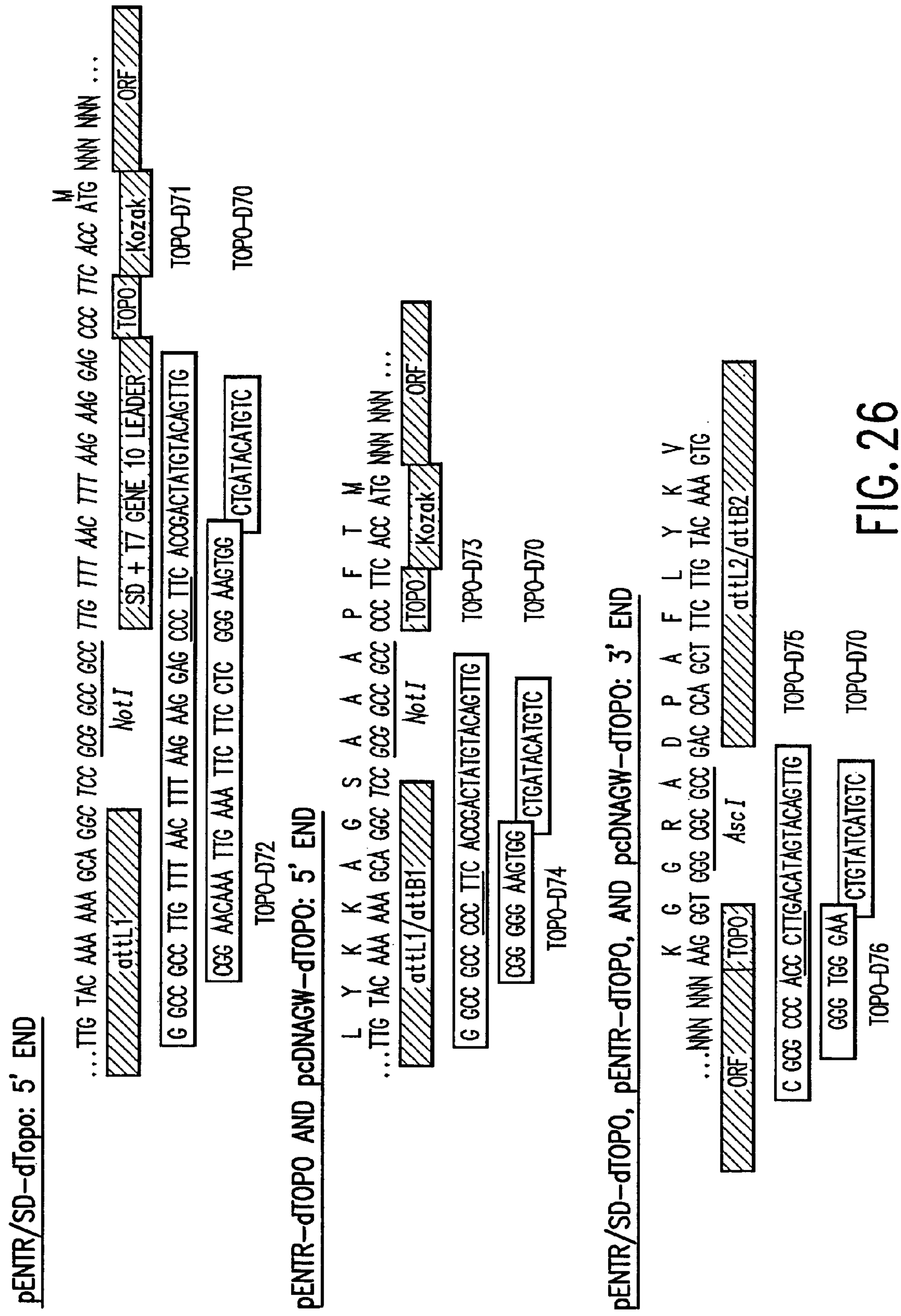

FIG. 26 is a depiction of an exemplary adaptation strategy for pENTR/SD-dTopo, (SEQ ID NO: 74: SEQ ID NO: 75; SEQ ID NO: 138; SEQ ID NO 139), pENTR-dTopo (SEQ ID NO: 76; SEQ ID NO: 78; SEQ ID NO: 140; SEQ ID NO: 141), and pcDNAGW-dTopo (SEQ ID NO: 77; SEQ ID NO: 79; SEQ ID NO: 142).

Figure 27:
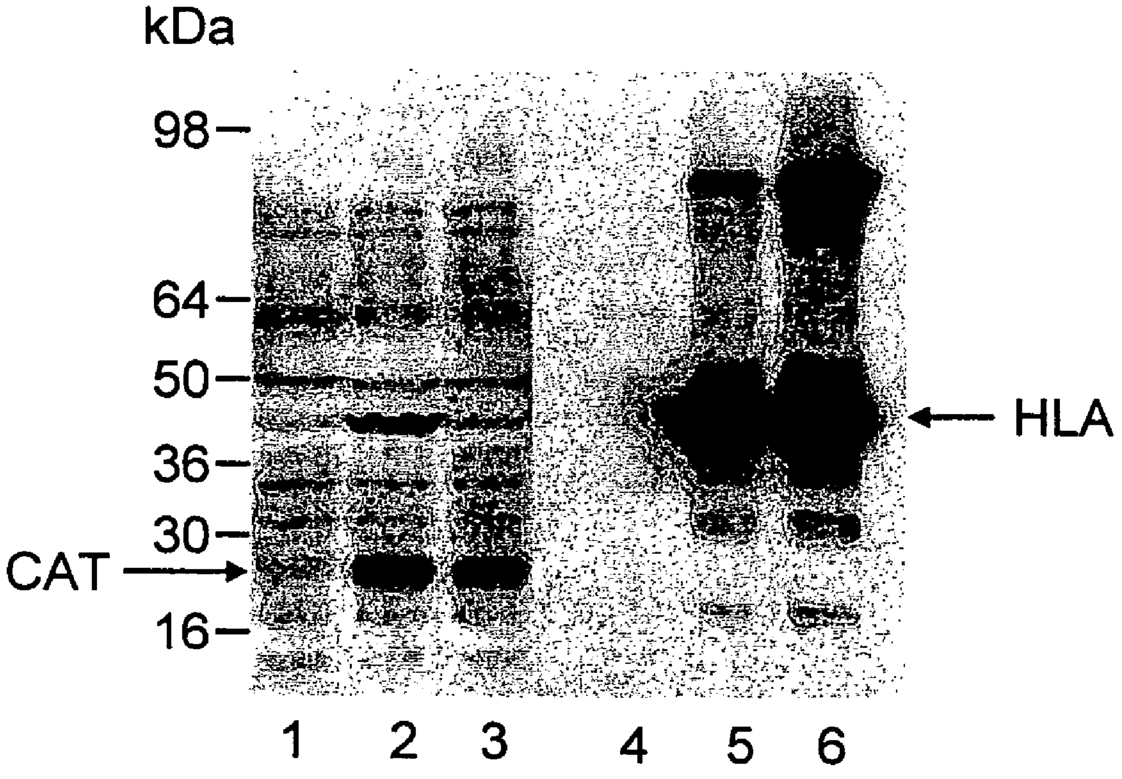

FIG. 27 is a photograph of a Western blot analysis of HLA and CAT expresed in COS cells. The genes encoding CAT (26 kDa) and HLA (41 kDa) were amplified by PCR and either Topo-cloned into pENTR-dTopo and transferred into pcDNA-DEST40 (lanes 2 and 5, respectively), or cloned directly into pcDNAGW-dTopo (lanes 3 and 6, respectively). These constructs were used to transfect COS cells and the lysates probed for recombinant V5tagged protein by Western blot, using V5-HRP antibody conjugate. Lanes 1 and 4 represent cells only controls.

Figure 28:
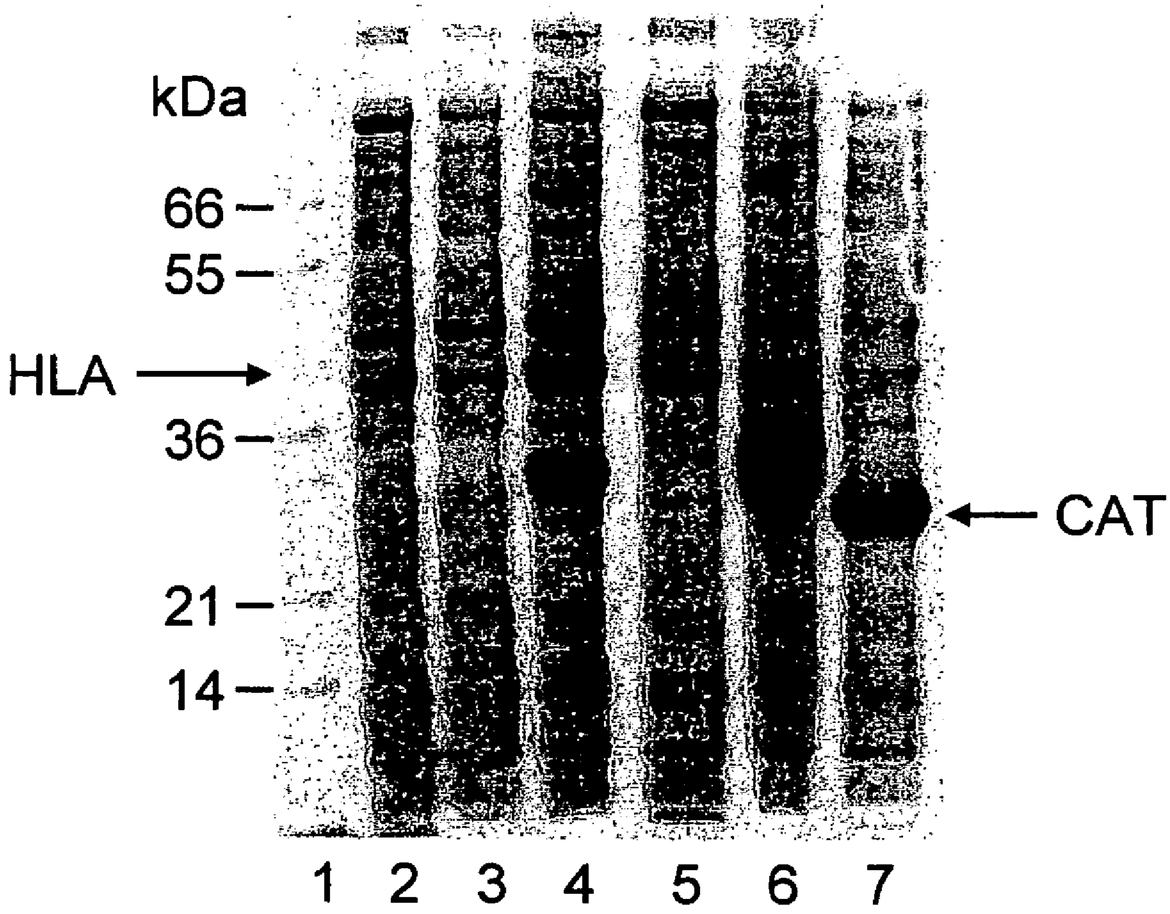

FIG. 28 is a photograph of a gel depicting HLA and CAT expression in *E. coli*. The genes encoding HLA (41 kDa) and CAT (26 kDa) were amplified by PCR and either topo cloned into pENTR/SD-dTopo and transferred into pET-DEST42 (lanes 3 and 6, respectively) or cloned directly into pET101-dTopo (lanes 4 and 7, respectively). These constructs were used to transform BL21(DE3) cells and induced to express by addition of IPTG to 1 mM for 3 hours at 37C. Cell lysates were run on a NuPage and stained with SafeStain™. Lanes 2 and 5 represent cells uninduced cell lysates from the respective pET-DEST42 cultures.

Figure 29:
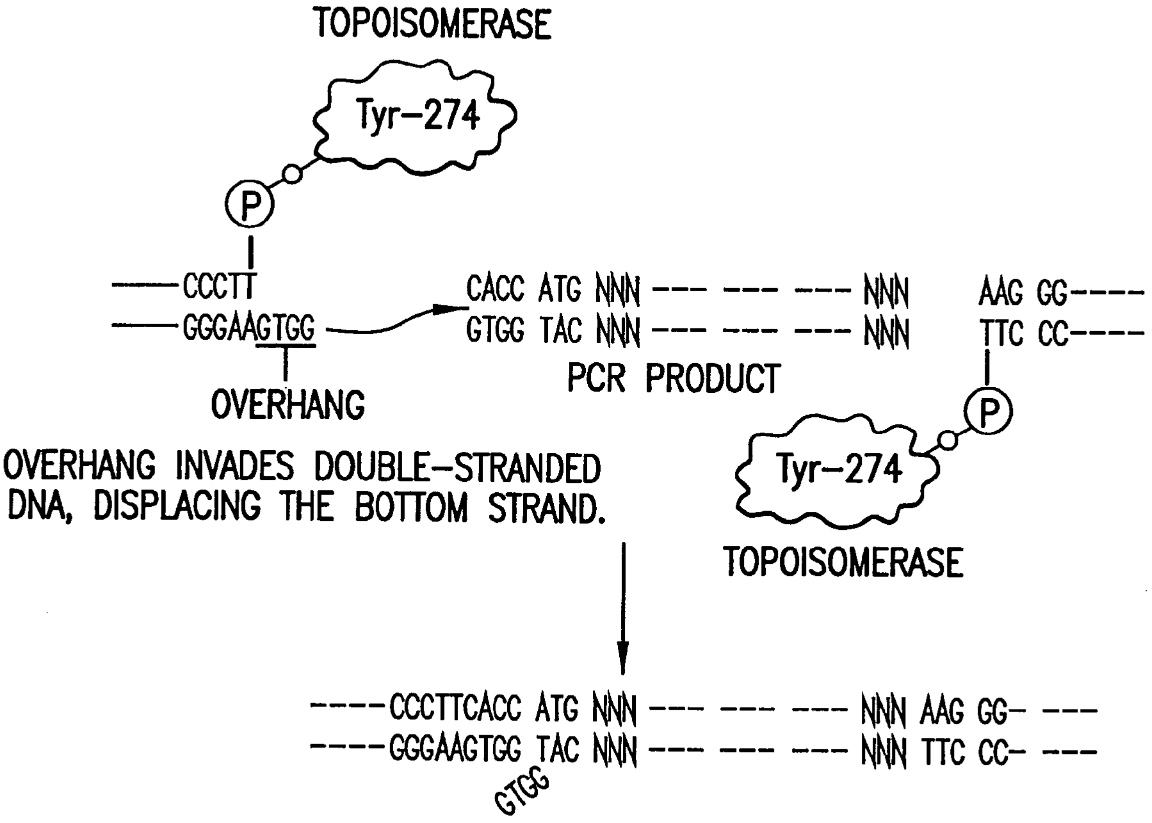

FIG. 29 is a schematic depiction of the binding of a topoisomerase to a recognition site near the 3' terminus of a target nucleic acid molecule. Upon binding of the topoisomerase, the downstream sequence (3' to the cleavage site) can dissociate, leaving a nucleic acid molecule having the topoisomerase covalently bound to the newly generated 3' end. (SEQ ID NO: 80)

Figure 30C:
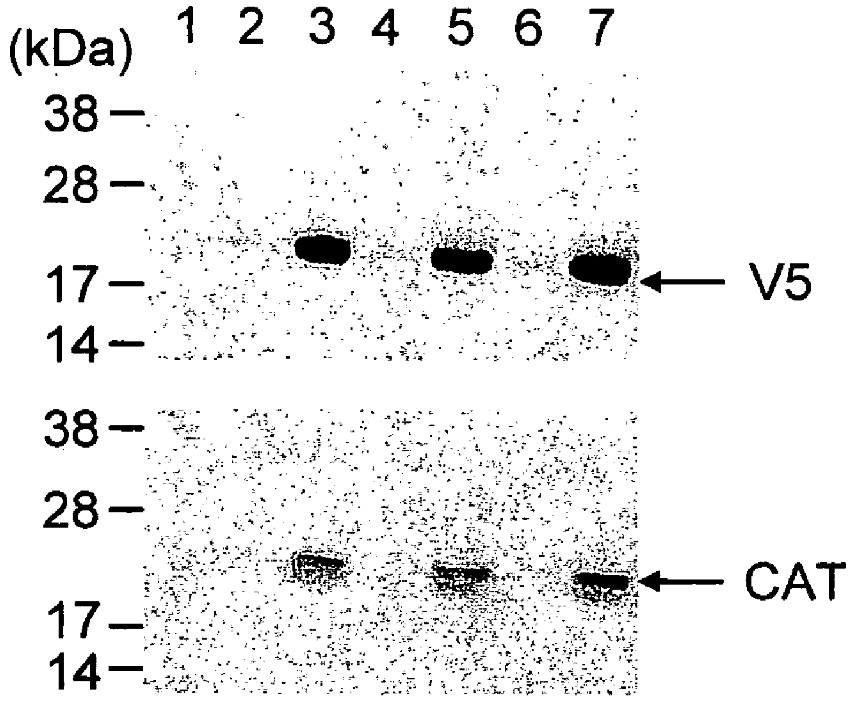

FIG. 30 depicts protein expression results (Western blot) for mammalian expression cassettes that were constructed by PCR amplification of expression elements and a gene of interest (CAT or V5) followed by a TOPO joining reaction performed with or without secondary PCR. Protein expression data from the expression cassette transfected into suspension TRex-CHO cells (FIG. 30A), adherent TRex-CHO cells (FIG. 30B), and adherent TRex-293 cells (FIG. 30C). For the Western blot, anti-V5 or anti-CAT antibodies were used for detection. Arrows indicate the position of the bands corresponding to the V5 or CAT proteins.

Figure 31:
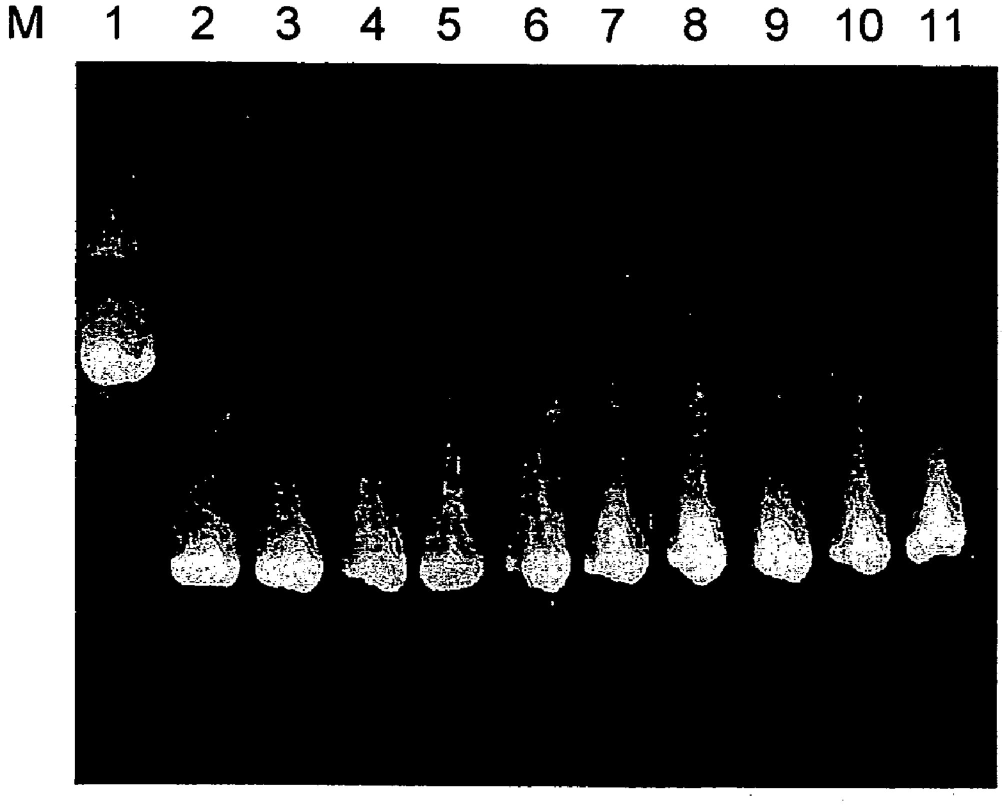

FIG. 31 is a photograph of an ethidium bromide-stained agarose gel containing PCR products showing that the Gateway-compatible cassette contained inserts of the expected size. The Gateway-compatible cassette was constructed by first generating a CAT insert by PCR and then using a TOPO joining reaction to introduce attB1 and attB2 adaptors. The purified DNA product was inserted into pDONR 222 using a BP reaction. Following transformation into *E. coli*, PCR was performed on the colonies and the PCR product was checked on an ethidium bromide-stained agarose gel.

Figure 32:
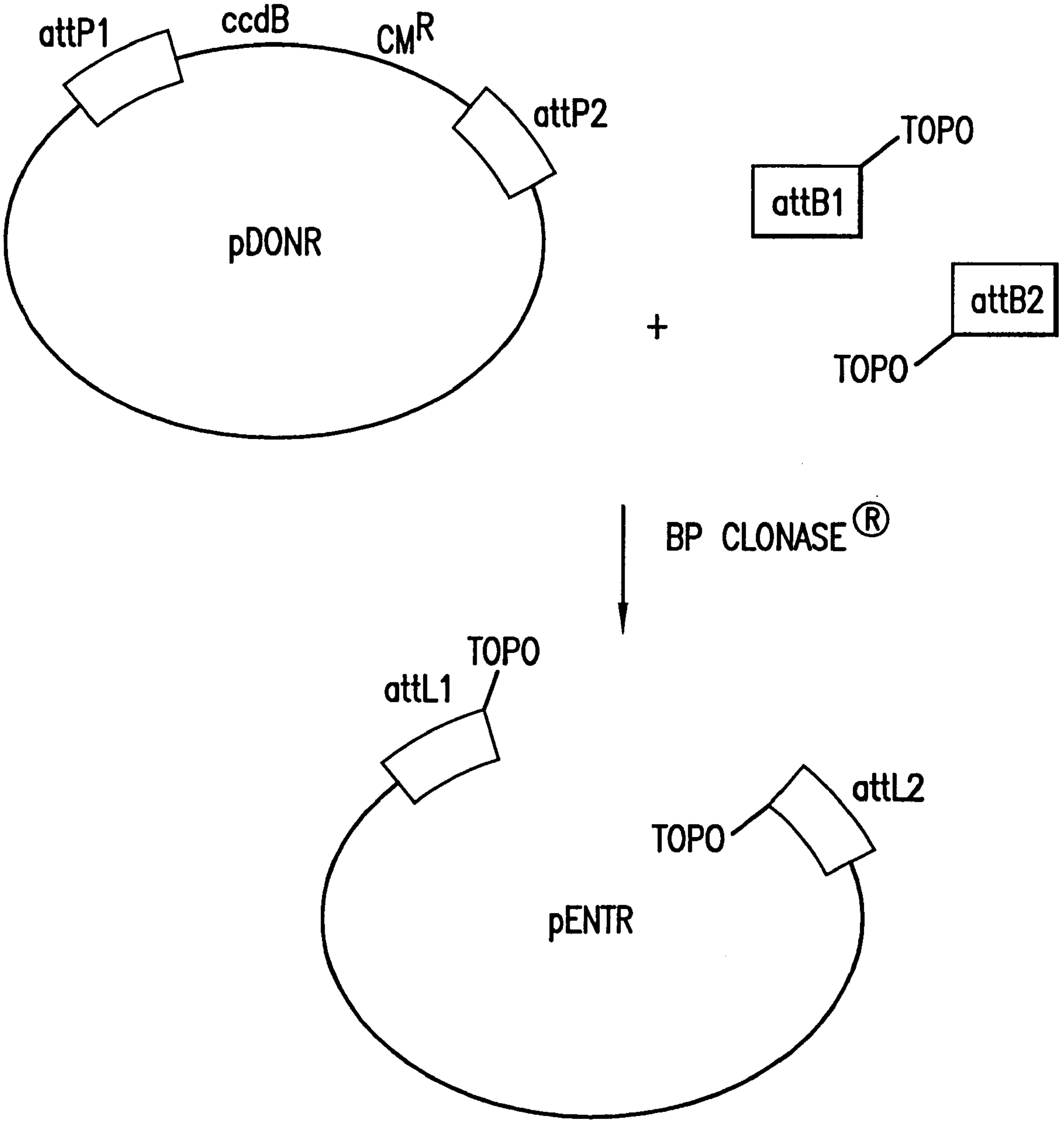

FIG. 32 is a schematic diagram depicting the preparation of topoisomerase-charged pENTR vectors, by charging pDONR vectors with topoisomerase and carrying out a BxP GATEWAY cloning reaction according to methods of the invention.

Figure 33:
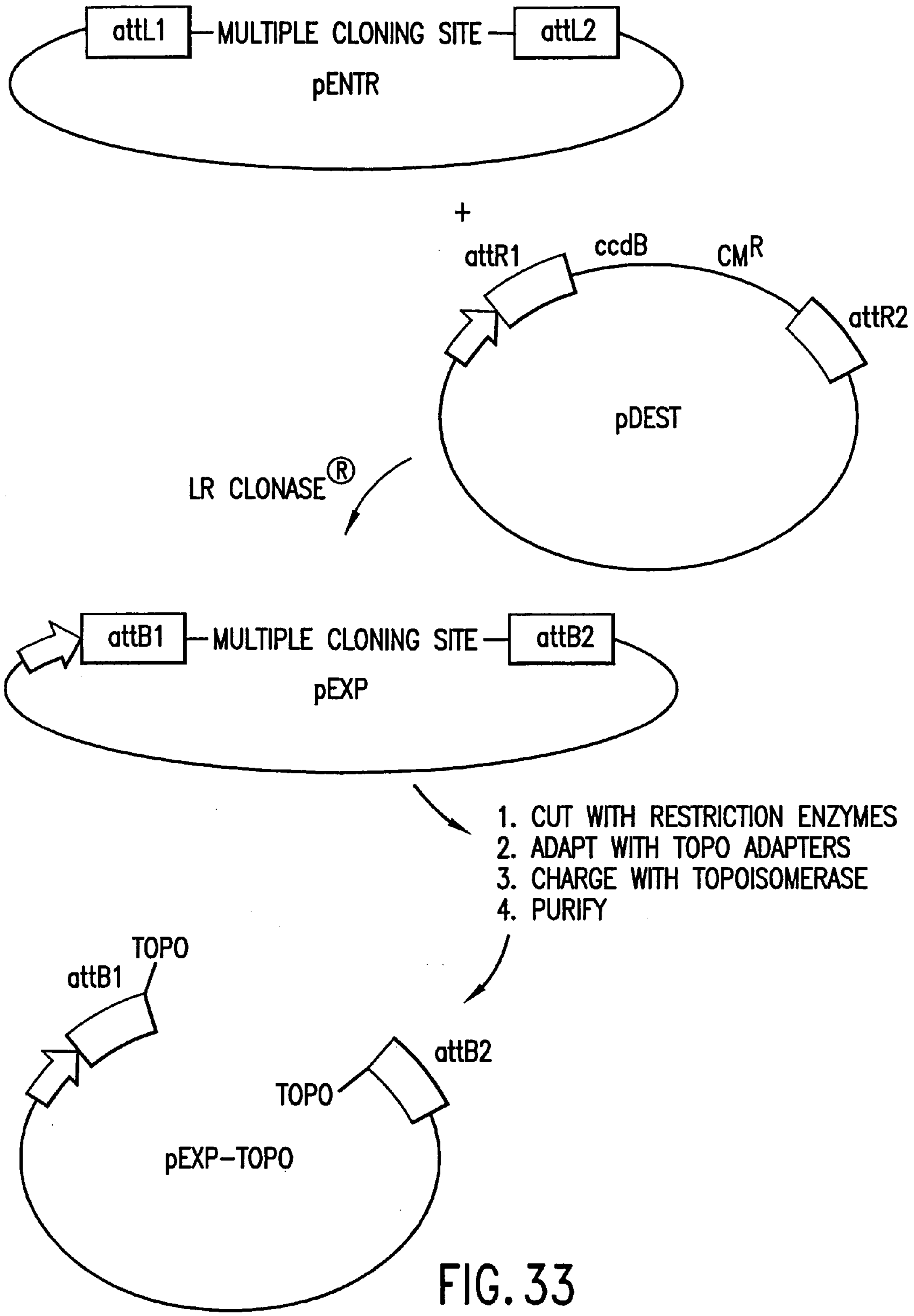

FIG. 33 is a schematic diagram depicting the preparation of topoisomerase-charged pEXP vectors, by charging pDEST vectors with topoisomerase and carrying out an LxR GATEWAY cloning reaction, then adding TOPO adaptors to the cut ends of the pEXP vector, according to methods of the invention.

Figure 34:
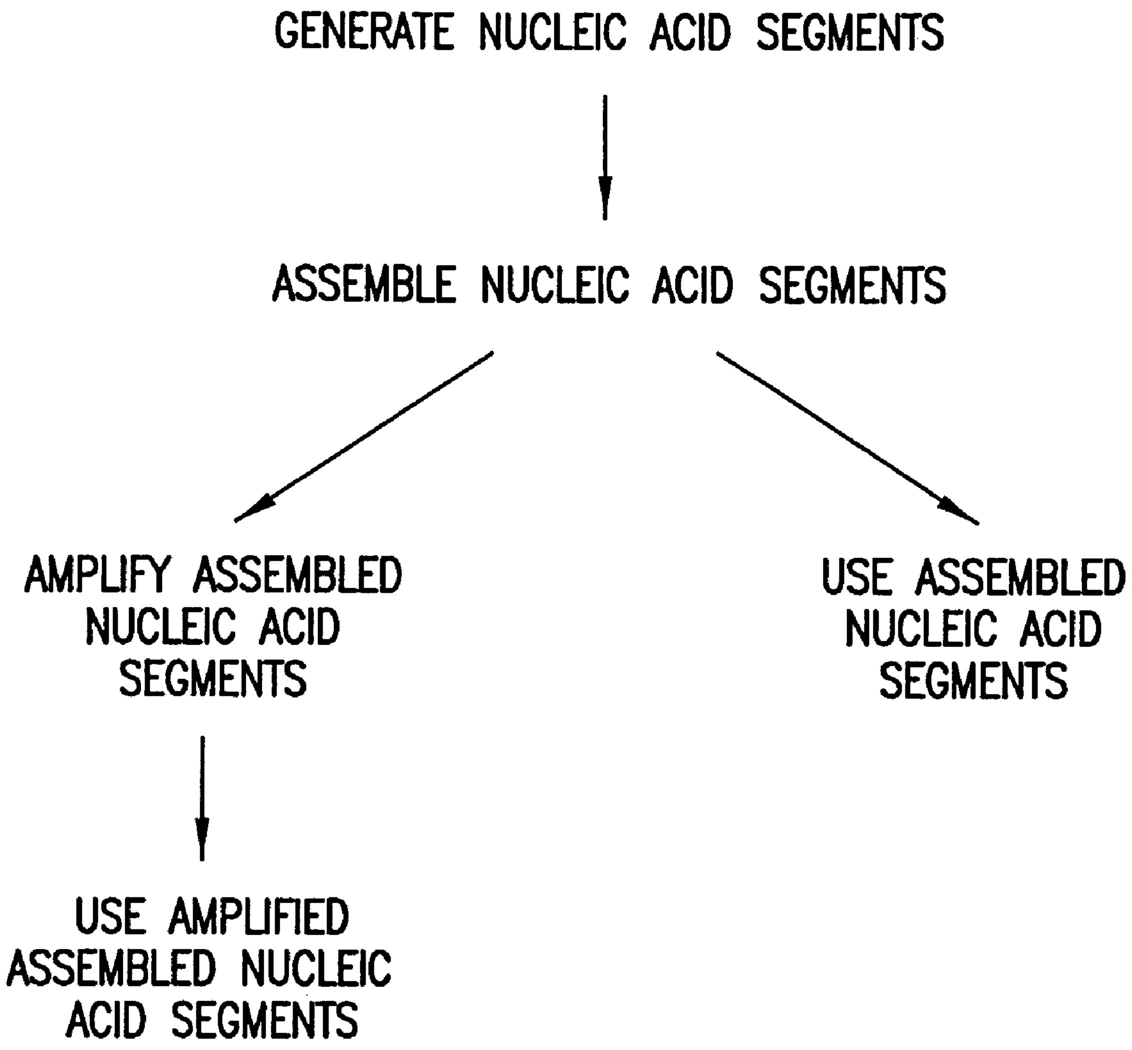

FIG. 34 shows a schematic outline of methods of the invention. In the first step, nucleic acid molecules to be assembled are generated using, for example, PCR. In the second step, nucleic acid molecules of the first step are assembled using methods of the invention (e.g., methods involving the use of topoisomerase to covalently linking at least one strand of one nucleic acid segments to another nucleic acid segment). In the third step, assembled nucleic acid molecules generated in the second step either may be used directly or may be amplified and then used. Examples of uses of the assembled molecules are described elsewhere herein.

Figure 35:
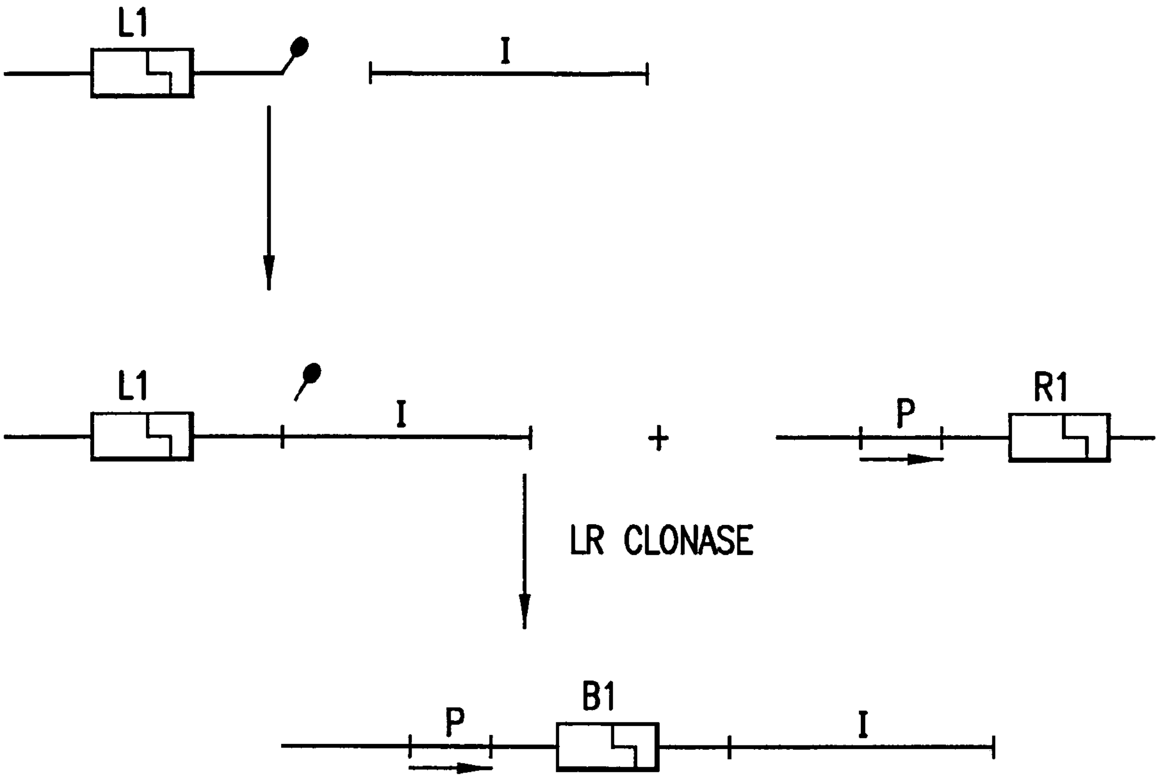

FIG. 35 shows a schematic representation of a process for using topoisomerase to link two nucleic acid segments, followed by single site recombination to recombine the linked nucleic acid segment with another nucleic acid segment. In the first step, a topoisomerase adapted nucleic acid segment which contains an attL1 recombination site is linked to another nucleic acid segment, referred to here as an insert (labeled "I"), using any of the topoisomerase mediated methods described herein for connecting nucleic acid molecules. The topoisomerase assembled nucleic acid segments are then contacted with another nucleic acid segment which contains a promoter, labeled "P", and an attR1 recombination site in the presence of LR Clonase™ under conditions which allow for recombination between the two recombination sites. Recombination results in the formation of a nucleic acid molecule which contains the insert nucleic acid segment in operable linkage with the promoter. Further, an attB1 recombination site is located between the promoter and the insert in the end product. The recombination sites shown in this figure are attL and attB sites, but any suitable recombination sites could be used.

Figure 36:
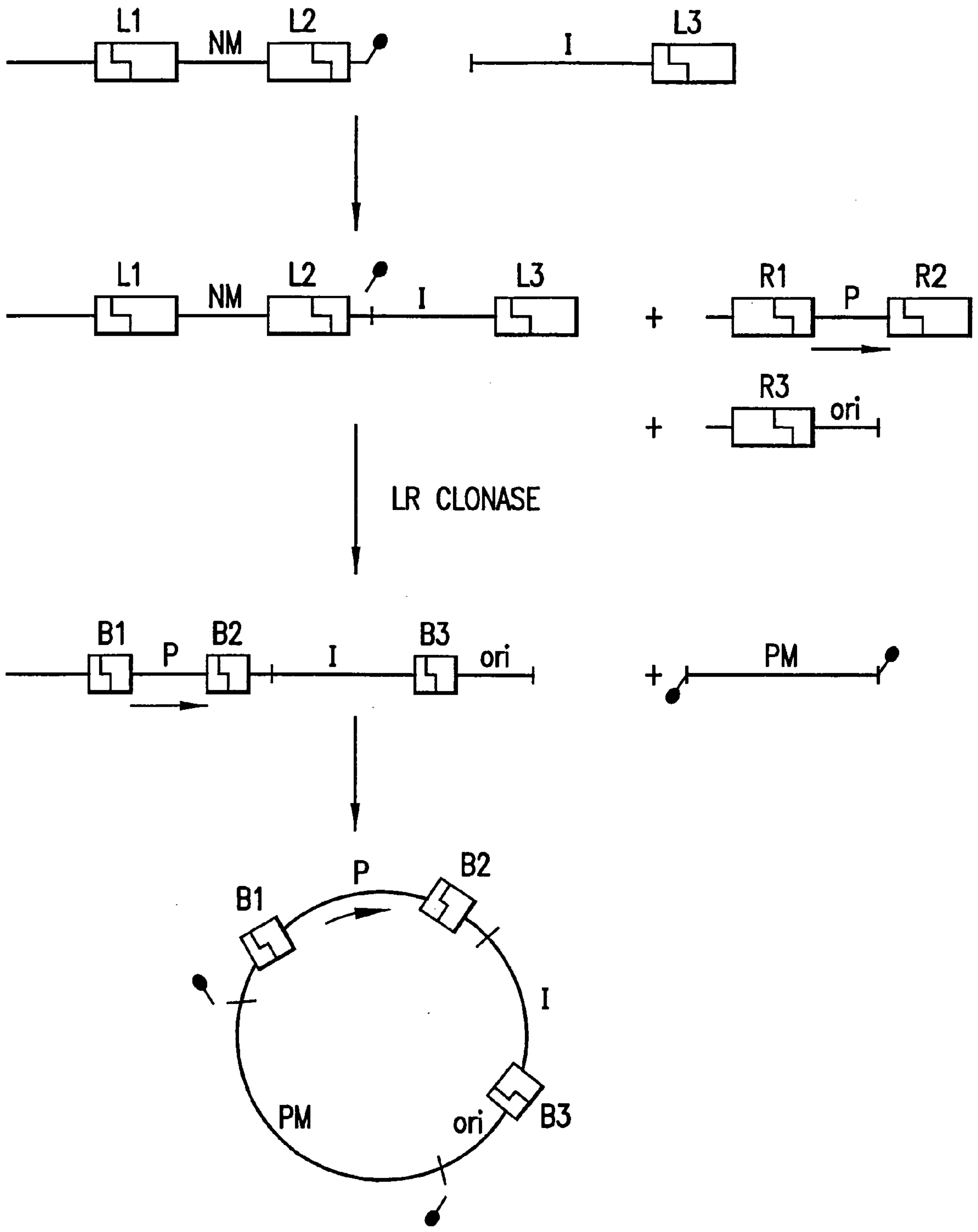

FIG. 36 shows a schematic representation of a process for using topoisomerase and recombination to recombine and/or link five separate nucleic acid segments and circularize the resulting product. In the first step, a topoisomerase adapted nucleic acid segment which contains attL1 and attL2 recombination sites and a negative selection marker (labeled "NM") is linked to another nucleic acid segment, referred to here as an insert (labeled "I"), using any of the topoisomerase mediated methods described herein for connecting nucleic acid molecules. The topoisomerase assembled nucleic acid segments are then contacted with two additional nucleic acid segments, each of which contains at least one attR recombination site, in the presence of LR CLONASE™ (Invitrogen Corporation, Carlsbad, Calif.) under conditions which allow for recombination between the various recombination sites. In certain such methods, for example, TOPO-adapted vectors are incubated with one or more nucleic acid segments (e.g., one or more PCR products) at room temperature (e.g., about 20-20° C.) for about 5–30 (and preferably about 10) minutes; the reaction is then heat-treated by incubation at about 80° C. for about 20 minutes, and the reaction mixture then used in a standard LR reaction according to manufacturer's instructions (Invitrogen Corporation, Carlsbad Calif.), except the incubation time for the LR reaction is increased to about 3 hours. The recombination reactions result in the formation of a product molecule in which the promoter is linked to (1) the insert molecule and (2) an origin of replication (labeled "ori"). This product molecule is then connected to a nucleic acid segment which is topoisomerase adapted at both termini and contains a positive selection marker (labeled "PM"). Further, the final topoisomerase linkage step results in the formation of a circular nucleic acid molecule. The recombination sites shown in this figure are attL and attB sites, but any suitable recombination sites could be used.

Figure 37:
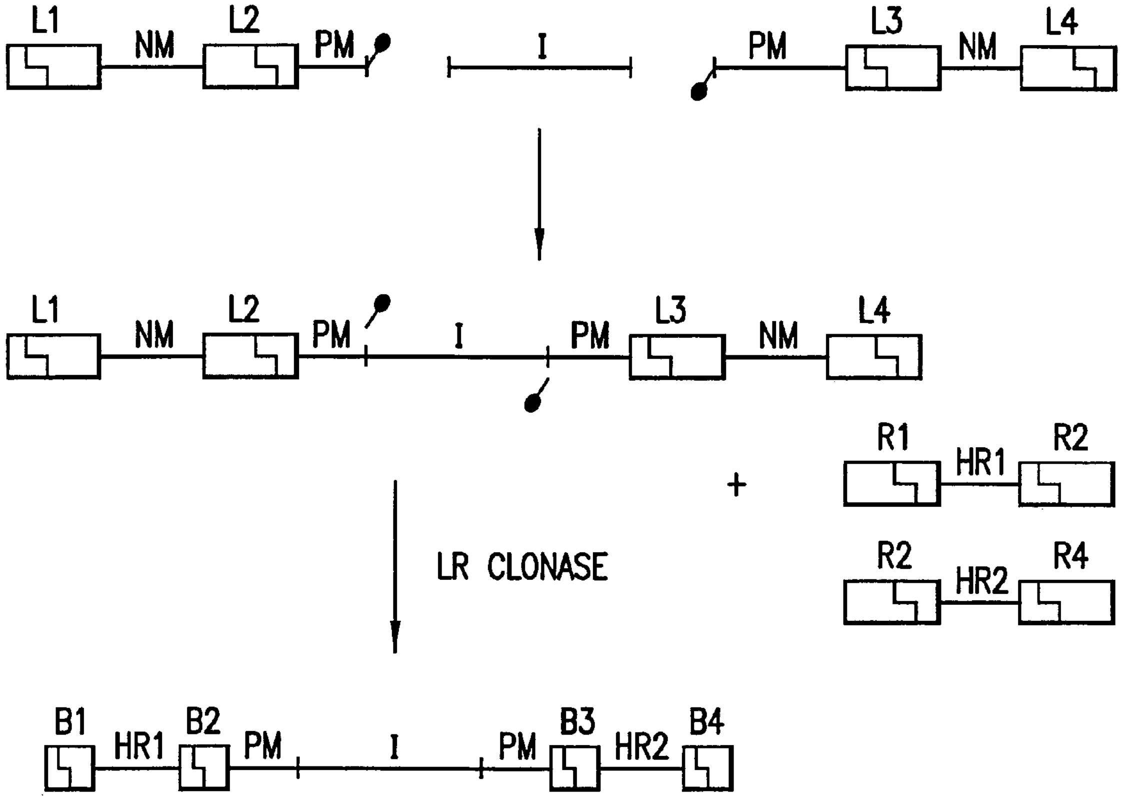

FIG. 37 shows a schematic representation of a process for the preparation of nucleic acid molecules for performing homologous recombination. In this instance, three nucleic acid segments are connected to each other using methods which involve topoisomerase mediated covalent linkage of nucleic acid strands of the individual segments. Two of these nucleic acid segments each contain a positive selection marker and two attL sites which flank a negative selection marker. Thus, the nucleic acid molecule which results from the first step contains a nucleic acid segment, referred to here as an insert. On each side of the insert is (1) a positive selection marker and (2) two recombination sites which flank a negative selection marker. LR CLONASE™ catalyzed recombination in the presence of two nucleic acid segments which contain regions that share homology to a chromosomal locus where the nucleic acid end product is designed to integrate (labeled "HR1" and HR2") results in the formation of the end product nucleic acid molecule shown. As one skilled in the art would recognize, any suitable recombination sites could be used in the process set out in this figure.

Figure 38:
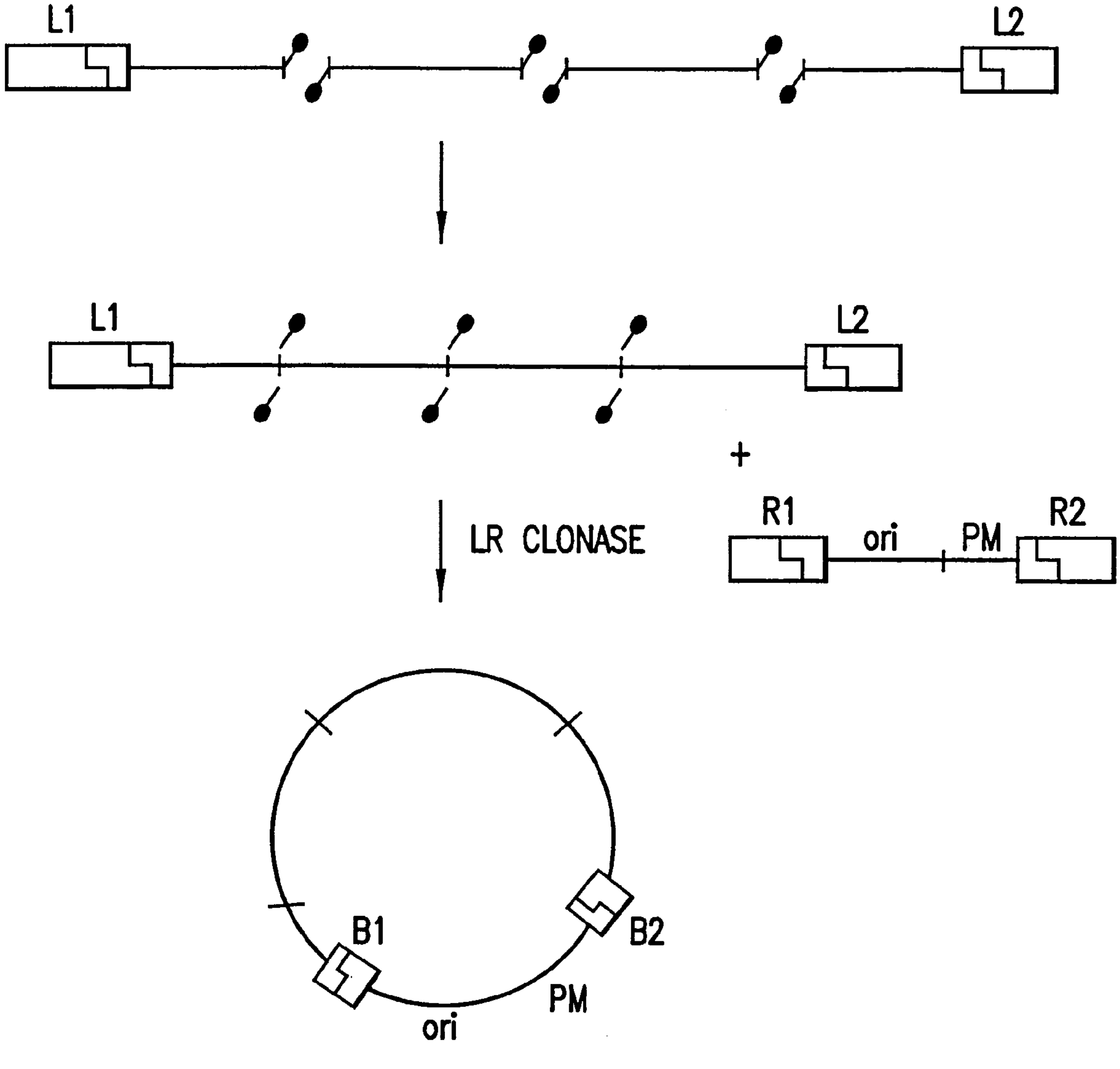

FIG. 38 shows a schematic representation of the linking of four nucleic acid segments using toposiomerase to generate a linear nucleic acid molecule with recombination sites (labeled "L1" and "L2") located near the termini. Upon toposiomerase mediated linkage of the nucleic acid strands, no nicks are present at the junction points. In a second step, the topoisomerase assembled nucleic acid segments are contacted with another nucleic acid segment which contains an origin of replication (labeled "ori"), a positive selection marker (labeled "PM"), an attR1 recombination site, and an attR2 recombination site in the presence of LR CLONASE™ under conditions which allow for recombination between the recombination sites. Recombination results in the formation of a circular nucleic acid molecule as shown. The recombination sites shown in this figure are attL and attB sites, but any suitable recombination sites could be used.

Figure 39:
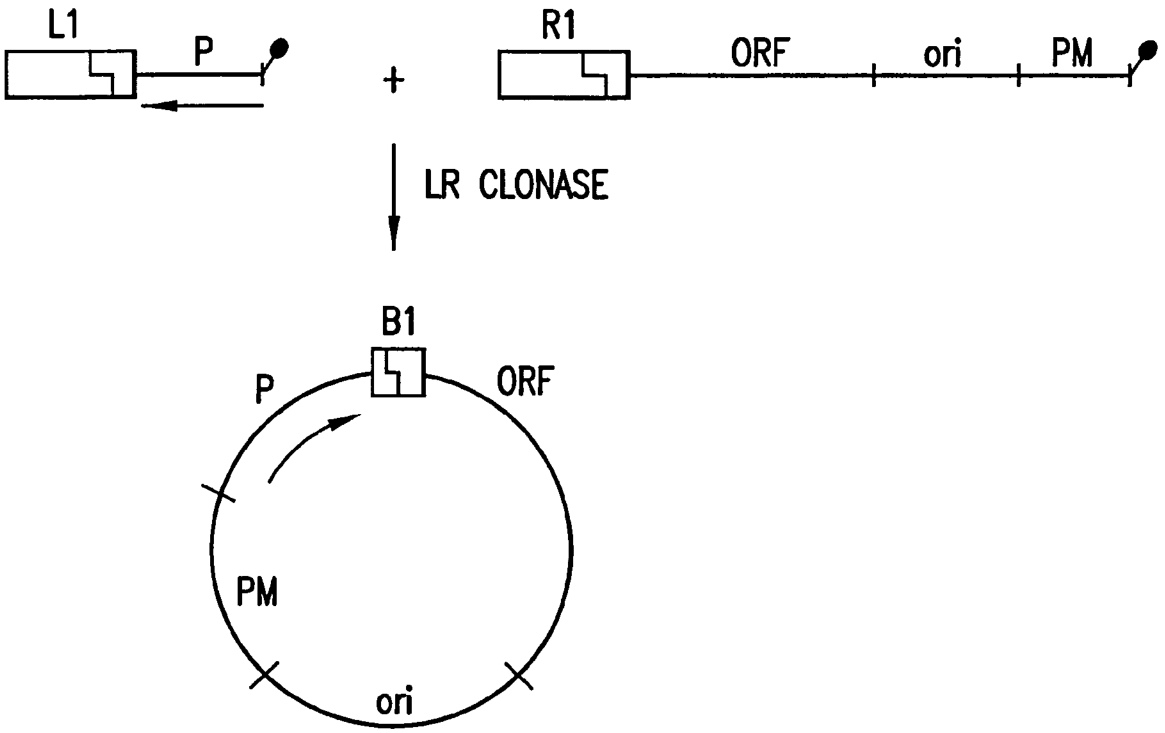

FIG. 39 shows a schematic representation of the linking of two nucleic acid segments in a single step process using toposiomerase and recombination sites to generate a circular nucleic acid molecule. One of the nucleic acid segments contains an attL1 recombination site (labeled "L1"), a promoter (labeled "P"), and toposiomerase molecule covalently linked to one terminus. The other nucleic acid segment contains an attR1 recombination site (labeled "R1"), an open reading frame (labeled "ORF"), an origin of replication (labeled "ORI"), a positive selection marker (labeled "PM"), and topoisomerase molecule covalently linked to one terminus. Thus, when these two nucleic acid segments are contacted with each other in the presence of LR CLONASE™ under conditions which allow for recombination between the attL and attR recombination sites and topoisomerase mediated linkage of nucleic acid strands, a circular molecule is formed having the structure indicated. The recombination sites shown in this figure are attL and attB sites, but any suitable recombination sites could be used.

Figure 40:
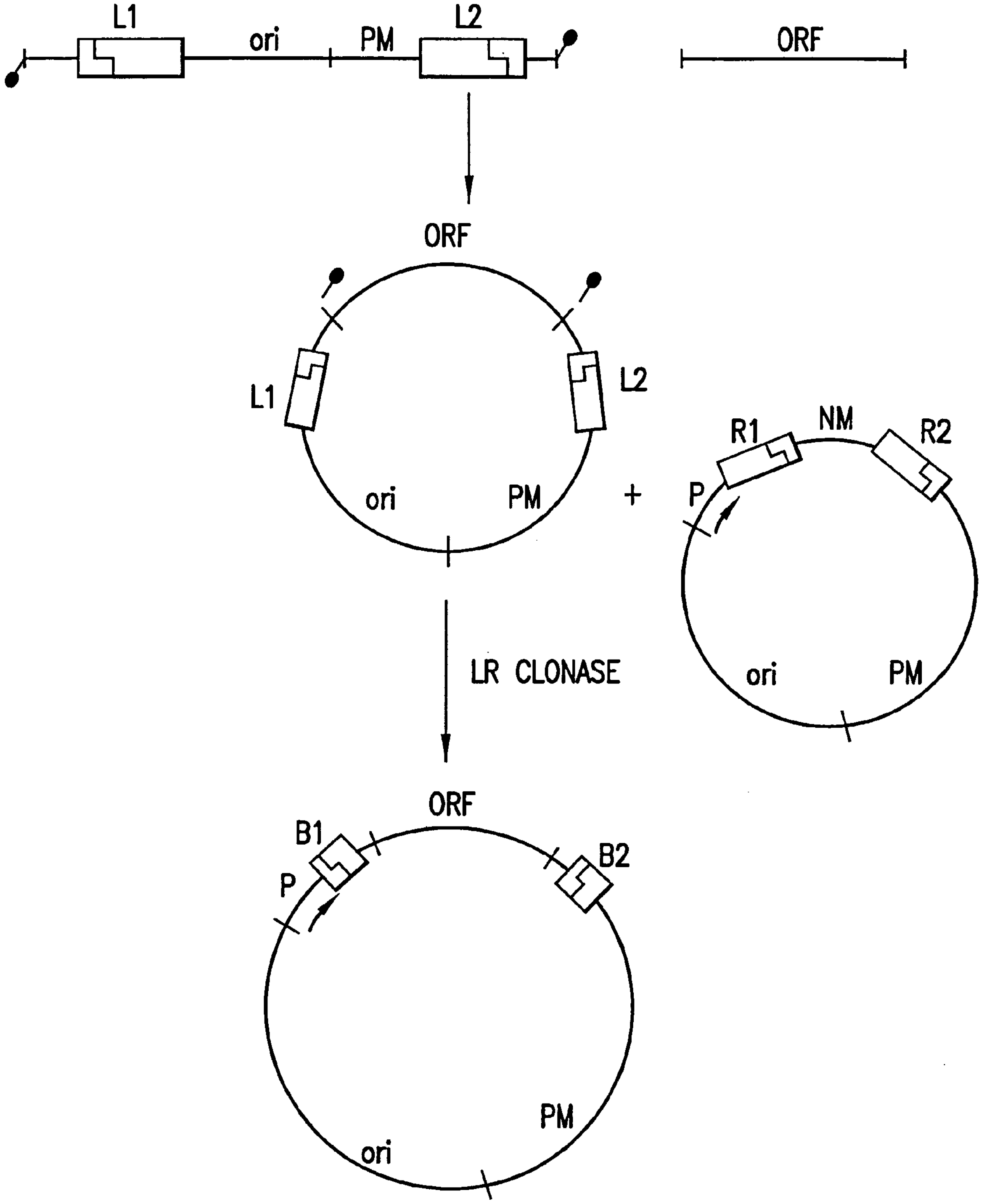

FIG. 40 shows a schematic representation of the linking of two nucleic acid segments using toposiomerase mediated methods to generate a circular nucleic acid molecule. This circular molecule contains an open reading frame (labeled "ORF") positioned between attL1 and attL2 recombination site (labeled "L1" and "L2"). The topoisomerase assembled product then undergoes recombination with another circular molecule which contains attR1 and attR2 recombination sites to generate a third circular nucleic acid molecule which contains the open reading frame positioned between attB 1 and attB2 recombination sites. Further, the open reading frame is operably linked to a promoter. The recombination sites shown in this figure are attL and attB sites, but any suitable recombination sites could be used.

Figure 41:
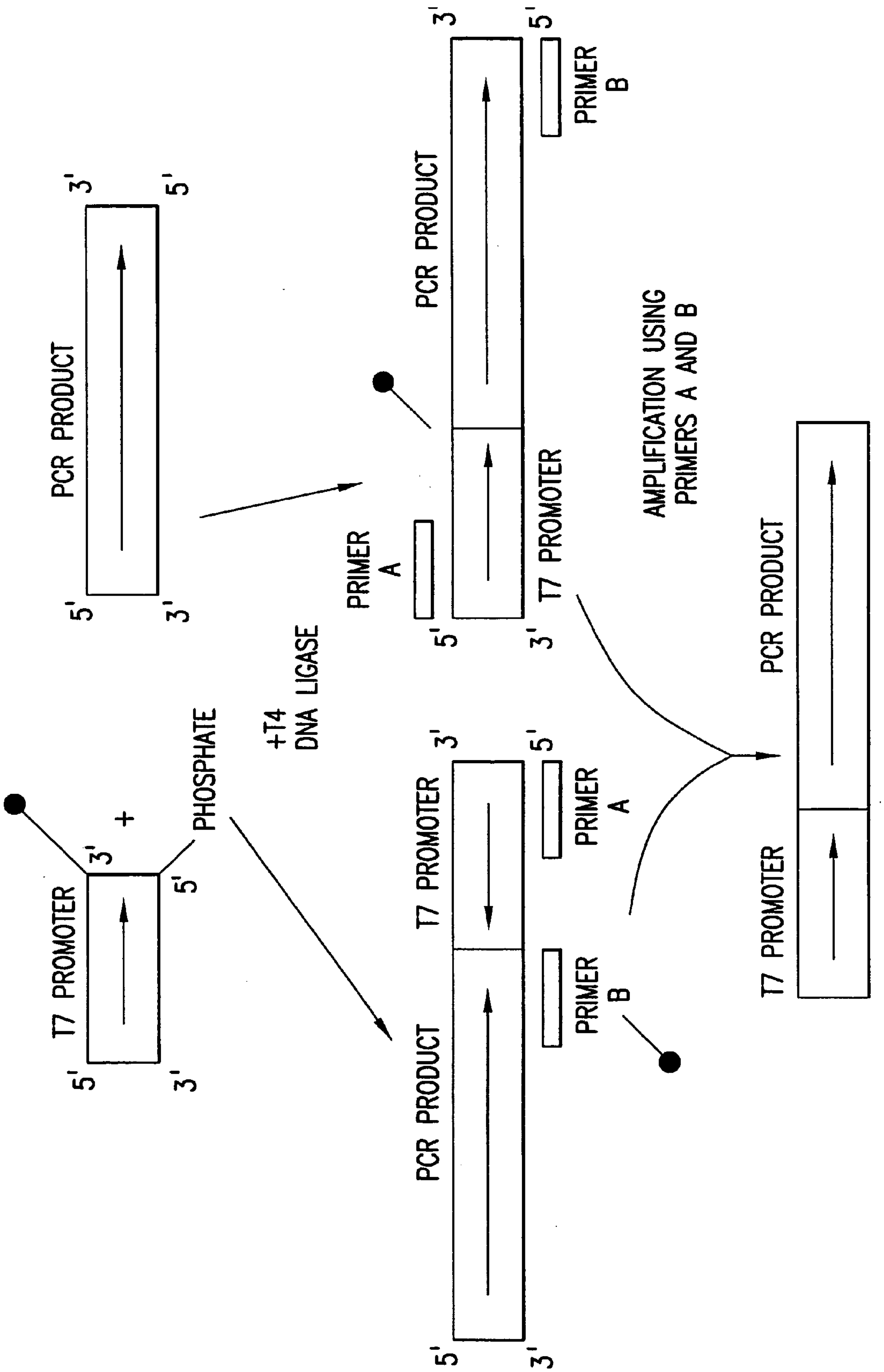

FIG. 41 shows an example of a process by which two nucleic acid segments may be covalently linked to each other in both strands at the junction where the two nucleic acid segments are connected. As in other figures presented herein, the "lollipop" type symbol represents a topoisomerase molecule. Further, the arrows within the boxes represent the functional directionality of the particular nucleic acid segment. For example, if the PCR product is an open reading frame, then the 3' end of the coding region (i.e., the end of the coding region which encodes the C-terminal end of the polypeptide) would be at the point of the arrow and the 5' end would be at the other end.

FIG. 42. T7 TOPO-linker. (A) Diagram of TOPO-activated T7 linker. Three oligonucleotides were annealed, incubated with TOPO, and the diagrammed TOPO-DNA covalent complex was purified as described in Materials and Methods. The T7 promoter is shown in bold, and the TOPO recognition site is underlined. (B) Use of TOPO-linker to add a T7 RNA polymerase promoter to a PCR product generated by Taq polymerase (A-tailed).

FIG. 43. FPLC purification. (A) Chromatogram of FPLC purification of TOPO-activated T7 linker. $A_{254}$ trace is shown in blue, conductivity (salt concentration) in brown, and the relative concentration of buffer B in the mixing chamber in green. The boundaries of eleven 1 ml flow-through fractions and 39–0.2 ml elution fractions are designated with broken red lines. The $A_{254}$ trace is actually shifted approximately 3 elution fractions to the left as determined by gel analysis (see FIG. 44A). (B) Magnified $A_{254}$ peak showing small right shoulder corresponding to the position of free topoisomerase (see also FIG. 44B).

FIG. 44. Gel analysis of fractions. (A) EtBr-stained 10% TBE polyacrylamide gels. Except the undigested load, all fractions were incubated with proteinase K prior to loading. 10 bp DNA ladder, annealed oligos, the load, flow-through (F-T) fractions 2–5, and elution fractions 29–40 are shown. (B) Coomassie-stained 4–12% Bis-Tris NuPAGE gels. The sizes of some of the marker bands in kDa are shown. "TOPO" designates the free topoisomerase control lane (see Materials & Methods). Load, flow-through, and elution fractions are labeled as in (A).

FIG. 45. PCR, linking reactions, and transcription. (A–D). EtBr-stained 1.2% agarose-TAE gels. (A,C) The 1.2 kb ladder band corresponds to 25 ng DNA. (A) Primary PCR reactions loaded to estimate product yields. "T7–" indicates that the reverse primer contained a 5' T7 promoter sequence. (B) The products of linking reactions with ("+") or without ("–") T7 TOPO linker and with actin or GFP primary PCR products from (A). (C) Products from the secondary amplification of the linking reactions in (B). The volume loaded from each PCR reaction is indicated. "F+T" indicates that gene-specific forward primers and T7amp1 primer were used in the amplification. "T" indicates that the T7amp1 primer alone was used. Negative control ("neg ctrl") reactions used the mock linking reactions in (B) as templates. (D) Products of transcription. "neg ctrl" transcriptions used the negative control "F+T" secondary amplification products shown in (C). The "T7–" transcriptions were performed with the "T7–" primary PCR products in (A) as templates.

FIG. 46. pUC19/actin positive control plasmid. (A) Vector map of the positive control plasmid. The actin template sequence was cloned into BamHI and HindIII sites in the pUC19 polylinker as described in Materials & Methods. (B)–(D) Photographs of ethidium bromide stained gels. (B) 6% polyacrylamide TBE gel of linking reactions of a primary PCR product amplified from pUC19/actin with actinF and actinR primers in the presence (right) or absence (left) of T7 TOPO linker. (C) 1.2% agarose-TAE gel of secondary amplification product of linked actin from (B) and the primary product of pUC19/actin amplified with actinF and T7-actinR primers. (D) 1.2% agarose-TAE gel DNase I digested transcription reactions using the PCR products in (C) as templates.

DETAILED DESCRIPTION OF THE INVENTION

Definitions

In the description that follows, a number of terms used in recombinant nucleic acid technology are utilized extensively. In order to provide a clear and more consistent understanding of the specification and claims, including the scope to be given such terms, the following definitions are provided.

Gene: As used herein, a gene is a nucleic acid sequence that contains information necessary for expression of a polypeptide, protein or functional RNA (e.g., a ribozyme, tRNA, rRNA, mRNA, etc.). It includes the promoter and the structural gene open reading flame sequence (orf) as well as other sequences involved in expression of the protein.

Structural gene: As used herein, a structural gene refers to a nucleic acid sequence that is transcribed into messenger RNA that is then translated into a sequence of amino acids characteristic of a specific polypeptide.

Host: As used herein, a host is any prokaryotic or eukaryotic organism that is a recipient of a replicable expression vector, cloning vector or any nucleic acid molecule. The nucleic acid molecule may contain, but is not limited to, a structural gene, a transcriptional regulatory sequence (such as a promoter, enhancer, repressor, and the like) and/or an origin of replication. As used herein, the terms "host," "host cell," "recombinant host" and "recombinant host cell" may be used interchangeably. For examples of such hosts, see Maniatis et al., *Molecular Cloning: A Laboratory Manual*, Cold Spring Harbor Laboratory, Cold Spring Harbor, N.Y. (1982).

Derivative: As used herein, a "derivative" of a specified host is a progeny of the specified host, a modified or mutated host obtained or derived from the specified host or its progeny, or other recipient host that contains genetic material obtained directly or indirectly from the specified host. Such a derivative host may, for example, be formed by removing genetic material from a specified host and subsequently introducing it into another host (i.e., the progeny or other recipient host) by any conventional methodology including, but not limited to, transformation, conjugation, electroporation, transduction and the like. A derivative may be formed by introducing one or more mutations or modifications into the genome or other genetic material (e.g. vectors, plasmids, extrachromosomal elements, etc.) of a host. Such mutations or modifications may include one or more insertion mutations, deletion mutations and/or substitutions or various combinations thereof. The mutations or modifications may be insertions into the genome or other genetic material (e.g. vectors, plasmids, extrachromosomal elements, etc.) of the host. Alternatively, the mutations may be deletions of one or more bases and/or nucleic acid sequences from the genome or other genetic material (e.g. vectors, plasmids, extrachromosomal elements, etc.) of the host. In some instances, the mutations may be the alteration of one or more bases in the genome of the host. Such modifications or mutations may also comprise substituting one or more nucleic acid bases and/or nucleic acid molecules for other nucleic acid molecules and/or bases. In addition, one host is a derivative of a parent host if it contains the genome of the parent host but does not contain some or all of the same extrachromosomal nucleic acid molecules. Thus, a strain produced by curing some or all of the endogenous vectors from a parent strain is a derivative of the parent strain. Derivatives of a host of the invention may also include those hosts obtained by the addition of one or more nucleic acid molecules into the host of interest. Nucleic acid molecules which may be introduced into a host will be recognized by one skilled in the art and may include, but is not limited to, vectors, plasmids, transposons, oligonucleotides, RNA, DNA, RNA/DNA hybrids, phage sequences, virus sequences, regardless of the form or conformation (e.g. linear, circular, supercoiled, single stranded, double stranded, single/double stranded hybrids and the like). Examples of mutations or other genetic alterations which may be incorporated into the hosts of the present invention include, but are not limited to, mutations or alterations that create: a recA$^-$ genotype such as recA1/recA13 or recA deletions, a lacZ$^-$ genotype that allows alpha complementation such as lacX74, lacZΔM15 or other lacZ deletion, a protease deficient genotype such as Δlon and/or ompT$^-$, an endonuclease minus genotype such as endA1, a genotype suitable for M13 phage infection by including the F' episome, a restriction negative, modification positive genotype such as hsdR17($r_K^-$, $m_K^+$), a restriction negative, modification negative genotype such as hsdS20($r_B^-$, $m_B^-$), a methylase deficient genotype such as mcrA and/or mcrB and/or mrr, a genotype suitable for taking up large plasmids such as deoR, a genotype containing suppressor mutations such as supE and/or supF. Other suitable modifications are known to those skilled in the art and such modifications are considered to be within the scope of the present invention.

Transcriptional Regulatory Sequence: As used herein, transcriptional regulatory sequence is a functional stretch of nucleotides contained on a nucleic acid molecule, in any configuration or geometry, that acts to regulate the transcription of one or more structural genes into messenger RNA. Examples of transcriptional regulatory sequences include, but are not limited to, promoters, operators, enhancers, repressors, and the like. Transcriptional regulatory sequences may also regulate the transcription of nucleic acid molecules which encode functional RNAs (e.g., ribozymes, tRNAs, rRNAs, mRNAs, etc.).

Promoter: As used herein, a promoter is an example of a transcriptional regulatory sequence, and is specifically a nucleic acid sequence generally described as the 5'-region of a gene located proximal to the start codon. The transcription of an adjacent nucleic acid segment is initiated at the promoter region. A repressible promoter's rate of transcription decreases in response to a repressing agent. An inducible promoter's rate of transcription increases in response to an inducing agent. A constitutive promoter's rate of transcription is not specifically regulated, though it can vary under the influence of general metabolic conditions.

Insert: As used herein, an insert is a desire nucleic acid segment that is a part of a larger nucleic acid molecule.

Target Nucleic Acid Molecule: As used herein, target nucleic acid molecule is a nucleic acid segment of interest preferably nucleic acid which is to be acted upon using the compounds and methods of the present invention. Such target nucleic acid molecules preferably contain one or more genes or portions of genes.

Insert Donor: As used herein, an insert donor is one of the two parental nucleic acid molecules (e.g. RNA or DNA) of the present invention which carries the Insert. The Insert Donor molecule comprises the Insert flanked on both sides with recombination sites. The Insert Donor can be linear or circular. In one embodiment of the invention, the Insert Donor is a circular nucleic acid molecule, optionally supercoiled, and further comprises a cloning vector sequence outside of the recombination signals (see FIG. 1). When a population of Inserts or population of nucleic acid segments are used to make the Insert Donor, a population of Insert Donors result and may be used in accordance with the invention.

Product: As used herein, a product is one the desired daughter molecules comprising the A and D sequences which is produced after the second recombination event during the recombinational cloning process (see FIG. 1). The Product contains the nucleic acid which was to be cloned or subcloned. In accordance with the invention, when a population of Insert Donors are used, the resulting population of Product molecules will contain all or a portion of the population of Inserts of the Insert Donors and preferably will contain a representative population of the original molecules of the Insert Donors.

Recognition sequence: As used herein, a recognition sequence (alternatively and equivalently referred to herein as a "recognition site") is a particular sequence to which a protein, chemical compound, DNA, or RNA molecule (e.g., restriction endonuclease, a topoisomerase, a modification methylase, or a recombinase) recognizes and binds. In the present invention, a recognition sequence will usually refer to a recombination site (which may alternatively be referred to as a recombinase recognition site) or a topoisomerase recognition site. For example, the recognition sequence for Cre recombinase is loxP which is a 34 base pair sequence comprised of two 13 base pair inverted repeats (serving as the recombinase binding sites) flanking an 8 base pair core sequence. See FIG. 1 of Sauer, B., Current Opinion in Biotechnology 5:521–527 (1994). Other examples of such recognition sequences are the attB, attP, attL, and attR sequences which are recognized by the recombinase enzyme (Integrase. attB is an approximately 25 base pair sequence containing two 9 base pair core-type Int binding sites and a 7 base pair overlap region. attP is an approximately 240 base pair sequence containing core-type Int binding sites and arm-type Int binding sites as well as sites for auxiliary proteins integration host factor (IHF), FIS and excisionase (Xis). See Landy, Current Opinion in Biotechnology 3:699–707 (1993). Such sites may also be engineered according to the present invention to enhance production of products in the methods of the invention. When such engineered sites lack the P1 or H1 domains to make the recombination reactions irreversible (e.g., attR or attP), such sites may be designated attR' or attP' to show that the domains of these sites have been modified in some way. Examples of topoisomerase recognitions sites include, but are not limited to, the sequence 5'-GCAACTT-3' that is recognized by *E. coli* topoisomerase III (a type I topoisomerase); the sequence 5'-(C/T)CCTT-3' which is a topoisomerase recognition site that is bound specifically by most poxvirus topoisomerases, including vaccinia virus DNA topoisomerase I; and others that are known in the art as discussed elsewhere herein.

Recombination proteins: As used herein, recombination proteins include excisive or integrative proteins, enzymes, co-factors or associated proteins that are involved in recombination reactions involving one or more recombination sites, which may be wild-type proteins (See Landy, Current Opinion in Biotechnology 3:699–707 (1993)), or mutants, derivatives (e.g., fusion proteins containing the recombination protein sequences or fragments thereof), fragments, and variants thereof.

Recombination site: A used herein, a recombination site is a recognition sequence on a nucleic acid molecule participating in an integration/recombination reaction by recombination proteins. Recombination sites are discrete sections or segments of nucleic acid on the participating nucleic acid molecules that are recognized and bound by a site-specific recombination protein during the initial stages of integration or recombination. For example, the recombination site for Cre recombinase is loxP which is a 34 base pair sequence comprised of two 13 base pair inverted repeats (serving as the recombinase binding sites) flanking an 8 base pair core sequence. See FIG. 1 of Sauer, B., Curr. Opin. Biotech. 5:521–527 (1994). Other examples of recognition sequences include the attB, attP, attL, and attR sequences described herein, and mutants, fragments, variants and derivatives thereof, which are recognized by the recombination protein (Int and by the auxiliary proteins integration host factor (IHF), FIS and excisionase (Xis). See Landy, Curr. Opin. Biotech. 3:699–707 (1993).

Recombinational Cloning: As used herein, recombinational cloning is a method, such as that described in U.S. Pat. Nos. 5,888,732, 6,143,557, 6,171,861, 6,270,969, and 6,277,608 (the contents of which are fully incorporated herein by reference), and as also described herein, whereby segments of nucleic acid molecules or populations of such molecules are exchanged, inserted, replaced, substituted or modified, in vitro or in vivo. Preferably, such cloning method is an in vitro method.

Repression cassette: As used herein, repression cassette is a nucleic acid segment that contains a repressor or a Selectable marker present in the subcloning vector.

Selectable marker: As used herein, selectable marker is a nucleic acid segment that allows one to select for or against a molecule (e.g., a replicon) or a cell that contains it, often under particular conditions. These markers can encode an activity, such as, but not limited to, production of RNA, peptide, or protein, or can provide a binding site for RNA, peptides, proteins, inorganic and organic compounds or compositions and the like. Examples of selectable markers include but are not limited to: (1) nucleic acid segments that encode products which provide resistance against otherwise toxic compounds (e.g., antibiotics); (2) nucleic acid segments that encode products which are otherwise lacking in the recipient cell (e.g., tRNA genes, auxotrophic markers); (3) nucleic acid segments that encode products which suppress the activity of a gene product; (4) nucleic acid segments that encode products which can be readily identified (e.g., phenotypic markers such as (-galactosidase, green fluorescent protein (GFP), and cell surface proteins); (5) nucleic acid segments that bind products which are otherwise detrimental to cell survival and/or function; (6) nucleic acid segments that otherwise inhibit the activity of any of the nucleic acid segments described in Nos. 1–5 above (e.g., antisense oligonucleotides); (7) nucleic acid segments that bind products that modify a substrate (e.g. restriction endonucleases); (8) nucleic acid segments that can be used to isolate or identify a desired molecule (e.g. specific protein binding sites); (9) nucleic acid segments that encode a specific nucleotide sequence which can be otherwise non-functional (e.g., for PCR amplification of subpopulations of molecules); (10) nucleic acid segments, which when absent, directly or indirectly confer resistance or sensitivity to particular compounds; and/or (11) nucleic acid segments that encode products which are toxic in recipient cells.

Selection scheme: As used herein, selection scheme is any method which allows selection, enrichment, or identification of a desired Product or Product(s) from a mixture containing an Entry Clone or Vector, a Destination Vector, a Donor Vector, an Expression Clone or Vector, any intermediates (e.g. a Cointegrate or a replicon), and/or Byproducts. The selection schemes of one preferred embodiment have at least two components that are either linked or unlinked during recombinational cloning. One component is a Selectable marker. The other component controls the expression in vitro or in vivo of the Selectable marker, or survival of the cell (or the nucleic acid molecule, e.g., a replicon) harboring the plasmid carrying the Selectable marker. Generally, this controlling element will be a repressor or inducer of the Selectable marker, but other means for controlling expression or activity of the Selectable marker can be used. Whether a repressor or activator is used will depend on whether the marker is for a positive or negative selection, and the exact arrangement of the various nucleic acid segments, as will be readily apparent to those skilled in the art. In some preferred embodiments, the selection scheme results in selection of or enrichment for only one or more desired Products. As defined herein, selecting for a nucleic acid molecule includes (a) selecting or enriching for the presence of the desired nucleic acid molecule, and (b) selecting or enriching against the presence of nucleic acid molecules that are not the desired nucleic acid molecule.

Figure 1:
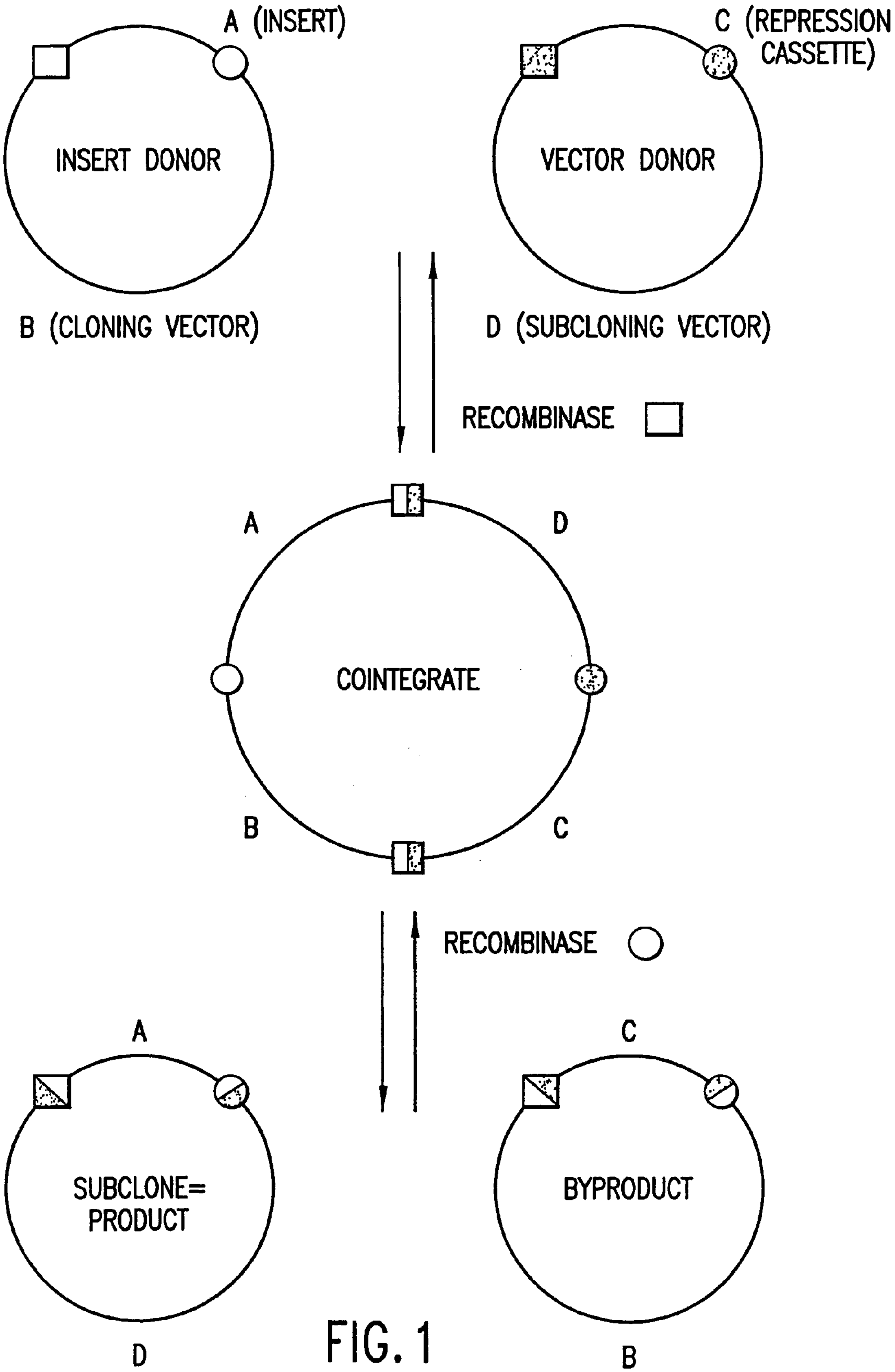
FIG. 1 is a schematic representation of a basic recombinational cloning reaction.
Figure 2:
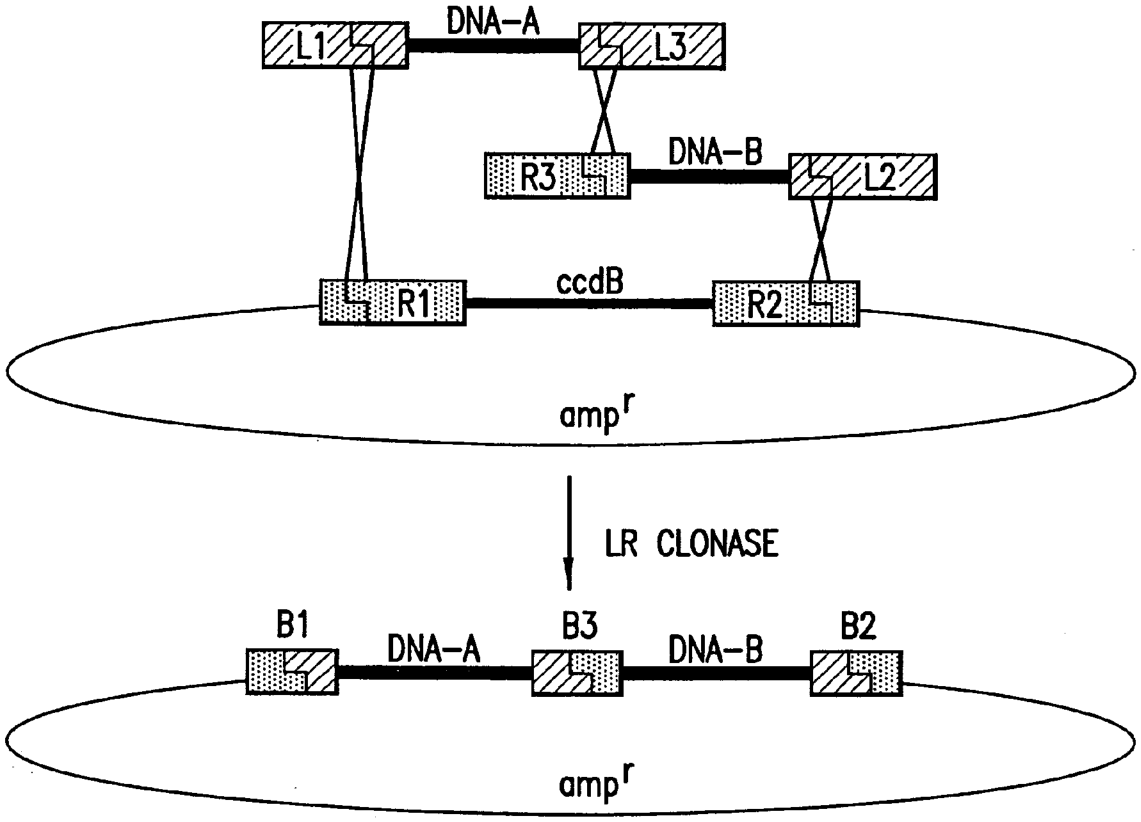
FIG. 2 is a schematic representation of the use of the present invention to clone two nucleic acid segments by performing an LR recombination reaction.
Figure 3:
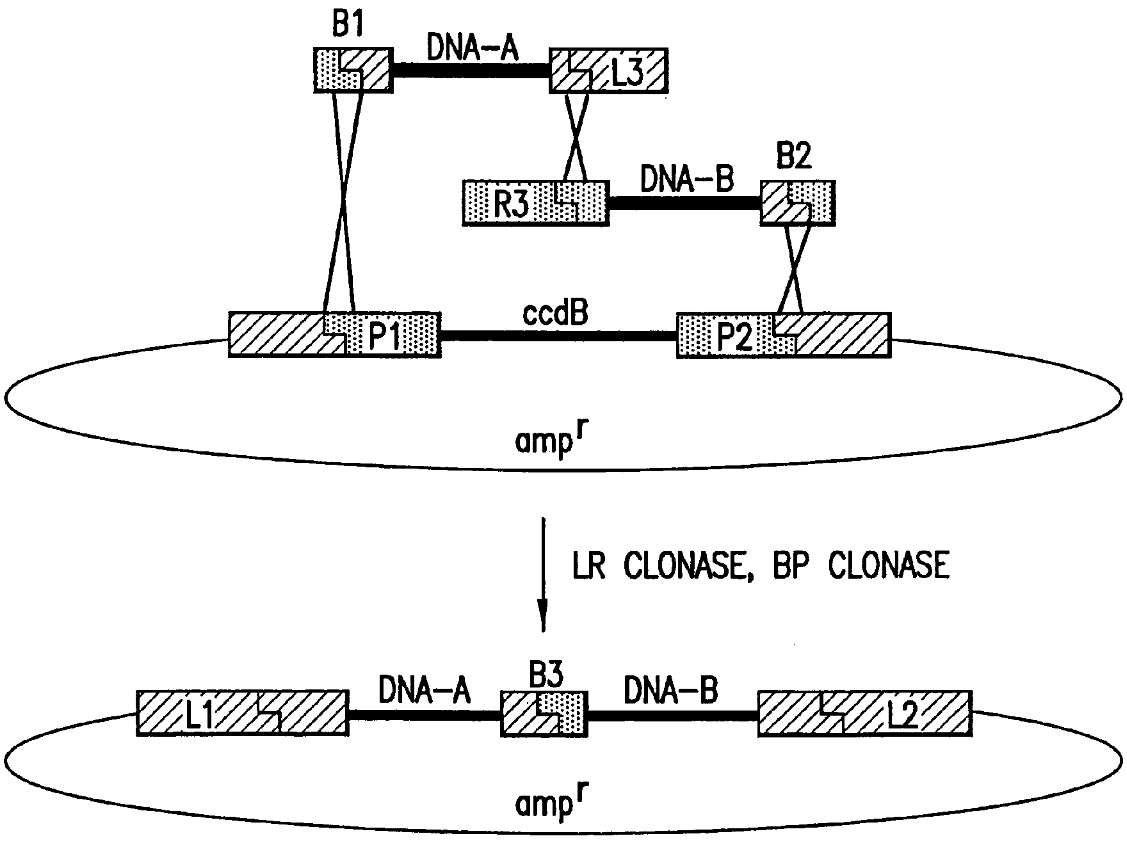
FIG. 3 is a schematic representation of the use of the present invention to clone two nucleic acid segments by joining the segments using an LR reaction and then inserting the joined fragments into a Destination Vector using a BP recombination reaction.
Figure 4:
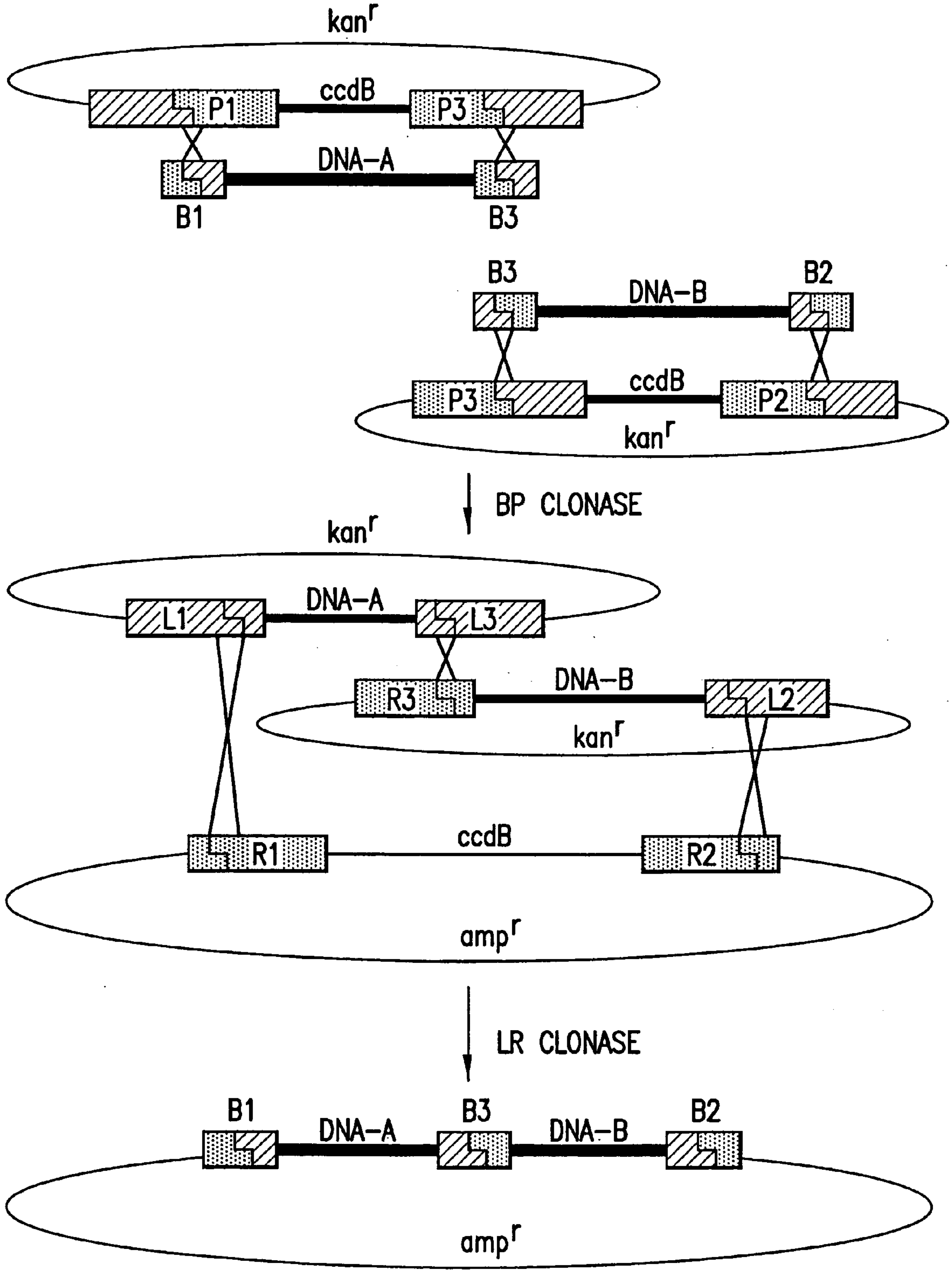
FIG. 4 is a schematic representation of the use of the present invention to clone two nucleic acid segments by performing a BP reaction followed by an LR reaction.
Figure 5:
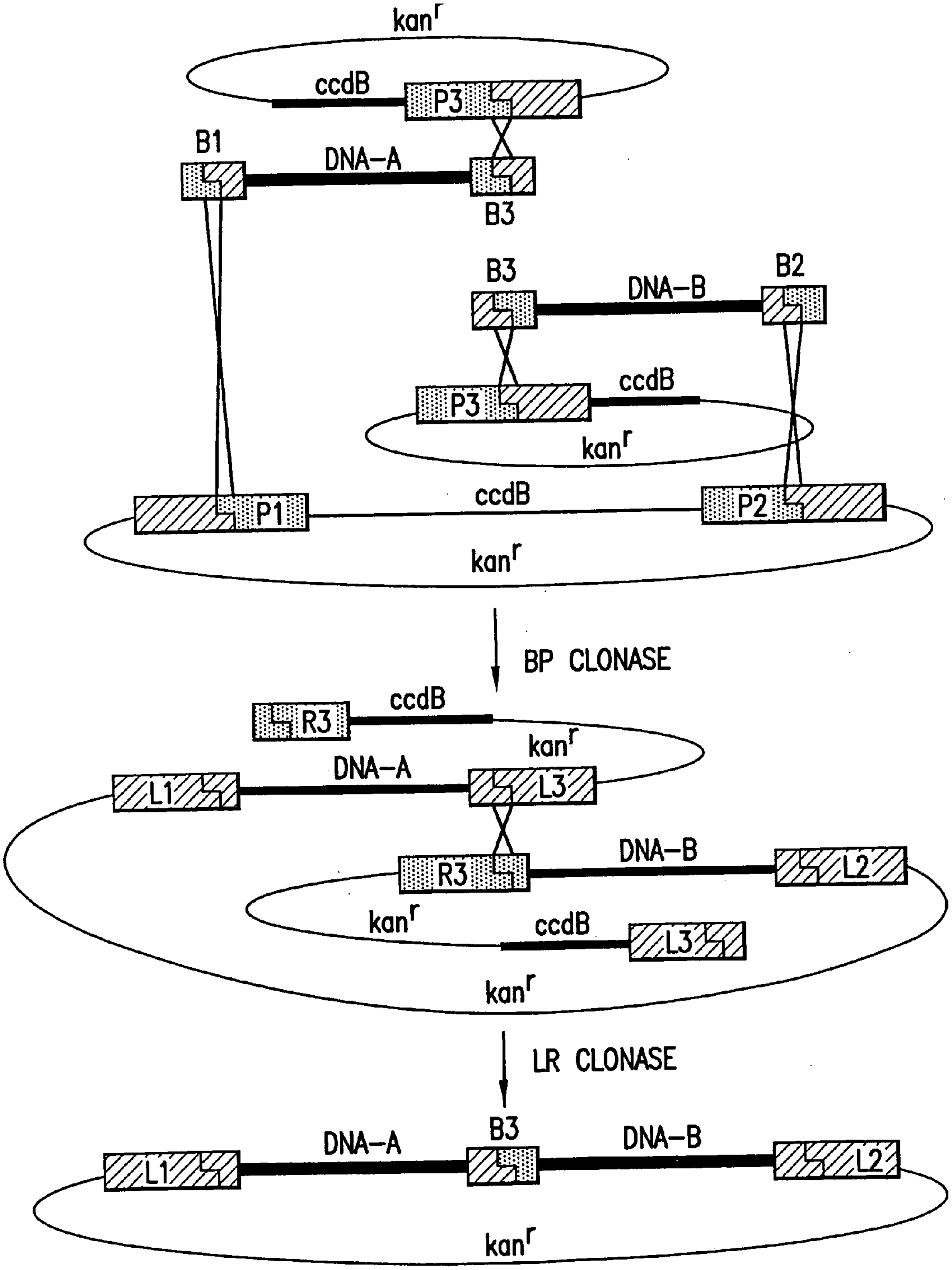
FIG. 5 is a schematic representation of two nucleic acid segments having attB sites being cloned by performing a first BP reaction to generate an attL site on one segment and an attR on the other followed by an LR reaction to combine the segments. In variations of this process, P1, P2, and/or P3 can be oligonucleotides or linear stretches of nucleotides.
Figure 6:
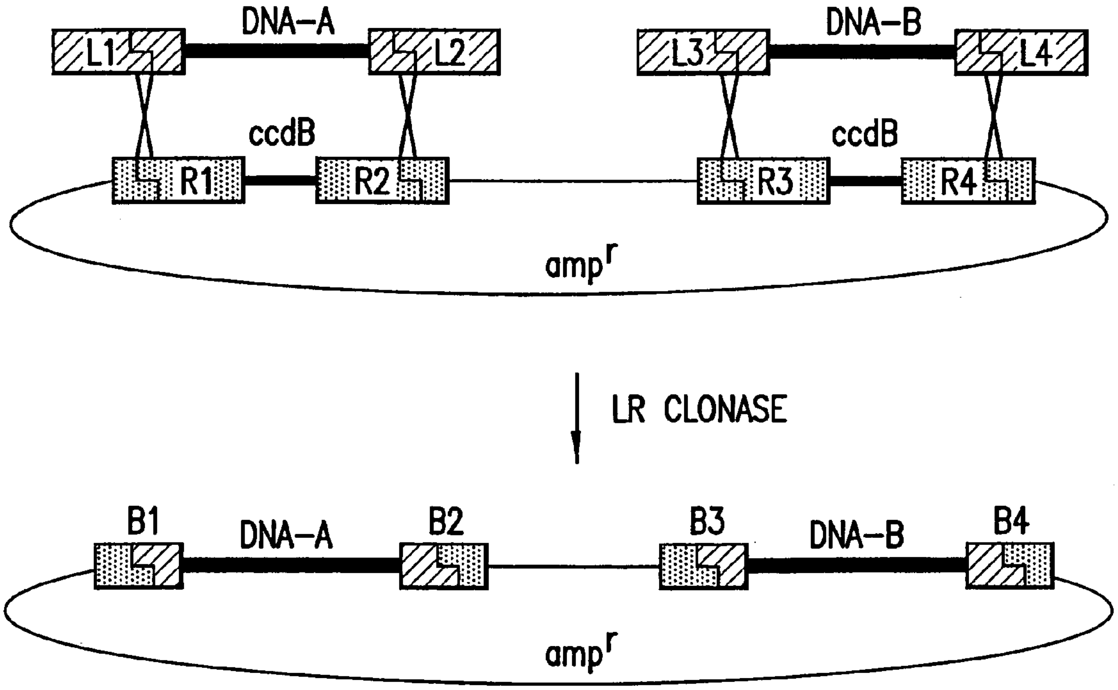
FIG. 6 is a schematic representation of the cloning of two nucleic acid segments into two separate sites in a Destination Vector using an LR reaction.
Figure 7:
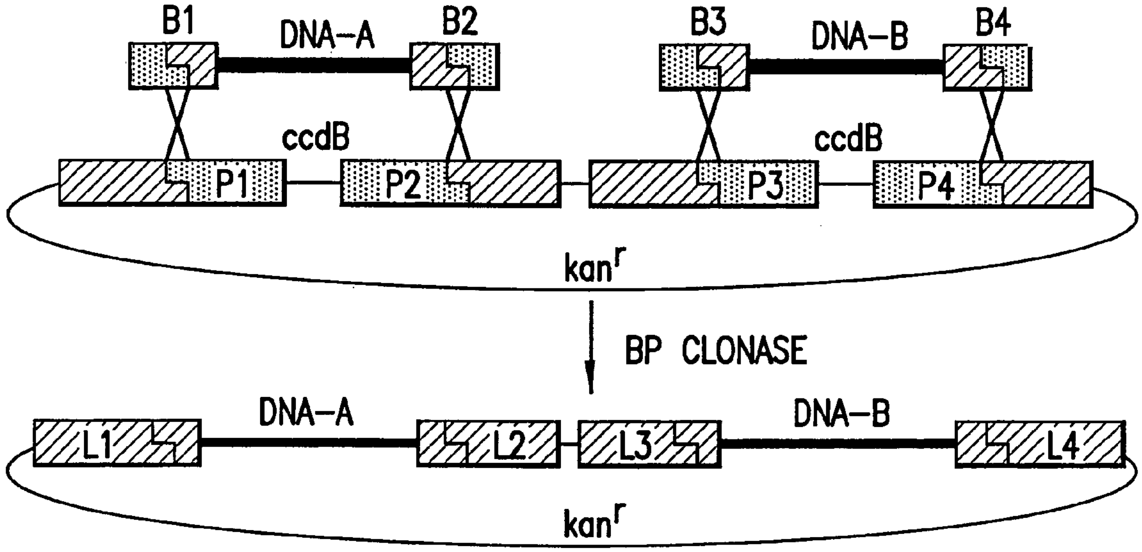
FIG. 7 is a schematic representation of the cloning of two nucleic acid segments into two separate sites in a Destination Vector using a BP reaction.

In one embodiment, the selection schemes (which can be carried out in reverse) will take one of three forms, which will be discussed in terms of FIG. 1. The first, exemplified herein with a Selectable marker and a repressor therefore, selects for molecules having segment D and lacking segment C. The second selects against molecules having segment C and for molecules having segment D. Possible embodiments of the second form would have a nucleic acid segment carrying a gene toxic to cells into which the in vitro reaction products are to be introduced. A toxic gene can be a nucleic acid that is expressed as a toxic gene product (a toxic protein or RNA), or can be toxic in and of itself. (In the latter case, the toxic gene is understood to carry its classical definition of "heritable trait".)

Examples of such toxic gene products are well known in the art, and include, but are not limited to, restriction endonucleases (e.g., DpnI), apoptosis-related genes (e.g. ASK1 or members of the bcl-2/ced-9 family), retroviral genes including those of the human immunodeficiency virus (HIV), defensins such as NP-1, inverted repeats or paired palindromic nucleic acid sequences, bacteriophage lytic genes such as those from (X174 or bacteriophage T4; antibiotic sensitivity genes such as rpsL, antimicrobial sensitivity genes such as pheS, plasmid killer genes, eukaryotic transcriptional vector genes that produce a gene product toxic to bacteria, such as GATA-1, and genes that kill hosts in the absence of a suppressing function, e.g., kicB, ccdb, (X174 E (Liu, Q. et al., *Curr. Biol.* 8:1300–1309 (1998)), and other genes that negatively affect replicon stability and/or replication. A toxic gene can alternatively be selectable in vitro, e.g., a restriction site.

Many genes coding for restriction endonucleases operably linked to inducible promoters are known, and may be used in the present invention. See, e.g. U.S. Pat. Nos. 4,960,707 (DpnI and DpnII); 5,000,333, 5,082,784 and 5,192,675 (KpnI); 5,147,800 (NgoAIII and NgoAI); 5,179,015 (FspI and HaeIII): 5,200,333 (HaeII and TaqI); 5,248,605 (HpaII); 5,312,746° ClaI); 5,231,021 and 5,304,480 (XhoI and XhoII); 5,334,526 (AluI); 5,470,740 (NsiI); 5,534,428 (SstI/SacI); 5,202,248 (NcoI); 5,139,942 (NdeI); and 5,098,839 (PacI). See also Wilson, G. G., Nucl. Acids Res. 19:2539–2566 (1991); and Lunnen, K. D., et al., *Gene* 74:25–32 (1988).

In the second form, segment D carries a Selectable marker. The toxic gene would eliminate transformants harboring the Vector Donor, Cointegrate, and Byproduct molecules, while the Selectable marker can be used to select for cells containing the Product and against cells harboring only the Insert Donor.

The third form selects for cells that have both segments A and D in cis on the same molecule, but not for cells that have both segments in trans on different molecules. This could be embodied by a Selectable marker that is split into two inactive fragments, one each on segments A and D.

The fragments are so arranged relative to the recombination sites that when the segments are brought together by the recombination event, they reconstitute a functional Selectable marker. For example, the recombinational event can link a promoter with a structural nucleic acid molecule (e.g., a gene), can link two fragments of a structural nucleic acid molecule, or can link nucleic acid molecules that encode a heterodimeric gene product needed for survival, or can link portions of a replicon.

Site-specific recombinase: As used herein, a site specific recombinase is a type of recombinase which typically has at least the following four activities (or combinations thereof): (1) recognition of one or two specific nucleic acid sequences; (2) cleavage of said sequence or sequences; (3) topoisomerase activity involved in strand exchange; and (4) ligase activity to reseal the cleaved strands of nucleic acid. See Sauer, B., Current Opinions in Biotechnology 5:521–527 (1994). Conservative site-specific recombination is distinguished from homologous recombination and transposition by a high degree of specificity for both partners. The strand exchange mechanism involves the cleavage and rejoining of specific nucleic acid sequences in the absence of DNA synthesis (Landy, A. (1989) Ann. Rev. Biochem. 58:913–949).

Vector: As used herein, a vector is a nucleic acid molecule (preferably DNA) that provides a useful biological or biochemical property to an Insert. Examples include plasmids, phages, autonomously replicating sequences (ARS), centromeres, and other sequences which are able to replicate or be replicated in vitro or in a host cell, or to convey a desired nucleic acid segment to a desired location within a host cell. A Vector can have one or more restriction endonuclease recognition sites at which the sequences can be cut in a determinable fashion without loss of an essential biological function of the vector, and into which a nucleic acid fragment can be spliced in order to bring about its replication and cloning. Vectors can further provide primer sites, e.g., for PCR, transcriptional and/or translational initiation and/or regulation sites, recombinational signals, replicons, Selectable markers, etc. Clearly, methods of inserting a desired nucleic acid fragment which do not require the use of recombination, transpositions or restriction enzymes (such as, but not limited to, UDG cloning of PCR fragments (U.S. Pat. No. 5,334,575, entirely incorporated herein by reference), TA Cloning® brand PCR cloning (Invitrogen Corporation, Carlsbad, Calif.) (also known as direct ligation cloning), and the like) can also be applied to clone a fragment into a cloning vector to be used according to the present invention. The cloning vector can further contain one or more selectable markers suitable for use in the identification of cells transformed with the cloning vector.

Subcloning vector: As used herein, a subcloning vector is a cloning vector comprising a circular or linear nucleic acid molecule which includes preferably an appropriate replicon. In the present invention, the subcloning vector (segment D in FIG. 1) can also contain functional and/or regulatory elements that are desired to be incorporated into the final product to act upon or with the cloned nucleic acid Insert (segment A in FIG. 1). The subcloning vector can also contain a Selectable marker (preferably DNA).

Vector Donor: As used herein, a Vector Donor is one of the two parental nucleic acid molecules (e.g. RNA or DNA) of the present invention which carries the nucleic acid segments comprising the nucleic acid vector which is to become part of the desired Product. The Vector Donor comprises a subcloning vector D (or it can be called the cloning vector if the Insert Donor does not already contain a cloning vector) and a segment C flanked by recombination sites (see FIG. 1). Segments C and/or D can contain elements that contribute to selection for the desired Product daughter molecule, as described above for selection schemes. The recombination signals can be the same or different, and can be acted upon by the same or different recombinases. In addition, the Vector Donor can be linear or circular.

Primer: As used herein, a primer is a single stranded or double stranded oligonucleotide that is extended by covalent bonding of nucleotide monomers during amplification or polymerization of a nucleic acid molecule (e.g. a DNA molecule). In one aspect, the primer may be a sequencing primer (for example, a universal sequencing primer). In another aspect, the primer may comprise a recombination site or portion thereof.

Template: As used herein, a template is a double stranded or single stranded nucleic acid molecule which is to be amplified, synthesized or sequenced. In the case of a double-stranded DNA molecule, denaturation of its strands to form a first and a second strand is preferably performed before these molecules may be amplified, synthesized or sequenced, or the double stranded molecule may be used directly as a template. For single stranded templates, a primer complementary to at least a portion of the template is hybridized under appropriate conditions and one or more polypeptides having polymerase activity (e.g. DNA polymerases and/or reverse transcriptases) may then synthesize a molecule complementary to all or a portion of the template. Alternatively, for double stranded templates, one or more transcriptional regulatory sequences (e.g., one or more promoters) may be used in combination with one or more polymerases to make nucleic acid molecules complementary to all or a portion of the template. The newly synthesized molecule, according to the invention, may be of equal or shorter length compared to the original template. Mismatch incorporation or strand slippage during the synthesis or extension of the newly synthesized molecule may result in one or a number of mismatched base pairs. Thus, the synthesized molecule need not be exactly complementary to the template. Additionally, a population of nucleic acid templates may be used during synthesis or amplification to produce a population of nucleic acid molecules typically representative of the original template population.

Incorporating: As used herein, incorporating means becoming a part of a nucleic acid (e.g., DNA) molecule or primer.

Library: As used herein, a library is a collection of nucleic acid molecules (circular or linear). In one embodiment, a library may comprise a plurality (i.e., two or more) of nucleic acid molecules, which may or may not be from a common source organism, organ, tissue, or cell. In another embodiment, a library is representative of all or a portion or a significant portion of the nucleic acid content of an organism (a "genomic" library), or a set of nucleic acid molecules representative of all or a portion or a significant portion of the expressed nucleic acid molecules (a cDNA library or segments derived therefrom) in a cell, tissue, organ or organism. A library may also comprise random sequences made by de novo synthesis, mutagenesis of one or more sequences and the like. Such libraries may or may not be contained in one or more vectors.

Amplification: As used herein, amplification is any in vitro method for increasing a number of copies of a nucleotide sequence with the use of one or more polypeptides having polymerase activity (e.g., one or more nucleic acid polymerases or one or more reverse transcriptases). Nucleic acid amplification results in the incorporation of nucleotides into a DNA and/or RNA molecule or primer thereby forming a new nucleic acid molecule complementary to a template. The formed nucleic acid molecule and its template can be used as templates to synthesize additional nucleic acid molecules. As used herein, one amplification reaction may consist of many rounds of nucleic acid replication. DNA amplification reactions include, for example, polymerase chain reaction (PCR). One PCR reaction may consist of 5 to 100 cycles of denaturation and synthesis of a DNA molecule.

Nucleotide: As used herein, a nucleotide is a base-sugar-phosphate combination. Nucleotides are monomeric units of a nucleic acid molecule (DNA and RNA). The term nucleotide includes ribonucleoside triphosphates ATP, UTP, CTG, GTP and deoxyribonucleoside triphosphates such as dATP, dCTP, dITP, dUTP, dGTP, dTTP, or derivatives thereof. Such derivatives include, for example, [S]dATP, 7-deaza-dGTP and 7-deaza-dATP. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels.

Nucleic acid molecule: As used herein, a nucleic acid molecule is a sequence of contiguous nucleotides (riboNTPs, dNTPs or ddNTPs, or combinations thereof) of any length, which may encode a full-length polypeptide or a fragment of any length thereof, or which may be non-coding. As used herein, the terms "nucleic acid molecule" and "polynucleotide" may be used interchangeably.

Oligonucleotide: As used herein, an oligonucleotide is a synthetic or natural molecule comprising a covalently linked sequence of nucleotides which are joined by a phosphodiester bond between the 3' position of the pentose of one nucleotide and the 5' position of the pentose of the adjacent nucleotide.

Polypeptide: As used herein, a polypeptide is a sequence of contiguous amino acids, of any length. As used herein, the terms "peptide," "oligopeptide," or "protein" may be used interchangeably with the term "polypeptide."

Hybridization: As used herein, the terms hybridization and hybridizing refer to base pairing of two complementary single-stranded nucleic acid molecules (RNA and/or DNA) to give a double stranded molecule. As used herein, two nucleic acid molecules may be hybridized, although the base pairing is not completely complementary. Accordingly, mismatched bases do not prevent hybridization of two nucleic acid molecules provided that appropriate conditions, well known in the art, are used. In some aspects, hybridization is said to be under "stringent conditions." By "stringent conditions" as used herein is meant overnight incubation at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 g/ml denatured, sheared salmon sperm DNA, followed by washing the filters in 0.1×SSC at about 65° C.

Other terms used in the fields of recombinant nucleic acid technology and molecular and cell biology as used herein will be generally understood by one of ordinary skill in the applicable arts.

Overview

The present invention relates to methods, compositions and kits for the recombinational and/or topoisomerase-mediated joining of two or more segments or molecules of nucleic acid or other molecules and/or compounds (or combinations thereof). The invention also relates to attaching such linked nucleic acids or other molecules and/or compounds to one or more supports or structures preferably through recombination sites (which may include recombination protein recognition sequences, topoisomerase recognition sequences, etc.) or portions thereof. Thus, the invention generally relates to linking any number of nucleic acids or other molecules and/or compounds via nucleic acid linkers comprising one or more topoisomerase recognition sites and/or one or more recombination sites or portions thereof. The linked products produced by the invention may comprise any number of the same or different nucleic acids or other molecules and/or compounds, depending on the starting materials. Such starting materials inlcude, but are not limited to, any nucleic acids (or derivatives thereof such as peptide nucleic acids (PNAs)), chemical compounds, detectably labeled molecules (such as fluorescent molecules and chemiluminescent molecules), drugs, peptides or protesins, lipids, carbohydrates and other molecules and/or compounds comprising one or more recombination sites or portions thereof. Through recombination of such recombination sites and/or topoisomerase-mediated joining reactions according to the invention, any number or combination of such starting molecules and/or compounds can be linked to make linked products of the invention. In addition, deletion or replacement of certain portions or components of the linked products of the invention can be accomplished by recombination.

In some embodiments, the joined segments may be inserted into a different nucleic acid molecule such as vectors, such as by recombinational cloning methods and/or topoisomerase-mediated joining methods of the invention. Thus, in some embodiments, the present invention relates to the construction of nucleic acid molecules (RNA or DNA) by combining two or more segments of nucleic acid by a recombination reaction and/or a topoisomerase-mediated joining reaction and inserting the joined two or more segments into a vector by recombinational cloning. In embodiments where the joined nucleic acid molecules are to be further combined with an additional nucleic acid molecule by a recombination reaction, the timing of the two recombination events, i.e. the joining of the segments and the insertion of the segments into a vector, is not critical. That is to say, it is not critical to the present invention whether the two or more nucleic acid segments are joined together before insertion into the vector or whether, for example, one recombination site on each segment first reacts with a recombination site on the vector and subsequently the recombination sites on the nucleic acid segments react with each other to join the segments. Moreover, the nucleic acid segments can be cloned in any one or a number of positions within the vector and do not need to be inserted adjacent to each other, although, in some embodiments, joining of two or more of such segments within the vector is preferred. In accordance with the invention, recombinational cloning allows efficient selection and identification of molecules (particularly vectors) containing the combined nucleic acid segments. Thus, two or more nucleic acid segments of interest can be combined and, optionally, inserted into a single vector suitable for further manipulation of the combined nucleic acid molecule.

In additional embodiments, at least two (e.g., 2, 3, 4, 5, 6, 7, 8, etc.) nucleic acid segments, each comprising at least one (e.g., 1, 2, 3, 4, 5, 6, 7, 8, etc.) recombination site and optionally with at least one (e.g., 1, 2, 3, 4, 5, 6, 7, 8, etc.) topoisomerase recognition site, are contacted with suitable recombination proteins and/or with topoisomerase to effect the joining all or a portion of the two molecules, depending on the position of the recombination sites in the molecules. In certain such embodiments, such as in nucleic acid molecules comprising at least two recombination sites, at least one of the two recombination sites flanks each end of a topoisomerase recognitino site in the molecule. By a recombination site (or a topoisomerase recognition site) that "flanks" another recognition site (e.g., another recombination site or topoisomerase recognition site) is meant that the two sites are within about 20 nucleotides of each other, or within about 20, 19, 18, 17, 16, 15, 14, 13, 12, 11, 10, 9, 8, 7, 6, 5, 4, 3, 2, 1 or 0 nucleotides of each other. Each individual nucleic acid segment may comprise a variety of sequences including, but not limited to sequences suitable for use as primer sites (e.g., sequences for which a primer such as a sequencing primer or amplification primer may hybridize to initiate nucleic acid synthesis, amplification or sequencing), transcription or translation signals or regulatory sequences such as promoters, ribosomal binding sites, Kozak sequences, and start codons, termination signals such as stop codons, origins of replication, recombination sites (or portions thereof), topoisomerase recognition sites (or portions thereof), selectable markers, and genes or portions of genes to create protein fusions (e.g., N-terminal or carboxy terminal) such as GST, GUS, GFP, 6 histidines, epitopes haptens and the like and combinations thereof. The vectors used for cloning such segments may also comprise these functional sequences (e.g., promoters, primer sites etc.). After combination of the segments comprising such sequences and optimally the cloning of the sequences into one or more vectors, the molecules may be manipulated in a variety of ways including sequencing or amplification of the target sequence (i.e., by using at least one or the primer sites introduced by the integration sequence), mutation of the target sequence (i.e., by insertion, deletion or substitution in or on the target sequences), and protein expression from the target sequence or portions thereof (i.e., by expression of translation and/or transcription signals contained by the segments and/or vectors).

The present invention also relates to the generation of combinatorial libraries using the recombinational cloning methods disclosed. Thus, one or more of the nucleic acid segments joined may comprise a nucleic acid library. Such a library may comprise, for example, nucleic acid sequences corresponding to permutations of a sequence coding for a peptide, polypeptide or protein sequence. The permutations can be joined to another nucleic acid segment consisting of a single sequence or, alternatively, the second nucleic acid segment may also be a library corresponding to permutation of another peptide, polypeptide or protein sequence such that joining of the two segments may produce a library representing all possible combinations of all the permutations of the two peptide, polypeptide or proteins sequences. Numerous examples of the use of combinatorial libraries are known in the art. See, for example, Waterhouse, et al., Nucleic Acids Research, 1993, Vol. 21, No. 9, 2265–2266, Tsurushita, et al., Gene, 1996, Vol. 172 No. 1, 59–63, Persson, Int Rev Immunol 1993 10:2–3 153–63, Chanock, et al., Infect Agents Dis 1993 Jun 2:3 118–31, Burioni, et al., Res Virol 1997 Mar-Apr 148:2 161–4, Leung, Thromb Haemost 1995 Jul 74:1 373–6, Sandhu, Crit Rev Biotechnol 1992 12:5–6 437–62 and U.S. Pat. Nos. 5,733,743, 5,871,907 and 5,858,657 all of which are specifically incorporated herein by reference.

Recombination Sites

Recombination sites for use in the invention may be any nucleic acid sequence that can serve as a substrate in a recombination reaction. Such recombination sites may be wild-type or naturally occurring recombination sites or modified or mutant recombination sites. Examples of recombination sites for use in the invention include, but are not limited to, phage-lambda recombination sites (such as attP, attB, attL, and attR and mutants or derivatives thereof) and recombination sites from other bacteriophage such as phi80, P22, P2, 186, P4 and P1 (including lox sites such as loxp and loxP511). Novel mutated att sites (e.g., attB 1-10, attP 1-10, attR 1-10 and attL 1-10) are described in previous patent application Ser. No. 60/136,744, filed May 28, 1999, which is specifically incorporated herein by reference. Other recombination sites having unique specificity (i.e., a first site will recombine with its corresponding site and will not recombine with a second site having a different specificity) are known to those skilled in the art and may be used to practice the present invention. Other suitable recombination proteins and mutant, modified, variant, or derivative recombination sites for use in the invention include those described in U.S. Pat. Nos. 5,888,732, 6,143,557, 6,171,861, 6,270,969, and 6,277,608 and in U.S. application Ser. No. 09/438,358 (filed Nov. 12, 1999), based upon U.S. provisional application No. 60/108,324 (filed Nov. 13, 1998). Mutated att sites (e.g., attB 1–10, attP 1-10, attR 1-10 and attL 1–10) are described in U.S. provisional patent application No. 60/122,389, filed Mar. 2, 1999, 60/126,049, filed Mar. 23, 1999, 60/169,983, filed Dec. 10, 1999, and 60/188,000, filed Mar. 9, 2000, and in U.S. application Ser. No. 09/517,466, filed Mar. 2, 2000, and Ser. No. 09/732,914, filed Dec. 11, 2000 (published as 20020007051-A1) the disclosures of which are specifically incorporated herein by reference in their entirety. Other suitable recombination sites and proteins are those associated with the GATEWAY™ Cloning Technology available from Invitrogen Corporation, Carlsbad, Calif., and described in the product literature of the GATEWAY™ Cloning Technology, the entire disclosures of all of which are specifically incorporated herein by reference in their entireties.

Sites that may be used in the present invention include att sites. The 15 bp core region of the wildtype att site (GCTTTTTTAT ACTAA (SEQ ID NO: 81)), which is identical in all wildtype att sites, may be mutated in one or more positions. The inventors have determined that att sites that specifically recombine with other att sites can be constructed by altering nucleotides in and near the 7 base pair overlap region, bases 6–12 of the core region. Thus, recombination sites suitable for use in the methods, compositions, and vectors of the invention include, but are not limited to, those with insertions, deletions or substitutions of one, two, three, four, or more nucleotide bases within the 15 base pair core region (see U.S. application Ser. No. 08/663,002, filed Jun. 7, 1996 (now U.S. Pat. No. 5,888,732) and Ser. No. 09/177,387, filed Oct. 23, 1998, which describes the core region in further detail, and the disclosures of which are incorporated herein by reference in their entireties). Recombination sites suitable for use in the methods, compositions, and vectors of the invention also include those with insertions, deletions or substitutions of one, two, three, four, or more nucleotide bases within the 15 base pair core region that are at least 50% identical, at least 55% identical, at least 60% identical, at least 65% identical, at least 70% identical, at least 75% identical, at least 80% identical, at least 85% identical, at least 90% identical, or at least 95% identical to this 15 base pair core region.

Analogously, the core regions in attB1, attP1, attL1 and attR1 are identical to one another, as are the core regions in attB2, attP2, attL2 and attR2. Nucleic acid molecules suitable for use with the invention also include those comprising insertions, deletions or substitutions of one, two, three, four, or more nucleotides within the seven base pair overlap region (TTTATAC, bases 6–12 in the core region). The overlap region is defined by the cut sites for the integrase protein and is the region where strand exchange takes place. Examples of such mutants, fragments, variants and derivatives include, but are not limited to, nucleic acid molecules in which (1) the thymine at position 1 of the seven bp overlap region has been deleted or substituted with a guanine, cytosine, or adenine; (2) the thymine at position 2 of the seven bp overlap region has been deleted or substituted with a guanine, cytosine, or adenine; (3) the thymine at position 3 of the seven bp overlap region has been deleted or substituted with a guanine, cytosine, or adenine; (4) the adenine at position 4 of the seven bp overlap region has been deleted or substituted with a guanine, cytosine, or thymine; (5) the thymine at position 5 of the seven bp overlap region has been deleted or substituted with a guanine, cytosine, or adenine; (6) the adenine at position 6 of the seven bp overlap region has been deleted or substituted with a guanine, cytosine, or thymine; and (7) the cytosine at position 7 of the seven bp overlap region has been deleted or substituted with a guanine, thymine, or adenine; or any combination of one or more such deletions and/or substitutions within this seven bp overlap region. The nucleotide sequences of the above described seven base pair core regions are set out below in Table 1.

Altered att sites have been constructed that demonstrate that (1) substitutions made within the first three positions of the seven base pair overlap (TTTATAC) strongly affect the specificity of recombination, (2) substitutions made in the last four positions (TTTATAC) only partially alter recombination specificity, and (3) nucleotide substitutions outside of the seven bp overlap, but elsewhere within the 15 base pair core region, do not affect specificity of recombination but do influence the efficiency of recombination. Thus, nucleic acid molecules and methods of the invention include those comprising or employing one, two, three, four, five, six, eight, ten, or more recombination sites which affect recombination specificity, particularly one or more (e.g., one, two, three, four, five, six, eight, ten, twenty, thirty, forty, fifty, etc.) different recombination sites that may correspond substantially to the seven base pair overlap within the 15 base pair core region, having one or more mutations that affect recombination specificity. Particularly preferred such molecules may comprise a consensus sequence such as NNNATAC wherein "N" refers to any nucleotide (ie., may be A, G, T/U or C). Preferably, if one of the first three nucleotides in the consensus sequence is a T/U, then at least one of the other two of the first three nucleotides is not a T/U.

The core sequence of each att site (attB, attP, attL and attR) can be divided into functional units consisting of integrase binding sites, integrase cleavage sites and sequences that determine specificity. Specificity determinants are defined by the first three positions following the integrase top strand cleavage site. These three positions are shown with underlining in the following reference sequence: CAACTTTTTTATAC AAAGTTG (SEQ ID NO: 82). Modification of these three positions (64 possible combinations) can be used to generate att sites that recombine with high specificity with other att sites having the same sequence for the first three nucleotides of the seven base pair overlap region. The possible combinations of first three nucleotides of the overlap region are shown in Table 1.

TABLE 1

Modifications of the First Three Nucleotides of the att Site Seven Base Pair Overlap Region that Alter Recombination Specificity.

| | | | |
|---|---|---|---|
| AAA | CAA | GAA | TAA |
| *AAC* | CAC | GAC | TAC |
| | CAG | GAG | TAG |
| AAG | CAT | GAT | TAT |
| AAT | CCA | GCA | TCA |
| ACA | CCC | GCC | TCC |
| ACC | CCG | GCG | TCG |
| ACG | CCT | GCT | TCT |

TABLE 1-continued

Modifications of the First Three Nucleotides of the att Site Seven Base Pair Overlap Region that Alter Recombination Specificity.

| | | | |
|---|---|---|---|
| ACT | CGA | GGA | TGA |
| AGA | CGC | GGC | TGC |
| AGC | CGG | GGG | TGG |
| AGG | CGT | GGT | TGT |
| AGT | CTA | GTA | TTA |
| ATA | CTC | GTC | TTC |
| ATC | CTG | GTG | TTG |
| ATG | CTT | GTT | TTT |
| ATT | | | |

Representative examples of seven base pair att site overlap regions suitable for in methods, compositions and vectors of the invention are shown in Table 2. The invention further includes nucleic acid molecules comprising one or more (e.g., one, two, three, four, five, six, eight, ten, twenty, thirty, forty, fifty, etc.) nucleotides sequences set out in Table 2. Thus, for example, in one aspect, the invention provides nucleic acid molecules comprising the nucleotide sequence GAAATAC, GATATAC, ACAATAC, or TGCATAC.

TABLE 2

Representative Examples of Seven Base Pair att Site Overlap Regions Suitable for use in the recombination sites of the Invention.

| | | | |
|---|---|---|---|
| AAAATAC | CAAATAC | GAAATAC | TAAATAC |
| AACATAC | CACATAC | GACATAC | TACATAC |
| AAGATAC | CAGATAC | GAGATAC | TAGATAC |
| AATATAC | CATATAC | GATATAC | TATATAC |
| ACAATAC | CCAATAC | GCAATAC | TCAATAC |
| ACCATAC | CCCATAC | GCCATAC | TCCATAC |
| ACGATAC | CCGATAC | GCGATAC | TCGATAC |
| ACTATAC | CCTATAC | GCTATAC | TCTATAC |
| AGAATAC | CGAATAC | GGAATAC | TGAATAC |
| AGCATAC | CGCATAC | GGCATAC | TGCATAC |
| AGGATAC | CGGATAC | GGGATAC | TGGATAC |
| AGTATAC | CGTATAC | GGTATAC | TGTATAC |
| ATAATAC | CTAATAC | GTAATAC | TTAATAC |
| ATCATAC | CTCATAC | GTCATAC | TTCATAC |
| ATGATAC | CTGATAC | GTGATAC | TTGATAC |
| ATTATAC | CTTATAC | GTTATAC | TTTATAC |

As noted above, alterations of nucleotides located 3' to the three base pair region discussed above can also affect recombination specificity. For example, alterations within the last four positions of the seven base pair overlap can also affect recombination specificity.

For example, mutated att sites that may be used in the practice of the present invention include attB1 (AGCCT-GCTTT TTTGTACAAA CTTGT (SEQ ID NO: 83)), attP1 (TACAGGTCAC TAATACCATC TAAGTAGTTG ATTCATAGTG ACTGGATATG TTGTGTTTTA CAGTAT-TATG TAGTCTGTTT TTTATGCAAA ATCTAATTTA ATATATTGAT ATTTATATCA TTTTACGTTT CTCGT-TCAGC TTTTTTGTAC AAAGTTGGCA TTATAAAAAA GCATTGCTCA TCAATTTGTT GCAACGAACA GGT-CACTATC AGTCAAAATA AAATCATTAT TTG (SEQ ID NO: 84)), attL1 (CAAATAATGA TTTTATTTTG ACTGAT-AGTG ACCTGTTCGT TGCAACAAAT TGATAAGCAA TGCTTTTTTA TAATGCCAAC TTTGTACAAA AAAG-CAGGCT (SEQ ID NO: 85)), and attR1 (ACAAGTTTGT ACAAAAAAGC TGAACGAGAA ACGTAAAATG ATATAAATAT CAATATATTA AATTAGATTT TGCAT-AAAAA ACAGACTACA TAATACTGTA AAACA-CAACA TATCCAGTCA CTATG (SEQ ID NO: 86)). Table 3 provides the sequences of the regions surrounding the core region for the wild type att sites (attB0, P0, R0, and L0) as well as a variety of other suitable recombination sites. Those skilled in the art will appreciated that the remainder of the site is the same as the corresponding site (B, P, L, or R) listed above.

TABLE 3

| Nucleotide sequences of representative att sites. | |
|---|---|
| attB0<br>AGCCTGCTTT TTTATACTAA CTTGAGC | (SEQ ID NO:87) |
| attP0<br>GTTCAGCTTT TTTATACTAA GTTGGCA | (SEQ ID NO:88) |
| attL0<br>AGCCTGCTTT TTTATACTAA GTTGGCA | (SEQ ID NO:89) |
| attR0<br>GTTCAGCTTT TTTATACTAA CTTGAGC | (SEQ ID NO:90) |
| attB1<br>AGCCTGCTTT TTTGTACAAA CTTGT | (SEQ ID NO:83) |
| attP1<br>GTTCAGCTTT TTTGTACAAA GTTGGCA | (SEQ ID NO:91) |
| attL1<br>AGCCTGCTTT TTTGTACAAA GTTGGCA | (SEQ ID NO:92) |
| attR1<br>GTTCAGCTTT TTTGTACAAA CTTGT | (SEQ ID NO:93) |
| attB2<br>ACCCAGCTTT CTTGTACAAA GTGGT | (SEQ ID NO:94) |
| attP2<br>GTTCAGCTTT CTTGTACAAA GTTGGCA | (SEQ ID NO:95) |
| attL2<br>ACCCAGCTTT CTTGTACAAA GTTGGCA | (SEQ ID NO:96) |
| attR2<br>GTTCAGCTTT CTTGTACAAA GTGGT | (SEQ ID NO:97) |
| attB5<br>CAACTTTATT ATACAAAGTT GT | (SEQ ID NO:98) |
| attP5<br>GTTCAACTTT ATTATACAAA GTTGGCA | (SEQ ID NO:99) |

TABLE 3-continued

| Nucleotide sequences of representative att sites. | |
|---|---|
| attL5<br>CAACTTTATT ATACAAAGTT GGCA | (SEQ ID NO:100) |
| attR5<br>GTTCAACTTT ATTATACAAA GTTGT | (SEQ ID NO:101) |
| attB11<br>CAACTTTTCT ATACAAAGTT GT | (SEQ ID NO:102) |
| attP11<br>GTTCAACTTT TCTATACAAA GTTGGCA | (SEQ ID NO:103) |
| attL11<br>CAACTTTTCT ATACAAAGTT GGCA | (SEQ ID NO:104) |
| attR11<br>GTTCAACTTT TCTATACAAA GTTGT | (SEQ ID NO:105) |
| attB17<br>CAACTTTTGT ATACAAAGTT GT | (SEQ ID NO:106) |
| attP17<br>GTTCAACTTT TGTATACAAA GTTGGCA | (SEQ ID NO:107) |
| attL17<br>CAACTTTTGT ATACAAAGTT GGCA | (SEQ ID NO:108) |
| attR17<br>GTTCAACTTT TGTATACAAA GTTGT | (SEQ ID NO:109) |
| attB19<br>CAACTTTTTC GTACAAAGTT GT | (SEQ ID NO:110) |
| attP19<br>GTTCAACTTT TTCGTACAAA GTTGGCA | (SEQ ID NO:111) |
| attL19<br>CAACTTTTTC GTACAAAGTT GGCA | (SEQ ID NO:112) |
| attR19<br>GTTCAACTTT TTCGTACAAA GTTGT | (SEQ ID NO:113) |
| attB20<br>CAACTTTTTG GTACAAAGTT GT | (SEQ ID NO:114) |
| attP20<br>GTTCAACTTT TTGGTACAAA GTTGGCA | (SEQ ID NO:115) |
| attL20<br>CAACTTTTTG GTACAAAGTT GGCA | (SEQ ID NO:116) |
| attR20<br>GTTCAACTTT TTGGTACAAA GTTGT | (SEQ ID NO:117) |
| attB21<br>CAACTTTTTA ATACAAAGTT GT | (SEQ ID NO:118) |
| attP21<br>GTTCAACTTT TTAATACAAA GTTGGCA | (SEQ ID NO:119) |
| attL21<br>CAACTTTTTA ATACAAAGTT GGCA | (SEQ ID NO:120) |
| attR21<br>GTTCAACTTT TTAATACAAA GTTGT | (SEQ ID NO:121) |

Other recombination sites having unique specificity (i.e., a first site will recombine with its corresponding site and will not recombine with a second site having a different specificity) are known to those skilled in the art and may be used to practice the present invention. Corresponding recombination proteins for these systems may be used in accordance with the invention with the indicated recombination sites. Other systems providing recombination sites and recombination proteins for use in the invention include the FLP/FRT system from *Saccharomyces cerevisiae*, the resolvase family (e.g., γδ, TndX, TnpX, Tn3 resolvase, Hin, Hjc, Gin, SpCCEl, ParA, and Cin), and IS231 and other *Bacillus thuringiensis* transposable elements. Other suitable recombination systems for use in the present invention include the XerC and XerD recombinases and the psi, dif and cer recombination sites in *E. coli*. Other suitable recombination sites may be found in U.S. Pat. No. 5,851,808 issued to Elledge and Liu which is specifically incorporated herein by reference.

Recombination sites used with the invention may also have embedded functions or properties. An embedded functionality is a function or property conferred by a nucleotide sequence in a recombination site that is not directly associated with recombination efficiency or specificity. For example, recombination sites may contain protein coding sequences (e.g. intein coding sequences), intron/exon splice sites, origins of replication, and/or stop codons. Further, recombination sites that have more than one (e.g., two, three, four, five, etc.) embedded functions or properties may also be prepared.

In some instances it will be advantageous to remove either RNA corresponding to recombination sites from RNA transcripts or amino acid residues encoded by recombination sites from polypeptides translated from such RNAs. Removal of such sequences can be performed in several ways and can occur at either the RNA or protein level. One instance where it may be advantageous to remove RNA transcribed from a recombination site will be when constructing a fusion polypeptide between a polypeptide of interest and a coding sequence present on the vector. The presence of an intervening recombination site between the ORF of the polypeptide of interest and the vector coding sequences may result in the recombination site (1) contributing codons to the mRNA that result in the inclusion of additional amino acid residues in the expression product, (2) contributing a stop codon to the mRNA that prevents the production of the desired fusion protein, and/or (3) shifting the reading frame of the mRNA such that the two protein are not fused "in-frame."

In one aspect, the invention provides methods for removing nucleotide sequences encoded by recombination sites from RNA molecules. One example of such a method employs the use of intron/exon splice sites to remove RNA encoded by recombination sites from RNA transcripts. Nucleotide sequences that encode intron/exon splice sites may be fully or partially embedded in the recombination sites used in the present invention and/or may encoded by adjacent nucleic acid sequence. Sequences to be excised from RNA molecules may be flanked by splice sites that are appropriately located in the sequence of interest and/or on the vector. For example, one intron/exon splice site may be encoded by a recombination site and another intron/exon splice site may be encoded by other nucleotide sequences (e.g., nucleic acid sequences of the vector or a nucleic acid of interest). Nucleic acid splicing is well known to those skilled in the art and is discussed in the following publications: R. Reed, *Curr. Opin. Genet. Devel.* 6:215–220 (1996); S. Mount, *Nucl. Acids. Res.* 10:459–472, (1982); P. Sharp, *Cell* 77:805–815, (1994); K. Nelson and M. Green, Genes and Devel. 23:319–329 (1988); and T. Cooper and W. Mattox, Am. J. Hum. Genet. 61:259–266 (1997).

Splice sites can be suitably positioned in a number of locations. For example, a Destination Vector designed to express an inserted ORF with an N-terminal fusion—for example, with a detectable marker—the first splice site could be encoded by vector sequences located 3' to the detectable marker coding sequences and the second splice site could be partially embedded in the recombination site that separates the detectable marker coding sequences from the coding sequences of the ORF. Further, the second splice site either could abut the 3' end of the recombination site or could be positioned a short distance (e.g., 2, 4, 8, 10, 20 nucleotides) 3' to the recombination site. In addition, depending on the length of the recombination site, the second splice site could be fully embedded in the recombination site.

A modification of the method described above involves the connection of multiple nucleic acid segments that, upon expression, results in the production of a fusion protein. In one specific example, one nucleic acid segment encodes detectable marker—for example, GFP—and another nucleic acid segment that encodes an ORF of interest. Each of these segments is flanked by recombination sites. In addition, the nucleic acid segments that encodes the detectable marker contains an intron/exon splice site near its 3' terminus and the nucleic acid segments that contains the ORF of interest also contains an intron/exon splice site near its 5' terminus. Upon recombination, the nucleic acid segment that encodes the detectable marker is positioned 5' to the nucleic acid segment that encodes the ORF of interest. Further, these two nucleic acid segments are separated by a recombination site that is flanked by intron/exon splice sites. Excision of the intervening recombination site thus occurs after transcription of the fusion mRNA. Thus, in one aspect, the invention is directed to methods for removing RNA transcribed from recombination sites from transcripts generated from nucleic acids described herein.

Splice sites may introduced into nucleic acid molecules to be used in the present invention in a variety of ways. One method that could be used to introduce intron/exon splice sites into nucleic acid segments is by the use of PCR. For example, primers could be used to generate nucleic acid segments corresponding to an ORF of interest and containing both a recombination site and an intron/exon splice site.

The above methods can also be used to remove RNA corresponding to recombination sites when the nucleic acid segment that is recombined with another nucleic acid segment encodes RNA that is not produced in a translatable format. One example of such an instance is where a nucleic acid segment is inserted into a vector in a manner that results in the production of antisense RNA. As discussed below, this antisense RNA may be fused, for example, with RNA that encodes a ribozyme. Thus, the invention also provides methods for removing RNA corresponding to recombination sites from such molecules.

The invention further provides methods for removing amino acid sequences encoded by recombination sites from protein expression products by protein splicing. Nucleotide sequences that encode protein splice sites may be fully or partially embedded in the recombination sites that encode amino acid sequences excised from proteins or protein splice sites may be encoded by adjacent nucleotide sequences. Similarly, one protein splice site may be encoded by a recombination site and another protein splice sites may be encoded by other nucleotide sequences (e.g., nucleic acid sequences of the vector or a nucleic acid of interest).

It has been shown that protein splicing can occur by excision of an intein from a protein molecule and ligation of flanking segments (see, e.g., Derbyshire et al., *Proc. Natl. Acad. Sci.* (USA) 95:1356–1357 (1998)). In brief, inteins are amino acid segments that are post-translationally excised from proteins by a self-catalytic splicing process. A considerable number of intein consensus sequences have been identified (see, e.g., Perler, *Nucleic Acids Res.* 27:346–347 (1999)).

Similar to intron/exon splicing, N- and C-terminal intein motifs have been shown to be involved in protein splicing. Thus, the invention further provides compositions and methods for removing amino acid residues encoded by recombination sites from protein expression products by protein splicing. In particular, this aspect of the invention is related to the positioning of nucleic acid sequences that encode intein splice sites on both the 5' and 3' end of recombination sites positioned between two coding regions. Thus, when the protein expression product is incubated under suitable conditions, amino acid residues encoded these recombination sites will be excised.

Protein splicing may be used to remove all or part of the amino acid sequences encoded by recombination sites. Nucleic acid sequence that encode inteins may be fully or partially embedded in recombination sites or may adjacent to such sites. In certain circumstances, it may be desirable to remove considerable numbers of amino acid residues beyond the N- and/or C-terminal ends of amino acid sequences encoded by recombination sites. In such instances, intein coding sequence may be located a distance (e.g., 30, 50, 75, 100, etc. nucleotides) 5' and/or 3' to the recombination site.

While conditions suitable for intein excision will vary with the particular intein, as well as the protein that contains this intein, Chong et al., *Gene* 192:271–281 (1997), have demonstrated that a modified *Saccharomyces cerevisiae* intein, referred to as Sce VMA intein, can be induced to undergo self-cleavage by a number of agents including 1,4-dithiothreitol (DTT), β-mercaptoethanol, and cysteine. For example, intein excision/splicing can be induced by incubation in the presence of 30 mM DTT, at 4° C. for 16 hours.

Corresponding recombination proteins for these systems may be used in accordance with the invention with the indicated recombination sites. Other systems providing recombination sites and recombination proteins for use in the invention include the FLP/FRT system from *Saccharomyces cerevisiae*, the resolvase family (e.g., ((, Tn3 resolvase, Hin, Gin and Cin), and IS231 and other *Bacillus thuringiensis* transposable elements. Other suitable recombination systems for use in the present invention include the XerC and XerD recombinases and the psi, dif and cer recombination sites in *E. coli*. Other suitable recombination sites may be found in U.S. Pat. No. 5,851,808 issued to Elledge and Liu which is specifically incorporated herein by reference. Preferred recombination proteins and mutant or modified recombination sites for use in the invention include those described in U.S. Pat. Nos. 5,888,732, 6,171,861, 6,143,557, 6,270,969 and 6,277,608, and commonly owned, co-pending U.S. application Ser. Nos. 09/438,358 (filed Nov. 12, 1999), 09/517,466 (filed Mar. 2, 2000), 09/695,065 (filed Oct. 25, 2000) and 09/732,914 (filed Dec. 11, 2000), the disclosures of all of which are incorporated herein by reference in their entireties, as well as those associated with the GATEWAY™ Cloning Technology available from Invitrogen Corporation (Carlsbad, Calif.).

Topoisomerase Cloning

The present invention also relates to methods of using one or more topoisomerases to generate a recombinant nucleic acid molecule from two or more nucleotide sequences. In a first aspect, the invention provides a method for generating a ds recombinant nucleic acid molecule that is covalently linked in one strand. Such a method is directed to linking a first and at least a second nucleotide sequence with at least one (e.g., 1, 2, 3, 4, 5, 6, 7, 8, 9, 10, etc.) topoisomerase (e.g., a type IA, type IB, and/or type II topoisomerase) such that one strand, but not both strands, is covalently linked (see, for example, FIGS. 11A–F). In a second aspect, the invention provides a method for generating a ds recombinant nucleic acid molecule covalently linked in both strands. Such a method is directed to linking a first and at least a second nucleotide sequence with at least one topoisomerase, such that ligated ends are covalently linked in both strands (i.e., the ds recombinant nucleic acid molecule contain no nicks at the positions where ends were ligated; see, for example, FIGS. 12A–D). In a third aspect, the invention provides a method for generating a recombinant nucleic acid molecule covalently linked in one strand, wherein the substrate nucleotide sequences linked according to the method include at least one single stranded nucleotide sequence, which can be covalently linked to a second (or more) single stranded nucleotide sequence or to a nucleic acid molecule (see, for example, FIG. 15).

A method for generating a ds recombinant nucleic acid molecule covalently linked in one strand can be performed by contacting a first nucleic acid molecule which has a site-specific topoisomerase recognition site (e.g., a type IA or a type II topoisomerase recognition site), or a cleavage product thereof, at a 5' or 3' terminus, with a second (or other) nucleic acid molecule, and optionally, a topoisomerase (e.g., a type IA, type IB, and/or type II topoisomerase), such that the second nucleotide sequence can be covalently attached to the first nucleotide sequence. As disclosed herein, the methods of the invention can be performed using any number of nucleotide sequences, typically nucleic acid molecules wherein at least one of the nucleotide sequences has a site-specific topoisomerase recognition site (e.g., a type IA, or type II topoisomerase), or cleavage product thereof, at one or both 5' termini (see, for example, FIGS. 11A–11F).

A method for generating a ds recombinant nucleic acid molecule covalently linked in both strands can be performed, for example, by contacting a first nucleic acid molecule having a first end and a second end, wherein, at the first end or second end or both, the first nucleic acid molecule has a topoisomerase recognition site (or cleavage product thereof) at or near the 3' terminus; at least a second nucleic acid molecule having a first end and a second end, wherein, at the first end or second end or both, the at least second double stranded nucleotide sequence has a topoisomerase recognition site (or cleavage product thereof) at or near a 3' terminus; and at least one site specific topoisomerase (e.g., a type IA and/or a type IB topoisomerase), under conditions such that all components are in contact and the topoisomerase can effect its activity. A covalently linked ds recombinant nucleic acid generated according to a method of this aspect of the invention is characterized, in part, in that it does not contain a nick in either strand at the position where the nucleic acid molecules are joined. In one embodiment, the method is performed by contacting a first nucleic acid molecule and a second (or other) nucleic acid molecule, each of which has a topoisomerase recognition site, or a cleavage product thereof, at the 3' termini or at the 5' termini of two ends to be covalently linked. In another embodiment, the method is performed by contacting a first nucleic acid molecule having a topoisomerase recognition site, or cleavage product thereof, at the 5' terminus and the 3' terminus of at least one end, and a second (or other) nucleic acid molecule having a 3' hydroxyl group and a 5' hydroxyl group at the end to be linked to the end of the first nucleic acid molecule containing the recognition sites. As disclosed herein, the methods can be performed using any number of nucleic acid molecules having various combinations of termini and ends (see, for example, FIG. 12A–12D).

Topoisomerases are categorized as type I, including type IA and type IB topoisomerases, which cleave a single strand of a double stranded nucleic acid molecule, and type II topoisomerases (gyrases), which cleave both strands of a nucleic acid molecule. Type IA and IB topoisomerases cleave one strand of a nucleic acid molecule. Cleavage of a nucleic acid molecule by type IA topoisomerases generates a 5' phosphate and a 3' hydroxyl at the cleavage site, with the type IA topoisomerase covalently binding to the 5' terminus of a cleaved strand. In comparison, cleavage of a nucleic acid molecule by type IB topoisomerases generates a 3' phosphate and a 5' hydroxyl at the cleavage site, with the type IB topoisomerase covalently binding to the 3' terminus of a cleaved strand. As disclosed herein, type I and type II topoisomerases, as well as catalytic domains and mutant forms thereof, are useful for generating ds recombinant nucleic acid molecules covalently linked in both strands according to a method of the invention.

Type IA topoisomerases include *E. coli* topoisomerase I, *E. coli* topoisomerase III, eukaryotic topoisomerase II, archeal reverse gyrase, yeast topoisomerase III, *Drosophila* topoisomerase III, human topoisomerase m, *Streptococcus pneumoniae* topoisomerase III, and the like, including other type IA topoisomerases (see Berger, *Biochim. Biophys. Acta* 1400:3–18, 1998; DiGate and Marians, *J. Biol. Chem.* 264:17924–17930, 1989; Kim and Wang, *J. Biol. Chem.* 267:17178–17185, 1992; Wilson et al., *J. Biol. Chem.* 275: 1533–1540, 2000; Hanai et al., *Proc. Natl. Acad. Sci. USA* 93:3653–3657, 1996, U.S. Pat. No. 6,277,620, each of which is incorporated herein by reference). *E. coli* topoisomerase III, which is a type IA topoisomerase that recognizes, binds to and cleaves the sequence 5'-GCAACTT-3', can be particularly useful in a method of the invention (Zhang et al., *J. Biol. Chem.* 270:23700–23705, 1995, which is incorporated herein by reference). A homolog, the traE protein of plasmid RP4, has been described by Li et al., *J. Biol. Chem.* 272:19582–19587 (1997) and can also be used in the practice of the invention. A DNA-protein adduct is formed with the enzyme covalently binding to the 5'-thymidine residue, with cleavage occurring between the two thymidine residues.

Type IB topoisomerases include the nuclear type I topoisomerases present in all eukaryotic cells and those encoded by *vaccinia* and other cellular poxviruses (see Cheng et al., *Cell* 92:841–850, 1998, which is incorporated herein by reference). The eukaryotic type IB topoisomerases are exemplified by those expressed in yeast, *Drosophila* and mammalian cells, including human cells (see Caron and Wang, *Adv. Pharmacol.* 29B,:271–297, 1994; Gupta et al., *Biochim. Biophys. Acta* 1262:1–14, 1995, each of which is incorporated herein by reference; see, also, Berger, supra, 1998). Viral type IB topoisomerases are exemplified by those produced by the vertebrate poxviruses (vaccinia, Shope fibroma virus, ORF virus, fowlpox virus, and molluscum contagiosum virus), and the insect poxvirus (Amsacta moorei entomopoxvirus) (see Shuman, *Biochim. Biophys. Acta* 1400:321–337, 1998; Petersen et al., *Virology* 230:197–206, 1997; Shuman and Prescott, *Proc. Natl. Acad. Sci. USA* 84:7478–7482, 1987; Shuman, *J. Biol. Chem.* 269:32678–32684, 1994; U.S. Pat. No. 5,766,891; PCT/US95/16099; PCT/US98/12372, each of which is incorporated herein by reference; see, also, Cheng et al., supra, 1998).

Type II topoisomerases include, for example, bacterial gyrase, bacterial DNA topoisomerase IV, eukaryotic DNA topoisomerase II, and T-even phage encoded DNA topoisomerases (Roca and Wang, *Cell* 71:833–840, 1992; Wang, *J. Biol. Chem.* 266:6659–6662, 1991, each of which is incorporated herein by reference; Berger, supra, 1998;). Like the type IB topoisomerases, the type II topoisomerases have both cleaving and ligating activities. In addition, like type IB topoisomerase, substrate nucleic acid molecules can be prepared such that the type II topoisomerase can form a covalent linkage to one strand at a cleavage site. For example, calf thymus type II topoisomerase can cleave a substrate nucleic acid molecule containing a 5' recessed topoisomerase recognition site positioned three nucleotides from the 5' end, resulting in dissociation of the three nucleotide sequence 5' to the cleavage site and covalent binding the of the topoisomerase to the 5' terminus of the nucleic acid molecule (Andersen et al., supra, 1991). Furthermore, upon contacting such a type II topoisomerase charged nucleic acid molecule with a second nucleotide sequence containing a 3' hydroxyl group, the type II topoisomerase can ligate the sequences together, and then is released from the recombinant nucleic acid molecule. As such, type II topoisomerases also are useful for performing methods of the invention.

Structural analysis of topoisomerases indicates that the members of each particular topoisomerase families, including type IA, type IB and type II topoisomerases, share common structural features with other members of the family (Berger, supra, 1998). In addition, sequence analysis of various type IB topoisomerases indicates that the structures are highly conserved, particularly in the catalytic domain (Shuman, supra, 1998; Cheng et al., supra, 1998; Petersen et al., supra, 1997). For example, a domain comprising amino acids 81 to 314 of the 314 amino acid *vaccinia* topoisomerase shares substantial homology with other type IB topoisomerases, and the isolated domain has essentially the same activity as the full length topoisomerase, although the isolated domain has a slower turnover rate and lower binding affinity to the recognition site (see Shuman, supra, 1998; Cheng et.al., supra, 1998). In addition, a mutant *vaccinia* topoisomerase, which is mutated in the amino terminal domain (at amino acid residues 70 and 72) displays identical properties as the full length topoisomerase (Cheng et al., supra, 1998). In fact, mutation analysis of *vaccinia* type IB topoisomerase reveals a large number of amino acid residues that can be mutated without affecting the activity of the topoisomerase, and has identified several amino acids that are required for activity (Shuman, supra, 1998). In view of the high homology shared among the *vaccinia* topoisomerase catalytic domain and the other type IB topoisomerases, and the detailed mutation analysis of *vaccinia* topoisomerase, it will be recognized that isolated catalytic domains of the type IB topoisomerases and type IB topoisomerases having various amino acid mutations can be used in the methods of the invention.

The various topoisomerases exhibit a range of sequence specificity. For example, type II topoisomerases can bind to a variety of sequences, but cleave at a highly specific recognition site (see Andersen et al., *J. Biol. Chem.* 266: 9203–9210, 1991, which is incorporated herein by reference.). In comparison, the type IB topoisomerases include site specific topoisomerases, which bind to and cleave a specific nucleotide sequence ("topoisomerase recognition site"). Upon cleavage of a nucleic acid molecule by a topoisomerase, for example, a type IB topoisomerase, the energy of the phosphodiester bond is conserved via the formation of a phosphotyrosyl linkage between a specific tyrosine residue in the topoisomerase and the 3' nucleotide of the topoisomerase recognition site. Where the topoisomerase cleavage site is near the 3' terminus of the nucleic acid molecule, the downstream sequence (3' to the cleavage site) can dissociate, leaving a nucleic acid molecule having the topoisomerase covalently bound to the newly generated 3' end (see FIG. 29).

A method of the invention for generating a ds recombinant nucleic acid molecule covalently linked in one strand, can be performed by contacting 1) a first nucleic acid molecule having a first end and a second end, wherein the first nucleic acid molecule has a site-specific topoisomerase recognition site (e.g., a type IA or a type II topoisomerase recognition site) at or near the 5' terminus of the first end or the second end or both and, optionally, comprising one or more recombination sites; 2) at least a second nucleic acid molecule that has, or can be made to have, a first end and a second end; and 3) at least one (e.g., 1, 2, 3, 4, 5, 6, 7, 8, 9, 10, etc.) site-specific topoisomerase (e.g., a type IA or a type IB topoisomerase), under conditions such that all components are in contact and the at least one topoisomerase can effect its activity. For example, the topoisomerase can be a type IA topoisomerase such as *E. coli* topoisomerase I, *E. coli* topoisomerase III, or a eukaryotic topoisomerase III. Upon cleavage of a nucleic acid molecule, the topoisomerase preferably is stably bound to the 5' terminus. Upon cleavage by the topoisomerase, the cleaved nucleic acid molecule often may comprise a 3' overhanging sequence. Once nucleic acid molecules are joined by the methods described above, the resulting molecules may then be used in recombination reactions, such as those described elsewhere herein.

A method of the invention for generating a ds recombinant nucleic acid molecule covalently linked in one strand can be performed such that any combination of ends are linked, and wherein one strand at the ends being linked is covalently linked and the other strand is not covalently linked, but contains a nick. For example, the first nucleic acid molecule can comprise a coding sequence, wherein the ATG start codon is at or near the first end and a poly A signal is encoded at or near the second end; and a second nucleic acid molecule can comprise a promoter element, which functions when positioned upstream of a coding sequence, and the first end is upstream of the second end, the method can be performed wherein a site-specific topoisomerase recognition site (e.g., a type IA or a type II topoisomerase recognition site) is at or near the 5' terminus of the first end of the first nucleic acid molecule, and wherein the contacting is performed under conditions such that the topoisomerase (e.g., a type IA or a type II topoisomerase) can covalently link the 5' terminus of the first end of the first nucleic acid molecule to the 3' terminus of the first end of the second nucleic acid molecule, thereby generating a ds recombinant nucleic acid molecule, in which a polypeptide can be expressed from the coding sequence. Alternatively, the method can be performed wherein the topoisomerase recognition site (e.g., a type IA or a type II topoisomerase recognition site) is at or near the 5' terminus of the second end of the first nucleic acid molecule, and wherein the contacting is performed under conditions such that the topoisomerase (e.g., a type IA or a type II topoisomerase recognition site) can covalently link the 5' terminus of the second end of the first nucleic acid molecule to the 3' terminus of the first end of the second nucleic acid molecule, thereby generating a ds recombinant nucleic acid molecule from which an antisense molecule can be expressed. Once nucleic acid molecules are joined by the methods described above, the resulting molecules may then be used in recombination reactions, such as those described elsewhere herein.

As another example using the first nucleic acid molecule and second nucleic acid molecule described above, the method can be performed, wherein the topoisomerase recognition site (e.g., a type IA or a type II topoisomerase recognition site) is at or near the 5' terminus of each of the first end and the second end of the first nucleic acid molecule, and wherein the contacting is performed under conditions such that the type IA topoisomerase can covalently link the 5' terminus of the first end of the first nucleic acid molecule to the 3' terminus of the first end of the second nucleic acid molecule, and the 5' terminus of the second end of the first nucleic acid molecule to the 3' terminus of the second end of the second nucleic acid molecule. As such, the ds recombinant nucleic acid molecule generated by the method is circularized, and includes a nick in each strand opposite the location where a strand was covalently linked by a topoisomerase (e.g., a type IA or a type II topoisomerase). Furthermore, the promoter of the second nucleic acid molecule can initiate expression of the first nucleic acid molecule. In one embodiment, the circularized ds recombinant nucleic acid molecule comprises a vector. Once nucleic acid molecules are joined by the methods described above, the resulting molecules may then be used in recombination reactions, such as those described elsewhere herein.

As another example using the first nucleic acid molecule and second nucleic acid molecule described above, the method can be performed, wherein the topoisomerase recognition site (e.g., a type IA or a type II topoisomerase recognition site) is at or near the 5' terminus of each of the first end and the second end of the first nucleic acid molecule, and wherein the contacting is performed under conditions such that the topoisomerase (e.g., a type IA or a type II topoisomerase) can covalently link the 5' terminus of the first end of the first nucleic acid molecule to the 3' terminus of the second end of the second nucleic acid molecule, and the 5' terminus of the second end of the first nucleic acid molecule to the 3' terminus of the first end of the second nucleic acid molecule. As such, the ds recombinant nucleic acid molecule generated by the method is circularized, and includes a nick in each strand opposite the location where a strand was covalently linked by topoisomerase (e.g., a type IA or a type II topoisomerase recognition site). Furthermore, the promoter of the second nucleic acid molecule can initiate expression of an antisense sequence. In one embodiment, the circularized ds recombinant nucleic acid molecule comprises a vector. Once nucleic acid molecules are joined by the methods described above, the resulting molecules may then be used in recombination reactions, such as those described elsewhere herein.

As disclosed herein, a method of generating a ds recombinant nucleic acid molecule covalently linked in one strand, involving a first nucleic acid molecule and at least a second nucleic acid molecule, can further include a step for amplifying the ds recombinant nucleic acid molecule covalently linked in one strand. The amplification reaction can be carried out by contacting the ds recombinant nucleic acid molecule with an amplification reaction primer pair, wherein a first primer of the pair is capable of binding to the covalently linked strand, at or near one end of the first or second nucleic acid molecule, and priming an amplification reaction toward the other nucleic acid molecule to generate a first extension product that is identical in nucleotide sequence to the nicked strand of the ds recombinant nucleic acid molecule; and the second primer of the pair is capable of binding to the first extension product, typically at or near the 3' terminus, and, in the presence of the first primer, can generate an amplification product using the covalently linked strand and the extension product (or extension products generated therefrom) as templates. For example, the method can be performed such that the type IA topoisomerase recognition site is at or near a first end of the first nucleic acid molecule, and the method further includes contacting the ds recombinant nucleic acid molecule with an amplification reaction primer pair, wherein a forward primer is capable of binding at or near the second end of the first nucleic acid molecule, and wherein a reverse primer is capable of binding to a nucleotide sequence complementary to at least a portion of the second end of the second nucleic acid molecule; and amplifying the ds recombinant nucleic acid molecule. The first nucleic acid molecule can include a coding region and the second nucleic acid molecule can include a regulatory element. Once nucleic acid molecules are joined by the methods described above, the resulting molecules may then be used in recombination reactions, such as those described elsewhere herein.

A method of generating a ds recombinant nucleic acid molecule covalently linked in one strand also can be performed by contacting 1) a first nucleic acid molecule having a first end and a second end, wherein the first nucleic acid molecule has a site-specific topoisomerase recognition site (e.g., a type IA or a type II topoisomerase recognition site) at or near the 5' terminus of the first end or the second end or both; 2) at least a second nucleic acid molecule that has, or can be made to have, a first end and a second end; 3) at least a third nucleic acid molecule which has, or can be made to have, a first end and a second end, each end further comprising a 5' terminus and a 3' terminus; and 4) at least one (e.g., 1, 2, 3, 4, 5, 6, 7, 8, 9, 10, etc.) site-specific topoisomerase (e.g., a type IA or a type II topoisomerase), under conditions such that all components are in contact and the at least one topoisomerase can effect its activity. For example, the topoisomerase can be a type IA topoisomerase such as *E. coli* topoisomerase I, *E. coli* topoisomerase III, or a eukaryotic topoisomerase III. Upon cleavage of a nucleic acid molecule, the topoisomerase preferably is stably bound to the 5' terminus. Preferably, upon cleavage by the topoisomerase, the cleaved nucleic acid molecule comprises a 3' overhanging sequence. Once nucleic acid molecules are joined by the methods described above, the resulting molecules may then be used in recombination reactions, such as those described elsewhere herein.

A method of the invention for generating a ds recombinant nucleic acid molecule covalently linked in one strand, involving a first nucleic acid molecule that contains a site-specific topoisomerase recognition site (e.g., a type IA or a type IB topoisomerase recognition site), or cleavage product thereof, at least a second nucleic acid molecule, and at least a third nucleic acid molecule can be performed such that any combination of ends are linked, and one strand at the ends being linked is covalently linked and one strand is nicked. According to this embodiment, any of the ends can contain a type IA, type II, or type IB topoisomerase recognition site, or can comprise a cleavage product thereof, provided that the first ds recombinant nucleotide molecule contains a topoisomerase recognition site (e.g., a type IA or a type H topoisomerase recognition site) at or near a 5' terminus, or a cleavage product thereof, and only one topoisomerase or topoisomerase recognition site is present at the ends that are to be linked. For example, where the first nucleic acid molecule comprises a site-specific type IA topoisomerase recognition site at or near each of the first end and the second end, the method further can include contacting the first nucleic acid molecule and the second nucleic acid molecule with at least a third nucleic acid molecule which has, or can be made to have, a first end and a second end, each end further comprising a 5' terminus and a 3' terminus, under conditions such that the topoisomerase (e.g., a type IA or a type II topoisomerase) can covalently link the 5' terminus of the first end of the first nucleic acid molecule with the 3' terminus of the first end of the second nucleotide sequence, and the 5' terminus of the second end of the first nucleic acid molecule with the 3' terminus of the first end of the third nucleotide sequence. It will be recognized that other combinations of ends and topoisomerase recognition sites, or cleavage products thereof, can be used to perform such a method of the invention. Once nucleic acid molecules are joined by the methods described above, the resulting molecules may then be used in recombination reactions, such as those described elsewhere herein.

A method of the invention also can be performed by contacting a first nucleic acid molecule and a second nucleic acid molecule with at least a third nucleic acid molecule, which comprises a first end and a second end, each end further comprising a 5' terminus and a 3' terminus, wherein the third nucleic acid molecule comprises a type IB topoisomerase recognition site at or near the 3' terminus of said first end, or said second end, or both said first end and said second end; and at least one (e.g., 1, 2, 3, 4, 5, 6, 7, 8, 9, 10, etc.) type IB topoisomerase under conditions such that the type IB topoisomerase can covalently link the 3' terminus of the first end or second end of the third nucleic acid molecule to the 5' terminus of the first end or second end of the second nucleic acid molecule. In such a method, where the third nucleic acid molecule comprises a type IB topoisomerase recognition site at or near the 3' terminus of the first end, the contacting can be performed under conditions such that the type IB topoisomerase can covalently link the 3' terminus of the first end of the third nucleic acid molecule to the 5' terminus of the first end of the second nucleic acid molecule. It will be recognized that other combinations of ends and topoisomerase recognition sites, or cleavage products thereof, can be used to perform such a method of the invention. Once nucleic acid molecules are joined by the methods described above, the resulting molecules may then be used in recombination reactions, such as those described elsewhere herein.

In another embodiment, a method for generating a ds recombinant nucleic acid molecule covalently linked in one strand can be performed by contacting 1) a first nucleic acid molecule having a first end and a second end, wherein the first nucleic acid molecule has a site-specific topoisomerase recognition site (e.g., a type IA or a type II topoisomerase recognition site) at or near the 5' terminus of an end and a type BB topoisomerase recognition site at or near the 3' terminus of the other end; 2) at least a second nucleic acid molecule that has, or can be made to have, a first end and a second end; 3) at least one (e.g., 1, 2, 3, 4, 5, 6, 7, 8, 9, 10, etc.) site-specific topoisomerase (e.g., a type IA or a type II topoisomerase); and 4) at least one (e.g., 1, 2, 3, 4, 5, 6, 7, 8, 9, 10, etc.) type BB topoisomerase under conditions such that all components are in contact and the at least one topoisomerase can effect its activity. For example, the topoisomerase, for which a recognition site is at or near the 5' terminus, can be a type IA topoisomerase such as *E. coli* topoisomerase I, *E. coli* topoisomerase III, or a eukaryotic topoisomerase III. Upon cleavage of a nucleic acid molecule, the type IA topoisomerase preferably is stably bound to the 5' terminus, and the type IB topoisomerase preferably is stably bound at the 3' terminus. Preferably, upon cleavage by the topoisomerases, the cleaved nucleic acid molecule comprises a 3' overhanging sequence and a 5' overhanging sequence. The method can further include contacting the ds recombinant nucleic acid molecule with a DNA ligase, thereby generating a ds recombinant nucleic acid molecule covalently linked in both strands. Once nucleic acid molecules are joined by the methods described above, the resulting molecules may then be used in recombination reactions, such as those described elsewhere herein.

A method of generating a ds recombinant nucleic acid molecule covalently linked in one strand by contacting a first nucleic acid molecule, a second nucleic acid molecule, and at least a third nucleic acid molecule, can further include a step for amplifying the ds recombinant nucleic acid molecule, particularly the covalently linked strand. The amplification can be carried out by contacting the ds recombinant nucleic acid molecule with an amplification reaction primer pair, wherein a first primer of the pair can bind selectively to the covalently linked strand at or near one end of the first or second nucleic acid molecule and prime an amplification reaction toward the other nucleic acid molecule to generate a first extension product that is complementary to the covalently-linked strand; and the second primer of the pair can bind selectively to the first extension product, typically at or near the 3' terminus, and, in the presence of the first primer, can generate an amplification product using the covalently linked strand and the extension product (or extension products derived therefrom) as templates. The method can be performed such that the topoisomerase recognition site (e.g., a type IA or a type IB topoisomerase recognition site) is at or near the first end of the first nucleic acid molecule, and can further include contacting the ds recombinant nucleic acid molecule with an amplification reaction primer pair, wherein a forward primer is capable of binding to a nucleotide sequence at or near the second end of the first nucleic acid molecule and wherein a reverse primer is capable of binding to a nucleotide sequence complementary to at least a portion of the third nucleic acid molecule; and amplifying the ds recombinant nucleic acid molecule. The first nucleic acid molecule can include a coding region and the third nucleic acid molecule can include a regulatory element. Furthermore, the ends being linked can contain complementary overhanging sequences. Once nucleic acid molecules are joined by the methods described above, the resulting molecules may then be used in recombination reactions, such as those described elsewhere herein.

Figure 11A:
Figure 11B:
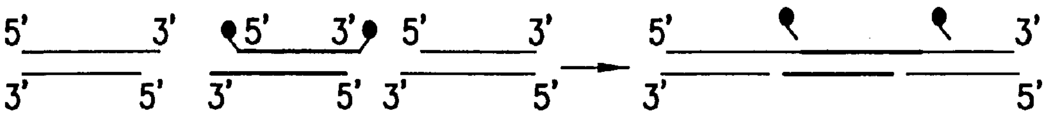
Figure 11C:
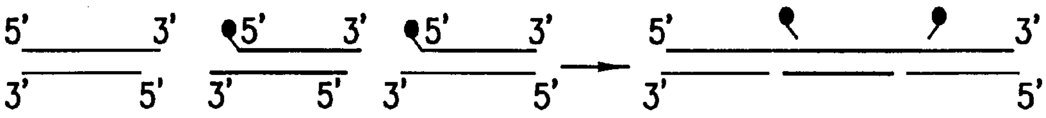
Figure 11D:
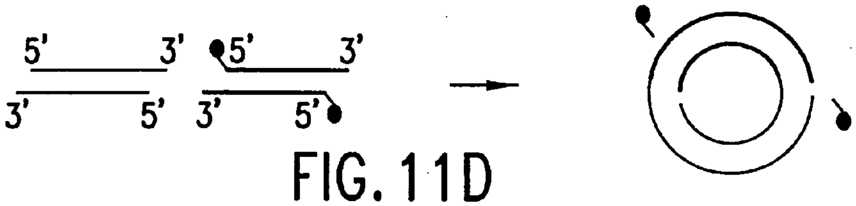
Figure 11E:
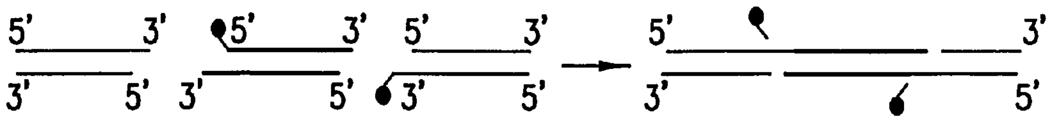
Figure 11F:
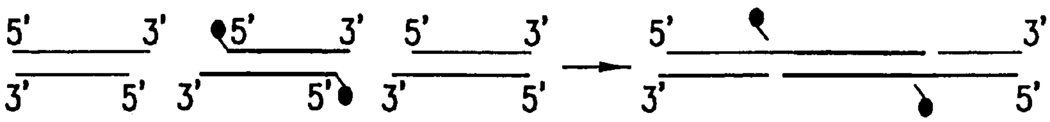

Representative embodiments of the disclosed methods for generating a ds recombinant nucleic acid molecule covalently linked in one strand and, optionally, comprising one or more recombination sites, are illustrated in FIGS. 11A–11F. In FIG. 11A, one of the nucleic acid molecules has a topoisomerase attached to the 5' terminus of one end such that, when this molecule, which has a 3' overhang, is contacted with a second nucleic acid molecule having a substantially complementary 3' overhang, under suitable conditions, the nucleotides comprising the 3' overhangs can hybridize and the topoisomerases can catalyze ligation. FIG. 11B shows a first nucleic acid molecule having topoisomerase molecules linked to the 5' terminus and 3' terminus of two different ends of one nucleotide sequence, and further shows linkage of the first nucleic acid molecule to two other nucleotide sequences to generate a nucleic acid molecule which has one strand without any nicks and another strand with two nicks. FIG. 11C shows a first nucleic acid molecule having a topoisomerase molecule linked to the 5' terminus of one end and a second nucleic acid molecule having a topoisomerase molecule linked to the 5' terminus of one end, and further shows linkage of the first and second nucleic acid molecule to one other nucleotide sequence to generate a nucleic acid molecule which has one strand without any nicks and another strand with two nicks. In FIG. 11D, one of the nucleic acid molecules to be linked has site-specific type IA topoisomerases attached to the 5' terminus of both ends such that, when the nucleotide sequences are contacted the complementary 3' overhangs can hybridize and the topoisomerases catalyze ligation. FIG. 11E shows another example of linking three nucleic acid molecules together, using one nucleic acid molecule that is topoisomerase-charged with a type IA topoisomerase at a 5' terminus and another nucleic acid molecule that is topoisomerase-charged with a type IB topoisomerase at a 3' terminus of the opposite strand to be linked, such that when the nucleotide sequences are contacted the complementary 3' overhangs can hybridize and the topoisomerases catalyze ligation. FIG. 11F illustrates another example of linking three nucleic acid molecules together, in this case using one nucleic acid molecule that is topoisomerase-charged with a topoisomerase (e.g., a type IA or a type II topoisomerase) at a first 5' terminus and is charged with a topoisomerase at a second 5'-terminus of the opposite strand, such that when the nucleotide sequences are contacted under suitable conditions, the complementary 3' overhangs can hybridize and the topoisomerases catalyze ligation. Once nucleic acid molecules are joined by the methods described above, the resulting molecules may then be used in recombination reactions, such as those described elsewhere herein.

The examples set forth in FIGS. 11A–11F show the ends of the nucleic acid molecules opposite those being linked as having blunt ends, and shows the being linked as having 3' overhanging sequences. However, the substrate nucleic acid molecules can have any ends and overhangs as desired, including both ends being blunt and/or complementary, or combinations thereof, such that the ends can be ligated to each other, for example, to form circular molecules or to other nucleic acid molecules having an appropriate end. Thus, one or more of the blunt ends as shown in FIGS. 11A–11F can be substituted with a nucleotide sequence comprising a 5' overhang or a 3' overhang, either of which can constitute a single nucleotide such as a thymidine residue or multiple nucleotides (e.g., two, three, four, five, six, seven, eight, nine, ten, eleven, twelve, thirteen, fourteen, fifteen, etc. nucleotides), which can be the same or different. In certain embodiments of the disclosed methods, a first nucleic acid molecule contains a blunt end to be linked, and a second nucleic acid molecule contains an overhang at the end which is to be linked by a site-specific topoisomerase (e.g., a type IA or a type IB topoisomerase), wherein the overhang includes a sequence complementary to that comprising the blunt end, thereby facilitating strand invasion as a means to properly position the ends for the linking reaction.

As exemplified in FIGS. 11A–11C, the ds recombinant nucleic acid molecule generated using the methods of this aspect of the invention include those in which one strand (not both strands) is covalently linked at the ends to be linked (i.e. ds recombinant nucleic acid molecules generated using these methods contain a nick at each position where two ends were joined). These embodiments are particularly advantageous in that a polymerase can be used to replicate the ds recombinant nucleic acid molecule by initially replicating the covalently linked strand. For example, a thermostable polymerase such as a polymerase useful for performing an amplification reaction such as PCR can be used to replicate the covalently strand, whereas the strand containing the nick does not provide a suitable template for replication.

The present invention also provides methods of covalently ligating the ends of two different nucleic acid molecules or two ends of the same nucleic acid molecule, such that the product generated is ligated in both strands and, therefore, does not contain a nick. Representative embodiments of this aspect of the invention are illustrated in FIG. 12. For example, in FIG. 12A, one of the nucleic acid molecules has topoisomerase molecules attached to the 3' terminus and the 5' terminus of one end such that, when this molecule, which has a 5' overhang, is contacted with a second nucleic acid molecule having a substantially complementary 5' overhang, under suitable conditions, the nucleotides comprising the 5' overhangs can hybridize and the topoisomerases can catalyze ligation of both strands of the nucleic acid molecules. In FIG. 12B, each end of the nucleic acid molecules to be linked has a topoisomerase molecule attached to the 3' terminus such that, when the nucleotide sequences are contacted under suitable conditions, nucleotides comprising the 5' overhangs can hybridize and the topoisomerases catalyze ligation (compare FIG. 12C, in which each of the nucleic acid molecules to be linked has a topoisomerase attached to the 5' termini of the ends to be linked). FIG. 12D illustrates linking three nucleic acid molecules together via a nucleic acid molecule that is topoisomerase-charged at both termini of both ends. Similarly to FIG. 11, the examples set forth in FIGS. 12A–12D show the ends of the nucleic acid molecules that are not being linked as having blunt ends. As discussed with respect to FIG. 11, however, the substrate nucleic acid molecules utilized in methods as exemplified in FIG. 12 can have any ends as desired, including topoisomerase-charged ends, such that the ends can be ligated to each other, for example, to form circular molecules or to other nucleic acid molecules having an appropriate end, blunt ends, 5' overhangs, 3' overhangs, and the like, as desired. Once nucleic acid molecules are joined by the methods described above, the resulting molecules may then be used in recombination reactions, such as those described elsewhere herein.

A covalently bound topoisomerase, in addition to catalyzing a ligation reaction, also can catalyze the reverse reaction, for example, religation of the 3' nucleotide of the recognition sequence, to which the type IB topoisomerase is linked through the phosphotyrosyl bond, and the nucleotide sequence that, prior to cleavage, comprised the 3' terminus of the nucleic acid molecule, and which, following cleavage, contains a free 5' hydroxy group. As such, methods have been developed for using a type IB topoisomerase to produce recombinant nucleic acid molecules. For example, cloning vectors containing a bound type IB topoisomerase have been developed and are commercially available (Invitrogen Corporation, Carlsbad, Calif.). Such cloning vectors, when linearized, contain a covalently bound type IB topoisomerase at each 3' end ("topoisomerase charged"). Nucleotide sequences such as those comprising a cDNA library, or restriction fragments, or sheared genomic DNA sequences that are to be cloned into such a vector are treated, for example, with a phosphatase to produce 5' hydroxyl termini, then are added to the linearized topoisomerase-charged vector under conditions that allow the topoisomerase to ligate the nucleotide sequences at the 5' terminus containing the hydroxyl group and the 3' terminus of the vector that contains the covalently bound topoisomerase. A nucleotide sequence such as a PCR amplification product, which is generated containing 5' hydroxyl ends, can be cloned into a topoisomerase-charged vector in a rapid joining reaction (approximately 5 minutes at room temperature). The rapid joining and broad temperature range inherent to the topoisomerase joining reaction makes the use of topoisomerase-charged vectors ideal for high throughput applications, which generally are performed using automated systems.

Type II topoisomerases have not generally been used for generating recombinant nucleic acid molecules or cloning procedures, whereas type IB topoisomerases, as indicated above, are used in a variety of procedures. As disclosed herein, type IA topoisomerases can be used in a variety of procedures similar to those described for the type IB topoisomerases. However, previously described methods of using type IB topoisomerases to ligate two or more nucleotide sequences have suffered from the disadvantage that the bound topoisomerase only effects the joining of the 3' end of the strand to which it is attached and a second strand containing a 5' hydroxyl group. Since the topoisomerase cannot ligate the complementary strands, the nucleic acid molecules that are generated contain nicks. While the presence of such nicks does not prevent the use of the recombinant molecules for transfection of a host cells, as the nicks generally are resolved intracellularly, the presence of such nicks in double stranded nucleic acid molecules significantly limits direct use of the recombinant molecules. For example, a strand of a nucleic acid molecule containing a nick cannot be amplified by PCR because the primer extension reaction terminates at the nick. Thus, nucleic acid constructs prepared using a topoisomerase according to previously described methods generally must be further treated, for example, with a DNA ligase, to obtain a ds recombinant nucleic acid molecule that is covalently linked in both strands and, therefore, useful for subsequent manipulations such as PCR.

Previously described methods for preparing nucleic acid constructs also generally required numerous steps, particularly where more than two nucleotide sequences are to be ligated, and even more so where the sequences must be ligated in a predetermined orientation. For example, the nucleotide sequences to be linked generally are ligated sequentially to produce intermediate constructs, each of which must be cloned, amplified in a host cell, isolated, and characterized. The constructs containing the correct sequences then must be isolated in a sufficient quantity and form such that the next nucleotide sequence can be ligated, and the process of cloning, amplifying, isolating and characterizing performed again to identify the proper construct. Clearly, as the number of different nucleotide sequences to be joined increases, so do the number of essentially repetitive procedures that must be performed, thus resulting in an expensive, laborious and lengthy process.

As disclosed herein, an advantage of a method of the invention for generating a ds recombinant nucleic acid molecule covalently linked in both strands is that there is no need to perform a separate ligation reaction in order to obtain a functional ds recombinant nucleic acid molecule covalently linked in both strands (see FIGS. 8 and 12). In addition, a method of this aspect of the invention can be performed such that, where a number of different nucleic acid molecules are to be covalently linked in a predetermined orientation, there is no requirement that intermediate constructs be cloned, characterized and isolated before proceeding to a subsequent step (see Example 1.B). As such, the methods of this aspect of the invention provide a means to generate a ds recombinant nucleic acid molecule covalently linked in both strands much more quickly and at a substantially lower cost than was possible using previously known methods.

As an additional advantage, the generated ds recombinant nucleic acid molecules covalently linked in both strands are in a form that can be used directly in further procedures, for example, particular procedures involving extension of a primer such as a PCR amplification procedure, or other transcription or translation procedure, because the generated construct does not contain nicks at the sites where the ds nucleotides sequences have been joined. As disclosed herein, a method of the invention for generating a ds recombinant nucleic acid molecule covalently linked in one strand, in certain embodiments, also is advantageous in that the generated ds recombinant nucleic acid molecules are in a form that can be used directly in further procedures, for example, particular procedures involving extension of a primer such as a PCR amplification procedure, or other transcription or translation procedure, because in certain embodiments, the generated ds recombinant nucleic acid molecule contains one strand that does not contain a nick at the sites where the ds nucleotides sequences were joined.

The term "nucleotide sequence" or "nucleic acid molecule" is used herein to refer to a discrete nucleic acid molecule. When used as such, the term "nucleotide sequence" is used merely for convenience such that the components in a composition or used in a method of the invention can be clearly distinguished. Thus, reference is made, for example, to "nucleic acid molecules", which, in a method of the invention, correspond to the reactants (substrates) used to produce a recombinant "nucleic acid molecule" product.

Certain methods of the invention are exemplified generally herein with reference to the use of type IB topoisomerase such as the *Vaccinia* topoisomerase, or a type IA topoisomerase. However, it will be recognized that the methods also can be performed using a topoisomerase other than that exemplified, merely by adjusting the components accordingly. For example, as described in greater detail below, methods are disclosed for incorporating a type IB topoisomerase recognition site at one or both 3' termini of a linear nucleic acid molecule using a PCR primer comprising, at least in part, a nucleotide sequence complementary to the topoisomerase recognition site. In comparison, a topoisomerase recognition site for a type IA or, if desired, type II topoisomerase, can be incorporated into a nucleic acid molecule by using a PCR primer that contains the recognition site.

Cleavage of a nucleic acid molecule by a site specific type IB topoisomerase results in the generation of a 5' overhanging sequence in the strand complementary to and at the same end as that containing the covalently bound topoisomerase. Furthermore, as disclosed herein, PCR primers can be designed that can incorporate a type IB topoisomerase recognition site into a nucleic acid molecule, and that further can produce, upon cleavage of the nucleic acid molecule by the topoisomerase, a 5' overhanging sequence in the complementary strand that has a defined and predetermined sequence. As such, the methods are readily adaptable to generating a ds recombinant nucleic acid molecule having the component nucleic acid molecule operatively linked in a predetermined orientation. In view of the present disclosure, it will be recognized that PCR primers also can be designed such that a type IA topoisomerase recognition site can be introduced into a nucleic acid molecule, including a library of diverse sequences, and, if desired, such that upon cleavage by a site-specific topoisomerase, generates a 3' overhanging sequence.

A method of generating a ds recombinant nucleic acid molecule covalently linked in both strands, as disclosed herein, extends the previously known methods by providing a topoisomerase at or near the terminus of each nucleic acid molecule to be covalently linked. For example, with respect to a type IB topoisomerase, the method provides a topoisomerase recognition site, or a cleavage product thereof (i.e., a covalently bound type IB topoisomerase), at or near the 3' terminus of each linear nucleic acid molecule to be linked. As used herein, the term "topoisomerase recognition site" means a defined nucleotide sequence that is recognized and bound by a site specific topoisomerase. For example, the nucleotide sequence 5'-(C/T)CCTT-3' is a topoisomerase recognition site that is bound specifically by most poxvirus topoisomerases, including vaccinia virus DNA topoisomerase I, which then can cleave the strand after the 3'-most thymidine of the recognition site to produce a nucleotide sequence comprising 5'-(C/T)CCTT-$PO_4$-TOPO, i.e., a complex of the topoisomerase covalently bound to the 3' phosphate through a tyrosine residue in the topoisomerase (see Shuman, *J. Biol. Chem.* 266:11372–11379, 1991; Sekiguchi and Shuman, *Nucl. Acids Res.* 22:5360–5365, 1994; each of which is incorporated herein by reference; see, also, U.S. Pat. No. 5,766,891; PCT/US95/16099; PCT/US98/12372). In comparison, the nucleotide sequence 5'-GCAACTT-3' is the topoisomerase recognition site for type IA *E. coli* topoisomerase III.

Topoisomerase-charged nucleic acid molecules, including those containing a topoisomerase covalently attached to a 5' terminus or 3' terminus or both, of one or both ends of the nucleic acid molecule, can be generated by any of a number of methods. In some cases and under the appropriate conditions, type I topoisomerases can cleave a single stranded nucleotide sequence. For example, a domain comprising the amino-terminal 67 kDa domain of *E. coli* topoisomerase I, which is a type IA topoisomerase, can cleave a single stranded nucleotide sequence containing the topoisomerase recognition site. Where conditions are such that the topoisomerases can cleave a single stranded nucleotide sequence, cleavage of a nucleic acid molecule containing topoisomerase recognition sites at the 5' and 3' termini of one end of nucleic acid molecule can be performed in parallel. Alternatively, where one or both of the topoisomerases requires a nucleic acid molecule for recognition and cleavage, the reactions are performed serially, wherein the more terminal (distal) of the topoisomerase recognition sites is cleaved first, then the more internal (proximal) site, which remains in a double stranded context, is cleaved. For example, a nucleic acid molecule containing an *E. coli* topoisomerase III recognition site at or near a 5' terminus of an end and a *Vaccinia* type IB topoisomerase recognition site at or near the 3' terminus of the same end, and wherein the type IB recognition site is closer to the end than the type IA recognition site, the nucleic acid molecule can be incubated with the *Vaccinia* topoisomerase, to produce a type IB topoisomerase charged nucleic acid molecule, then with the *E. coli* topoisomerase, to produce a nucleic acid molecule having the type IA topoisomerase bound to the 5' terminus and the type IB topoisomerase bound to the 3' terminus. Accordingly, the invention includes methods for producing nucleic acid molecule comprising a topoisomerase attached to one or both termini of at least one end, and further provides such topoisomerase-charged nucleic acid molecules.

As used herein, the term "cleavage product," when used in reference to a topoisomerase recognition site, refers to a nucleotide sequence that has been cleaved by a topoisomerase, generally at its recognition site, and comprises a complex of the topoisomerase covalently bound, in the case of type IA or type II topoisomerase, to the 5' phosphate group of the 5' terminal nucleotide in the topoisomerase recognition site, or in the case of a type IB topoisomerase to the 3' phosphate group of the 3' terminal nucleotide in the topoisomerase recognition site. Such a complex, which comprises a topoisomerase cleaved nucleic acid molecule having the topoisomerase covalently bound thereto, is referred to herein as a "topoisomerase-activated" or a "topoisomerase-charged" nucleotide sequence. Topoisomerase-activated nucleic acid molecules can be used in a method of the invention, as can nucleic acid molecules that contain an uncleaved topoisomerase recognition site and a topoisomerase, wherein the topoisomerase can cleave the nucleic acid molecule at the recognition site and become covalently bound thereto.

In one embodiment of a method of generating a ds recombinant nucleic acid molecule covalently linked in both strands, a topoisomerase recognition site is present at or near the 3' terminus of the end of each nucleotide sequence to be linked such that, in the presence of a type IB topoisomerase, each nucleotide sequence is cleaved to produce a 3' terminus, which contains the topoisomerase covalently bound thereto (see FIG. 8). The nucleotide sequences to be covalently linked also can contain a 5' hydroxy group at the same end as that containing the topoisomerase recognition site, or a 5' hydroxyl group can be generated using a phosphatase. Upon contact of such nucleotide sequences, the site specific topoisomerase can ligate each strand containing a 3' phosphate to a respective 5' hydroxyl group, thereby generating a ds recombinant nucleic acid molecule covalently linked in both strands, which can be produced as a linear, circular, or positively or negatively supercoiled nucleic acid molecule.

Preferably, the 5' termini of the ends of the nucleotide sequences to be linked by a type IB topoisomerase according to a method of certain aspects of the invention contain complementary 5' overhanging sequences, which can facilitate the initial association of the nucleotide sequences, including, if desired, in a predetermined directional orientation. Alternatively, the 5' termini of the ends of the nucleotide sequences to be linked by a type IB topoisomerase according to a method of certain aspects of the invention contain complementary 5' sequences wherein one of the sequences contains a 5' overhanging sequence and the other nucleotide sequence contains a complementary sequence at a blunt end of a 5' terminus, to facilitate the initial association of the nucleotide sequences through strand invasion, including, if desired, in a predetermined directional orientation. The term "5' overhang" or "5' overhanging sequence" is used herein to refer to a strand of a nucleic acid molecule that extends in a 5' direction beyond the terminus of the complementary strand of the nucleic acid molecule. Conveniently, a 5' overhang can be produced as a result of site specific cleavage of a nucleic acid molecule by a type IB topoisomerase (see Example 1).

Preferably, the 3' termini of the ends of the nucleotide sequences to be linked by a type IA topoisomerase according to a method of certain aspects of the invention contain complementary 3' overhanging sequences, which can facilitate the initial association of the nucleotide sequences, including, if desired, in a predetermined directional orientation. Alternatively, the 3' termini of the ends of the nucleotide sequences to be linked by a topoisomerase (e.g., a type IA or a type II topoisomerase) according to a method of certain aspects of the invention contain complementary 3' sequences wherein one of the sequences contains a 3' overhanging sequence and the other nucleotide sequence contains a complementary sequence at a blunt end of a 3' terminus, to facilitate the initial association of the nucleotide sequences through strand invasion, including, if desired, in a predetermined directional orientation. The term "3' overhang" or "3' overhanging sequence" is used herein to refer to a strand of a nucleic acid molecule that extends in a 3' direction beyond the terminus of the complementary strand of the nucleic acid molecule. Conveniently, a 3' overhang can be produced upon cleavage by a type IA or type II topoisomerase.

The 3' or 5' overhanging sequences can have any sequence, though generally the sequences are selected such that they allow ligation of a predetermined end of one nucleic acid molecule to a predetermined end of a second nucleotide sequence according to a method of the invention (FIG. 9C, see, also Example 1.B). As such, while the 3' or 5' overhangs can be palindromic, they generally are not because nucleic acid molecules having palindromic overhangs can associate with each other, thus reducing the yield of a ds recombinant nucleic acid molecule covalently linked in both strands comprising two or more nucleic acid molecules in a predetermined orientation. For example, the 5' overhanging sequences of nucleic acid molecules shown in FIG. 9A are palindrome and, therefore, the association, for example, of a first CMV element with a second CMV element through the AGCT overhang is just as likely as the association of a CMV element with a GFP element through the AGCT overhang. As such, the efficiency of generating a construct comprising an operatively covalently linked construct containing, in order from 5' to 3', a CMV element, a GFP element and a BGH element would be reduced as compared to the efficiency of generating such a construct using the elements as shown in FIG. 9C. The elements shown in FIG. 9B contain palindromic overhangs at one end of the GFP element and at the end of the BGH element shown and, therefore, would be less efficient than the elements of FIG. 9C, but more efficient than those in FIG. 9A, for generating the desired construct.

A nucleotide sequence used in the methods and kits of the current invention can be designed to contain a bridging phosphorothioate to prevent religation after topoisomerase-cleavage. For example, where the topoisomerase is *E. coli* topoisomerase III, the bridging phosphorothioate can be incorporated between the two thymidines of the GCAACTT cleavage/recognition sequence. When cleaved, the clipped sequence contains a 3'-SH instead of a 3'-OH, thus preventing religation (see Burgin, et al, *Nucl. Acids Res.* 23:2973–2979, 1995).

A nucleic acid molecule useful in a method or kit of an aspect of the invention can be amplified by an amplification method such as PCR to contain a topoisomerase recognition site at a 3' or 5' terminus of an end. Furthermore, one or both primers used for PCR can be designed such that, upon cleavage of an amplified nucleic acid molecule, the cleaved nucleic acid molecule contains a 5' or 3' overhang at one or both ends. In one embodiment, PCR primers are designed such that the 5' overhanging sequence on a first nucleic acid molecule is complementary to a 5' overhanging sequence on a second (or other) nucleic acid molecule, thereby facilitating the association of the nucleotide sequences, preferably in a predetermined orientation, whereupon they can be covalently linked according to a method of the invention. In accordance with the invention, by designing unique overhanging sequences for the different nucleic acid molecule to be linked, any number of nucleic acid molecules can be linked in a desired order and/or orientation.

It should be recognized that PCR is used in two ways with respect to the methods of the invention. In one aspect, PCR primers are designed to impart particular characteristics to a desired nucleic acid molecule, for example, a nucleic acid molecule that encodes a transcriptional or translational regulatory element or a coding sequence of interest such as an epitope tag or cell compartmentalization domain. In this aspect, the PCR primers can be designed such that, upon amplification, the nucleic acid molecule contains a topoisomerase recognition site at one or both ends, as desired. As disclosed herein, the PCR primer also can include an additional sequence such that, upon cleavage of the amplification product by a site specific topoisomerase, the cleaved nucleic acid molecule contains a 5' or 3' overhanging sequence at the topoisomerase cleaved end. In an embodiment of the invention involving a topoisomerase that binds and cleaves a 5' terminus (e.g., an embodiment involving a type IA topoisomerase), the PCR primers can be designed to contain a bridging phosphorothioate linkage (see above), which can block religation after topoisomerase cleavage and can assist in the generation of a topoisomerase charged amplification product.

Overhanging sequences generated using PCR can include a single nucleotide overhang that is generated as an artifact of the PCR reaction. For example, a polymerase such at Taq, which does not have a proof-reading function and has an inherent terminal transferase activity, is commonly used, and produces PCR products containing a single, non-template derived 3' A overhang at each end. These amplification products can be linked to topoisomerase charged nucleic acid molecules containing a single 3' T overhang or a single 3' dU overhang, which, for a T/A cloning reaction, can be a vector (see U.S. Pat. Nos. 5,487,993 and 5,856,144, each of which is incorporated herein by reference), at one or both ends, using the methods of the invention.

PCR also is used to amplify a covalently linked ds recombinant nucleic acid molecule covalently linked in one or both strands, generated by a method of the invention. For example, as illustrated in FIG. 13, a method of the invention can generate an expressible ds recombinant nucleic acid molecule from three substrate nucleic acid molecules including a nucleotide sequence comprising a promoter, a nucleotide sequence comprising a coding sequence, and a nucleotide sequence comprising a polyadenylation signal. The generation of the ds recombinant nucleic acid molecule can be facilitated by the incorporation of complementary 3' (or 5') overhanging sequences at the ends of the ds nucleotides sequences to be joined. For example, the expressible ds recombinant nucleic acid molecule can be generated by contacting a first nucleic acid molecule having a type IA topoisomerase at a 5' terminus of a first end and a type IB topoisomerase at a 3' terminus of a second end with a second nucleic acid molecule and a third double stranded nucleotide sequence. By designing a PCR primer pair containing a first primer that is specific for a portion of the nucleotide sequence comprising the promoter that is upstream from the promoter, and a second primer that is specific for a portion of the nucleotide sequence comprising the polyadenylation signal that is down stream of the signal, only a full length functional ds recombinant nucleic molecule containing the promoter, coding sequence and polyadenylation signal in the correct (predetermined) orientation will be amplified. In particular, partial reaction products, for example, containing only a promoter linked to the coding sequence, and reaction products containing nicks are not amplified. Thus, PCR can be used to specifically design a nucleic acid molecule such that it is useful in a method of the invention, and to selectively amplify only those reaction products having the desired components and characteristics.

As used herein, the term "covalently linked," when used in reference to a ds recombinant nucleic acid molecule, means that the nucleic acid molecule is generated from at least two nucleic acid molecules that are ligated together, in both strands, by a topoisomerase mediated ligation. It should be recognized, for example, that a topoisomerase covalently bound to one of the nucleic acid molecules to be covalently linked can be the same as or different from the topoisomerase covalently bound to the other nucleic acid molecule. Thus, a *Vaccinia* topoisomerase can be covalently bound to one nucleic acid molecule and another poxvirus or eukaryotic nuclear type IB topoisomerase can be bound to the other strand. Generally, however, the topoisomerases, where different, are members of the same family, for example, type IA or type IB or type II, although, where the topoisomerases are covalently bound, for example, to a 5' phosphate and generate complementary 3' overhangs, the topoisomerase can be from different families, for example, type IA and type II.

The term "covalently linked" also is used herein in reference to a single stranded or double stranded nucleic acid molecule that is generated from at least two nucleotide sequences that are ligated together in one strand. For example, a ds recombinant nucleic acid molecule that is generated when a first topoisomerase-charged nucleic acid molecule that includes one topoisomerase bound at or near a 5' terminus contacts a second ds nucleotide sequence under conditions such that the topoisomerases can covalently link the 5' terminus of the first nucleic acid molecule to which it is bound, to the 3' terminus of the second nucleic acid molecule, can generate a ds recombinant nucleic acid molecule covalently linked in one strand.

In one embodiment, a ds recombinant nucleic acid molecule covalently linked in both strands generated according to a method of the invention does not contain a nick in either strand at the site where two nucleotide sequences are ligated, although it can contain nicks elsewhere in the molecule. In a method for generating a ds recombinant nucleic acid molecule covalently linked in one strand, a ds recombinant nucleic acid molecule is generated that contains a nick at least at the position where ends were linked in the complementary strands. This nicked ds recombinant nucleic acid molecule can be converted to a ds recombinant nucleic acid molecule covalently linked in both strands by introducing the nicked ds recombinant nucleic acid molecule into a cell, or by subjecting the ds recombinant nucleic acid molecule to a ligation reaction, such as using a ligase, as is well known in the art.

The term "recombinant" is used herein to refer to a nucleic acid molecule that is produced by linking at least two nucleotide sequences according to a method of the invention. As such, a ds recombinant nucleic acid molecule encompassed within the present invention is distinguishable from a nucleic acid molecule that may be produced in nature, for example, during meiosis. For example, a ds recombinant nucleic acid molecule covalently linked in both strands generated according to a method of certain aspects of the invention can be identified by the presence of the two topoisomerase recognition sites, one present in each of the complementary strands, at or near the site at which the nucleic acid molecules were joined.

A method of the invention can be performed by contacting a first nucleic acid molecule having a first end and a second end, wherein at the first end or second end or both, the first nucleic acid molecule has a topoisomerase recognition site, or cleavage product thereof, at or near the 3' terminus and has (or can be made to have, for example, by contact with a phosphatase) a hydroxyl group at the 5' terminus of the same end; at least a second nucleic acid molecule having a first end and a second end, wherein at the first end or second end or both, the at least second nucleic acid molecule has a topoisomerase recognition site, or cleavage product thereof, at or near the 3' terminus and has (or can be made to have) a hydroxyl group at the 5' terminus of the same end; and a topoisomerase, under conditions such that the components are in contact and the topoisomerase can effect its activity. Upon contact of the topoisomerase with the first and second (or other) nucleic acid molecules, and cleavage, where necessary, each nucleotide sequence comprises at the cleavage site a covalently bound topoisomerase at the 3' terminus and has, or can have, a hydroxyl group at the 5' terminus such that, upon contact, the first and at least second nucleotide sequences are covalently linked in both strands. Accordingly, the invention provides a ds recombinant nucleic acid molecule covalently linked in both strands produced by such a method.

As used herein, the term "at or near," when used in reference to the proximity of a topoisomerase recognition site to the 3' (type IB) or 5' (type IA or type II) terminus of a nucleotide sequence, means that the site is within about 1 to 100 nucleotides from the 3' terminus or 5' terminus, respectively, generally within about 1 to 20 nucleotides from the terminus, and particularly within about 2 to 12 nucleotides from the respective terminus. An advantage of positioning the topoisomerase recognition site within about 10 to 15 nucleotides of a terminus is that, upon cleavage by the topoisomerase, the portion of the sequence downstream of the cleavage site can spontaneously dissociate from the remaining nucleotide sequence, which contains the covalently bound topoisomerase (referred to generally as "suicide cleavage"; see, for example, Shuman, supra, 1991; Andersen et al., supra, 1991). Where a topoisomerase recognition site is greater than about 12 to 15 nucleotides from the terminus, the nucleotide sequence upstream or downstream of the cleavage site can be induced to dissociate from the remainder of the sequence by modifying the reaction conditions, for example, by providing an incubation step at a temperature above the melting temperature of the portion of the duplex including the topoisomerase cleavage site.

An additional advantage of constructing a first or second (or other) nucleic acid molecule to comprise, for example, a type IB topoisomerase recognition site about 2 to 15 nucleotides from one or both ends is that a 5' overhang is generated following cleavage of the nucleic acid molecule by a site specific topoisomerase. Such a 5' overhanging sequence, which would contain 2 to 15 nucleotides, respectively, can be designed using a PCR method as disclosed herein to have any sequence as desired. Thus, where a cleaved first nucleic acid molecule is to be covalently linked to a selected second (or other) nucleic acid molecule according to a method of the invention, and where the selected sequence has a 5' overhanging sequence, the 5' overhang on the first nucleic acid molecule can be designed to be complementary to the 5' overhang on the selected second (or other) ds sequence such that the two (or more) sequences are covalently linked in a predetermined orientation due to the complementarity of the 5' overhangs. As discussed above, similar methods can be utilized with respect to 3' overhanging sequences generated upon cleavage by, for example, a type IA or type II topoisomerase.

As used herein, reference to a nucleotide sequence having "a first end" and "a second end" means that the nucleotide sequence is linear. A substrate nucleic acid molecule can be linear or circular, including supercoiled, although, as a result of cleavage by one or more topoisomerases, a linear topoisomerase-charged nucleic acid molecule generally is produced. For example, a circular nucleic acid molecule containing two type IB topoisomerase recognition sites within about 100 nucleotides of each other and in the complementary strands, preferably within about twenty nucleotides of each other and in the complementary strands, can be contacted with a site specific type IB topoisomerase such that each strand is cleaved and the intervening sequence dissociates, thereby generating a linear nucleic acid molecule having a topoisomrerase covalently bound to each end.

It should be recognized that reference to a first end or a second end of a nucleic acid molecule is not intended to imply any particular orientation of the nucleotide sequence, and is not intended to imply a relative importance of the ends with respect to each other. Where a nucleotide sequence having a first end and second end is a double stranded nucleotide sequence, each end contains a 5' terminus and a 3' terminus. Thus, reference is made herein, for example, to a nucleotide sequence containing a topoisomerase recognition site at a 3' terminus and a hydroxyl group at the 5' terminus of the same end, which can be the first end or the second end.

A method of the invention can be performed using only a first nucleic acid molecule and a second nucleic acid molecule, or can additionally include a third, fourth or more nucleic acid molecules as desired. Generally, each such nucleotide sequence contains a topoisomerase recognition site, or a cleavage product thereof, at or near at least one 3' or 5' terminus, and can contain a hydroxyl group at the 5' terminus of the same end, or a hydroxyl group can be generated using a phosphatase. Where a nucleotide sequence does not contain a topoisomerase recognition site at or near an end to be linked to a second nucleotide sequence, a topoisomerase recognition site can be introduced into the nucleotide sequence using a method as disclosed herein, for example, by PCR amplification of the sequence using a primer comprising a complement of the topoisomerase recognition site.

The terms "first nucleotide sequence," "second nucleotide sequence," "third nucleotide sequence," and the like, are used herein only to provide a means to indicate which of several nucleotide sequences is being referred to. Thus, absent any specifically defined characteristic with respect to a particular nucleotide sequence, the terms "first," "second," "third" and the like, when used in reference to a nucleotide sequence, or a population or plurality of nucleotide sequences, are not intended to indicate any particular order, importance or other information about the nucleotide sequence. Thus, where an exemplified method refers, for example, to using PCR to amplify a first nucleic acid molecule such that the amplification product contains a topoisomerase recognition site at one or both ends, it will be recognized that, similarly, a second (or other) nucleic acid molecule also can be so amplified.

The term "at least a second nucleotide sequence" is used herein to mean one or more nucleotide sequences in addition to a first nucleotide sequence. Thus, the term can refer to only a second nucleotide sequence, or to a second nucleotide sequence and a third nucleotide sequence (or more). As such, the term "second (or other) nucleotide sequence" or second (and other) nucleotide sequences" is used herein in recognition of the fact that the term "at least a second nucleotide sequence" can refer to a second, third or more nucleotide sequences. It should be recognized that, unless indicated otherwise, a nucleotide sequence encompassed within the meaning of the term "at least a second nucleotide sequence" can be the same or substantially the same as a first nucleotide sequence. For example, a first and second nucleic acid molecule can be the same except for having complementary 5' overhanging sequences produced upon cleavage by a topoisomerase such that the first and second nucleic acid molecules can be covalently linked using a method of the invention. As such, a method of the invention can be used to produce a concatenate of first and second nucleic acid molecules, which, optionally, can be interspersed, for example, by a third nucleic acid molecule such as a regulatory element, and can contain the covalently linked sequences in a predetermined directional orientation, for example, each in a 5' to 3' orientation with respect to each other.

As disclosed herein, a method of the invention provides a means to covalently link, two or more ds nucleotides in a predetermined directional orientation. The term "directional orientation" or "predetermined directional orientation" or "predetermined orientation" is used herein to refer to the covalent linkage, of two or more nucleotide sequences in a particular order. Thus, a method of the invention provides a means, for example, to covalently link, a promoter regulatory element upstream of a coding sequence, and to covalently link a polyadenylation signal downstream of the coding region to generate a functional expressible ds recombinant nucleic acid molecule; or to covalently link two coding sequences such that they can be transcribed and translated in frame to produce a fusion polypeptide.

A method of the invention also can be performed by contacting a first nucleic acid molecule having a first end and a second end, wherein at the first end or second end or both, the first nucleic acid molecule has a type IB topoisomerase covalently bound at the 3' terminus (topoisomerase-charged) and has (or can be made to have) a hydroxyl group at the 5' terminus of the same end; and at least a second type IB topoisomerase-charged nucleic acid molecule, which has (or can be made to have) a hydroxyl group at the 5' terminus at the same end. Upon contact of the topoisomerase-activated first and at least second nucleotide sequences at the ends containing the topoisomerase and a 5' hydroxyl group, phosphodiester bonds are formed in each strand, thereby generating a ds recombinant nucleic acid molecule covalently linked in both strands.

The invention further provides methods for linking two or more (e.g., two, three, four, five, six, seven, etc.) nucleotide sequences, wherein the linked ds recombinant nucleic acid molecule is covalently linked in one strand, but not both strands, (i.e. the ds recombinant nucleic acid molecule contains a nick in one strand at each position where two ends were joined to generate the ds recombinant nucleic acid molecule). Further, one or more of the nucleotide sequences may comprise one or more recombination sites. Using the schematic shown in FIG. 11A for purposes of illustration, the invention includes methods for linking at least two nucleotide sequences comprising contacting a first nucleic acid molecule having a first end and a second end, wherein at the first end at the second end or at both ends, the first nucleic acid molecule has a site-specific type IA topoisomerase covalently bound to the 5' termini; and a second nucleic acid molecule which does not have topoisomerase covalently bound to either termini of at least one end. Further, the second nucleotide sequence will typically have hydroxyl groups at the 3' termini of the end being joined to the first nucleic acid molecule. In many instances, the two nucleotide sequences to be joined will have either 3' or 5' overhangs with sufficient sequence complementarity to allow for hybridization. In related embodiments, the first and second nucleic acid molecules described above may be first and second ends of the same nucleic acid molecule. Thus, connection of the two ends results in the formation of a circularized molecule. Once nucleic acid molecules are joined by the methods described above, the resulting molecules may then be used in recombination reactions, such as those described elsewhere herein. The invention further includes nucleic acid molecules prepared by methods of the invention, compositions comprising such nucleic acid molecules, and methods for using such nucleic acid molecules.

Using the schematic shown in FIG. 11B for purposes of illustration, the invention includes methods for joining three or more nucleotide sequences. While any number of variations of the invention are possible, three nucleotide sequences may be joined by the use of a linker molecule which contains topoisomerases at or near both the 5' and 3' termini of one strand, and optionally one or more recombination site. Thus, upon joining of the three nucleotide sequences, a single nucleotide sequence is formed which contains a first strand with no nicks at the junction points, and a second strand with nicks at the junction points. This process-has the advantage of employing a single topoisomerase modified molecule to join three nucleotide sequences together. Once nucleic acid molecules are joined by the methods described above, the resulting molecules may then be used in recombination reactions, such as those described elsewhere herein. The invention further includes nucleic acid molecules prepared by methods of the invention, compositions comprising such nucleic acid molecules, and methods for using such nucleic acid molecules.

The invention further provides methods for covalently linking both strands of two or more (e.g., two, three, four, five, six, seven, etc.) nucleic acid molecules. Using the schematic shown in FIG. 12A for purposes of illustration, the invention includes methods for linking at least two nucleotide sequences comprising contacting a first nucleic acid molecule having a first end and a second end, wherein at the first end, at the second end, or at both ends, the first nucleic acid molecule has two topoisomerases (e.g., a type IA and a type IB topoisomerase) one each covalently bound to the 3' and 5' termini; and a second nucleic acid molecule which does not have topoisomerase covalently bound to either termini of at least one end. Further, the second nucleotide sequence will often have hydroxyl groups at the 51 and 3' termini of the end being joined to the first nucleic acid molecule. In many instances, the two nucleotide sequences to be joined will have either 3' or 5' overhangs with sufficient sequence complementarity to allow for hybridization, and, optionally, one or more recombination sites. In related embodiments, the first and second nucleic acid molecules as described above can be first and second ends of the same nucleic acid molecule. Thus, connection of the two ends results in the formation of a circularized molecule. Once nucleic acid molecules are joined by the methods described above, the resulting molecules may then be used in recombination reactions, such as those described elsewhere herein. The invention further includes nucleic acid molecules prepared by methods of the invention, compositions comprising such nucleic acid molecules, and methods for using such nucleic acid molecules.

Using the schematic shown in FIG. 12D for purposes of illustration, the invention includes methods for joining three or more nucleotide sequences. While any number of variations of the invention are possible, three nucleotide sequences may be joined by the use of a linker molecule which contains topoisomerases at or near both the 5' and 3' termini of each end and, optionally, one or more recombination sites. Thus, upon joining of the three nucleotide sequences, a single nucleotide sequence is formed which contains no nicks at the junction points. This process has the advantage of employing a single topoisomerase modified molecule to join three nucleotide sequences together. Once nucleic acid molecules are joined by the methods described above, the resulting molecules may then be used in recombination reactions, such as those described elsewhere herein. The invention further includes nucleic acid molecules prepared by methods of the invention, compositions comprising such nucleic acid molecules, and methods for using such nucleic acid molecules.

Substrates which particular reagents (e.g., enzymes) recognize and/or catalyze reactions with can be used in methods of the invention to produce nucleic acid molecules having particular characteristics. For example, reagents which catalyze nucleic acid modifications may recognize termini and/or generate termini having particular features. One example of such a feature is the presence or absence of a terminal phosphate group on the 3' or 5' strand. Such reagents, or combinations of such reagents, may be used to prepare, for example, nucleic acid molecules (1) from particular segments and/or (2) having a specific “pattern” of nicks (e.g., a nick in only one strand where two or more segments are joined, nicks in alternating strands where three or more segments are joined, etc.) or having no nicks in either strand.

Reagents (e.g., enzymes) which can be used in methods of the invention include, but are not limited to, the following: ligases (e.g. DNA and RNA Ligases such as T4 DNA Ligase, T4 RNA ligase, *E. coli* DNA ligase, etc.), restriction enzymes (e.g., EcoRI, HpaII, BamHI, etc.), kinases (e.g., T4 polynucleotide kinase, etc.), phosphatases (e.g., calf intestinal alkaline phosphatase), topoisomerases, and polymerases (e.g., proof-reading polymerases such as Pfu, Pfx, THERMALAcE™ (Invitrogen Corp., Carlsbad, Calif.), etc.), and non-proof-reading polymerases such as Taq polymerase, Tfl polymerase, Tth polymerase, Thr polymerase, etc.).

The cleavage of nucleic acid molecules by many endonucleases (e.g., restriction endonucleases) results in the formation of two new ends, wherein a hydroxyl group is present at the 3' terminus of one end and a phosphate group is present at the 5' terminus of the other end. Also, when exonucleases (e.g., snake venom phosphodiesterase, bovine spleen phosphodiesterase, *E. coli* exonuclease VII, lambda exonuclease, *E. coli* exonuclease III, etc.) digest nucleic acid molecules, they often generate ends with (1) 5' terminal hydroxyl groups and 3' terminal phosphate groups or (2) 3' terminal hydroxyl groups and 5' terminal phosphate groups. Further, exonucleases typically digest only a single stranded of a nucleic acid molecule but can use either single stranded and/or double stranded nucleic acids as substrates. In addition, exonucleases (e.g., exonucleases used in methods of the invention) may digest nucleic acid molecules from the 3' terminus, 5' terminus, or both the 3' and 5' termini. Also, kinases (e.g., T4 polynucleotide kinase, etc.) may be used to replace 5' and/or 3' terminal hydroxyl groups of nucleic acid molecules with phosphate groups.

Many polymerases used for the amplification of nucleic acid molecules, for example, by PCR, generate nucleic acid products having 3' terminal hydroxyl groups. In addition, the presence or absence of a phosphate group, or other chemical group, at the 5' terminus of a PCR product is typically determined by whether the primer used in the PCR reaction(s) contains a 5' terminal phosphate or other chemical group. Thus, 5' terminal phosphate groups, hydroxyl groups, or other groups can be introduced into PCR products by the use of primers which contain these groups at their 5' termini. As a result, PCR can be used to generate nucleic acid molecules (i.e., the first nucleic acid molecule referred to below) which contain a desired arrangement of hydroxyl groups, phosphate groups and/or other groups on the 5' and/or 3' termini of one or both ends of a linear nucleic acid molecule (e.g., 5' phosphate group and a 3' hydroxyl group at one end and a 5' hydroxyl group and a 3' hydroxyl group at the other end).

Each of the enzymes types listed above represents a general class of tools which can be used to generate nucleic acid molecules having particular characteristics (e.g., having a desired arrangement of hydroxyl, phosphate and/or other groups on the 3' and/or 5' termini of one or more ends). For example, double stranded, linear nucleic acid molecules may be prepared in which the 5' terminus and the 3' terminus at one end each contain terminal hydroxyl groups and the 5' terminus and the 3' terminus at the other end each contain terminal phosphate groups. Such ends may be prepared using the enzymes discussed above and/or other reagents and methods known in the art.

Thus, the present invention contemplates the construction and use of nucleic acid segments having particular characteristics (e.g., having a desired arrangement of hydroxyl, phosphate and/or other groups on the 3' and/or 5' termini of one or more ends). Such nucleic acids include, but are not limited to, double-stranded, linear nucleic acid molecules which have first and second ends with the characteristics set out in Table 4.

TABLE 4

| First End | | Second End | |
|---|---|---|---|
| 5' Terminus | 3' Terminus | 5' Terminus | 3' Terminus |
| Phosphate Group | Phosphate Group | Phosphate Group | Phosphate Group |
| Phosphate Group | Phosphate Group | Phosphate Group | Hydroxyl Group |
| Phosphate Group | Phosphate Group | Hydroxyl Group | Phosphate Group |
| Phosphate Group | Phosphate Group | Hydroxyl Group | Hydroxyl Group |
| Hydroxyl Group | Hydroxyl Group | Phosphate Group | Phosphate Group |
| Hydroxyl Group | Hydroxyl Group | Phosphate Group | Hydroxyl Group |
| Hydroxyl Group | Hydroxyl Group | Hydroxyl Group | Phosphate Group |
| Hydroxyl Group | Hydroxyl Group | Hydroxyl Group | Hydroxyl Group |
| Hydroxyl Group | Phosphate Group | Phosphate Group | Phosphate Group |
| Hydroxyl Group | Phosphate Group | Phosphate Group | Hydroxyl Group |
| Hydroxyl Group | Phosphate Group | Hydroxyl Group | Phosphate Group |
| Hydroxyl Group | Phosphate Group | Hydroxyl Group | Hydroxyl Group |
| Phosphate | Hydroxyl | Phosphate | Phosphate |

TABLE 4-continued

| First End | | Second End | |
|---|---|---|---|
| 5' Terminus | 3' Terminus | 5' Terminus | 3' Terminus |
| Group | Group | Group | Group |
| Phosphate | Hydroxyl | Phosphate | Hydroxyl |
| Group | Group | Group | Group |
| Phosphate | Hydroxyl | Hydroxyl | Phosphate |
| Group | Group | Group | Group |
| Phosphate | Hydroxyl | Hydroxyl | Hydroxyl |
| Group | Group | Group | Group |

Nucleic acid molecules having a desired arrangement of hydroxyl, phosphate and/or other groups on the 3' and/or 5' termini of one or more ends can be directionally linked to other nucleic acid molecules using linking reactions which require, for example, the presence of a particular group on one or more termini of the molecule (e.g., either a 5' hydroxyl group or a 5' phosphate group and/or a 3' hydroxyl group or a 3' phosphate group).

A number of reagents which catalyze the linkage of nucleic acid segments to each other will generally only recognize termini with particular chemical groups (e.g., a hydroxyl group or a phosphate group) present. For example, T4 DNA ligase will catalyze the ligation of the 3' terminus of an end of a nucleic acid molecule to the 5' terminus of a separate end of the same nucleic acid molecule or of a different nucleic acid molecule, when the 5' terminus contains a terminal phosphate group. Further, a number of topoisomerases (e.g., a type IB topoisomerases) will cleave and bind to the 3' terminus of the end of a nucleic acid molecule and catalyze the linkage of this 3' terminus to the 5' terminus of the end of the same nucleic acid molecule or of a different nucleic acid molecule, when the 5' end contains a terminal hydroxyl group. Additionally, a number of topoisomerases (e.g. a type IA topoisomerases) will cleave and bind to the 5' terminus of the end of a nucleic acid molecule and catalyze the linkage of this 5' terminus to the 3' terminus of the end of the same nucleic acid molecule or of a different nucleic acid molecule, when the 3' end contains a terminal hydroxyl group.

One example of such a linking reaction is where a first nucleic acid molecule having a desired arrangement of groups on one or more termini (for example, a 5' phosphate on one terminus and a 5' hydroxyl on the other terminus) is linked to a second nucleic acid molecule that contains a type IB toposiomerase molecule covalently attached to a phosphate group at the 3' terminus of only one end of the molecule, i.e., attached to the 3' terminus of one strand of a double-stranded nucleic acid molecule. In such an instance, the 3' terminus of the end of the second nucleic acid molecule that contains the bound toposiomerase can only be joined to the 5' terminus of the end of the first nucleic acid molecule that contains the hydroxyl group. Thus, these two nucleic acid molecules can only be covalently linked in one orientation.

A linear double stranded nucleic acid molecule which has phosphate groups at both of the 5' and 3' termini at both ends (see Table 4) may be generated by any number of methods. One example of methods which may be used to produce such molecules involves chemical synthesis of both strands of the double stranded nucleic acid molecule. These individual strands may then be mixed under conditions which allow for the formation of the double stranded molecule.

Using reagents referred to above, as well as other reagents, nucleic acid molecules with various chemical groups at their termini can be covalently linked to each other in one or both strands. For example, a first nucleic acid segment which contains a 5' terminal phosphate group and a 3' terminal phosphate group with a type IB toposiomerase bound to it at one end may be linked in both strands to a second nucleic acid segment which contains 5' and 3' terminal hydroxyl groups at one end. In this instance, the 3' terminus of first nucleic acid segment which contains the toposiomerase molecule bound to it may be joined to the 5' terminus of the end of the second nucleic acid molecule. This linking reaction may be catalyzed by the bound topoisomerase molecule. Further, the 5' terminus of the same end of the first nucleic acid segments may be covalently linked to the 3' terminus of the end of the second nucleic acid segment to which it is joined by a ligase (e.g., T4 DNA ligase). As a second example, a first nucleic acid segments is prepared with a "sticky end" (i.e., an overhang) generated by digestion with a restriction endonuclease that leaves a 5' terminal phosphate group present on the "sticky end". The first nucleic acid segment is contacted with a second nucleic acid segment which contains a compatible "sticky end" and a toposiomerase molecule bound to the 5' terminus of this "sticky end". The result is the covalent connection of these two nucleic acid segments in a single strand. Further, the nick in the other strand at the junction point may be sealed by the inclusion of a ligase, such as T4 DNA ligase, in the reaction mixture.

Any number of variations of the above are possible depending on the available ends and the reagents used to prepare nucleic acid segments with ends for ligation by particular mechanisms or catalyzed by particular reagents. One example of such a variation is where the 5' terminus of the "sticky end" of the first nucleic acid molecule referred contains a hydroxyl group (e.g., the 5' phosphate is removed by a phosphatase) and the second nucleic acid molecule contain a type IB topoisomerase bound to the 3' terminus of the compatible "sticky end".

Thus, enzymes used to generate termini of nucleic acid molecules (e.g., by amplification, by cleavage of a larger molecule, etc.) can be selected such that termini suitable for "downstream" reactions (e.g., ligation reactions) may be generated. One example of such a process is shown in the upper portion of FIG. 41 and described as follows. A nucleic acid molecule may be amplified by PCR using a proofreading polymerase (e.g. Pfx, Pfu, etc.) which generates amplification products having predominantly blunt ends (i.e., neither terminus of the amplification product has an overhanging adenine or other residue) and 3' terminal hydroxyl groups at both ends. Blunt ended linkers which contain (1) nucleic acid of a T7 promoter and (2) a molecule of type IB topoisomerase linked at or near the 3' terminus of the end downstream of the promoter element (see FIG. A). The 5' terminus of the end of the linker which contains the covalently bound topoisomerase contains a terminal phosphate. The result of the linking reaction, when conducted in the presence of T4 DNA ligase, is nucleic acid molecules which are covalently linked in both strands at the junction point where the T7 promoter element is joined to the PCR product. As one skilled in the art would recognize, the process set out above and in FIG. 41 may be performed with nucleic acid segments other than promoters and PCR products. In other words, essentially any nucleic acid segments may be used. Example of nucleic acid molecules which may be used in methods of the invention include those which have termini such as those set out in Table 4. Also, non-proof-reading polymerases (e.g., Taq polymerase) may be used to generate the PCR product and the linkers containing the T7 promoter element may have a "T" overhang for use in T/A cloning.

Further, the invention is not limited to methods for connecting two nucleic acid segments. Thus, the invention also includes methods for connecting two or more nucleic acid segments to each other, wherein at each connection point the nucleic acid segments are covalently linked to each other in either one or both strands. The invention further includes nucleic acid molecules prepared by methods of the invention, as well as compositions and reaction mixtures which contain the reaction products and reaction precursors (e.g., nucleic acid segments which are to be connected to each other by methods of the invention).

The process shown in FIG. 41 for the linkage of two nucleic acid segments is non-directional. In other words, the two segments will be connected to each other without regard to orientation. Methods of the invention further include those directed to the selection, isolation and/or preparation of nucleic acid molecules which contain two or more (e.g., two, three, four, five, six eight, ten, etc.) nucleic acid molecules connected in a particular order and/or orientation. In performing these methods, joining reactions may be designed, for example, so that nucleic acid segments are connected to each other (1) in a particular order or orientation or (2) without regard to orientation and then assembled nucleic acid molecules which contain two or more segments connected to each other in a particular order and/or orientation are selected and/or isolated.

One example of a method for performing the second process referred to immediately above is shown in FIG. 41. The process shown in FIG. 41 involves the connection of two nucleic acid molecules using methods described elsewhere herein, followed by the amplification of nucleic acid molecules which contain segments connected in a particular orientation. The amplification process employs primers (i.e., primers A and B) which hybridize to different stands and at opposite ends of the linkage product which is sought. Thus, when the T7 promoter is connected to the PCR product in one orientation (e.g., the desired orientation), primers A and B hybridize to opposite strands and can be used to amplify the nucleic acid molecule. However, when the T7 promoter is connected to the PCR product in the other orientation (e.g., the non-desired orientation), primers A and B hybridize to the same strand and can not be used to amplify the nucleic acid molecule.

Thus, the invention includes, in part, methods for selectively amplifying nucleic acid molecules based on the order and/or orientation of nucleic acid segments which are joined by methods described elsewhere herein. In particular aspects, these methods involve performing amplification reactions in the presence of two or more primers which have been selected to amplify one or more desired nucleic acid molecules assembled using methods described elsewhere herein. Nucleic acid molecules selectively amplified by methods of the invention may be assembled by the joining of two or more nucleic acid segments. As one skilled in the art would recognize, the selective amplification process described above can be used to amplify nucleic acid molecules which are assembled from three, four, five, six, seven, etc. nucleic acid segments. When three or more nucleic acid segments selectively amplified by methods described above, only those which contain the segments corresponding to the primers in the proper orientation will be amplified. Nucleic acid molecules which contain the correct segments and segments in the proper order may be selected and/or isolated by the use of additional processes. For example, if nucleic acid segments 1, 2, and 3 are connected to each other by methods of the invention, then assembled nucleic acid segments containing nucleic acid segments 1 and 3 in the desired orientation can be selectively amplified using primers corresponding to sequences present in segments 1 and 3. Further, separation of nucleic acid molecules to obtain those which are of the size represented by nucleic acid molecules comprising segments 1, 2, and 3 may be performed to isolate these molecules. In such an instance, depending on how the nucleic acid segments are assembled, segment 2 could be in either one particular orientation or in both orientations Any number of such methods may be performed to obtain assembled nucleic acid molecules which contain nucleic acid segments connected to each other in a desired orientation and/or order. The invention further includes reaction mixtures and compositions for performing the methods described above, as well as nucleic acid molecules generated by these methods.

In the embodiment of the invention shown in FIG. 41, it is not necessary to covalently link both strands at the junction between the linker containing the T7 Promoter element and the PCR product. After the first round of amplification, both strands will be represented in the population because, even if one strand contains a nick, the first round of amplification will generate a full-length nucleic acid strand corresponding to the nicked strand. Thus, both primers will hybridize to nucleic acid strands in the second and subsequent rounds of amplification. As a result of the above, the T4 DNA ligase may be omitted from the methods schematically represented in FIG. 41.

Again using the process shown in FIG. 41 for reference, when a nucleic acid molecule is prepared as shown in the upper portion of FIG. 41, it may be desirable to link both strands of the nucleic acid segments being joined when the product nucleic acid molecule is to be directly used (e.g., without one or more additional rounds of amplification) in a process such as transcription. This is so because strand separation occurs during the transcription process and the presence of a nick in one of the strands often interferes with the transcription process. Thus, when nucleic acid molecules assembled as shown in FIG. 41 are intended for use for transcription, it will often be desirable to generate nucleic acid molecules in which both strands are covalently linked at the junction between the nucleic acid segments. One exception to the above is where the template strand does not contain a nick after linking of the nucleic acid segments being joined. In other words, in instances where the template strand is not nicked, transcription will efficiently occur even if a nick is present in the non-template strand.

The invention further provides methods for performing topoisomerase mediated joining reactions and recombination reactions which can be performed in either a single tube or multiple tubes. For instance, all of the components necessary to perform both topoisomerase mediated joining reactions and recombination reactions can be combined in one tube and both reactions can occur essentially simultaneously. Examples of topoisomerase/recombination reactions which can be performed in either a single tube or in multiple tubes are shown in FIGS. 35–40. Thus, in particular embodiments, the invention provides single tube reactions in which (1) one or more nucleic acid molecules or two ends of one nucleic acid molecule are linked to each other by a topoisomerase mediated reaction and (2) one or more recombination sites undergo recombination with one or more other recombination sites. Any number of topoisomerase mediated joining reaction and/or recombination reactions may occur in processes of the invention. Further, these reactions may occur in any order. In particular embodiments, one or more nucleic acid molecules in reaction mixtures of the invention will contain (1) one or more recombination sites and (2) one or more topoisomerases or one or more topoisomerase recognition sites.

As explained below in Example 9, in certain instances, topoisomerases have been found to inhibit particular recombination reactions. In such instances, nucleic acid molecules which have undergone toposiomerase mediated joining reaction(s) may be separated from topoisomerases present in the reaction mixture and then may used as substrates for recombination reaction(s). Often in such instances, the topoisomerase mediated joining reaction(s) and the recombination reaction(s) will occur in separate tubes. Examples of process by which products of topoisomerase mediated joining reactions may be separated from topoisomerase include, but are not limited to, phenol/chloroform extraction, typically followed by precipitation of the nucleic acid (e.g., ethanol precipitation), and chromatography (e.g., column chromatography).

Alternatively, topoisomerases present in the reaction mixture may be inactivated, for example, by heating (e.g., heating to about 65° C. for about 60 min., about 70° C. for about 60 min., about 75° C. for about 60 min., about 70° C. for about 40 min., about 75° C. for about 40 min., about 80° C. for about 40 min., about 80° C. for about 30 min., about 85° C. for about 20 min., about 90° C. for about 15 min., about 95° C. for about 5 min. or about 99° C. for about 1 min.) or by the use of proteases (e.g., proteinase K). In this instance, it will generally be possible for the topoisomerase mediated joining reaction(s) and the recombination reaction(s) to occur in the same tube.

In specific embodiments of single tube reactions, two or more nucleic acid segments, each comprising one or more topoisomerases or toposiomerase recognition sites are joined to each other using a topoisomerase mediated joining reaction (e.g., a topoisomerase mediated joining reaction). After which, the tube is heated to about 85° C. for about 20 min. and one or more recombinases are added. Further, if one or more of the two or more nucleic acid segments do not comprise recombination sites or if recombination with additional nucleic acid segments is desired, then nucleic acid segments which comprise one or more recombination sites may be added. Typically, the recombination sites present in the tube will be ones which are capable of recombining with each other.

In other specific embodiments of single tube reactions, two or more nucleic acid segments undergo recombination catalyzed by one or more recombinases. After recombination has occurred, toposiomerase is then added to the tube to facilitate topoisomerase mediated joining of nucleic acid segments. As above, additional nucleic acid segments may, optionally, be added to the reaction mixture along with the topoisomerase. Further, when nucleic acid segments to which one or more toposiomerases are attached are added to the reaction mixture, it will often not be necessary to add additional topoisomerase. Thus, in particular embodiments, topoisomerase modified nucleic segments may be added to the above reaction mixtures and, depending on the particular reaction conditions, additional topoisomerase may or may not be added.

The invention also provides methods for preparing nucleic acid molecules which contain one or more (e.g., one, two, three, four, five, six, etc.) multiple cloning sites. For example, one or more nucleic acid segments used in methods of the invention may comprise one or more multiple cloning sites. As another example, multiple cloning sites may be added to nucleic acid segments used to prepare nucleic acid molecules by methods of the invention or to nucleic acid molecules prepared by methods of the invention by the attachment of linkers which contain one or more multiple cloning sites. In related aspects, the invention includes nucleic acid molecules prepared by methods of the invention which contain one or more multiple cloning sites, as well as the use of one or more these multiple cloning sites to modify nucleic acid molecules prepared by methods of the invention. The invention also provides nucleic acid molecules produced by the methods described above, as well as uses of these molecules and compositions comprising these molecules.

Viral Vectors

The invention further provides methods for preparing nucleic acid molecules having regions of viral nucleic acids, as well as nucleic acid molecules prepared by such methods and compositions comprising these nucleic acid molecules.

Adenoviruses are viral vectors that can be used, for example, in gene therapy. Adenoviruses are especially attractive vehicles for delivering genes to respiratory epithelia and the use of such vectors are included within the scope of the invention. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development* 3:499–503 (1993), present a review of adenovirus-based gene therapy. Bout et al., *Human Gene Therapy* 5:3–10 (1994), demonstrated the use of adenovirus vectors to transfer genes to the respiratory epithelia of rhesus monkeys. Other instances of the use of adenoviruses in gene therapy can be found in Rosenfeld et al., *Science* 252:431–434 (1991); Rosenfeld et al., *Cell* 68:143–155 (1992); Mastrangeli et al., *J. Clin. Invest.* 91:225–234 (1993); PCT Publication Nos. WO94/12649 and WO 96/17053; U.S. Pat. No. 5,998,205; and Wang et al., *Gene Therapy* 2:775–783 (1995), the disclosures of all of which are incorporated herein by reference in their entireties.

Adeno-associated virus (AAV) and Herpes viruses, as well as vectors prepared from these viruses have also been proposed for use in gene therapy (Walsh et al., 1993, *Proc. Soc. Exp. Biol. Med.* 204:289–300; U.S. Pat. No. 5,436,146; Wagstaff et al., *Gene Ther.* 5:1566–70 (1998)). Herpes viral vectors are particularly useful for applications where gene expression is desired in nerve cells.

The invention thus includes methods for preparing nucleic acid molecules which have one or more functional properties of viral vectors (e.g., adenoviral vectors, alphaviral vectors, herpes viral vectors, adeno-associated viral vectors, etc.). In particular embodiments, methods of the invention include the joining of nucleic acid segments, wherein one or more of the nucleic acid segments contains regions which confer upon product nucleic acid molecules the ability to function as viral vectors (e.g., the ability to replicate in specific host cells, the ability to be packaged into viral particles, etc.).

In particular embodiments, the invention includes methods for preparing adenoviral vectors by joining at least one (e.g., one, two, three, four, etc.) nucleic acid segment which comprises adenoviral sequences to one or more other nucleic acid segments. Specific examples of adenoviral vectors, and nucleic acid segments which can be used to prepare adenoviral vectors are disclosed in U.S. Pat. Nos. 5,932,210, 6,136,594, and 6,303,362, the entire disclosures of which are incorporated herein by reference. Adenoviral vector prepared by methods of the invention may be replication competent or replication deficient.

One example of an adenoviral vector may be prepared by joining a nucleic acid segment comprising adenoviral nucleic acid to one or more other nucleic acid segments. For example, when a replication deficient adenoviral vector is desired, the adenoviral nucleic acid may have deletions of all or part of one or more of the following regions: the E1a region, the E1b region, and/or the E3 region. Adenoviral vectors which contain deletions in these regions are described, for example, in U.S. Pat. No. 6,136,594. The invention further includes adenoviral vectors prepared by methods of the invention, as well as uses of these vectors and compositions comprising these vectors. One example of a use of adenoviral vectors prepared by methods of the invention include the delivery of nucleic acid segments to cells of a mammal (e.g., a human). Thus, the invention provides methods for preparing vector suitable for use in gene therapy protocols. Typically, such vectors will be replication deficient.

In specific embodiments, adenoviral vectors of the invention will comprise substantially the entire adenoviral genome with the exception that are deletions of all or part of one or more of the following regions: the E1a region, the E1b region, and/or the E3 region. In further specific embodiments, non-adenoviral nucleic acid may be present in one or more of the E1a region, the E1b region, and/or the E3 region.

In particular embodiments, adenoviral vectors prepared by methods of the invention will contain at least one origin of replication and/or a selection marker which allows for amplification of the vector in prokaryotic cells, such as *E. coli.*

Adeno-associated viral vectors and Herpes viral vectors may be prepared by methods of the invention which are similar to those described above. Thus, the invention further provides methods for preparing such vectors, as well as vectors produced by these methods, uses of these vectors, and compositions comprising these vectors.

The invention further provides methods for preparing alphaviral vectors (e.g., Sindbis virus vectors, Semliki Forest virus vectors, Ross River virus vectors, Venezuelan equine encephalitis virus vectors, Western equine encephalitis virus vectors, Eastern equine encephalitis virus vectors, etc.), as well as alphaviral vectors prepared by such methods, methods employing these alphaviral vectors and compositions comprising these alphaviral vectors.

In particular embodiments, the invention includes methods for preparing alphaviral vectors by joining at least one nucleic acid segment which comprises alphaviral sequences to one or more other nucleic acid segments. Specific examples of alphaviral vectors and nucleic acids which can be used to prepare alphaviral vectors are described in U.S. Pat. Nos. 5,739,026 and 6,224,879, the GibcoBRL's Instruction Manual No. 10179-018, "SFV Gene Expression System", and Sindbis Expression System manual (Invitrogen Corporation, Carlsbad, Calif.), catalog no. K750-01 (version E), the entire disclosures of which are incorporated herein by reference.

In specific embodiments, alphaviral vector sequences used in methods of the invention to prepare alphaviral vectors will comprise one or more of the following components: one or more packaging signals (which may or may not be of alphaviral origin), one or more subgenomic promoters, and/or nucleic acid encoding one or more non-structural protein (e.g., nsp1, nsp2, nsp3, nsp4, etc.).

Alphaviral vectors of the invention may be introduced into cells as DNA or RNA molecules. When DNA forms of such vectors are introduced into cells, expression control sequences (e.g., inducible, repressible or constitutive expression control sequences) may then be used to generate RNA molecules from which one or more non-structural proteins may be translated. In specific embodiments, these non-structural proteins will form an RNA-dependent RNA polymerase which will amplify RNA molecules corresponding to all or part of the transcript generated from the DNA form of the alphaviral vector. Thus, these non-structural proteins may catalyze the production of additional copies of RNA molecules from RNA templates, resulting in RNA amplification. Further, a nucleic acid segment for which high levels of expression is desired may be operably linked to a subgenomic promoter, thus resulting in the production of high levels of RNA corresponding to the nucleic acid segment.

In one exemplary embodiment, alphaviral vectors prepared by methods of the invention comprise DNA wherein an inducible promoter directs transcription of an RNA molecule which encodes nsp1, nsp2, nsp3, and nsp4 of a Sindbis virus and a Sindbis subgenomic promoter operatively linked to a nucleic acid segment which is not of Sindbis viral origin. The invention also provides alphaviral vectors prepared by methods of the invention, methods of using such alphaviral vectors, and compositions comprising such alphaviral vectors.

The invention further provides methods for joining nucleic acid segments wherein one or more of the nucleic acid segments contains one or more (e.g., one, two, three, four, etc.) viral packaging signal (e.g., one or more packaging signal derived from a virus referred to above). These packaging signals can be used to direct the packaging of nucleic acid molecules prepared by methods of the invention. One method for preparing packaged nucleic acid molecules is by the introduction or expression of nucleic acid molecules of the invention into packaging cell lines which express proteins suitable for the production of virus-like particles. The invention further includes packaged nucleic acid molecules of the invention, methods for preparing packaged nucleic acid molecules of the invention, and compositions comprising packaged nucleic acid molecules of the invention.

The present invention also provides compositions, and kits containing such compositions, including kits containing component useful for performing methods of the invention. In one aspect, a composition of the invention comprises isolated components characteristic of a step of a method of the invention. For example, a composition of the invention can comprise two or more of the same or different topoisomerase-charged nucleic acid molecules. As used herein, the term "different," when used in reference to the nucleic acid molecules of a composition of the invention, means that the nucleic acid molecules share less than 95% sequence identity with each when optimally aligned, generally less than 90% sequence identity, and usually less than 70% sequence identity. Thus, nucleic acid molecules that, for example, differ only in being polymorphic variants of each other or that merely contain different 5' or 3' overhanging sequences are not considered to be "different" for purposes of a composition of the invention. In comparison, different nucleic acid molecules are exemplified by a first sequence encoding a polypeptide and second sequence comprising a regulatory element, or a first sequence encoding a first polypeptide a second sequence encoding a non-homologous polypeptide.

Where a composition of the invention comprises more than two different isolated nucleic acid molecules or more than two different topoisomerase-charged nucleic acid molecules, each of the nucleic acid molecules is different from each other, i.e., they are all different from each other. However, it will be recognized that each of the nucleic acid molecules, for example, a sequence referred to as a first nucleic acid molecule, generally comprises a population of such nucleotide sequences, which are identical or substantially identical to each other. Thus, it should be clear that the term "different" is used in comparing, for example, a first (or population of first) nucleic acid molecules with a second (and other) nucleic acid molecule. A composition comprising two or more different topoisomerase-charged nucleic acid molecules can further comprise a topoisomerase. Examples of such nucleic acid molecules comprising the components of a composition of the invention are disclosed herein and include, for example, coding sequences, transcriptional regulatory element, translational regulatory elements, elements encoding a detectable or selectable markers such as an epitope tag or an antibiotic resistance gene, elements encoding polypeptide domains such as cell compartmentalization domains or signal peptides, and the like.

As used herein, the term "isolated" means that a molecule being referred to is in a form other than that in which it exists in nature. In general, an isolated nucleotide sequence, for example, can be any nucleotide sequence that is not part of a genome in a cell, or is separated physically from a cell that normally contains the nucleotide sequence. It should be recognized that various compositions of the invention comprise a mixture of isolated nucleic acid molecules. As such, it will be understood that the term "isolated" only is used in respect to the isolation of the molecule from its natural state, but does not indicate that the molecule is an only constituent.

A composition of the invention can comprise two different nucleic acid molecules, each of which contains a topoisomerase recognition site at or near one or both ends, and a site specific topoisomerase, which can bind to and cleave the nucleic acid molecules at the topoisomerase recognition site. Optionally, at least one of the different nucleic acid molecules can be a topoisomerase-charged nucleic acid molecule. Preferably, the topoisomerase covalently bound to the topoisomerase-charge nucleic acid molecule is of the same family as the topoisomerase in the composition.

Various combinations of components can be used in a method of the invention. For example, the method can be performed by contacting a topoisomerase-activated first nucleic acid molecule, which optionally comprises one or more recombination sites; a second nucleic acid molecule having a first end and a second end, wherein at the first end or second end or both, the second nucleotide sequence has a topoisomerase recognition site at or near the 3' terminus, and a hydroxyl group at the 5' terminus of the same end; and a topoisomerase. Where the 5' terminus of one or both ends to be linked has a 5' phosphate group, a phosphatase also can be contacted with the components of the reaction mixture. Upon such contacting, the topoisomerase can cleave the second nucleotide sequence to produce a topoisomerase-activated second nucleic acid molecule, the phosphatase, if necessary, can generate a 5' hydroxyl group at the same end, and the second nucleic acid molecule then can be covalently linked to the topoisomerase-activated first nucleic acid molecule. As such, it will be recognized that a composition of the invention can comprise any of various combinations of components useful for performing a method of the invention. Once nucleic acid molecules are joined by the methods described above, the resulting molecules may then be used in recombination reactions, such as those described elsewhere herein. The invention further includes nucleic acid molecules prepared by methods of the invention, compositions comprising such nucleic acid molecules, and methods for using such nucleic acid molecules.

In general, a method of the invention for generating a ds recombinant nucleic acid molecule covalently linked in both strands is based on the determination that a ds recombinant nucleic acid molecule covalently linked in both strands can be produced by contacting a first nucleic acid molecule with a second nucleic acid molecule, wherein the first and second sequences each have, at the ends to be linked, a topoisomerase recognition site, for example, 5'-(C/T)CCTT-3' (Shuman, supra, 1991; U.S. Pat. No. 5,766,891). Upon cleavage, the site specific topoisomerase is covalently bound at the 3' terminus. Where the cleaved nucleotide sequences also contain a 5' hydroxy group at the same end as the bound topoisomerase, and the ends of the two nucleotide sequences associate, the topoisomerase on each 3' terminus can covalently link that terminus to a 5' hydroxyl group on the associated nucleotide sequence (see FIG. 12B).

As used herein, reference to contacting a first nucleotide sequence and at least a second nucleotide sequence "under conditions such that all components are in contact" means that the reaction conditions are appropriate for the topoisomerase-cleaved ends of the nucleotide sequences to come into sufficient proximity such that a topoisomerase can effect its enzymatic activity and covalently link the 3' or 5' terminus of a first nucleotide sequence to a 5' or 3' terminus, respectively, of a second nucleotide sequence. Examples of such conditions, which include the reaction temperature, ionic strength, pH, and the like, are disclosed herein, and other appropriate conditions as required, for example, for particular 5' overhanging sequences of the termini generated upon topoisomerase cleavage, can be determined empirically or using formulas that predict conditions for specific hybridization of nucleotide sequences, as is well known in the art (see, for example, (Sambrook et al., *Molecular Cloning: A laboratory manual* (Cold Spring Harbor Laboratory Press 1989); Ausubel et al., *Current Protocols in Molecular Biology*, John Wiley and Sons, Baltimore, Md. (1987, and supplements through 1995), each of which is incorporated herein by reference).

In one embodiment, a method of the invention provides a means to render an open reading from a cDNA or an isolated genomic DNA sequence expressible by operatively linking one or more regulatory elements to the putative coding sequence. Accordingly, a first nucleic acid molecule comprising an open reading frame can be amplified by PCR using a primer pair that generates an amplified first nucleic acid molecule having a topoisomerase recognition site at one or both ends and, optionally, one or more recombination sites, as desired, such that, upon cleavage by the site specific topoisomerase, one or both ends contains a defined 5' or 3' overhang or is blunt. Where both ends of the amplified first nucleic acid molecule are so constructed, the 5' or 3' overhanging sequences generally, but not necessarily, are different from each other. The amplified first nucleic acid molecule then can be contacted with a second nucleic acid molecule comprising a desired regulatory element such as a promoter and, in certain embodiments, (a) one or more topoisomerase recognition sites, and with a topoisomerase and/or (b) one or more recombination sites, under conditions which facilitate recombination, such that the second nucleotide sequence is operatively covalently linked to the 5' end of the coding sequence according to a method of the invention.

In such a method, a second (or other) nucleic acid molecule also can comprise two or more regulatory elements, for example, a promoter, an internal ribosome entry site and an ATG initiator methionine codon, or the like, or other sequence of interest, for example, an sequence encoding an epitope tag, in operative linkage with each other, and which can be operatively covalently linked to the 5' end of a first nucleic acid molecule comprising a coding sequence. Such a method can further include contacting a third nucleic acid molecule comprising, for example, a polyadenylation signal, which can be operatively covalently linked according to a method of the invention to the 3' end of the coding sequence, thereby generating an expressible ds recombinant nucleic acid molecule. As such, a method of the invention provides a means for generating a functional ds recombinant nucleic acid molecule that can be transcribed, translated, or both as a functional unit. As disclosed herein, the inclusion of complementary 5' or 3' overhanging sequences generated by topoisomerase cleavage at the termini of the nucleic acid molecules to be linked together by the site specific topoisomerase facilitates the generation of a ds recombinant nucleic acid molecule having a desired directional orientation of the nucleotide sequences in the construct.

In another embodiment, a method of the invention is performed such that the first nucleic acid molecule or a second (or other) nucleic acid molecule, or combination thereof, is one of a plurality of nucleotide sequences. As used herein, the term "plurality," when used in reference to a first or at least a second nucleotide sequence, means that the nucleotide sequences are related but different. For purposes of the present invention, the nucleotide sequences of a plurality are "related" in that each nucleotide sequence in the plurality contains at least a topoisomerase recognition site, or a cleaved form thereof, at one or more termini and/or at least one recombination site. Furthermore, the nucleotide sequences of a plurality are "different" in that they can comprise, for example, a cDNA library, a combinatorial library of nucleotide sequences, a variegated population of nucleotide sequences, or the like. Methods of making cDNA libraries, combinatorial libraries, libraries comprising variegated populations of nucleotide sequences, and the like are well known in the art (see, for example, U.S. Pat. No. 5,837,500; U.S. Pat. No. 5,622,699; U.S. Pat. No. 5,206,347; Scott and Smith, *Science* 249:386–390, 1992; Markland et al., *Gene* 109:13–19, 1991; O'Connell et al., *Proc. Natl. Acad. Sci., USA* 93:5883–5887, 1996; Tuerk and Gold, *Science* 249:505–510, 1990; Gold et al., *Ann. Rev. Biochem.* 64:763–797, 1995; each of which is incorporated herein by reference).

The present invention further provides a method of generating a ds recombinant nucleic acid molecule covalently linked in both strands by amplifying a portion of a first nucleotide sequence using a PCR primer pair, wherein at least one primer of the primer pair encodes a topoisomerase recognition site or a complement thereof and, optionally, one or more recombination sites, thereby producing a first nucleic acid molecule having a first end and a second end, wherein the first end or second end or both has a topoisomerase recognition site at the 3' terminus and/or the 5' terminus; and contacting the first nucleic acid molecule with at least a second nucleic acid molecule having a first end and a second end, wherein the first end or second end or both has a topoisomerase recognition site at the 3' terminus and/or the 5' terminus, or a cleavage product thereof; and a topoisomerase (see FIG. 12). When contacted under conditions such that an end of the first nucleic acid molecule having a topoisomerase recognition site and an end of the at least second nucleic acid molecule having a topoisomerase recognition site can associate, a ds recombinant nucleic acid molecule covalently linked in both strands is generated. Once nucleic acid molecules are joined by the methods described above, the resulting molecules may then be used in recombination reactions, such as those described elsewhere herein. The invention further includes nucleic acid molecules prepared by methods of the invention, compositions comprising such nucleic acid molecules, and methods for using such nucleic acid molecules.

As disclosed herein, a PCR method using primers designed to incorporate one or more topoisomerase recognition sites and, optionally, one or more recombination sites at one or both ends of an amplified nucleic acid molecule provides a convenient means for producing nucleic acid molecules useful in a method of the invention. In certain embodiments, at least one of the primers of a primer pair is designed such that it comprises, in a 5' to 3' orientation, a nucleotide sequence complementary to a topoisomerase recognition site, such that PCR introduces a functional recognition site in the opposite strand (see primer sequences in FIG. 9D), and a nucleotide sequence complementary to the 3' end of a target nucleic acid molecule to be amplified (i.e., a target specific region). In addition, the primer can contain, in a position 5' to the complement of the topoisomerase recognition site, a desired nucleotide sequence of any length (generally about 1 to 100 nucleotide, usually about 2 to 20 nucleotides, and particularly about 4 to 12 nucleotides), which, upon cleavage of the amplification product by a site specific topoisomerase, forms a desired 5' overhang. The second primer of the PCR primer pair can be complementary to a desired sequence of the nucleotide sequence to be amplified, and can comprise a complement to a topoisomerase recognition site, a sequence that would generate a 5' overhang upon cleavage by a site specific topoisomerase, or any other sequence, as desired.

Such a primer can comprise or encode any other sequence of interest, including, for example, a site specific integration recognition site such as an att site, a lox site, or the like, or, as discussed above, can simply be used to introduce a topoisomerase recognition site into a nucleic acid molecule comprising such a sequence of interest. A ds recombinant nucleic acid molecule generated according to a method of the invention and containing a site specific integration recognition site such as an att site or lox site can be integrated specifically into a desired locus such as into a vector, a gene locus, or the like, that contains the required integration site, for example, an att site or lox site, respectively, and upon contact with the appropriate enzymes required for the site specific event, for example, lambda Int and IHF proteins or Cre recombinase, respectively. The incorporation, for example, of attB or attP sequences into a ds recombinant nucleic acid molecule covalently linked in both strands according to a method of the invention allows for the convenient manipulation of the nucleic acid molecule using the GATEWAY™ Cloning System (Invitrogen Corporation, Carlsbad, Calif.).

In one embodiment, a construct generated according to a method of the invention is further amplified by a PCR reaction or other amplification reaction. Direct PCR of a ds recombinant nucleic acid molecule generated according to a method of the invention is possible because the construct is covalently linked in at least one strand. As such, PCR can be used to generate a large amount of the construct. More importantly, as indicated above, PCR provides an in vitro selection method for obtaining only a desired product generated according to a method of the invention, without obtaining partial reaction products. For example, a method of the invention can be used to generate a ds recombinant nucleic acid molecule covalently linked in both strands comprising, operatively linked in a 5' to 3' orientation, a first nucleic acid molecule comprising a promoter, a second nucleic acid molecule comprising a coding region, and a third nucleic acid molecule comprising a polyadenylation signal.

As disclosed herein, a construct having a predetermined orientation can be generated by including complementary 5' overhanging sequences on the ends of the nucleic acid molecules to be joined. By selecting a PCR primer pair including a first primer complementary to the first nucleic acid molecule and upstream of the promoter sequence, and a second primer complementary to the third nucleic acid molecule and downstream of the polyadenylation signal, a functional amplification product comprising the promoter, coding region and polyadenylation signal can be generated. In contrast, partial reaction products that lack either the first nucleic acid molecule or third ds nucleotide is not amplified because either the first or second primer, respectively, would not hybridize to the partial product. In addition, a construct lacking the second nucleic acid molecule would not be generated due to the lack of complementarity of the 5' overhanging sequences of the first and third nucleic acid molecules. As such, a method of the invention provides a means to obtain a desired functional ds recombinant nucleic acid molecule covalently linked in both strands.

The use of PCR in such a manner further provides a means to screen a large number of nucleic acid molecules generated according to a method of the invention in order to identify constructs of interest. Since methods for utilizing PCR in automated high throughput analyses are routine and well known, it will be recognized that the methods of the invention can be readily adapted to use in a high throughput system. Using such a system, a large number of constructs can be screened in parallel, and partial or incomplete reaction products can be identified and disposed of, thereby preventing a waste of time and expense that would otherwise be required to characterize the constructs or examine the functionality of the constructs in further studies.

The methods of the invention have broad application to the field of molecular biology. As discussed in greater detail below, the methods of the invention can be used, for example, to label DNA or RNA probes, to perform directional cloning (see Example 1.B), to generate sense or antisense RNA molecules (see Example 2.A), to prepare bait or prey constructs for performing a two hybrid assay (see Example 2.C), to prepare linear expression elements (see Examples 2.A and 2.B), and to prepare constructs useful for coupled in vitro transcription/translation assays (see Example 2.B). For example, a method of generating ds recombinant nucleic acid molecules covalently linked in both strands provides a means to generate linear expression elements (LEEs), which consist of a linear nucleic acid molecule comprising two or more nucleotide sequences such as a promoter or other regulatory element linked to an open reading frame (see Example 1). LEEs have been reported to efficiently transfect cells, thus bypassing a requirement for cloning the expression element in a vector (Sykes and Johnston, *Nat. Biotechnol.* 17:355–359, 1999). The components of a LEE can be noncovalently linked, or can be covalently linked via a ligation reaction. The preparation of noncovalently linked LEEs requires using PCR primers containing deoxyuridine residues to amplify each nucleotide sequence component, then treating the PCR products with uracil-DNA glycosylase to generate overhanging ends that can hybridize. However, the efficiency of transfection using such noncovalently linked LEEs is variable, and, in some cases, much lower than the efficiency of covalently linked LEEs (Sykes and Johnston, supra, 1999). Furthermore, such LEEs are not suitable for use as templates for PCR amplification because the primer extension reaction cannot proceed past nicks in the template and, therefore, is terminated producing incomplete reaction products.

A method of the invention provides a straightforward and simple means to generate covalently linked LEEs, thereby avoiding the inconvenient and additional steps previously described for preparing a LEE, as well as reducing variability in transfection efficiency as observed using noncovalently linked LEEs. For example, a first nucleic acid molecule, which encodes an open reading frame of interest, can be amplified by PCR as disclosed herein to contain a topoisomerase recognition site, or cleavage product thereof, on one or both ends. Furthermore, the PCR primers can be designed such that, upon cleavage of the amplified first nucleic acid molecule by a site specific topoisomerase, the cleavage product contains a predetermined and desired 5' overhanging sequence. A second nucleotide sequence (and a third or more, as desired), in addition to containing a topoisomerase recognition site, or cleavage product thereof, can include or encode a regulatory element, for example, a promoter, an enhancer, a silencer, a splice acceptor site, a translation start site, a ribosome recognition site or internal ribosome entry site, a polyadenylation signal, an initiator methionine codon, or a STOP codon, or can encode any other desired sequence such as an epitope tag or cell compartmentalization domain. Preferably, the second (or other) nucleic acid molecule to be covalently linked to the first nucleic acid molecule has a 5' overhanging sequence that is complementary to the 5' overhang at the end of the first nucleic acid molecule to which it is to be linked. Upon contact of such nucleotide sequences in presence of a topoisomerase a promoter, for example, can be operatively covalently linked to the 5' terminus of the open reading frame, and a polyadenylation signal can be operatively covalently linked to the 3' terminus of the open reading frame, thereby generating a covalently linked functional LEE (see Example 1).

Examples of regulatory elements useful in the present invention are disclosed herein and include transcriptional regulatory elements, translational regulatory elements, elements that facilitate the transport or localization of a nucleotide sequence or polypeptide in (or out of) a cell, elements that confer a detectable phenotype, and the like. Transcriptional regulatory elements include, for example, promoters such as those from cytomegalovirus, Moloney leukemia virus, and herpes virus, as well as those from the genes encoding metallothionein, skeletal actin, phosphoenolpyruvate carboxylase, phosphoglycerate, dihydrofolate reductase, and thymidine kinase, as well as promoters from viral long terminal repeats (LTRs) such as Rous sarcoma virus LTR and operators; enhancers, which can be constitutively active such as an immunoglobulin enhancer, or inducible such as SV40 enhancer; and the like. For example, a metallothionein promoter is a constitutively active promoter that also can be induced to a higher level of expression upon exposure to a metal ion such as copper, nickel or cadmium ion. In comparison, a tetracycline (tet) inducible promoter is an example of a promoter that is induced upon exposure to tetracycline, or a tetracycline analog, but otherwise is inactive. A transcriptional regulatory element also can be a tissue specific regulatory element, for example, a muscle cell specific regulatory element, such that expression of an encoded product is restricted to the muscle cells in an individual, or to muscle cells in a mixed population of cells in culture, for example, an organ culture. Muscle cell specific regulatory elements including, for example, the muscle creatine kinase promoter (Sternberg et al., *Mol. Cell. Biol.* 8:2896–2909, 1988, which is incorporated herein by reference) and the myosin light chain enhancer/promoter (Donoghue et al., *Proc. Natl. Acad. Sci., USA* 88:5847–5851, 1991, which is incorporated herein by reference) are well known in the art. Other tissue specific promoters, as well as regulatory elements only expressed during particular developmental stages of a cell or organism are well known in the art.

In additional embodiments, the regulatory elements contained in the nucleotide sequences used in or produced by the practice of the invention can be one or more operators. A number of operators are known in the art. An example of an operator suitable for use with the invention is the tryptophan operator of the tryptophan operon of *E. coli*. The tryptophan repressor, when bound to two molecules of tryptophan, binds to the *E. coli* tryptophan operator and, when suitably positioned with respect to the promoter, blocks transcription. Another example of an operator suitable for use with the invention is operator of the *E. coli* tetracycline operon. Components of the tetracycline resistance system of *E. coli* have also been found to function in eukaryotic cells and have been used to regulate gene expression. For example, the tetracycline repressor, which binds to tetracycline operator in the absence of tetracycline and represses gene transcription, has been expressed in plant cells at sufficiently high concentrations to repress transcription from a promoter containing tetracycline operator sequences (Gatz et al., *Plants* 2:397–404 (1992)). The tetracycline regulated expression systems are described, for example in U.S. Pat. No. 5,789,156, the entire disclosure of which is incorporated herein by reference. Additional examples of operators which can be used with the invention include the Lac operator and the operator of the molybdate transport operator/promoter system of *E. coli* (see, e.g., Cronin et al., *Genes Dev.* 15:1461–1467 (2001) and Grunden et al., *J. Biol. Chem.,* 274:24308–24315 (1999)).

Thus, in particular embodiments, the invention provides methods for preparing nucleic acid molecules that contain one or more operators which can be used to regulate expression in prokaryotic or eukaryotic cells. As one skilled in the art would recognize, when a nucleic acid molecule which contains an operator is placed under conditions in which transcriptional machinery is present, either in vivo or in vitro, regulation of expression will often be modulated by contacting the nucleic acid molecule with a repressor and one or more metabolites which facilitate binding of an appropriate repressor to the operator. Thus, the invention further provides methods for preparing nucleic acid molecules which encode repressors which modulate the function of operators, as well as nucleic acid molecules produced by these methods, compositions comprising these molecules, and uses of these molecules and compositions.

Regulatory or other elements useful in generating a construct according to a method of the invention can be obtained in various ways. In particular, many of the elements are included in commercially available vectors and can be isolated therefrom and can be modified to contain a topoisomerase recognition site at one or both ends, for example, using a PCR method as disclosed herein. In addition, the sequences of or encoding the elements useful herein generally are well known and disclosed in publications. In many cases, the elements, for example, many transcriptional and translational regulatory elements, as well as cell compartmentalization domains, are relatively short sequences and, therefore, are amenable to chemical synthesis of the element or a nucleotide sequence encoding the element. Thus, in one embodiment, an element comprising a composition of the invention, useful in generating a ds recombinant nucleic acid molecule according to a method of the invention, or included within a kit of the invention, can be chemically synthesized and, if desired, can be synthesized to contain a topoisomerase recognition site at one or both ends of the element and, further, to contain an overhanging sequence following cleavage by a site specific topoisomerase.

A topoisomerase-charged vector can be generated in the following manner (*Genome Res.* 9: 383–392, 1999): A vector is linearized with a restriction enzyme that leaves “sticky ends”. Using a ligase such as T4 DNA ligase, adapter oligonucleotides are ligated to both ends, and both strands, of the linearized DNA. The adapter oligonucleotides contain and position a 5'-CCCTT-3' *Vacccinia* topoisomerase type I recognition sequence such that it can be cleaved by topoisomerase and trap the covalent topoisomerase-DNA complex at each 3' end of the vector. The adapted vector is then incubated with purified *Vaccinia* topoisomerase and an annealing oligonucleotide that complete the “topoisomerase sites” at each end of the vector. The annealing oligonucleotide acts to leave a break, or nick, in the “bottom” strand opposite the last T in the 5'-CCCTT-3' containing oligonucleotide. The oligonucleotide adapter fragments that are “downstream” of the topoisomerase cleavage site (the “leaving groups”) are released upon topoisomerase cleavage and are removed in the topoisomerase-vector purification process. In the absence of the 5' hydroxyl from the “leaving group”, topoisomerase is trapped in a covalent complex with the DNA ends to produce a topoisomerase-charged vector.

Where nucleic acid molecules are to be covalently linked according to a method of the invention, the nucleotide sequences generally are operatively linked such that the recombinant nucleic acid molecule that is generated has a desired structure and performs a desired function or encodes a desired expression product. As used herein, the term “operatively linked” means that two or more nucleotide sequences are positioned with respect to each other such that they act as a unit to effect a function attributable to one or both sequences or a combination thereof. The term “operatively covalently linked” is used herein to refer to operatively linked nucleotide sequences generated according to a method of the invention for generating a ds recombinant nucleic acid molecule covalently linked in one or both strands. For example, a nucleotide sequence containing an open reading frame can be operatively linked to a promoter such that the promoter confers its regulatory effect on the open reading frame similarly to the way in which it would effect expression of an open reading frame that it normally is associated with in a genome in a cell. Similarly, two or more nucleotide sequences comprising open reading frames can be operatively linked in frame such that, upon transcription and translation, a chimeric fusion polypeptide is produced.

Although a ds recombinant nucleic acid molecule covalently linked in one or both strands, generated according to a method of the invention generally is linear, the construct generated also can be a circularized ds recombinant nucleic acid molecule. Furthermore, a circular ds recombinant nucleic acid molecule can be generated such that it has the characteristics of a vector, and contains, for example, regulatory elements required for replication in a prokaryotic host cell, a eukaryotic host cell, or both, and can contain a nucleotide sequence encoding a polypeptide that confers antibiotic resistance or the like. An advantage of such a method is that the generated ds recombinant nucleic acid molecule, which is circularized according to a method of the invention, can be transformed or transfected into an appropriate host cell, wherein the construct is amplified. Thus, in addition to an in vitro method such as PCR, which can be used to generate large amounts of a linear ds recombinant nucleic acid molecule generated according to a method of the invention, an in vivo method using a host cell can be used for obtaining a large amount of a circularized product generated according to a method of the invention. Such elements including bacterial origins of replication, antibiotic resistance genes, and the like, which comprise a topoisomerase recognition site according to the present invention, can be useful components to include in a kit of the invention as disclosed herein.

It should be recognized that a linear ds recombinant nucleic acid molecule covalently linked in one or both strands, also can be cloned into a vector, which can be a plasmid vector or a viral vector such as a bacteriophage, baculovirus, retrovirus, lentivirus, adenovirus, vaccinia virus, semliki forest virus and adeno-associated virus vector, all of which are well known and can be purchased from commercial sources (Promega, Madison Wis.; Stratagene, La Jolla Calif.; GIBCO/BRL, Gaithersburg Md.). If desired, the vector can be linearized and modified according to a method of the invention, for example, using a PCR method, to contain a topoisomerase recognition site, or cleavage product thereof, at one or both 3' termini, or can be constructed by one skilled in the art (see, generally, *Meth. Enzymol*., Vol. 185, Goeddel, ed. (Academic Press, Inc., 1990); Jolly, *Canc. Gene Ther.* 1:51–64, 1994; Flotte, *J. Bioenerg. Biomemb.* 25:37–42, 1993; Kirshenbaum et al., *J. Clin. Invest.* 92:381–387, 1993; each of which is incorporated herein by reference).

Viral expression vectors can be particularly useful where a method of the invention is practiced for the purpose of generating a ds recombinant nucleic acid molecule covalently linked in one or both strands, that is to be introduced into a cell, particularly a cell in a subject. Viral vectors provide the advantage that they can infect host cells with relatively high efficiency and can infect specific cell types or can be modified to infect particular cells in a host.

Viral vectors have been developed for use in particular host systems and include, for example, baculovirus vectors, which infect insect cells; retroviral vectors, other lentivirus vectors such as those based on the human immunodeficiency virus (HIV), adenovirus vectors, adeno-associated virus (AAV) vectors, herpesvirus vectors, vaccinia virus vectors, and the like, which infect mammalian cells (see Miller and Rosman, *BioTechniques* 7:980–990, 1992; Anderson et al., *Nature* 392:25–30 Suppl., 1998; Verma and Somia, *Nature* 389:239–242, 1997; Wilson, *New Engl. J. Med.* 334:1185–1187 (1996), each of which is incorporated herein by reference). For example, a viral vector based on an HIV can be used to infect T cells, a viral vector based on an adenovirus can be used, for example, to infect respiratory epithelial cells, and a viral vector based on a herpesvirus can be used to infect neuronal cells. Other vectors, such as AAV vectors can have greater host cell range and, therefore, can be used to infect various cell types, although viral or non-viral vectors also can be modified with specific receptors or ligands to alter target specificity through receptor mediated events.

A method of the invention can be used to operatively covalently link a first nucleic acid molecule containing an open reading frame to a second (and other) nucleic acid molecule containing an open reading frame such that a nucleic acid molecule encoding a chimeric polypeptide is generated. The chimeric polypeptide comprises a fusion polypeptide, in which the two (or more) encoded peptides (or polypeptides) are translated into a single product, i.e., the peptides are covalently linked through a peptide bond. For example, a first nucleic acid molecule can encode a cell compartmentalization domain, such as a plasma membrane localization domain, a nuclear localization signal, a mitochondrial membrane localization signal, an endoplasmic reticulum localization signal, or the like, or a protein transduction domain such as the human immunodeficiency virus TAT protein transduction domain, which can facilitate translocation of a peptide linked thereto into a cell (see Schwarze et al., *Science* 285:1569–1572, 1999; Derossi et al., *J. Biol. Chem.* 271:18188, 1996; Hancock et al., *EMBO J.* 10:4033–4039, 1991; Buss et al., *Mol. Cell. Biol.* 8:3960–3963, 1988; U.S. Pat. No. 5,776,689 each of which is incorporated herein by reference). Such a domain can be useful to target a fusion polypeptide comprising the domain and a polypeptide encoded by a second nucleic acid molecule, to which it is covalently linked according to a method of the invention, to a particular compartment in the cell, or for secretion from or entry into a cell. As such, the invention provides a means to generate ds recombinant nucleic acid molecules covalently linked in both strands that encode a chimeric polypeptide.

A fusion polypeptide expressed from a nucleic acid molecule generated according to a method of the invention also can comprise a peptide having the characteristic of a detectable label or a tag such that the express fusion polypeptide can be detected, isolated, or the like. For example, a nucleic acid molecule containing a topoisomerase recognition site, or cleavage product thereof, as disclosed herein, can encode an enzyme such as alkaline phosphatase, β-galactosidase, chloramphenicol acetyltransferase, luciferase, or other enzyme; or can encode a peptide tag such as a polyhistidine sequence (e.g., hexahistidine), a V5 epitope, a c-myc epitope; a hemagglutinin A epitope, a FLAG epitope, or the like. Expression of a fusion polypeptide comprising a detectable label can be detected using the appropriate reagent, for example, by detecting light emission upon addition of luciferin to a fusion polypeptide comprising luciferase, or by detecting binding of nickel ion to a fusion polypeptide comprising a polyhistidine tag. Similarly, isolation of a fusion polypeptide comprising a tag can be performed, for example, by passing a fusion polypeptide comprising a myc epitope over a column having an anti-c-myc epitope antibody bound thereto, then eluting the bound fusion polypeptide, or by passing a fusion polypeptide comprising a polyhistidine tag over a nickel ion or cobalt ion affinity column and eluting the bound fusion polypeptide. Methods for detecting or isolating such fusion polypeptides will be well known to those in the art, based on the selected detectable label or tag (see, for example, Hopp et al., *BioTechnology* 6:1204, 1988; U.S. Pat. No. 5,011,912; each of which is incorporated herein by reference).

A method of the invention also can be used to detectably label a nucleotide sequence with a chemical or small organic or inorganic moiety such that the nucleotide sequence is useful as a probe. For example, a nucleic acid molecule, which has a topoisomerase recognition site, or cleavage product thereof, at a 3' terminus, can have bound thereto a detectable moiety such as a biotin, which can be detected using avidin or streptavidin, a fluorescent compound (e.g., Cy3, Cy5, Fam, fluorescein, or rhodamine), a radionuclide (e.g., sulfur-35, technicium-99, phosphorus-32, or tritium), a paramagnetic spin label (e.g., carbon-13), a chemiluminescent compound, or the like, such that, upon generating a covalently linked double stranded recombinant nucleic acid molecule according to a method of the invention, the generated nucleic acid molecule will be labeled. Methods of detectably labeling a nucleotide sequence with such moieties are well known in the art (see, for example, Hermanson, "Bioconjugate Techniques" (Academic Press 1996), which is incorporated herein by reference). Furthermore, a detectable label can be used to allow capture of a ds nucleic acid molecule that is generated by the present invention. Finally, a detectable label, for example biotin, can be used to block ligation of a topoisomerase-charged end of a first nucleic acid molecule to a labeled end of a second nucleic acid molecule, thus providing a method to direct ligation to the unlabelled end of the second nucleic acid molecule. It should be recognized that such elements as disclosed herein or otherwise known in the art, including nucleotide sequences encoding cell compartmentalization domains, or detectable labels or tags, or comprising transcriptional or translation regulatory elements can be useful components of a kit as disclosed herein.

A method of the invention provides a means to conveniently generate ds recombinant nucleic acid molecules that encode chimeric polypeptides useful, for example, for performing a two hybrid assay. In such a method, the first nucleic acid molecule encodes a polypeptide, or a relevant domain thereof, that is suspected of having or being examined for the ability to interact specifically with one or more other polypeptides. The first nucleic acid molecule is modified as disclosed herein to contain a topoisomerase recognition site at one or both ends and, if desired, a 5' overhanging sequence. The second nucleic acid molecule, to which the first nucleic acid molecule is to be covalently-linked according to a method of the invention, can encode a transcription activation domain or a DNA binding domain (Example 2.C), and contains a topoisomerase recognition site, or cleavage product thereof, and a 5' overhanging sequence complementary to that at the end of the first nucleic acid molecule to which it is to be linked. Upon contact with a topoisomerase, if the nucleotide sequences are not already topoisomerase-charged, a first hybrid useful for performing a two hybrid assay (see, for example, Fields and Song, *Nature* 340:245–246, 1989; U.S. Pat. No. 5,283,173; Fearon et al., *Proc. Natl. Acad. Sci., USA* 89:7958–7962, 1992; Chien et al., *Proc. Natl. Acad. Sci., USA* 88:9578–9582, 1991; Young, *Biol. Reprod.* 58:302–311(1998), each of which is incorporated herein by reference), or modified form of a two hybrid assay such as the reverse two hybrid assay (Leanna and Hannink, *Nucl. Acids Res.* 24:3341–3347, 1996, which is incorporated herein by reference), the repressed transactivator system (U.S. Pat. No. 5,885,779, which is incorporated herein by reference), the protein recruitment system (U.S. Pat. No. 5,776,689, which is incorporated herein by reference), and the like, is generated. Similar methods are used to generate the second hybrid protein, which can comprise a plurality of polypeptides to be tested for the ability to interact with the polypeptide, or domain thereof, of the first hybrid protein.

Similarly, such a method of generating a chimeric protein can be performed according to a method of the current invention for generating a ds recombinant nucleic acid molecule covalently linked in one strand, using first and second nucleic acid molecules comprising a site-specific topoisomerase recognition site (e.g., a type IA or a type II topoisomerase recognition site), or cleavage product thereof, at least at one 5' terminus of an end to be joined, wherein the nucleic acid molecules can further comprise complementary 3' overhangs upon cleavage by the topoisomerase.

Similarly, such a method of generating a chimeric protein can be performed according to a method of the current invention for generating a ds recombinant nucleic acid molecule covalently linked in both strands using first and second nucleic acid molecules comprising a topoisomerase recognition site, or cleavage product thereof, at least at the 5' terminus of the ends to be joined, wherein the nucleic acid molecules can further comprise complementary 3' overhangs upon cleavage by the topoisomerase; or one of the first or second nucleic acid molecules can comprise topoisomerase recognition sites, or cleavage products thereof, at the 5' terminus and the 3' terminus of at least one end, and the other nucleic acid molecule can contain a 3' hydroxyl group and a 5' hydroxyl group at the end to be joined, and wherein, upon cleavage by the topoisomerases, the topoisomerase-charged nucleic acid molecule can contain a 5' or 3' overhang that is complementary to, and facilitates hybridization to, a 5' or 3' overhang, respectively, or a blunt end, at the end of the other nucleic acid molecule to be joined.

In an alternative embodiment, the present invention also provides a method for the directional insertion of DNA fragments into cloning or expression vectors with the ease and efficiency of topoisomerase-mediated cloning. This invention also has advantages over current cloning systems because it decreases the laborious screening process necessary to identify cloned inserts in the desired orientation. This aspect of the invention consists, in its simplest form, of a linearized expression vector having a single topoisomerase molecule covalently attached at both 3' ends. At least one end of the linearized vector contains a 5' single-stranded overhang, while the opposite end can be either blunt, possess a single 3' T extension for T/A cloning, or may itself contain a second 5' single-stranded overhang sequence. These single-stranded sequence overhangs are alternatively referred to herein as "SSS" and may consist of any convenient sequence.

Construction of a topoisomerase-charged cloning vector according to this aspect of the invention may be accomplished, for example, by endonuclease digestion of the vector (which may be a pDONR vector (see FIG. 32) or a pDEST vector (see FIG. 33)), followed by complementary annealing of synthetic oligonucleotides and site-specific cleavage of the heteroduplex by *Vaccinia* topoisomerase I. Digestion of a vector with any compatible endonuclease creates specific sticky ends. Custom oligonucleotides may be annealed to these sticky ends, and possess sequences that, following topoisomerase I modification, form custom ends of the vector (see FIGS. 32 and 33). The sequence and length of the SSS will vary based on the desires of the user.

In one use of the TOPO SSS vectors provided by this aspect of the present invention, the DNA fragment to be inserted into the vector is a PCR product. Following PCR amplification with custom primers, the product can be directionally inserted into a topoisomerase I charged cloning vector having a SSS on one or both ends of the insertion site. The custom primers may be designed such that at least one primer of a given primer pair contains an additional sequence at its 5' end. The added sequence may be designed to be complementary to the sequence of the single-stranded overhang in the vector. The complementarity between the 5' single-stranded overhang in the vector and the 5' end of the PCR product mediates the directional insertion of the PCR product into the topoisomerase-mediated vector. Specifically, since only one end of the vector and one end of the PCR product possess complimentary SSS regions, the insertion of the product is directional. Topoisomerase I catalyzes the ligation of the PCR product to the vector.

This aspect of the invention also provides a modified cloning vector, having an overhanging single stranded piece of DNA, (the SSS) charged with topoisomerase, or "TOPO SSS vector". The modified vector allows the directional insertion of PCR amplified, or otherwise suitable, open reading frames (ORF) for subsequent expression, and takes advantage of the efficiency of topoisomerase-mediated cloning.

As noted above, topoisomerases are a class of enzymes that modify the topological state of DNA via the breakage and rejoining of DNA strands, (Shuman et al., U.S. Pat. No. 5,766,891, incorporated herein by reference). *Vaccinia* virus encodes a 314 aa type I topoisomerase enzyme capable of site-specific single-strand nicking of double stranded DNA, as well as 5' hydroxyl driven religation. Site-specific type I topoisomerases include, but are not limited to, viral topoisomerases such as pox virus topoisomerase. Examples of pox virus topoisomerases include shope fibroma virus and ORF virus. Other site-specific topoisomerases are well known to those skilled in the art and can be used to practice this invention.

Shuman teaches that *Vaccinia* topoisomerase binds to duplex DNA and cleaves the phosphodiester backbone of one strand while exhibiting a high level of sequence specificity. Cleavage occurs at a consensus pentapyrimidine element 5'-(C/T)CCTT-3' or related sequences in the scissile strand. In one embodiment the scissile bond is situated in the range of 2–12 bp from the 3' end of the duplex DNA. In another embodiment cleavable complex formation by *Vaccinia* topoisomerase requires six duplex nucleotides upstream and two nucleotides downstream of the cleavage site. Examples of *Vaccinia* topoisomerase cleavable sequences include, but are not limited to, +6/−6 duplex G CCCTTATTCCC (SEQ ID NO: 29), +8/−4 duplex TCG CCCTTATTC (SEQ ID NO: 30), +10/−2 duplex TGTCG CCCTTAT (SEQ ID NO: 31), +11/−1 duplex GTGTCG CCCTTA (SEQ ID NO: 32).

Examples of other site-specific type I topoisomerases are well known in the art. These enzymes are encoded by many organisms including, but not limited to *Saccharomyces cerevisiae, Saccharomyces pombe* and *Tetrahymena*, however these species' topoisomerase I enzymes have less specificity for a consensus sequence than does *Vaccinia*'s. (Lynn, R. M., Bjornsti, M., Caron, P. R. and Wang, J. C., (1989) Peptide sequencing and site-directed mutagenesis identify tyrosine-727 as the active site tyrosine of *Saccharomyces cerevisiae* DNA topoisomerase I, Proc. Natl. Acad. Sci. USA, 86: 3559–3563), (Eng, W., Pandit, S. D., and Sternglanz, R., (1989) Mapping of the active site tyrosine of eukaryotic DNA topoisomerase I, J. Biol. Chem., 264: 13373–13376) and (Busk, H., Thomsen, B., Bonven, B. J., Nielsen, O. F., and Westergaard, O. (1987) Preferential relaxation of supercoiled DNA containing a hexadecameric recognition for topoisomerase I, Nature, 327: 638–640), respectively.

As used herein with regard to this aspect of the invention, the term donor signifies a duplex DNA which contains a 5'-CCCTT cleavage site near the 3' end, and the term acceptor signifies a duplex DNA which contains a 5'-OH terminus. Once covalently activated by topoisomerase the donor will be transferred to those acceptors to which it has SSS complementation.

According to this aspect of the present invention, topoisomerase-modified vectors are further adapted to contain at least one 5' single-stranded overhang sequence to facilitate the directional insertion of DNA segments. In a preferred embodiment, the segment to be cloned is a PCR product constituting an open reading frame (ORF) which will be expressed from the resultant recombinant vector. The primers used for amplifying the ORF are designed such that at least one primer of the primer pair contains an additional sequence at its 5' end. This sequence is designed to be complementary to the sequence of the 5' single-stranded overhang present in the topoisomerase-modified vector of the present invention.

Certain preferred, but non-exclusive, embodiments according to this aspect of the present invention are described in detail below in Examples 5–8.

Nucleic acid molecules assembled using methods of the invention either may be used directly or may be amplified and then used for any number of purposes. With reference to FIG. 34, nucleic acid segments to be assembled using methods of the invention may be generated by any number of methods. For example, these segments may be obtained by any method known in the art. In instances where the nucleic acid segments do not have one or more (e.g., one, two, three, four, etc.) termini and/or regions suitable for assembly using methods of the invention, such termini and/or regions may be added. Suitable termini and/or regions may be added, for example, by amplifying nucleic acids using PCR or by the addition of one or more (e.g., one, two, three, four, etc.) adapter linkers (e.g., adapter linkers which contain one or more topoisomerase recognition sites). Nucleic acid segments having suitable termini and/or regions may then be assembled using methods of the invention described elsewhere herein.

As shown in FIG. 34, once assembled, the linked nucleic acid segments may be amplified (e.g., in vivo or in vitro) and then used in any number of methods or processes, many of which are described elsewhere herein. Alternatively, the assembled nucleic acid segments may be used directly for applications such as in vitro transcription/translation, recombinational cloning, or for transforming or transfecting cells. The invention thus provides versatile compositions and methods for manipulating nucleic acids.

As also indicated in FIG. 34, the invention further provides methods for linking nucleic acid segments which then may be used in any number of methods or processes. As one example of such a method, the initial ligation products generated by the first step set out in FIG. A, which is referred to here solely for illustrative purposes, are directly transcribed (e.g., used for in vitro transcription). This process is facilitated by the fact that the nucleic acid which is transcribed is covalently linked in both strands at the junction point between the linker containing the T7 promoter element and the PCR product. Further, transcription of the linkage products from the T7 promoter results in the production of both sense and antisense RNA which can be used to form, for example, double stranded RNA. This double stranded RNA can be used for inhibiting gene expression. In particular, methods of the invention may be used to produce double stranded RNA for RNAi applications. Such RNAi molecules may be prepared from RNA molecules prepared in two separate tubes and then mixed or in the same tube. In the first case, transcription of sense strand and antisense strand RNA may occur after DNA molecules which encode these strand have been separated and placed in separate tubes. In the second case, transcription of both sense strand and antisense strand RNA may occur in the same tube. Thus, the invention also provides one and two tube methods for the preparation RNA for, for example, the preparation of RNAi.

As one skilled in the art would recognize, any number of variations of the above are possible and within the scope of the invention. For example, a promoter other than a T7 promoter may be used. Further, any of the nucleic acid molecules described above, as well as elsewhere herein, may be designed to contain one or more recombination sites which can then be used to connect these molecules with other nucleic acid molecules (e.g., other nucleic acid molecules with cognate recombination sites).

The invention provides compositions and methods for linking nucleic acid molecules using topoisomerase and recombination. In particular embodiments of the invention, nucleic acid molecules undergo one or more (e.g., one, two, three, four, five, six, seven, eight, nine, ten, etc.) recombination reactions and are then linked to one or more (e.g., one, two, three, four, five, six, seven, eight, nine, ten, etc.) other nucleic acid molecules by methods involving covalent linking of strands catalyzed by one or more (e.g. one, two, three, four, etc.) topoisomerases. In other embodiments, nucleic acid molecules are linked to other nucleic acid molecules by methods involving covalent linking of strands catalyzed by one or more (e.g., one, two, three, four, etc.) topoisomerases and then undergo one or more (e.g., one, two, three, four, five, six, seven, eight, nine, ten, etc.) recombination reactions. As one skilled in the art would recognize, the invention is not tied to any particular order of topoisomerase-mediated linkage of nucleic acid molecules or recombination reactions. Thus, in general, the invention is directed to compositions and methods for performing both recombination reactions and linking nucleic acid segments using topoisomerases.

The invention thus also provides adapter-linker molecules for use in accordance with the methods and compositions of the invention. The adapter linkers that are provided by, and that may be used in connection with, the present invention can contain both a topoisomerase site and a recombination site. One example of a process of the invention is set out schematically in FIG. 35. FIG. 35 shows a process which involves the connection of a topoisomerase-adapted nucleic acid segment ("adapter linker") which contains a single recombination site to another nucleic acid segment, referred to as an insert. These two nucleic acid segments may be connected by any topoisomerase-mediated process described herein.

Adapter linkers of the invention may comprise (1) one or more recombination sites and/or (2) one or more topoisomerase recognition sites or one or more topoisomerases. In particular embodiments, at least one of the one or more recombination sites of the adapter linkers will be located within zero, one, two, three, four, five, six, seven, eight, nine, ten, fifteen, or twenty nucleotides of at least one of the one or more topoisomerase recognition site or one or more topoisomerase. In specific embodiments, recombination sites present in adapter linkers of the invention are attL, attB, attP, or attL recombination sites. In additional specific embodiments, the topoisomerase recognition sites recognition are recognition sites for type IB topoisomerases, type IA topoisomerases or type II topoisomerases, or the topoisomerases are type IB topoisomerases, type IA topoisomerases or type II topoisomerases. In addition, topoisomerase recognition sites or topoisomerases may be located, with respect to recombination sites, in adapter linkers of the invention such that upon recombination, particular recombination sites become associated with the product molecules. For example, a topoisomerase recognition site may be located on either end of an attL site in an adapter linker such that when the linker is attached to a nucleic acid molecule and recombination occurs, either an attB or an attP site is generated on the nucleic acid molecule to which the adapter linker was attached. Thus, adapter linkers may contain toposiomerase recognition sites and/or topoisomerases positioned, with respect to recombination sites, such that upon ligation to a nucleic acid molecule and recombination any number of variations of recombination sites are present on the product nucleic acid molecules. Examples of such recombination sites include attL, attB, attP, and attR recombination sites.

The invention further provides methods for linking any number of nucleic acid segments using adapter linkers which contain recombination sites having the same or different specificities, as well as adapter linkers which contain recombination sites having the same or different specificities and kits which contain such adapter linkers. For example, three separate PCR products, referred to as segments A, B, and C, may be linked to adapter linkers such that attL1 and attL3 sites are present at the ends of segment A, attR3 and attR4 sites are present at the ends of segment B, and attL4 and attL2 sites are present at the ends of segment C. Thus, upon recombination with a linearized vector which contains attR1 and attR2 recombination sites at or near the termini, all three PCR products are joined to each other and inserted into the vector to generate a circularized nucleic acid molecule. Any number of variations of the above are possible and are within the scope of the invention.

The invention further includes sets of two or more (e.g., two, three, four, five, six, seven eight, nine, etc.) adapter linkers which contain (1) one or more recombination sites having the same or different specificities and/or (2) one or more topoisomerases or toposiomerase recognition sites, as well as methods for using these sets of adapter linkers to generate nucleic acid molecules which contain one or more recombination sites, compositions comprising such adapter linker sets or individual member of these sets, nucleic acid molecules which have been adapted with one or more adapter linkers of these sets, and methods for using these nucleic acid molecules.

After topoisomerase-mediated assembly, the assembled nucleic acid molecule may be recombined with another nucleic acid segment which contains one or more (e.g., one, two, three, four, etc.) suitable recombination sites. The recombination sites shown in FIG. 35 are attL1 and attR1 sites but any suitable recombination sites may be used (e.g. lox sites, attR sites, attL sites, attB sites, attP sites, etc.). Additional suitable recombination sites are described elsewhere herein.

The invention thus includes methods for generating nucleic acid molecules using topoisomerase recognition sites and recombination sites with recombine with each other. The invention also includes nucleic acid molecules prepared by and used in methods of the invention, as well as methods for using nucleic acid molecules generated by methods described herein.

The invention further includes methods for generating nucleic acid molecules using multiple (e.g., two, three, four, five, six, seven, eight, nine, ten, etc.) recombination sites and topoisomerase recognition sites, as well as nucleic acid molecules prepared by and used in such methods. Further, these recombination sites may have multiple (e.g., two, three, four, five, six, seven, eight, nine, ten, etc.) specificities. In addition, the topoisomerase recognition sites may be designed to generate termini which will result in the connection of these termini to different nucleic acid segments. For example, these termini may be designed to generate different "sticky ends" upon cleavage with a topoisomerase.

Another example of methods described above is shown in FIG. 36. FIG. 36 shows a process in which two nucleic acid segments are connected using a process which involves topoisomerase-mediated covalent linkage of strands of the termini of the nucleic acid segments. The resulting nucleic acid molecule then undergoes recombination, which results in (1) the topoisomerase assembled nucleic acid molecule becoming linked to a nucleic acid segment which contains an origin of replication and (2) replacement of a negative selection marker (e.g., a ccdB gene) with a promoter. The recombined nucleic acid product is then connected to a nucleic acid segment which is topoisomerase adapted at both termini and contains a positive selection marker. This last step results in the nucleic acid molecule being circularized.

The circularized nucleic acid end product shown in FIG. 36 may be introduced into host cells, which may be prokaryotic (e.g., bacterial) or eukaryotic (e.g., yeast, plant, animal (including mammalian, such as human)) cells such as those described elsewhere herein. Further, cells which contain this end product can be selected for using positive and negative selection. Thus, for example, cells which have acquired a nucleic acid molecule wherein the negative selection marker has not been replaced by the promoter will be selected against. The invention further includes methods and compositions similar to those set out in FIGS. 35 and 36 in which any number of the steps and components are varied. Examples of steps and components which may be varied are described elsewhere herein. The invention further includes methods for using nucleic acid molecules generated by methods described above.

As one skilled in the art would recognize, nucleic acid segments used in processes such as those shown in FIGS. 35 and 36 could contain any number of different elements. For example, a positive selection marker could be substituted for the promoters shown in FIG. 36. Further, the insert shown in FIG. 35 may contain nucleic acid which has any number of functionalities. In particular, when the insert contains a regions which is transcribed, the transcript can be a mRNA or an RNA which serves a function in the absence of translation. Examples of RNA which serves a function in the absence of translation include transfer RNAs (e.g., suppressor tRNAs), antisense RNAs, ribosomal RNAs, and ribozymes. Additionally, more than one of the nucleic acid segments connected and/or recombined by methods of the invention may contain all or part of one or more (e.g., one, two, three, four, five, six, seven, etc.) open reading frames. In such instances, nucleic acid segments may be connected to each other such that transcription and translation result in the production of one or more fusion proteins. Additional nucleic acid elements which can be used in methods of the invention are described elsewhere herein.

Once a nucleic acid molecule, such as the end product of the process shown in FIG. 35, has been generated by methods of the invention, the nucleic acid molecule may optionally be connected to one or more (e.g., one, two, three, four, etc.) other nucleic acid molecules or may be circularized by joining of the termini to each other. Further, when three or more nucleic acid molecules are connected to each other by methods of the invention, the termini of various intermediate molecules or the end product may be joined to each other to circularize these molecules.

The invention further provides compositions and methods for performing homologous recombination and for producing transgenic animals. Gene targeting by homologous recombination between an exogenous DNA construct and cognate chromosomal sequences allows precise modifications to be made at predetermined sites in the genome. Gene targeting is well-established in, e.g., mouse embryonic stem (ES) cells, and has been used to effect modifications in a large number of murine genes. (See e.g., Brandon et al., *Curr. Biol.* 5:625–634, 758–765, 873–881 (1995)). Gene targeting can also be accomplished in somatic cells. (See e.g., Itzhaki et al., *Nat. Genet.* 15:258–265 (1997)). Cells that have been modified by gene targeting via homologous recombination can then be manipulated by methods known in the art to establish transgenic animals.

One example of a composition of the invention that can be used in homologous recombination applications is the end product nucleic acid molecule set out in FIG. 37. FIG. 37 further shows an example of a method for preparing such compositions. In particular, FIG. 37 shows the linkage of topoisomerase adapted nucleic acid segments to a non-topoisomerase adapted nucleic acid segment. In this instance, the nucleic acid segment which the designer of the nucleic acid end product seeks to integrate into a chromosome, referred to here as an insert, is flanked by regions which contain (1) a positive selection marker and (2) a negative selection marker positioned between two recombination sites. Recombination may then be used to replace the two negative selection markers with nucleic acid having homology to a chromosomal region into which the end product is to integrate (labeled “HR1” and “HR2” in FIG. 37).

Regions of homology used in the practice of the invention will vary with the chromosomes of cells into which nucleic acid molecules are to integrate. Further, in many instances, regions of homology will be selected to facilitate integration into cells of a particular organism. Such an organism may be unicellular organism (e.g., a yeast, a protozoan, etc.) or multicellular organism (e.g., a plant, an animal, etc.).

The invention thus provides nucleic acid molecules and compositions for perforing homologous recombination and cells produced via homologous recombination involving these molecules and compositions. Methods of the present invention can be used in the linking of multiple nucleic acid segments. FIG. 38, for example, shows a schematic representation of the linking of four nucleic acid segments using toposiomerase to generate a linear nucleic acid molecule with recombination sites (labeled “L1” and “L2”) located near the termini. In the first step, topoisomerase adapted nucleic acid segment which contains an attL1 recombination site and an attL2 recombination site are linked to two other nucleic acid segments using topoisomerase. In this particular instance, each strand of the termini which are joined to each other is covalently linked to a topoisomerase molecule. Thus, upon toposiomerase mediated linkage of the nucleic acid strands, no nicks are present at the junction points. In the second step, the topoisomerase assembled nucleic acid segments are contacted with another nucleic acid segment which contains an origin of replication (labeled “ori”), a positive selection marker (labeled “PM”), an attR1 recombination site, and an attR2 recombination site in the presence of LR CLONASE™ under conditions which allow for recombination between the attL and attR recombination sites. In certain such methods, for example, TOPO-adapted vectors are incubated with one or more nucleic acid segments (e.g., one or more PCR products) at room temperature (e.g., about 20–20° C.) for about 5–30 (and preferably about 10) minutes; the reaction is then heat-treated by incubation at about 80° C. for about 20 minutes, and the reaction mixture then used in a standard LR reaction according to manufacturer’s instructions (Invitrogen Corporation, Carlsbad, Calif.), except the incubation time for the LR reaction is increased to about 3 hours. Recombination results in the formation of a circular nucleic acid molecule which contains the various starting nucleic acid segments separated from the origin and selection marker by attB1 and attB2 recombination sites. As one skilled in the art would recognize, any suitable recombination sites could be used in place of the aut recombination sites shown in this figure. The invention thus also provides compositions comprising such nucleic acids, compositions used for producing such nucleic acids, and uses of such nucleic acids and compositions in the recombination and topoisomerase-mediated joining methods of the invention described elsewhere herein.

The invention further provides nucleic acid molecules suitable for performing cloning reactions in which a first nucleic acid molecule, which shares one or more region of homology with a second nucleic acid molecule, is used to insert nucleic acid from the second nucleic acid molecule into the first nucleic acid molecule. The invention further provides compositions and methods for performing such cloning reactions.

One example of a process referred to above is RecE/T cloning, which is described in PCT Publication WO 01/04288, the entire disclosure of which is incorporated herein by reference. Typically, in RecE/T cloning, a linear first nucleic acid molecule (e.g., a vector) is introduced into a cell which contains (1) regions at the termini that share homology with two separate, nearby regions (e.g., nucleic acid regions which are about 20 to about 30, about 20 to about 40, about 20 to about 50, about 30 to about 40, about 40 to about 50, about 40 to about 60, about 40 to about 80, about 50 to about 90, etc. nucleotides in length) of a nucleic acid molecule present in the cell (e.g., a plasmid, a bacterial artificial chromosome, a natural chromosome, etc.), referred to here as "a second nucleic acid molecule", (2) a selection marker, and (3) an origin of replication. The linear first nucleic acid molecule will generally only replicate if it becomes circularized. Further, the first nucleic acid molecule will typically become circularized when it has undergone recombination with the second nucleic acid molecule and acquired nucleic acid from the second nucleic acid molecule which is intervening between the regions of homology. In such embodiments, the regions of homology in the first nucleic acid molecule will typically be in a reverse orientation as compared to the second nucleic acid molecule. Generally, the cell in which recombination occurs will be one which expresses a recombinase such as RecE/T or RecAlpha/Beta. Thus, the invention provides, in part, methods for performing RecE/T cloning, nucleic acid molecules prepared by such methods, compositions comprising such nucleic acid molecules, and methods for using such nucleic acid molecules and compositions.

Modifications of the RecE/T process may be employed to generate a number of different end products. For example, when the regions of homology are arranged in various ways, the first nucleic acid molecule can be designed to (1) insert into the second nucleic acid molecule, or (2) delete nucleic acid from the second nucleic acid molecule. Typically, when insertion of the second nucleic acid molecule into the second nucleic acid molecule is desired, the regions of homology of the first nucleic acid molecule will be in the same orientation with respect to the regions of homology in the second nucleic acid molecule. Further, when deletion of nucleic acid from the second nucleic acid molecule is desired, the regions of homology of the first nucleic acid molecule will generally be in an inverse orientation with respect to the regions of homology in the second nucleic acid molecule. Also, when insertion of the first nucleic acid molecule into the second nucleic acid molecule is desired, typically the first nucleic acid molecule will not contain an origin of replication. The invention provides methods for performing the above processes. The invention also provides nucleic acid molecules and compositions for use in the above processes.

The present invention can also be used to link two nucleic acid segments in a single step process using topoisomerase and recombination sites to generate a circular nucleic acid molecule. An example of this embodiment is depicted in FIG. 39 where one of the nucleic acid segments contains an attL1 recombination site (labeled "L1"), a promoter (labeled "P"), and toposiomerase molecule covalently linked to one terminus. The other nucleic acid segment contains an attR1 recombination site (labeled "R1"), an open reading frame (labeled "ORF"), an origin of replication (labeled "ORI"), a positive selection marker (labeled "PM"), and topoisomerase molecule covalently linked to one terminus. Thus, when these two nucleic acid segments are contacted with each other in the presence of LR CLONASE™ under conditions which allow for recombination between the attL and attR recombination sites and topoisomerase mediated linkage of nucleic acid strands, a circular molecule is formed having the structure indicated. In certain such methods, for example, TOPO-adapted vectors are incubated with one or more nucleic acid segments (e.g., one or more PCR products) at room temperature (e.g., about 20-20° C.) for about 5–30 (and preferably about 10) minutes; the reaction is then heat-treated by incubation at about 80° C. for about 20 minutes, and the reaction mixture then used in a standard LR reaction according to manufacturer's instructions (Invitrogen Corporation, Carlsbad, Calif.), except the incubation time for the LR reaction is increased to about 3 hours. As one skilled in the art would recognize, any suitable recombination sites could be used in place of the att recombination sites shown in this figure.

The present invention can also be used to link two nucleic acid segments using toposiomerase mediated methods to generate a circular nucleic acid molecule. A schematic representation of one embodiment of this aspect of the invention is illustrated in FIG. 40. As shown in FIG. 40, the circular molecule contains an open reading frame (labeled "ORF") positioned between attL1 and attL2 recombination site (labeled "L1" and "L2"). The topoisomerase assembled product then undergoes recombination with another circular molecule which contains attR1 and attR2 recombination sites to generate a third circular nucleic acid molecule which contains the open reading frame positioned between attB1 and attB2 recombination sites. Further, the open reading frame is operably linked to a promoter. Thus, the final nucleic acid molecule produced by this process is an expression construct. As one skilled in the art would recognize, any suitable recombination sites could be used in place of the att recombination sites shown in this figure.

As disclosed herein, a first nucleic acid molecule can be one of a plurality of nucleotide sequences, for example, a cDNA library, a combinatorial library of nucleotide sequences, or a population of variegated nucleotide sequences. As such, a particularly useful embodiment of a method of the invention is in generating recombinant polynucleotides encoding chimeric polypeptides for performing a high throughput two hybrid assay for identifying protein-protein interactions that occur among populations of polypeptides (see U.S. Pat. No. 6,057,101 and U.S. Pat. No. 6,083,693, each of which is incorporated herein by reference). In such a method, two populations (pluralities) of nucleotide sequences encoding polypeptides are examined, each plurality having a complexity of from a few related but different nucleotide sequences to as high as tens of thousands of such sequences. By performing a method of the invention, for example, using a PCR primer pair to amplify each nucleotide sequence in the plurality, wherein at least one primer of the PCR primer pair comprises (a) at least one topoisomerase recognition site or complement thereof or (b) at least one recombination site, covalently linked recombinant polynucleotides encoding a population of chimeric bait polypeptides and a population of chimeric prey polypeptides readily can be generated by contacting the amplified pluralities of nucleotide sequences, each of which comprises (a) at least one topoisomerase recognition site, with at least one topoisomerase and a nucleotide sequence, which contains at least one topoisomerase recognition site and encodes a transcription activation domain or a DNA binding domain or (b) at least one recombination site site, with at least one topoisomerase and a nucleotide sequence, which contains at least one recombination site and encodes a transcription activation domain or a DNA binding domain.

In practicing a method of the invention, a first nucleic acid molecule also can encode a ribonucleic acid (RNA) molecule, which can function, for example, as a riboprobe, an antisense nucleotide sequence, a ribozyme, or a triplexing nucleotide sequence, or can be used in an in vitro translation reaction, and the second nucleic acid molecule can encode a regulatory element useful for expressing an RNA from the first nucleotide sequence (see Example 2.A). For example, where it is desired to produce a large amount of RNA, a second nucleic acid molecule component for performing a method of the invention can comprise an RNA polymerase promoter such as a T7, T3 or SP6 RNA polymerase promoter. Where the RNA molecule is to be expressed in a cell, for example, an antisense molecule to be expressed in a mammalian cell, the second (or other) nucleic acid molecule can include a promoter that is active in a mammalian cell, particularly a tissue specific promoter, which is active only in a target cell. Furthermore, where the RNA molecule is to be translated, for example, in a coupled in vitro transcription/translation reaction, the first nucleotide sequence or second (or other) nucleotide sequence can contain appropriate translational regulatory elements (see Example 2.B).

Methods of the invention may also be used to produce constructs which allow for silencing of genes in vivo. One method of silencing genes involves the production of double-stranded RNA, termed RNA interference (RNAi). (See, e.g., Mette et al., *EMBO J,* 19:5194–5201 (2000)). The mechanism by which RNAi is believed to function, which is reviewed in Fjose et al., *Biotechnol. Annu. Rev.* 7:31–57 (2001), appears to be based on the ability of double stranded RNA to induce the degradation of specific RNA molecules. This mechanism is reported to involve the conversion of double-stranded RNA into short RNAs that direct ribonucleases to homologous RNA targets (e.g., mRNA targets). Methods of the invention can be used in a number of ways to produce molecules such as RNAi. Thus, expression products of nucleic acid molecules of the invention can be used to silence gene expression.

One example of a nucleic acid molecule designed to produce RNAi is a molecule in which a nucleic acid segment is linked to one or more promoters such that RNA corresponding to both strands are produced as two separate transcripts or as part of the same transcript. For example, a nucleic acid molecule could be prepared using methods of the invention wherein two copies of an open reading frame are connected by an intervening nucleic acid segment with two promoters that drive transcription in different directions. Thus, one of the promoters drives transcription of sense strand mRNA and the other promoter drives transcription of antisense mRNA. Another example of a nucleic acid molecule which could be used to produce RNAi is one in which an open reading frame is flanked on each end by promoters which, drive transcription of the open reading frame in opposing directions. As a third example, doubles stranded RNA can be produced from a nucleic acid molecule which encode RNA having a “snapback” region (e.g., a region that is six, seven, eight, nine ten, etc. nucleotides in length) at one terminus. Thus, an RNA transcript of this type will form a hairpin turn at or near one terminus. When such an RNA molecule is incubated, under appropriate conditions, in the presence of an RNA dependent RNA polymerase, the double stranded region formed by the hairpin can be used to prime second strand synthesis to form double stranded RNA molecule.

Nucleic acid segments designed to produce RNAi, such as the nucleic acid molecules described above, need not correspond to the full-length gene or open reading frame. For example, when the nucleic acid segment corresponds to all or part of an ORF or encode an RNA molecule which does not correspond to all or part of an ORF, the segment may only correspond to part of the ORF (e.g., about 15, about 16, about 17, about 18, about 19, about 20, about 21, about 22, about 23, about 24, about 25, about 26, about 27, about 28, about 29, about 30, about 40, about 50, about 60, etc. nucleotides at the 5' or 3' end of the ORF).

Thus, in particular embodiments, the invention provides methods for preparing nucleic acid molecules comprising at least three segments. In some embodiments, at least two of these segments share at least one region of sequence identity (e.g., a region at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, at least about 30, at least about 40, at least about 50, at least about 60, at least about 70, at least about 80, at least about 90, at least about 100 nucleotides, etc. nucleotides in length). In other embodiments, one nucleic acid segment is flanked by a region which can confer transcription of the interior portion of the molecule in opposing directions (e.g., to produce sense and antisense transcripts). The invention further provides nucleic acid molecules prepared by methods of the invention and the use of such molecules to either inhibit gene expression or facilitate the degradation of specific RNA molecules.

The invention further includes methods for preparing nucleic acid molecules which express one or more RNA molecules which can be used to prepare double stranded RNA having overhangs on one or both ends. For example, methods of the invention can be used to express two single stranded RNA molecules which are 21 nucleotides in length and share sequence complementarity over 19 of their nucleotides. Thus, when these two single stranded RNA molecules hybridize to each other, there will be a two nucleotide overhang on each end. Double stranded RNA molecules similar to those described above have been shown to be capable of inhibiting gene expression when introduced into mammalian cells (Elbashir et al., *Nature* 411:494–498 (2001)).

The invention thus includes methods for generating nucleic acid molecules which can be used to produce short RNA molecules, as well as RNA molecules produced by nucleic acid molecules prepared by these methods and methods for preparing these RNA molecules. These short RNA molecules will typically be about 15, about 16, about 17, about 18, about 19, about 20, about 21, about 22, about 23, about 24, about 25, about 26, about 27, about 28, about 29, about 30 nucleotides in length. Further, these short RNA molecules will typically be between from about 15 to about 30, from about 15 to about 25, from about 15 to about 24, from about 23 to about 22, from about 15 to about 21, from about 15 to about 20, from about 15 to about 19, from about 15 to about 18, from about 20 to about 30, from about 20 to about 28, from about 20 to about 25, from about 20 to about 24, from about 20 to about 23, from about 20 to about 22, or from about 20 to about 21 nucleotides in length.

The invention further includes methods for generating nucleic acid molecules which can be used to produce short double stranded RNA molecules, as well as RNA molecules produced by nucleic acid molecules prepared by these methods. These short double stranded RNA molecules may comprise a double stranded region which is about 10, about 12, about 14, about 15, about 16, about 17, about 18, about 19, about 20, about 21, about 22, about 23, about 24, about 25, about 26, about 27, about 28, about 29, about 30 nucleotides in length. Further, the double stranded region of these RNA molecules may be between from about 10 to about 30, from about 10 to about 25, from about 10 to about 20, from about 10 to about 18, from about 10 to about 17, from about 15 to about 30, from about 15 to about 25, from about 15 to about 24, from about 23 to about 22, from about 15 to about 21, from about 15 to about 20, from about 15 to about 19, from about 15 to about 18, from about 20 to about 30, from about 20 to about 28, from about 20 to about 25, from about 20 to about 24, from about 20 to about 23, from about 20 to about 22, or from about 20 to about 21 nucleotides in length. Further, these double stranded RNA molecules may comprise overhangs at one or both termini which are about 1, about 2, about 3, about 4, about 5, about 6, about 7, or about 8 nucleotides in length and/or are between from about 1 to about 10, from about 1 to about 8, from about 1 to about 6, from about 1 to about 4, from about 1 to about 2, from about 2 to about 10, from about 2 to about 8, from about 2 to about 6, or from about 2 to about 4 nucleotides in length.

The invention also provides methods for preparing nucleic acid molecules which can be used to express antisense RNA (e.g., antisense mRNA). Methods similar to those described above for the production of nucleic acid molecules which can be used for RNAi may be employed; however, only the antisense strand will typically be transcribed in molecules prepared by methods of the invention which may be used to generate antisense RNA.

In related embodiments, promoters which drive transcription of the sense RNA or antisense RNA can be either constitutive (e.g., CMV promoter, SV40 promoter, etc.), inducible (e.g., a metallothionein promoter, etc.), or repressible. Thus, for example, two different inducible promoters can be used to drive transcription of sense RNA and antisense RNA. In such an instance, promoter activation can be used to induce production of sense RNA, antisense RNA, or both sense RNA and antisense RNA. Further, the amount of sense RNA and/or antisense RNA produced can be related by using, for example, graduated induction and/or derepression of the promoters.

Gene silencing methods involving the use of compounds such as RNAi and antisense RNA, for examples, are particularly useful for identifying gene functions. More specifically, gene silencing methods can be used to reduce or prevent the expression of one or more genes in a cell or organism. Phenotypic manifestations associated with the selective inhibition of gene functions can then be used to assign role to the "silenced" gene or genes. As an example, Chuang et al., *Proc. Natl. Acad. Sci.* (USA) 97:4985–4990 (2000), have demonstrated that in vivo production of RNAi can alter gene activity in *Arabidopsis thaliana*. Thus, the invention provides methods for regulating expression of nucleic acid molecules in cells and tissues comprising the expression of RNAi and antisense RNA. The invention further provides methods for preparing nucleic acid molecules which can be used to produce RNA corresponding to one or both strands of a DNA molecule.

The invention thus provides methods for regulating expression of nucleic acid molecules in vivo (e.g., in cells and tissues) and/or in vitro comprising the expression of sense RNA and/or antisense RNA. The invention further provides methods for preparing nucleic acid molecules which can be used to produce RNA corresponding to one or both strands of a nucleic acid molecule (e.g., a DNA molecule). The invention also provides compositions for performing the methods described above and nucleic acid molecules produced by the above methods (e.g., RNA and DNA molecules).

The invention also relates to compounds and methods for gene silencing involving ribozymes. In particular, the invention provides antisense RNA/ribozymes fusions, which comprise 1) antisense RNA corresponding to a target gene and 2) one or more ribozymes that cleave RNA (e.g., hammerhead ribozyme, hairpin ribozyme, delta ribozyme, *Tetrahymena* L-21-ribozyme, etc.). Further provided by the invention are vectors that express such fusions, methods for producing such vectors, and methods for using such vector to suppress gene expression.

Expression of antisense molecules fused to ribozymes can be used, for example, to cleave specific RNA molecules in a cell because the antisense RNA portion of the transcript can be designed to hybridize to particular "mRNA molecules. Further, the ribozyme portion of the transcript can be designed to cleave the RNA molecule to which it has hybridized. For example, the ribozyme can be one which cleaves double stranded RNA (e.g., a *Tetrahymena* L-21 ribozyme).

A method of the invention can be particularly useful for generating an expressible ds recombinant nucleic acid molecule that can be inserted in a site specific manner into a target DNA sequence. The target DNA sequence can be any DNA sequence, particularly a genomic DNA sequence, and preferably a gene for which some or all of the nucleotide sequence is known. The method can be performed utilizing a first nucleic acid molecule, which has a first end and a second end and encodes a polypeptide, for example, a selectable marker, wherein the first nucleic acid molecule comprises at least one topoisomerase recognition site and/or at least one recombination site or cleavage product thereof at the 3' terminus of each end and, optionally, a hydroxyl group at the 5' terminus of each end, and wherein, preferably, the 5' termini comprise 5' overhanging sequences, which are different from each other; and covalently linking the first nucleic acid molecule to first and second PCR amplification products according to a method of the invention. The first and second amplification products are generated from sequences upstream and downstream of the site at which the construct is to be inserted, and each amplification product contains at least one topoisomerase recognition site and optionally at least one recombination site, preferably, a 5' overhanging sequence, which is generated following contact with the site specific topoisomerase. Preferably, the first and second amplification products have different 5' overhanging sequences such that each can be linked to a predetermined end of the first nucleic acid molecule. Such a method similarly can be performed using a ds amplification product comprising at least one topoisomerase recognition site and, optionally, at least one recombination site, or cleavage product thereof, at the 5' terminus of one or both ends, wherein, upon cleavage by the topoisomerase, the topoisomerase-charged molecule can comprise a 3' overhang at one or both ends containing the topoisomerase. In addition, the method can be performed using a ds amplification product comprising topoisomerase recognition sites and, optionally, recombination sites, or cleavage products thereof, at or near the 5' terminus and the 3' terminus of one or both ends, wherein, upon cleavage by the topoisomerases, the topoisomerase-charged nucleic acid molecule preferably contains a 5' or 3' overhang at one or both ends containing the topoisomerases. Once nucleic acid molecules are joined by the methods described above, the resulting molecules may then be used in recombination reactions, such as those described elsewhere herein.

The first and second amplification products may be generated using two sets of PCR primer pairs. The two sets of PCR primer pairs may be selected such that, in the presence of an appropriate polymerase such as Taq polymerase and a template comprising the sequences to be amplified, the primers amplify portions of a target DNA sequence that are upstream of and adjacent to, and downstream of and adjacent to, the site for insertion of the selectable marker. In addition, the sets of PCR primer pairs may be designed such that the amplification products contain a topoisomerase recognition site and, following cleavage by the site specific topoisomerase, a 5' overhanging sequence at the end to be covalently linked to the selectable marker. As such, the first PCR primer pair includes 1) a first primer, which comprises, in an orientation from 5' to 3', a nucleotide sequence complementary to a 5' overhanging sequence of the end of the selectable marker to which the amplification product is to be covalently linked, a nucleotide sequence complementary to a topoisomerase recognition site, such that PCR introduces a functional recognition site in the opposite strand (see primer sequences in FIG. 9D), and a nucleotide sequence complementary to a 3' sequence of a target DNA sequence upstream of the insertion site; and 2) a second primer, which comprises a nucleotide sequence of the target genomic DNA upstream of the 3' sequence to which the first primer is complementary, i.e., downstream of the insertion site. The second PCR primer pair includes 1) a first primer, which comprises, from 5' to 3', a nucleotide sequence complementary to the 5' overhanging sequence of the end of the selectable marker to which it is to be covalently linked, a nucleotide sequence complementary to a topoisomerase recognition site, such that PCR introduces a functional recognition site in the opposite strand (see primer sequences in FIG. 9D), and a nucleotide sequence of a 5' sequence of a target DNA sequence, wherein the 5' sequence of the target genomic DNA is downstream of the 3' sequence of the target DNA sequence to which the first primer of the first PCR primer pair is complementary; and the second primer of the second primer pair comprises a nucleotide sequence complementary to a 3' sequence of the target DNA sequence that is downstream of the 5' sequence of the target genomic DNA contained in the first primer. The skilled artisan will recognize that the sequences of the primer that are complementary to the target genomic DNA are selected based on the sequence of the target DNA. These primers may further comprise one or more recombination sites.

Upon contact of the nucleic acid molecule comprising the selectable marker, the first and second amplification products, and a topoisomerase (if the molecules are not topoisomerase-charged), a ds recombinant nucleic acid molecule covalently linked in both strands is generated according to a method of the invention. The generated ds recombinant nucleic acid molecule can be further amplified, if desired, using PCR primers that are specific for an upstream and downstream sequence of the target genomic DNA, thus ensuring that only functional constructs are amplified. The generated ds recombinant nucleic acid molecule is useful for performing homologous recombination in a genome, for example, to knock-out the function of a gene in a cell, or to confer a novel phenotype on the cell containing the generated recombinant nucleic acid molecule. The method can further be used to produce a transgenic non-human organism having the generated ds recombinant nucleic acid molecule stably maintained in its genome.

A method of the invention also is useful for covalently linking, an adapter or linker sequence to one or both ends of a nucleic acid molecule of interest, including to each of a plurality of nucleic acid molecules. For example, where it is desired to put linkers on both ends of a first nucleic acid molecule, the method can be performed by contacting a topoisomerase with a first nucleic acid molecule, which has a topoisomerase recognition site, or cleavage product thereof, at one or both 3' or 5' termini and which can include hydroxyl groups at both 5' termini and one or more recombination sites; and a second nucleic acid molecule and at least a third double stranded nucleotide sequence, each of which can include a topoisomerase recognition site, or cleavage product thereof at the appropriate 3' or 5' terminus and which can also include, where desirable, a 5' hydroxyl group at the same terminus and one or more recombination sites. An appropriate terminus is the terminus to which the linker is to be covalently linked in at least one strand to the first nucleotide sequence. In one embodiment, one or both linker sequences contain an overhanging sequence that is complementary to a sequence at the 5' terminus of the end of the first nucleic acid molecule to which the linker is to be covalently linked, thereby facilitating the initial association of the nucleotide sequences in the proper (predetermined) orientation (see, for example, FIG. 9 and Example 1.B). In performing such a method, the linker sequences comprising the second and at least third nucleotide sequence can be the same or different.

FIG. 14 shows one example of a process for preparing a nucleic acid molecule containing a topoisomerase (e.g., a type IA topoisomerase) bound to the 5' terminus of one end of the sequence, and wherein the same end further comprise a 3' overhang (see (4) in FIG. 14). In step A, a nucleotide sequence to be modified with topoisomerase is digested with a restriction enzyme that generates a “sticky” end. The restricted nucleotide sequence is then contacted in step B with a linear, single stranded nucleotide sequence which contains a topoisomerase attached the 5' terminus and a ligase (e.g., a DNA ligase such as T4 DNA ligase). The linear, single stranded nucleotide sequence also contains a region at the 3' terminus which shares sufficient sequence complementarity to the “sticky” end generated by the restriction enzyme, such that the two molecules will hybridize. Thus, in step B, the two nucleotide sequences are ligated to each other. In step C, the product of the second step is contacted with a third nucleotide sequence which shares sequence complementarity to portions of the linear, single stranded nucleic acid molecule generated in step B, and a ligase. The product of step C, shown in (4), is a nucleic acid molecule containing a topoisomerase attached to the 5' terminus of one end and a 3' overhang on the same end. It will be recognized that numerous variations of the exemplified method are within the scope of the invention. For example, similar processes can be performed to prepare nucleic acid molecules which comprise topoisomerase attached to the 3' terminus of one end or which have a 5' overhang or are blunt ended at the end to which a topoisomerase is attached. In another example, the nucleotide sequence labeled number 3 in FIG. 14 can be produced in the following manner: a nucleic acid molecule can be digested with a restriction enzyme to generate a nucleic acid molecule with a single-stranded 5' overhang that includes a type IA topoisomerase recognition site. The nucleic acid molecule with the single stranded overhang can then be contacted with type IA topoisomerase to generate a type IA topoisomerase-charged nucleic acid molecule.

FIG. 15 shows two embodiments of the invention in which single stranded or double stranded DNA is covalently linked to single stranded RNA. Where single stranded DNA is joined to single stranded RNA, the 3' end of the ribonucleotide sequence is covalently linked to the 5' end of the deoxyribonucleotide sequence. Where double stranded DNA is joined to single stranded RNA, the 3' terminus of the ribonucleotide sequence shares sufficient sequence complementarity to the 3' overhang of the deoxyribonucleotide sequence such that the two molecules hybridize. As above, the 3' end of the ribonucleotide sequence is also covalently linked to the 5' end of the deoxyribonucleotide sequence. As will be recognized, numerous variations of the above are within the scope of the invention. For example, the RNA molecule can be double stranded. In another example, all of the nucleotide sequences can be deoxyribonucleotide sequences and/or can comprise one or more recombination sites.

The present invention provides a ds recombinant nucleic acid molecule having, or which can be made to have, a first end and a second end, each end including a 5' terminus and a 3' terminus, wherein the molecule comprises a site-specific type IA topoisomerase recognition site at or near a 5' terminus of the first end, the second end, or both the first end and the second end. The ds recombinant nucleic acid molecule can further include a type IB topoisomerase recognition site at or near a 3' termini of an end that does not include a type IA topoisomerase recognition site. The ds recombinant nucleic acid molecule can be a vector.

The present invention further provides a topoisomerase-charged ds recombinant nucleic acid molecule having a first end and a second end, each end having a 5' terminus and a 3' terminus, wherein a site-specific type IA topoisomerase is bound at the 5' terminus of the first end, the second end, or both the first end and the second end. For example, the topoisomerase-charged ds recombinant nucleic acid molecule can include a type IA topoisomerase bound at the 5' termini of each of the first and second ends. The topoisomerase-charged nucleic acid ds recombinant nucleic acid molecule can include a type IB topoisomerase bound at a 3' termini of an end not bound by a type IA topoisomerase. The topoisomerase-charged ds recombinant nucleic acid molecule can be a vector.

Kits

The present invention also provides kits, which contain components useful for conveniently practicing the methods of the invention. In one embodiment, a kit of the invention contains a first nucleic acid molecule, which encodes a polypeptide, particularly a selectable marker, and contains a topoisomerase recognition site at each end. Preferably, the first nucleotide sequence comprises a topoisomerase-activated nucleotide sequence. More preferably, the topoisomerase-charged first nucleotide sequence comprises a 5' overhanging sequence at each end, and most preferably the 5' overhanging sequences are different from each other. Optionally, each of the 5' termini comprises a 5' hydroxyl group.

In addition, the kit can contain at least a nucleotide sequence (or complement thereof) comprising a regulatory element, which can be an upstream or downstream regulatory element, or other element, and which contains a topoisomerase recognition site at one or both ends. Preferably, the kit contains a plurality of nucleic acid molecules, each comprising a different regulatory element or other element, for example, a sequence encoding a tag or other detectable molecule or a cell compartmentalization domain. The different elements can be different types of a particular regulatory element, for example, constitutive promoters, inducible promoters and tissue specific promoters, or can be different types of elements including, for example, transcriptional and translational regulatory elements, epitope tags, and the like. Such nucleic acid molecules can be topoisomerase-activated, and can contain 5' overhangs or 3' overhangs that facilitate operatively covalently linking the elements in a predetermined orientation, particularly such that a polypeptide such as a selectable marker is expressible in vitro or in one or more cell types.

The kit also can contain primers, including first and second primers, such that a primer pair comprising a first and second primer can be selected and used to amplify a desired ds recombinant nucleic acid molecule covalently linked in one or both strands, generated using components of the kit. For example, the primers can include first primers that are complementary to elements that generally are positioned at the 5' end of a generated ds recombinant nucleic acid molecule, for example, a portion of a nucleic acid molecule comprising a promoter element, and second primers that are complementary to elements that generally are positioned at the 3' end of a generated ds recombinant nucleic acid molecule, for example, a portion of a nucleic acid molecule comprising a transcription termination site or encoding an epitope tag. Depending on the elements selected from the kit for generating a ds recombinant nucleic acid molecule covalently linked in both strands, the appropriate first and second primers can be selected and used to amplify a full length functional construct.

In another embodiment, a kit of the invention contains a plurality of different elements, each of which can comprise one or more recombination sites and/or can be topoisomerase-activated at one or both ends, and each of which can contain a 5' overhanging sequence or a 3' overhanging sequence or a combination thereof. The 5' or 3' overhanging sequences can be unique to a particular element, or can be common to plurality of related elements, for example, to a plurality of different promoter element. Preferably, the 5' overhanging sequences of elements are designed such that one or more elements can be operatively covalently linked to provide a useful function, for example, an element comprising a Kozak sequence and an element comprising a translation start site can have complementary 5' overhangs such that the elements can be operatively covalently linked according to a method of the invention.

The plurality of elements in the kit can comprise any elements, including transcription or translation regulatory elements; elements required for replication of a nucleotide sequence in a bacterial, insect, yeast, or mammalian host cell; elements comprising recognition sequences for site specific nucleic acid binding proteins such as restriction endonucleases or recombinases; elements encoding expressible products such as epitope tags or drug resistance genes; and the like. As such, a kit of the invention provides a convenient source of different elements that can be selected depending, for example, on the particular cells that a construct generated according to a method of the invention is to be introduced into or expressed in. The kit also can contain PCR primers, including first and second primers, which can be combined as described above to amplify a ds recombinant nucleic acid molecule covalently linked in one or both strands, generated using the elements of the kit. Optionally, the kit further contains a site specific topoisomerase in an amount useful for covalently linking in at least one strand, a first nucleic acid molecule comprising a topoisomerase recognition site to a second (or other) nucleic acid molecule, which can optionally be topoisomerase-activated nucleic acid molecules or nucleotide sequences that comprise a topoisomerase recognition site.

In still another embodiment, a kit of the invention contains a first nucleic acid molecule, which encodes a selectable marker, and contains a topoisomerase recognition site and/or a recombination site at each end; a first and second PCR primer pair, which can produce a first and second amplification products that can be covalently linked in one or both strands, to the first nucleic acid molecule in a predetermined orientation according to a method of the invention. Such a generated construct can be introduced into a cell and can incorporate into the genome of the cell by homologous recombination in a site specific manner, where it can be stably maintained and can express a heterologous polypeptide in the cell or can knock-out a target gene function. A target gene to be knocked-out, for example, can be any gene for which at least part of the sequence is known or can be readily determined and the function of which it is desired to disrupt, for example, an oncogene, a gene involved in apoptosis, a gene encoding a serine/threonine or a tyrosine kinase, or any other gene.

The first PCR primer pair in a kit of the invention useful for generating a ds recombinant nucleic acid molecule covalently linked in both strands, includes a first primer that comprises, in an orientation from 5' to 3', a nucleotide sequence complementary to a 5' overhanging sequence of a nucleic acid molecule to which it is to be covalently linked (for example, an end of the nucleic acid molecule encoding the selectable marker), a nucleotide sequence complementary to a topoisomerase recognition site, such that PCR introduces a functional recognition site in the opposite strand (see primer sequences in FIG. 9D), and/or a recombination site, and a nucleotide sequence complementary to a 3' sequence of the target DNA sequence. The first PCR primer pair also includes a second primer that comprises a nucleotide sequence of the target DNA sequence upstream of the 3' sequence to which the first primer is complementary.

The second PCR primer pair of a kit useful for generating a ds recombinant nucleic acid molecule covalently linked in both strands, includes a first primer that comprises, from 5' to 3', a nucleotide sequence complementary to a 5' overhanging sequence of a nucleic acid molecule to which it is to be covalently linked, a nucleotide sequence complementary to a topoisomerase recognition, such that PCR introduces a functional recognition site in the opposite strand (see primer sequences in FIG. 9D), site and/or a recombination site, and a nucleotide sequence of a 5' sequence of the target DNA sequence, wherein the 5' sequence of the target gene is downstream of the 3' sequence of the target DNA sequence to which the first primer of the first primer pair is complementary. The second PCR primer pair also includes a second primer that comprises a nucleotide sequence complementary to a 3' sequence of the target gene that is downstream of the 5' sequence of the target DNA sequence contained in the first primer.

In another embodiment, a kit of the invention useful for generating a ds recombinant nucleic acid molecule covalently linked in both strands contains a first nucleic acid molecule, which encodes a transcription activation domain and comprises a topoisomerase recognition site, or cleavage product thereof, at a 3' terminus; and a second nucleic acid molecule, which encodes a DNA binding domain and comprises a topoisomerase recognition site and/or a recombination site, or cleavage product thereof, at a 3' terminus. Upon cleavage by the site specific topoisomerase, the first or second nucleic acid molecule can have a 5' overhang, or both sequences can have 5' overhangs, which are the same or are different from each other. Where the nucleic acid molecules have a 5' overhang, the overhang generally is complementary to a nucleic acid molecule to which first or second nucleic acid molecule is to be covalently linked according to a method of the invention. The kit also can contain one or a pair of adapters, linkers or the like, which can comprise a topoisomerase recognition site, or cleavage product thereof, at one or both 3' termini, and, optionally, a hydroxyl group at the same terminus/termini. Such adapters, linkers, or the like are selected such that they contain a 5' overhang that is complementary to one or the other of the two nucleic acid molecules described above and part of the kit.

Similarly, a kit of the invention can contain one or a pair of adapters, linkers or the like, which comprise a topoisomerase recognition site and/or a recombination site, or cleavage product thereof, at one or both 5' termini, and, optionally, a hydroxyl group at the same terminus (or termini). Such adapters, linkers, or the like are selected such that they contain a 3' overhang that is complementary to one or the other of the two nucleic acid molecules described above and part of the kit. In addition, the kit can contain one or a pair of adapters, linkers or the like, which comprise a topoisomerase recognition site, or cleavage product thereof, at one or both 5' and/or 3' termini, and, optionally, a hydroxyl group at the same terminus/termini.

Adapters, linkers, or the like generally are selected such that they contain a 5' and/or a 3' overhang that is complementary to one or the other of the two nucleic acid molecules as disclosed herein and part of the kit. Such adapters, linkers, or the like can be joined to the ends of nucleic acid molecules that are to covalently linked to one or the other of the first or second nucleic acid molecules provided with the kit, thus facilitating the construction of chimeric polynucleotides encoding the bait and prey polypeptides useful in a two hybrid assay. Such a kit also can contain a PCR primer or primer pair, which can be used to prepare an amplified plurality of nucleotide sequences comprising a topoisomerase recognition site, or cleavage product thereof (see Example 1).

A PCR primer pair in a kit of the invention, which can be used for generating a ds recombinant nucleic acid molecule covalently linked in one strand, can include a first primer that comprises, in an orientation from 5' to 3', a nucleotide sequence of a 5' overhanging sequence of a nucleic acid molecule to which it is to be linked (for example, an end of the nucleic acid molecule encoding the selectable marker), a topoisomerase recognition site (e.g., a type IA or type II topoisomerase recognition site) and, optionally, a recombination site, and a nucleotide sequence complementary to a 5' sequence of the target DNA sequence. The PCR primer pair also includes a second primer that comprises a nucleotide sequence of the target DNA sequence downstream of the 5' sequence to which the first primer is complementary.

In another embodiment, a kit of the invention contains a first nucleic acid molecule, which encodes a transcription activation domain and comprises a site-specific topoisomerase recognition site (e.g., a type IA or a type II topoisomerase recognition site) and, optionally, a recombination site, or cleavage product thereof, at a 5' terminus; and a second nucleic acid molecule, which encodes a DNA binding domain and comprises a site-specific topoisomerase recognition site (e.g., a type IA or a type II topoisomerase recognition site), or cleavage product thereof, at a 5' terminus. Upon cleavage by the site specific topoisomerase, the first or second nucleic acid molecule can have a 3' overhang, or both sequences can have 3' overhangs, which are the same or are different from each other. Where the nucleic acid molecules have a 3' overhang, the overhang generally is complementary to a nucleic acid molecule to which first or second nucleic acid molecule is to be linked according to a method of the invention. The kit also can contain one or a pair of adapters, linkers or the like, which may comprise a site-specific topoisomerase recognition site (e.g., a type IA or a type II topoisomerase recognition site), a cleavage product thereof, and/or a recombination site, at one or both 5' and/or 3' termini and/or located internally, and which can contain a 5' overhang that is complementary to one or the other of the two nucleic acid molecules of the kit.

A ds recombinant nucleic acid molecule covalently linked in one or both strands, and generated according to a method of the invention, can be used for various purposes, including, for example, for expressing a polypeptide in a cell, for diagnosing or treating a pathologic condition, or the like. As such, the present invention provides a medicament, which can be useful for treating a pathologic condition by expressing a polypeptide in one or more cells or by expressing an antisense molecule, or the like. Such a ds recombinant nucleic acid molecule can be provided to a cell by contacting the cell ex vivo, then administering the cell to the subject, such a method also allowing for selection and/or expansion of the cells containing the ds recombinant nucleic acid molecule prior to such administration, or can be provided directly to the subject. For administration to a living subject, the ds recombinant nucleic acid molecule, which is covalently linked in one or both strands, generally is formulated in a composition suitable for administration to the subject. Thus, the invention provides compositions containing a ds recombinant nucleic acid molecule covalently linked in one or both strands, generated according to a method of the invention. As disclosed herein, such nucleic acid molecules are useful as medicaments for treating a subject suffering from a pathological condition.

A composition for administration generally is formulated using one or more pharmaceutically acceptable carriers as well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition, which can be, for example, orally or parenterally such as intravenously, and by injection, intubation, or other such method known in the art. A composition of the invention also can contain a second reagent such as a diagnostic reagent, nutritional substance, toxin, or therapeutic agent, for example, a cancer chemotherapeutic agent.

The ds recombinant nucleic acid molecule covalently linked in one or both strands, can be incorporated within an encapsulating material such as into an oil-in-water emulsion, a microemulsion, micelle, mixed micelle, liposome, microsphere or other polymer matrix (see, for example, Gregoriadis, *Liposome Technology*, Vol. I (CRC Press, Boca Raton, Fla. 1984); Fraley, et al., *Trends Biochem. Sci.*, 6:77 (1981), each of which is incorporated herein by reference). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395,619; and 5,225,212, each of which is incorporated herein by reference) are an example of such encapsulating materials particularly useful for preparing a pharmaceutical composition, and other "masked" liposomes similarly can be used, such liposomes extending the time that a nucleic acid molecule remains in the circulation. Cationic liposomes, for example, also can be modified with specific receptors or ligands (Morishita et al., *J. Clin. Invest.*, 91:2580–2585 (1993), which is incorporated herein by reference). The nucleic acid molecule also can be introduced into a cell by complexing it with an adenovirus-polylysine complex (see, for example, Michael et al., *J. Biol. Chem.* 268:6866–6869 (1993), which is incorporated herein by reference). Such compositions can be particularly useful for introducing a nucleic acid molecule into a cell in vivo or in vitro, including ex vivo, wherein the cell containing the nucleic acid molecule is administered back to the subject (see U.S. Pat. No. 5,399,346, which is incorporated herein by reference). A nucleic acid molecule generated according to a method of the invention also can be introduced into a cell using a biolistic method (see, for example, Sykes and Johnston, supra, 1999).

Host Cells

The invention also relates to host cells, or derivatives thereof, comprising one or more of the nucleic acid molecules or vectors of the invention, particularly those nucleic acid molecules and vectors described in detail herein. Representative host cells that may be used according to this aspect of the invention include, but are not limited to, bacterial cells, yeast cells, plant cells and animal cells, and derivatives thereof. Preferred bacterial host cells include *Escherichia* spp. cells (particularly *E. coli* cells and most particularly *E. coli* strains DH10B, Stbl2, DH5α, DB3, DB3.1 (preferably *E. coli* LIBRARY EFFICIENCY® DB3.1™ Competent Cells; Invitrogen Corporation, Carlsbad, Calif.), DB4, DB5, JDP682 and ccdA-over (see U.S. application Ser. No. 09/518,188, filed Mar. 2, 2000, and U.S. provisional Application No. 60/475,004, filed Jun. 3, 2003, by Louis Leong et al., entitled "Cells Resistant to Toxic Genes and Uses Thereof," the disclosures of which are incorporated by reference herein in their entireties); *Bacillus* spp. cells (particularly *B. subtilis* and *B. megaterium* cells); *Streptomyces* spp. cells; *Erwinia* spp. cells; *Klebsiella* spp. cells; *Serratia* spp. cells (particularly *S. marcessans* cells); *Pseudomonas* spp. cells (particularly *P. aeruginosa* cells); and *Salmonella* spp. cells (particularly *S. typhimurium* and *S. typhi* cells). Preferred animal host cells include insect cells (most particularly *Drosophila melanogaster* cells, *Spodoptera frugiperda* Sf9 and Sf21 cells and Trichoplusa High-Five cells), nematode cells (particularly *C. elegans* cells), avian cells, amphibian cells (particularly *Xenopus laevis* cells), reptilian cells, and mammalian cells (most particularly NIH3T3, CHO, COS, VERO, BHK and human cells). Preferred yeast host cells include *Saccharomyces cerevisiae* cells and *Pichia pastoris* cells. In addition, derivatives of such host cells are suitable for use in accordance with the present invention. These and other suitable host cells are available commercially, for example from Invitrogen Corporation (Carlsbad, Calif.), American Type Culture Collection (Manassas, Va.), and Agricultural Research Culture Collection (NRRL; Peoria, Ill.).

Methods for introducing the nucleic acid molecules and/or vectors of the invention into the host cells described herein, to produce host cells comprising one or more of the nucleic acid molecules and/or vectors of the invention, will be familiar to those of ordinary skill in the art. For instance, the nucleic acid molecules and/or vectors of the invention may be introduced into host cells using well known techniques of infection, transduction, electroporation, transfection, and transformation. The nucleic acid molecules and/or vectors of the invention may be introduced alone or in conjunction with other the nucleic acid molecules and/or vectors and/or proteins, peptides or RNAs. Alternatively, the nucleic acid molecules and/or vectors of the invention may be introduced into host cells as a precipitate, such as a calcium phosphate precipitate, or in a complex with a lipid. Electroporation also may be used to introduce the nucleic acid molecules and/or vectors of the invention into a host. Likewise, such molecules may be introduced into chemically competent cells such as *E. coli*. If the vector is a virus, it may be packaged in vitro or introduced into a packaging cell and the packaged virus may be transduced into cells. Hence, a wide variety of techniques suitable for introducing the nucleic acid molecules and/or vectors of the invention into cells in accordance with this aspect of the invention are well known and routine to those of skill in the art. Such techniques are reviewed at length, for example, in Sambrook, J., et al., Molecular Cloning, a Laboratory Manual, 2nd Ed., Cold Spring Harbor, N.Y.: Cold Spring Harbor Laboratory Press, pp. 16.30–16.55 (1989), Watson, J. D., et al., *Recombinant DNA,* 2nd Ed., New York: W.H. Freeman and Co., pp. 213–234 (1992), and Winnacker, E.-L., From Genes to Clones, New York: VCH Publishers (1987), which are illustrative of the many laboratory manuals that detail these techniques and which are incorporated by reference herein in their entireties for their relevant disclosures.

Polymerases

Polymerases for use in the invention include but are not limited to polymerases (DNA and RNA polymerases), and reverse transcriptases. DNA polymerases include, but are not limited to, *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (*Tli* or VENT™) DNA polymerase, *Pyrococcus furiosus* (Pfi) DNA polymerase, DEEPVENT™ DNA polymerase, *Pyrococcus woosii* (*Pwo*) DNA polymerase, Pyrococcus sp KOD2 (KOD) DNA polymerase, *Bacillus sterothermophilus* (*Bst*) DNA polymerase, *Bacillus caldophilus* (*Bca*) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, mycobacterium DNA polymerase (Mtb, Mlep), *E. coli* pol I DNA polymerase, T5 DNA polymerase, T7 DNA polymerase, and generally pol I type DNA polymerases and mutants, variants and derivatives thereof. RNA polymerases such as T3, T5, T7 and SP6 and mutants, variants and derivatives thereof may also be used in accordance with the invention.

The nucleic acid polymerases used in the present invention may be mesophilic or thermophilic, and are preferably thermophilic. Preferred mesophilic DNA polymerases include Pol I family of DNA polymerases (and their respective Klenow fragments) any of which may be isolated from organism such as *E. coli, H. influenzae, D. radiodurans, H. pylori*, C. aurantiacus, *R. prowazekii, T. pallidum*, Synechocystis sp., *B. subtilis, L. lactis, S. pneumoniae, M. tuberculosis, M. leprae, M. smegmatis*, Bacteriophage L5, phi-C31, T7, T3, T5, SP01, $SP_{02}$, mitochondrial from *S. cerevisiae* MIP-1, and eukaryotic *C. elegans*, and *D. melanogaster* (Astatke, M. et al., 1998, *J. Mol. Biol.* 278, 147–165), pol III type DNA polymerase isolated from any sources, and mutants, derivatives or variants thereof, and the like. Preferred thermostable DNA polymerases that may be used in the methods and compositions of the invention include Taq, Tne, Tma, Pfu, KOD, Tfl, Tth, Stoffel fragment, VENT™ and DEEPVENT™ DNA polymerases, and mutants, variants and derivatives thereof (U.S. Pat. No. 5,436,149; U.S. Pat. No. 4,889,818; U.S. Pat. No. 4,965,188; U.S. Pat. No. 5,079,352; U.S. Pat. No. 5,614,365; U.S. Pat. No. 5,374,553; U.S. Pat. No. 5,270,179; U.S. Pat. No. 5,047,342; U.S. Pat. No. 5,512,462; WO 92/06188; WO 92/06200; WO 96/10640; WO 97/09451; Barnes, W. M., Gene 112:29–35 (1992); Lawyer, F. C., et al., *PCR Meth. Appl.* 2:275–287 (1993); Flaman, J.-M, et al., *Nucl. Acids Res.* 22(15):3259–3260 (1994)).

Reverse transcriptases for use in this invention include any enzyme having reverse transcriptase activity. Such enzymes include, but are not limited to, retroviral reverse transcriptase, retrotransposon reverse transcriptase, hepatitis B reverse transcriptase, cauliflower mosaic virus reverse transcriptase, bacterial reverse transcriptase, *Tth* DNA polymerase, Taq DNA polymerase (Saiki, R. K., et al., *Science* 239:487–491 (1988); U.S. Pat. Nos. 4,889,818 and 4,965,188), Tne DNA polymerase (WO 96/10640 and WO 97/09451), Tma DNA polymerase (U.S. Pat. No. 5,374,553) and mutants, variants or derivatives thereof (see, e.g., WO 97/09451 and WO 98/47912). Preferred enzymes for use in the invention include those that have reduced, substantially reduced or eliminated RNase H activity. By an enzyme "substantially reduced in RNase H activity" is meant that the enzyme has less than about 20%, more preferably less than about 15%, 10% or 5%, and most preferably less than about 2%, of the RNase H activity of the corresponding wildtype or RNase $H^+$ enzyme such as wildtype Moloney Murine Leukemia Virus (M-MLV), Avian Myeloblastosis Virus (AMV) or Rous Sarcoma Virus (RSV) reverse transcriptases. The RNase H activity of any enzyme may be determined by a variety of assays, such as those described, for example, in U.S. Pat. No. 5,244,797, in Kotewicz, M. L., et al., *Nucl. Acids Res.* 16:265 (1988) and in Gerard, G. F., et al., *FOCUS* 14(5):91 (1992), the disclosures of all of which are fully incorporated herein by reference. Particularly preferred polypeptides for use in the invention include, but are not limited to, M-MLV $H^-$ reverse transcriptase, RSV $H^-$ reverse transcriptase, AMV $H^-$ reverse transcriptase, RAV (rous-associated virus) $H^-$ reverse transcriptase, MAV (myeloblastosis-associated virus) $H^-$ reverse transcriptase and HIV $H^-$ reverse transcriptase. (See U.S. Pat. No. 5,244,797 and WO 98/47912). It will be understood by one of ordinary skill, however, that any enzyme capable of producing a DNA molecule from a ribonucleic acid molecule (i.e., having reverse transcriptase activity) may be equivalently used in the compositions, methods and kits of the invention.

The enzymes having polymerase activity for use in the invention may be obtained commercially, for example from Invitrogen Corporation (Carlsbad, Calif.), Perkin-Elmer (Branchburg, N.J.), New England BioLabs (Beverly, Mass.) or Boehringer Mannheim Biochemicals (Indianapolis, Ind.). Enzymes having reverse transcriptase activity for use in the invention may be obtained commercially, for example from Invitrogen Corporation (Carlsbad, Calif.), Pharmacia (Piscataway, N.J.), Sigma (Saint Louis, Mo.) or Boehringer Mannheim Biochemicals (Indianapolis, Ind.). Alternatively, polymerases or reverse transcriptases having polymerase activity may be isolated from their natural viral or bacterial sources according to standard procedures for isolating and purifying natural proteins that are well-known to one of ordinary skill in the art (see, e.g., Houts, G. E., et al., *J. Virol.* 29:517 (1979)). In addition, such polymerases/reverse transcriptases may be prepared by recombinant DNA techniques that are familiar to one of ordinary skill in the art (see, e.g., Kotewicz, M. L., et al., *Nucl. Acids Res.* 16:265 (1988); U.S. Pat. No. 5,244,797; WO 98/47912; Soltis, D. A., and Skalka, A. M., Proc. Natl. Acad. Sci. USA 85:3372–3376 (1988)). Examples of enzymes having polymerase activity and reverse transcriptase activity may include any of those described in the present application.

Methods of Nucleic Acid Synthesis, Amplification and Sequencing

The present invention may be used in combination with any method involving the synthesis of nucleic acid molecules, such as DNA (including cDNA) and RNA molecules. Such methods include, but are not limited to, nucleic acid synthesis methods, nucleic acid amplification methods and nucleic acid sequencing methods. Such methods may be used to prepare molecules (e.g., starting molecules) used in the invention or to further manipulate molecules or vectors produced by the invention.

Nucleic acid synthesis methods according to this aspect of the invention may comprise one or more steps. For example, the invention provides a method for synthesizing a nucleic acid molecule comprising (a) mixing a nucleic acid template (e.g., a nucleic acid molecules or vectors of the invention) with one or more primers and one or more enzymes having polymerase or reverse transcriptase activity to form a mixture; and (b) incubating the mixture under conditions sufficient to make a first nucleic acid molecule complementary to all or a portion of the template. According to this aspect of the invention, the nucleic acid template may be a DNA molecule such as a cDNA molecule or library, or an RNA molecule such as a mRNA molecule. Conditions sufficient to allow synthesis such as pH, temperature, ionic strength, and incubation times may be optimized by those skilled in the art. If desired, recombination sites and/or topoisomerase recognition sites may be added to such synthesized molecules during or after the synthesis process (see for sample, U.S. patent application Ser. No. 09/177,387 filed Oct. 23, 1998 based on U.S. provisional patent application No. 60/065,930 filed Oct. 24, 1997).

In accordance with the invention, the target or template nucleic acid molecules or libraries may be prepared from nucleic acid molecules obtained from natural sources, such as a variety of cells, tissues, organs or organisms. Cells that may be used as sources of nucleic acid molecules may be prokaryotic (bacterial cells, including those of species of the genera *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium*, and *Streptomyces*) or eukaryotic (including fungi (especially yeast's), plants, protozoans and other parasites, and animals including insects (particularly *Drosophila* spp. cells), nematodes (particularly *Caenorhabditis elegans* cells), and mammals (particularly hurrian cells)).

Of course, other techniques of nucleic acid synthesis which may be advantageously used will be readily apparent to one of ordinary skill in the art.

In other aspects of the invention, the invention may be used in combination with methods for amplifying or sequencing nucleic acid molecules. Nucleic acid amplification methods according to this aspect of the invention may include the use of one or more polypeptides having reverse transcriptase activity, in methods generally known in the art as one-step (e.g., one-step RT-PCR) or two-step (e.g., two-step RT-PCR) reverse transcriptase-amplification reactions. For amplification of long nucleic acid molecules (i.e., greater than about 3–5 Kb in length), a combination of DNA polymerases may be used, as described in WO 98/06736 and WO 95/16028.

Amplification methods according to the invention may comprise one or more steps. For example, the invention provides a method for amplifying a nucleic acid molecule comprising (a) mixing one or more enzymes with polymerase activity with one or more nucleic acid templates; and (b) incubating the mixture under conditions sufficient to allow the enzyme with polymerase activity to amplify one or more nucleic acid molecules complementary to all or a portion of the templates. The invention also provides nucleic acid molecules amplified by such methods. If desired, recombination sites may be added to such amplified molecules during or after the amplification process (see for example, U.S. patent application Ser. No. 09/177,387 filed Oct. 23, 1998, based on U.S. provisional patent application No. 60/065,930 filed Oct. 24, 1997, the disclosures of which are incorporated herein by reference in their entireties).

General methods for amplification and analysis of nucleic acid molecules or fragments are well known to one of ordinary skill in the art (see, e.g., U.S. Pat. Nos. 4,683,195; 4,683,202; and 4,800,159; Innis, M. A., et al., eds., PCR Protocols: A Guide to Methods and Applications, San Diego, Calif.: Academic Press, Inc. (1990); Griffin, H. G., and Griffin, A. M., eds., PCR Technology: Current Innovations, Boca Raton, Fla.: CRC Press (1994)). For example, amplification methods which may be used in accordance with the present invention include PCR (U.S. Pat. Nos. 4,683,195 and 4,683,202), Strand Displacement Amplification (SDA; U.S. Pat. No. 5,455,166; EP 0 684 315), and Nucleic Acid Sequence-Based Amplification (NASBA; U.S. Pat. No. 5,409,818; EP 0 329 822).

Typically, these amplification methods comprise: (a) mixing one or more enzymes with polymerase activity with the nucleic acid sample in the presence of one or more primer sequences, and (b) amplifying the nucleic acid sample to generate a collection of amplified nucleic acid fragments, preferably by PCR or equivalent automated amplification technique.

Following amplification or synthesis by the methods of the present invention, the amplified or synthesized nucleic acid fragments may be isolated for further use or characterization. This step is usually accomplished by separation of the amplified or synthesized nucleic acid fragments by size or by any physical or biochemical means including gel electrophoresis, capillary electrophoresis, chromatography (including sizing, affinity and immunochromatography), density gradient centrifugation and immunoadsorption. Separation of nucleic acid fragments by gel electrophoresis is particularly preferred, as it provides a rapid and highly reproducible means of sensitive separation of a multitude of nucleic acid fragments, and permits direct, simultaneous comparison of the fragments in several samples of nucleic acids. One can extend this approach, in another preferred embodiment, to isolate and characterize these fragments or any nucleic acid fragment amplified or synthesized by the methods of the invention. Thus, the invention is also directed to isolated nucleic acid molecules produced by the amplification or synthesis methods of the invention.

In this embodiment, one or more of the amplified or synthesized nucleic acid fragments are removed from the gel which was used for identification (see above), according to standard techniques such as electroelution or physical excision. The isolated unique nucleic acid fragments may then be inserted into standard vectors, including expression vectors, suitable for transfection or transformation of a variety of prokaryotic (bacterial) or eukaryotic (yeast, plant or animal including human and other mammalian) cells. Alternatively, nucleic acid molecules produced by the methods of the invention may be further characterized, for example by sequencing (i.e., determining the nucleotide sequence of the nucleic acid fragments), by methods described below and others that are standard in the art (see, e.g., U.S. Pat. Nos. 4,962,022 and 5,498,523, which are directed to methods of DNA sequencing).

Nucleic acid sequencing methods according to the invention may comprise one or more steps. For example, the invention may be combined with a method for sequencing a nucleic acid molecule comprising (a) mixing an enzyme with polymerase activity with a nucleic acid molecule to be sequenced, one or more primers, one or more nucleotides, and one or more terminating agents (such as a dideoxynucleotides) to form a mixture; (b) incubating the mixture under conditions sufficient to synthesize a population of molecules complementary to all or a portion of the molecule to be sequenced; and (c) separating the population to determine the nucleotide sequence of all or a portion of the molecule to be sequenced.

Nucleic acid sequencing techniques which may be employed include dideoxy sequencing methods such as those disclosed in U.S. Pat. Nos. 4,962,022 and 5,498,523.

Kits

In another aspect, the invention provides kits which may be used in conjunction with the invention. Kits of the invention may contain any number of components but typically will contain at least two components. Kits according to this aspect of the invention may comprise one or more containers, which may contain one or more components selected from the group consisting of one or more nucleic acid molecules or vectors of the invention, one or more primers, the molecules and/or compounds of the invention, supports of the invention, one or more polymerases, one or more reverse transcriptases, one or more recombination proteins (or other enzymes for carrying out the methods of the invention), one or more topoisomerases, one or more buffers, one or more detergents, one or more restriction endonucleases, one or more nucleotides, one or more terminating agents (e.g., ddNTPs), one or more transfection reagents, pyrophosphatase, and the like. The kits of the invention may also comprise instructions for carrying out methods of the invention.

For example, a kit of the invention may comprise (1) a first nucleic acid molecule which comprises one or more (e.g., 1, 2, 3, 4, 5, 6, 7, 8, 9, 10, etc.) recombination sites and/or one or more (e.g., 1, 2, 3, 4, 5, 6, 7, 8, 9, 10, etc.) toposiomerase recognition sites and (2) instructions for covalently linking the first nucleic molecule to another nucleic acid molecule using methods described herein. In particular embodiments, the instructions describe methods for linking two or more nucleic molecules in either one or both strands. In a related embodiment, the first nucleic acid molecule is topoisomerase adapted prior to inclusion in the kit.

Additional kits of the invention can contain, for example, one or more topoisomerase-charged nucleic acid molecule substrates, which can include one or more control nucleic acid sequences which can be useful, for example, to test the accuracy or fidelity of the components of the kit; one or more topoisomerases; one or more compositions comprising one or more topoisomerases; one or more recombinases (or recombination proteins); one or more compositions comprising one or more recombinases (or recombination proteins); one or more primers, which can comprise at least one topoisomerase recognition site and/or at least one recombination site, a nucleotide sequence complementary to at least one topoisomerase recognition site and/or at least one recombination site, or both at least one topoisomerase recognition site and at least one nucleotide sequence complementary to at least one topoisomerase recognition site; one or more cells, which can contain or be useful for containing a nucleic acid molecule of the kit or generated using the kit; one or more reagents, polymers, buffers, or the like, for performing a method using the kit; instructions for performing a method using the kit; and the like.

In another aspect, a kit of the invention may contain a nucleic acid molecule having a first end and a second end, and encoding a polypeptide to be expressed, for example, a selectable marker, wherein the nucleic acid molecule comprises a topoisomerase recognition site or cleavage product thereof at the 3' terminus of one or both ends. Optionally, the nucleic acid molecule contains a hydroxyl group at the 5' terminus of one or both of the other ends, i.e., at the ends that do not contain a topoisomerase recognition site or that are not topoisomerase-charged. Further, one or both 5' termini may comprise overhanging sequences, which are different from each other. A kit of the invention also can contain a nucleic acid molecule having a first end and a second end, and encoding a polypeptide to be expressed, for example, a selectable marker, wherein the nucleic acid molecule comprises a topoisomerase recognition site or cleavage product thereof at the 5' terminus of one or both ends. Optionally, the nucleic acid molecule contains a hydroxyl group at the 3' terminus of one or both ends, and preferably, one or both 3' termini comprise overhanging sequences, which are different from each other. In addition, a kit of the invention can contain a nucleic acid molecule having a first end and a second end, and encoding a polypeptide to be expressed, for example, a selectable marker, wherein the nucleic acid molecule comprises a topoisomerase recognition site or cleavage product thereof at the 5' terminus and the 3' terminus of one or both ends. As such, it should be recognized that a kit of the invention can include any of various combinations of such nucleic acid molecules comprising one or more topoisomerase recognition sites or topoisomerase-charged nucleic acid molecules.

A kit of the invention also can contain a nucleic acid molecule comprising a regulatory element or other nucleotide sequence, for example, a coding sequence, and a topoisomerase recognition site and/or a recombination site, or cleavage product thereof, at a 3' terminus of at least a first end and, optionally, a hydroxyl group at the 5' terminus of an end containing the recognition site; or comprising a topoisomerase recognition site or cleavage product thereof at a 5' terminus of at least a first end, and, optionally, a hydroxyl group at the 3' terminus of the end containing the recognition site; or comprising a topoisomerase recognition site at the 5' terminus and 3' terminus of at least a first end. In certain embodiments, the kit may contain a variety of upstream regulatory elements, a variety of downstream regulatory elements, a variety of elements useful detecting or identifying a molecule containing the element, and combinations thereof. For example, the kit can contain a variety of gene promoter elements, which are active constitutively or inducibly and in a few or many different types of cells, elements that permit ribosome binding such as an internal ribosome entry site, an element encoding a Kozak sequence or an initiator methionine, or the like. In addition, or alternatively, the kit can contain a variety of downstream regulatory elements such a polyadenylation signal sequences, sequences that terminate transcription or translation, or the like. Similarly, the kit can contain elements encoding detectable markers such as epitope tags, or the like. In certain such aspects of the invention, the kit contains a variety of such elements, each of which contains at least one topoisomerase recognition site and/or at least one recombination site. In certain other such aspects, these elements may contain an overhanging sequence such that they can be operably covalently linked to each other or to a nucleic acid molecule encoding a polypeptide such as a selectable marker according to a method of the invention.

Optionally, the kit contains element specific primers, which can amplify a construct containing one of the variety of elements included in the kit. Where the kit contains such primers, the nucleic acid molecules comprising the regulatory or other element has a nucleotide sequence that can be specifically recognized by the primer and that results in extension of the primer through and including the regulatory element. In particular, the kit can contain element specific forward and reverse primers, which can be combined to produce a primer pair that amplifies, for example, a construct containing a particular 5' regulatory element and a particular 3' regulatory element of the kit. Such a primer pair can selectively amplify a desired functional covalently linked ds nucleic acid molecule generated according to a method of the invention, but does not amplify partial reaction products.

In another embodiment, a kit of the invention contains a first nucleic acid molecule, which has a first end and a second end, contains a topoisomerase recognition site, or cleavage product thereof, and/or a recombination site, at or near one or both 3' termini, and encodes a transcription activation domain; and a second nucleic acid molecule, which has a first end and a second end, contains a topoisomerase recognition site, or cleavage product thereof, at or near one or both 3' termini, and encodes a DNA binding domain; or contains a first nucleic acid molecule, which has a first end and a second end, contains a topoisomerase recognition site, or cleavage product thereof, and/or a recombination site, at or near one or both 5' termini, and encodes a transcription activation domain; and a second nucleic acid molecule, which has a first end and a second end, contains a topoisomerase recognition site, or cleavage product thereof, and/or a recombination site, at or near one or both 5' termini, and encodes a DNA binding domain. A kit of the invention also can contain a first nucleic acid molecule, which has a first end and a second end, and encodes a transcription activation domain, and a second nucleic acid molecule, which has a first end and a second end, and encodes a DNA binding domain, wherein at least the first nucleic acid molecule-or the second nucleic acid molecule contains a topoisomerase recognition site, or cleavage product thereof, at or near a 5' terminus and at or near 3' terminus of at least one end, and wherein the other ds nucleotide contains a 3' hydrdxyl and 5' hydroxyl at the end to be covalently linked to the end of the nucleic acid molecule comprising the recognition sites. Such a kit is useful, for example, for generating covalently linked ds recombinant nucleic acid molecules encoding chimeric polypeptides for performing a two hybrid assay. The kit can further contain a primer pair, which can amplify a nucleotide sequence to be operably linked to the first or second nucleic acid molecule, wherein at least one primer of the primer pair comprises a topoisomerase recognition site, a complement of a topoisomerase recognition site, or both. Preferably, an amplification product generated using such a primer pair contains, following cleavage by a site-specific topoisomerase, a 3' or 5' overhanging sequence that is complementary to the first or second nucleic acid molecule to which it is to be covalently linked. Such a kit can facilitate the generation of recombinant polynucleotides that comprise a first or second nucleotide sequence of the kit and encode a chimeric polypeptide useful for performing a two hybrid assay.

The present invention also relates to additional kits for carrying out the methods of the invention, and particularly for use in creating the product nucleic acid molecules of the invention. The invention also relates to kits for carrying out homologous recombination (particularly gene targeting) according to the methods of the invention. Such kits of the invention may also comprise further components for further manipulating the recombination site-containing molecules and/or compounds produced by the methods of the invention. The kits of the invention may comprise one or more nucleic acid molecules of the invention (particularly starting molecules comprising one or more recombination sites and optionally comprising one or more reactive functional moieties), one or more molecules and/or compounds of the invention, one or more supports of the invention and/or one or more vectors of the invention. Such kits may optionally comprise one or more additional components selected from the group consisting of one or more host cells or derivatives thereof, one or more nucleotides, one or more polymerases and/or reverse transcriptases, one or more suitable buffers, one or more primers, one or more terminating agents, one or more populations of molecules for creating combinatorial libraries and one or more combinatorial libraries.

In another embodiment, a kit of the invention contains a first nucleic acid molecule, which encodes a polypeptide, particularly a selectable marker, and contains a topoisomerase recognition site at each end. In certain preferred such embodiments, the first nucleic acid molecule is a circular molecule (for example, a plasmid, vector, etc.) and comprises at least one recombination site, and more preferably at least two recombination sites, flanking the one or more, preferably two or more, topoisomerase recognition sites on the molecule. Preferably, the first nucleotide sequence comprises a topoisomerase-activated nucleotide sequence. More preferably, the topoisomerase-charged first nucleotide sequence comprises a 5' overhanging sequence at each end, and most preferably the 5' overhanging sequences are different from each other. Optionally, each of the 5' termini comprises a 5' hydroxyl group.

Kits according to this aspect of the invention may also contain at least a nucleotide sequence comprising a regulatory element, which can be an upstream or downstream regulatory element, or other element, which contains one or more topoisomerase recognition sites and, optionally, contains one or more recombination sites at one or both ends. Preferably, the kit contains a plurality of nucleic acid molecules, each comprising a different regulatory element or other element, for example, a sequence encoding a tag or other detectable molecule or a cell compartmentalization domain. The different elements can be different types of a particular regulatory element, for example, constitutive or inducible promoters or tissue specific promoters, or can be different types of elements including, for example, transcriptional and translational regulatory elements, epitope tags, and the like. Such nucleic acid molecules can be topoisomerase-activated, and can contain 5' overhanging sequences that facilitate operably covalently linking the elements in a predetermined orientation, particularly such that a polypeptide such as a selectable marker is expressible in vitro or in one or more cell types.

Such kits also may contain primers, including first and second primers, such that a primer pair comprising a first and second primer can be selected and used to amplify a desired covalently linked ds recombinant nucleic acid molecule generated using components of the kit. For example, the primers can include first primers that are complementary to elements that generally are positioned at the 5' end of a generated ds recombinant nucleic acid molecule, for example, a portion of a nucleic acid molecule comprising a promoter element, and second primers that are complementary to elements that generally are positioned at the 3' end of a generated ds recombinant nucleic acid molecule, for example, a portion of a nucleic acid molecule comprising a transcription termination site or encoding an epitope tag. Depending on the elements selected from the kit for generating a covalently linked ds recombinant nucleic acid molecule, the appropriate first and second primers can be selected and used to amplify a full length functional construct.

In another embodiment, a kit of the invention contains a plurality of different elements, each of which can be topoisomerase-activated at one or both ends, and each of which can contain a 5' overhanging sequence. The 5' overhanging sequences can be unique to a particular element, or can be common to plurality of related elements, for example, to a plurality of different promoter element. Preferably, the 5' overhanging sequences of elements are designed such that one or more elements can be operably covalently linked to provide a useful function, for example, an element comprising a Kozak sequence and an element comprising a translation start site can have complementary 5' overhangs such that the elements can be operably covalently linked according to a method of the invention.

The plurality of elements in the kit can comprise any elements, including transcription or translation regulatory elements; elements required for replication of a nucleotide sequence in a bacterial, insect, yeast, or mammalian host cell; elements comprising recognition sequences for site specific nucleic acid binding proteins such as restriction endonucleases or recombinases; elements encoding expressible products such as epitope tags or drug resistance genes; and the like. As such, a kit of the invention provides a convenient source of different elements that can be selected depending, for example, on the particular cells that a construct generated according to a method of the invention is to be introduced into or expressed in. The kit also can contain PCR primers, including first and second primers, which can be combined as described above to amplify a covalently linked ds recombinant nucleic acid molecule generated using the elements of the kit. Optionally, the kit further contains one or more topoisomerases (e.g., one or more site-specific topoisomerases) and/or one or more recombinases (or recombination proteins) in an amount useful for covalently linking a first nucleic acid molecule comprising a topoisomerase recognition site to a second (or other) nucleic acid molecule, which can be topoisomerase-activated nucleic acid molecules or can be nucleotide sequences that comprise a topoisomerase recognition site.

In still another embodiment, a kit of the invention contains a first nucleic acid molecule, which encodes a selectable marker, and contains a topoisomerase recognition site at each end; a first and second PCR primer pair, which can produce a first and second amplification products that can be covalently linked to the first nucleic acid molecule in a predetermined orientation according to a method of the invention. Such a generated construct can be introduced into a cell and can incorporate into the genome of the cell by homologous recombination in a site specific manner, where it can be stably maintained and can express a heterologous polypeptide in the cell or can knock-out a target gene function. A target gene to be knocked-out, for example, can be any gene for which at least part of the sequence is known or can be readily determined and the function of which it is desired to disrupt, for example, an oncogene, a gene involved in apoptosis, a gene encoding a serine/threonine or a tyrosine kinase, or any other gene.

The first PCR primer pair in a kit of the invention includes a first primer that comprises, in an orientation from 5' to 3', a nucleotide sequence complementary to a 5' overhanging sequence of a nucleic acid molecule to which it is to be covalently linked (for example, an end of the nucleic acid molecule encoding the selectable marker), a nucleotide sequence complementary to a topoisomerase recognition site, such that PCR introduces a functional recognition site in the opposite strand (see primer sequences in FIG. 9D), and/or to a recombination site, and a nucleotide sequence complementary to a 3' sequence of the target DNA sequence. The first PCR primer pair also includes a second primer that comprises a nucleotide sequence of the target DNA sequence upstream of the 3' sequence to which the first primer is complementary.

The second PCR primer pair of a kit of the invention includes a first primer that comprises, from 5' to 3', a nucleotide sequence complementary to a 5' overhanging sequence of a nucleic acid molecule to which it is to be covalently linked, a nucleotide sequence complementary to a topoisomerase recognition site, such that PCR introduces a functional recognition site in the opposite strand (see primer sequences in FIG. 9D), and optionally, a nucleotide sequence complementary to a recombination site, and a nucleotide sequence of a 5' sequence of the target DNA sequence, wherein the 5' sequence of the target gene is downstream of the 3' sequence of the target DNA sequence to which the first primer of the first primer pair is complementary. The second PCR primer pair also includes a second primer that comprises a nucleotide sequence complementary to a 3' sequence of the target gene that is downstream of the 5' sequence of the target DNA sequence contained in the first primer.

In another embodiment, a kit of the invention contains a first nucleic acid molecule, which encodes a transcription activation domain and comprises a topoisomerase recognition site, or cleavage product thereof, at or near a 3' terminus; and a second nucleic acid molecule, which encodes a DNA binding domain and comprises a topoisomerase recognition site and optionally a recombination site, or cleavage product thereof, at or near a 3' terminus. Upon cleavage by the site specific topoisomerase, the first or second nucleic acid molecule can have a 5' overhang, or both sequences can have 5' overhangs, which are the same or are different from each other. Where the nucleic acid molecules have a 5' overhang, the overhang generally is complementary to a nucleic acid molecule to which first or second nucleic acid molecule is to be covalently linked according to a method of the invention.

The kit also can contain one or a pair of adapters, linkers or the like, which comprise a topoisomerase recognition site and, optionally, a recombination site, or cleavage product thereof, at one or both 3' termini, and, optionally, a hydroxyl group at the same terminus/termini. Such adapters, linkers, or the like are selected such that they contain a 5' overhang that is complementary to one or the other of the two nucleic acid molecules described above and part of the kit. Similarly, the kit also can contain one or a pair of adapters, linkers or the like, which comprise a topoisomerase recognition site and, optionally, a recombination site, or cleavage product thereof, at one or both 5' termini, and, optionally, a hydroxyl group at the same terminus/termini. Such adapters, linkers, or the like are selected such that they contain a 3' overhang that is complementary to one or the other of the two nucleic acid molecules described above and part of the kit. In addition, the kit can contain one or a pair of adapters, linkers or the like, which comprise a topoisomerase recognition site, or cleavage product thereof, at or near one or both 5' and/or 3' termini, and, optionally, a hydroxyl group at the same terminus/termini. Such adapters, linkers, or the like are selected such that they contain a 5' and/or a 3' overhang that is complementary to one or the other of the two nucleic acid molecules described above and part of the kit. Such adapters, linkers, or the like can be joined to the ends of nucleic acid molecules that are to covalently linked to one or the other of the first or second nucleic acid molecules provided with the kit, thus facilitating the construction of chimeric polynucleotides encoding the bait and prey polypeptides useful in a two hybrid assay. Such a kit also can contain a PCR primer or primer pair, which can be used to prepare an amplified plurality of nucleotide sequences comprising a topoisomerase recognition site, or cleavage product thereof. Additional kits according to this aspect of the invention may optionally comprise one or more additional components such as one or more topoisomerases, one or more recombination proteins, one or more vectors, one or more polypeptides having polymerase activity, and one or more host cells.

It will be understood by one of ordinary skill in the relevant arts that other suitable modifications and adaptations to the methods and applications described herein are readily apparent from the description of the invention contained herein in view of information known to the ordinarily skilled artisan, and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

EXAMPLE 1

Construction of Covalently Linked Double Stranded Recombinant Nucleic Acid Molecules Using Topoisomerase This example demonstrates that topoisomerase can be used to produce covalently linked double stranded (ds) recombinant nucleic acid molecules.

A. Methods

Except where indicated, studies were performed using the following methods. PCR was performed in 50 μl reactions, including 10 ng plasmid (template), 100 ng each primer, 2.5 Units Taq DNA polymerase (Sigma), 5 μl 10× PCR buffer, and 4 μl of dNTPs (200 μM each). An initial denaturation was performed by incubating the reaction at 94° C. for 4 min; followed by 30 cycles of PCR using 94° C. (45 sec) for denaturation, 55° C. (45 sec) for primer annealing and 72° C. (1 min per kb of target sequence) for extension. After cycling, the reactions were incubated at 72° C. (10 min), and then placed at 4° C.

Topoisomerase joining reactions were performed in 5 μl, including 50–100 ng each amplified element (PCR-generated or synthetic), 0.5 μl 500 mM Tris (pH 7.5), and 0.5 μg topoisomerase. Reactions were incubated at room temperature for 5 min, then 1–2 μl of the Topo-linked product was used for linear fragment generation.

Linear fragment generation by PCR was performed in 50 μl reactions, including 1–2 μl of the Topo-linked product (template), 100 ng each primer, 2.5 U Taq DNA polymerase (Sigma), 5 μl 10× PCR buffer, and 4 μl dNTPs (200 μM each). PCR was performed as described above.

The resultant linear fragment was purified using a SNAP Miniprep Kit (Invitrogen Corporation, Carlsbad, Calif.) as described by the manufacturer. Essentially, 100 μl PCR product was mixed with 300 μl Binding Buffer; 750 μl isopropanol, and the mixture was applied to a SNAP Miniprep Column/Collection Tube and centrifuged at 7,000 rpm for 30 sec. The column was washed with 700 μl Wash Buffer, centrifuged at 7,000 rpm for 30 sec; then washed with 900 μl 1× Final Wash and centrifuged at 7,000 rpm for 30 sec. The column was then centrifuged at 7,000 rpm for an additional 30 sec to remove all remaining liquid. Water (30 to 50 μl) was added and the column was centrifuged at 7,000 rpm for 30 sec to elute the purified DNA. DNA concentration was determined by spectrophotometry.

B. Generation of Topoisomerase Linked Linear Nucleic Acid Molecules

PCR primers were designed to examine the directional addition of elements to the coding sequence of green fluorescent protein (GFP; see FIG. 9A–C). The CMV promoter (approximately 700 bp) and BGH polyadenylation signal sequence (approximately 380 bp) were amplified from a pCMV/myc/nuc plasmid template, and the GFP element (approximately 700 bp) was amplified from a pcDNA3.1/GFP plasmid template (Invitrogen Corporation, Carlsbad, Calif.) using the primers indicated in FIG. 9D. The resultant amplification products were joined using topoisomerase as described above, and a portion of the ligation reaction was used as template for PCR with primers F6945 (SEQ ID NO: 11) and F6948 (SEQ ID NO: 15) to amplify the entire construct (CMV+GFP+BGH; approximately 1,700 bp). In addition, 5 μl of the ligation mixture was treated with proteinase K for 30 min at 37° C. to remove any bound topoisomerase, and then subjected to electrophoresis on a 3–8% NuPAGE Tris-acetate gel to examine the ligated products.

Only a small amount of ligation product of the correct size (1.7 kb) was observed when the recombinant nucleic acid molecules were generated using elements having palindromic overhanging sequence (FIG. 9A or 9B), whereas significant quantities of the desired product were generated using elements having non-palindromic overhangs (FIG. 9C). These results demonstrate that the efficiency of generating ds recombinant nucleic acid molecule covalently linked in both strands containing nucleotide sequences operatively linked in a predetermined orientation is related to the nature of the overhang sequence. In particular, the selection of overhanging sequences that lack palindromic regions result in the efficient generation of a desired ds recombinant nucleic acid molecule covalently linked in both strands, whereas the presence of palindromic sequences in the overhangs allows the formation of ligation products other than the intended product, thus decreasing the efficiency of generating a desired product.

EXAMPLE 2

Functional Characterization of Topoisomerase-generated ds Recombinant Nucleic Acid Molecules This example demonstrates that a method of the invention provides a means to generate functional ds recombinant nucleic acid molecules covalently linked in both strands.

A. Expression of Sense and Antisense mRNA from a Topo-Ligated Construct

The ability to create a ds recombinant nucleic acid molecule containing functional upstream and downstream elements flanking a gene of interest was examined using two synthetic elements containing either a T7 or a T3 promoter sequence. The elements were made by annealing pairs of synthetic oligonucleotides. The T7 linker was generated by mixing equal molar amounts of T7top (F9304; SEQ ID NO: 20) and T7bottom (F9305; SEQ ID NO: 21) oligonucleotides (FIG. 9D). The T3 linker was generated by mixing equal molar amounts of T3top (F9661; SEQ ID NO: 23) and T3bottom (F9662; SEQ ID NO: 24) oligonucleotides (FIG. 9D). The mixtures were heated in boiling water for 5 min, then allowed to cool to room temperature. Both elements were designed to contain a topoisomerase recognition site at one end.

The GFP gene was amplified with GFP primers F8418 (SEQ ID NO: 17) and F8420 (SEQ ID NO: 18, FIG. 9D; see, also, FIG. 9C). Unpurified GFP PCR product (2 μl) was mixed with 50 ng of T7 linker and 50 ng of T3 linker, topoisomerase was added, and the topo-joining reaction was allowed to proceed at room temperature for 5 min. Two μl of the joining reaction was used as template for a 50 μl PCR reaction with primers for the T7 and T3 sequences.

After amplification, a 4 μl aliquot of the PCR reaction was used as template for in vitro transcription. The reaction was performed using a Promega RiboProbe In Vitro Transcription Systems kit according to the manufacturer's instruction. The reaction was allowed to proceed for 60 min at 37° C. with T7 or T3 RNA polymerase (final volume, 20 μl). Aliquots of the in vitro transcription reactions were digested with RNase or DNase, then undigested and digested samples were subjected to electrophoresis in a 2% TBE gel. A predominant band of the predicted size (either sense or antisense orientation) was observed in the undigested samples. No decrease in the product band was noted in samples treated with DNase. The product bands disappeared when samples were treated with RNase indicating the product was RNA. These results demonstrate that topoisomerase can be used according to a method of the invention to generate a ds recombinant nucleic acid molecule covalently linked in both strands in a predetermined orientation, and that an RNA transcript can be expressed from such a nucleic acid molecule.

B. Expression of a Translation Product from a Topo-Ligated Construct

The ability of topoisomerase ligated polynucleotide to support coupled in vitro transcription/translation was examined. A ds recombinant nucleic acid molecule was generated according to a method of the invention by linking an element containing a T7 promoter (plus a Kozak sequence) to lacZ PCR products of 1 kb, 2 kb, or 3 kb. Two 2 μl of the generated products were used as template for PCR amplification reactions (primers, SEQ ID NOS: 25–28; FIG. 9D). Unpurified aliquots of the amplification reactions (3 μl) were used as templates for coupled transcription/translation with a TNT T7 Quick for PCR DNA Kit according to the manufacturer's instructions (Promega).

Two μl aliquots from each reaction were separated by electrophoresis on a Tris-glycine gel (Novex), then visualized by autoradiography, which revealed protein products that migrated at the expected sizes. These results demonstrate that a method of the invention can be used to produce a ds recombinant nucleic acid molecule covalently linked in both strands useful as a template for expressing a polypeptide by a coupled in vitro transcription/translation reaction.

C. Generation of Topo-ligated Constructs for Performing a Two Hybrid Assay

Two hybrid assays provide a powerful method for detecting protein-protein interactions in vivo. These assays are based on the fact that many eukaryotic transcriptional activators consist of two physically and functionally separable domains, including a DNA binding domain, which binds to a specific DNA sequence, and a transcriptional activation domain, which interacts with the basal transcriptional machinery. The association of a transactivation domain with a DNA binding domain can promote the assembly of a functional RNA polymerase II complex, thereby allowing transcriptional activation, for example, of a detectable reporter gene (Field and Song, *Nature* 340:245–246, 1989). Where a first protein, X, is fused to a DNA binding domain, for example, a GAL4 binding domain, and a second protein, Y, which can be the same or different from X, is fused into a transactivation domain, for example, a VP16 domain, an interaction of proteins X and Y can be identified by detecting transcription of a reporter gene having a GAL4 promoter.

The ability of a method of the invention to generate linear constructs for expressing fusion proteins for performing a mammalian two-hybrid assay was examined. PCR was used to generate GAL4 (F10779 and F12667 primers; SEQ ID NOS: 1 and 3, respectively), VP16 (F10779 and F12668 primers; SEQ ID NOS: 1 and 5, respectively), p53 (F12669 and F12505 primers; SEQ ID NOS: 8 and 4, respectively), T antigen (F12670 and F12505 primers; SEQ ID NOS: 9 and 4, respectively), and SV40pA (F12016 and F561 primers; SEQ ID NOS: 6 and 7, respectively) elements containing topoisomerase sites at the appropriate ends. Topoisomerase was used to create the covalently linked, double stranded constructs GAL4+p53+SV40pA and VP16+T antigen+

SV40pA, and the resultant ligation products were used as templates for PCR amplification.

Purified GAL4+p53+SV40pA and VP16+T antigen+SV40pA PCR constructs were co-transfected with a lacZ reporter gene (pGene/lacZ plasmid; Invitrogen Corporation, Carlsbad, Calif.) into CHO cells (6 well plate, $1\times10^5$ cells/well). In parallel studies, the use of plasmid vectors containing the expression constructs was examined, as was the use of PCR reaction mixtures containing the unpurified constructs. Control reactions were performed using GAL4+pA and VP16+pA without inserts (negative controls) or p53+VP16 (positive control). Cells were lysed 48 hr after transfection and reporter gene activity was measured using a beta-galactosidase assay kit.

A high level of reporter gene activity was detected with the positive control (FIG. 10, sample 3) and in the sample co-transfected with the reporter gene and the linear GAI4+p53+SV40pA and VP16+T antigen+SV40pA constructs (FIG. 10, sample 4). Low level activity (but greater than that of the negative controls; samples 5, 6, 8 and 9) was detected when the plasmid version of the constructs was used (FIG. 10, sample 1). Low level activity was also observed in the sample co-transfected with the unpurified, PCR-generated prey and bait constructs (sample 7). These results demonstrate that a method of the invention can be used to prepare constructs useful for performing a two hybrid assay.

EXAMPLE 3

Production and Use of Directionally Topo-Charged Gateway Vectors Introduction

As a combination of Topoisomerase and GATEWAY™ recombinational cloning technologies, directionally Topo-charged Gateway vectors were developed. These tools facilitate easy entry into the Gateway system by alleviating the necessity of adding attB sites (25 base pairs) to either side of a PCR amplified ORF prior to recombination into a Donor vector. Instead, a four base tag recognition sequence (CACC) is added to the 5' end of the ORF and PCR products are then directionally TOPO-cloned to create an Entry or a Gateway compatible expression vector (See FIG. 29).

In the present Example, three Topo-Gateway vectors and one Destination vector were created in all. Two topo entry vectors have been produced: (1) pENTR/D-TOPO® (FIG. 22), which allows ORFs directionally cloned between attL sites to be transferred to any of the N-terminal fusion prokaryotic and all of the eukaryotic DEST vectors; and (2) pENTR/SD/D-TOPO® (FIG. 23), which allows ORFs to be directionally topo cloned downstream of a prokaryotic ribosome binding site Shine-Dalgarno). Genes cloned in this manner can be transferred to prokaryotic DEST vectors without N-terminal tags and expressed in bacteria yielding proteins with native N-termini.

One directional Topo Gateway mammalian expression vector has also been constructed, pcDNA/GW-DT (FIG. 19). This vector allows directional cloning of an ORF into a pcDNA 3.1 derivative. ORFs cloned into this vector are expressed in mammalian cells under the control of the CMV promoter. Cloned ORFs are flanked by attB sites in the vector, allowing them to be moved around in the Gateway system via BP and LR Clonase reactions. This vector also encodes a C-terminal V5 tag, the TK poly adenylation signal, and the neomycin (G418) resistance marker for selection of stable clones in mammalian cell lines. Finally, a Gateway Destination vector was constructed from pcDNA/GW-DT by transferring the ccdB and chloramphenicol resistance cassettes.

These Topo Gateway Entry and Expression vectors improve the ease of entry into the Gateway system by allowing the researcher to directly clone a PCR amplified gene without the necessity of adding attB sites to the primers and performing a BP clonase reaction.

Materials and Methods

Construction of pcDNA/GW-DT. pcDNA/GW-DT was constructed by first replacing the multiple cloning site in pcDNA3.1attB (an early version with the BGH polyadenylation signal). This was done by digesting the parent vector with BsrG I (which cuts within each att site flanking the MCS) and inserting a double stranded oligonucleotide encoding the new MCS (FIG. 18). Once the proper insertion was confirmed, the V5/His tag and BGH polyadenylation signal were replaced with a V5 tag followed by three stop codons (TAG, TGA, TAA) and the thymidine kinase (TK) polyadenylation signal from Herpes Simplex Virus. This was accomplished by digesting the vector with AscI and AvrII, purification of the vector fragment, and inserting two fragments encoding the new sequences in a triple ligation (see FIG. 19). Construction of pcDNA-DEST 40. pcDNA-DEST 40 was created from pcDNA/GW-DT via a BP clonase reaction with pDONR221. pDONR221 was combined with pcDNAGW-DT(sc) and BP clonase (Invitrogen Corporation; Carlsbad, Calif.) in the appropriate buffer. The reaction was incubated according to the standard protocol and transformants selected for on Kanamycin plates. The product, a pcDNA destination vector containing attP sites flanking the ccdB, ccdA, and chloramphenicol resistance genes was selected on ampicillin/chloramphenicol containing media. In one alternative of this aspect of the invention, the chloramphenicol resistance gene in the cassette can be replaced by a spectinomycin resistance gene (see Hollingshead et al., *Plasmid* 13(1):17–30 (1985), NCBI accession no. X02340 M10241), and the Destination Vector can be selected on ampicillin/spectinomycin-containing media. It has recently been found that the use of spectinomycin selection instead of chloramphenicol selection results in an increase in the number of colonies obtained on selection plates, indicating that use of the spectinomycin resistance gene may lead to an increased efficiency of cloning from that observed using cassettes containing the chloramphenicol resistance gene.

Construction of pENTR/D-TOPO™ (sc). pDONOR221 was modified by adding an adaptation sequence cassette between the attP sites by BP recombination with pcDNA/GW-DT(sc) creating pENTR/D-TOPO® (sc) (FIG. 22). pDONR221 was combined with pcDNA/GW-DT (sc) and BP clonase in the appropriate buffer. The reaction was incubated according to the standard protocol except that DH10BsbcC cells were used for transformation and propagation of pENTR/D-TOPO® (sc). This cell line carries a mutation that allows maintenance of plasmids that carry hairpin structures (e.g. attL sites) that are in close proximity. This plasmid did not support growth of Top 10 cells in selective media.

Creation of pENTR/D-TOPO® and pENTR/SD/D-TOPO®. The vector pENTR/D-TOPO®(sc) was directionally topo charged by sequential digestion with Not I, Asc I, and Xho I followed by ligation with the directional topo adapters Topo-D71, -D72, -D75 and -D76 for pENTR/SD/D-TOPO® or Topo D-73, -D74, -D75, and -D76 for pENTR/D-TOPO® overnight at 15° C. (see FIG. 26). The adapted vectors were separated from free oligonucleotides by isopropanol precipitation at room temerature. The purified, adapted vector was topo charged by addition of the common annealing oligo Topo D-70, T4 Kinase, and recombinant *vaccinia* topoisomerase I. After incubation at 37° C. for 15 minutes, charged vector was purified either by agarose gel electrophoresis (NB JC-12, 2001-035, pg. 3) or chromatography on a 25 Q MacroPrep column (BioRad) (NB2000-0342, pg. 45). Directional topo cloning efficiency was assayed by incubation of 1 ng purified vector with 5 ng directional (CACC) 750 bp test insert for 5 minutes at room temperature. Top 10 chemically competent cells were then transformed with 2 ul of the cloning reaction and grown out on LB plates containing Kanamycin as antibiotic selection.

Topo-Gateway cloning and gene expression. To test the ability of these vectors to support Topo cloning, Gateway cloning and protein production, the gene encoding human HLA class I (accession No. D32129) was amplified by PCR with primers that incorporated the four base CACC tag at its 5' end immediately upstream of the ATG start codon. This PCR product was cloned into both pENTR/D-TOPO® and pENTR/SD/D-TOPO®. Ten clones from each HLA reaction were used in colony directional PCR reactions (d-PCR). In this study, clones were amplified with a T7 primer (binds 5' to the attL 1 site) and 129 reverse primer (specific for the 3' end of HLA).

In addition to the HLA gene, the gene for chloramphenicol acetyl transferase (CAT) was similarly amplified and cloned into the two entry vectors. After miniprep and digestion analysis, single clones from each reaction were isolated and sequenced using the M13 Forward and M13 Reverse primers. All entry clones were confirmed by sequencing and recombined by L/R Clonase reaction with pcDNA/GW DEST 40 (pENTR-D-TOPO® clones) or pET DEST 42 (pENTR/SD/D-TOPO® clones). Positive clones were confirmed by digestion with NcoI (site appears at the 5' end of directionally adapted ORFs, caCCATGG), and NotI (data not shown). The resulting pcDNA-DEST 40 (HLA and CAT) and pcDNA/GW-DT (HLA and CAT) constructs were then used to transfect COS cells. Cells were transfected using Lipofectamine 2000, 8 μg DNA and Optimem buffer. Reactions were applied to the cells for 5 hours then the media changed. After an overnight incubation at 37° C., the cells were harvested, lysed and run on a 4–20% Tris-Glycine gel using standard procedures. After electrophoresis, proteins were transferred to nitrocellulose membranes, blocked, and probed with V5-HRP antibody and ECL detection.

One positive clone from each pET DEST 42 reaction was used to transform BL21(DE3) cells and grown overnight in LB/Amp. The culture was then diluted 1:25 in the same medium and allowed to grow to O.D.(600 nm)=0.5 at which time expression of recombinant protein was induced by addition of IPTG to a final concentration of 1 mM. After the cultures were allowed to grow 3 hours at 37° C., cells were harvested by centrifigation. Aliquots of cell pellets were boiled in NuPage denaturing sample buffer, run on 4–12% NuPage polyacrylamide gels, and stained using SafeStain™ (Invitrogen Corporation, Carlsbad, Calif.). As a positive control for expression of test genes in the pET DEST 42 vector, the HLA and CAT genes were directly topo cloned into pET100 CAT and HLA (dTopo, no attB sites). These constructs were used to transfect BL21(DE3) *E. coli* cells, grown to log phase and induced with IPTG as described above.

Results and Discussion

Directional cloning efficiency of HLA and CAT clones in pENTR-dTopo and pENTR/SD-dTopo. Directional PCR reactions were designed to ensure that the HLA ORF cloned into pENTR/D-TOPO®" and pENTR/SD/D-TOPO® were in the correct orientation. Ten colonies were picked from each of the Topo cloning transformations and put directly into PCR reactions as described in "Materials and Methods." Eight of ten pENTR/SD-HLA clones tested were correctly oriented while nine of ten pENTR-HLA clones were correct. These tests were done with gel purified vector which had approximately 10–15% no insert background (data not shown).

Alternatively, restriction analysis of the CAT clones was done. Clones were isolated and the DNA digested with NcoI and AscI. One of the two NcoI sites in a correctly oriented CAT clone appears at the 5' end of each ORF as part of the Kozac directional adaptation sequence and the first two codons of the CAT gene (caCCATGG). AscI is present in the vector at the 3' end of the ORF. A correctly oriented clone will have two NcoI sites (one at the 5' end and one internal) and will yield 500 bp and 150 bp fragments after a double digest with Asc I. The CAT ORF encodes at its 3' end the sequence, CGCC, which is a one base pair mismatch to the optimum tag sequence. This close homology caused the CAT PCR product to directionally clone with only 50% efficiency (four of eight clones, data not shown).

Sequencing of Entry Clones. Each of the Entry clones chosen for recombination into DEST vectors and subsequent expression were sequenced from both ends to confirm that the adapters and ORFs ligated correctly. M13 forward and reverse primers were used and the reactions were sent to ResGen for sequencing on an ABI 3700 capillary sequencer. From these reactions a minimum of 600 bases of readable sequence were obtained. It is clear that there is some loss of signal as the reaction proceeds through the attL sites but significant signal remains after this point using this procedure (data not shown).

Expression of HLA and CAT in COS cells. Expression from pcDNA/GW/D-TOPO® and pcDNA-DEST 40 was tested by transfection of COS cells with HLA and CAT as the test gene in these constructs. Harvested lysates were probed for V5-tagged recombinant protein by Western blot using the V5 antibody. Data shown in FIG. 27 indicates that both the HLA and CAT genes express in these vectors whether the genes were cloned directly via Topo cloning (FIG. 27, lanes 3 and 6) or after LR clonase transfer from pENTR/D-TOPO® (FIG. 27, lanes 2 and 5).

Bacterial expression of HLA and CAT. The CAT and HLA genes cloned into pENTR/SD/D-TOPO® were transferred via LR Clonase reaction to pDEST-42 (pET, C-terminal V5/His). The results shown in FIG. 28 suggest that the CAT gene expressed in bacteria whether it is flanked by attB sites or not (FIG. 28, compare lanes 6 and 7). The finding that the CAT gene expresses well in *E. coli* after being transferred to a pET DEST vector from pENTR/SD/D-TOPO® validates the utility of this system for cloning and expressing ORFs using the Topo-Gateway system.

Interestingly, HLA cloned into pDEST 42 (flanked by attB sites) failed to express in BL21(DE3) cells in two independent studies (FIG. 28, lanes 3 and 4). As seen above, the HLA gene from the same Entry clone expressed well in COS cells when recombined into a mammalian DEST vector. Further, the fact that the pET system was unable to support expression of the HLA gene when it was flanked by attB sites suggests that there can be gene specific variations on expression using the Gateway system at least in bacteria. One factor that may be involved in this result is that HLA expressed from the control vector (pET 100 d-Topo) ran anomalously in the gel (30 kDa instead of the predicted 41 kDa). This human protein may not express well in bacteria in any case and the expression problem may be exacerbated by addition of attB sites.

In conclusion, we have described the construction and testing of two new Topo Gateway Entry vectors, one new Topo Gateway Expression vector and a new DEST vector that followed from that. In all, these new tools that combine the ease and efficiency of Topo cloning and the versatility of the Gateway system permit the cloning and expression of large numbers of genes in many different contexts with a minimum of expense and effort.

EXAMPLE 4

Alternative Methods of Topoisomerase Cloning

In one preferred alternative embodiment of the present invention, a TOPO SSS vector is made by first obtaining a commercially available cloning vector. One such vector is pUni/V5-His version A (Invitrogen Corporation, Carlsbad, Calif.), a circular supercoiled vector that contains uniquely designed elements. These elements include a BGH polyadenylation sequence to increase mRNA stability in eukaryotic hosts, a T7 transcription termination region, an R6Kg DNA replication origin and a kanamycin resistance gene and promoter for antibiotic resistance selection. Additionally, pUni/V5-His version A contains a multiple cloning site, which is a synthetic DNA sequence encoding a series of restriction endonuclease recognition sites. These sites are engineered for cloning of DNA into a vector at a specific position. Also within the vector's multiple cloning site is a loxP site inserted 5' to the endonuclease recognition sites thereby facilitating Cre recombinase-mediated fusion into a variety of other expression vectors, (Echo™ Cloning System, Invitrogen Corporation, Carlsbad, Calif.). An optional C-terminal V5 epitope tag is present for easy detection of expressed fusion proteins using an Anti-V5 Antibody. An optional C-terminus polyhistidine (6×His) tag is also present to enable rapid purification and detection of expressed proteins. A bacterial ribosomal binding site downstream from the loxP site makes transcription initiation in *E. coli* possible. Though this combination of elements is specific for pUni/V5-His version A cloning vector, many similar cloning and expression vectors are commercially available or may be assembled from sequences and by methods well known in the art. pUni/V5-His version A is a 2.2 kb double stranded plasmid.

Construction of a topoisomerase I charged cloning vector from pUni/V5-His version A is accomplished by endonuclease digestion of the vector, followed by complementary annealing of synthetic oligonucleotides and site-specific cleavage of the heteroduplex by *Vaccinia* topoisomerase I. SacI and EcoRI are two of the many restriction endonuclease sites present within the multiple cloning site of pUni/V5-His version A. Digestion of pUni/V5-His version A with the corresponding restriction enzymes, *Sac*I and EcoRI will leave cohesive ends on the vector (5'-AGCT-3' and 5'-AATT-3'). These enzymes are readily available from numerous vendors including New England Biolabs (Beverly, Mass., Catalogue Nos. R0156S, SacI and RO101S, EcoRI). The digested pUni/V5-His version A is easily separated from the digested fragments using isopropanol precipitation. These and other methods for digesting and isolating DNA are well known to those of ordinary skill in the art (Sambrook, J., Fritsch, E. F., and T. Maniatis. (1989) Molecular Cloning, A Laboratory Manual. Second edition. Cold Spring Harbor Laboratory Press. pp 5.28–5.32.)

The purified, digested vector is then incubated with two specific oligonucleotide adapters and T4 DNA ligase. The adapters are oligonucleotide duplexes containing ends that are compatible with the SacI and EcoRI ends of the vector. One of skill in the art will readily appreciate that other adapter oligonucleotides with appropriate sequences can be made for other vectors having different restriction sites. Following incubation with T4 DNA ligase, the vector containing the ligated adapters is purified using isopropanol. The adapter duplex that results from the annealing of TOPO D1 and TOPO D2 has a single-stranded Eco R1 overhang at one end and a 12-nucleotide single-stranded overhang at the other end.

The first adapter oligonucleotide, (TOPO D1), has complementation to the EcoRI cohesive end, 3'-TTAA-5'. Furthermore, TOPO D1 has an additional 24-bp including the topoisomerase consensus pentapyriridine element 5'-CCCTT located 16-bp upstream of the 3' end. The remaining sequence and size of TOPO D1 adapter oligo is variable, and may be modified to fit a researcher's particular needs. According to one such aspect of this preferred embodiment of the invention, 5'-AATTGAT CCCTTCACCGACATAGTACAG-3 (SEQ ID NO: 33) is the full sequence of the adapter used.

The second adapter oligonucleotide, (TOPO D2), must have full complementation to TOPO. D1. TOPO D2 complements directly 5' of the EcoRI cohesive flap, extending the bottom strand of the linearized vector. Additionally, TOPO D2 contains the sequence 3'-GTGG, which is the necessary SSS for directional cloning. In this embodiment, the SSS was chosen to complement the Kozak sequence known to help expression of ORFs in eukaryotic cells by increasing the efficiency of ribosome binding on the mRNA, however, sequence and length are highly variable to meet the specific needs of individual users. The complete sequence of TOPO D2 is 3-CTAGGGAAGTGG-5 (SEQ ID NO: 34). Similar to above, the adapter duplex that results from the annealing of oligonucleotides TOPO D4 and TOPO D5 has a single-stranded SacI overhang at one end, and a 12 nucleotide single-stranded overhang at the other end.

The third adapter oligonucleotide (TOPO D5), has complementation to the SacI cohesive end, 3'-TCGA-5'. Similar to TOPO D1, TOPO D5 has additional bases creating a single stranded overhang. The length and sequence can vary based on the needs of the user. In the current embodiment TOPO D5's sequence is 5'-AAGGGCGAGCT-3' (SEQ ID NO: 35).

The fourth adapter oligonucleotide (TOPO D4), has full complementation to TOPO D5, and complements directly 5' of the SacI cohesive flap extending the top strand of the linearized vector. TOPO D4 also contains the topoisomerase consensus sequence 5'-CCCTT. The remaining sequence and size of TOPO D4 adapter oligo is variable and may be modified to fit particular needs. In the current embodiment, the sequence of TOPO D4 is 3'-GACATGATACAG TTCCCGC-5' (SEQ ID NO: 36), which includes an additional 12 bp single stranded overhang.

These adapter oligonucleotides can be chemically synthesized using any of numerous techniques, including the phosphoramadite method, (Caruthers, M. H., Barone, A. D., Beaucage, S. L., Dodds, D. R., Fisher, E. F., McBride, L. J., Matteucci, M., Stabinsky, Z., and Tang, J. Y., (1987) Chemical Synthesis of Deoxyoligonucleotides, Methods Enzymol. 154: 287–313). This and other methods for the chemical synthesis of oligos are well known to those of ordinary skill in the art.

Complementary annealing of the purified digested vector and the adapter oligonucleotides is done by incubation of the DNA in the presence of T4 DNA ligase. Typical ligation reactions are performed by incubation of a cloning vector with suitable DNA fragments in the presence of ligase and an appropriate reaction buffer. Buffers for ligation reactions should contain ATP to provide energy to for the reaction, as well as, reducing reagents like dithiothreitol and pH stabilizers like Tris-HCl. The ratio of concentrations for the cloning vector and the DNA fragments are dependent on each individual reaction, and formulae for their determination are abundant in the literature, (See e.g. Protocols and Applications Guide (1991), Promega Corporation, Madison, Wis., p.45). T4 Ligase will catalyze the formation of a phosphodiester bond between adjacent 5'-phosphates and 3'-hydroxyl termini during the incubation. Cohesive end ligation can generally be accomplished in 30 minutes at 12–15° C., while blunt end ligation requires 4–16 hours at room temperature, (Ausubel, F. M., Brent, R., Kingston, R. E., Moore, D. D., Seidman, J. G., Smith, J. A., Struhl, K. (1992) Second Edition; Short Protocols in Molecular Biology, John Wiley & Sons, Inc., New York, N.Y., pp. 3.14–3.37), however parameter range varies for each study. In the current embodiment, purified, digested pUni/V5-His version A and the adapter oligos were incubated in the presence of T4 ligase and a suitable buffer for sixteen hours at 12.5° C. The resulting linearized and adapted vector comprises the purified cloning vector attached to the adapter oligonucleotides through base pair complementation and T4 ligase-catalyzed, phosphodiester bonds.

Efficient modification of the adapted vector with topoisomerase requires the addition of an annealing oligo to generate double, stranded DNA on TOPO D1's and TOPO D4's single stranded overhangs. Vaccinia topoisomerase I initially binds non-covalently to double stranded DNA. The enzyme then diffuses along the duplex until locating and covalently attaching to the consensus pentapyrimidine sequence 5'-CCCTT, forming the topoisomerase adapted complex (See Shuman et al., U.S. Pat. No. 5,766,891). Modification of the adapted vector takes place in the absence of DNA ligase to prevent the formation of phosphodiester bonds between the adapted vector and the annealing oligo, since phosphodiester bonds in the non-scissile strand will prevent the dissociation of the leaving group upon cleavage.

The annealing oligonucleotide (TOPO D3), must have complementation to the single stranded DNA overhangs of TOPO D1 and TOPO D4. In the current embodiment the overhangs both share the following sequence, 5'-GACATAGTACAG-3' (SEQ ID NO: 37). Therefore, TOPO D3 has the following sequence, 3-CTGTATCATGTCAAC-5 (SEQ ID NO: 38), which comprises full complementation to the adapter oligos' single stranded overhang and an additional 3 bp overhang, 3'-AAC-5'.

Incubation of the adapted vector with the annealing oligo in the presence of topoisomerase will create double stranded DNA to which topoisomerase can non-covalently bind. Bound topoisomerase will search the double stranded DNA by a facilitated diffusion mechanism, until the 5'-CCCTT recognition motif is located. Cleavage of the phosphodiester backbone of the scissile strand 3' of the motif is catalyzed via a nucleophilic attack on the 3' phosphorus atom of the preferred oligonucleotide cleavage sequence 5-CCCTT, resulting in covalent attachment of the DNA to the enzyme by a 3'-phosphotyrosyl linkage, (See Shuman, S., Kane, E. M., Morham, S. G. (1989) Proc. Natl. Acad. Sci. U.S.A. 86, 9793–9796). Cleavage of the scissile strand creates a double stranded leaving group comprising the 3' end adapter oligo, downstream from the 5'-CCCTT motif, and the annealing oligo TOPO D3. Although the leaving group can religate to the topoisomerase-modified end of the vector via 5' hydroxyl-mediated attack of the phosphotyrosyl linkage, this reaction is disfavored when the leaving group is no longer covalently attached to the vector. The addition of T4 polynucleotide kinase and ATP to the cleavage/religation reaction further shifts the equilibrium toward the accumulation of trapped topoisomerase since the kinase can phosphorylate the 5' hydroxyl of the leaving group to prevent the rejoining from taking place, (Ausubel, F. M., Brent, R., Kingston, R. E., Moore, D. D., Seidman, J. G., Smith, J. A., Struhl, K. (1992) Second Edition; Short Protocols in Molecular Biology, John Wiley & Sons, Inc., New York, N.Y., pp. 3.14–3.30). The resulting linearized vector comprises a blunt end from the TOPO D4/D3 leaving group and a SSS bearing end from the TOPO D1/D3 leaving group. Both of the linearized cloning vector's ends are charged with topoisomerase, enabling fast, efficient and directional topoisomerase mediated insertion of an acceptor molecule.

Although the above example details the modification of pUni/V5-His version A to form the topoisomerase-modified directional cloning vector, a person of ordinary skill in the art will appreciate how to apply these methods to any plasmid, cosmid, virus, or other DNA. It should also be noted that this example demonstrates a vector containing a 5' single-stranded overhang comprising the sequence 5'-GGTG-3', however the design of adapter duplexes and annealing oligonucleotides would allow one of skill in the art to custom design overhangs of any sequence or length at one or both ends of a given vector.

Specifically, any plasmid, cosmid, virus or other DNA can be modified to possess a SSS of any convenient sequence and length. These are the basic steps: the vector is first subjected to a treatment that is known to linearize the DNA. Common procedures include, but are not limited to, restriction digestion and treatment with topoisomerase II. Following linearization, a custom SSS is added. In the above example, complementary oligonucleotides are added to the sticky ends of a restriction digestion giving the desired SSS, however SSS forming oligonucleotides can be added by T4 blunt end ligation, as well. The SSS sequence is exposed by a topoisomerase I mediated, single strand nicking. In turn, this SSS can be used to directionally insert a PCR product comprising one or more complimentary SSS.

Likewise, topoisomerase modification can be applied to any double-stranded plasmid, cosmid, virus or other piece of DNA. Methods for the attachment of topoisomerase I to double stranded DNA are well known in the art, (See Shuman et al., U.S. Pat. No. 5,766,891). The strategic placement of topoisomerase on to a piece of double stranded DNA is determined by the incorporation of a topoisomerase I consensus sequence, (See Shuman et al., U.S. Pat. No. 5,766,891). The topoisomerase I will bind the double stranded DNA, nick the scissile strand thus revealing the predetermined single-stranded overhang sequence, and ligate the incoming PCR product in the correct, SSS mediated orientation.

EXAMPLE 5

Production of Custom Topoisomerase I-adapted Vectors

As an example of the application of this aspect of the current invention to another plasmid, pCR 2.1 (Invitrogen Corporation; Carlsbad, Calif.) was modified to create a topoisomerase I adapted vector with a custom single stranded sequence.

Plasmid pCR 2.1 is 3.9 kb T/A cloning vector. Within the sequence of this vector are many uniquely designed elements. These elements include an f1 origin, a ColE1 origin, a kanamycin resistance gene, an ampicillin resistance gene, a LacZ-alpha fragment and a multiple cloning sequence located within the LacZ-alpha fragment allowing for blue-white selection of recombinant plasmids. The multiple cloning sequence of pCR 2.1 contains; numerous restriction sites, including but not limited to, HindIII, SpeI and EcoRI; M13 forward and reverse primers and a T7 RNA polymerase promoter.

Construction of the topoisomerase I charged vector possessing a custom single stranded sequence consists of endonuclease digestion followed by complementary annealing of synthetic oligonucleotides and the site specific cleavage of the heteroduplex by *Vaccinia* topoisomerase I. Digestion of pCR 2.1 with the restriction enzymes HindIII, SpeI and EcoRI leaves HindIII and EcoRI cohesive ends on the vector. The dissociated fragment of pCR 2.1 downstream from the HindIII cleavage site is further cleaved with SpeI in order to reduce its size. By reducing the size of the fragment, the digested vector is easily purified away from the smaller digested pieces by isopropanol precipitation. These enzymes are readily available from numerous vendors including New England Biolabs, (Beverly, Mass., Catalogue Nos.; RO104S, HindIII; RO133S, SpeI; RO101S, EcoRI). Methods for the digestion and the isolation of DNA are well known to those skilled in the art, (Sambrook, J., Fritsch, E. F., and T. Maniatis. (1989) Molecular Cloning, A Laboratory Manual. Second edition. Cold Spring Harbor Laboratory Press. pp. 5.28–5.32.)

The purified digested vector is incubated with four adapter oligonucleotides and T4 DNA ligase. These adapter oligonucleotides are designed to have complementation to either the HindIII cohesive end, the EcoRI cohesive end, or to each other. Following incubation with T4 DNA ligase the adapted vector is purified using isopropanol.

The first adapter oligonucleotide, (TOPO H), has complementation to the HindIII cohesive end, 3'-TCGA-5'. Furthermore, TOPO H has an additional 24 bp including the topoisomerase consensus pentapyrimidine element 5'-CCCTT located 19-bp upstream of the 3' end. The remaining sequence and size of TOPO H adapter oligo is variable, and may be modified to fit a researcher=s particular needs. In the current embodiment 5'-AGCTCG CCCTTATTCCGATAGTG-3' (SEQ ID NO: 39) is the full sequence of the adapter used.

The second adapter oligonucleotide (TOPO 16), must have full complementation to TOPO H. TOPO 16 complements directly 5' of the HindIII cohesive end, extending the bottom strand of the linearized vector. Additionally, TOPO 16 contains the sequence 3'-TAAG, which is the chosen single stranded sequence for directional cloning. The complete sequence of TOPO 16 is 3'-GCGGGAATAAG-5' (SEQ ID NO: 40).

The third adapter oligonucleotide (TOPO 1), has complementation to the EcoRI cohesive end, 3'-TTAA-5'. Similar to TOPO H, TOPO 1 has additional bases containing the topoisomerase I consensus sequence CCCTT located 12 bp upstream of the 3' end. The length and sequence of TOPO 1 can vary based on the needs of the user. In the current embodiment TOPO 1's sequence is 5'-AATTCGCCCTTATTCCGATAGTG-3' (SEQ ID NO: 41).

The fourth adapter oligonucleotide (TOPO 2), has full complementation to TOPO 1, and complements directly 5' of the EcoRI cohesive end extending the top strand of the linearized vector. In the current embodiment, the sequence of TOPO 2 is 3'-GCGGGAA-5'.

Complementary annealing of the purified digested vector and the adapter oligonucleotides is done by incubation of the DNA in the presence of T4 DNA ligase. T4 Ligase will catalyze the formation of a phosphodiester bond between adjacent 5'-phosphates and 3'-hydroxyl termini during the incubation. In the current embodiment, purified, digested pCR 2.1 and the adapter oligos were incubated in the presence of T4 ligase and a suitable buffer for sixteen hours at 12.5° C. The resulting linearized and adapted vector comprises the purified cloning vector attached to the adapter oligonucleotides through base pair complementation and T4 ligase-catalyzed, phosphodiester bonds. Ligation techniques are abundant in the literature, (see Ausubel, F. M., et al, (1992) Second Edition; Short Protocols in Molecular Biology, John Wiley & Sons, Inc., New York, N.Y., pp. 3.14–3.37)

Charging of the adapted vector with topoisomerase requires the addition of annealing oligonucleotides to generate double stranded DNA on TOPO H's and TOPO1's single stranded overhangs. Charging of the adapted vector takes place in the absence of DNA ligase to prevent the formation of phosphodiester bonds between the adapted vector and the annealing oligo, since phosphodiester bonds in the non-scissile strand will prevent the dissociation of the leaving group upon cleavage.

The annealing oligonucleotide (TOPO 17), must have complementation to the single stranded DNA overhang of TOPO H. In the current embodiment the overhang has the following sequence, 5'-CGATAGTG-3'. Therefore, TOPO 17 has the following sequence, 3'-GCTATCAC-5', which comprises full complementation to the adapter oligo's single stranded overhang.

The annealing oligonucleotide (TOPO 3), must have complementation to the single stranded DNA overhang of TOPO 1. In the current embodiment the overhang has the following sequence, 3'-GTGATAGCCTTA-5' (SEQ ID NO: 42). Therefore, TOPO 3 has the following sequence, 5'-CAACACTATCGGAAT-3' (SEQ ID NO: 43), which comprises full complementation to the adapter oligo's single stranded overhang and an additional 3 bp overhang, 5'-CAA-3'.

Incubation of the adapted vector with the annealing oligo in the presence of topoisomerase will create double stranded DNA to which topoisomerase can non-covalently bind. Bound topoisomerase will search the double stranded DNA by a facilitated diffusion mechanism, until the 5'-CCCTT recognition motif is located. Cleavage of the phosphodiester backbone of the scissile strand 3' of the motif will result in the covalent attachment of the DNA to the enzyme by a 3'-phosphotyrosyl linkage, (See Shuman, S., et al (1989) Proc. Natl. Acad. Sci. U.S.A. 86, 9793–9796). Cleavage of the scissile strand creates a double stranded leaving group comprising the 3' end the adapter oligos, downstream from the 5'-CCCTT motif, and the complementary annealing oligonucleotide. The leaving group can religate to the topoisomerase adapted vector through its 5' hydroxyl's attack of the phosphotyrosyl linkage, also catalyzed by topoisomerase. Addition of T4 polynucleotide kinase to the equilibrium reaction prevents the back reaction via the kinase-mediated phosphorylation of the leaving group's 5' hydroxyl, (Ausubel, F. M., et al (1992) Second Edition; Short Protocols in Molecular Biology, John Wiley & Sons, Inc., New York, N.Y., pp. 3.14–3.30). The resulting linearized vector comprises a blunt end from the TOPO 1/3 leaving group and a single stranded sequence end from the TOPO H/17 leaving group. Both of the linearized cloning vector's ends are charged with topoisomerase, enabling fast, efficient and directional topoisomerase mediated insertion of an acceptor molecule.

EXAMPLE 6

Directional Cloning Using Topoisomerase

This aspect of the invention also provides a method for directional cloning of DNA. In such methods, the TOPO SSS vector constructed from pUni/V5-His version A was used for the directional insertion of ORFs from the GeneStorm Expression Ready Clones (Invitrogen Corporation, Carlsbad, Calif.). The modified pUni vector was selected for the cloning of these ORF's because the single strand added to the vector has homology to the Kozak sequence known to enhance ORF expression. Note, however, that, as before, any plasmid, cosmid, virus or other DNA could be modified to possess the necessary single stranded sequence. Likewise, any DNA fragment could be modified to possess a homologous sequence to any vector SSS. As a point of interest, the sequence of the SSS can effect directional cloning efficiencies. For example, SSSs with low GC content will have lower annealing stability, also SSSs that have high complementation to both ends of a DNA fragment to be cloned will loose the capability to direct these DNA inserts. Thus the sequence of a SSS should be carefully designed to avoid these and similar problems.

This aspect of the present invention is particularly useful in the directional insertion of PCR products into vectors constructed according to the present invention. In the PCR amplification of the desired insert, the PCR primers are designed so as to complement identified sequences of the insert(s) that are to be directionally cloned into the TOPO SSS vector. The primer designed to bind upstream of the DNA's coding strand is modified with an additional vector SSS complementation sequence on its 5' end. The resulting PCR product will possess a complementary sequence allowing SSS mediated directional insertion into the TOPO SSS cloning vector and subsequent expression of the product.

One such embodiment comprises introducing to a donor duplex DNA substrate a SSS site by PCR amplifying the donor duplex DNA molecule with the 5' oligonucleotide primer containing the SSS. PCR amplification of a region of DNA is achieved by designing oligonucleotide primers that complement a known area outside of the desired region. In a preferred embodiment the primer that has homology to the coding strand of the double stranded region of DNA will possess an additional sequence of nucleotides complementary to the SSS of the TOPO SSS cloning vector.

Using the current invention in a high throughput format, we selected 82 known ORFs from the GeneStorm expression system (Invitrogen Corporation, Carlsbad, Calif.) for directional cloning into the TOPO SSS vector, however, any sequence of DNA may be selected as desired by individual users. For each of these ORFs, primers are designed with homology to the coding and the non-coding strands. To clone PCR products in a directional fashion into the modified pUni/V5-His version A TOPO SSS vector as described in Example 4, one primer of a given pair was modified to contain the nucleotide sequence complementary to the SSS contained within the vector. In the current example, the coding primer contained the added sequence 5'-CACC-3', which complements the 'SSS', 3'-GTGG-5', of the TOPO SSS cloning vector. PCR amplification of the above ORFs with their respective primers will produce double stranded DNA fragments, which possess the SSS at their 5' end. We used Pfu polymerase in our PCR amplification, but it is well-known that PCR reactions can be performed with either a non-thermophillic polymerase such as Pfu or with a thermophillic polymerase like Taq followed by a blunting step to remove the non-template nucleotide these enzymes leave at the end of PCR products.

In the present example, 0.1 μg of each primer was combined with 0.05 μg of DNA containing an ORF in a PCR reaction mix totaling 50 μl total volume. Besides the primers and vector, the reaction mix also contained water, PCR buffer salts, 10mM dNTPs and 1.25 units of Pfu polymerase. Thermal cycling temperatures were as follows: an initial 94° C. denaturation; followed by 25 repetitions of 94° C. denaturation, 55° C. primer annealing, and 72° C. elongation, each at one minute; and ended with a 72° C., fifteen minute elongation. These parameters will vary with each DNA fragment to be amplified, and can be optimized for fragments of varying lengths and composition using methods well known to those of ordinary skill in the art (Ausubel, F. M., Brent, R., Kingston, R. E., Moore, D. D., Seidman, J. G., Smith, J. A., Struhl, K. (1992) Second Edition; Short Protocols in Molecular Biology, John Wiley & Sons, Inc., New York, N.Y., pp. 15.3–15.4). Techniques for the conversion of 3' overhangs to blunt end termini will also be familiar to those of ordinary skill in the art (Protocols and Applications Guide (1991), Promega Corporation, Madison, Wis., pp.43–44).

Incubation of the PCR amplified donor duplex DNA containing the SSS complementary sequence with the modified pUni/V5-His version A TOPO SSS vector results in the directional cloning of the donor DNA. For example, the eighty-two ORFs from the GeneStorm clone collection (Invitrogen Corporation, Carlsbad, Calif.) were amplified using SSS adapted primers. Amplification of the 82 GeneStorm ORFs with the described modified primer pairs resulted in PCR products that had the SSS complementary sequence at their 5' end. This ORF PCR product is combined with 10 ng of TOPO SSS cloning vector in either sterile water or a salt solution. The reaction is mixed gently and incubated for 5 minutes at room temperature (22–23° C.). After five minutes, we placed the reaction on ice then proceeded to the OneShot® Chemical Transformation or Electroporation (Invitrogen Corporation, Carlsbad, Calif., Catalogue Nos. C4040-10 and C4040-50, respectively) (Invitrogen TOPO Cloning Protocol. Invitrogen Corporation Carlsbad, Calif.). Topoisomerase had joined the adjacent strands of the vector and the product by catalyzing a rejoining reaction (FIG. 29). DNA fragments constructed with the SSS at their 5' ends were thus correctly inserted into TOPO SSS cloning vectors with a high efficiency.

Directional insertion of DNA fragments containing 5' SSS occurs with greater than 90% efficiency as shown by sequencing multiple colonies of transformed host cells. In the current example, the TOPO SSS cloning vectors containing the GeneStorm ORFs were incubated with transformation competent *E. coli* host cells. In 74 of the transformation reactions, the directional cloning of the ORFs into the TOPO SSS cloning vector occurred in at least seven of the eight colonies picked, and 59 of these cloning reactions were directional in all eight colonies picked. The overall directional cloning score was 609 of 656, thus, directional insertion was present in over 93% of the clones picked (see Table 5).

TABLE 5

| Directional Cloning of ORFs using a TOPO SSS Cloning Vector | |
|---|---|
| Positive colonies. dPCR reactions | Clones tested |
| 8/8 | 59 |
| 7/8 | 15 |
| 6/8 | 2 |
| 5/8 | 1 |
| 4/8 | 3 |
| 3/8 | 2 |

EXAMPLE 7

Directional Cloning of a Reporter Gene

In a similar example, using the above described modified pCR2.1 TOPO SSS vector, a PCR-generated ORF encoding the gene encoding the reporter molecule Green Fluorescent Protein (GFP) was directionally cloned in frame with the lacZ a fragment present in the vector. The primers used to amplify the GFP gene contained the requisite SSS complementation sequence 5'-ATTC-3', and the known sequence for translation initiating methionine, 5'-ATG-3'. Using the necessary cloning steps noted above, the PCR amplified GFP was inserted into the vector and transformed cells were grown on solid Agar plates. Glowing colonies represented a correctly inserted PCR product (see Table 6).

TABLE 6

In-frame and Directional Insertion of GFP Into Modified pCR2.1 TOPO SSS Cloning Vector.

| 5' sequence of PCR Product | Percentage of Correct Inserts | Total White Colonies |
|---|---|---|
| 5'-ATTCATG-3' (homologous) | 86% | 457 |
| 5'-CAAGATG-3' (non-homologous) | 35% | 118 |
| 5'-ATTCGGATG-3' (frame shift) | 0% | 268 |
| VECTOR ONLY | 0% | 31 |

These data represent a substantial improvement over the current state of the art in cloning, and furthermore present an invention in cloning that is highly compatible with high throughput techniques. Given directional cloning efficiencies greater than 90%, a user need only screen two colonies for each cloned DNA fragment. Thus, on a 96-well plate, 48 separate clones can be screened for directional insertion, 400% more than current cloning techniques. Use of this invention will streamline many high-throughput-gene-expression operations, and allow them to be run at a fraction of their current costs.

EXAMPLE 8

Directional Topoisomerase Cloning of Blunt-End PCR Products into Entry Vectors

Overview

In additional embodiments, the compositions, kits and methods of the invention combine a highly efficient, 5-minute cloning strategy ("TOPO® Cloning;" Invitrogen Corporation, Carlsbad, Calif.) to directionally clone blunt-end PCR products into vectors for entry into the recombinational cloning system of the invention (e.g., the GATEWAY™ System available from Invitrogen Corporation, Carlsbad, Calif.). Using this cloning strategy of the invention, blunt-end PCR products clone directionally at greater than 90% efficiency, with no ligase, post-PCR procedures, or restriction enzymes required.

For optimal expression of a PCR product after recombination with the GATEWAY™ destination vector of interest, any suitable expression vector may be used. Examples include, but are not limited to, the pENTR Directional TOPO® vectors available commercially (Invitrogen Corporation; Carlsbad, Calif.), which have a number of benefits including the following:

Vector Benefits pENTR/D-TOPO® For efficient expression of a gene of interest after recombination with a GATEWAY™ destination vector pENTR/SD/D-TOPO® Contains a T7 gene 10 translational enhancer and a ribosome binding site for optimal expression of native protein after recombination with a prokaryotic GATEWAY™ destination vector Also suitable for efficient expression of a gene of interest in other host cell systems (e.g., mammalian, insect, yeast) after recombination with a suitable GATEWAY™ destination vector These pENTR/D-TOPO® and pENTR/SD/D-TOPO® vectors are designed to facilitate rapid, directional TOPO® Cloning of blunt-end PCR products for entry into the GATEWAY™ System. Features of these vectors include:

attL1 and attL2 sites for site-specific recombination of the entry clone with a GATEWAY™ destination vector;

Directional TOPO® Cloning site for rapid and efficient directional cloning of blunt-end PCR products;

rrnB transcription termination sequences to prevent basal expression of the PCR product of interest in *E coli;*

Kanamycin resistance gene for selection in *E. coli;* pUC origin for high-copy replication and maintenance of the plasmid in *E. coli*; and T7 gene 10 translation enhancer and ribosome binding site for efficient translation of the PCR product in prokaryotic systems (pENTR/SD/D-TOPO® only).

Using these pENTR Directional TOPO® vectors in conjunction with the GATEWAY™ recombinational cloning system of the invention, genes of interest contained in blunt-end PCR products may be readily expressed by following several simple steps:

1. the blunt-end PCR product is cloned (using topoisomerase in the "TOPO® Cloning" procedures described herein) into one of the pENTR TOPO® vectors described above, to generate an entry clone;
2. an expression construct is generated by performing a recombination reaction between this entry clone and a GATEWAY™ destination vector of choice (such as those described elsewhere herein); and
3. the expression construct is introduced into an appropriate host cell (e.g., a bacterial, mammalian, yeast, insect, or other appropriate host cell, the choice depending on the specific destination vector chosen for production of the expression construct above), and the recombinant protein encoded by the gene of interest on the PCR product (and now contained on the expression construct) is expressed using expression conditions appropriate for the particular host cell system.

Directional TOPO® Cloning

Topoisomerase I from *Vaccinia* virus binds to duplex DNA at specific sites (CCCTT) and cleaves the phosphodiester backbone in one strand (Shuman, 1991). The energy from the broken phosphodiester backbone is conserved by formation of a covalent bond between the 3' phosphate of the cleaved strand and a tyrosyl residue (Tyr-274) of topoisomerase I. The phospho-tyrosyl bond between the DNA and enzyme can subsequently be attacked by the 5' hydroxyl of the original cleaved strand, reversing the reaction and releasing topoisomerase (Shuman, 1994). TOPO® Cloning exploits this reaction to efficiently clone PCR products.

Directional joining of double-stranded DNA using TOPO®-charged oligonucleotides occurs by adding a 3' single-stranded end (overhang) to the incoming DNA (Cheng and Shuman, 2000). This single-stranded overhang is identical to the 5' end of the TOPO®-charged DNA fragment. By the present invention, this approach has been modified by adding a 4 nucleotide overhang sequence to the TOPO®-charged DNA and adapting it to a "whole vector" format.

In this system, PCR products are directionally cloned by adding four bases to the forward primer (CACC). The overhang in the cloning vector (GTGG) invades the 5' end of the PCR product, anneals to the added bases, and stabilizes the PCR product in the correct orientation. Inserts can be cloned in the correct orientation with efficiencies equal to or greater than 90%.

Methods

Designing PCR Primers. The design of the PCR primers to amplify a gene of interest is critical for expression. Depending on the pENTR TOPO® vector being used, several considerations must be kept in mind during design of PCR primers, including:

- the sequences required to facilitate directional cloning;
- the sequences required for proper translation initiation of the PCR product; and
- whether or not the PCR product is to be fused in frame with an N- or C-terminal tag after recombination of the entry clone with a GATEWAY™ destination vector.

Guidelines to Design the Forward PCR Primer. When designing the forward PCR primer, the following points must be considered.

To enable directional cloning, the forward PCR primer MUST contain the sequence, CACC, at the 5' end of the primer. The four nucleotides, CACC, base pair with the overhang sequence, GTGG, in each pENTR TOPO® vector.

If the PCR product is to be expressed in mammalian cells (following recombination of the entry clone with a GATEWAY™ destination vector), the sequence of interest must include a Kozak translation initiation sequence with an ATG initiation codon for proper initiation of translation (Kozak, 1987; Kozak, 1991; Kozak, 1990). An example of a Kozak consensus sequence is (G/A)NNATGG. Other sequences are possible, but the G or A at position −3 and the G at position +4 are the most critical for function (shown in bold). The ATG initiation codon is shown underlined. Note: If the sequence of interest does not contain an initiation codon within the context of a Kozak sequence, the forward PCR primer may be designed so as to contain a Kozak sequence at the 5' end of the primer (see below).

If the PCR product is to be expressed in prokaryotic cells without an N-terminal fusion tag (following recombination of the entry clone with a GATEWAY™—destination vector), the PCR product should be TOPO® Cloned into a pENTR/SD/D-TOPO® entry vector. As noted above, pENTR/SD/D-TOPO® contains a T7 gene 10 translational enhancer and a ribosome binding site (RBS) to enable efficient translation of the PCR product in *E. coli*. To ensure optimal spacing for proper translation, the forward PCR primer should be designed such that that the ATG initiation codon of the PCR product directly follows the CACC necessary for directional cloning (see below).

Example of Forward Primer Design. Below is the DNA sequence of the N-terminus of a theoretical protein and the proposed sequence for a corresponding forward PCR primer. The ATG initiation codon is underlined.

```
DNA sequences:,               5'-ATG GGA TCT GAT AAA

Proposed Forward PCR primer:  5'-CACC ATG GGA TCT GAT AAA
```

If the forward PCR primer is designed as noted above, then (a) the ATG initiation codon falls within the context of a Kozak sequence (see boxed sequence), allowing proper translation initiation of the PCR product in mammalian cells (note that the first three base pairs of the PCR product following the 5' CACC overhang will constitute a functional codon); and (b) the ATG initiation codon is properly spaced from the RBS (in pENTR/SD/D-TOPO® only), allowing proper translation of the PCR product in prokaryotic cells.

Guidelines to Design the Reverse primer. When designing your reverse PCR primer, consider the following points below. See FIGS. 26 and 27 for diagrams of the TOPO® Cloning sites for pENTR/D-TOPO® and pENTR/SD/D-TOPO®, respectively.

To ensure that the PCR product clones directionally with high efficiency, the reverse PCR primer MUST NOT be complementary to the overhang sequence GTGG at the 5' end. A one base pair mismatch can reduce the directional cloning efficiency from 90% to 50%, increasing the likelihood that the ORF will be cloned in the opposite orientation (see "example A" below). We have not observed evidence of PCR products cloning in the opposite orientation from a two base pair mismatch.

If the PCR product is to be fused in frame with a C-terminal tag (following recombination of the entry clone with a GATEWAY™—destination vector), then the reverse PCR primer should be designed so as to remove the native stop codon in the gene of interest (see "example B" below).

If the PCR product is NOT to be fused in frame with a C-terminal tag (following recombination of the entry clone with a GATEWAY™-destination vector), then the native sequence containing the stop codon should be included in the reverse primer, or it should be ensured that the stop codon is upstream from the reverse PCR primer binding site (see "example B" below).

Example A of Reverse Primer Design. Below is the sequence of the C-terminus of a theoretical protein. The protein should be fused in frame with a C-terminal tag (following recombination of the entry clone with a GATEWAY™—destination vector). The stop codon is underlined.

DNA sequence: AAG TCG GAG CAC TCG ACG ACG GTG TAG-3' (SEQ ID NO: 46)

One solution is to design the reverse PCR primer to start with the codon just upstream of the stop codon, but the last two codons contain GTGG (underlined below), which is identical to the 4 bp overhang sequence. As a result, the reverse primer will be complementary to the 4 bp overhang sequence, increasing the probability that the PCR product will clone in the opposite orientation. This situation should be avoided.

```
DNA sequence:                           AAG TCG GAG CAC TCG ACG ACG GTG TAG-3'

Proposed Reverse PCR primer sequence: TG AGC TGC TG C CAC AAA-5'
```

Another solution is to design the reverse primer so that it hybridizes just downstream of the stop codon, but still includes the C-terminus of the ORF. Note that the stop codon will need to be replaced with a codon for an innocuous amino acid such as glycine, alanine, or lysine.

Example B of Reverse Primer Design. Below is the sequence for the C-terminus of a theoretical protein. The stop codon is underlined.

. . . GCG GTT AAG TCG GAG CAC TCG ACG ACT GCA TAG-3' (SEQ ID NO: 48 )

To fuse the ORF in frame with a C-terminal tag (supplied by the destination vector after recombination), remove the stop codon by starting with nucleotides homologous to the last codon (TGC) and continue upstream. The reverse primer will be:

5'-TGC AGT CGT CGA GTG CTC CGA CTT-3' (SEQ ID NO: 49)

This will amplify the C-terminus without the stop codon and allow the ORF to be joined in frame with a C-terminal tag. If it is not desirable to join the ORF in frame with a C-terminal tag, the reverse primer should simply be designed to include the stop codon:

5'-CTA TGC AGT CGT CGA GTG CTC CGA CTT-3' (SEQ ID NO: 50)

Important: It must be remembered that the pENTR TOPO® vectors accept blunt-end PCR products. 5' phosphates should not be added to the primers for PCR, as this will prevent ligation into the pENTR TOPO® vectors. In addition, it is recommended that the oligonucleotides be gel-purified prior to use, especially if they are long (>30 nucleotides).

Producing Blunt-End PCR Products

Once a PCR strategy has been chosen and primers synthesized according to the guidance presented above, the blunt-end PCR product can be produced. Any thermostable, proofreading polymerase may be used for this purpose, including ThermalAce™, PLATINUM®, Pfr, Pfu, or Vent® for PCR. To produce blunt-end PCR products, the instructions and recommendations of the manufacturer of the polymerase should be followed. It is important to optimize PCR conditions to produce a single, discrete PCR product. Gel purification of PCR fragments, according to methods outlined below, is also recommended.

Producing PCR Products

To produce amplification products via PCR, 25 µl or 50 µl PCR reaction mixtures are set up using the following guidelines:

Follow the manufacturer's instructions for the DNA polymerase that is being used.

Use the cycling parameters suitable for the primers and template.

Use a 7 to 30 minute final extension to ensure that all PCR products are completely extended.

After cycling, the tube should be placed on ice or stored at −20° C. for up to 2 weeks.

Checking the PCR Product

To verify quality and quantity of the PCR product, 5 µl to 10 µl should be removed from each PCR reaction and analyzed by agarose gel electrophoresis for the following:

The presence of a single, discrete band of the correct size. If there is not a single, discrete band, consult the manufacturer's recommendations for optimizing PCR reactions with the chosen polymerase. Alternatively, the desired product may be gel purified (see below).

Estimate the concentration of the PCR product. For TOPO® Cloning, a 5:1 molar ratio of PCR product to TOPO® vector is recommended to obtain the highest cloning efficiency. For example, 20 ng of a 500 bp PCR product, or 10 ng of a 1000 bp PCR product, may be used in a TOPO® Cloning reaction. The concentration of the PCR product may need to be adjusted before proceeding to TOPO® Cloning.

Note: If ThermalAce™ polymerase is being used to produce the blunt-end PCR product, it should be noted that ThermalAce™ can generate higher yields than other proofreading polymerases. When generating PCR products in the 0.5 to 1.0 kb range, we generally dilute the PCR reaction 1:5 in 1× ThermalAce™ buffer before performing the TOPO® Cloning reaction. For PCR products larger than 1.0 kb, dilution may not be required.

Setting Up the TOPO® Cloning Reaction

Introduction

Once you have produced the desired PCR product, you are ready to TOPO® Clone it into the pENTR TOPO® vector and transform the recombinant vector into TOP10 *E. coli*. It is important to have everything you need set up and ready to use to ensure that you obtain the best possible results. We suggest that you read the sections entitled Setting Up the TOPO® Cloning Reaction and Transforming One-Shot® TOP 10 Competent Cells before beginning. If this is the first time you have TOPO® Cloned, perform the control reactions described below in parallel with your samples.

If you are TOPO® Cloning in HTP format (see below), you may transform TOP10 *E. coli* using Bulk TOP10 cells (500 reaction kits) or MultiShot™ TOP10 cells (480 reaction kits). Depending on which kit you are using, see the TOPO® Cloning and transformation protocols below.

Note: Recent studies demonstrate that including salt (200 mM NaCl, 10 mM $MgCl_2$) in the TOPO® Cloning reaction may result in an increase in the number of transformants. From these results, we recommend adding salt to the TOPO® Cloning reaction. A stock salt solution is provided in the kit for this purpose. Please note that the amount of salt added to the TOPO® Cloning reaction varies depending on whether you plan to transform chemically competent cells or electrocompetent cells. For this reason two different TOPO® Cloning reactions are provided to help you obtain the best possible results.

Transforming Chemically Competent *E. coli*

For TOPO® Cloning and transformation into chemically competent *E. coli*, adding sodium chloride and magnesium chloride to a final concentration of 200 mM NaCl, 10 mM $MgCl_2$ in the TOPO® (Cloning reaction increases the number of colonies over time. A Salt Solution (1.2 M NaCl, 0.06 M $MgCl_2$) is provided to adjust the TOPO® Cloning reaction to the recommended concentration of NaCl and $MgCl_2$.

Transforming Electrocompetent *E. coli*

For TOPO® Cloning and transformation of electrocompetent *E. coli*, salt may also be included in the TOPO® Cloning reaction, but the amount of salt must be reduced to 50 mM NaCl, 2.5 mM $MgCl_2$ to prevent arcing when electroporating. Dilute the Salt Solution 4-fold with water to prepare a 300 mM NaCl, 15 mM $MgCl_2$ solution for convenient addition to the TOPO® Cloning reaction.

Setting Up the TOPO® Cloning Reaction

The table below describes how to set up your TOPO® Cloning reaction (6 μl) for eventual transformation into either chemically competent One Shot! TOP0 *E. coli* or electrocompetent *E. coli*. Additional information on optimizing the TOPO® Cloning reaction for your needs can be found below. If you generated your PCR product using ThermalAce-polymerase, please note that you may need to dilute your PCR reaction before proceeding.

Note: The blue color of the TOPO® vector solution is normal and is used to visualize the solution.

TABLE 7

Setting Up a TOPO ® Cloning Reaction Mixture.

| Reagents* | Chemically Competent *E. coli* | Electrocompetent *E. coli* |
|---|---|---|
| Fresh PCR product | 0.5 to 4 μl | 0.5 to 4 μl |
| Salt Solution | 1 μl | — |
| Dilute Salt Solution (1:4) | — | 1 μl |
| Sterile Water | add to a final volume of 5 μl | add to a final volume of 5 μl |
| TOPO ® vector | 1 μl | 1 μl |

*Store all reagents at −20° C. when finished. Salt solutions and water can be stored at room temperature or 4° C.

Performing the TOPO® Cloning Reaction

Mix reaction gently and incubate for 5 minutes at room temperature (22–23° C.).

Note: For most applications, 5 minutes will yield plenty of colonies for analysis. Depending on your needs, the length of the TOP011 Cloning reaction can be varied from 30 seconds to 30 minutes. For routine subcloning of PCR products, 30 seconds may be sufficient. For large PCR products (>1 kb) or if you are TOPO® Cloning a pool of PCR products, increasing the reaction time may yield more colonies.

Place the reaction on ice and proceed to Transforming One Shot7 TOP10 Competent Cells. Note: You may store the TOPO7 Cloning reaction at −20° C. overnight.

Transforming One Shot® TOP10 Competent Cells

Introduction

Once you have performed the TOPO® Cloning reaction, you will transform your pENTR TOPO® construct into competent *E. coli*i. One Shots TOP10 Chemically Competent *E. coli* are included with the 20 reaction kit to facilitate transformation, however, you may also transform electrocompetent cells (see page x for ordering information). Protocols to transform chemically competent or electrocompetent *E. coli* are provided in this section.

Materials Supplied by the User

In addition to general microbiological supplies (i.e. plates, spreaders), you will need the following reagents and equipment.

(a) 42° C. water bath (or electroporator with cuvettes, optional)

(b) LB plates containing 50 μg/ml kanamycin (two for each transformation)

(c) 37° C. shaking and non-shaking incubator

There is no blue-white screening for the presence of inserts. Most transformants will contain recombinant plasmids with the PCR product of interest cloned in the correct orientation. Sequencing primers are included in the kit to sequence across an insert in the multiple cloning site to confirm orientation and reading frame.

Preparing for Transformation

For each transformation, you will need one vial of competent cells and two selective plates.

Equilibrate a water bath to 42° C. (for chemical transformation) or set up your electroporator if you are using electrocompetent *E. coli*.

For electroporation, dilute a small portion of the Salt Solution 4-fold to prepare Dilute Salt Solution (e.g. add 5 μl of the Salt Solution to 150 sterile water).

Warm SOC medium to room temperature.

Warm LB plates containing 50 μg/ml kanamycin at 37° C. for 30 minutes.

Thaw on ice 1 vial of One Shot® TOP10 cells for each transformation.

Important: Please note that directional TOPO® Cloning generally yields 5 to 10-fold fewer colonies than traditional bidirectional TOPO TA Cloning®. When directionally TOPO® Cloning a 750 bp test insert, we generally obtain 1800–3000 colonies using the protocol desribed herein. Although fewer total colonies are obtained, greater than 90% of the colonies will contain plasmid with your PCR insert in the correct orientation.

One Shot® TOP10 Chemical Transformation Protocol

1. Add 2 μl of the TOPO® Cloning reaction from Performing the TOPO® Cloning Reaction (above) into a vial of One Shot TOP10 Chemically Competent *E. coli* and mix gently. Do not mix by pipetting up and down.

2. Incubate on ice for 5 to 30 minutes.

Note: Longer incubations on ice seem to have a minimal effect on transformation efficiency. The length of the incubation is at the user's discretion.

3. Heat-shock the cells for 30 seconds at 42° C. without shaking.

4. Immediately transfer the tubes to ice.

5. Add 250 μl of room temperature SOC medium.

6. Cap the tube tightly and shake the tube horizontally (200 rpm) at 37° C. for 30 minutes.

7. Spread 50–200 μl from each transformation on a prewarmed selective plate and incubate overnight at 37° C. We recommend that you plate two different volumes to ensure that at least one plate will have well-spaced colonies.

8. An efficient TOPO7 Cloning reaction may produce several hundred colonies. Pick ~5 colonies for analysis (see Analyzing Transformants, below).

Transformation by Eletroporation

Use ONLY electrocompetent cells for electroporation to avoid arcing. Do not use the One Shot® TOP10 chemically competent cells for electroporation.

1. Add 2 μl of the TOPO® Cloning reaction from Performing the TOPO® Cloning Reaction (above) into a 0.1 cm cuvette containing 50 μl of electrocompetent *E coli* and mix gently. Do not mix by pipetting up and down. Avoid formation of bubbles.

2. Electroporate your samples using your own protocol and your electroporator.

Note: If you have problems with arcing, see below.

3. Immediately add 250 μl of room temperature SOC medium.

4. Transfer the solution to a 15 ml snap-cap tube (i.e. Falcon) and shake for at least 1 hour at 37° C. to allow expression of the kanamycin resistance gene.

5. Spread 20–100 μl from each transformation on a prewarmed selective plate and incubate overnight at 37° C. To ensure even spreading of small volumes, add 20 μl of SOC. We recommend that you plate two different volumes to ensure that at least one plate will have well-spaced colonies.

6. An efficient TOPO7 Cloning reaction may produce several hundred colonies. Pick ~5 colonies for analysis (see Analyzing Transformants, below).

Addition of the Dilute Salt Solution in the TOPO® Cloning Reaction brings the final concentration of NaCl and $MgCl_2$ in the TOPO® Cloning Reaction to 50 mM and 2.5 mM, respectively. To prevent arcing of your samples during electroporation, the volume of cells should be between 50 and 80 μl (0.1 cm cuvettes) or 100 to 200 μl (0.2 cm curettes).

If you experience arcing during transformation, try one of the following suggestions:

Reduce the voltage normally used to charge your electroporator by 10%

Reduce the pulse length by reducing the load resistance to 100 ohms

Ethanol precipitate the TOPO® Cloning reaction and resuspend in water prior to electroporation.

High-Throughput Applications

The 480 and 500 reaction pENTR and pENTR/SD Directional TOPO® Cloning Kits are specifically designed to allow production of GATEWAY™ entry clones for use in high-throughput (HTP) applications. In these kits, the pENTR TOPO® vector is provided in bulk and chemically competent TOP10 *E. coli* are provided in a choice of two formats:

Cells are provided in bulk aliquots of 5 ml to allow simple transfer of the cells from a sterile trough into a 96-well plate containing the TOPO7 Cloning reaction (Catalog nos. K2400-500 and K2420-500).

Cells are provided pre-aliquoted in 96-well plates (in 12-well stripwells) to allow addition of the TOPO7 Cloning reaction to the cells (Invitrogen Corporation, Carlsbad, Calif.; Catalog nos. K2400-480 and K2420-480).

HTP TOPO® Cloning and Transformation with Bulk Cells

Description

In this protocol, the TOPO® Cloning reaction is set up in a 96-well U bottom, polystyrene plate (Costar, Catalog no. 3366, 330 μl/well) and the TOP10 competent cells are placed in a trough for dispensing.

Before Starting

Chill a 96-well metal heating block (VWR, Catalog no. 13259-260) on ice until the block is cold.

Bring a vial of SOC to room temperature.

Pre-heat a heat block or thermocycler containing a 96-well metal block to 42° C.

Note: You can also use a water bath, but be careful not to contaminate the cells.

Thaw 1 tube (5 ml) of TOP10 chemically competent *E. coli* on ice (30–60 minutes).

Warm LB agar plates containing 50 μg/ml kanamycin to 37° C. If you plan to include a pUC19 control to test the transformation efficiency of the cells, you will need LB agar plates containing 50–100 μg/ml ampicillin. Controls: For your convenience a 50 μl aliquot of competent cells is provided to perform a test TOPO® Cloning and transformation reaction. In addition, you can include the pUC19 plasmid as an internal control (see Procedure below).

Procedure

1. Set up the 6 μl TOPO® Cloning reaction in each well as follows. If you include pUC19 as a control, leave 2–3 wells empty.

| | |
|---|---|
| PCR product | 1 μl |
| Salt Solution | 1 μl |
| Sterile Water | 3 μl |
| pENTR TOPO ® vector | 1 μl |
| Final Volume | 6 μl |

2. Incubate 5–10 minutes at room temperature.

3. Place the 96-well plate on the cooling block for 5 minutes.

4. If you are including pUC19, add 1 μl (10 pg) of the plasmid to 2–3 empty wells.

5. Pour thawed TOP10 *E. coli* into a sterile trough and immediately dispense 45 μl/well. Gently pipet up and down 1–2 times to mix.

6. Cover the plate with Parafilm® and incubate it on the chilled block for 20 minutes.

7. Transfer the plate to either the pre-warmed heat block or the thermocycler and heat-shock the cells at 42° C. for 30 seconds.

8. Transfer the plate back to the cooling block and press down to ensure the plate is in complete contact with the cooling block. Incubate for 1 minute.

9. Remove the Parafilm® and add 150 μL/well of SOC.

10. Re-cover the plate and incubate the plate at 37° C. for 1 hour. Note: Gentle shaking (125 RPM) is optional.

11. Plate 50 μL from each well onto LB agar plates containing 50 μg/ml kanamycil. For the pUC19 controls, plate 10 μl of the transformation mixture plus 20 μl of SOC on LB plates containing 100 μg/ml ampicillin. Incubate overnight at 37° C.

12. The next day, select 5–10 colonies and process as desired.

Too Many Colonies

If you obtain too many colonies, reduce the amount of bacterial culture plated and/or dilute the transformation with additional SOC.

HTP TOPO Cloning and Transformation with MultiShot™ Cells

Description

In this protocol, the TOPO® Cloning reaction is set up in a 96-well plate and 2 μl are transferred to each well of a 96-well MultiShot™ plate containing 15 μl of chemically competent TOP 10 *E. coli* per well.

Before Starting

Chill two 96-well metal heating blocks (VWR, Catalog no. 13259-260) on ice until the blocks are cold.

Bring a vial of SOC to room temperature.

Warm LB agar plates containing 50 μg/ml kanamycin to 37° C. If you plan to include a pUC19 control to test the transformation efficiency of the cells, you will need LB agar plates containing 50–100 μg/ml ampicillin.

Pre-heat a heat block or thermocycler containing a 96-well metal block to 42° C.

Note: You can also use a water bath, but be careful not to contaminate the cells.

If you are using a thermocycler, program the machine to hold the temperature at 42° C.

Controls: A test plate containing 1 row (12 wells) of TOP10 cells is included to perform test TOPO® Cloning reactions and transformations. In addition, you can include the pUC19 plasmid as an internal control (see Procedure below).

Procedure

1. In a 96-well plate, set up the following 6 μl TOPO® Cloning reaction in each well.

| | |
|---|---|
| PCR product | 1 μl |
| Salt Solution | 1 μl |
| Sterile Water | 3 μl |
| pENTR TOPO ® vector | 1 μl |
| Final Volume | 6 μl |

2. Incubate 5–10 minutes at room temperature.

3. Place the 96-well plate on one of the cooling blocks for 5 minutes.

4. Remove a 96-well MultiShot™ plate of chemically competent TOP10 *E. coli* from the freezer and place it in the second cooling block. Cells should thaw within 30 seconds.

5. Carefully remove the aluminum foil seal.

6. Use a multi-channel pipet to add 2 μl of each TOPO® Cloning reaction (~3.3 ng) to each well of the 96-well plate containing cells. Keep the volume around 2 μl for uniform results. For the pUC19 control, add 1 μl (10 pg) of the DNA.

7. Cover the cells with the supplied plastic lid and incubate the cells and DNA in the chilled block for 20 minutes.

8. Transfer the cell plate to either the pre-warmed heat block or thermocycler and heat-shock for 30 seconds at 42° C.

9. Transfer the cell plate back to a cooling block, press the plate into the block and allow the plate to cool for 1 minute.

10. Remove the plastic lid and add 90 μl SOC to each well.

11. Cover the plate with the lid and incubate the plate at 37° C. for 1 hour. Note: Gentle shaking (125 RPM) is optional.

12. Plate 100 μl from each well onto LB agar plates containing 50 μg/ml kanamycin. For the pUC19 controls, plate 10 μl of the transformation mixture plus 20 μl of SOC on LB plates containing 100 μg/ml ampicillin. Incubate overnight at 37° C.

NOTE: If you obtain too many colonies, you can reduce the amount of cells plated or dilute the TOPO® Cloning reactions with sterile water or TE buffer prior to adding the reaction to the cells.

Analyzing Transformants

Analyzing Positive Clones

1. Pick 5 colonies and culture them overnight in LB or SOB medium containing 50–100 μg/ml kanamycin.

2. Isolate plasmid DNA using your method of choice. If you need ultra-pure plasmid DNA for automated or manual sequencing, we recommend using the S.N.A.P.J MidiPrep Kit (Catalog no. K1910-01).

3. Analyze the plasmids by restriction analysis to confirm the presence and correct orientation of the insert. Use a restriction enzyme or a combination of enzymes that cut once in the vector and once in the insert.

Sequencing

You may sequence your construct to confirm that your gene is cloned in the correct orientation. The M13 Forward (−20) and M13 Reverse primers are included in the kit to help you sequence your insert. The M13 Forward (−20) and M13 Reverse primers are also available separately from Invitrogen Corporation, Carlsbad, Calif.

Important: If you download the sequence for pENTR/D-TOPO® or pENTR/SD/D-TOPO® from the Invitrogen Corporation Web site (see description for FIG. 22), note that the overhang sequence (GTGG) will be shown already hybridized to CACC. No DNA sequence analysis program allows us to show the overhang without the complementary sequence.

Analyzing Transformants by PCR

You may analyze positive transformants using PCR. For PCR primers, use a combination of the M13 Forward (−20) primer or the M13 Reverse primer and a primer that hybridizes within your insert. You will have to deter-mine the amplification conditions. If you are using this technique for the first time, we recommend performing restriction analysis in parallel. Artifacts may be obtained because of mispriming or contaminating template.

The protocol below is provided for your convenience. Other protocols are suitable.

1. Prepare a PCR cocktail consisting of PCR buffer, dNTPs, primers, and Taq polymerase. Use a 20 μl reaction volume. Multiply by the number of colonies to be analyzed (e.g. 5).

2. Pick 5 colonies and resuspend them individually in 20 μl of the PCR cocktail (remember to make a patch plate to preserve the colonies for further analysis).

3. Incubate reaction for 10 minutes at 94° C. to lyse cells and inactivate nucleases.

4. Amplify for 20 to 30 cycles.

5. For the final extension, incubate at 72° C. for 10 minutes. Store at −4° C.

6. Visualize by agarose gel electrophoresis.

Important: If you have problems obtaining transformants or the correct insert, perform the control reactions described herein. These reactions will help you troubleshoot your experiment.

Long-Term Storage

Once you have identified the correct clone, be sure to purify the colony and make a glycerol stock for long term storage. We recommend that you store a stock of plasmid DNA at −20° C.

1. Streak the original colony out for single colony on LB plates containing 50 μg/ml kanamycin.

2. Isolate a single colony and inoculate into 1–2 ml of LB containing 50 μg/ml kanamycin.

3. Grow until culture reaches stationary phase.

4. Mix 0.85 ml of culture with 0.15 ml of sterile glycerol and transfer to a cryovial.

5. Store at −80° C.

Recombining the Entry Construct with a Destination Vector

Once you have obtained your entry clone, you may recombine the pENTR TOPO® construct with any GATEWAY™ destination vector of choice to generate an expression clone. This "LR" recombination reaction is mediated by LR CLONASE™, a cocktail of recombination proteins. LR CLONASE™ Enzyme Mix is available from Invitrogen Corporation (Carlsbad, Calif.). In certain such methods, for example, TOPO-adapted vectors are incubated with one or more nucleic acid segments (e.g., one or more PCR products) at room temperature (e.g., about 20-20° C.) for about 5–30 (and preferably about 10) minutes; the reaction is then heat-treated by incubation at about 80° C. for about 20 minutes, and the reaction mixture then used in a standard LR reaction according to manufacturer's instructions (Invitrogen Corporation, Carlsbad, Calif.), except the incubation time for the LR reaction is increased to about 3 hours.

Optimizing the TOPO® Cloning Reaction

Speeding up the Cloning Process. The high efficiency of TOPO® Cloning allows you to streamline the cloning process. If you routinely clone PCR products and wish to speed up the process, consider the following:

Incubate the TOPO® Cloning reaction for only 30 seconds instead of 5 minutes.

You may not obtain the highest number of colonies, but with the high efficiency of TOPO® Cloning, most of the transformants will contain your insert.

After adding 3 μl of the TOPO® Cloning reaction to chemically competent cells, incubate on ice for only 5 minutes.

Increasing the incubation time to 30 minutes does not significantly improve transformation efficiency.

Obtaining More Transformants. If you are TOPO® Cloning large PCR products, toxic genes, or cloning a pool of PCR products, you may need more transformants to obtain the clones you want. To increase the number of colonies:

Incubate the salt-supplemented TOPO® Cloning reaction for 20 to 30 minutes instead of 5 minutes.

Increasing the incubation time of the salt-supplemented TOPO® Cloning reaction allows more molecules to ligate, increasing the transformation efficiency. Addition of salt appears to prevent topoisomerase I from rebinding and nicking the DNA after it has ligated the PCR product and dissociated from the DNA.

Titrate the amount of PCR product used in the TOPO7 Cloning reaction for maximum colony output.

Cloning Dilute PCR Products

To clone dilute PCR products, you may:

Increase the amount of the PCR product

Incubate the TOPO® Cloning reaction for 20 to 30 minutes

Concentrate the PCR product

Performing the Control Reactions

Introduction

We recommend performing the following control TOPO® Cloning reactions the first time you use the 20 reaction kit to help you evaluate your results. Performing the control reactions involves producing a control PCR product using the reagents included in the kit and using this product directly in a TOPO® Cloning reaction.

Before Starting

For each transformation, prepare two LB plates containing 50 μg/ml kanamycin.

Producing the Control PCR Product

Use your thermostable, proofreading polymerase and the appropriate buffer to amplify the control PCR product. Follow the manufacturer's recommendations for the polymerase you are using.

1. To produce the 750 bp control PCR product, set up the following 50 μl PCR:

| | |
|---|---|
| Control DNA Template (100 ng) | 1 μl |
| 10X PCR Buffer (appropriate for enzyme) | 5 μl |
| dNTP Mix | 0.5 μl |
| Control PCR Primers (0.1 μg/μl each) | 1 μl |
| Sterile Water | 41.5 μl |
| Thermostable polymerase (1–2.5 units/μl) | 1 μl |
| Total Volume | 50 μl |

2. Overlay with 70 μl (1 drop) of mineral oil.

3. Amplify using the following cycling parameters:

| Stop | Time | Temperature | Cycles |
|---|---|---|---|
| Initial Denaturation | 2 minutes | 94° C. | 1X |
| Denaturation | 1 minute | 94° C. | 25X |
| Annealing | 1 minute | 55° C. | |
| Extension | 1 minute | 72° C. | |
| Final Extension | 7 minutes | 72° C. | 1X |

4. Remove 10 μl from the reaction and analyze by agarose gel electrophoresis. A discrete 750 bp band should be visible. Proceed to the Control TOPO7 Cloning Reactions.

Control TOPO® Cloning Reactions

Using the control PCR product produced on the previous page and the pENTR is TOPO® vector, set up two 6 μl TOPO® Cloning reactions as described below.

1. Set up control TOPO® Cloning reactions:

| Reagent | "Vector Only" | "Vector + PCR Insert" |
|---|---|---|
| Sterile Water | 4 μl | 3 μl |
| Salt Solution or Dilute Salt Solution | 1 μl | 1 μl |
| Control PCR Product | — | 1 μl |
| pENTR TOPO ® vector | 1 μl | 1 μl |

2. Incubate at room temperature for 5 minutes and place on ice.

3. Transform 3 μl of each reaction into separate vials of One Shot® TOP10 cells.

4. Spread 100–200 μl of each transformation mix onto LB plates containing 50 μg/ml kanamycin. Be sure to plate two different volumes to ensure that at least one plate has well-spaced colonies.

5. Incubate overnight at 37° C.

Analysis of Results

Hundreds of colonies from the vector+PCR insert reaction should be produced. To analyze the transformations, isolate plasmid DNA and digest with the appropriate restriction enzymes. Greater than 90% of the colonies should contain the 750 bp insert in the correct orientation. Relatively few colonies should be produced in the vector-only reaction.

Transformation Control pUC19 plasmid is included to check the transformation efficiency of the One Shot® TOP10 competent cells. Transform one vial of One Shot® TOP10 cells with 10 pg of pUC19 using the protocol described above. Plate 10 μl of the transformation mixture plus 20 μl of SOC on LB plates containing 100 μg/ml ampicillin. Transformation efficiency should be $-1\times10^9$ cfu/μg DNA.

Factors Affecting Cloning Efficiency

Please note that lower cloning efficiencies will result from the following variables. Most of these are easily corrected, but if you are cloning large inserts, you may not obtain the expected 90% directional cloning efficiency.

| Variable | Solution |
|---|---|
| Low efficiency of directional cloning | Forward primer should contain CACC at the 5' end. Reverse primer is complementary to the overhang at the 5' end. Re-design primer to avoid base pairing to the overhang. |
| pH >9 in PCR amplification reaction | Check the pH of the PCR amplification reaction and adjust with 1 M Tris-HCl, pH 8. |
| Incomplete extension during PCR | Be sure to include a final extension step of 7 to 30 minutes during PCR. Longer PCR products will need a longer extension time. |
| Cloning large inserts (>1 kh) | Increase amount of insert or gel-purify as described on pages 25–26. |
| Excess (or overly dilute) PCR product | Reduce (or concentrate) the amount of PCR product. |
| PCR cloning artifacts ("false positives") | TOPO ® Cloning is very efficient for small fragments (<100 bp) present in certain PCR reactions. Gel-purify your PCR product or optimize your PCR. |

Gel Purifying PCR Products

Introduction

Smearing, multiple banding, primer-dimer artifacts, or large PCR products (>3 kb) may necessitate gel purification. If you wish to purify your PCR product, be extremely careful to remove all sources of nuclease contamination. There are many protocols to isolate DNA fragments or remove oligonucleotides. Please refer to *Current Protocols in Molecular Biology*, Unit 2.6 (Ausubel et al., 1994) for the most common protocols. Three simple protocols are provided below.

Note: cloning efficiency may decrease with purification of the PCR product (e.g. PCR product too dilute). You may wish to optimize your PCR to produce a single band (see Producing Blunt-End PCR Products, herein).

Using the S.N.A.P.™ Gel Purification Kit

The S.N.A.P.™ Gel Purification Kit available from Invitrogen Corporation, Carlsbad, Calif. (Catalog no. K1999-25) allows you to rapidly purify PCR products from regular agarose gels.

1. Electrophorese amplification reaction on a 1 to 5% regular TAE agarose gel. (Note: Do not use TBE to prepare agarose gels. Borate interferes with the sodium iodide step, below.)

2. Cut out the gel slice containing the PCR product and melt it at 65° C. in 2 volumes of the 6 M sodium iodide solution.

3. Add 1.5 volumes Binding Buffer.

4. Load solution (no more than 1 ml at a time) from Step 3 onto a S.N.A.P.™ column. Centrifuge 1 minute at 3000× g in a microcentrifuge and discard the supernatant.

5. If you have solution remaining from Step 3, repeat Step 4.

6. Add 900 μl of the Final Wash Buffer.

7. Centrifuge 1 minute at full speed in a microcentrifuge and discard tile flowthrough.

8. Repeat Step 7.

9. Elute the purified PCR product in 40 μl of TE or sterile water. Use 4 μl for the TOPO® Cloning reaction and proceed as described above. Quick S.N.A.P.™ Method An even easier method is to simply cut out the gel slice containing your PCR product, place it on top of the S.N.A.P.™ column bed, and centrifuge at full speed for 10 seconds. Use 1–2 μl of the flow-through in the TOPO® Cloning reaction. Be sure to make the gel slice as small as possible for best results.

Low-Melt Agarose Method

If you prefer to use low-melt agarose, use the procedure below. Please note that gel purification will result in a dilution of your PCR product and a potential loss of cloning efficiency.

1. Electrophorese as much as possible of your PCR reaction on a low-melt agarose gel (0.8 to 1.2%) in TAE buffer.

2. Visualize the band of interest and excise the band.

3. Place the gel slice in a microcentrifuge tube and incubate the tube at 65° C. until the gel slice melts.

4. Place the tube at 37° C. to keep the agarose melted.

5. Add 4 μl of the melted agarose containing your PCR product to the TOPO® Cloning reaction as described above.

6. Incubate the TOPO® Cloning reaction at 37° C. for 5 to 10 minutes. This is to keep the agarose melted.

7. Transform 2 to 4 μl directly into OneShot® TOP10 cells using the method on page 13.

Note: the cloning efficiency may decrease with purification of the PCR product. You may wish to optimize your PCR to produce a single band.

EXAMPLE 9

Optimization of Reaction Conditions for TOPO Joining Reactions Using GATEWAY™ Vectors To use TOPO Cloning procedures in conjunction with GATEWAY vectors, the optimal conditions for the combined reactions were investigated. In carrying out these studies, several questions were addressed.

Sufficiency of Template for BP Reaction, and Inhibition of BP Reaction by TOPO Reaction Components To address these issues, TOPO Tools was used as described elsewhere herein to generate attB1+CAT+attB2 templates. Secondary PCR was then performed to generate sufficient template for testing studies, and BP reactions were performed using the products. The following reaction conditions were used for each step of the process:

| TOPO Joining Reaction: | BP Reaction: |
|---|---|
| X ng of PCR product (see below) | 2 µl salt-free buffer |
| 1 µl topoisomerase | 1 µl TOPO Joining Product |
| 0.5 µl of 500 mM Tris | 0.5 µl of pDONR222 (300 ng/µl) |
| 1 µl of 40 mM NaCl | 2 µl of BP Clonase (Invitrogen Corporation, Carlsbad, CA) |
| 37° C. for 15 min | room temp for 25 min → Proteinase |
| Transformation (chemical) | K treatment |

Following BP reactions, mixtures were chemically transformed into chemically competent *E. coli* cells (e.g., TOP10; Invitrogen Corporation Carlsbad, Calif.) and cells were plated to determine recombination efficiency.

Results

| | 1 | 2 | 3 | 4 | 5 | 6 |
|---|---|---|---|---|---|---|
| Colonies | 149 | 270 | 514 | 0 | 0 | 0 |
| Template Used | 0.8 ng | 1.6 ng | 4 ng | 1.6 ng | 4 ng | 0 ng |
| TOPO Joining? | No | No | No | Yes | Yes | No |

These results demonstrate that TOPO Tools generates sufficient template for the subsequent BP reaction. In addition, these results demonstrate that TOPO joining inhibits the subsequent BP reaction.

Effect of Presence of attB1 and attB2 Adapters on BP Reactions

In this portion of the studies, the effects of the presence of excess attB1 and attB2 adapters in the reaction mixtures on the subsequent BP reaction were examined. To address this issue, different amounts of attB1 and attB2 adapters were added to templates (attB1+CAT+attB2, 20 ng), and BP reactions were performed under standard conditions (60 minutes at room temperature). Following BP reactions, mixtures were chemically transformed into chemically competent *E. coli* cells (e.g., TOP10; Invitrogen Corporation, Carlsbad, Calif.) and cells were plated to determine recombination efficiency.

Results:

| | 1 | 2 | 3 | 4 | 5 | 6 |
|---|---|---|---|---|---|---|
| Adapter amount (ng) | 20 | 10 | 5 | 2.5 | 1 | 0 |
| No. of colonies formed | 270 | 475 | 760 | 590 | 340 | 460 |

These results demonstrate that the presence of an excess of attB1 and attB2 adapters has no significant effect on the transformation efficiencies observed, indicating that the BP reaction is not significantly influenced by the presence of attB1 and attB2 adapters in the reaction mixture.

Removal of Inhibitors from TOPO Joining Reactions

To address the optimal methods for removing inhibitors from TOPO Joining reactions prior to use of the products in BP reactions, various treatment methods were assessed. TOPO Joining reactions were performed using the following reaction mixtures, incubated at room temperature for 5 minutes:

| | |
|---|---|
| attB1 + attB2 (20 ng/µl each) | 2 µl |
| CAT (100 ng/µl) | 1.7 µl |
| attB1 + CAT + attB2 product (10 ng/µl) | 1 µl |
| 500 mM Tris | 0.5 µl |
| Topoisomerase (1 µg/µl) | 1 µl |

Following TOPO Joining reactions, seven different samples of the reaction mixtures were treated under one of the following conditions prior to carrying out BP reactions:

(1) add 1 µl of 0.6% SDS+3 mM EDTA to one reaction, 37° C. for 15 min;

(2) add 4 µl of 0.6% SDS+3 mM EDTA to four reactions, 37° C. for 15 min, then SNAP purify into 20 µl of water;

(3) add 4 µl of 0.6% SDS+3 mM EDTA+1 µl of proteinase K (2 µg/µl) to 4 reactions, 37° C. for 15 minutes, then SNAP purify into 20 µl of water;

(4) add 0.8 µl of 2.5 M NaCl to one reaction, 37° C. for 17 minutes;

(5) add 3.2 µl of 2.5 M NaCl to four reactions, 37° C. for 15 min, then SNAP purify into 20 µl of water;

(6) add 3.2 µl of 2.5 M NaCl and 1 µl of 2 µg/µl proteinase K to 4 reactions, 37° C. for 15 min, then SNAP purify into 20 µl of water (positive control; 0.8 ng template used);

(7) (negative control; no template used).

BP reactions were performed using salt-free buffer for 60 min at room temperature. For unpurified mixtures, 1 µl of TOPO Joining reaction mixture was used per 10 µl of BP reaction. For purified mixtures, 5.5 µl of TOPO Joining reaction mixture was used per 10 µl of BP reaction. Following BP reactions, mixtures were chemically transformed into chemically competent *E. coli* cells (e.g., TOP10; Invitrogen Corporation, Carlsbad, Calif.) and cells were plated to determine recombination efficiency.

Results

| | 1 | 2 | 3 | 4 | 5 | 6 | 7 | 8 |
|---|---|---|---|---|---|---|---|---|
| Treatment | SDS | SDS | SDS | NaCl | NaCl | NaCl | (+) | (−) |
| Proteinase K | − | − | + | − | − | + | | |
| Purification | − | + | + | − | + | + | | |
| No. of Colonies | 6 | 515 | 400 | 0 | 550 | 657 | 179 | 0 |

These results demonstrate that: (1) purification is not necessary to carry out the BP reaction efficiently; (2) treatment of reaction mixtures with proteinase K is not required following TOPO Joining reactions for maximum efficiency of subsequent BP reactions; and (3) SDS treatment and NaCl treatment of reaction mixtures give the same transformation efficiencies (and therefore have the same effects upon the BP reaction).

Optimization of BP Reaction Temperature

To determine the optimum reaction temperature for carrying out BP reactions following TOPO Joining, attB1+CAT+attB2 PCR product was used as the template for BP reactions conducted under various temperatures. Following BP reactions, mixtures were chemically transformed into chemically competent *E. coli* cells (e.g., TOP10; Invitrogen Corporation, Carlsbad, Calif.) and cells were plated to determine recombination efficiency.

Results

| | BP Reaction Temperature | | | |
|---|---|---|---|---|
| | 42° C. | 37° C. | Room Temp | 14° C. |
| No. of Colonies (+Template) | 3 | 337 | 588 | 195 |
| No. of Colonies (no Template) | 0 | 4 | 0 | 0 |

These results demonstrate that room temperature (about 20–25° C.) is the optimal reaction temperature for carrying out BP reactions.

Optimization of Molar Ratio of attB1:insert:attB2

To determine the optimal molar ratio for attB1, insert and attB2 templates in the BP reaction, these templates were mixed in various molar ratios and BP reactions carried out under optimal conditions described above. Following BP reactions, mixtures were chemically transformed into chemically competent *E. coli* cells (e.g., TOP10; invitrogen Corporation, Carlsbad, Calif.) and plated to determine recombination efficiency. Results

| Ratio of attB1:insert:attB2 | 2:1:2 | 1.5:1:1.5 | 1:1:1 | 1:2:1 | 0 (control) |
|---|---|---|---|---|---|
| No. of Colonies | 81 | 93 | 165 | 154 | 9 |

These results demonstrate that a ratio of attB1:insert:attB2 at 1:1:1 is optimal for carrying out BP reactions.

Determination of Effect of Salt on BP Reaction

To determine whether the presence of salt in the BP reaction solution influences the recombination efficiency, BP reactions were carried out in salt-free buffers, or in standard BP reaction buffers containing salt.

Results (No. of colonies formed)

| Buffer Salt | – | + |
|---|---|---|
| +template | 108 | 109 |
| –template (neg. control) | 1 | 0 |

These results demonstrate that the presence or absence of salt in the reaction buffer during the BP reaction has no impact upon the recombination efficiency.

Determination of Optimal Number of TOPO Joining Reactions

In the next series of studies, the question of whether one TOPO Joining reaction is sufficient to provide optimal recombination efficiency for BP reactions after purification was examined. A single TOPO Joining reaction was carried out using the following reaction mixture:

| | |
|---|---|
| attB1 and attB2 (20 ng/μl each) | 0.5 μl |
| CAT (100 ng/μl) | 1.7 μl |

-continued

| | |
|---|---|
| 500 mM Tris | 0.5 μl |
| Topoisomerase (1 μg/μl) | 1 μl |
| $dH_2O$ | sufficient to bring final volume to 5 μl |

The reaction mixture was incubated at 37° C. for 15 minutes, then 1 μl of 0.6% SDS+3 mM EDTA was added; the mixture was incubated at 37° C. for 15 minutes, and then purified using a SNAP column (see above) into 20 μl of water. A BP reaction was then carried out using the product of this TOPO Joining reaction as follows:

| | |
|---|---|
| standard BP reaction buffer | 2 μl |
| pDONR222 (300 ng/μl) | 0.5 μl |
| TOPO Joining product (from above) | 5.5 μl |
| BP Clonase | 2 μl |

The reaction mixture was incubated at room temperature for 60 minutes, then 1 μl of 2 μg/μl proteinase K was added; the mixture was incubated at 37° C. for 15 minutes, and then at 75° C. for 15 minutes. 4 μl of this reaction mixture was then used for chemical transformation into chemically competent *E. coli* cells (e.g., TOP10; Invitrogen Corporation, Carlsbad, Calif.) and cells were then plated to determine recombination efficiency.

Results (No. of Colonies Formed):

| +Template | –Template (neg. control) |
|---|---|
| 188 | 0 |

These results demonstrate that one TOPO Joining reaction provides sufficient template to carry out an efficient BP reaction.

Optimization of Purification Methods

Studies were also conducted to determine whether the SNAP purification column (Invitrogen Corporation, Carlsbad, Calif.) or the CONCERT purification system (Invitrogen Corporation, Carlsbad, Calif.) differed in providing optimal purified template for carrying out BP reactions after TOPO Joining. TOPO Joining reactions and BP reactions were conducted as described above, except that some samples were purified using SNAP columns, and other samples were purified using the CONCERT plasmid purification system after conducting the TOPO Joining reaction. Purified samples were then carried through a standard BP reaction, and reaction mixtures were then used either for transformation via chemical transformation or electroporation. Following transformation, cells were plated to determine recombination efficiency.

Results (No. of Colonies Formed)

| Transformation Method | SNAP | CONCERT | No template (neg. control) |
|---|---|---|---|
| Chemical | 188 | 254 | 0 |
| Electroporation | 8220 | 11,460 | 672 |

These results demonstrate that both SNAP and CONCERT purification systems work well to provide purified template for BP reactions after TOPO Joining reactions.

Optimal Conditions

Based on the results of the above studies taken together, it was determined that the optimal conditions for combination TOPO Joining-Gateway reactions are as follows:

(1) TOPO Joining Reaction (a) attB 1/insert at 1:1 molar ratio, in 5 μl reaction volume (b) incubate at 37° C. for 15 minutes (c) add 1 μl of 0.6% SDS+3 mM EDTA; incubate at 37° C. for 15 minutes (d) purify with SNAP column or CONCERT system into 20 μl of $dH_2O$ (2) BP Reaction (a) prepare reaction mixture:

| | | |
|---|---|---|
| (i) | purified TOPO Joining product | 5.5 μl; |
| (ii) | standard BP reaction buffer | 2 μl; |
| (iii) | pDONR222 (30 ng/μl) | 0.5 μl; |
| (iv) | BP Clonase | 2 μl; |

(b) incubate reaction mixture at room temperature for 60 minutes;

(c) add 1 μl of 2 μg/μl proteinase K;

(d) incubate at 37° C. for 15 minutes;

(e) incubate at 75° C. for 15 minutes;

(3) Transformation (a) use 2–4 μl of reaction mixture from BP reaction, and carry out either chemical transformation or electroporation.

To demonstrate the efficacy of these optimized conditions, studies were conducted using CAT and lacZ inserts of various sizes subjected to TOPO Joining and subsequent BP reactions, followed by transformation and plating.

Results

Chemical Transformation

| Insert | CAT | lacZ (1 kb) | lacZ (1.5 kb) | lacZ (2 kb) | lacZ (3.2 kb) | none |
|---|---|---|---|---|---|---|
| No. of Colonies | 188 | 180 | 182 | 177 | 71 | 3 |
| Right-sized Clone | 10/10 | 18/18 | 16/16 | 17/18 | 18/18 | — |

Electrical Transformation

| Insert | CAT | lacZ (1 kb) | lacZ (1.5 kb) | lacZ (2 kb) | lacZ (3.2 kb) | none |
|---|---|---|---|---|---|---|
| No. of Colonies | 8222 | 7335 | 7320 | 7500 | 6150 | 510 |

These results, taken together, demonstrate that the conditions described above are optimal for combination TOPO Joining-Gateway reactions on inserts of various sizes.

EXAMPLE 10

Construction of a Mammalian Expression Cassette Without Secondary PCR Methods

Preparation of Elements and Gene of Interest

The following primer sets (see Table 8 below) and templates were used for PCR amplification of elements and gene of interest:

(A) Primer set: Sequence #1 and #2; template: pcDNA 4/TetO. PCR product: 5' element.

(B) Primer set: Sequence #3 and #4; template: pcDNA 3.2/V5. PCR product: 3' element.

(C) Primer set: Sequence #5 and #6; template: pcDNA 3.1/CAT. PCR product: CAT insert.

TABLE 8

| Primers Used for Construction of Expression Cassette. | |
|---|---|
| Sequence #1 | GTTGACATTGATTATTGACTAG |
| Sequence #2 | GTTCCGAAGGGTTAACGCTAGAGTCCGGAGGC |
| Sequence #3 | GACTCAAAGGGAAGGTAAGCCTATCCCTAAGG |
| Sequence #4 | GCGCAGATCTGCTATGGCAG |
| Sequence #5 | CGGAACAAGGGACCATGGAGAAAAAAATCACTGGATA |
| Sequence #6 | TGAGTCAAGGGCGCCCCGCCCTGCTGCCACTCATCG |
| Sequence #7 | GGGGACAAGTTTGTACAAAAAAGCAGGCTTCCCTTCGGAAC |
| Sequence #8 | GTTCCGAAGGGAAGCCTGCTTTTTTGTACAAACTTGTCCCC |
| Sequence #9 | GACTCAAAGGGACCCAGCTTTCTTGTACAAAGTGGTCCCC |
| Sequence #10 | GGGGACCACTTTGTACAAGAAAGCTGGGTCCCTTTGAGTC |
| Sequence #11 | CACGACGTTGTAAAACGACG |
| Sequence #12 | ATGTAATACGACTCACTATAGG |

Platinum Taq DNA polymerase High Fidelity (Invitrogen Corporation; Carlsbad, Calif.) was used for PCR. The PCR conditions were as follows:

| Components | Volume | Final Concentration |
|---|---|---|
| $dH_2O$ | 35.5 µl | |
| 10 mM dNTP mixture (2.5 mM each) | 4 µl | 0.2 mM each |
| 10 × High Fidelity PCR Buffer | 5 µl | 1× |
| 50 mM $MgSO_4$ | 2 µl | 2 mM |
| Primer 1 (100 ng/µl) | 1 µl | |
| Primer 2 (100 ng/µl) | 1 µl | |
| Template (10 ng/µl) | 1 µl | |
| Platinum Taq High Fidelity (5 U/µl) | 0.5 µl | |

94° C.: 4 min (1 cycle)

94° C. 30 sec->55° C. 30 sec->68° C. 1 min (30 cycles)

68° C. 10 min (1 cycle)

4° C. (to completion)

The following conditions were used to purify PCR generated fragments:

Reagent: SNAP MiniPrep kit (Invitrogen Corporation, Carlsbad, Calif.).

Steps (1) Mix 50 µl PCR product with 150 µl Binding Buffer. Mix well.

(2) Add 350 µl of Isopropanol. Mix well.

(3) Load the sample onto a SNAP MiniPrep Column.

(4) Centrifuge at 14000 rpm for 1 min. Discard the column flow through.

(5) Add 500 µl of Wash Buffer and centrifuge at 14000 rpm for 1 min. Discard the column flow through.

(6) Add 700 µl of 1× Final Wash Buffer and centrifuge at 14000 rpm for 1 min. Discard the column flow through.

(7) Dry the column by centrifuge at 14000 rpm for 1 min.

(8) Transfer the column to a new centrifuge tube. Add 50 µl of $dH_2O$ to the column. Incubate at room temperature for 2–5 min. Centrifuge at 14000 rpm for 1 min. Collect the flow through.

(9) DNA concentration measurement by UV absorbance at 260 nm.

TOPO Joining Reaction

For production of expression cassettes with secondary PCR, the following joining conditions were used:

| | |
|---|---|
| 5' element (700 bp) | 75 ng |
| 3' element (350 bp) | 35 ng |
| 500 mM Tris (pH7.5) | 0.5 µl |
| Topoisomerase (1 µg/µl) | 0.5 µl |
| CAT insert (700 bp) | 150 ng |
| dH2O | enough to bring final volume to 5 µl |

The reaction was performed at room temperature for 5–15 min. Half volume of the reaction was used as template for the second round PCR with primer set sequence #1 and sequence #4. PCR conditions were the same as above except that the extension time was 2 min. After PCR, DNA was purified as mentioned above. Purified DNA was used for transfection.

For production of expression cassette without secondary PCR, the following joining conditions were used:

| | |
|---|---|
| 5' element (700 bp) | 510 ng |
| 3' element (350 bp) | 230 ng |
| 500 mM Tris (pH7.5) | 1.5 µl |
| Topoisomerase (1 µg/µl) | 3 µl |
| CAT insert (700 bp) | 450 ng |
| dH2O | enough to bring final volume to 15 µl |

The reaction was performed at 37° C. for 15 min. Proteinase K was added to a final concentration of 50 µg/ml and the mixture was incubated at 37° C. for 10 min. The treated DNA was ready for transfection.

Gene Expression Study

Three cell lines (suspension TRex-CHO, adherent TRex-CHO and adherent TRex-293 cell lines) were used as model cell lines to test these expression cassettes. Standard cell culture methods were used. Twenty-four well cell culture plates were used. Lipofectamine 2000 was used as transfection reagent. Twenty-four hours after transfection, tetracycline was added at a final concentration of 1 µg/ml. For control studies, no tetracycline was added. Cells were incubated for another 24 hours before lysis. Western blot was used for transfer of proteins and anti-V5 or anti-CAT antibody was used for detection.

Results and Discussion

The purpose of this study was to demonstrate that expression cassettes could be generated without secondary PCR. In this study, we compared the expression data generated from an expression cassette produced using a secondary PCR step to that obtained using an expression cassette produced without a secondary PCR step. For the expression cassette produced with secondary PCR, about 1.2 µg/well of DNA was used for transfection into 24-well plate format. For the expression cassette without secondary PCR, the product from one joining reaction was used (about 1.2 µg/well). The detection data showed that functional expression cassettes can be produced using the methods of the present invention, without using a secondary PCR step (FIG. 30).

EXAMPLE 11

Generation of Gateway Compatible Cassettes With Topo Tools Methods

Preparation of Adaptors

Equal amounts of sequence #7 and sequence #8 (see Table 8, above) were mixed in 40 mM NaCl and the mixture was denatured at 95° C. for 5 min and slowly cooled to room temperature to form the attB1adaptor. Equal amounts of sequence #9 and sequence #10 (see Table 8, above) were mixed in 40 mM NaCl and the mixture was denatured at 95° C. for 5 min and slowly cooled to room temperature to form the attB2 adaptor.

TOPO Joining

CAT insert was generated as in example 10. The joining conditions were as optimized above (see Examples 9 and 10):

| | |
|---|---|
| attB1 adaptor (40 bp) | 10 ng |
| attB2 adaptor (40 bp) | 10 ng |
| 500 mM Tris (pH7.5) | 0.5 µl |

-continued

| | |
|---|---|
| Topoisomerase (1 μg/μl) | 1 μl |
| CAT insert (700 bp) | 170 ng |
| $dH_2O$ | sufficient to bring final volume to 5 μl |

The reaction was performed at 37° C. for 15 min. SDS and EDTA were added to a final concentration of 0.1% and 0.5 mM respectively. The mixture was incubated at 37° C. for 15 min.

Purification

Water (15 Pμl ) was added to the treated mixture. DNA was purified with SNAP MiniPrep kit (Invitrogen Corporation, Carlsbad, Calif.).

Steps (1) Mix the treated product with 60 μl Binding Buffer. Mix well.

(2) Add 140 μl of Isopropanol. Mix well.

(3) Load the sample onto a SNAP MiniPrep Column.

(4) Centrifuge at 14000 rpm for 1 min. Discard the column flow through.

(5) Add 500 μl of Wash Buffer and centrifuge at 14000 rpm for 1 min. Discard the column flow through.

(6) Add 700 μl of 1× Final Wash Buffer and centrifuge at 14000 rpm for 1 min. Discard the column flow through.

(7) Dry the column by centrifuge at 14000 rpm for 1 min.

(8) Transfer the column to a new centrifuge tube. Add 20 μl of $dH_2O$ to the column. Incubate at room temperature for 2–5 min. Centrifuge at 14000 rpm for 1 min. Collect the flow through.

BP Reaction

| | |
|---|---|
| BP reaction buffer | 2 μl |
| Purified product | 5.5 μl |
| pDONR 222 (300 ng/μl) | 0.5 μl |
| BP clonase | 2 μl |

The reaction mixture was incubated at room temperature for 60 min then 1 μl of Proteinase K (2 μg/μl) was added. The mixture was incubated at 37° C. for 15 min followed by 15 min at 75° C. to inactive the enzyme.

Transformation

The treated mixture was transformed into TOP10 competent cells (chemical) or eletroporated into ElectroMax competent cells. Cells were plated onto LP-Kanamycin plates and incubated at 37° C. overnight. The number of colonies was counted. To make sure that insert was present in these colonies, we designed primer sets (sequence #11 and #12) to do colony PCR. If insert was present, the PCR product would have produced a band of about 700 bp; if no insert was present, however, the PCR product band would be about 2.2 kb in size.

Results and Discussion

In this study, we wanted to demonstrate that PCR products produced with TOPO Tools sticky ends can be directly joined to attB1 and attB2 adaptors. The joined product can be directly used in the BP recombination reaction to create GATEWAY™ entry clones (Table 9).

TABLE 9

Colonies Generated from BP Reaction.

| Transformation Type | attB1-Cat-attB2 | Vector only |
|---|---|---|
| Chemical | 188 | 0 |
| Electroporation | 8220 | 672 |

To further confirm the insert was present in these colonies, we picked 18 positive colonies and 2 negative colonies to do PCR. PCR results showed that right-sized product was present in all 18 colonies checked (FIG. 31).

The present invention has been described in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

The following commonly owned, co-pending U.S. patent applications are incorporated herein by reference in their entireties: U.S. Provisional Appl. No. 60/254,510, filed Dec. 8, 2000; U.S. application Ser. No. 09/732,914, filed Dec. 11, 2000; U.S. Provisional Appl. No. 60/291,972, filed May 21, 2001; U.S. Provisional Appl. No. 60/318,902, filed Sep. 14, 2001; and U.S. Provisional Appl. No. 60/326,092, filed Sep. 28, 2001.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

EXAMPLE 12

In vitro transcription with the T7 bacteriophage promoter and RNA polymerase is commonly used to generate RNAs for downstream studies such as probing of Northern blots, RNase protection assays, and RNA interference. In order to produce the template molecule, the sequence of interest is usually cloned into a vector downstream of a T7 promoter sequence or PCR amplified with primers including 20–30 nt T7 promoters at their 5' ends. The first method requires subcloning, growth, isolation, and sometimes sequencing of the recombinant plasmid. The second is rapid but requires 40–50 nt primers designed and synthesized in advance of transcription.

T7 TOPO linkers provide a way to quickly and easily add a T7 promoter to an existing PCR product without the need to order new primers and without subcloning. A TOPO-charged linker containing the T7 promoter sequence is joined to a Taq-generated PCR product in a 15 minute reaction. A secondary amplification with a linker-specific primer and one of the original gene-specific primers produces ample template for as many T7 transcription reactions as needed and determines the orientation of the RNA that will be produced.

Here we test conditions for purification of a T7 TOPO linker, and we show that it is capable of efficient ligation to actin and GFP PCR products and can direct T7 transcription from secondarily amplified templates at levels comparable to primary amplification products with a T7 promoter in one primer.

Materials and Methods

The following materials may be used to prepare T7 promoter linkers and attach them to a PCR product (e.g., the actin ORF), and then isolate a construct having the T7 promoter attached to the PCR product in the desired orientation such that an RNA molecule can be transcribed with a T7 polymerase that corresponds to the sense or the antisense or both strands of the PCR fragment (see FIG. 42). T7 TOPO linkers are prepared ase described below. A T7 secondary amplification primer having a sequence that anneals to all or a portion of the T7 promoter such that extension of the primer is in the direction of the attached PCR product. Various buffer, nucleotide and/or salt solutions may be mployed in the reactions described, for example, salt solution (available from Invitrogen Corporation, Carlsbad Calif., catalog number 46-0205), 10× PCR buffer (available from Invitrogen Corporation, Carlsbad Calif., catalog number 46-0121), 10 mM dNTPs (available from Invitrogen Corporation, Carlsbad Calif., catalog number 46-0344).

As an example of the use of the methods of the present invention, a PCR fragment containing all or portions of the actin gene is prepared using forward and reverse actin control primers described below to amplify a fragment from an actin control template. After attachment of the T7 promoter to the fragment, in vitro transcription was performed using a commercially available T7 transcription kit.

Construction and Purification of a T7 Promoter Linker

The following oligos were synthesized and gel-purified:

```
T7topG 5'-pGACTCGTAATACGACTCACTATAGGGCCCTTATTCCGATAGTG-3'  (SEQ ID NO:)

T7botG pAGGGCCCTATAGTGAGTCGTATTACGAGTCAAAAAAAAAAAA        (SEQ ID NO:)

TOPO-5 pCAACACTATCGGAATA                                  (SEQ ID NO:)
```

A total of 50 μg oligos were annealed in a 1:1:3 molar ratio (T7topG:T7botG:TOPO-5) in 1× PNK buffer (New England Biolabs) and 200 mM NaCl by incubation in a thermal cycler for 5 min at 95° C., 5 min at 65° C., 5 min at 37° C., and 5 min at 25° C. 10 μg of annealed oligos were charged in a 400 μl reaction consisting of 1×PNK buffer (New England Biolabs) with 1 mM ATP, 20U of polynucleotide kinase (New England Biolabs), and 50 μg Vaccinia topoisomerase I for 15 min at 37° C. This results in the attachment of the topoisomerase to the 3' terminus of the T7 promoter linker that is to be attached to the PCR product.

The topoisomerase-charged promoter linker was purified using an Akta-FPLC and Unicom software ver. 4.00 (Amersham). 360 μl of the linking reaction was loaded onto a 1 ml HiTrap SP Sepharose HP pre-packed column (Amersham) pre-equilibrated in buffer A (50 mM Tris-HCl pH 7.0), washed at 0.5 ml/min with 11 ml buffer A (collected in 1 ml fractions), and eluted with a 5 ml, 0–100% buffer B (50 mM Tris-HCl pH 7.0, 1M NaCl) gradient followed by 3 ml of 100% buffer B. The eluate was collected in 0.2 ml fractions. Representative chromatograms of the FPLC purification are shown in FIG. 43.

The peak fractions were identified by treating 4 μl of "load" fraction (unpurified linking reaction), 10 μl of each flow-through fraction, and 16 μl of each eluate fraction with 5 μg proteinase K for 30 min prior to loading on a 10% polyacrylamide Novex TBE gel and electrophoresing for 45 min at 200V. The gel was stained for 30 min in 0.2 μg/ml ethidium bromide and destained by washing 10 min in $ddH_2O$. Linker concentration can be estimated by running low DNA mass ladder on the same gel and comparing band intensities (see FIG. 44A).

The location of free topoisomerase among the fractions was determined by loading the same fraction volumes as above but without proteinase K treatment onto Novex 4–12% Tris-Bis NUPAGE gels. 0.3 μg of three topoisomerase were run for comparison. The gels were electrophoresed for 35 min at 200V in MES buffer and stained with Coomassie R-250 (see FIG. 44B).

Three peak fractions (#33–35) of T7 TOPO linker were pooled, diluted with 2 volumes of storage buffer (60% glycerol, 67 μg/ml BSA, 50 mM Tris-HCl pH 7.4, 0.3 mM EDTA, 1.3 mM DTT, 0.07% Triton-X 100), and stored at −20° C.

Plasmid templates pcDNA5/FRT/TO/GFP was from Invitrogen Corporation.

pBAD/TOPO-actin-as was created by TOPO cloning a blunt PCR product amplified with an actin forward, actinF, primer having the sequence 5'-GCTCACCATGGATGATGATATCGC-3' (SEQ ID NO: 127) and an actin reverse, actinR, primer having the sequence 5'-GGAGGAGCAATGATCTTGATCTTC-3' (SEQ ID NO: 128) from the HeLa cDNA PCR control template (available from Invitrogen Corporation, Carlsbad Calif., catalog number 46-0324) into pBAD/TOPO in the antisense orientation.

pUC 19/actin (FIG. 46A) was created by cloning of a BamHI-HindIII digested PCR product amplified from the HeLa cDNA template with BamHI-actinF primer having the sequence 5'-CACGGATCCGCTCACCATGGATGATGATATCGC-3' (SEQ ID NO: 129) and actinR-HindIII primer having the sequence 5'-CACAAGCTTGGAGGAGCAATGATCTTGATCTTC (SEQ ID NO: 130) into BamHI-HindIII digested pUC19.

50 μl reactions were used for both primary and secondary amplifications using 10 pmol each primer, 0.2 mM dNTPs, 1× PCR buffer (from 10× stock, Invitrogen Corporation, Carlsbad Calif.), and 2.5U Platinum Taq DNA polymerase or Recombinant Taq DNA polymerase. Primary reactions were performed using 1 ng of pBAD/TOPO-actin-as, pUC19/actin, or pcDNA5/FRT/TO/GFP plasmids as templates and actinF+actinR or GFPstart (5'-ATGGCTAGCAAAGGAGAAGAACTTT-3' (SEQ ID NO: 131))+GFP-stop2 (5'-TTATTTGTAGAGCTCATCCATGCCA-3' (SEQ ID NO: 132)) primers. For transcription control templates, the GFP and actin forward primers were paired with reverse primers appended with a 5' T7 promoter sequence (5'-GATGACTCGTAATACGACTCACTATAGGG-3' (SEQ ID NO: 133)). Secondary reactions were the same as the primary reactions except 1 μl of T7 TOPO linking reaction was used as template and either actinF or GFPstart primers were combined with the linker-specific primer T7amp1 (5'-GATGACTCGTAATACGACTCACTA-3' (SEQ ID NO: 134)).

GFP primary and secondary amplifications were incubated for 2 min at 94° C. followed by 30 cycles of 94° C. for 15s, 57° C. for 30s, and 72° C. for 45s. Actin primary and secondary amplifications were incubated for 2 min at 94° C.

followed by 30 cycles of 94° C. for 15s, 58° C. for 30s, and 72° C. for 1 min. All amplifications included a final extension step of 7 min at 72° C.

PCR product concentrations were estimated by running on 1.2% agarose-TAE gels with Low DNA Mass ladder and comparing band intensities.

T7 TOPO Linking Reactions

Linking was performed by combining 1 μl of pooled T7 TOPO linker eluate fractions in storage buffer with 1 μl of primary GFP or actin PCR reaction, 3 μl $ddH_2O$, and 1 μl salt solution (1.2M NaCl, 60 mM $MgCl_2$) and incubating at 37° C. for 15 min. Reactions were checked by running 8 μl from a double reaction on a 6% polyacrylamide Novex TBE gel for 1 hr at 200V, staining in 0.2 μg/ml ethidium bromide, and destaining for 10 min in $ddH_2O$. For the negative control, 1×TOPO storage buffer (2 vol. storage buffer, above, +1 vol. buffer A) was substituted for the pooled TOPO linker eluate in vitro transcription 1 μl-1.5 μl of secondary PCR reaction was mixed with 2 μl 75 mM NTPs (Amersham), 4.5 μl $ddH_{20}$, 1 μl 10× transcription buffer (400 mM Tris-HCl pH 8.0, 100 mM DTT, 20 mM spermidine, 100 mM $MgCl_2$), and 1.5 μl enzyme mix (4 parts 50U/μl T7 RNA polymerase, 1 part 40U/μl RNaseOUT, 1 part 0.6U/μl yeast inorganic pyrophosphatase). Reactions were incubated for 1 hr at 37° C. followed by addition of 0.51 μl DNase I (50U/μl) and continued incubation for 15 min. 0.5 μl of each reaction was then mixed with 4.5 μl $ddH_2O$ and 5 μl of Gel Loading Buffer II (Ambion), denatured for 5 min at 95° C., cooled on ice for 5 min, and run on a 1.2% agarose-TAE gel for 45 min at 100V. The gel was stained for 30 min in 1 μg/ml ethidium bromide and destained for 10 min in $ddH_2O$.

Results

T7 TOPO linker purification by FPLC

Figures 42A, 42B:
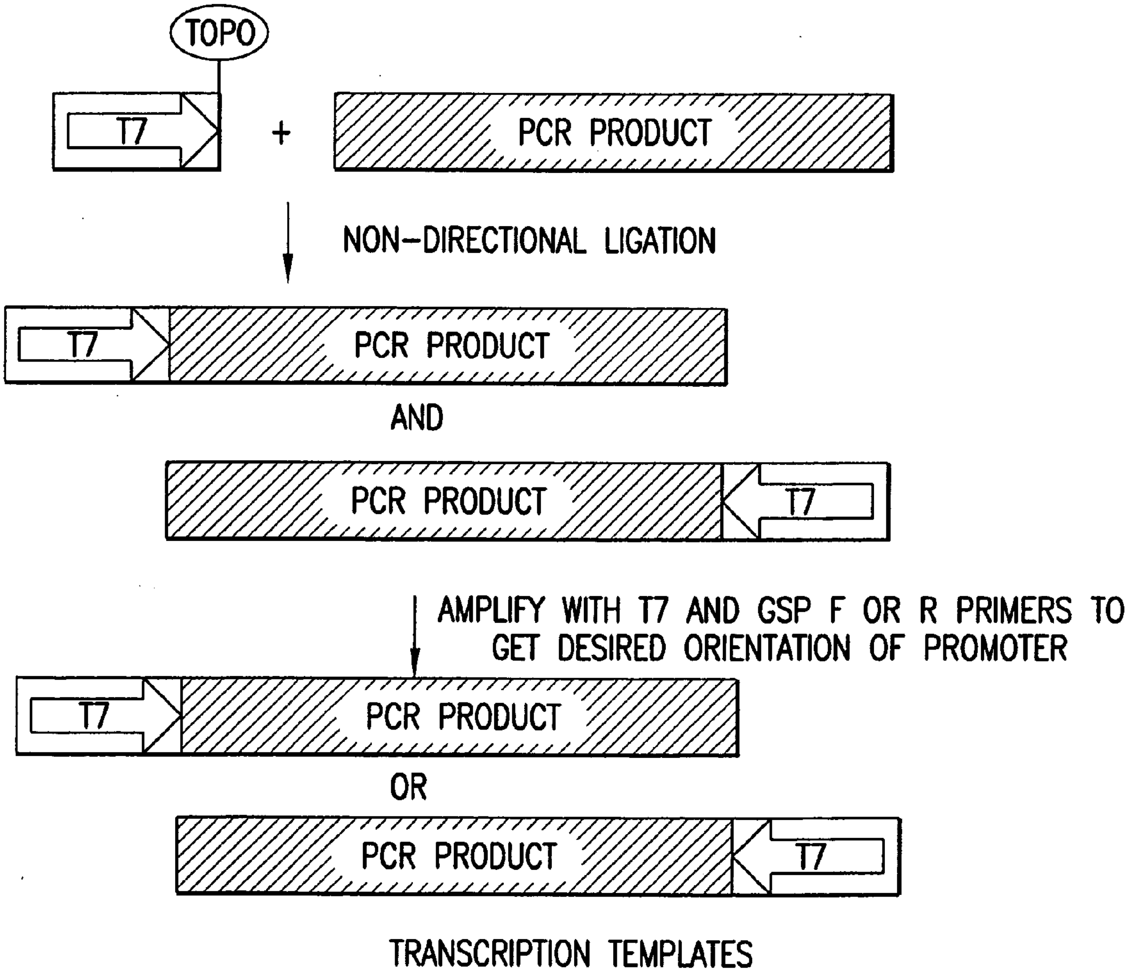

The T7 TOPO linker is produced by annealing three oligos, charging with *Vaccinia* topoisomerase I, and purifying over SP Sepharose as described in the Materials & Methods. The final product is a double-stranded oligo covalently bound to topoisomerase (FIG. 42A). The linker self-joins to Taq-generated PCR products in a 15 min reaction, forming a template for secondary PCR and subsequent transcription (FIG. 42B).

Figure 43A:
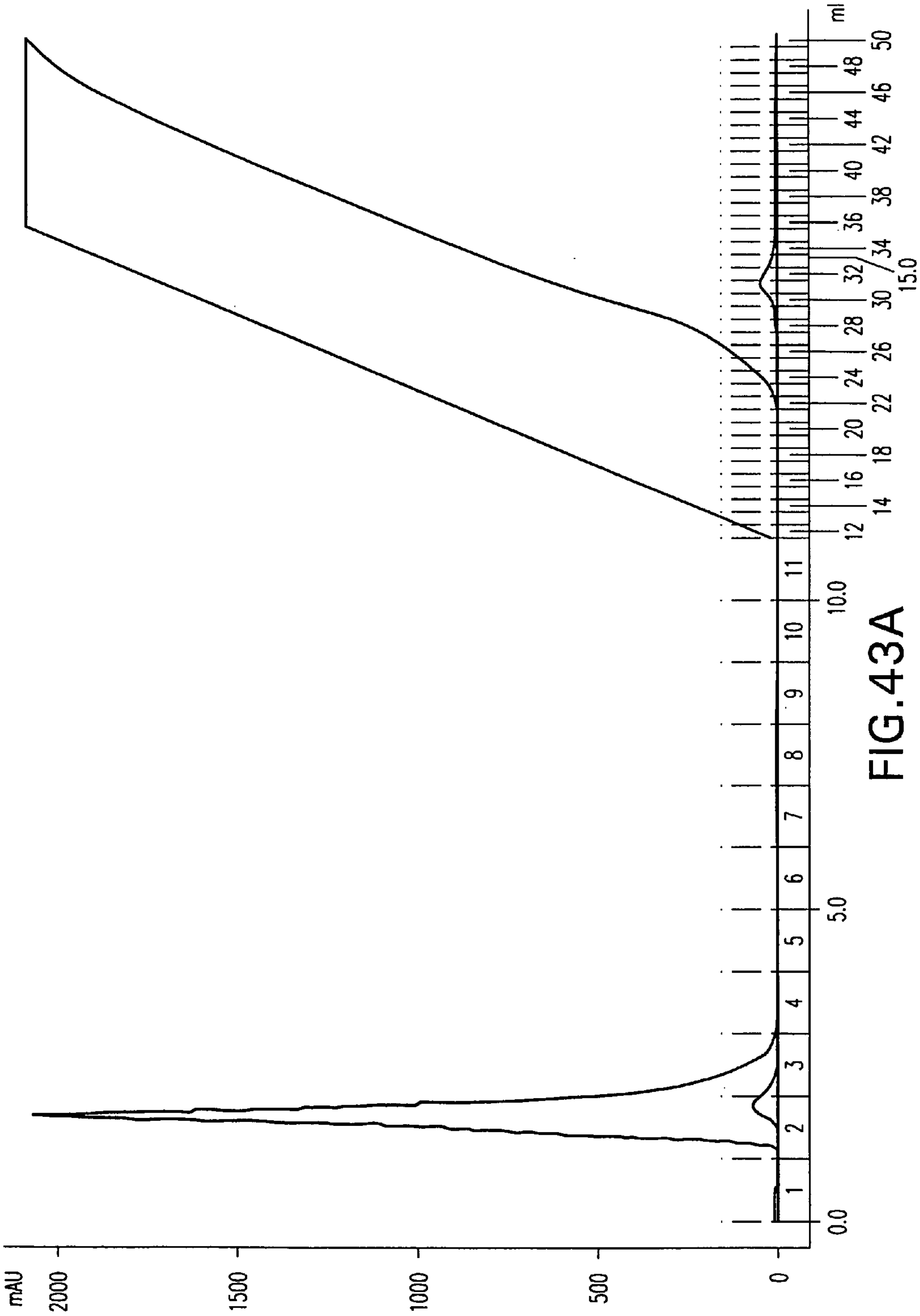
Figure 43B:
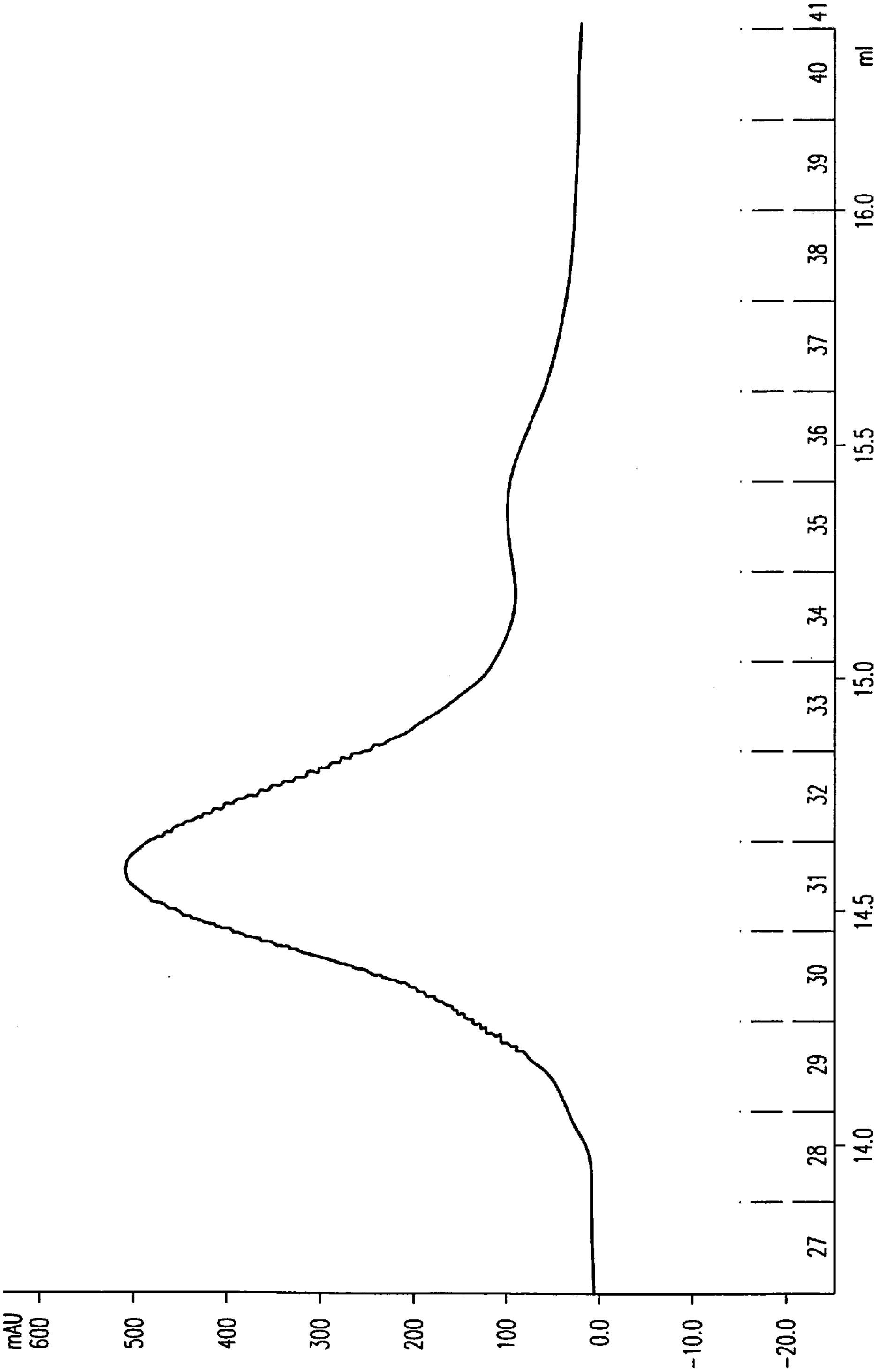
Figure 44A:
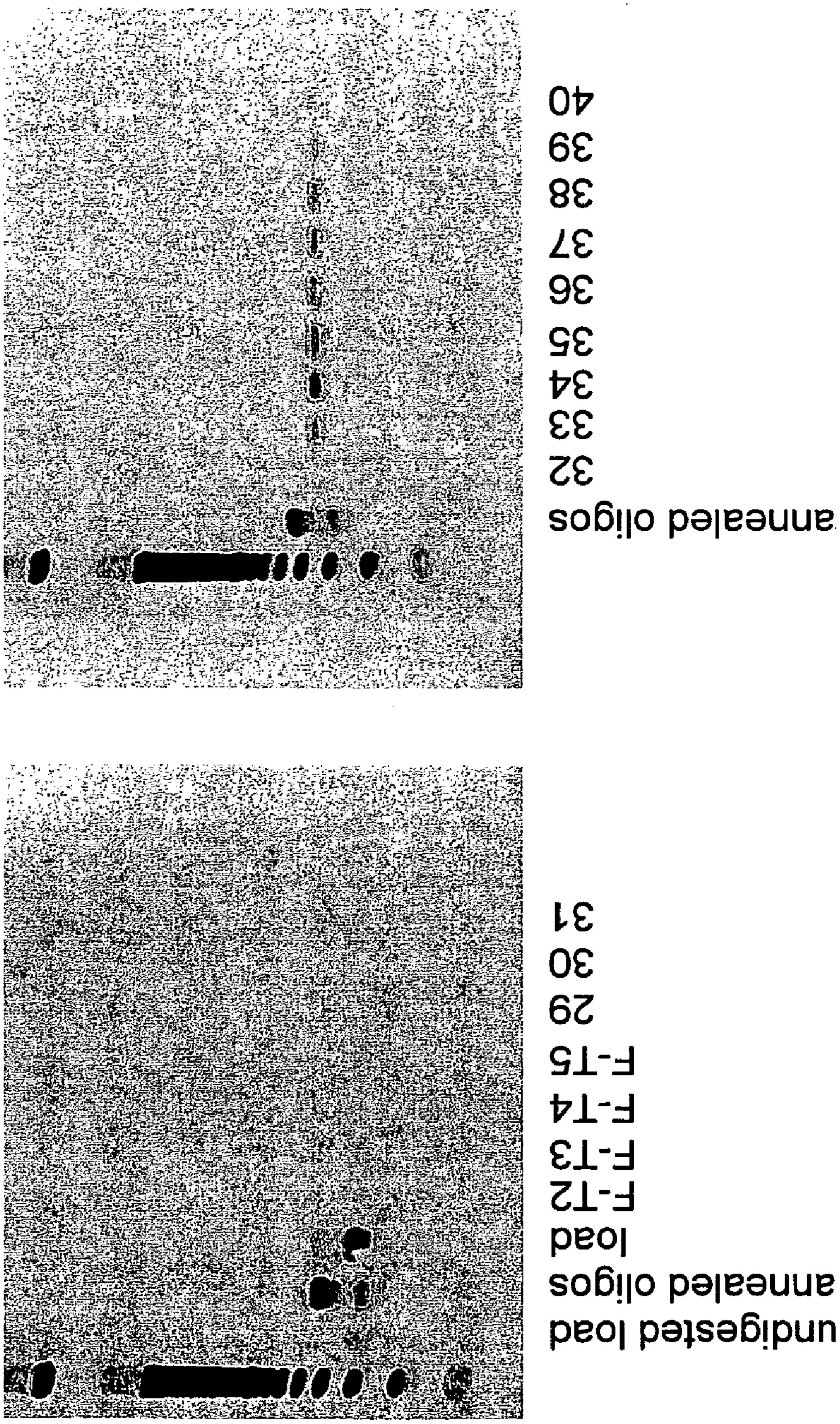

FIG. 43A shows a chromatogram from the FPLC purification. The peak in UV absorbance (254 nm) in flow-through fractions 2 and 3 corresponds to unbound linker, a small cleavage product, and ATP. The small peak corresponding to TOPO-bound linker appears in fractions 30–33 and is magnified in FIG. 43B. Gel electrophoresis (FIG. 44A) reveals that fractions digested with proteinase K can be visualized as discrete bands (compare undigested load with load). The digested topoisomerase/linker covalent complex runs at a lower molecular weight than annealed oligos alone due to cleavage of the oligo duplex by topoisomerase. Little covalent complex is evident in the flow-through fractions (F-T 2 through 5). The lanes corresponding to elution fractions 29–40 demonstrate that the peak elution position of the linker is offset from the UV absorbance trace on the chromatogram in FIG. 43A by approximately 3 fractions (0.6 ml) to fractions 33–36.

Figure 44B:
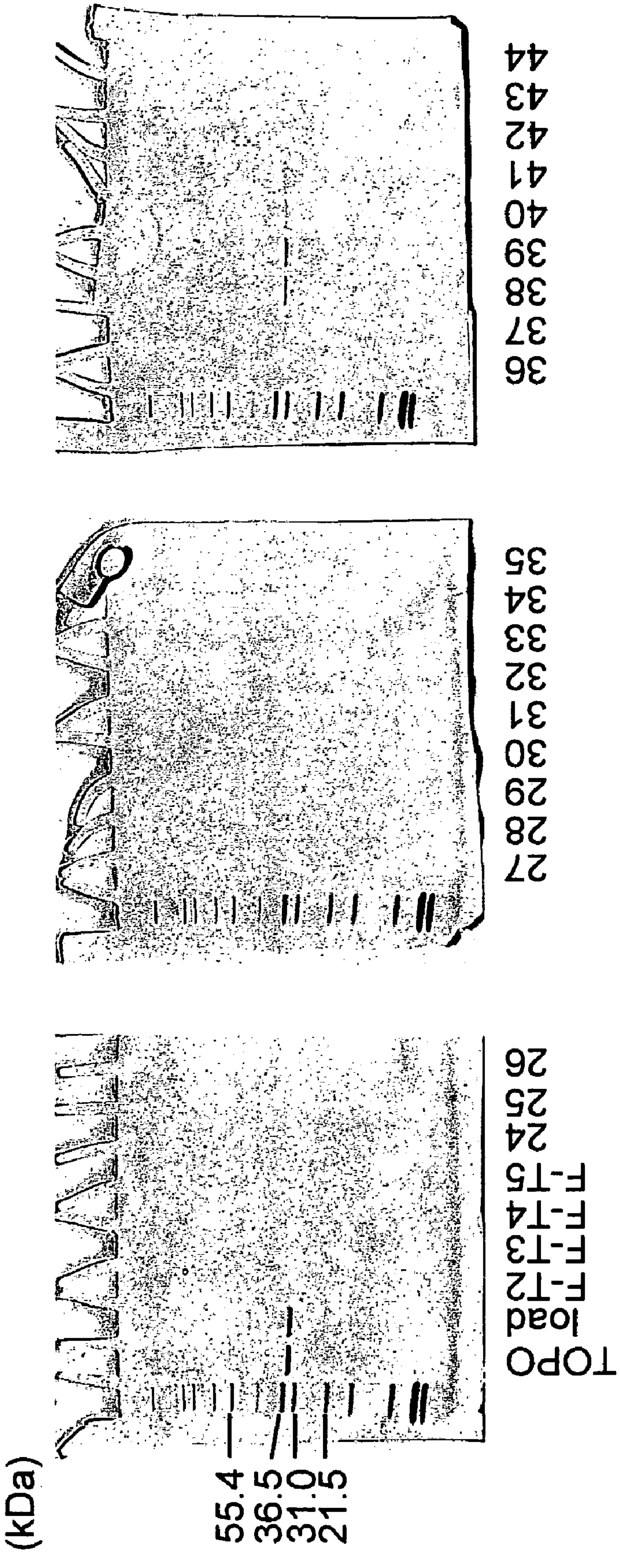
Figure 45B:
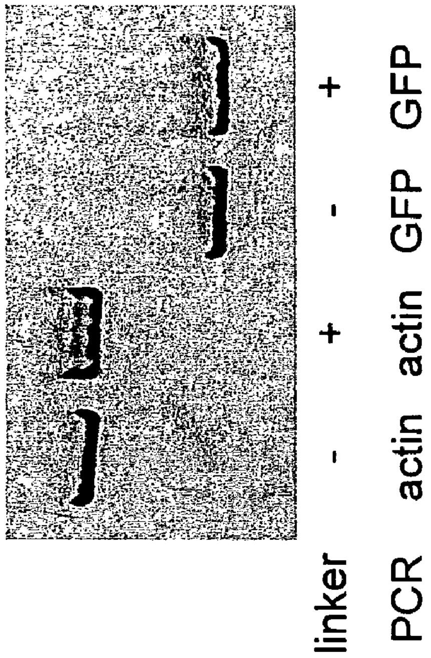

Undigested fractions run on protein gels and stained with Coomassie reveal that free topoisomerase elutes in fractions 37–42 (FIG. 44B, compare to free topoisomerase control lane). T7 TOPO linker can be joined to actin and GFP PCR products T7 TOPO linker from peak fractions #33–35 was pooled and tested for the ability to join with actin (pBAD/TOPO-actin-as template) and GFP (pcDNA5/FRT/TO/GFP template) test PCR products (see FIG. 45A and Materials & Methods). A brief incubation with the linker causes a portion of each Platinum Taq-generated PCR product to shift into a more slowly migrating band during agarose gel electrophoresis (FIG. 45B). This band presumably represents a single copy of the T7 linker joined to one end of the PCR product.

Figure 45A:
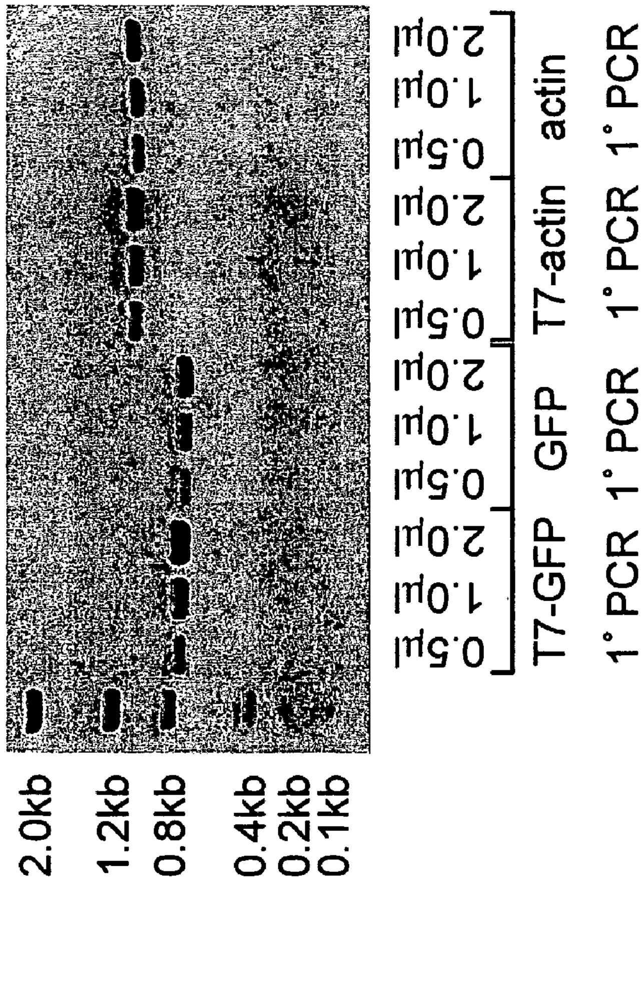
Figure 45D:
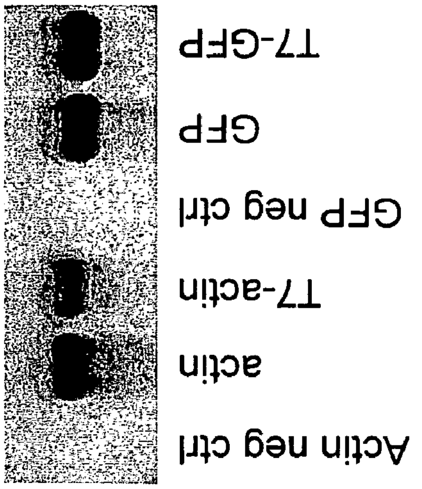
Figure 45C:
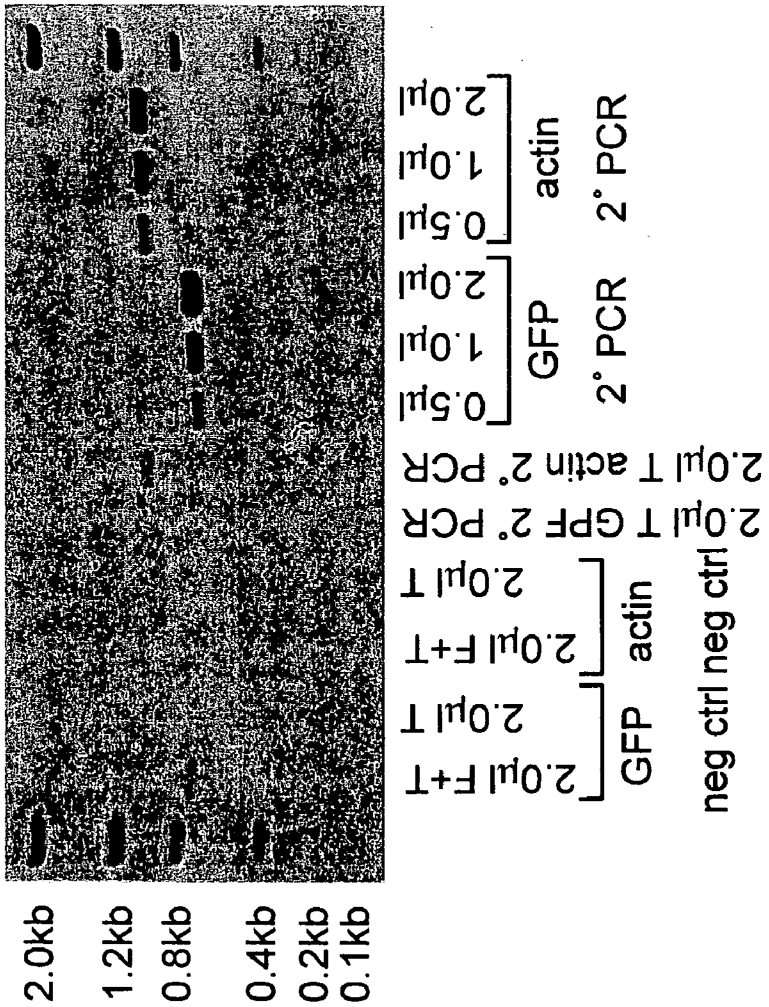
Figure 46A:
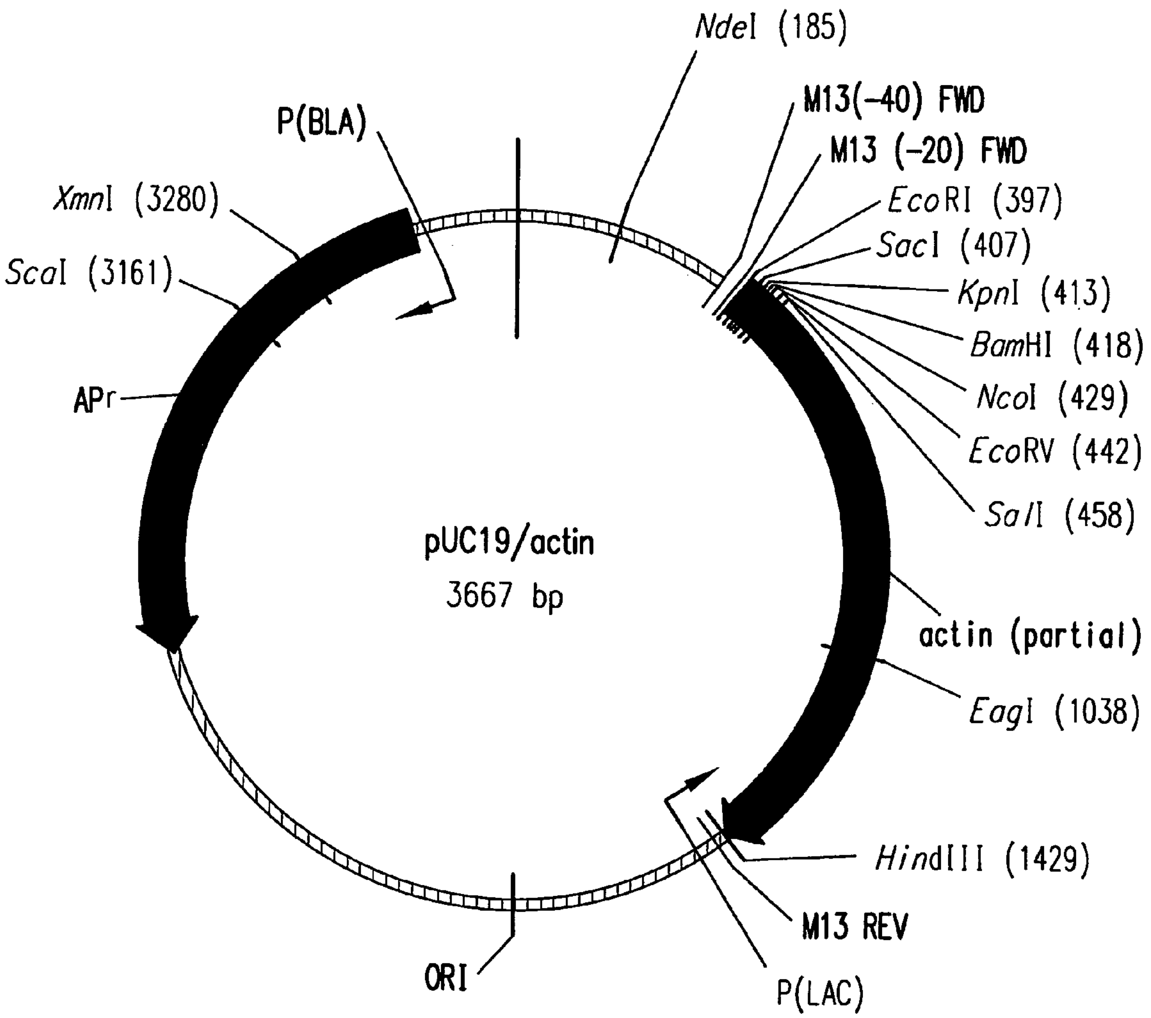
Figure 46D:
Figure 46C:
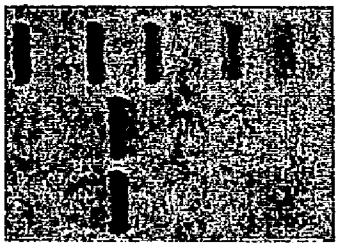
Figure 46B:
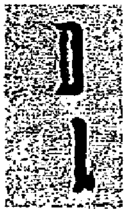

Secondary PCR reactions using the T7 linker specific primer T7amp1 and the appropriate gene-specific forward primer (actinF or GFPstart) produce strong bands when the linker reaction is used as the template but not when control reactions lacking linker are used (FIG. 45C). Relatively weak bands are seen when only the T7amp1 primer is used in the secondary amplification, possibly created from a small amount of template carrying T7 linkers on both ends. Background bands are also evident in some negative control lanes, in which the mock linking reactions (no T7 TOPO linker) were used as templates for the secondary amplification.

T7 TOPO Linkers can be Used to Generate Competent Templates for Transcription

Approximately 40–50 ng of actin and GFP secondary PCR products (1.0 μl) (see FIG. 45C) or T7-actin (1.0 μl) and T7-GFP (1.5 μl) primary PCR products (see FIG. 45A) were used as templates in 10 μl transcription reactions as described in the Materials & Methods. The secondary amplification products from both the actin and GFP linking reactions, but not from the corresponding negative controls, are competent templates for transcription by T7 RNA polymerase (FIG. 45D).

Transcription reactions using these secondary PCR reactions as templates produce equivalent or greater amounts of RNA to those using primary PCR reactions with the T7 promoter sequence added to the 5' end of one of the primers, another common method of generating transcription templates (FIG. 45D). Thus the amplified product of the T7 TOPO linking reaction is a fully competent template. pUC19/actin can also function as an actin template for use with the T7 TOPO linker Similar results were obtained using Recombinant Taq DNA Polymerase and a pUC19/actin template (FIG. 46). Success with a non-Platinum polymerase shows that use of the linkers does not require automatic hot start.

The amount of T7 TOPO linker in the peak fraction (#34) was estimated to be 0.1 ng/μl in the final storage buffer. The linker concentration can be roughly quantitated by running Low DNA Mass Ladder on a gel along with the proteinase K digested peak fractions as in FIG. 44A.

The success of PCR reactions, both primary and secondary, can be estimated by rough quantitation of the products on agarose gels as in FIG. 45A. 20–60 ng/μl should be acceptable for the primary reaction, as the PCR products are in excess in the linking reactions. For the secondary reaction, at least 25 ng/μl should be produced as significantly lower levels will influence the yield of the transcription reaction.

Transcription reaction yields should be judged according to the criteria developed for the forthcoming transcription kit.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. An in vitro method of cloning a nucleic acid molecule comprising:

(a) obtaining a first nucleic acid molecule to be cloned;

(b) mixing said first nucleic acid molecule to be cloned in vitro with a second nucleic acid molecule comprising at least a first topoisomerase recognition site flanked by at least a first recombination site, and at least a second topoisomerase recognition site flanked by at least a second recombation site, wherein said first and second recombination sites do not recombine with each other, and at least one topoisomerase; and (c) incubating said mixture under conditions such that said first nucleic acid molecule to be cloned is inserted into said second nucleic acid molecule between said first and second topoisomerase recognition sites, thereby producing a first product molecule comprising said first nucleic acid molecule to be cloned between said first and second recombination sites.

2. The method of claim 1, wherein the second nucleic acid molecule is a vector.

3. The method of claim 1, wherein said first nucleic acid molecule to be cloned is a linear nucleic acid molecule.

4. The method of claim 1, wherein said linear nucleic acid molecule is a blunt-end nucleic acid molecule.

5. The method of claim 1, wherein said first nucleic acid molecule to be cloned is a PCR product.

6. The method of claim 1, wherein said first nucleic acid molecule to be cloned comprises at least one open reading frame.

7. The method of claim 1, further comprising contacting said first product molecule with at least one third nucleic acid molecule comprising at least a third and fourth recombination sites that do not recombine with each other, under conditions favoring recombination between said first and third and between said second and fourth recombination sites, thereby producing at least one second product molecule.

8. The method of claim 7, wherein the third nucleic acid molecule is a vector.

9. The method of claim 1, further comprising inserting said first product molecule into a host cell.

10. The method of claim 2, further comprising inserting said first product molecule into a host cell.

11. The method of claim 7, further comprising inserting said second product molecule into a host cell.

12. The method of claim 8, further comprising inserting said second product molecule into a host cell.

13. The method of 2, wherein said vector is an expression vector.

14. The method of 8, wherein said vector is an expression vector.

15. The method of claim 1, wherein said second nucleic acid molecule comprises at least one additional nucleic acid sequence selected from the group consisting of a selectable marker, a cloning site, a restriction site, a promoter, an operator, an operon, an origin of replication, and a gene or partial gene.

16. The method of claim 7, wherein said third nucleic acid molecule comprises at least one additional nucleic acid sequence selected from the group consisting of a selectable marker, a cloning site, a restriction site, a promoter, an operator, an operon, an origin of replication, and a gene or partial gene.

17. The method of claim 1, wherein said first and second recombination sites are selected from the group consisting of:

(a) attB sites,
(b) attP sites,
(c) attL sites,
(d) attR sites,
(e) lox sites,
(f) psi sites,
(g) dif sites,
(h) cer sites, and
(i) frt sites.

18. The method of claim 7, wherein said third and fourth recombination sites are selected from the group consisting of:

(a) attB sites,
(b) attP sites,
(c) attL sites,
(d) attR sites,
(e) lox sites,
(f) psi sites,
(g) dif sites,
(h) cer sites, and
(i) frt sites.

19. The method of claim 17, wherein said lox sites are selected from the group consisting of loxP sites and loxP511 sites.

20. The method of claim 18, wherein said lox sites are selected from the group consisting of loxP sites and loxP511 sites.

21. The method of claim 1, wherein said topoisomerase is a type I topoisomerase.

22. The method of claim 7, wherein said product nucleic acid molecule and said third nucleic acid molecule are combined in the presence of at least one recombination protein.

23. The method of claim 22, wherein said recombination protein is selected from the group consisting of:

(a) Cre;

(b) Int;

(c) IHF;

(d) Xis;

(e) Fis;

(f) Hin;

(g) Gin;

(h) Cin;

(i) Tn3 resolvase;

(j) TndX;

(k) XerC; and (l) XerD.

24. The method of claim 22, wherein said recombination protein is Cre.

25. The method of claim 22, wherein said recombination protein is selected from the group consisting of Int, Xis, IHF and Fis.

* * * * *

SEQUENCE LISTING

<160> NUMBER OF SEQ ID NOS: 142

<210> SEQ ID NO 1
<211> LENGTH: 27
<212> TYPE: DNA
<213> ORGANISM: artificial sequence
<220> FEATURE:
<223> OTHER INFORMATION: oligonucleotide primer

<400> SEQUENCE: 1
tatgtatcat acacatacga tttaggt 27

<210> SEQ ID NO 2
<211> LENGTH: 20
<212> TYPE: DNA
<213> ORGANISM: artificial sequence
<220> FEATURE:
<223> OTHER INFORMATION: oligonucleotide primer

<400> SEQUENCE: 2
accgcctctc cccgcgcgtt 20

<210> SEQ ID NO 3
<211> LENGTH: 34
<212> TYPE: DNA
<213> ORGANISM: artificial sequence
<220> FEATURE:
<223> OTHER INFORMATION: oligonucleotide primer

<400> SEQUENCE: 3
gttccgaagg gggcgataca gtcaactgtc tttg 34

<210> SEQ ID NO 4
<211> LENGTH: 36
<212> TYPE: DNA
<213> ORGANISM: artificial sequence
<220> FEATURE:
<223> OTHER INFORMATION: oligonucleotide primer

<400> SEQUENCE: 4
ttggccaagg gtatctagaa gcttctgcag acgcgt 36

<210> SEQ ID NO 5
<211> LENGTH: 34
<212> TYPE: DNA
<213> ORGANISM: artificial sequence
<220> FEATURE:
<223> OTHER INFORMATION: oligonucleotide primer

<400> SEQUENCE: 5
gttccgaagg gccaccgtac tcgtcaattc caag 34

<210> SEQ ID NO 6
<211> LENGTH: 36
<212> TYPE: DNA
<213> ORGANISM: artificial sequence
<220> FEATURE:

-continued

<223> OTHER INFORMATION: oligonucleotide primer

<400> SEQUENCE: 6
ggccaaaagg gaacttgttt attgcagctt ataatg 36

<210> SEQ ID NO 7
<211> LENGTH: 22
<212> TYPE: DNA
<213> ORGANISM: artificial sequence
<220> FEATURE:
<223> OTHER INFORMATION: oligonucleotide primer

<400> SEQUENCE: 7
ctctgacttg agcgtcgatt tt 22

<210> SEQ ID NO 8
<211> LENGTH: 32
<212> TYPE: DNA
<213> ORGANISM: artificial sequence
<220> FEATURE:
<223> OTHER INFORMATION: oligonucleotide primer

<400> SEQUENCE: 8
cggaacaagg ggaattccct gtcaccgaga cc 32

<210> SEQ ID NO 9
<211> LENGTH: 34
<212> TYPE: DNA
<213> ORGANISM: artificial sequence
<220> FEATURE:
<223> OTHER INFORMATION: oligonucleotide primer

<400> SEQUENCE: 9
cggaacaagg ggaattcccg gggatctgga attc 34

<210> SEQ ID NO 10
<211> LENGTH: 29
<212> TYPE: DNA
<213> ORGANISM: artificial sequence
<220> FEATURE:
<223> OTHER INFORMATION: oligonucleotide primer

<400> SEQUENCE: 10
tcgaaagggt cgaggtcgac ctgcagctg 29

<210> SEQ ID NO 11
<211> LENGTH: 26
<212> TYPE: DNA
<213> ORGANISM: artificial sequence
<220> FEATURE:
<223> OTHER INFORMATION: oligonucleotide primer

<400> SEQUENCE: 11
aattcacatt gattattgag tagtta 26

<210> SEQ ID NO 12
<211> LENGTH: 30
<212> TYPE: DNA
<213> ORGANISM: artificial sequence
<220> FEATURE:
<223> OTHER INFORMATION: oligonucleotide primer

<400> SEQUENCE: 12
tcgaaagggt aatggccagc aaaggagaag 30

-continued

<210> SEQ ID NO 13
<211> LENGTH: 27
<212> TYPE: DNA
<213> ORGANISM: artificial sequence
<220> FEATURE:
<223> OTHER INFORMATION: oligonucleotide primer

<400> SEQUENCE: 13
ggccaagggt ttgtagagct catccat 27

<210> SEQ ID NO 14
<211> LENGTH: 29
<212> TYPE: DNA
<213> ORGANISM: artificial sequence
<220> FEATURE:
<223> OTHER INFORMATION: oligonucleotide primer

<400> SEQUENCE: 14
ggccaagggt ctgaatgggg ccgcatagt 29

<210> SEQ ID NO 15
<211> LENGTH: 20
<212> TYPE: DNA
<213> ORGANISM: artificial sequence
<220> FEATURE:
<223> OTHER INFORMATION: oligonucleotide primer

<400> SEQUENCE: 15
aagccataga gcccgggcca 20

<210> SEQ ID NO 16
<211> LENGTH: 31
<212> TYPE: DNA
<213> ORGANISM: artificial sequence
<220> FEATURE:
<223> OTHER INFORMATION: oligonucleotide primer

<400> SEQUENCE: 16
gttccgaagg gtcgaggtcg acctgcagct g 31

<210> SEQ ID NO 17
<211> LENGTH: 30
<212> TYPE: DNA
<213> ORGANISM: artificial sequence
<220> FEATURE:
<223> OTHER INFORMATION: oligonucleotide primer

<400> SEQUENCE: 17
cggaacaagg gatggccagc aaaggagaag 30

<210> SEQ ID NO 18
<211> LENGTH: 31
<212> TYPE: DNA
<213> ORGANISM: artificial sequence
<220> FEATURE:
<223> OTHER INFORMATION: oligonucleotide primer

<400> SEQUENCE: 18
taggccaagg gtttgtagag ctcatccatg c 31

<210> SEQ ID NO 19
<211> LENGTH: 29
<212> TYPE: DNA
<213> ORGANISM: artificial sequence
<220> FEATURE:
<223> OTHER INFORMATION: oligonucleotide primer -continued

<400> SEQUENCE: 19
ggcctaaagg gtgaatgggg ccgcatagt 29

<210> SEQ ID NO 20
<211> LENGTH: 50
<212> TYPE: DNA
<213> ORGANISM: artificial sequence
<220> FEATURE:
<223> OTHER INFORMATION: oligonucleotide primer

<400> SEQUENCE: 20
gaaggagtaa tacgactcac tatagggagc caccatgggc ccttcggaac 50

<210> SEQ ID NO 21
<211> LENGTH: 50
<212> TYPE: DNA
<213> ORGANISM: artificial sequence
<220> FEATURE:
<223> OTHER INFORMATION: oligonucleotide primer

<400> SEQUENCE: 21
gttccgaagg gcccatggtg gctccctata gtgagtcgta ttactccttc 50

<210> SEQ ID NO 22
<211> LENGTH: 21
<212> TYPE: DNA
<213> ORGANISM: artificial sequence
<220> FEATURE:
<223> OTHER INFORMATION: oligonucleotide primer

<400> SEQUENCE: 22
gaaggagtaa tacgactcac t 21

<210> SEQ ID NO 23
<211> LENGTH: 38
<212> TYPE: DNA
<213> ORGANISM: artificial sequence
<220> FEATURE:
<223> OTHER INFORMATION: oligonucleotide primer

<400> SEQUENCE: 23
ggcctaaagg gtccctttag tgagggttaa ttgcgcgc 38

<210> SEQ ID NO 24
<211> LENGTH: 38
<212> TYPE: DNA
<213> ORGANISM: artificial sequence
<220> FEATURE:
<223> OTHER INFORMATION: oligonucleotide primer

<400> SEQUENCE: 24
gcgcgcaatt aaccctcact aaagggaccc tttaggcc 38

<210> SEQ ID NO 25
<211> LENGTH: 34
<212> TYPE: DNA
<213> ORGANISM: artificial sequence
<220> FEATURE:
<223> OTHER INFORMATION: oligonucleotide primer

<400> SEQUENCE: 25
cggaacaagg gatgatagat cccgtcgttt taca 34

<210> SEQ ID NO 26
<211> LENGTH: 32

-continued

<212> TYPE: DNA
<213> ORGANISM: artificial sequence
<220> FEATURE:
<223> OTHER INFORMATION: oligonucleotide primer

<400> SEQUENCE: 26
taggccaagg ggaccatttt caatccgcac ct 32

<210> SEQ ID NO 27
<211> LENGTH: 32
<212> TYPE: DNA
<213> ORGANISM: artificial sequence
<220> FEATURE:
<223> OTHER INFORMATION: oligonucleotide primer

<400> SEQUENCE: 27
taggccaagg ggaggcactt caccgcttgc ca 32

<210> SEQ ID NO 28
<211> LENGTH: 33
<212> TYPE: DNA
<213> ORGANISM: artificial sequence
<220> FEATURE:
<223> OTHER INFORMATION: oligonucleotide primer

<400> SEQUENCE: 28
taggccaagg gtttgacacc agaccaactg gta 33

<210> SEQ ID NO 29
<211> LENGTH: 12
<212> TYPE: DNA
<213> ORGANISM: artificial sequence
<220> FEATURE:
<223> OTHER INFORMATION: Vaccinia topoisomerase cleavable sequence

<400> SEQUENCE: 29
gcccttattc cc 12

<210> SEQ ID NO 30
<211> LENGTH: 12
<212> TYPE: DNA
<213> ORGANISM: artificial sequence
<220> FEATURE:
<223> OTHER INFORMATION: Vaccinia topoisomerase cleavable sequence

<400> SEQUENCE: 30
tcgcccttat tc 12

<210> SEQ ID NO 31
<211> LENGTH: 12
<212> TYPE: DNA
<213> ORGANISM: artificial sequence
<220> FEATURE:
<223> OTHER INFORMATION: Vaccinia topoisomerase cleavable sequence

<400> SEQUENCE: 31
tgtcgccctt at 12

<210> SEQ ID NO 32
<211> LENGTH: 12
<212> TYPE: DNA
<213> ORGANISM: artificial sequence
<220> FEATURE:
<223> OTHER INFORMATION: Vaccinia topoisomerase cleavable sequence

<400> SEQUENCE: 32

-continued gtgtcgccct ta 12

<210> SEQ ID NO 33
<211> LENGTH: 28
<212> TYPE: DNA
<213> ORGANISM: artificial sequence
<220> FEATURE:
<223> OTHER INFORMATION: adapter oligonucleotide, TOPO D1

<400> SEQUENCE: 33
aattgatccc ttcaccgaca tagtacag 28

<210> SEQ ID NO 34
<211> LENGTH: 12
<212> TYPE: DNA
<213> ORGANISM: artificial sequence
<220> FEATURE:
<223> OTHER INFORMATION: adapter oligonucleotide, TOPO D2

<400> SEQUENCE: 34
ggtgaaggga tc 12

<210> SEQ ID NO 35
<211> LENGTH: 11
<212> TYPE: DNA
<213> ORGANISM: artificial sequence
<220> FEATURE:
<223> OTHER INFORMATION: adapter oligonucleotide, TOPO D5

<400> SEQUENCE: 35
aagggcgagc t 11

<210> SEQ ID NO 36
<211> LENGTH: 19
<212> TYPE: DNA
<213> ORGANISM: artificial sequence
<220> FEATURE:
<223> OTHER INFORMATION: adapter oligonucleotide, TOPO D4

<400> SEQUENCE: 36
cgcccttgac atagtacag 19

<210> SEQ ID NO 37
<211> LENGTH: 12
<212> TYPE: DNA
<213> ORGANISM: artificial sequence
<220> FEATURE:
<223> OTHER INFORMATION: oligonucleotide overhang sequence of TOPO D1
      and TOPO D4

<400> SEQUENCE: 37
gacatagtac ag 12

<210> SEQ ID NO 38
<211> LENGTH: 15
<212> TYPE: DNA
<213> ORGANISM: artificial sequence
<220> FEATURE:
<223> OTHER INFORMATION: annealing oligonucleotide sequence, TOPO D3

<400> SEQUENCE: 38
caactgtact atgtc 15

<210> SEQ ID NO 39
<211> LENGTH: 23
<212> TYPE: DNA

-continued

<213> ORGANISM: artificial sequence
<220> FEATURE:
<223> OTHER INFORMATION: adapter oligonucleotide, TOPO H

<400> SEQUENCE: 39
agctcgccct tattccgata gtg 23

<210> SEQ ID NO 40
<211> LENGTH: 11
<212> TYPE: DNA
<213> ORGANISM: artificial sequence
<220> FEATURE:
<223> OTHER INFORMATION: adapter oligonucleotide, TOPO 16

<400> SEQUENCE: 40
gaataagggc g 11

<210> SEQ ID NO 41
<211> LENGTH: 23
<212> TYPE: DNA
<213> ORGANISM: artificial sequence
<220> FEATURE:
<223> OTHER INFORMATION: adapter oligonucleotide, TOPO 1

<400> SEQUENCE: 41
aattcgccct tattccgata gtg 23

<210> SEQ ID NO 42
<211> LENGTH: 12
<212> TYPE: DNA
<213> ORGANISM: artificial sequence
<220> FEATURE:
<223> OTHER INFORMATION: oligonucleotide overhang sequence of TOPO 1

<400> SEQUENCE: 42
attccgatag tg 12

<210> SEQ ID NO 43
<211> LENGTH: 15
<212> TYPE: DNA
<213> ORGANISM: artificial sequence
<220> FEATURE:
<223> OTHER INFORMATION: annealing oligonucleotide, TOPO 3

<400> SEQUENCE: 43
caacactatc ggaat 15

<210> SEQ ID NO 44
<211> LENGTH: 14
<212> TYPE: DNA
<213> ORGANISM: artificial sequence
<220> FEATURE:
<223> OTHER INFORMATION: DNA sequence of the N-terminus of a
theoretical protein

<400> SEQUENCE: 44
atggatctga taaa 14

<210> SEQ ID NO 45
<211> LENGTH: 14
<212> TYPE: DNA
<213> ORGANISM: artificial sequence
<220> FEATURE:
<223> OTHER INFORMATION: PCR primer

<400> SEQUENCE: 45

-continued

```
accgatctga taaa                                                14


<210> SEQ ID NO 46
<211> LENGTH: 27
<212> TYPE: DNA
<213> ORGANISM: artificial sequence
<220> FEATURE:
<223> OTHER INFORMATION: DNA sequence of the C-terminus of a
      theoretical protein

<400> SEQUENCE: 46

aagtcggagc actcgacgac ggtgtag                                  27


<210> SEQ ID NO 47
<211> LENGTH: 17
<212> TYPE: DNA
<213> ORGANISM: artificial sequence
<220> FEATURE:
<223> OTHER INFORMATION: reverse PCR primer sequence

<400> SEQUENCE: 47

aaacaccgtc gtcgagt                                             17


<210> SEQ ID NO 48
<211> LENGTH: 33
<212> TYPE: DNA
<213> ORGANISM: artificial sequence
<220> FEATURE:
<223> OTHER INFORMATION: DNA sequence of the C-teminus of a
      theoretical protein

<400> SEQUENCE: 48

gcggttaagt cggagcactc gacgactgca tag                           33


<210> SEQ ID NO 49
<211> LENGTH: 24
<212> TYPE: DNA
<213> ORGANISM: artificial sequence
<220> FEATURE:
<223> OTHER INFORMATION: sequence of reverse primer without stop codon

<400> SEQUENCE: 49

tgcagtcgtc gagtgctccg actt                                     24


<210> SEQ ID NO 50
<211> LENGTH: 27
<212> TYPE: DNA
<213> ORGANISM: artificial sequence
<220> FEATURE:
<223> OTHER INFORMATION: sequence of reverse primer with stop codon

<400> SEQUENCE: 50

ctatgcagtc gtcgagtgct ccgactt                                  27


<210> SEQ ID NO 51
<211> LENGTH: 22
<212> TYPE: DNA
<213> ORGANISM: artificial sequence
<220> FEATURE:
<223> OTHER INFORMATION: oligonucleotide primer

<400> SEQUENCE: 51

gttgacattg attattgact ag                                       22


<210> SEQ ID NO 52
<211> LENGTH: 32
```

-continued

<212> TYPE: DNA
<213> ORGANISM: artificial sequence
<220> FEATURE:
<223> OTHER INFORMATION: oligonucleotide primer

<400> SEQUENCE: 52
gttccgaagg gttaacgcta gagtccggag gc 32

<210> SEQ ID NO 53
<211> LENGTH: 32
<212> TYPE: DNA
<213> ORGANISM: artificial sequence
<220> FEATURE:
<223> OTHER INFORMATION: oligonucleotide primer

<400> SEQUENCE: 53
gactcaaagg gaaggtaagc ctatccctaa gg 32

<210> SEQ ID NO 54
<211> LENGTH: 20
<212> TYPE: DNA
<213> ORGANISM: artificial sequence
<220> FEATURE:
<223> OTHER INFORMATION: oligonucleotide primer

<400> SEQUENCE: 54
gcgcagatct gctatggcag 20

<210> SEQ ID NO 55
<211> LENGTH: 37
<212> TYPE: DNA
<213> ORGANISM: artificial sequence
<220> FEATURE:
<223> OTHER INFORMATION: oligonucleotide primer

<400> SEQUENCE: 55
cggaacaagg gaccatggag aaaaaaatca ctggata 37

<210> SEQ ID NO 56
<211> LENGTH: 36
<212> TYPE: DNA
<213> ORGANISM: artificial sequence
<220> FEATURE:
<223> OTHER INFORMATION: oligonucleotide primer

<400> SEQUENCE: 56
tgagtcaagg gcgccccgcc ctgctgccac tcatcg 36

<210> SEQ ID NO 57
<211> LENGTH: 41
<212> TYPE: DNA
<213> ORGANISM: artificial sequence
<220> FEATURE:
<223> OTHER INFORMATION: oligonucleotide sequence

<400> SEQUENCE: 57
ggggacaagt ttgtacaaaa aagcaggctt cccttcggaa c 41

<210> SEQ ID NO 58
<211> LENGTH: 41
<212> TYPE: DNA
<213> ORGANISM: artificial sequence
<220> FEATURE:
<223> OTHER INFORMATION: oligonucleotide primer

<400> SEQUENCE: 58

-continued gttccgaagg gaagcctgct tttttgtaca aacttgtccc c 41

<210> SEQ ID NO 59
<211> LENGTH: 40
<212> TYPE: DNA
<213> ORGANISM: artificial sequence
<220> FEATURE:
<223> OTHER INFORMATION: oligonucleotide primer

<400> SEQUENCE: 59
gactcaaagg gacccagctt tcttgtacaa agtggtcccc 40

<210> SEQ ID NO 60
<211> LENGTH: 40
<212> TYPE: DNA
<213> ORGANISM: artificial sequence
<220> FEATURE:
<223> OTHER INFORMATION: oligonucleotide primer

<400> SEQUENCE: 60
ggggaccact ttgtacaaga aagctgggtc cctttgagtc 40

<210> SEQ ID NO 61
<211> LENGTH: 20
<212> TYPE: DNA
<213> ORGANISM: artificial sequence
<220> FEATURE:
<223> OTHER INFORMATION: oligonucleotide primer

<400> SEQUENCE: 61
cacgacgttg taaaacgacg 20

<210> SEQ ID NO 62
<211> LENGTH: 22
<212> TYPE: DNA
<213> ORGANISM: artificial sequence
<220> FEATURE:
<223> OTHER INFORMATION: oligonucleotide primer

<400> SEQUENCE: 62
atgtaatacg actcactata gg 22

<210> SEQ ID NO 63
<211> LENGTH: 11
<212> TYPE: DNA
<213> ORGANISM: artificial sequence
<220> FEATURE:
<223> OTHER INFORMATION: nucleotide primer

<400> SEQUENCE: 63
cggaacaagg g 11

<210> SEQ ID NO 64
<211> LENGTH: 11
<212> TYPE: DNA
<213> ORGANISM: artificial sequence
<220> FEATURE:
<223> OTHER INFORMATION: nucleotide primer

<400> SEQUENCE: 64
taggccaagg g 11

<210> SEQ ID NO 65
<211> LENGTH: 16
<212> TYPE: DNA
<213> ORGANISM: artificial sequence -continued
<220> FEATURE:
<223> OTHER INFORMATION: amplified end of PCR product

<400> SEQUENCE: 65
cccttcggaa caaggg 16

<210> SEQ ID NO 66
<211> LENGTH: 16
<212> TYPE: DNA
<213> ORGANISM: artificial sequence
<220> FEATURE:
<223> OTHER INFORMATION: amplified end of PCR product

<400> SEQUENCE: 66
cccttggcca taaggg 16

<210> SEQ ID NO 67
<211> LENGTH: 75
<212> TYPE: DNA
<213> ORGANISM: artificial sequence
<220> FEATURE:
<223> OTHER INFORMATION: map of multiple cloning sites in plasmids pcDNAGW-DT9(sc) and pENTR-DT(sc)

<400> SEQUENCE: 67
ttgtacaaaa aagcaggctc cgcggccgcc gtactcgaga aagggcgcgc cgacccagct 60
ttcttgtaca aagtg 75

<210> SEQ ID NO 68
<211> LENGTH: 10
<212> TYPE: PRT
<213> ORGANISM: artificial sequence
<220> FEATURE:
<223> OTHER INFORMATION: Amino acid sequence for pcDNAGW-DT9(sc) and pENTR-DT(sc)

<400> SEQUENCE: 68

Leu Tyr Lys Lys Ala Gly Ser Ala Ala Ala
1 5 10

<210> SEQ ID NO 69
<211> LENGTH: 11
<212> TYPE: PRT
<213> ORGANISM: artificial sequence
<220> FEATURE:
<223> OTHER INFORMATION: Amino acid sequence for pcDNAGW-DT9(sc) and pENTR-DT(sc)

<400> SEQUENCE: 69

Gly Arg Ala Asp Pro Ala Phe Leu Tyr Lys Val
1 5 10

<210> SEQ ID NO 70
<211> LENGTH: 2591
<212> TYPE: DNA
<213> ORGANISM: artificial sequence
<220> FEATURE:
<223> OTHER INFORMATION: Nucleotide sequence of plasmid pENTR/D-TOPO
<220> FEATURE:
<221> NAME/KEY: unsure
<222> LOCATION: (691)..(699)
<223> OTHER INFORMATION: N can be any nucleotide: a, t, c, g

<400> SEQUENCE: 70
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120

-continued gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggcccca aataatgatt ttattttgac tgatagtgac 600
ctgttcgttg caacaaattg atgagcaatg cttttttata atgccaactt tgtacaaaaa 660
agcaggctcc gcggccgccc cttcaccatg nnnnnnnnna agggtgggcg cgccgaccca 720
gctttcttgt acaaagttgg cattataaga aagcattgct tatcaatttg ttgcaacgaa 780
caggtcacta tcagtcaaaa taaaatcatt atttgccatc cagctgatat cccctatagt 840
gagtcgtatt acatggtcat agctgtttcc tggcagctct ggcccgtgtc tcaaaatctc 900
tgatgttaca ttgcacaaga taaaaatata tcatcatgaa caataaaact gtctgcttac 960
ataaacagta atacaagggg tgttatgagc catattcaac gggaaacgtc gaggccgcga 1020
ttaaattcca acatggatgc tgatttatat gggtataaat gggctcgcga taatgtcggg 1080
caatcaggtg cgacaatcta tcgcttgtat gggaagcccg atgcgccaga gttgtttctg 1140
aaacatggca aaggtagcgt tgccaatgat gttacagatg agatggtcag actaaactgg 1200
ctgacggaat ttatgcctct tccgaccatc aagcatttta tccgtactcc tgatgatgca 1260
tggttactca ccactgcgat ccccggaaaa acagcattcc aggtattaga agaatatcct 1320
gattcaggtg aaaatattgt tgatgcgctg gcagtgttcc tgcgccggtt gcattcgatt 1380
cctgtttgta attgtccttt taacagcgat cgcgtatttc gtctcgctca ggcgcaatca 1440
cgaatgaata acggtttggt tgatgcgagt gattttgatg acgagcgtaa tggctggcct 1500
gttgaacaag tctggaaaga aatgcataaa cttttgccat tctcaccgga ttcagtcgtc 1560
actcatggtg atttctcact tgataacctt atttttgacg aggggaaatt aataggttgt 1620
attgatgttg gacgagtcgg aatcgcagac cgataccagg atcttgccat cctatggaac 1680
tgcctcggtg agttttctcc ttcattacag aaacggcttt ttcaaaaata tggtattgat 1740
aatcctgata tgaataaatt gcagtttcat ttgatgctcg atgagttttt ctaatcagaa 1800
ttggttaatt ggttgtaaca ctggcagagc attacgctga cttgacggga cggcgcaagc 1860
tcatgaccaa aatcccttaa cgtgagttac gcgtcgttcc actgagcgtc agaccccgta 1920
gaaaagatca aaggatcttc ttgagatcct ttttttctgc gcgtaatctg ctgcttgcaa 1980
acaaaaaaac caccgctacc agcggtggtt tgtttgccgg atcaagagct accaactctt 2040
tttccgaagg taactggctt cagcagagcg cagataccaa atactgtcct tctagtgtag 2100
ccgtagttag gccaccactt caagaactct gtagcaccgc ctacatacct cgctctgcta 2160
atcctgttac cagtggctgc tgccagtggc gataagtcgt gtcttaccgg gttggactca 2220
agacgatagt taccggataa ggcgcagcgg tcgggctgaa cggggggttc gtgcacacag 2280
cccagcttgg agcgaacgac ctacaccgaa ctgagatacc tacagcgtga gcattgagaa 2340
agcgccacgc ttcccgaagg gagaaaggcg gacaggtatc cggtaagcgg cagggtcgga 2400
acaggagagc gcacgaggga gcttccaggg ggaaacgcct ggtatcttta tagtcctgtc 2460

-continued

```
gggtttcgcc acctctgact tgagcgtcga tttttgtgat gctcgtcagg ggggcggagc   2520

ctatggaaaa acgccagcaa cgcggccttt ttacggttcc tggccttttg ctggcctttt   2580

gctcacatgt t                                                        2591
```

<210> SEQ ID NO 71
<211> LENGTH: 2607
<212> TYPE: DNA
<213> ORGANISM: artificial sequence
<220> FEATURE:
<223> OTHER INFORMATION: Nucleotide sequence of plasmid pENTR/SD/D-TOPO
<220> FEATURE:
<221> NAME/KEY: unsure
<222> LOCATION: (710)..(715)
<223> OTHER INFORMATION: N can be any nucleotide: a, t, c, g

<400> SEQUENCE: 71

```
ctttcctgcg ttatcccctg attctgtgga taaccgtatt accgcctttg agtgagctga     60

taccgctcgc cgcagccgaa cgaccgagcg cagcgagtca gtgagcgagg aagcggaaga    120

gcgcccaata cgcaaaccgc ctctccccgc gcgttggccg attcattaat gcagctggca    180

cgacaggttt cccgactgga aagcgggcag tgagcgcaac gcaattaata cgcgtaccgc    240

tagccaggaa gagtttgtag aaacgcaaaa aggccatccg tcaggatggc cttctgctta    300

gtttgatgcc tggcagttta tggcgggcgt cctgcccgcc accctccggg ccgttgcttc    360

acaacgttca aatccgctcc cggcggattt gtcctactca ggagagcgtt caccgacaaa    420

caacagataa aacgaaaggc ccagtcttcc gactgagcct ttcgttttat ttgatgcctg    480

gcagttccct actctcgcgt taacgctagc atggatgttt tcccagtcac gacgttgtaa    540

aacgacggcc agtcttaagc tcgggcccca aataatgatt ttattttgac tgatagtgac    600

ctgttcgttg caacaaattg atgagcaatg cttttttata atgccaactt tgtacaaaaa    660

agcaggctcc gcggccgcct tgtttaactt taagaaggag cccttcaccn nnnnnaaggg    720

tgggcgcgcc gacccagctt tcttgtacaa agttggcatt ataagaaagc attgcttatc    780

aatttgttgc aacgaacagg tcactatcag tcaaaataaa atcattattt gccatccagc    840

tgatatcccc tatagtgagt cgtattacat ggtcatagct gtttcctggc agctctggcc    900

cgtgtctcaa aatctctgat gttacattgc acaagataaa aatatatcat catgaacaat    960

aaaactgtct gcttacataa acagtaatac aaggggtgtt atgagccata ttcaacggga   1020

aacgtcgagg ccgcgattaa attccaacat ggatgctgat ttatatgggt ataaatgggc   1080

tcgcgataat gtcgggcaat caggtgcgac aatctatcgc ttgtatggga agcccgatgc   1140

gccagagttg tttctgaaac atggcaaagg tagcgttgcc aatgatgtta cagatgagat   1200

ggtcagacta aactggctga cggaatttat gcctcttccg accatcaagc attttatccg   1260

tactcctgat gatgcatggt tactcaccac tgcgatcccc ggaaaaacag cattccaggt   1320

attagaagaa tatcctgatt caggtgaaaa tattgttgat gcgctggcag tgttcctgcg   1380

ccggttgcat tcgattcctg tttgtaattg tccttttaac agcgatcgcg tatttcgtct   1440

cgctcaggcg caatcacgaa tgaataacgg tttggttgat gcgagtgatt ttgatgacga   1500

gcgtaatggc tggcctgttg aacaagtctg gaaagaaatg cataaacttt tgccattctc   1560

accggattca gtcgtcactc atggtgattt ctcacttgat aaccttattt ttgacgaggg   1620

gaaattaata ggttgtattg atgttggacg agtcggaatc gcagaccgat accaggatct   1680

tgccatccta tggaactgcc tcggtgagtt ttctccttca ttacagaaac ggctttttca   1740

aaaatatggt attgataatc ctgatatgaa taaattgcag tttcatttga tgctcgatga   1800
```

-continued

```
gtttttctaa tcagaattgg ttaattggtt gtaacactgg cagagcatta cgctgacttg   1860

acgggacggc gcaagctcat gaccaaaatc ccttaacgtg agttacgcgt cgttccactg   1920

agcgtcagac cccgtagaaa agatcaaagg atcttcttga gatccttttt ttctgcgcgt   1980

aatctgctgc ttgcaaacaa aaaaaccacc gctaccagcg gtggtttgtt tgccggatca   2040

agagctacca actctttttc cgaaggtaac tggcttcagc agagcgcaga taccaaatac   2100

tgtccttcta gtgtagccgt agttaggcca ccacttcaag aactctgtag caccgcctac   2160

atacctcgct ctgctaatcc tgttaccagt ggctgctgcc agtggcgata agtcgtgtct   2220

taccgggttg gactcaagac gatagttacc ggataaggcg cagcggtcgg gctgaacggg   2280

gggttcgtgc acacagccca gcttggagcg aacgacctac accgaactga gatacctaca   2340

gcgtgagcat tgagaaagcg ccacgcttcc cgaagggaga aaggcggaca ggtatccggt   2400

aagcggcagg gtcggaacag gagagcgcac gagggagctt ccagggggaa acgcctggta   2460

tctttatagt cctgtcgggt ttcgccacct ctgacttgag cgtcgatttt tgtgatgctc   2520

gtcagggggg cggagcctat ggaaaaacgc cagcaacgcg gcctttttac ggttcctggc   2580

cttttgctgg ccttttgctc acatgtt                                       2607
```

<210> SEQ ID NO 72
<211> LENGTH: 5543
<212> TYPE: DNA
<213> ORGANISM: artificial sequence
<220> FEATURE:
<223> OTHER INFORMATION: Nucleotide sequence of plasmid
pcDNA3.2/V5/GWD-TOPO
<220> FEATURE:
<221> NAME/KEY: unsure
<222> LOCATION: (958)..(966)
<223> OTHER INFORMATION: N can be any nucleotide: a, t, c, g

<400> SEQUENCE: 72

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagt    900

taagctatca acaagtttgt acaaaaaagc aggctccgcg gccgcccctt caccatgnnn    960

nnnnnnaagg gtgggcgcgc cgacccagct ttcttgtaca aagtggttga tctagagggc   1020

ccgcggttcg aaggtaagcc tatccctaac cctctcctcg gtctcgattc tacgcgtacc   1080
```

-continued

```
ggttagtaat gagtttaaac gggggaggct aactgaaaca cggaaggaga caataccgga   1140
aggaacccgc gctatgacgg caataaaaag acagaataaa acgcacgggt gttgggtcgt   1200
ttgttcataa acgcggggtt cggtcccagg gctggcactc tgtcgatacc ccaccgagac   1260
cccattgggg ccaatacgcc cgcgtttctt ccttttcccc accccacccc ccaagttcgg   1320
gtgaaggccc agggctcgca gccaacgtcg gggcggcagg ccctgccata gcagatctgc   1380
gcagctgggg ctctaggggg tatccccacg cgccctgtag cggcgcatta agcgcggcgg   1440
gtgtggtggt tacgcgcagc gtgaccgcta cacttgccag cgccctagcg cccgctcctt   1500
tcgctttctt cccttccttt ctcgccacgt tcgccggctt tccccgtcaa gctctaaatc   1560
ggggcatccc tttagggttc cgatttagtg ctttacggca cctcgacccc aaaaaacttg   1620
attagggtga tggttcacgt agtgggccat cgccctgata gacggttttt cgccctttga   1680
cgttggagtc cacgttcttt aatagtggac tcttgttcca aactggaaca acactcaacc   1740
ctatctcggt ctattctttt gatttataag ggattttggg gatttcggcc tattggttaa   1800
aaaatgagct gatttaacaa aaatttaacg cgaattaatt ctgtggaatg tgtgtcagtt   1860
agggtgtgga aagtccccag gctccccagc aggcagaagt atgcaaagca tgcatctcaa   1920
ttagtcagca accaggtgtg gaaagtcccc aggctcccca gcaggcagaa gtatgcaaag   1980
catgcatctc aattagtcag caaccatagt cccgccccta actccgccca tcccgcccct   2040
aactccgccc agttccgccc attctccgcc ccatggctga ctaatttttt ttatttatgc   2100
agaggccgag gccgcctctg cctctgagct attccagaag tagtgaggag gcttttttgg   2160
aggcctaggc ttttgcaaaa agctcccggg agcttgtata tccattttcg gatctgatca   2220
agagacagga tgaggatcgt ttcgcatgat tgaacaagat ggattgcacg caggttctcc   2280
ggccgcttgg gtggagaggc tattcggcta tgactgggca caacagacaa tcggctgctc   2340
tgatgccgcc gtgttccggc tgtcagcgca ggggcgcccg gttctttttg tcaagaccga   2400
cctgtccggt gccctgaatg aactgcagga cgaggcagcg cggctatcgt ggctggccac   2460
gacgggcgtt ccttgcgcag ctgtgctcga cgttgtcact gaagcgggaa gggactggct   2520
gctattgggc gaagtgccgg ggcaggatct cctgtcatct caccttgctc ctgccgagaa   2580
agtatccatc atggctgatg caatgcggcg gctgcatacg cttgatccgg ctacctgccc   2640
attcgaccac caagcgaaac atcgcatcga gcgagcacgt actcggatgg aagccggtct   2700
tgtcgatcag gatgatctgg acgaagagca tcaggggctc gcgccagccg aactgttcgc   2760
caggctcaag gcgcgcatgc ccgacggcga ggatctcgtc gtgacccatg gcgatgcctg   2820
cttgccgaat atcatggtgg aaaatggccg cttttctgga ttcatcgact gtggccggct   2880
gggtgtggcg gaccgctatc aggacatagc gttggctacc cgtgatattg ctgaagagct   2940
tggcggcgaa tgggctgacc gcttcctcgt gctttacggt atcgccgctc ccgattcgca   3000
gcgcatcgcc ttctatcgcc ttcttgacga gttcttctga gcgggactct ggggttcgcg   3060
aaatgaccga ccaagcgacg cccaacctgc catcacgaga tttcgattcc accgccgcct   3120
tctatgaaag gttgggcttc ggaatcgttt tccgggacgc cggctggatg atcctccagc   3180
gcggggatct catgctggag ttcttcgccc accccaactt gtttattgca gcttataatg   3240
gttacaaata aagcaatagc atcacaaatt tcacaaataa agcatttttt tcactgcatt   3300
ctagttgtgg tttgtccaaa ctcatcaatg tatcttatca tgtctgtata ccgtcgacct   3360
ctagctagag cttggcgtaa tcatggtcat agctgtttcc tgtgtgaaat tgttatccgc   3420
```

-continued tcacaattcc acacaacata cgagccggaa gcataaagtg taaagcctgg ggtgcctaat 3480
gagtgagcta actcacatta attgcgttgc gctcactgcc cgctttccag tcgggaaacc 3540
tgtcgtgcca gctgcattaa tgaatcggcc aacgcgcggg gagaggcggt ttgcgtattg 3600
ggcgctcttc cgcttcctcg ctcactgact cgctgcgctc ggtcgttcgg ctgcggcgag 3660
cggtatcagc tcactcaaag gcggtaatac ggttatccac agaatcaggg gataacgcag 3720
gaaagaacat gtgagcaaaa ggccagcaaa aggccaggaa ccgtaaaaag gccgcgttgc 3780
tggcgttttt ccataggctc cgcccccctg acgagcatca caaaaatcga cgctcaagtc 3840
agaggtggcg aaacccgaca ggactataaa gataccaggc gtttccccct ggaagctccc 3900
tcgtgcgctc tcctgttccg accctgccgc ttaccggata cctgtccgcc tttctccctt 3960
cgggaagcgt ggcgctttct caatgctcac gctgtaggta tctcagttcg gtgtaggtcg 4020
ttcgctccaa gctgggctgt gtgcacgaac cccccgttca gcccgaccgc tgcgccttat 4080
ccggtaacta tcgtcttgag tccaacccgg taagacacga cttatcgcca ctggcagcag 4140
ccactggtaa caggattagc agagcgaggt atgtaggcgg tgctacagag ttcttgaagt 4200
ggtggcctaa ctacggctac actagaagga cagtatttgg tatctgcgct ctgctgaagc 4260
cagttacctt cggaaaaaga gttggtagct cttgatccgg caaacaaacc accgctggta 4320
gcggtggttt ttttgtttgc aagcagcaga ttacgcgcag aaaaaaagga tctcaagaag 4380
atcctttgat cttttctacg gggtctgacg ctcagtggaa cgaaaactca cgttaaggga 4440
ttttggtcat gagattatca aaaaggatct tcacctagat ccttttaaat taaaaatgaa 4500
gttttaaatc aatctaaagt atatatgagt aaacttggtc tgacagttac caatgcttaa 4560
tcagtgaggc acctatctca gcgatctgtc tatttcgttc atccatagtt gcctgactcc 4620
ccgtcgtgta gataactacg atacgggagg gcttaccatc tggccccagt gctgcaatga 4680
taccgcgaga cccacgctca ccggctccag atttatcagc aataaaccag ccagccggaa 4740
gggccgagcg cagaagtggt cctgcaactt tatccgcctc catccagtct attaattgtt 4800
gccgggaagc tagagtaagt agttcgccag ttaatagttt gcgcaacgtt gttgccattg 4860
ctacaggcat cgtggtgtca cgctcgtcgt ttggtatggc ttcattcagc tccggttccc 4920
aacgatcaag gcgagttaca tgatccccca tgttgtgcaa aaaagcggtt agctccttcg 4980
gtcctccgat cgttgtcaga agtaagttgg ccgcagtgtt atcactcatg gttatggcag 5040
cactgcataa ttctcttact gtcatgccat ccgtaagatg cttttctgtg actggtgagt 5100
actcaaccaa gtcattctga gaatagtgta tgcggcgacc gagttgctct tgcccggcgt 5160
caatacggga taataccgcg ccacatagca gaactttaaa agtgctcatc attggaaaac 5220
gttcttcggg gcgaaaactc tcaaggatct taccgctgtt gagatccagt tcgatgtaac 5280
ccactcgtgc acccaactga tcttcagcat cttttacttt caccagcgtt tctgggtgag 5340
caaaaacagg aaggcaaaat gccgcaaaaa agggaataag ggcgacacgg aaatgttgaa 5400
tactcatact cttccttttt caatattatt gaagcattta tcagggttat tgtctcatga 5460
gcggatacat atttgaatgt atttagaaaa ataaacaaat aggggttccg cgcacatttc 5520
cccgaaaagt gccacctgac gtc 5543

<210> SEQ ID NO 73
<211> LENGTH: 5173
<212> TYPE: DNA
<213> ORGANISM: artificial sequence
<220> FEATURE:
<223> OTHER INFORMATION: Nucleotide sequence of plasmid -continued pcDNA6.2/V5/GWD-TOPO
<220> FEATURE:
<221> NAME/KEY: unsure
<222> LOCATION: (958)..(966)
<223> OTHER INFORMATION: N can be any nucleotide: a, t, c, g

<400> SEQUENCE: 73

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagt    900
taagctatca acaagtttgt acaaaaaagc aggctccgcg gccgcccctt caccatgnnn    960
nnnnnnaagg gtgggcgcgc cgacccagct ttcttgtaca aagtggttga tctagagggc   1020
ccgcggttcg aaggtaagcc tatccctaac cctctcctcg gtctcgattc tacgcgtacc   1080
ggttagtaat gagtttaaac gggggaggct aactgaaaca cggaaggaga caataccgga   1140
aggaacccgc gctatgacgg caataaaaag acagaataaa acgcacgggt gttgggtcgt   1200
ttgttcataa acgcggggtt cggtcccagg gctggcactc tgtcgatacc ccaccgagac   1260
cccattgggg ccaatacgcc cgcgtttctt ccttttcccc accccacccc ccaagttcgg   1320
gtgaaggccc agggctcgca gccaacgtcg gggcggcagg ccctgccata gcagatctgc   1380
gcagctgggg ctctaggggg tatccccacg cgccctgtag cggcgcatta agcgcggcgg   1440
gtgtggtggt tacgcgcagc gtgaccgcta cacttgccag cgccctagcg cccgctcctt   1500
tcgctttctt cccttccttt ctcgccacgt tcgcaggctt tccccgtcaa gctctaaatc   1560
ggggcatccc tttagggttc cgatttagtg ctttacggca cctcgacccc aaaaaacttg   1620
attagggtga tggttcacgt agtgggccat cgccctgata gacggttttt cgccctttga   1680
cgttggagtc cacgttcttt aatagtggac tcttgttcca aactggaaca acactcaacc   1740
ctatctcggt ctattctttt gatttataag ggattttggg gatttcggcc tattggttaa   1800
aaaatgagct gatttaacaa aaatttaacg cgaattaatt ctgtggaatg tgtgtcagtt   1860
agggtgtgga aagtccccag gctccccagc aggcagaagt atgcaaagca tgcatctcaa   1920
ttagtcagca accaggtgtg gaaagtcccc aggctcccca gcaggcagaa gtatgcaaag   1980
catgcatctc aattagtcag caaccatagt cccgccccta actccgccca tcccgcccct   2040
aactccgccc agttccgccc attctccgcc ccatggctga ctaatttttt ttatttatgc   2100
agaggccgag gccgcctctg cctctgagct attccagaag tagtgaggag gcttttttgg   2160
```

-continued

```
aggcctaggc ttttgcaaaa agctcccggg agcttgtata tccattttcg gatctgatca   2220
gcacgtgttg acaattaatc atcggcatag tatatcggca tagtataata cgacaaggtg   2280
aggaactaaa ccatggccaa gcctttgtct caagaagaat ccaccctcat tgaaagagca   2340
acggctacaa tcaacagcat ccccatctct gaagactaca gcgtcgccag cgcagctctc   2400
tctagcgacg gccgcatctt cactggtgtc aatgtatatc attttactgg gggaccttgt   2460
gcagaactcg tggtgctggg cactgctgct gctgcggcag ctggcaacct gacttgtatc   2520
gtcgcgatcg gaaatgagaa caggggcatc ttgagcccct gcggacggtg ccgacaggtg   2580
cttctcgatc tgcatcctgg gatcaaagcc atagtgaagg acagtgatgg acagccgacg   2640
gcagttggga ttcgtgaatt gctgccctct ggttatgtgt gggagggcta agcacttcgt   2700
ggccgaggag caggactgac acgtgctacg agatttcgat tccaccgccg ccttctatga   2760
aaggttgggc ttcggaatcg ttttccggga cgccggctgg atgatcctcc agcgcgggga   2820
tctcatgctg gagttcttcg cccaccccaa cttgtttatt gcagcttata atggttacaa   2880
ataaagcaat agcatcacaa atttcacaaa taaagcattt ttttcactgc attctagttg   2940
tggtttgtcc aaactcatca atgtatctta tcatgtctgt ataccgtcga cctctagcta   3000
gagcttggcg taatcatggt catagctgtt tcctgtgtga aattgttatc cgctcacaat   3060
tccacacaac atacgagccg gaagcataaa gtgtaaagcc tggggtgcct aatgagtgag   3120
ctaactcaca ttaattgcgt tgcgctcact gcccgctttc cagtcgggaa acctgtcgtg   3180
ccagctgcat taatgaatcg gccaacgcgc ggggagaggc ggtttgcgta ttgggcgctc   3240
ttccgcttcc tcgctcactg actcgctgcg ctcggtcgtt cggctgcggc gagcggtatc   3300
agctcactca aaggcggtaa tacggttatc cacagaatca ggggataacg caggaaagaa   3360
catgtgagca aaaggccagc aaaaggccag gaaccgtaaa aaggccgcgt tgctggcgtt   3420
tttccatagg ctccgccccc ctgacgagca tcacaaaaat cgacgctcaa gtcagaggtg   3480
gcgaaacccg acaggactat aaagatacca ggcgtttccc cctggaagct ccctcgtgcg   3540
ctctcctgtt ccgaccctgc cgcttaccgg atacctgtcc gcctttctcc cttcgggaag   3600
cgtggcgctt tctcatagct cacgctgtag gtatctcagt tcggtgtagg tcgttcgctc   3660
caagctgggc tgtgtgcacg aaccccccgt tcagcccgac cgctgcgcct tatccggtaa   3720
ctatcgtctt gagtccaacc cggtaagaca cgacttatcg ccactggcag cagccactgg   3780
taacaggatt agcagagcga ggtatgtagg cggtgctaca gagttcttga agtggtggcc   3840
taactacggc tacactagaa gaacagtatt tggtatctgc gctctgctga agccagttac   3900
cttcggaaaa agagttggta gctcttgatc cggcaaacaa accaccgctg gtagcggttt   3960
ttttgtttgc aagcagcaga ttacgcgcag aaaaaaagga tctcaagaag atcctttgat   4020
cttttctacg gggtctgacg ctcagtggaa cgaaaactca cgttaaggga ttttggtcat   4080
gagattatca aaaaggatct tcacctagat ccttttaaat taaaaatgaa gttttaaatc   4140
aatctaaagt atatatgagt aaacttggtc tgacagttac caatgcttaa tcagtgaggc   4200
acctatctca gcgatctgtc tatttcgttc atccatagtt gcctgactcc ccgtcgtgta   4260
gataactacg atacgggagg gcttaccatc tggccccagt gctgcaatga taccgcgaga   4320
cccacgctca ccggctccag atttatcagc aataaaccag ccagccggaa gggccgagcg   4380
cagaagtggt cctgcaactt tatccgcctc catccagtct attaattgtt gccgggaagc   4440
tagagtaagt agttcgccag ttaatagttt gcgcaacgtt gttgccattg ctacaggcat   4500
```

-continued

```
cgtggtgtca cgctcgtcgt ttggtatggc ttcattcagc tccggttccc aacgatcaag   4560

gcgagttaca tgatccccca tgttgtgcaa aaaagcggtt agctccttcg gtcctccgat   4620

cgttgtcaga agtaagttgg ccgcagtgtt atcactcatg gttatggcag cactgcataa   4680

ttctcttact gtcatgccat ccgtaagatg cttttctgtg actggtgagt actcaaccaa   4740

gtcattctga gaatagtgta tgcggcgacc gagttgctct tgcccggcgt caatacggga   4800

taataccgcg ccacatagca gaactttaaa agtgctcatc attggaaaac gttcttcggg   4860

gcgaaaactc tcaaggatct taccgctgtt gagatccagt tcgatgtaac ccactcgtgc   4920

acccaactga tcttcagcat cttttacttt caccagcgtt tctgggtgag caaaaacagg   4980

aaggcaaaat gccgcaaaaa agggaataag ggcgacacgg aaatgttgaa tactcatact   5040

cttccttttt caatattatt gaagcattta tcagggttat tgtctcatga gcggatacat   5100

atttgaatgt atttagaaaa ataaacaaat aggggttccg cgcacatttc cccgaaaagt   5160

gccacctgac gtc                                                      5173
```

<210> SEQ ID NO 74
<211> LENGTH: 69
<212> TYPE: DNA
<213> ORGANISM: artificial sequence
<220> FEATURE:
<223> OTHER INFORMATION: Partial sequence of pENTR/SD-dTOPO
<220> FEATURE:
<221> NAME/KEY: unsure
<222> LOCATION: (64)..(69)
<223> OTHER INFORMATION: N can be any nucleotide: a, t, c, g

<400> SEQUENCE: 74

```
ttgtacaaaa aagcaggctc cgcggccgcc ttgtttaact ttaagaagga gcccttcacc     60

atgnnnnnn                                                             69
```

<210> SEQ ID NO 75
<211> LENGTH: 52
<212> TYPE: DNA
<213> ORGANISM: artificial sequence
<220> FEATURE:
<223> OTHER INFORMATION: Nucleotide sequence of TOPO-D71

<400> SEQUENCE: 75

```
ggccgccttg tttaacttta agaaggagcc cttcaccgac tatgtacagtt g             52
```

<210> SEQ ID NO 76
<211> LENGTH: 31
<212> TYPE: DNA
<213> ORGANISM: artificial sequence
<220> FEATURE:
<223> OTHER INFORMATION: Nucleotide sequence of TOPO-D73

<400> SEQUENCE: 76

```
ggccgccccc ttcaccgact atgtacagtt g                                    31
```

<210> SEQ ID NO 77
<211> LENGTH: 28
<212> TYPE: DNA
<213> ORGANISM: artificial sequence
<220> FEATURE:
<223> OTHER INFORMATION: Nucleotide sequence of TOPO-D75

<400> SEQUENCE: 77

```
cgcgcccacc cttgacatag tacagttg                                        28
```

```
<210> SEQ ID NO 78
<211> LENGTH: 14
<212> TYPE: PRT
<213> ORGANISM: artificial sequence
<220> FEATURE:
<223> OTHER INFORMATION: Partial amino acid sequence of pENTR-dTOPO and
      pcDNAGW-dTOPO

<400> SEQUENCE: 78

Leu Tyr Lys Lys Ala Gly Ser Ala Ala Ala Pro Phe Thr Met
1               5                   10

<210> SEQ ID NO 79
<211> LENGTH: 13
<212> TYPE: PRT
<213> ORGANISM: artificial sequence
<220> FEATURE:
<223> OTHER INFORMATION: Partial amino acid sequence of pENTR/SD-dTOPO,
      pENTR-dTOPO, and pcDNAGW-dTOPO

<400> SEQUENCE: 79

Lys Gly Gly Arg Ala Asp Pro Ala Phe Leu Tyr Lys Val
1               5                   10

<210> SEQ ID NO 80
<211> LENGTH: 15
<212> TYPE: DNA
<213> ORGANISM: artificial sequence
<220> FEATURE:
<223> OTHER INFORMATION: Product of binding a topoisomerase to part of
      a nucleic acid molecule
<220> FEATURE:
<221> NAME/KEY: unsure
<222> LOCATION: (13)..(15)
<223> OTHER INFORMATION: N can be any nucleotide: a, t, c, g

<400> SEQUENCE: 80

cccttcacca tgnnn                                                        15

<210> SEQ ID NO 81
<211> LENGTH: 15
<212> TYPE: DNA
<213> ORGANISM: Unknown
<220> FEATURE:
<223> OTHER INFORMATION: 15 bp core region of the wildtype att site

<400> SEQUENCE: 81

gcttttttat actaa                                                        15

<210> SEQ ID NO 82
<211> LENGTH: 21
<212> TYPE: DNA
<213> ORGANISM: Unknown
<220> FEATURE:
<223> OTHER INFORMATION: att site

<400> SEQUENCE: 82

caactttttt atacaaagtt g                                                 21

<210> SEQ ID NO 83
<211> LENGTH: 25
<212> TYPE: DNA
<213> ORGANISM: Unknown
<220> FEATURE:
<223> OTHER INFORMATION: attB1 site

<400> SEQUENCE: 83

agcctgcttt tttgtacaaa cttgt                                             25
```

-continued

<210> SEQ ID NO 84
<211> LENGTH: 233
<212> TYPE: DNA
<213> ORGANISM: Unknown
<220> FEATURE:
<223> OTHER INFORMATION: attP1 site

<400> SEQUENCE: 84
tacaggtcac taataccatc taagtagttg attcatagtg actggatatg ttgtgtttta 60
cagtattatg tagtctgttt tttatgcaaa atctaattta atatattgat atttatatca 120
ttttacgttt ctcgttcagc ttttttgtac aaagttggca ttataaaaaa gcattgctca 180
tcaatttgtt gcaacgaaca ggtcactatc agtcaaaata aaatcattat ttg 233

<210> SEQ ID NO 85
<211> LENGTH: 100
<212> TYPE: DNA
<213> ORGANISM: Unknown
<220> FEATURE:
<223> OTHER INFORMATION: attL1 site

<400> SEQUENCE: 85
caaataatga ttttattttg actgatagtg acctgttcgt tgcaacaaat tgataagcaa 60
tgctttttta taatgccaac tttgtacaaa aaagcaggct 100

<210> SEQ ID NO 86
<211> LENGTH: 125
<212> TYPE: DNA
<213> ORGANISM: Unknown
<220> FEATURE:
<223> OTHER INFORMATION: attR1 site

<400> SEQUENCE: 86
acaagtttgt acaaaaaagc tgaacgagaa acgtaaaatg atataaatat caatatatta 60
aattagattt tgcataaaaa acagactaca taatactgta aaacacaaca tatccagtca 120
ctatg 125

<210> SEQ ID NO 87
<211> LENGTH: 27
<212> TYPE: DNA
<213> ORGANISM: Unknown
<220> FEATURE:
<223> OTHER INFORMATION: attB0 site

<400> SEQUENCE: 87
agcctgcttt tttatactaa cttgagc 27

<210> SEQ ID NO 88
<211> LENGTH: 27
<212> TYPE: DNA
<213> ORGANISM: Unknown
<220> FEATURE:
<223> OTHER INFORMATION: attP0 site site

<400> SEQUENCE: 88
gttcagcttt tttatactaa gttggca 27

<210> SEQ ID NO 89
<211> LENGTH: 27
<212> TYPE: DNA
<213> ORGANISM: Unknown
<220> FEATURE:

-continued

<223> OTHER INFORMATION: attL0 site

<400> SEQUENCE: 89
agcctgcttt tttatactaa gttggca 27

<210> SEQ ID NO 90
<211> LENGTH: 27
<212> TYPE: DNA
<213> ORGANISM: Unknown
<220> FEATURE:
<223> OTHER INFORMATION: attR0 site

<400> SEQUENCE: 90
gttcagcttt tttatactaa cttgagc 27

<210> SEQ ID NO 91
<211> LENGTH: 27
<212> TYPE: DNA
<213> ORGANISM: Unknown
<220> FEATURE:
<223> OTHER INFORMATION: attP1 site

<400> SEQUENCE: 91
gttcagcttt tttgtacaaa gttggca 27

<210> SEQ ID NO 92
<211> LENGTH: 27
<212> TYPE: DNA
<213> ORGANISM: Unknown
<220> FEATURE:
<223> OTHER INFORMATION: attL1 site

<400> SEQUENCE: 92
agcctgcttt tttgtacaaa gttggca 27

<210> SEQ ID NO 93
<211> LENGTH: 25
<212> TYPE: DNA
<213> ORGANISM: Unknown
<220> FEATURE:
<223> OTHER INFORMATION: attR1 site

<400> SEQUENCE: 93
gttcagcttt tttgtacaaa cttgt 25

<210> SEQ ID NO 94
<211> LENGTH: 25
<212> TYPE: DNA
<213> ORGANISM: Unknown
<220> FEATURE:
<223> OTHER INFORMATION: attB2 site

<400> SEQUENCE: 94
acccagcttt cttgtacaaa gtggt 25

<210> SEQ ID NO 95
<211> LENGTH: 27
<212> TYPE: DNA
<213> ORGANISM: Unknown
<220> FEATURE:
<223> OTHER INFORMATION: attP2 site

<400> SEQUENCE: 95
gttcagcttt cttgtacaaa gttggca 27

-continued

<210> SEQ ID NO 96
<211> LENGTH: 27
<212> TYPE: DNA
<213> ORGANISM: Unknown
<220> FEATURE:
<223> OTHER INFORMATION: attL2 site

<400> SEQUENCE: 96
acccagcttt cttgtacaaa gttggca 27

<210> SEQ ID NO 97
<211> LENGTH: 25
<212> TYPE: DNA
<213> ORGANISM: Unknown
<220> FEATURE:
<223> OTHER INFORMATION: attR2 site

<400> SEQUENCE: 97
gttcagcttt cttgtacaaa gtggt 25

<210> SEQ ID NO 98
<211> LENGTH: 22
<212> TYPE: DNA
<213> ORGANISM: Unknown
<220> FEATURE:
<223> OTHER INFORMATION: attB5 site

<400> SEQUENCE: 98
caactttatt atacaaagtt gt 22

<210> SEQ ID NO 99
<211> LENGTH: 27
<212> TYPE: DNA
<213> ORGANISM: Unknown
<220> FEATURE:
<223> OTHER INFORMATION: attP5 site

<400> SEQUENCE: 99
gttcaacttt attatacaaa gttggca 27

<210> SEQ ID NO 100
<211> LENGTH: 24
<212> TYPE: DNA
<213> ORGANISM: Unknown
<220> FEATURE:
<223> OTHER INFORMATION: attL5 site

<400> SEQUENCE: 100
caactttatt atacaaagtt ggca 24

<210> SEQ ID NO 101
<211> LENGTH: 25
<212> TYPE: DNA
<213> ORGANISM: Unknown
<220> FEATURE:
<223> OTHER INFORMATION: attR5 site

<400> SEQUENCE: 101
gttcaacttt attatacaaa gttgt 25

<210> SEQ ID NO 102
<211> LENGTH: 22
<212> TYPE: DNA
<213> ORGANISM: Unknown
<220> FEATURE:
<223> OTHER INFORMATION: attB11 site -continued

<400> SEQUENCE: 102
caacttttct atacaaagtt gt 22

<210> SEQ ID NO 103
<211> LENGTH: 27
<212> TYPE: DNA
<213> ORGANISM: Unknown
<220> FEATURE:
<223> OTHER INFORMATION: attP11 site

<400> SEQUENCE: 103
gttcaacttt tctatacaaa gttggca 27

<210> SEQ ID NO 104
<211> LENGTH: 24
<212> TYPE: DNA
<213> ORGANISM: Unknown
<220> FEATURE:
<223> OTHER INFORMATION: attL11 site

<400> SEQUENCE: 104
caacttttct atacaaagtt ggca 24

<210> SEQ ID NO 105
<211> LENGTH: 25
<212> TYPE: DNA
<213> ORGANISM: Unknown
<220> FEATURE:
<223> OTHER INFORMATION: attR11 site

<400> SEQUENCE: 105
gttcaacttt tctatacaaa gttgt 25

<210> SEQ ID NO 106
<211> LENGTH: 22
<212> TYPE: DNA
<213> ORGANISM: Unknown
<220> FEATURE:
<223> OTHER INFORMATION: attB17 site

<400> SEQUENCE: 106
caacttttgt atacaaagtt gt 22

<210> SEQ ID NO 107
<211> LENGTH: 27
<212> TYPE: DNA
<213> ORGANISM: Unknown
<220> FEATURE:
<223> OTHER INFORMATION: attP17 site

<400> SEQUENCE: 107
gttcaacttt tgtatacaaa gttggca 27

<210> SEQ ID NO 108
<211> LENGTH: 24
<212> TYPE: DNA
<213> ORGANISM: Unknown
<220> FEATURE:
<223> OTHER INFORMATION: attL17 site

<400> SEQUENCE: 108
caacttttgt atacaaagtt ggca 24

<210> SEQ ID NO 109
<211> LENGTH: 25

-continued

<212> TYPE: DNA
<213> ORGANISM: Unknown
<220> FEATURE:
<223> OTHER INFORMATION: attR17 site

<400> SEQUENCE: 109
gttcaacttt tgtatacaaa gttgt 25

<210> SEQ ID NO 110
<211> LENGTH: 22
<212> TYPE: DNA
<213> ORGANISM: Unknown
<220> FEATURE:
<223> OTHER INFORMATION: attB19 site

<400> SEQUENCE: 110
caactttttc gtacaaagtt gt 22

<210> SEQ ID NO 111
<211> LENGTH: 27
<212> TYPE: DNA
<213> ORGANISM: Unknown
<220> FEATURE:
<223> OTHER INFORMATION: attP19 site

<400> SEQUENCE: 111
gttcaacttt ttcgtacaaa gttggca 27

<210> SEQ ID NO 112
<211> LENGTH: 24
<212> TYPE: DNA
<213> ORGANISM: Unknown
<220> FEATURE:
<223> OTHER INFORMATION: attL19 site

<400> SEQUENCE: 112
caactttttc gtacaaagtt ggca 24

<210> SEQ ID NO 113
<211> LENGTH: 25
<212> TYPE: DNA
<213> ORGANISM: Unknown
<220> FEATURE:
<223> OTHER INFORMATION: attR19 site

<400> SEQUENCE: 113
gttcaacttt ttcgtacaaa gttgt 25

<210> SEQ ID NO 114
<211> LENGTH: 22
<212> TYPE: DNA
<213> ORGANISM: Unknown
<220> FEATURE:
<223> OTHER INFORMATION: attB20 site

<400> SEQUENCE: 114
caactttttg gtacaaagtt gt 22

<210> SEQ ID NO 115
<211> LENGTH: 27
<212> TYPE: DNA
<213> ORGANISM: Unknown
<220> FEATURE:
<223> OTHER INFORMATION: attP20 site

<400> SEQUENCE: 115

-continued gttcaacttt ttggtacaaa gttggca 27

<210> SEQ ID NO 116
<211> LENGTH: 24
<212> TYPE: DNA
<213> ORGANISM: Unknown
<220> FEATURE:
<223> OTHER INFORMATION: attL20 site

<400> SEQUENCE: 116
caactttttg gtacaaagtt ggca 24

<210> SEQ ID NO 117
<211> LENGTH: 25
<212> TYPE: DNA
<213> ORGANISM: Unknown
<220> FEATURE:
<223> OTHER INFORMATION: attR20 site

<400> SEQUENCE: 117
gttcaacttt ttggtacaaa gttgt 25

<210> SEQ ID NO 118
<211> LENGTH: 22
<212> TYPE: DNA
<213> ORGANISM: Unknown
<220> FEATURE:
<223> OTHER INFORMATION: attB21 site

<400> SEQUENCE: 118
caacttttta atacaaagtt gt 22

<210> SEQ ID NO 119
<211> LENGTH: 27
<212> TYPE: DNA
<213> ORGANISM: Unknown
<220> FEATURE:
<223> OTHER INFORMATION: attP21 site

<400> SEQUENCE: 119
gttcaacttt ttaatacaaa gttggca 27

<210> SEQ ID NO 120
<211> LENGTH: 24
<212> TYPE: DNA
<213> ORGANISM: Unknown
<220> FEATURE:
<223> OTHER INFORMATION: attL21 site

<400> SEQUENCE: 120
caacttttta atacaaagtt ggca 24

<210> SEQ ID NO 121
<211> LENGTH: 25
<212> TYPE: DNA
<213> ORGANISM: Unknown
<220> FEATURE:
<223> OTHER INFORMATION: attR21 site

<400> SEQUENCE: 121
gttcaacttt ttaatacaaa gttgt 25

<210> SEQ ID NO 122
<211> LENGTH: 15
<212> TYPE: DNA
<213> ORGANISM: Unknown

-continued

<220> FEATURE:
<223> OTHER INFORMATION: Theoretical protein N-terminus DNA sequence

<400> SEQUENCE: 122
atgggatctg ataaa 15

<210> SEQ ID NO 123
<211> LENGTH: 19
<212> TYPE: DNA
<213> ORGANISM: Unknown
<220> FEATURE:
<223> OTHER INFORMATION: Theoretical PCR primer

<400> SEQUENCE: 123
caccatggga tctgataaa 19

<210> SEQ ID NO 124
<211> LENGTH: 43
<212> TYPE: DNA
<213> ORGANISM: Unknown
<220> FEATURE:
<223> OTHER INFORMATION: Oligonucleotide linker

<400> SEQUENCE: 124
gactcgtaat acgactcact atagggccct tattccgata gtg 43

<210> SEQ ID NO 125
<211> LENGTH: 42
<212> TYPE: DNA
<213> ORGANISM: Unknown
<220> FEATURE:
<223> OTHER INFORMATION: Oligonucleotide linker

<400> SEQUENCE: 125
agggccctat agtgagtcgt attacgagtc aaaaaaaaaa aa 42

<210> SEQ ID NO 126
<211> LENGTH: 16
<212> TYPE: DNA
<213> ORGANISM: Unknown
<220> FEATURE:
<223> OTHER INFORMATION: Oligonucleotide linker

<400> SEQUENCE: 126
caacactatc ggaata 16

<210> SEQ ID NO 127
<211> LENGTH: 24
<212> TYPE: DNA
<213> ORGANISM: Unknown
<220> FEATURE:
<223> OTHER INFORMATION: PCR Primer

<400> SEQUENCE: 127
gctcaccatg gatgatgata tcgc 24

<210> SEQ ID NO 128
<211> LENGTH: 24
<212> TYPE: DNA
<213> ORGANISM: Unknown
<220> FEATURE:
<223> OTHER INFORMATION: PCR Primer

<400> SEQUENCE: 128
ggaggagcaa tgatcttgat cttc 24

-continued

<210> SEQ ID NO 129
<211> LENGTH: 33
<212> TYPE: DNA
<213> ORGANISM: Unknown
<220> FEATURE:
<223> OTHER INFORMATION: PCR Primer

<400> SEQUENCE: 129
cacggatccg ctcaccatgg atgatgatat cgc 33

<210> SEQ ID NO 130
<211> LENGTH: 33
<212> TYPE: DNA
<213> ORGANISM: Unknown
<220> FEATURE:
<223> OTHER INFORMATION: PCR Primer

<400> SEQUENCE: 130
cacaagcttg gaggagcaat gatcttgatc ttc 33

<210> SEQ ID NO 131
<211> LENGTH: 25
<212> TYPE: DNA
<213> ORGANISM: Unknown
<220> FEATURE:
<223> OTHER INFORMATION: PCR Primer

<400> SEQUENCE: 131
atggctagca aaggagaaga acttt 25

<210> SEQ ID NO 132
<211> LENGTH: 25
<212> TYPE: DNA
<213> ORGANISM: Unknown
<220> FEATURE:
<223> OTHER INFORMATION: PCR Primer

<400> SEQUENCE: 132
ttatttgtag agctcatcca tgcca 25

<210> SEQ ID NO 133
<211> LENGTH: 29
<212> TYPE: DNA
<213> ORGANISM: Unknown
<220> FEATURE:
<223> OTHER INFORMATION: PCR Primer

<400> SEQUENCE: 133
gatgactcgt aatacgactc actataggg 29

<210> SEQ ID NO 134
<211> LENGTH: 24
<212> TYPE: DNA
<213> ORGANISM: Unknown
<220> FEATURE:
<223> OTHER INFORMATION: PCR Primer

<400> SEQUENCE: 134
gatgactcgt aatacgactc acta 24

<210> SEQ ID NO 135
<211> LENGTH: 11
<212> TYPE: DNA
<213> ORGANISM: Unknown
<220> FEATURE:
<223> OTHER INFORMATION: 5' end of Element 2

-continued

<400> SEQUENCE: 135
ggccataagg g 11

<210> SEQ ID NO 136
<211> LENGTH: 11
<212> TYPE: DNA
<213> ORGANISM: Unknown
<220> FEATURE:
<223> OTHER INFORMATION: 3' end of Element 1

<400> SEQUENCE: 136
gttccgaagg g 11

<210> SEQ ID NO 137
<211> LENGTH: 11
<212> TYPE: DNA
<213> ORGANISM: Unknown
<220> FEATURE:
<223> OTHER INFORMATION: oligonucleotide

<400> SEQUENCE: 137
ggcctaaagg g 11

<210> SEQ ID NO 138
<211> LENGTH: 33
<212> TYPE: DNA
<213> ORGANISM: Unknown
<220> FEATURE:
<223> OTHER INFORMATION: TOPO-D71 5' end

<400> SEQUENCE: 138
cggaacaaat tgaaattctt cctcgggaag tgg 33

<210> SEQ ID NO 139
<211> LENGTH: 12
<212> TYPE: DNA
<213> ORGANISM: Unknown
<220> FEATURE:
<223> OTHER INFORMATION: TOPO-D70 5' end

<400> SEQUENCE: 139
ctgatacatg tc 12

<210> SEQ ID NO 140
<211> LENGTH: 48
<212> TYPE: DNA
<213> ORGANISM: Unknown
<220> FEATURE:
<223> OTHER INFORMATION: pENTR-dTOPO and pcDNAGW-dTOPO 5'end
<220> FEATURE:
<221> NAME/KEY: misc_feature
<222> LOCATION: (43)..(48)
<223> OTHER INFORMATION: n is a, c, g, or t

<400> SEQUENCE: 140
ttgtacaaaa aagacggctc cgcggccgcc cccttcacca tgnnnnnn 48

<210> SEQ ID NO 141
<211> LENGTH: 12
<212> TYPE: DNA
<213> ORGANISM: Unknown
<220> FEATURE:
<223> OTHER INFORMATION: TOPO-D74 5' end

<400> SEQUENCE: 141

-continued

```
cgggggaagt gg                                                         12


<210> SEQ ID NO 142
<211> LENGTH: 45
<212> TYPE: DNA
<213> ORGANISM: Unknown
<220> FEATURE:
<223> OTHER INFORMATION: pENTR/SD-dTOPO, pENTR-dTOPO, and pcDNAGW-dTOPO
      3' end
<220> FEATURE:
<221> NAME/KEY: misc_feature
<222> LOCATION: (1)..(6)
<223> OTHER INFORMATION: n is a, c, g, or t

<400> SEQUENCE: 142

nnnnnnaagg gtgggcgcgc cgacccagct ttcttgtaca aagtg                     45
```